United States Patent
Luengo et al.

(10) Patent No.: US 11,220,524 B2
(45) Date of Patent: Jan. 11, 2022

(54) SELECTIVE INHIBITORS OF PROTEIN ARGININE METHYLTRANSFERASE 5 (PRMT5)

(71) Applicant: PRELUDE THERAPEUTICS, INCORPORATED, Wilmington, DE (US)

(72) Inventors: Juan Luengo, Phoenixville, PA (US); Raul A. Leal, Newark, DE (US); Hong Lin, Exton, PA (US); Rupa Shetty, Blue Bell, PA (US); Krishna Vaddi, Chadds Ford, PA (US)

(73) Assignee: Prelude Therapeutics Incorporated, Wilmington, DE (US)

( * ) Notice: Subject to any disclaimer, the term of this patent is extended or adjusted under 35 U.S.C. 154(b) by 126 days.

(21) Appl. No.: 16/486,545

(22) PCT Filed: Feb. 20, 2018

(86) PCT No.: PCT/US2018/018856
§ 371 (c)(1),
(2) Date: Aug. 16, 2019

(87) PCT Pub. No.: WO2018/152548
PCT Pub. Date: Aug. 23, 2018

(65) Prior Publication Data
US 2021/0130388 A1    May 6, 2021

Related U.S. Application Data

(60) Provisional application No. 62/461,122, filed on Feb. 20, 2017, provisional application No. 62/461,106, (Continued)

(51) Int. Cl.
*C07H 19/23* (2006.01)
*C07H 19/16* (2006.01)
(Continued)

(52) U.S. Cl.
CPC .............. *C07H 19/23* (2013.01); *A61P 35/00* (2018.01); *C07D 473/34* (2013.01); *C07D 487/04* (2013.01); *C07H 19/16* (2013.01)

(58) Field of Classification Search
None
See application file for complete search history.

(56) References Cited

U.S. PATENT DOCUMENTS

2016/0244475 A1*  8/2016 Tatlock .................. C07H 19/23

FOREIGN PATENT DOCUMENTS

| WO | 2012075500 A2 | 6/2012 |
| WO | 2015200680 A2 | 12/2015 |
| WO | 2016178870 A1 | 11/2016 |

OTHER PUBLICATIONS

International Search Report and Written Opinion issued in PCT/US2018/018856, dated Jun. 28, 2018.
(Continued)

*Primary Examiner* — Traviss C McIntosh, III
(74) *Attorney, Agent, or Firm* — BakerHostetler

(57) ABSTRACT

The disclosure is directed to compounds of Formula I, Formula II, Formula III, Formula IV, Formula V, or Formula VI: Methods of their use in inhibiting a protein arginine methyltransferase 5 (PRMT5) enzyme and treating disease, as well as methods of their preparation are also described.

I

II

III (Continued)

-continued

IV

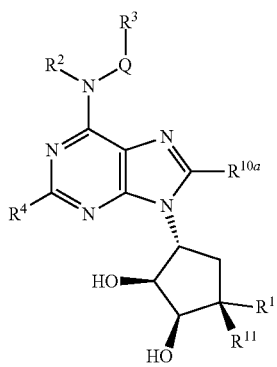

V

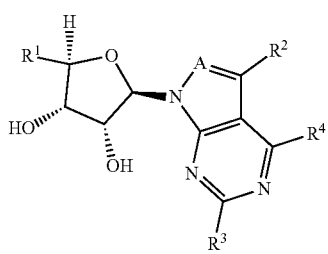

VI

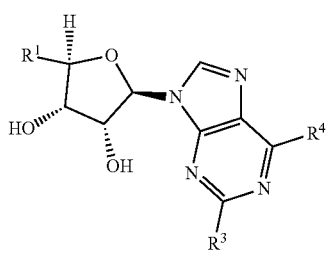

20 Claims, 4 Drawing Sheets

Related U.S. Application Data filed on Feb. 20, 2017, provisional application No. 62/546,444, filed on Aug. 16, 2017, provisional application No. 62/582,528, filed on Nov. 7, 2017, provisional application No. 62/590,038, filed on Nov. 22, 2017.

(51) Int. Cl.
  *A61P 35/00* (2006.01)
  *C07D 473/34* (2006.01)
  *C07D 487/04* (2006.01)

(56) References Cited

OTHER PUBLICATIONS

International Preliminary Report on Patentability and Written Opinion issued in PCT/US2018/018856, dated Aug. 29, 2019.

Mogensen et al., "The Synthesis of New Adenosine A3 Selective Ligands Containing Bioisosteric Isoxazoles" Bioorganic & Medicinal Chemistry Letters, XP004137125, vol. 8, No. 13, 1998, pp. 1767-1770.

Umino et al., "Nucleosides and nucleotides. Part 201: Alternative method to synthesize 9-(6, 7-dideoxy-B-D-allo-hept-5-ynofuranosyl) adenine, a selective and potent ligand for P3 purinoceptor-like protein: a stereoselective reduction based on sugar puckering of the furanose ring" Tetrahedron Letters, XP004215079, vol. 41, No. 33, 2000, pp. 6419-6423.

Database Registry [Online] Chemical Abstracts Service, Columbus, Ohio, US; Sep. 29, 2008 (Sep. 29, 2008), XP002779701, Database accession No. 1054626-26-4; compound cas RN: 1054626-26-4, 1 Page.

* cited by examiner

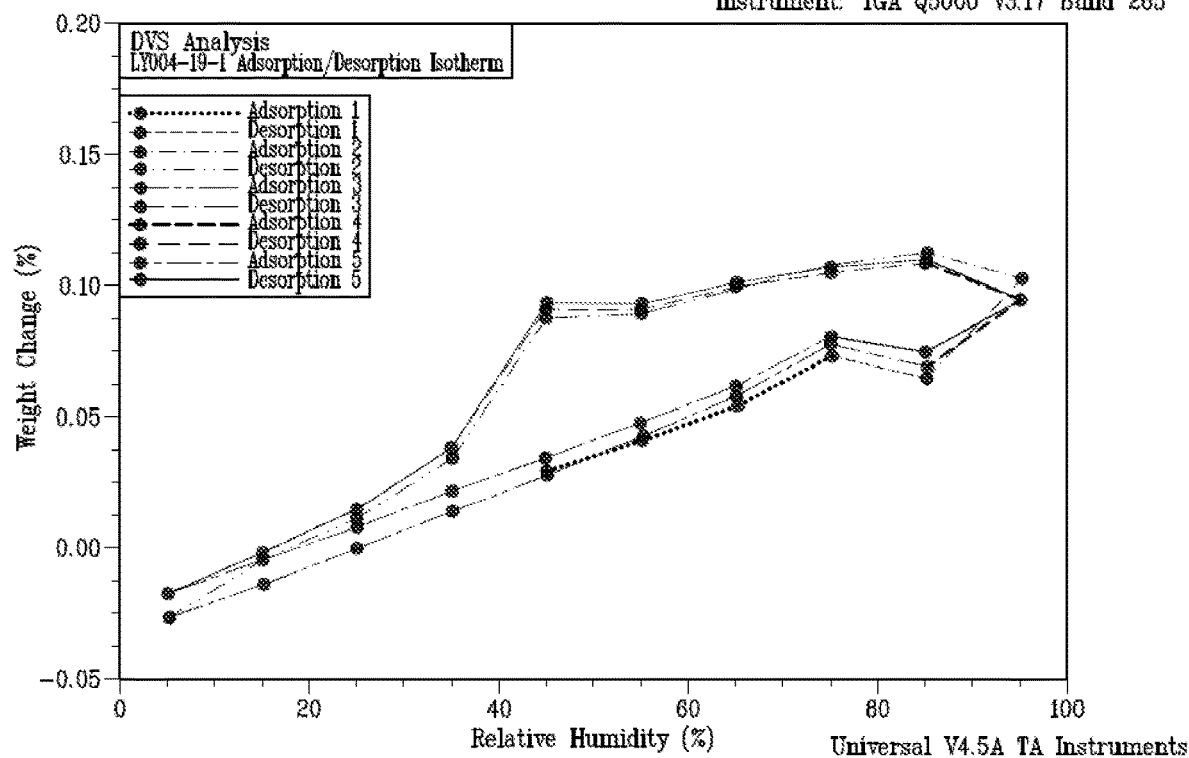

SELECTIVE INHIBITORS OF PROTEIN ARGININE METHYLTRANSFERASE 5 (PRMT5)

CROSS-REFERENCE TO RELATED APPLICATIONS

This application is the National Stage Application of International Patent Application No. PCT/US2018/018856 filed Feb. 20, 2018, which claims the benefit of priority to U.S. Provisional Patent Application No. 62/461,106, filed Feb. 20, 2017, U.S. Provisional Patent Application No. 62/461,122, filed Feb. 20, 2017, U.S. Provisional Patent Application No. 62/546,444, filed Aug. 16, 2017, U.S. Provisional Patent Application No. 62/590,038, filed Nov. 22, 2017, and U.S. Provisional Patent Application No. 62/582,528, filed Nov. 7, 2017, each of which is incorporated herein by reference in its entirety.

TECHNICAL FIELD

The disclosure is directed to PRMT5 inhibitors and methods of their use.

BACKGROUND

Protein arginine methylation is a common post-translational modification that regulates numerous cellular processes, including gene transcription, mRNA splicing, DNA repair, protein cellular localization, cell fate determination, and signaling. Three types of methyl-arginine species exist: ω NG monomethylarginine (MMA), ω NG, NG asymmetric dimethylarginine (ADMA) and ω NG,N'G symmetric dimethylarginine (SDMA). The formation of methylated arginines is catalyzed by the protein arginine methyl transferases (PRMTs) family of methyltransferases. Currently, there are nine PRMTs annotated in the human genome The majority of these enzymes are Type I enzymes (PRMT1, -2, -3, -4, -6, -8) that are capable of mono- and asymmetric dimethylation of arginine, with S-adenosylmethionine (SAM) as the methyl donor. PRMT-5, -7 and -9 are considered to be Type II enzymes that catalyze symmetric dimethylation of arginines. Each PRMT species harbors the characteristic motifs of seven beta strand methyltransferases (Katz et al., 2003), as well as additional "double E" and "THW" sequence motifs particular to the PRMT subfamily.

PRMT5 is as a general transcriptional repressor that functions with numerous transcription factors and repressor complexes, including BRG1 and hBRM, Blimp1, and Snail. This enzyme, once recruited to a promoter, symmetrically dimethylates H3R8 and H4R3. Importantly, the H4R3 site is a major target for PRMT1 methylation (ADMA) and is generally regarded as a transcriptional activating mark. Thus, both H4R3me2s (repressive; me2s indicates SDMA modification) and H4R3me2a (active; me2a indicates ADMA modification) marks are produced in vivo. The specificity of PRMT5 for H3R8 and H4R3 can be altered by its interaction with COPR5 and this could perhaps play an important role in determining PRMT5 corepressor status.

Role of PRMTs in Cancer

Aberrant expression of PRMTs has been identified in human cancers, and PRMTs are considered to be therapeutic targets. Global analysis of histone modifications in prostate cancer has shown that the dimethylation of histone H4R3 is positively correlated with increasing grade, and these changes are predictive of clinical outcome.

PRMT5 levels have been shown to be elevated in a panel of lymphoid cancer cell lines as well as mantle cell lymphoma clinical samples. PRMT5 interacts with a number of substrates that are involved in a variety of cellular processes, including RNA processing, signal transduction, and transcriptional regulation. PRMT5 can directly modify histone H3 and H4, resulting in the repression of gene expression. PRMT5 overexpression can stimulate cell growth and induce transformation by directly repressing tumor suppressor genes. Pal et al., Mol. Cell. Biol. 2003, 7475; Pal et al. Mol. Cell. Biol. 2004, 9630; Wang et al. Mol. Cell. Biol. 2008, 6262; Chung et al. J Biol Chem 2013, 5534. In addition to its well-documented oncogenic functions in transcription and translation, the transcription factor MYC also safeguards proper pre-messenger-RNA splicing as an essential step in lymphomagenesis. Koh et al. Nature 2015, 523 7558; Hsu et al. Nature 2015 525, 384.

The discovery of cancer dependencies has the potential to inform therapeutic strategies and to identify putative drug targets. Integrating data from comprehensive genomic profiling of cancer cell lines and from functional characterization of cancer cell dependencies, it has been recently discovered that loss of the enzyme methylthioadenosine phosphorylase (MTAP) confers a selective dependence on protein arginine methyltransferase 5 (PRMT5) and its binding partner WDR77. MTAP is frequently lost due to its proximity to the commonly deleted tumor suppressor gene, CDKN2A. Cells harboring MTAP deletions possess increased intracellular concentrations of methylthioadenosine (MTA, the metabolite cleaved by MTAP). Furthermore, MTA specifically inhibits PRMT5 enzymatic activity. Administration of either MTA or a small-molecule PRMT5 inhibitor shows a preferential impairment of cell viability for MTAP-null cancer cell lines compared to isogenic MTAP-expressing counterparts. Together, these findings reveal PRMT5 as a potential vulnerability across multiple cancer lineages augmented by a common "passenger" genomic alteration.

Role of PRMT5 in Hemoglobinopathies

The developmental switch in human globin gene subtype from fetal to adult that begins at birth heralds the onset of the hemoglobinopathies, b-thalassemia and sickle cell disease (SCD). The observation that increased adult globin gene expression (in the setting of hereditary persistence of fetal hemoglobin [HPFH] mutations) significantly ameliorates the clinical severity of thalassemia and SCD has prompted the search for therapeutic strategies to reverse gamma-globin gene silencing. Central to silencing of the gamma-genes is DNA methylation, which marks critical CpG dinucleotides flanking the gene transcriptional start site in adult bone marrow erythroid cells. It has been shown that these marks are established as a consequence of recruitment of the DNA methyltransferase, DNMT3A to the gamma-promoter by the protein arginine methyltransferase PRMT5. Zhao et al. Nat Struct Mol Biol. 2009 16, 304. PRMT5-mediated methylation of histone H4R3 recruits DNMT3A, coupling histone and DNA methylation in gene silencing.

PRMT5 induces the repressive histone mark, H4R3me2s, which serves as a template for direct binding of DNMT3A, and subsequent DNA methylation. Loss of PRMT5 binding or its enzymatic activity leads to demethylation of the CpG dinucleotides and gene activation. In addition to the H4R3me2s mark and DNA methylation, PRMT5 binding to the gamma-promoter, and its enzymatic activity are essential for assembly of a multiprotein complex on the gamma-promoter, which induces a range of coordinated repressive epigenetic marks. Disruption of this complex leads to reactivation of gamma gene expression. These studies provide the basis for developing PRMT5 inhibitors as targeted therapies for thalassemia and SCD.

SUMMARY

The disclosure is directed to compounds of Formula I or Formula II:

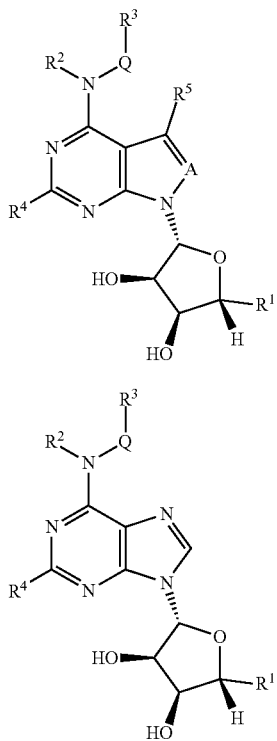

or a pharmaceutically acceptable salt or solvate thereof; wherein

A is CH or N;
Q is NH, $NR^6$ or O;
$R^1$ is —$C_0$-$C_6$alk-$C_3$-$C_6$cycloalkyl, —$C_0$-$C_6$alk-$C_3$-$C_6$halocycloalkyl; —$C_2$-$C_6$alkenyl, —$C_2$-$C_6$haloalkenyl, —$C_0$-$C_6$alk-$C_1$-$C_6$alkyl, —$C_0$-$C_6$alk-$C_1$-$C_6$haloalkyl, —$C_0$-$C_6$alk-C≡CH, —$C_0$-$C_6$alk-C≡C—$C_1$-$C_6$alkyl, —$C_0$-$C_6$alk-C≡C—$C_1$-$C_6$haloalkyl, —$C_0$-$C_6$alk-C≡C—$C_3$-$C_6$cycloalkyl, —$C_1$-$C_6$alk-aryl, —$C_1$-$C_6$alk-S—$C_1$-$C_6$alkyl, —$C_1$-$C_6$alk-S—$C_1$-$C_6$haloalkyl, —$C_1$-$C_6$alk-S—$C_3$-$C_6$cycloalkyl; —$C_1$-$C_6$alk-S—$C_3$-$C_6$halocycloalkyl; —$C_1$-$C_6$alk-O—$C_1$-$C_6$alkyl, —$C_1$-$C_6$alk-O—$C_3$-$C_6$cycloalkyl, —$C_1$-$C_6$alk-S—$CH_2$-aryl, or —$C_1$-$C_6$alk-C(O)NH-aryl, —$C_0$-$C_6$alk-heteroaryl, —$C_1$-$C_6$alk-O-heteroaryl, —$C_1$-$C_6$alk-S-heteroaryl, or —$C_1$-$C_6$alk-NH-heteroaryl;
$R^2$ is H, —$C_1$-$C_6$alkyl, —$C_1$-$C_6$haloalkyl, or —$C_0$-$C_6$alk-$C_3$-$C_6$cycloalkyl;
$R^3$ is H, —$C_1$-$C_6$alkyl, —$C_1$-$C_6$haloalkyl, —$C_0$-$C_6$alk-$C_3$-$C_6$cycloalkyl, —C(O)$R^7$, —C(O)O$R^7$, or —C(O)$NR^{8a}R^{8b}$;
$R^4$ is H, halo, —$C_1$-$C_6$alkyl, or $NH_2$;
$R^5$ is H, halo, CN, —$C_1$-$C_6$alkyl, —$C_2$-$C_4$alkenyl, —$C_2$-$C_4$haloalkenyl, $C_2$-$C_4$cyanoalkenyl, —$C_0$-$C_6$alk-C≡CH, —$C_0$-$C_6$alk-C≡C—$C_1$-$C_6$alkyl, —$C_1$-$C_4$haloalkyl, —$C_2$-$C_6$heterocycloalkyl, oxo-substituted-$C_2$-$C_6$heterocycloalkyl, —$C_3$-$C_6$cycloalkyl, —$C_0$-$C_3$-alk-C(O)$R^9$, —$CR^8R^{8'}$CN, —$CH_2NR^8R^{8'}$, —$C_0$-$C_6$alk-OH, —$NR^8R^{8'}$, —N($R^9$)CN, —O—$C_1$-$C_4$alkyl, —$NR^9CONR^8R^{8'}$, —OCO$NR^8R^{8'}$, or —$NR^9C(O)OR^{9a}$;
$R^6$ is —$C_1$-$C_6$alkyl or $C_0$-$C_6$alk-$C_3$-$C_6$cycloalkyl;
$R^7$ is H, $C_0$-$C_6$alkyl, or $C_0$-$C_6$alk-$C_3$-$C_6$cycloalkyl;
$R^{8a}$ and $R^{8b}$ are each independently H, $C_0$-$C_6$alkyl, or —$C_0$-$C_6$alk-O$C_1$-$C_6$alkyl, or $R^{8a}$ and $R^{8b}$, together with the atom to which they are attached, form a $C_2$-$C_6$heterocycloalkyl ring;
$R^8$ and $R^{8'}$ are each independently H, $C_1$-$C_6$alkyl, or —$C_0$-$C_6$alk-O$C_1$-$C_6$alkyl;
or $R^8$ and $R^{8'}$, together with the atom to which they are attached, form a $C_3$-$C_6$cycloalkyl ring or a $C_2$-$C_6$heterocycloalkyl ring;
$R^9$ is H, —$C_1$-$C_6$alkyl, or —$C_0$-$C_6$alk-$C_3$-$C_6$cycloalkyl; and
$R^{9a}$ is —$C_1$-$C_6$alkyl, or —$C_0$-$C_6$alk-$C_3$-$C_6$cycloalkyl.

Stereoisomers of the compounds of Formula I or Formula II, and the pharmaceutical salts and solvates thereof, are also described. Methods of using compounds of Formula I or Formula II are described, as well as pharmaceutical compositions including the compounds of Formula I or Formula II.

The disclosure is also directed to compounds of Formula III or IV:

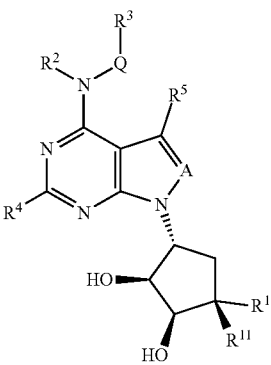

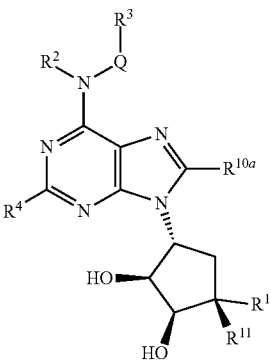

or a pharmaceutically acceptable salt or solvate thereof; wherein

A is CH, $CR^{10}$, or N;
Q is NH, $NR^6$, or O;
$R^1$ is —$C_0$-$C_6$alk-$C_3$-$C_6$cycloalkyl, —$C_0$-$C_6$alk-$C_3$-$C_6$halocycloalkyl; —$C_2$-$C_6$alkenyl, —$C_2$-$C_6$haloalkenyl, —$C_0$-$C_6$alk-$C_1$-$C_6$alkyl, —$C_0$-$C_6$alk- $C_1$-$C_6$haloalkyl, —$C_0$-$C_6$alk-C≡CH, —$C_0$-$C_6$alk-C≡C—$C_1$-$C_6$alkyl, —$C_0$-$C_6$alk-C≡C—$C_1$-$C_6$haloalkyl, —$C_0$-$C_6$alk-C≡C—$C_3$-$C_6$cycloalkyl, —$C_1$-$C_6$alk-aryl, —$C_1$-$C_6$alk-S—$C_1$-$C_6$alkyl, —$C_1$-$C_6$alk-S—$C_1$-$C_6$haloalkyl, —$C_1$-$C_6$alk-S—$C_3$-$C_6$cycloalkyl; —$C_1$-$C_6$alk-S—$C_3$-$C_6$halocycloalkyl, —$C_1$-$C_6$alk-O—$C_1$-$C_6$alkyl, —$C_1$-$C_6$alk-O—$C_3$-$C_6$cycloalkyl, —$C_1$-$C_6$alk-S—$CH_2$-aryl, —$C_1$-$C_6$alk-C(O)NH-aryl, —$C_0$-$C_6$alk-S-aryl, —$C_0$-$C_6$alk-S(O) aryl, —$C_0$-$C_6$alk-S(O)$_2$aryl, —$C_0$-$C_6$alk-Oaryl, —$C_0$-$C_6$alk-heteroaryl, —$C_1$-$C_6$alk-O-heteroaryl, —$C_1$-$C_6$alk-S-heteroaryl, or —$C_1$-$C_6$alk-NH-heteroaryl;

$R^2$ is H, —$C_1$-$C_6$alkyl, —$C_1$-$C_6$haloalkyl, or —$C_0$-$C_6$alk-$C_3$-$C_6$cycloalkyl;

$R^3$ is H, —$C_1$-$C_6$alkyl, —$C_1$-$C_6$haloalkyl, —$C_0$-$C_6$alk-$C_3$-$C_6$cycloalkyl, —C(O)$R^7$, —C(O)O$R^7$, or —C(O)N$R^{8a}R^{8b}$;

$R^4$ is H, halo, —$C_1$-$C_6$alkyl, or $NH_2$;

$R^5$ is H, halo, CN, —$C_1$-$C_6$alkyl, —$C_2$-$C_4$alkenyl, —$C_2$-$C_4$haloalkenyl, $C_2$-$C_4$cyanoalkenyl, —$C_0$-$C_6$alk-C≡CH, —$C_0$-$C_6$alk-C≡C—$C_1$-$C_6$alkyl, —$C_1$-$C_4$haloalkyl, —$C_2$-$C_6$heterocycloalkyl, oxo-substituted-$C_2$-$C_6$heterocycloalkyl, —$C_3$-$C_6$cycloalkyl, —$C_0$-$C_3$alk-C(O)$R^9$, —C$R^8R^{8'}$CN, —$CH_2$N$R^8R^{8'}$, —$C_0$-$C_6$alk-OH, —N$R^8R^{8'}$, —N($R^9$)CN, —O—$C_1$-$C_4$alkyl, —N$R^9$CON$R^8R^{8'}$, —OCON$R^8R^{8'}$, or —N$R^9$C(O)O$R^{9a}$;

$R^6$ is $C_1$-$C_6$alkyl, or $C_0$-$C_6$alk-$C_3$-$C_6$cycloalkyl $R^7$ is H, $C_1$-$C_6$alkyl, or $C_0$-$C_6$alk-$C_3$-$C_6$cycloalkyl;

$R^{8a}$ and $R^{8b}$ are each independently H, $C_1$-$C_6$alkyl, or —$C_0$-$C_6$alk-O$C_1$-$C_6$alkyl, or $R^{8a}$ and $R^{8b}$, together with the atom to which they are attached, form a $C_2$-$C_6$heterocycloalkyl ring;

$R^8$ and $R^{8'}$ are each independently H, $C_1$-$C_6$alkyl, or —$C_0$-$C_6$alk-O$C_1$-$C_6$alkyl;

or $R^8$ and $R^{8'}$, together with the atom to which they are attached, form a $C_3$-$C_6$cycloalkyl ring or a $C_2$-$C_6$heterocycloalky ring;

$R^9$ is H, —$C_1$-$C_6$alkyl, or $C_0$-$C_6$alk-$C_3$-$C_6$cycloalkyl;

$R^{9a}$ is —$C_1$-$C_6$alkyl, or $C_0$-$C_6$alk-$C_3$-$C_6$cycloalkyl;

$R^{10}$ is halo or —$C_1$-$C_6$alkyl;

$R^{10a}$ is H, halo or —$C_1$-$C_6$alkyl;

$R^{11}$ is H, —$C_1$-$C_6$alkyl, —$C_1$-$C_6$haloalkyl, —$C_0$-$C_6$alk-$C_3$-$C_6$cycloalkyl, —$C_0$-$C_6$alk-$C_3$-$C_6$halocycloalkyl, —$C_0$-$C_6$alk-OH, —$C_0$-$C_6$alk-$NH_2$, —$C_0$-$C_6$alk-NH—$C_1$-$C_6$alkyl, —$C_0$-$C_6$alk-N($C_1$-$C_6$alkyl)-$C_1$-$C_6$alkyl, —$C_0$-$C_6$alk-NH—$C_3$-$C_6$cycloalkyl, or —$C_0$-$C_6$alk-N($C_1$-$C_6$alkyl)-$C_3$-$C_6$cycloalkyl;

or $R^{11}$ and $R^1$, together with the atom to which they are attached, form a $C_3$-$C_6$cycloalkyl ring or a heterocycloalkyl ring.

Stereoisomers of the compounds of Formula III or Formula IV, and the pharmaceutical salts and solvates thereof, are also described. Methods of using compounds of Formula III or Formula IV are described, as well as pharmaceutical compositions including the compounds of Formula III or Formula IV.

The disclosure is also directed to compounds of Formula V or Formula VI:

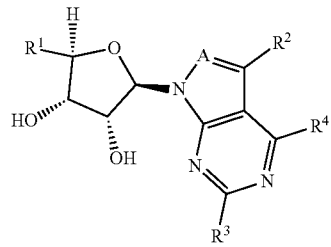

V

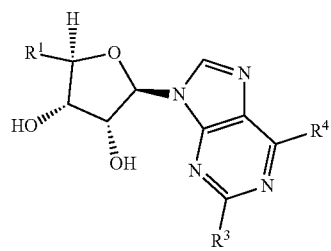

VI or a pharmaceutically acceptable salt or solvate thereof; wherein

A is CH or N;

$R^1$ is —$C_1$-$C_6$alk-aryl, —$C_1$-$C_6$alk-heteroaryl, —$C_1$-$C_6$alk-C≡CH, —$C_1$-$C_6$alk-C≡C—$C_1$-$C_6$alkyl, —$C_1$-$C_6$alk-C≡C—$C_1$-$C_6$haloalkyl, or —$C_1$-$C_6$alk-C≡C—$C_3$-$C_6$cycloalkyl;

$R^2$ is H, or halo;

$R^3$ is H, halo, $NH_2$, or $C_1$-$C_6$alkyl; and $R^4$ is $NH_2$ or $CH_3$.

Stereoisomers of the compounds of Formula V or Formula VI, and the pharmaceutical salts and solvates thereof, are also described. Methods of using compounds of Formula V or Formula VI, are described, as well as pharmaceutical compositions including the compounds of Formula V or Formula VI.

BRIEF DESCRIPTION OF THE DRAWINGS

FIG. 5 is a Dynamic Vapor Sorption ("DVS") profile of Example 92A.

DETAILED DESCRIPTION OF ILLUSTRATIVE EMBODIMENTS

Figure 1:
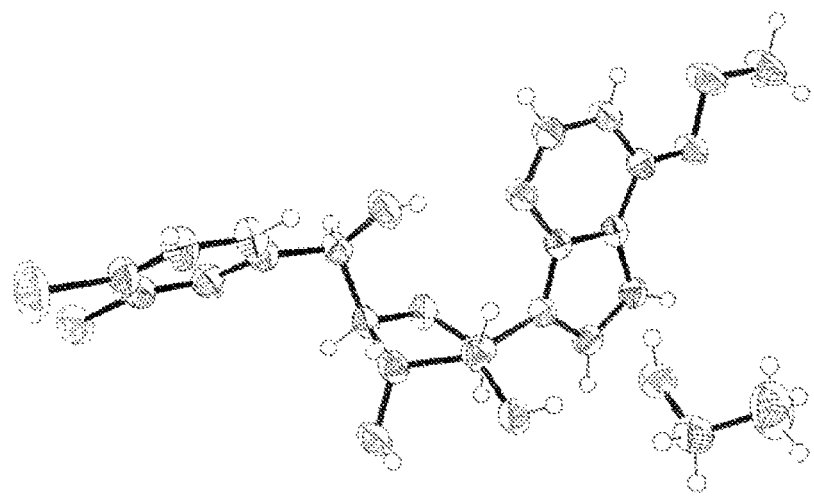
FIG. 1 is an ORTEP representation of Example 69.

The disclosure may be more fully appreciated by reference to the following description, including the following definitions and examples. Certain features of the disclosed compositions and methods which are described herein in the context of separate aspects, may also be provided in combination in a single aspect. Alternatively, various features of the disclosed compositions and methods that are, for brevity, described in the context of a single aspect, may also be provided separately or in any subcombination.

The term "alkyl," when used alone or as part of a substituent group, refers to a straight- or branched-chain hydrocarbon group having from 1 to 12 carbon atoms ("$C_1$-$C_{12}$"), preferably 1 to 6 carbons atoms ("$C_1$-$C_6$"), in the group. Examples of alkyl groups include methyl (Me, $C_1$alkyl), ethyl (Et, $C_2$alkyl), n-propyl ($C_3$alkyl), isopropyl ($C_3$alkyl), butyl ($C_4$alkyl), isobutyl ($C_4$alkyl), sec-butyl ($C_4$alkyl), tert-butyl ($C_4$alkyl), pentyl ($C_5$alkyl), isopentyl ($C_5$alkyl), tert-pentyl ($C_5$alkyl), hexyl ($C_6$alkyl), isohexyl ($C_6$alkyl), and the like.

The term "halo" when used alone or as part of a substituent group refers to chloro, fluoro, bromo, or iodo.

The term "haloalkyl" when used alone or as part of a substituent group refers to refers to an alkyl group wherein one or more of the hydrogen atoms has been replaced with one or more halogen atoms. Halogen atoms include chlorine, fluorine, bromine, and iodine. Examples of haloalkyl groups of the disclosure include, for example, trifluoromethyl ($-CF_3$), chloromethyl ($-CH_2Cl$), and the like.

The term "cycloalkyl" when used alone or as part of a substituent group refers to cyclic-containing, non-aromatic hydrocarbon groups having from 3 to 10 carbon atoms ("$C_3$-$C_{10}$"), preferably from 3 to 6 carbon atoms ("$C_3$-$C_6$"). Examples of cycloalkyl groups include, for example, cyclopropyl ($C_3$), cyclobutyl ($C_4$), cyclopropylmethyl ($C_4$), cyclopentyl ($C_5$), cyclohexyl (C), 1-methylcyclopropyl ($C_4$), 2-methylcyclopentyl ($C_4$), adamantanyl ($C_{10}$), and the like.

The term "halocycloalkyl" when used alone or as part of a substituent group refers to a cycloalkyl group wherein one or more of the hydrogen atoms has been replaced with one or more halogen atoms. Halogen atoms include chlorine, fluorine, bromine, and iodine. Examples of cycloalkyl groups include, for example, chlorocyclopropyl ($C_3$), fluorocyclobutyl ($C_4$), bromocyclopentyl ($C_5$), iodocyclohexyl ($C_6$), and the like.

The term "heterocycloalkyl" when used alone or as part of a substituent group refers to any three to ten membered monocyclic or bicyclic, saturated ring structure containing at least one heteroatom selected from the group consisting of O, N and S. Where N is a heteroatom in the heterocycloalkyl group, the N may be substituted with H, $-C_1$-$C_3$alkyl, $-C_1$-$C_3$haloalkyl, or $C_3$-$C_6$cycloalkyl. The heterocycloalkyl group may be attached at any heteroatom or carbon atom of the ring such that the result is a stable structure. Examples of suitable heterocycloalkyl groups include, but are not limited to, azepanyl, aziridinyl, azetidinyl, pyrrolidinyl, dioxolanyl, imidazolidinyl, pyrazolidinyl, piperazinyl, piperidinyl, dioxanyl, morpholinyl, dithianyl, thiomorpholinyl, oxazepanyl, oxiranyl, oxetanyl, quinuclidinyl, tetrahydrofuranyl, tetrahydropyranyl, piperazinyl, and the like.

The term "oxo-substituted-heterocycloalkyl" when used alone or as part of a substituent group refers to a heterocycloalkyl group wherein at least one of the carbon atoms in the ring is substituted with an oxo group. Examples of oxo-substituted heterocycloalkyl groups include, but are not limited to, 2-aziridinonyl, 2-azetidinonyl, pyrrolidinonyl, dioxolanonyl, imidazolidinonyl, pyrazolidinonyl, piperazinonyl, piperidinonyl, dioxanonyl, dithianonyl, thiomorpholinonyl, oxazepanonyl, oxiranonyl, oxetanonyl, quinuclidinonyl, tetrahydrofuranonyl, tetrahydropyranonyl, piperazinonyl, and the like.

The term "alkenyl" when used alone or as part of a substituent group refers to a straight- or branched-chain group having from 2 to 12 carbon atoms ("$C_2$-$C_{12}$"), preferably 2 to 4 carbons atoms ("$C_2$-$C_4$"), in the group, wherein the group includes at least one carbon-carbon double bond. Examples of alkenyl groups include vinyl ($-CH=CH_2$; $C_2$alkenyl) allyl ($-CH_2-CH=CH_2$; $C_3$alkenyl), propenyl ($-CH=CHCH_3$; $C_3$alkenyl); isopropenyl ($-C(CH_3)=CH_2$; $C_3$alkenyl), butenyl ($-CH=CHCH_2CH_3$; $C_4$alkenyl), sec-butenyl ($-C(CH_3)=CHCH_3$; $C_4$alkenyl), iso-butenyl ($-CH=C(CH_3)_2$; $C_4$alkenyl), 2-butenyl ($-CH_2CH=CHCH_3$; $C_4$alkenyl), pentenyl ($-CH=CHCH_2CH_2CH_3$; $C_5$alkenyl), and the like.

The term "haloalkenyl" when used alone or as part of a substituent group refers to an alkenyl group wherein at least one carbon atom in the group is substituted by one or more halogen atoms. Halogen atoms include chlorine, fluorine, bromine, and iodine.

The term "cyanoalkenyl" when used alone or as part of a substituent group refers to an alkenyl group wherein at least one carbon atom in the group is substituted by one or more cyano groups.

The term "cycloalkenyl," when used alone or as part of a substituent group refers to cyclic, non-aromatic hydrocarbon groups having from 3 to 10 carbon atoms ("$C_3$-$C_{10}$"), preferably from 3 to 6 carbon atoms ("$C_3$-$C_6$") and containing at least one carbon-carbon double bond. For example, cycloalkenyl groups include, but are not limited to cyclopropenyl, cyclobutenyl, and the like.

The term "aryl" when used alone or as part of a substituent group refers to a mono- or bicyclic-aromatic hydrocarbon ring structure having 6 to 10 carbon atoms in the ring, wherein one or more of the carbon atoms in the ring is optionally substituted with a halogen (halo) atom, a $-C_1$-$C_3$ alkyl group, an amino-substituted $-C_1$-$C_3$alkyl group, a $-C_1$-$C_3$haloalkyl group, an amino group (i.e., $NH_2$), or a substituted amino group. Amino-substituted $-C_1$-$C_3$ alkyl groups include $-CH_2-NH_2$, $-CH_2CH_2-NH_2$, and the like. $C_1$-$C_3$haloalkyl groups include, for example, $-CF_3$, $-CH_2CF_3$, and the like. Substituted amino groups include, for example, $-NH-C(O)-NH_2$. Halogen atoms include chlorine, fluorine, bromine, and iodine. Examples of aryl groups (substituted and unsubstituted) include phenyl, naphtyl, fluorophenyl, difluorophenyl, chlorophenyl, dichlorophenyl, bromophenyl, iodophenyl, chlorofluorophenyl, fluoronaphthyl, difluoronaphthyl, chloronaphthyl, bromonaphthyl, iodonaphthyl, methylphenyl, ethylphenyl, (trifluoromethyl)phenyl, methyl-trifluoromethylphenyl, fluoro-trifluoromethylphenyl and the like. The term "aryl" also includes a mono- or bicyclic-aromatic hydrocarbon ring structure having 6 or 10 carbon atoms in the ring, wherein two adjacent carbon atoms in the ring are optionally substituted such that said two adjacent carbon atoms and their respective substituents form a heterocyclic ring. Thus, aryl groups include, for example, 2,3-dihydrobenzofuran and 1,3-benzodioxole.

The term "heteroaryl" when used alone or as part of a substituent group refers to a mono- or bicyclic-aromatic ring structure including carbon atoms as well as up to four heteroatoms selected from nitrogen, oxygen, and sulfur. Heteroaryl rings can include a total of 5, 6, 9, or 10 ring atoms. The heteroaryl moiety can be unsubstituted or one or more of the carbon atoms in the ring can be substituted with a halogen atom; an amino group; a substituted amino group, including an amino group substituted with a $-C_1$-$C_6$ cycloalkyl group or a $-C_1$-$C_6$ alkyl group; $-C_1$-$C_3$ alkyl group, or a $-C_1$-$C_3$ haloalkyl group. Halogen atoms include chlorine, fluorine, bromine, and iodine. Examples of heteroaryl groups include but are not limited to, pyrrolyl, furyl, thiophenyl (thienyl), 5-chlorothiophen-2-yl, oxazolyl, imidazolyl, purazolyl, isoxazolyl, isothiazolyl, triazolyl, thiadiazolyl, pyrazolyl, pyridyl, pyridazinyl, pyrimidinyl, pyrazinyl, pyranyl, furazanyl, indolizinyl, indolyl, isoindolinyl, indazolyl, benzofuranyl, benzothiophenyl, benzimidazolyl, benzthiazolyl, purinyl, quinolizinyl, quinolinyl, 2-amino-3-bromoquinolin-7-yl, 2-amino-3-chloroquinolin-7-yl, 2-((cyclopropylmethyl)amino)quinolin-7-yl, 2-(methylamino)quinolin-7-yl, 2-aminoquinolin-7-yl, isoquinolinyl, isothiazolyl, cinnolinyl, phthalazinyl, quinazolinyl, quinoxalinyl, naphthyridinyl, pteridinyl, and the like.

When a range of carbon atoms is used herein, for example, $C_1$-$C_6$, all ranges, as well as individual numbers of carbon atoms are encompassed. For example, "$C_1$-$C_3$" includes $C_1$-$C_3$, $C_1$-$C_2$, $C_2$-$C_3$, $C_1$, $C_2$, and $C_3$.

The term "$C_1$-$C_6$alk" when used alone or as part of a substituent group refers to an aliphatic linker having 1, 2, 3, 4, 5, or 6 carbon atoms and includes, for example, —$CH_2$—, —$CH(CH_3)$—, —$CH(CH_3)$—$CH_2$—, and —$C(CH_3)_2$—. The term "—$C_0$alk-" refers to a bond. In some aspects, the $C_1$-$C_6$alk can be substituted with one or more —OH, —O—$C_1$-$C_6$alkyl (e.g., —$OCH_3$), —$NH_2$, or halo (e.g., —F, —Cl, —Br, with —F being preferred) substituents. Thus, $C_1$-$C_6$alk encompasses, for example, —CH(Me)-, —CH(OH)—, —CH($CH_2$OH)—, —CH(Me)(OH)—, —CH($NH_2$)—, —CH(Me)($NH_2$)—, —CH(F)—, —CH(Me)(F)—, and the like. $C_1$alk groups, for example, include:

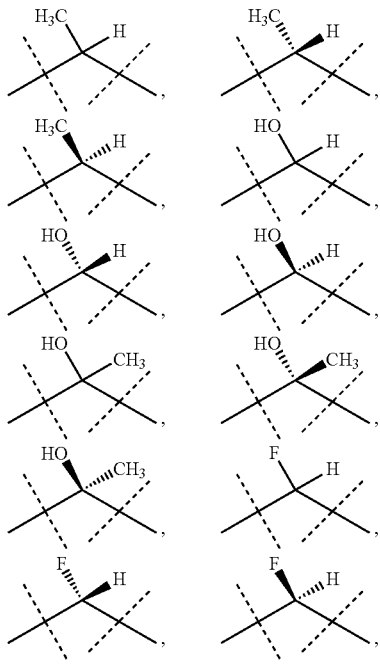

and the like.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, e.g., in humans.

"Pharmaceutically acceptable salt" refers to a salt of a compound of the disclosure that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

A "solvate" refers to a physical association of a compound of Formula I or Formula II with one or more solvent molecules.

"Subject" includes mammals, for example, humans. The terms "human," "patient," and "subject" are used interchangeably herein.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

"Compounds of the present disclosure," and equivalent expressions, are meant to embrace compounds of Formula I, Formula II, Formula III, Formula IV, Formula V, and/or Formula VI as described herein, as well as their subgenera, which expression includes the stereoisomers of compounds of Formula I, Formula II, Formula III, Formula IV, Formula V, and/or Formula VI, as well as the pharmaceutically acceptable salts and solvates, where the context so permits.

As used herein, the term "isotopic variant" refers to a compound that contains proportions of isotopes at one or more of the atoms that constitute such compound that is greater than natural abundance. For example, an "isotopic variant" of a compound can be radiolabeled, that is, contain one or more radioactive isotopes, or can be labeled with non-radioactive isotopes such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be 2H/D, any carbon may be $^{13}C$, or any nitrogen may be $^{15}N$, and that the presence and placement of such atoms may be determined within the skill of the art.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers," for example, diastereomers, enantiomers, and atropisomers. The compounds of this disclosure may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. Where a chiral center exists in a structure, but no specific stereochemistry is shown for that center, both enantiomers, individually or as a mixture of enantiomers, are encompassed by that structure. The methods for the determination of stereochemistry and the separation of stereoisomers are well-known in the art.

The disclosure is directed to compounds of Formula I or Formula II. In some aspects, the disclosure is directed to compounds of Formula I:

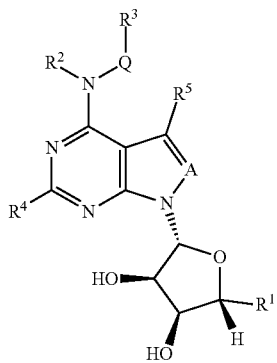

I

In other aspects, the disclosure is directed to compounds of Formula II:

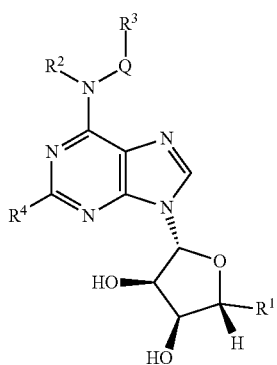

II

According to the disclosure, A in Formula I is N or CH. In some aspects, A is N and the compounds of Formula I are of Formula IA:

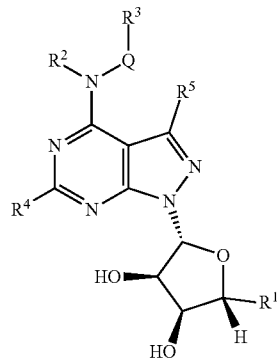

IA

In other aspects, A is CH and the compounds of Formula I are of Formula IB:

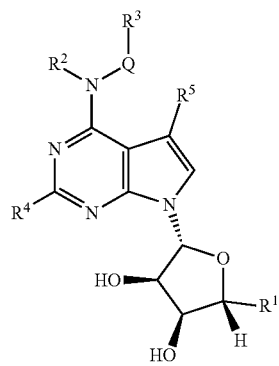

IB

According to the disclosure, Q in Formula I or Formula II is NH, $NR^6$ or O. In some embodiments of Formula I or II, Q is NH. In other embodiments, Q is O. In yet other embodiments, Q is $NR^6$.

According to the disclosure, $R^1$ in Formula I or Formula II is —$C_0$-$C_6$alk-$C_3$-$C_6$cycloalkyl, —$C_0$-$C_6$alk-$C_3$-$C_6$halocycloalkyl; —$C_2$-$C_6$alkenyl, —$C_2$-$C_6$haloalkenyl, —$C_0$-$C_6$alk-$C_1$-$C_6$alkyl, —$C_0$-$C_6$alk-$C_1$-$C_6$haloalkyl, —$C_0$-$C_6$alk-C≡CH, —$C_0$-$C_6$alk-C≡C—$C_1$-$C_6$alkyl, —$C_0$-$C_6$alk-C≡C—$C_1$-$C_6$haloalkyl, —$C_0$-$C_6$alk-C≡C—$C_3$-$C_6$cycloalkyl, —$C_1$-$C_6$alk-aryl, —$C_1$-$C_6$alk-S—$C_1$-$C_6$alkyl, —$C_1$-$C_6$alk-S—$C_1$-$C_6$haloalkyl, —$C_1$-$C_6$alk-S—$C_3$-$C_6$cycloalkyl; —$C_1$-$C_6$alk-S—$C_3$-$C_6$halocycloalkyl; —$C_1$-$C_6$alk-O—$C_1$-$C_6$alkyl, —$C_1$-$C_6$alk-O—$C_3$-$C_6$cycloalkyl, —$C_1$-$C_6$alk-S—$CH_2$-aryl, —$C_1$-$C_6$alk-C(O)NH-aryl, —$C_0$-$C_6$alk-heteroaryl, —$C_1$-$C_6$alk-O-heteroaryl, —$C_1$-$C_6$alk-S-heteroaryl, or —$C_1$-$C_6$alk-NH-heteroaryl.

In some aspects, $R^1$ in Formula I or Formula II is —$C_0$-$C_6$alk-$C_1$-$C_6$alkyl, —$C_0$-$C_6$alk-$C_1$-$C_6$haloalkyl, —$C_0$-$C_6$alk-C≡CH, —$C_0$-$C_6$alk-C≡C—$C_1$-$C_6$alkyl, —$C_0$-$C_6$alk-C≡C—$C_1$-$C_6$haloalkyl, —$C_0$-$C_6$alk-C≡C—$C_3$-$C_6$cycloalkyl, or —$C_1$-$C_6$alk-aryl.

In other aspects, $R^1$ in Formula I or Formula II is —$C_0$-$C_6$alk-$C_3$-$C_6$cycloalkyl, for example, —$C_0$alk-$C_3$cycloalkyl, —$C_1$alk-$C_3$cycloalkyl, —$C_2$alk-$C_3$cycloalkyl, —$C_3$alk-$C_3$cycloalkyl, —$C_4$alk-$C_3$cycloalkyl, —$C_5$alk- C₃cycloalkyl, —C₆alk-C₃cycloalkyl, —C₀alk-C₄cycloalkyl, —C₁alk-C₄cycloalkyl, —C₂alk-C₄cycloalkyl, —C₃alk-C₄cycloalkyl, —C₄alk-C₄cycloalkyl, —C₅alk-C₄cycloalkyl, —C₆alk-C₄cycloalkyl, —C₀alk-C₅cycloalkyl, —C₁alk-C₅cycloalkyl, —C₂alk-C₅cycloalkyl, —C₃alk-C₅cycloalkyl, —C₄alk-C₅cycloalkyl, —C₅alk-C₅cycloalkyl, —C₆alk-C₅cycloalkyl, —C₀alk-C₆cycloalkyl, —C₁alk-C₆cycloalkyl, —C₂alk-C₆cycloalkyl, —C₃alk-C₆cycloalkyl, —C₄alk-C₆cycloalkyl, —C₅alk-C₆cycloalkyl, or —C₆alk-C₆cycloalkyl. Thus, in some aspects, R¹ is —CH₂-cyclopropyl.

In some aspects, R¹ in Formula I or Formula II is —C₀-C₆alk-C₃-C₆halocycloalkyl, for example, —C₀alk-C₃halocycloalkyl, —C₁alk-C₃halocycloalkyl, —C₂alk-C₃halocycloalkyl, —C₃alk-C₃halocycloalkyl, —C₄alk-C₃halocycloalkyl, —C₅alk-C₃halocycloalkyl, —C₆alk-C₃halocycloalkyl, —C₀alk-C₄halocycloalkyl, —C₁alk-C₄halocycloalkyl, —C₂alk-C₄halocycloalkyl, —C₃alk-C₄halocycloalkyl, —C₄alk-C₄halocycloalkyl, —C₅alk-C₄halocycloalkyl, —C₆alk-C₄halocycloalkyl, —C₀alk-C₅halocycloalkyl, —C₁alk-C₅halocycloalkyl, —C₂alk-C₅halocycloalkyl, —C₃alk-C₅halocycloalkyl, —C₄alk-C₅halocycloalkyl, —C₅alk-C₅halocycloalkyl, —C₆alk-C₅halocycloalkyl, —C₀alk-C₆halocycloalkyl, —C₁alk-C₆halocycloalkyl, —C₂alk-C₆halocycloalkyl, —C₃alk-C₆halocycloalkyl, —C₄alk-C₆halocycloalkyl, —C₅alk-C₆halocycloalkyl, or —C₆alk-C₆halocycloalkyl.

In some aspects, R¹ in Formula I or Formula II is —C₂-C₆alkenyl, for example, vinyl, allyl, and the like.

In some aspects, R¹ in Formula I or Formula II is —C₂-C₆haloalkenyl, for example, —C(F)=CHMe, —C(F)=CH₂, and the like.

In some aspects, R¹ in Formula I or Formula II is —C₀-C₆alk-C₁-C₆alkyl, for example, —C₀alk-C₁alkyl, —C₁alk-C₁alkyl, —C₂alk-C₁alkyl, —C₆alk-C₁alkyl, —C₄alk-C₁alkyl, —C₅alk-C₁alkyl, —C₆alk-C₁alkyl, —C₀alk-C₂alkyl, —C₁alk-C₂alkyl, —C₂alk-C₂alkyl, —C₃alk-C₂alkyl, —C₄alk-C₂alkyl, —C₅alk-C₂alkyl, —C₆alk-C₂alkyl, —C₀alk-C₃alkyl, —C₁alk-C₃alkyl, —C₂alk-C₃alkyl, —C₃alk-C₃alkyl, —C₄alk-C₃alkyl, —C₆alk-C₃alkyl, —C₆alk-C₃alkyl, —C₀alk-C₄alkyl, —C₁alk-C₄alkyl, —C₂alk-C₄alkyl, —C₃alk-C₄alkyl, —C₄alk-C₄alkyl, —C₅alk-C₄alkyl, —C₆alk-C₄alkyl, —C₀alk-C₅alkyl, —C₁alk-C₅alkyl, —C₂alk-C₅alkyl, —C₃alk-C₅alkyl, —C₄alk-C₅alkyl, —C₆alk-C₅alkyl, —C₆alk-C₅alkyl, —C₀alk-C₆alkyl, —C₁alk-C₆alkyl, —C₂alk-C₆alkyl, —C₃alk-C₆alkyl, —C₄alk-C₆alkyl, —C₅alk-C₆alkyl, —C₀alk-C₆alkyl, methyl, ethyl, propyl, isopropyl, butyl, isobutyl, s-butyl, t-butyl, pentyl, —CH(OH)—C₁-C₆alkyl, —CH(F)—C₁-C₆alkyl, —CH(NH₂)—C₁-C₆alkyl, —CH(Me)-C₁-C₆alkyl, —C(Me)(OH)—C₁-C₆alkyl, and the like.

In other aspects, R¹ in Formula I or Formula II is —C₀-C₆alk-C₁-C₆haloalkyl, for example, —C₀alk-C₁haloalkyl, —C₁alk-C₁haloalkyl, —C₂alk-C₁haloalkyl, —C₆alk-C₁haloalkyl, —C₄alk-C₁haloalkyl, —C₅alk-C₁haloalkyl, —C₀alk-C₁haloalkyl, —C₀alk-C₂haloalkyl, —C₁alk-C₂haloalkyl, —C₂alk-C₂haloalkyl, —C₃alk-C₂haloalkyl, —C₄alk-C₂haloalkyl, —C₅alk-C₂haloalkyl, —C₆alk-C₂haloalkyl, —C₀alk-C₃haloalkyl, —C₁alk-C₃haloalkyl, —C₂alk-C₃haloalkyl, —C₃alk-C₃haloalkyl, —C₄alk-C₃haloalkyl, —C₅alk-C₃haloalkyl, —C₆alk-C₃haloalkyl, —C₀alk-C₄haloalkyl, —C₁alk-C₄haloalkyl, —C₂alk-C₄haloalkyl, —C₄haloalkyl, —C₃alk-C₄haloalkyl, —C₄alk-C₄haloalkyl, —C₅alk-C₄haloalkyl, —C₆alk-C₄haloalkyl, —C₀alk-C₅haloalkyl, —C₁alk-C₅haloalkyl, —C₂alk-C₅haloalkyl, —C₃alk-C₅haloalkyl, —C₄alk-C₅haloalkyl, —C₅alk-C₅haloalkyl, —C₆alk-C₅haloalkyl, —C₀alk-C₆haloalkyl, —C₁alk-C₆haloalkyl, —C₂alk-C₆haloalkyl, —C₃alk-C₆haloalkyl, —C₄alk-C₆haloalkyl, —C₅alk-C₆haloalkyl, —C₆alk-C₆haloalkyl, fluoromethyl, fluoroethyl, fluoropropyl, fluorobutyl, fluoropentyl, chloromethyl, chloroethyl, chloropropyl, chlorobutyl, chloropentyl, bromomethyl, bromoethyl, bromopropyl, bromobutyl, bromopentyl, iodomethyl, iodoethyl, iodopropyl, iodobutyl, iodopentyl, —CH(OH)—C₁-C₆haloalkyl, —CH(F)—C₁-C₆haloalkyl, —CH(NH₂)—C₁-C₆haloalkyl, —CH(Me)-C₁-C₆haloalkyl, —C(Me)(OH)—C₁-C₆haloalkyl, and the like.

In some aspects, R¹ in Formula I or Formula II is —C₀-C₆alk-C≡CH, for example, —C₀alk-C≡CH, —C₁alk-C≡CH, —C₂alk-C≡CH, —C₃alk-C≡CH, —C₄alk-C≡CH, —C₅alk-C≡CH, —C₆alk-C≡CH, ethynyl, propargyl, —CH(OH)—C≡CH, —CH(F)—C≡CH, —CH(NH₂)—C≡CH, —CH(Me)-C≡CH, —C(Me)(OH)—C≡CH, and the like.

In some aspects, R¹ in Formula I or Formula II is —C₀-C₆alk-C≡C—C₁-C₆alkyl, for example, —C₀alk-C≡C—C₁alkyl, —C₁alk-C≡C—C₁alkyl, —C₂alk-C≡C—C₁alkyl, —C₃alk-C≡C—C₁alkyl, —C₄alk-C≡C—C₁alkyl, —C₅alk-C≡C—C₁alkyl, —C₀alk-C≡C—C₁alkyl, —C₀alk-C≡C—C₂alkyl, —C₁alk-C≡C—C₂alkyl, —C₂alk-C≡C—C₂alkyl, —C₃alk-C≡C—C₂alkyl, —C₄alk-C≡C—C₂alkyl, —C₅alk-C≡C—C₂alkyl, —C₆alk-C≡C—C₂alkyl, —C₀alk-C≡C—C₃alkyl, —C₁alk-C≡C—C₃alkyl, —C₂alk-C≡C—C₃alkyl, —C₃alk-C≡C—C₃alkyl, —C₄alk-C≡C—C₃alkyl, —C₆alk-C≡C—C₃alkyl, —C₆alk-C≡C—C₃alkyl, —C₀alk-C≡C—C₄alkyl, —C₁alk-C≡C—C₄alkyl, —C₂alk-C≡C—C₄alkyl, —C₃alk-C≡C—C₄alkyl, —C₄alk-C≡C—C₄alkyl, —C₅alk-C≡C—C₄alkyl, —C₆alk-C≡C—C₄alkyl, —C₀alk-C≡C—C₅alkyl, —C₁alk-C≡C—C₅alkyl, —C₂alk-C≡C—C₅alkyl, —C₃alk-C≡C—C₅alkyl, —C₄alk-C≡C—C₅alkyl, —C₆alk-C≡C—C₅alkyl, —C₆alk-C≡C—C₅alkyl, —C₀alk-C≡C—C₆alkyl, —C₁alk-C≡C—C₆alkyl, —C₂alk-C≡C—C₆alkyl, —C₃alk-C≡C—C₆alkyl, —C₄alk-C≡C—C₆alkyl, —C₅alk-C≡C—C₆alkyl, —C₆alk-C≡C—C₆alkyl, propynyl, butynyl, —CH(OH)—C≡C—C₁-C₆alkyl, —CH(F)—C≡C—C₁-C₆alkyl, —CH(NH₂)—C≡C—C₁-C₆alkyl, —CH(Me)-C≡C—C₁-C₆alkyl, —C(Me)(OH)—C≡C—C₁-C₆alkyl, and the like. In some embodiments wherein —C₀-C₆alk-C≡C—C₁-C₆alkyl is —C₀-C₆alk-C≡C—CH₃, R¹ is —CH(OH)—C≡C—CH₃, —CH(F)—C≡C—CH₃, —CH(NH₂)—C≡C—CH₃, —CH(Me)-C≡C—CH₃, or —C(Me)(OH)—C≡C—CH₃. Thus, in some embodiments, R¹ is —CH(OH)—C≡C—CH₃.

In some aspects, R¹ in Formula I or Formula II is —C₀-C₆alk-C≡C—C₁-C₆haloalkyl, for example, —C₀alk-C≡C—C₁haloalkyl, —C₁alk-C≡C—C₁haloalkyl, —C₂alk-C≡C—C₁haloalkyl, —C₆alk-C≡C—C₁haloalkyl, —C₄alk-C≡C—C₁haloalkyl, —C₅alk-C≡C—C₁haloalkyl, —C₀alk-C≡C—C₁haloalkyl, —C₀alk-C≡C—C₂haloalkyl, —C₁alk-C≡C—C₂haloalkyl, —C₂alk-C≡C—C₂haloalkyl, —C₃alk-C≡C—C₂haloalkyl, —C₄alk-C≡C—C₂haloalkyl, —C₅alk-C≡C—C₂haloalkyl, —C₆alk-C≡C—C₂haloalkyl, —C₀alk-C≡C—C₃haloalkyl, —C₁alk-C≡C—C₃haloalkyl, —C₂alk-C≡C—C₃haloalkyl, —C₃alk-C≡C—C₃haloalkyl, —C₄alk-C≡C—C₃haloalkyl, —C₅alk-C≡C—C₃haloalkyl, —C₆alk-C≡C—C₃haloalkyl, —C₀alk-C≡C—C₄haloalkyl, —C₁alk-C≡C—C₄haloalkyl, —C₂alk-C≡C—C₄haloalkyl, —C₃alk-C≡C—C₄haloalkyl, —C₄alk-C≡C—C₄haloalkyl, —C₅alk-C≡C—C₄haloalkyl, —C₆alk-C≡C—C₄haloalkyl, —C₀alk-C≡C—C₅haloalkyl, —C₁alk-C≡C—C₅haloalkyl, —C₂alk-C≡C—C₅haloalkyl, —C₃alk-C≡C—C₅haloalkyl, —C₄alk-C≡C—C₅haloalkyl, —C₅alk-C≡C—C₅haloalkyl, —C₆alk-C≡C—C₅haloalkyl, —C₆alk- C≡C—C₅haloalkyl, —C₀alk-C≡C—C₆haloalkyl, —C₁alk-C≡C—C₆haloalkyl, —C₂alk-C≡C—C₆haloalkyl, —C₃alk-C≡C—C₆haloalkyl, —C₄alk-C≡C—C₆haloalkyl, —C₅alk-C≡C—C₆haloalkyl, —C₆alk-C≡C—C₆haloalkyl, —CH(OH)—C≡C—C₁-C₆ haloalkyl, —CH(F)—C≡C—C₁-C₆ haloalkyl, —CH(NH₂)—C≡C—C₁-C₆ haloalkyl, —CH(Me)-C≡C—C₁-C₆ haloalkyl, —C(Me)(OH)—C≡C—C₁-C₆ haloalkyl, and the like. In some embodiments wherein —C₀-C₆alk-C≡C—C₁-C₆haloalkyl is —C₀-C₆alk-C≡C—CF₃, R¹ is —CH(OH)—C≡C—CF₃, —CH(F)—C≡C—CF₃, —CH(NH₂)—C≡C—CF₃, —CH(Me)-C≡C—CF₃, —C(Me)(OH)—C≡C—CF₃, and the like. Thus, in some embodiments, R¹ is —CH(OH)—C≡C—CF₃.

In some aspects, R¹ in Formula I or Formula II is —C₀-C₆alk-C≡C—C₃-C₆cycloalkyl, for example, —C₀alk-C≡C—C₃cycloalkyl, —C₀alk-C≡C—C₄cycloalkyl, —C₀alk-C≡C—C₅cycloalkyl, —C₀alk-C≡C—C₆cycloalkyl, —C₁alk-C≡C—C₃cycloalkyl, —C₁alk-C≡C—C₄cycloalkyl, —C₁alk-C≡C—C₅-cycloalkyl, —C₁alk-C≡C—C₆cycloalkyl, —C₂alk-C≡C—C₃cycloalkyl, —C₂alk-C≡C—C₄cycloalkyl, —C₂alk-C≡C—C₅cycloalkyl, —C₂alk-C≡C—C₆cycloalkyl, —C₃alk-C≡C—C₃cycloalkyl, —C₃alk-C≡C—C₄cycloalkyl, —C₃alk-C≡C—C₅cycloalkyl, —C₃alk-C≡C—C₆cycloalkyl, —C₄alk-C≡C—C₃cycloalkyl, —C₄alk-C≡C—C₄cycloalkyl, —C₄alk-C≡C—C₅cycloalkyl, —C₄alk-C≡C—C₆cycloalkyl, —C₅alk-C≡C—C₃cycloalkyl, —C₅alk-C≡C—C₄cycloalkyl, —C₅alk-C≡C—C₅cycloalkyl, —C₅alk-C≡C—C₆cycloalkyl, —C₆alk-C≡C—C₃cycloalkyl, —C₆alk-C≡C—C₄cycloalkyl, —C₆alk-C≡C—C₅cycloalkyl, —C₆alk-C≡C—C₆cycloalkyl, —CH(OH)—C≡C—C₃-C₆cycloalkyl, —CH(F)—C≡C—C₃-C₆cycloalkyl, —CH(NH₂)—C≡C—C₃-C₆cycloalkyl, —CH(Me)-C≡C—C₃-C₆cycloalkyl, or —C(Me)(OH)—C≡C—C₃-C₆cycloalkyl. In some embodiments wherein —C₀-C₆alk-C≡C—C₃-C₆cycloalkyl is —C₀-C₆alk-C≡C-cyclopropyl, R¹ is —CH(OH)—C≡C-cyclopropyl, —CH(F)—C≡C-cyclopropyl, —CH(NH₂)—C≡C-cyclopropyl, —CH(Me)-C≡C-cyclopropyl, —C(Me)(OH)—C≡C-cyclopropyl, and the like. Thus, in some embodiments, R¹ is —CH(OH)—C≡C-cyclopropyl.

In some aspects, R¹ in Formula I or Formula II is —C₁-C₆alk-aryl, for example, —C₁alk-aryl, —C₂alk-aryl, —C₃alk-aryl, —C₄alk-aryl, —C₅alk-aryl, —C₀alk-aryl, —CH(OH)-aryl, —C(OCH₃)-aryl, —CH(F)-aryl, —CH(NH₂)-aryl, —CH(Me)-aryl, —C(Me)(OH)-aryl, —C(CF₃)(OH)-aryl, and the like. In some embodiments wherein R¹ is —C₁-C₆alk-aryl, the -aryl is -4-chlorophenyl, -3,4-dichlorophenyl, -3,4-difluorophenyl, -3-fluoro-4-chlorophenyl, -3-chloro-4-fluorophenyl, 4-(trifluoromethyl)phenyl, 3-fluoro-4-(trifluoromethyl)phenyl, -3-methyl-4-chlorophenyl, 2,3-dihydrobenzofuran-5-yl, 3-methyl-4-(trifluoromethyl)phenyl, or -benzo[d][1,3]dioxol-5-yl. Thus in some embodiments, R¹ is —CH(OH)-4-chlorophenyl, —CH(OH)-3,4-dichlorophenyl, —CH(OH)-3,4-difluorophenyl, —CH(OH)-3-fluoro-4-chlorophenyl, —CH(OH)-3-chloro-4-fluorophenyl, —CH(OH)-4-(trifluoromethyl)phenyl, —CH(OH)-3-fluoro-4-(trifluoromethyl)phenyl, —CH(OH)-2,3-dihydrobenzofuran-5-yl, —CH(OH)-3-methyl-4-(trifluoromethyl)phenyl, —CH(OH)-benzo[d][1,3]dioxol-5-yl, —C(CF₃)(OH)-4-chlorophenyl, —CH(OH)-3-methyl-4-chlorophenyl, —CH(F)-4-chlorophenyl, —CH(F)-3,4-dichlorophenyl, —CH(F)-3,4-difluorophenyl, —CH(F)-3-fluoro-4-chlorophenyl, —CH(F)-3-chloro-4-fluorophenyl, —CH(F)-4-(trifluoromethyl)phenyl, —CH(F)-3-fluoro-4-(trifluoromethyl)phenyl, —C(CF₃)(F)-4-chlorophenylphenyl, —CH(F)-3-methyl-4-chlorophenyl, —CH(F)-2,3-dihydrobenzofuran-5-yl, —CH(F)-3-methyl-4-(trifluoromethyl)phenyl, —CH(F)-benzo[d][1,3]dioxol-5-yl, —CH(NH₂)-4-chlorophenyl, —CH(NH₂)-3,4-dichlorophenyl, —CH(NH₂)-3,4-difluorophenyl, —CH(NH₂)-3-fluoro-4-chlorophenyl, —CH(NH₂)-3-chloro-4-fluorophenyl, —CH(NH₂)-4-(trifluoromethyl)phenyl, —CH(NH₂)-3-fluoro-4-(trifluoromethyl)phenyl, —C(CF₃)(NH₂)-4-chlorophenylphenyl, CH(NH₂)-3-methyl-4-chlorophenyl, —CH(NH₂)-2,3-dihydrobenzofuran-5-yl, —CH(NH₂)-3-methyl-4-(trifluoromethyl)phenyl, —CH(NH₂)-benzo[d][1,3]dioxol-5-yl, —CH(Me)-4-chlorophenyl, —CH(Me)-3,4-dichlorophenyl, —CH(Me)-3,4-difluorophenyl, —CH(Me)-3-fluoro-4-chlorophenyl, —CH(Me)-3-chloro-4-fluorophenyl, —CH(Me)-4-(trifluoromethyl)phenyl, —CH(Me)-3-fluoro-4-(trifluoromethyl)phenyl, —CH(Me)-3-methyl-4-chlorophenyl, —CH(Me)-2,3-dihydrobenzofuran-5-yl, —CH(Me)-3-methyl-4-(trifluoromethyl)phenyl, —CH(Me)-benzo[d][1,3]dioxol-5-yl, —C(CF₃)(Me)-4-chlorophenylphenyl, —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, or —C(Me)(OH)-3-chloro-4-fluorophenyl, —C(Me)(OH)-4-(trifluoromethyl)phenyl, —C(Me)(OH)-3-fluoro-4-(trifluoromethyl)phenyl, —C(Me)(OH)-3-methyl-4-chlorophenyl, —C(Me)(OH)-2,3-dihydrobenzofuran-5-yl, —C(Me)(OH)-benzo[d][1,3]dioxol-5-yl, —C(Me)(OH)-3-methyl-4-(trifluoromethyl)phenyl, —CH(OCH₃)-4-chlorophenyl, —CH(OCH₃)-3,4-dichlorophenyl, —CH(OCH₃)-3,4-difluorophenyl, —CH(OCH₃)-3-fluoro-4-chlorophenyl, —CH(OCH₃)-3-chloro-4-fluorophenyl, —CH(OCH₃)-4-(trifluoromethyl)phenyl, —CH(OCH₃)-3-fluoro-4-(trifluoromethyl)phenyl, —CH(OCH₃)-2,3-dihydrobenzofuran-5-yl, —CH(OCH₃)-benzo[d][1,3]dioxol-5-yl, —CH(OCH₃)-3-methyl-4-(trifluoromethyl)phenyl, —C(CF₃)(OCH₃)-4-chlorophenyl, —CH(OCH₃)-3-methyl-4-chlorophenyl.

In some aspects, R¹ in Formula I or Formula II is —C₁-C₆alk-S—C₁-C₆alkyl, for example —C₁alk-S—C₁alkyl, —C₂alk-S—C₁alkyl, —C₃alk-S—C₁alkyl, —C₄alk-S—C₁alkyl, —C₅alk-S—C₁alkyl, —C₆alk-S—C₁alkyl, —C₁alk-S—C₂alkyl, —C₂alk-S—C₂alkyl, —C₃alk-S—C₂alkyl, —C₄alk-S—C₂alkyl, —C₅alk-S—C₂alkyl, —C₆alk-S—C₂alkyl, —C₁alk-S—C₃alkyl, —C₂alk-S—C₃alkyl, —C₃alk-S—C₃alkyl, —C₄alk-S—C₃alkyl, —C₅alk-S—C₃alkyl, —C₆alk-S—C₃alkyl, —C₁alk-S—C₄alkyl, —C₂alk-S—C₄alkyl, —C₃alk-S—C₄alkyl, —C₄alk-S—C₄alkyl, —C₅alk-S—C₄alkyl, —C₆alk-S—C₄alkyl, —C₁alk-S—C₅alkyl, —C₂alk-S—C₅alkyl, —C₃alk-S—C₅alkyl, —C₄alk-S—C₅alkyl, —C₅alk-S—C₅alkyl, —C₆alk-S—C₅alkyl, —C₁alk-S—C₆alkyl, —C₂alk-S—C₆alkyl, —C₃alk-S—C₆alkyl, —C₄alk-S—C₆alkyl, —C₅alk-S—C₆alkyl, —C₆alk-S—C₆alkyl, —CH₂S—C₂alkyl, —CH₂S—C₃alkyl, —CH₂S—C₄alkyl, —CH₂S—C₅alkyl, —CH₂S—C₆alkyl, and the like. Thus, in some aspects R¹ is —CH₂S—C₁alkyl. In some aspects, R¹ is —CH₂—S—CH₃.

In some aspects, R¹ in Formula I or Formula II is —C₁-C₆alk-S—C₁-C₆haloalkyl, for example —C₁alk-S—C₁haloalkyl, —C₂alk-S—C₁haloalkyl, —C₃alk-S—C₁haloalkyl, —C₄alk-S—C₁haloalkyl, —C₅alk-S—C₁haloalkyl, —C₆alk-S—C₁haloalkyl, —C₁alk-S—C₂haloalkyl, —C₂alk-S—C₂haloalkyl, —C₃alk-S—C₂haloalkyl, —C₄alk-S—C₂haloalkyl, —C₅alk-S—C₂haloalkyl, —C₆alk-S—C₂haloalkyl, —C₁alk-S—C₃haloalkyl, —C₂alk-S—C₃haloalkyl, —C₃alk-S—C₃haloalkyl, —C₄alk-S—C₃haloalkyl, —C₅alk-S—C₃haloalkyl, —C₆alk-S—C₃haloalkyl, —C₁alk-S—

$C_4$haloalkyl, —$C_2$alk-S—$C_4$haloalkyl, —$C_3$alk-S—$C_4$haloalkyl, —$C_4$alk-S—$C_4$haloalkyl, —$C_5$alk-S—$C_4$haloalkyl, —$C_6$alk-S—$C_4$haloalkyl, —$C_1$alk-S—$C_5$haloalkyl, —$C_2$alk-S—$C_5$haloalkyl, —$C_3$alk-S—$C_5$haloalkyl, —$C_4$alk-S—$C_5$haloalkyl, —$C_5$alk-S—$C_5$haloalkyl, —$C_6$alk-S—$C_5$haloalkyl, —$C_1$alk-S—$C_6$haloalkyl, —$C_2$alk-S—$C_6$haloalkyl, —$C_3$alk-S—$C_6$haloalkyl, —$C_4$alk-S—$C_6$haloalkyl, —$C_5$alk-S—$C_6$haloalkyl, —$C_6$alk-S—$C_6$haloalkyl, —$CH_2$S—$C_1$haloalkyl, —$CH_2$S—$C_2$haloalkyl, —$CH_2$S—$C_3$haloalkyl, —$CH_2$S—$C_4$haloalkyl, —$CH_2$S—$C_5$haloalkyl, and —$CH_2$S—$C_6$haloalkyl.

In some aspects, $R^1$ in Formula I or Formula II is —$C_1$-$C_6$alk-S—$C_3$-$C_6$cycloalkyl, for example —$C_1$alk-S—$C_3$cycloalkyl, —$C_2$alk-S—$C_3$cycloalkyl, —$C_3$alk-S—$C_3$cycloalkyl, —$C_4$alk-S—$C_3$cycloalkyl, —$C_5$alk-S—$C_3$cycloalkyl, —$C_6$alk-S—$C_3$cycloalkyl, —$C_1$alk-S—$C_4$cycloalkyl, —$C_2$alk-S—$C_4$cycloalkyl, —$C_3$alk-S—$C_4$cycloalkyl, —$C_4$alk-S—$C_4$cycloalkyl, —$C_5$alk-S—$C_4$cycloalkyl, —$C_6$alk-S—$C_4$cycloalkyl, —$C_1$alk-S—$C_5$cycloalkyl, —$C_2$alk-S—$C_5$cycloalkyl, —$C_3$alk-S—$C_5$cycloalkyl, —$C_4$alk-S—$C_5$cycloalkyl, —$C_5$alk-S—$C_5$cycloalkyl, —$C_6$alk-S—$C_5$cycloalkyl, —$C_1$alk-S—$C_6$cycloalkyl, —$C_2$alk-S—$C_6$cycloalkyl, —$C_3$alk-S—$C_6$cycloalkyl, —$C_4$alk-S—$C_6$cycloalkyl, —$C_5$alk-S—$C_6$cycloalkyl, —$C_6$alk-S—$C_6$cycloalkyl, —$CH_2$S—$C_3$cycloalkyl, —$CH_2$S—$C_4$cycloalkyl, —$CH_2$S—$C_5$cycloalkyl, —$CH_2$S—$C_6$cycloalkyl, and the like.

In some aspects, $R^1$ in Formula I or Formula II is —$C_1$-$C_6$alk-S—$C_3$-$C_6$halocycloalkyl, for example —$C_1$alk-S—$C_3$halocycloalkyl, —$C_2$alk-S—$C_3$halocycloalkyl, —$C_3$alk-S—$C_3$halocycloalkyl, —$C_4$alk-S—$C_3$halocycloalkyl, —$C_5$alk-S—$C_3$halocycloalkyl, —$C_6$alk-S—$C_3$halocycloalkyl, —$C_1$alk-S—$C_4$halocycloalkyl, —$C_2$alk-S—$C_4$halocycloalkyl, —$C_3$alk-S—$C_4$halocycloalkyl, —$C_4$alk-S—$C_4$halocycloalkyl, —$C_5$alk-S—$C_4$halocycloalkyl, —$C_6$alk-S—$C_4$halocycloalkyl, —$C_1$alk-S—$C_5$halocycloalkyl, —$C_2$alk-S—$C_5$halocycloalkyl, —$C_3$alk-S—$C_5$halocycloalkyl, —$C_4$alk-S—$C_5$halocycloalkyl, —$C_5$alk-S—$C_5$halocycloalkyl, —$C_6$alk-S—$C_5$halocycloalkyl, —$C_1$alk-S—$C_6$halocycloalkyl, —$C_2$alk-S—$C_6$halocycloalkyl, —$C_3$alk-S—$C_6$halocycloalkyl, —$C_4$alk-S—$C_6$halocycloalkyl, —$C_5$alk-S—$C_6$halocycloalkyl, —$C_6$alk-S—$C_6$halocycloalkyl, —$CH_2$S—$C_3$halocycloalkyl, —$CH_2$S—$C_4$halocycloalkyl, —$CH_2$S—$C_5$halocycloalkyl, —$CH_2$S—$C_6$halocycloalkyl, and the like.

In some aspects, $R^1$ in Formula I or Formula II is —$C_1$-$C_6$alk-O$C_1$-$C_6$alkyl, for example, —$C_1$alk-O—$C_1$alkyl, —$C_2$alk-O—$C_1$alkyl, —$C_3$alk-O—$C_1$alkyl, —$C_4$alk-O—$C_1$alkyl, —$C_5$alk-O—$C_1$alkyl, —$C_6$alk-O—$C_1$alkyl, —$C_1$alk-O—$C_2$alkyl, —$C_2$alk-O—$C_2$alkyl, —$C_3$alk-O—$C_2$alkyl, —$C_4$alk-O—$C_2$alkyl, —$C_5$alk-O—$C_2$alkyl, —$C_6$alk-O—$C_2$alkyl, —$C_1$alk-O—$C_3$alkyl, —$C_2$alk-O—$C_3$alkyl, —$C_3$alk-O—$C_3$alkyl, —$C_4$alk-O—$C_3$alkyl, —$C_5$alk-O—$C_3$alkyl, —$C_6$alk-O—$C_3$alkyl, —$C_1$alk-O—$C_4$alkyl, —$C_2$alk-O—$C_4$alkyl, —$C_3$alk-O—$C_4$alkyl, —$C_4$alk-O—$C_4$alkyl, —$C_5$alk-O—$C_4$alkyl, —$C_6$alk-O—$C_4$alkyl, —$C_1$alk-O—$C_5$alkyl, —$C_2$alk-O—$C_5$alkyl, —$C_3$alk-O—$C_5$alkyl, —$C_4$alk-O—$C_5$alkyl, —$C_5$alk-O—$C_5$alkyl, —$C_6$alk-O—$C_5$alkyl, —$C_1$alk-O—$C_6$alkyl, —$C_2$alk-O—$C_6$alkyl, —$C_3$alk-O—$C_6$alkyl, —$C_4$alk-O—$C_6$alkyl, —$C_5$alk-O—$C_6$alkyl, —$C_6$alk-O—$C_6$alkyl, —$CH_2$O$C_1$alkyl, —$CH_2$O$C_2$alkyl, —$CH_2$O$C_3$alkyl, —$CH_2$O$C_4$alkyl, —$CH_2$O$C_5$alkyl, —$CH_2$O$C_6$alkyl, and the like.

In some aspects, $R^1$ in Formula I or Formula II is —$C_1$-$C_6$alk-O—$C_3$-$C_6$cycloalkyl, for example, —$C_1$alk-O—$C_3$cycloalkyl, —$C_2$alk-O—$C_3$cycloalkyl, —$C_3$alk-O—$C_3$cycloalkyl, —$C_4$alk-O—$C_3$cycloalkyl, —$C_5$alk-O—$C_3$cycloalkyl, —$C_6$alk-O—$C_3$cycloalkyl, —$C_1$alk-O—$C_4$cycloalkyl, —$C_2$alk-O—$C_4$cycloalkyl, —$C_3$alk-O—$C_4$cycloalkyl, —$C_4$alk-O—$C_4$cycloalkyl, —$C_5$alk-O—$C_4$cycloalkyl, —$C_6$alk-O—$C_4$cycloalkyl, —$C_1$alk-O—$C_5$cycloalkyl, —$C_2$alk-O—$C_5$cycloalkyl, —$C_3$alk-O—$C_5$cycloalkyl, —$C_4$alk-O—$C_5$cycloalkyl, —$C_5$alk-O—$C_5$cycloalkyl, —$C_6$alk-O—$C_5$cycloalkyl, —$C_1$alk-O—$C_6$cycloalkyl, —$C_2$alk-O—$C_6$cycloalkyl, —$C_3$alk-O—$C_6$cycloalkyl, —$C_4$alk-O—$C_6$cycloalkyl, —$C_5$alk-O—$C_6$cycloalkyl, —$C_6$alk-O—$C_6$cycloalkyl, —$CH_2$O—$C_3$cycloalkyl, —$CH_2$O—$C_4$cycloalkyl, —$CH_2$O—$C_5$cycloalkyl, —$CH_2$O—$C_6$cycloalkyl, and the like.

In some aspects, $R^1$ in Formula I or Formula II is —$C_1$-$C_6$alk-S$CH_2$-aryl, for example —$C_1$alk-S$CH_2$-aryl, —$C_2$alk-S$CH_2$-aryl, —$C_3$alk-S$CH_2$-aryl, —$C_4$alk-S$CH_2$-aryl, —$C_5$alk-S$CH_2$-aryl, —$C_6$alk-S$CH_2$-aryl, —$CH_2$S$CH_2$-phenyl, —$CH_2$S$CH_2$-naphthyl, —$CH_2$S$CH_2$-fluorophenyl, —$CH_2$S$CH_2$-difluorophenyl, —$CH_2$S$CH_2$-fluoronaphthyl, —$CH_2$S$CH_2$-chlorophenyl, —$CH_2$S$CH_2$-bromophenyl, —$CH_2$S$CH_2$-iodophenyl, —$CH_2$S$CH_2$-methylphenyl, —$CH_2$S$CH_2$-4-chlorophenyl, —$CH_2$S$CH_2$-3,4-dichlorophenyl, —$CH_2$S$CH_2$-3,4-difluorophenyl, —$CH_2$S$CH_2$-3-fluoro-4-chlorophenyl, —$CH_2$S$CH_2$-3-chloro-4-fluorophenyl, and the like. Thus, in some aspects $R^1$ is —$CH_2$S$CH_2$-phenyl.

In some aspects, $R^1$ in Formula I or Formula II is —$C_1$-$C_6$alk-C(O)NH-aryl, for example, —$C_1$alk-C(O)NH-aryl, —$C_2$alk-C(O)NH-aryl, —$C_3$alk-C(O)NH-aryl, —$C_4$alk-C(O)NH-aryl, —$C_5$alk-C(O)NH-aryl, —$C_6$alk-C(O)NH-aryl, —$CH_2$C(O)NH-phenyl, —$CH_2$C(O)NH-naphthyl, —$CH_2$C(O)NH-fluorophenyl, —$CH_2$C(O)NH-difluorophenyl, —$CH_2$C(O)NH-fluoronaphthyl, —$CH_2$C(O)NH-chlorophenyl, —$CH_2$C(O)NH-bromophenyl, —$CH_2$C(O)NH-iodophenyl, —$CH_2$C(O)NH-methylphenyl, —$CH_2$C(O)NH-4-chlorophenyl, —$CH_2$C(O)NH-3,4-dichlorophenyl, —$CH_2$C(O)NH-3,4-difluorophenyl, —$CH_2$C(O)NH-3-fluoro-4-chlorophenyl, —$CH_2$C(O)NH-3-chloro-4-fluorophenyl and the like. Thus, in some aspects $R^1$ is —$CH_2$C(O)NH-phenyl.

In some aspects, $R^1$ in Formula I or Formula II is —$C_0$-$C_6$alk-heteroaryl, for example, —$C_0$alk-heteroaryl, —$C_1$alk-heteroaryl, —$C_2$alk-heteroaryl, —$C_3$alk-heteroaryl, —$C_4$alk-heteroaryl, —$C_5$alk-heteroaryl, and —$C_6$alk-heteroaryl. In some aspects, $R^1$ is 2-(2-amino-3-bromoquinolin-7-yl)ethyl, 2-(2-amino-3-chloroquinolin-7-yl)ethyl, 2-(2-((cyclopropylmethyl)amino)quinolin-7-yl)ethyl, 2-(2-(methylamino)quinolin-7-yl)ethyl, or 2-(2-aminoquinolin-7-yl)ethyl.

In some aspects, $R^1$ in Formula I or Formula II is —$C_1$-$C_6$alk-O-heteroaryl, for example, —$C_1$alk-O-heteroaryl, —$C_2$alk-O-heteroaryl, —$C_3$alk-O-heteroaryl, —$C_4$alk-O-heteroaryl, —$C_5$alk-O-heteroaryl, and —$C_6$alk-O-heteroaryl. In some aspects, $R^1$ is ((2-amino-3-bromoquinolin-7-yl)oxy)methyl.

In some aspects, $R^1$ in Formula I or Formula II is —$C_1$-$C_6$alk-S-heteroaryl, for example, —$C_1$alk-S-heteroaryl, —$C_2$alk-S-heteroaryl, —$C_3$alk-S-heteroaryl, —$C_4$alk-S-heteroaryl, —$C_5$alk-S-heteroaryl, and —$C_6$alk-S-heteroaryl. In some aspects, $R^1$ is ((2-amino-3-bromoquinolin-7-yl)thio)methyl.

In some aspects, $R^1$ in Formula I or Formula II is —$C_1$-$C_6$alk-NH-heteroaryl, for example, —$C_1$alk-NH-heteroaryl, —$C_2$alk-NH-heteroaryl, —$C_3$alk-NH-heteroaryl, —C$_4$alk-NH-heteroaryl, —C$_5$alk-NH-heteroaryl, and —C$_6$alk-NH-heteroaryl. In some aspects, R$^1$ is ((2-amino-3-bromoquinolin-7-yl)amino)methyl.

In some embodiments of Formula I or Formula II, R$^2$ is H, —C$_1$-C$_6$alkyl, —C$_1$-C$_6$haloalkyl, or —C$_0$-C$_6$alk-C$_3$-C$_6$cycloalkyl. Thus, in some embodiments, R$^2$ is H.

It will be apparent that when R$^2$ is H, the compounds of Formula I or Formula II may exist as tautomers having (E)- or (Z)-geometry at the exocyclic carbon-nitrogen double bond The compounds of Formula I and Formula II described and claimed herein are meant to encompass all such tautomers and geometric isomers. The depiction of a particular tautomer or geometric isomer is not intended to be limiting. Thus, when R$^2$ is H, compounds of Formula I may be represented by any of the following equivalent structures:

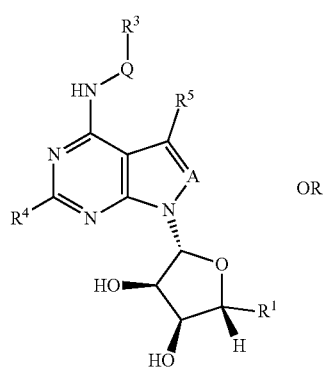

OR

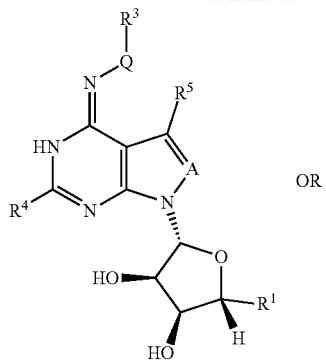

OR

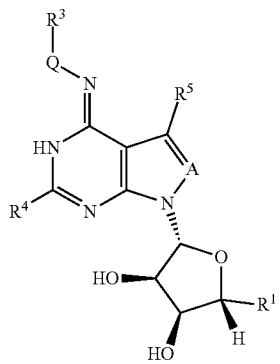

OR

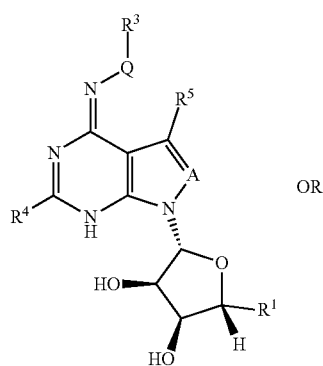

OR

Similarly, when R$^2$ is H, compounds of Formula II may be represented by any of the following equivalent structures:

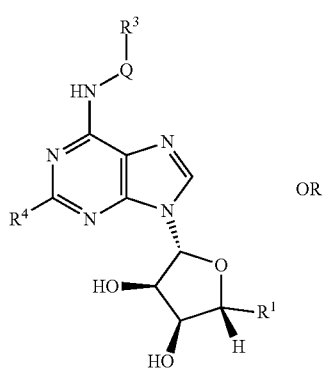

OR

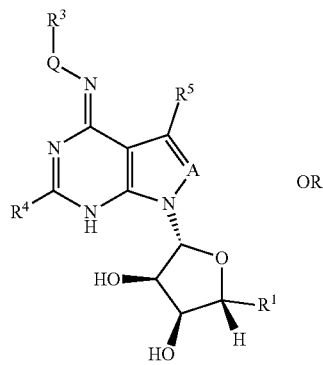

OR

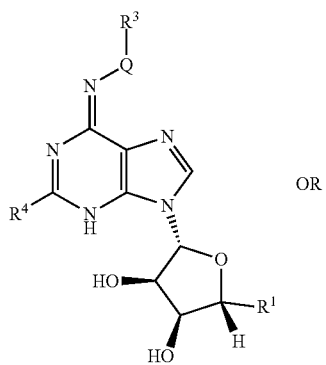

OR

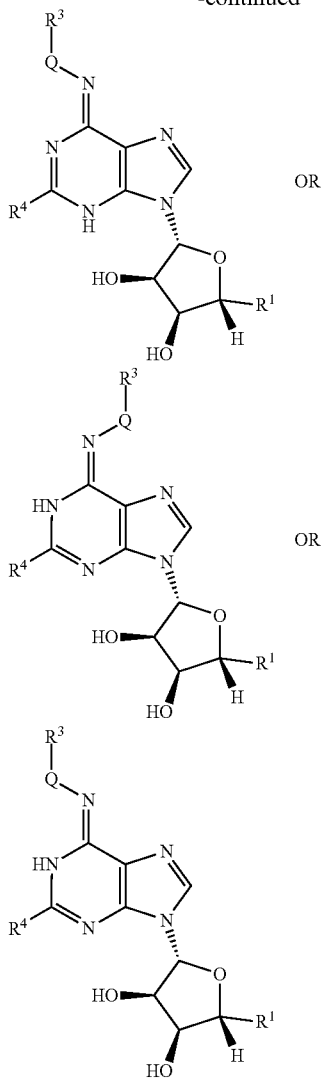

In some embodiments, $R^2$ in Formula I or Formula II is —$C_1$-$C_6$alkyl, for example, methyl, ethyl, propyl, isopropyl, butyl, isobutyl, s-butyl, t-butyl, pentyl, and the like. Thus, in some embodiments, $R^2$ is methyl (i.e., —$CH_3$, or Me).

In some aspects, $R^2$ in Formula I or Formula II is —$C_1$-$C_6$haloalkyl, for example, —$CF_3$ or —$CHF_2$ and the like.

In some aspects, $R^2$ in Formula I or Formula II is —$C_0$-$C_6$alk-$C_3$-$C_6$cycloalkyl, for example, —$C_0$alk-$C_3$cycloalkyl, —$C_1$alk-$C_3$cycloalkyl, —$C_2$alk-$C_3$cycloalkyl, —$C_3$alk-$C_3$cycloalkyl, —$C_4$alk-$C_3$cycloalkyl, —$C_5$alk-$C_3$cycloalkyl, —$C_6$alk-$C_3$cycloalkyl, —$C_0$alk-$C_4$cycloalkyl, —$C_1$alk-$C_4$cycloalkyl, —$C_2$alk-$C_4$cycloalkyl, —$C_3$alk-$C_4$cycloalkyl, —$C_4$alk-$C_4$cycloalkyl, —$C_5$alk-$C_4$cycloalkyl, —$C_6$alk-$C_4$cycloalkyl, —$C_0$alk-$C_5$cycloalkyl, —$C_1$alk-$C_5$cycloalkyl, —$C_2$alk-$C_5$cycloalkyl, —$C_3$alk-$C_5$cycloalkyl, —$C_4$alk-$C_5$cycloalkyl, —$C_5$alk-$C_5$cycloalkyl, —$C_6$alk-$C_5$cycloalkyl, —$C_0$alk-$C_6$cycloalkyl, —$C_1$alk-$C_6$cycloalkyl, —$C_2$alk-$C_6$cycloalkyl, —$C_3$alk-$C_6$cycloalkyl, —$C_4$alk-$C_6$cycloalkyl, and —$C_6$alk-$C_6$cycloalkyl. In some aspects wherein $R^2$ is —$C_0$-$C_6$alk-$C_3$-$C_6$cycloalkyl, the cycloalkyl is unsubstituted. In other aspects wherein $R^2$ is —$C_0$-$C_6$alk-$C_3$-$C_6$cycloalkyl, the cycloalkyl is substituted with one, two, or three R substituents independently selected from $C_1$-$C_6$alkyl, (e.g., methyl, ethyl, propyl, isopropyl, butyl), —$OC_1$-$C_6$alkyl (e.g., —Omethyl, —Oethyl, —Opropyl, —Oisopropyl, —Obutyl), and halo (e.g., F or Cl).

In some aspects of Formula I and Formula II, $R^3$ is H, —$C_1$-$C_6$alkyl, —$C_1$-$C_6$haloalkyl, —$C_0$-$C_6$alk-$C_3$-$C_6$cycloalkyl, —C(O)$R^7$, —C(O)O$R^7$, or —C(O)N$R^{8a}R^{8b}$. Thus, in some embodiments of Formula I or Formula II, $R^3$ is H.

In some aspects, $R^3$ in Formula I or Formula II is —$C_1$-$C_6$alkyl, for example, methyl, ethyl, propyl, isopropyl, butyl, isobutyl, s-butyl, t-butyl, pentyl, and the like. Thus, in some embodiments, $R^3$ is methyl. In other embodiments, $R^3$ is ethyl.

In some aspects, $R^3$ in Formula I or Formula II is —$C_1$-$C_6$haloalkyl, for example, —$CF_3$, —$CH_2CF_3$, —$CH_2CHF_2$ or —$CHF_2$ and the like.

In some aspects, $R^3$ in Formula I or Formula II is —$C_0$-$C_6$alk-$C_3$-$C_6$cycloalkyl, for example, —$C_0$alk-$C_3$cycloalkyl, —$C_1$alk-$C_3$cycloalkyl, —$C_2$alk-$C_3$cycloalkyl, —$C_3$alk-$C_3$cycloalkyl, —$C_4$alk-$C_3$cycloalkyl, —$C_5$alk-$C_3$cycloalkyl, —$C_6$alk-$C_3$cycloalkyl, —$C_0$alk-$C_4$cycloalkyl, —$C_1$alk-$C_4$cycloalkyl, —$C_2$alk-$C_4$cycloalkyl, —$C_3$alk-$C_4$cycloalkyl, —$C_4$alk-$C_4$cycloalkyl, —$C_5$alk-$C_4$cycloalkyl, —$C_6$alk-$C_4$cycloalkyl, —$C_0$alk-$C_5$cycloalkyl, —$C_1$alk-$C_5$cycloalkyl, —$C_2$alk-$C_5$cycloalkyl, —$C_3$alk-$C_5$cycloalkyl, —$C_4$alk-$C_5$cycloalkyl, —$C_5$alk-$C_5$cycloalkyl, —$C_6$alk-$C_5$cycloalkyl, —$C_0$alk-$C_6$cycloalkyl, —$C_1$alk-$C_6$cycloalkyl, —$C_2$alk-$C_6$cycloalkyl, —$C_3$alk-$C_6$cycloalkyl, —$C_4$alk-$C_6$cycloalkyl, —$C_6$alk-$C_6$cycloalkyl, and —$C_6$alk-$C_6$cycloalkyl. In some aspects wherein $R^3$ is —$C_0$-$C_6$alk-$C_3$-$C_6$cycloalkyl, the cycloalkyl is unsubstituted. In other aspects wherein $R^3$ is —$C_0$-$C_6$alk-$C_3$-$C_6$cycloalkyl, the cycloalkyl is substituted with one, two, or three R substituents independently selected from $C_1$-$C_6$alkyl, (e.g., methyl, ethyl, propyl, isopropyl, butyl), —$OC_1$-$C_6$alkyl (e.g., —Omethyl, —Oethyl, —Opropyl, —Oisopropyl, —Obutyl), and halo (e.g., F or Cl).

In some embodiments, $R^3$ in Formula I or Formula II is —C(O)R or —C(O)O$R^7$. In these embodiments, $R^7$ is H, $C_1$-$C_6$alkyl, or $C_0$-$C_6$alk-$C_3$-$C_6$cycloalkyl.

In some aspects, $R^7$ in Formula I or Formula II is H, $C_1$-$C_6$alkyl, or $C_0$-$C_6$alk-$C_3$-$C_6$cycloalkyl. Thus, in some aspects, $R^7$ is H.

In other aspects, $R^7$ in Formula I or Formula II is $C_1$-$C_6$alkyl, for example, methyl, ethyl, propyl, isopropyl, butyl, isobutyl, s-butyl, t-butyl, pentyl, and the like. Thus, in some embodiments, $R^7$ is methyl.

In other aspects, $R^7$ in Formula I or Formula II is —$C_0$-$C_6$alk-$C_3$-$C_6$cycloalkyl, for example, —$C_0$alk-$C_3$cycloalkyl, —$C_1$alk-$C_3$cycloalkyl, —$C_2$alk-$C_3$cycloalkyl, —$C_3$alk-$C_3$cycloalkyl, —$C_4$alk-$C_3$cycloalkyl, —$C_5$alk-$C_3$cycloalkyl, —$C_6$alk-$C_3$cycloalkyl, —$C_0$alk-$C_4$cycloalkyl, —$C_1$alk-$C_4$cycloalkyl, —$C_2$alk-$C_4$cycloalkyl, —$C_3$alk-$C_4$cycloalkyl, —$C_4$alk-$C_4$cycloalkyl, —$C_5$alk-$C_4$cycloalkyl, —$C_6$alk-$C_4$cycloalkyl, —$C_0$alk-$C_5$cycloalkyl, —$C_1$alk-$C_5$cycloalkyl, —$C_2$alk-$C_5$cycloalkyl, —$C_3$alk-$C_5$cycloalkyl, —$C_4$alk-$C_5$cycloalkyl, —$C_5$alk-$C_5$cycloalkyl, —$C_0$alk-$C_5$cycloalkyl, —$C_6$cycloalkyl, —$C_1$alk-$C_6$cycloalkyl, —$C_2$alk- $C_6$cycloalkyl, —$C_3$alk-$C_6$cycloalkyl, —$C_4$alk-$C_6$cycloalkyl, —$C_6$alk-$C_6$cycloalkyl, and —$C_6$alk-$C_6$cycloalkyl.

In some aspects, $R^3$ in Formula I or Formula II is —C(O)$R^7$. In some embodiments wherein $R^7$ is —$C_1$-$C_6$alkyl, $R^3$ is —C(O)$C_1$-$C_6$alkyl. Thus, in some embodiments wherein $R^7$ is methyl, $R^3$ is acetyl (i.e., —C(O)$CH_3$).

In some aspects, $R^3$ in Formula I or Formula II is —C(O)O$R^7$. In some embodiments wherein $R^7$ is —$C_1$-$C_6$alkyl, $R^3$ is —C(O)O$C_1$-$C_6$alkyl. Thus, in some embodiments wherein $R^7$ is methyl, $R^3$ is —C(O)O$CH_3$.

In some aspects, $R^3$ in Formula I or Formula II is or —C(O)N$R^{8a}R^{8b}$.

In some aspects, $R^{8a}$ and $R^{8b}$ in Formula I or Formula II are each independently H, $C_1$-$C_6$alkyl (e.g., methyl, ethyl, propyl, isopropyl, butyl, isobutyl, s-butyl, t-butyl, pentyl, and the like), or —$C_0$-$C_6$alk-O—$C_1$-$C_6$alkyl (e.g., —$C_0$alk-O—$C_1$alkyl, —$C_1$alk-O—$C_1$alkyl, —$C_2$alk-O—$C_1$alkyl, —$C_3$alk-O—$C_1$alkyl, —$C_4$alk-O—$C_1$alkyl, —$C_5$alk-O—$C_1$alkyl, —$C_0$alk-O—$C_2$alkyl, —$C_1$alk-O—$C_2$alkyl, —$C_2$alk-O—$C_2$alkyl, —$C_3$alk-O—$C_2$alkyl, —$C_4$alk-O—$C_2$alkyl, —$C_6$alk-O—$C_2$alkyl, —$C_6$alk-O—$C_2$alkyl, —$C_0$alk-O—$C_3$alkyl, —$C_1$alk-O—$C_3$alkyl, —$C_2$alk-O—$C_3$alkyl, —$C_3$alk-O—$C_3$alkyl, —$C_4$alk-O—$C_3$alkyl, —$C_5$alk-O—$C_3$alkyl, —$C_6$alk-O—$C_3$alkyl, —$C_0$alk-O—$C_4$alkyl, —$C_1$alk-O—$C_4$alkyl, —$C_2$alk-O—$C_4$alkyl, —$C_3$alk-O—$C_4$alkyl, —$C_4$alk-O—$C_4$alkyl, —$C_5$alk-O—$C_4$alkyl, —$C_6$alk-O—$C_4$alkyl, —$C_0$alk-O—$C_5$alkyl, —$C_1$alk-O—$C_5$alkyl, —$C_2$alk-O—$C_5$alkyl, —$C_3$alk-O—$C_5$alkyl, —$C_4$alk-O—$C_5$alkyl, —$C_5$alk-O—$C_5$alkyl, —$C_6$alk-O—$C_5$alkyl, —$C_0$alk-O—$C_6$alkyl, —$C_1$alk-O—$C_6$alkyl, —$C_2$alk-O—$C_6$alkyl, —$C_3$alk-O—$C_6$alkyl, —$C_4$alk-O—$C_6$alkyl, —$C_6$alk-O—$C_6$alkyl, —$C_6$alk-O—$C_6$alkyl). In some embodiments, $R^{8a}$ is $C_1$-$C_6$alkyl or —$C_0$-$C_6$alk-O$C_1$-$C_6$alkyl and $R^{8b}$ is H, $C_1$-$C_6$alkyl, and —$C_0$-$C_6$alk-O$C_1$-$C_6$alkyl.

In some embodiments, $R^{8a}$ in Formula I or Formula II is H or $C_1$-$C_6$alkyl. In some embodiments, $R^{8b}$ is H or $C_1$-$C_6$alkyl. In some embodiments, $R^{8a}$ and $R^{8b}$ are each H. In other embodiments, $R^{8a}$ and $R^{8b}$ are each independently $C_1$-$C_6$alkyl. In some aspects, $R^{8a}$ is $C_1$-$C_6$alkyl and $R^{8b}$ is H.

In other aspects, $R^{8a}$ and $R^{8b}$ in Formula I or Formula II are each independently —$C_0$-$C_6$alk-O$C_1$-$C_6$alkyl.

In other aspects, $R^{8a}$ in Formula I or Formula II is —$C_0$-$C_6$alk-O$C_1$-$C_6$alkyl and $R^{8b}$ is H.

In yet other aspects, $R^{8a}$ and $R^{8b}$ in Formula I or Formula II, together with the atom to which they are attached, form a $C_2$-$C_6$heterocycloalkyl ring, for example, aziridinyl, azetidinyl, pyrrolidinyl, piperidinyl, and the like.

In some aspects of Formula I or Formula II, $R^4$ is H, halo, $C_1$-$C_6$alkyl, or $NH_2$. Thus in some embodiments, $R^4$ is H. In other embodiments, $R^4$ is halo, for example, F, Cl, Br, or I, with Cl being preferred. In other embodiments, $R^4$ is —$C_1$-$C_6$alkyl, for example, methyl, ethyl, propyl, isopropyl, butyl, isobutyl, s-butyl, t-butyl, pentyl, and the like. Thus, in some embodiments, $R^4$ is methyl. In yet other embodiments, $R^4$ is $NH_2$.

In embodiments of the disclosure wherein the compounds are of Formula I, $R^5$ is H, halo, CN, —$C_1$-$C_6$alkyl, —$C_2$-$C_4$alkenyl, —$C_2$-$C_4$haloalkenyl, $C_2$-$C_4$cyanoalkenyl, —$C_0$-$C_6$alk-C≡CH, —$C_0$-$C_6$alk-C≡C—$C_1$-$C_6$alkyl, —$C_1$-$C_4$haloalkyl, —$C_2$-$C_6$heterocycloalkyl, oxo-substituted-$C_2$-$C_6$heterocycloalkyl, —$C_3$-$C_6$cycloalkyl, —$C_0$-$C_3$-alk-C(O)$R^9$, —$CR^8R^{8'}CN$, —$CH_2NR^8R^{8'}$, —$C_0$-$C_6$alk-OH, —$NR^8R^{8'}$, —$N(R^9)CN$, —O—$C_1$-$C_4$alkyl, —$NR^9CONR^8R^{8'}$, —$OCONR^8R^{8'}$, or —NRC(O)O$R^{9a}$.

In some embodiments, $R^5$ in the compounds of Formula I is H.

In some embodiments, $R^5$ in the compounds of Formula I is halo, for example, F, Cl, Br, or I. Thus, in some embodiments, $R^5$ is F.

In some embodiments, $R^5$ in the compounds of Formula I is CN.

In other embodiments, $R^5$ in the compounds of Formula I is —$C_1$-$C_6$alkyl, for example, methyl, ethyl, propyl, isopropyl, butyl, isobutyl, s-butyl, t-butyl, pentyl, and the like. Thus, in some aspects, $R^5$ is methyl.

In some aspects, $R^5$ in the compounds of Formula I is —$C_2$-$C_4$alkenyl, for example, vinyl, allyl, and the like. Thus, in some embodiments, $R^5$ is vinyl (—CH=$CH_2$).

In some aspects, $R^5$ in the compounds of Formula I is —$C_2$-$C_4$haloalkenyl, for example, —C(F)=$CH_2$, C($CF_3$)=$CH_2$, and the like. Thus, in some embodiments, $R^5$ is —C(F)=$CH_2$.

In other aspects, $R^5$ is —$C_2$-$C_4$cyanoalkenyl, for example, —C(CN)=$CH_2$, —CH=CHCN, and the like. Thus, in some embodiments, $R^5$ is —C(CN)=$CH_2$.

In other embodiments, $R^5$ in the compounds of Formula I is —$C_0$-$C_6$alk-C≡CH, for example, —$C_0$alk-C≡CH, —$C_1$alk-C≡CH, —$C_2$alk-C≡CH, —$C_3$alk-C≡CH, —$C_4$alk-C≡CH, —$C_5$alk-C≡CH, —$C_6$alk-C≡CH, ethynyl, propargyl, and the like. Thus, in some embodiments, $R^5$ is ethynyl (—C≡CH).

In some aspects, $R^5$ in the compounds of Formula I is —$C_0$-$C_6$alk-C≡C—$C_1$-$C_6$alkyl, for example, —$C_0$alk-C≡C—$C_1$alkyl, —$C_1$alk-C≡C—$C_1$alkyl, —$C_2$alk-C≡C—$C_1$alkyl, —$C_3$alk-C≡C—$C_1$alkyl, —$C_4$alk-C≡C—$C_1$alkyl, —$C_5$alk-C≡C—$C_1$alkyl, —$C_0$alk-C≡C—$C_1$alkyl, —$C_0$alk-C≡C—$C_2$alkyl, —$C_1$alk-C≡C—$C_2$alkyl, —$C_2$alk-C≡C—$C_2$alkyl, —$C_3$alk-C≡C—$C_2$alkyl, —$C_4$alk-C≡C—$C_2$alkyl, —$C_5$alk-C≡C—$C_2$alkyl, —$C_6$alk-C≡C—$C_2$alkyl, —$C_0$alk-C≡C—$C_3$alkyl, —$C_1$alk-C≡C—$C_3$alkyl, —$C_2$alk-C≡C—$C_3$alkyl, —$C_3$alk-C≡C—$C_3$alkyl, —$C_4$alk-C≡C—$C_3$alkyl, —$C_6$alk-C≡C—$C_3$alkyl, —$C_6$alk-C≡C—$C_3$alkyl, —$C_0$alk-C≡C—$C_4$alkyl, —$C_1$alk-C≡C—$C_4$alkyl, —$C_2$alk-C≡C—$C_4$alkyl, —$C_3$alk-C≡C—$C_4$alkyl, —$C_4$alk-C≡C—$C_4$alkyl, —$C_5$alk-C≡C—$C_4$alkyl, —$C_6$alk-C≡C—$C_4$alkyl, —$C_0$alk-C≡C—$C_5$alkyl, —$C_1$alk-C≡C—$C_5$alkyl, —$C_2$alk-C≡C—$C_5$alkyl, —$C_3$alk-C≡C—$C_5$alkyl, —$C_4$alk-C≡C—$C_5$alkyl, —$C_6$alk-C≡C—$C_5$alkyl, —$C_6$alk-C≡C—$C_5$alkyl, —$C_0$alk-C≡C—$C_6$alkyl, —$C_1$alk-C≡C—$C_6$alkyl, —$C_2$alk-C≡C—$C_6$alkyl, —$C_3$alk-C≡C—$C_6$alkyl, —$C_4$alk-C≡C—$C_6$alkyl, —$C_5$alk-C≡C—$C_6$alkyl, and —$C_6$alk-C≡C—$C_6$alkyl.

In some embodiments, $R^5$ in the compounds of Formula I is —$C_1$-$C_4$haloalkyl, for example, —$CF_3$ or —$CHF_2$.

In some embodiments, $R^5$ in the compounds of Formula I is —$C_2$-$C_6$heterocycloalkyl, for example $C_2$heterocycloalkyl, $C_3$heterocycloalkyl, $C_4$heterocycloalkyl, $C_5$heterocycloalkyl, and $C_6$heterocycloalkyl, including azepanyl, aziridinyl, azetidinyl, pyrrolidinyl, dioxolanyl, imidazolidinyl, pyrazolidinyl, piperazinyl, piperidinyl, dioxanyl, morpholinyl, dithianyl, thiomorpholinyl, oxazepanyl, oxiranyl, oxetanyl, tetrahydrofuranyl, tetrahydropyranyl, piperazinyl, and the like. Thus, in some embodiments, $R^5$ is 2-oxiranyl. In other embodiments, $R^5$ is 1-azetidinyl.

In some embodiments, $R^5$ in the compounds of Formula I is oxo-substituted-$C_2$-$C_6$heterocycloalkyl, for example, oxo-substituted-$C_2$heterocycloalkyl, oxo-substituted-$C_3$heterocycloalkyl, oxo-substituted-$C_4$heterocycloalkyl, oxo-substituted-$C_5$heterocycloalkyl, oxo-substituted-$C_6$heterocycloalkyl, including aziridinonyl, azetidinonyl, pyrrolidinonyl, dioxolanonyl, imidazolidinonyl, pyrazolidinonyl, piperazinonyl, piperidinonyl, dioxanonyl, dithianonyl, thiomorpholinonyl, oxazepanonyl, oxiranonyl, oxetanonyl, quinuclidinonyl, tetrahydrofuranonyl, tetrahydropyranonyl, piperazinonyl, and the like. Thus, in some embodiments, $R^5$ is azetidin-2-one-1-yl.

In some embodiments, $R^5$ in the compounds of Formula I is —$C_3$-$C_6$cycloalkyl, for example —$C_3$cycloalkyl, —$C_4$cycloalkyl, —$C_5$cycloalkyl, —$C_6$cycloalkyl, and the like. In some embodiments, $R^5$ is —$C_3$cycloalkyl. Thus, in some embodiments, $R^5$ is cyclopropyl.

In other embodiments, $R^5$ in the compounds of Formula I is —$C_0$-$C_3$-alk-C(O)$R^9$, for example —$C_0$-alk-C(O)$R^9$, —$C_1$-alk-C(O)$R^9$, —$C_2$-alk-C(O)$R^9$, and —$C_3$-alk-C(O)$R^9$. In some embodiments wherein $R^9$ is $C_1$-$C_6$alkyl, $R^5$ is —$C_0$-$C_3$-alk-C(O)$C_1$-$C_6$alkyl. Thus, in some embodiments wherein $R^9$ is methyl, $R^5$ is acetyl (i.e., —C(O)CH$_3$). In some embodiments wherein $R^9$ is —$C_0$-$C_6$alk-$C_3$-$C_6$cycloalkyl, $R^5$ is —C(O)$C_0$-$C_6$alk-$C_3$-$C_6$cycloalkyl. In some embodiments wherein $R^9$ is H, $R^5$ is —CHO.

In some embodiments, $R^5$ in the compounds of Formula I is —CR$^8$R$^{8'}$CN. Thus, in some embodiments wherein $R^8$ and $R^{8'}$ are both H, $R^5$ is cyanomethyl (i.e., —CH$_2$CN). In some embodiments wherein $R^8$ is —$C_1$-$C_6$alkyl and $R^{8'}$ is H, $R^5$ is —CH(—$C_1$-$C_6$alkyl)CN. In some embodiments wherein $R^8$ and $R^{8'}$ are both —$C_1$-$C_6$alkyl, $R^5$ is —C($C_1$-$C_6$alkyl)($C_1$-$C_6$alkyl)CN. In some embodiments wherein $R^8$ is —$C_0$-$C_6$alk-O$C_1$-$C_6$alkyl and $R^{8'}$ is H, $R^5$ is —CH(—$C_0$-$C_6$alk-O$C_1$-$C_6$alkyl)CN. In some embodiments wherein $R^8$ and $R^{8'}$ are both —$C_0$-$C_6$alk-O$C_1$-$C_6$alkyl, $R^5$ is —C(—$C_0$-$C_6$alk-O$C_1$-$C_6$alkyl)(—$C_0$-$C_6$alk-O$C_1$-$C_6$alkyl)CN.

In some embodiments, $R^5$ in the compounds of Formula I is CH$_2$NR$^8$R$^{8'}$. Thus, in some embodiments wherein $R^8$ and $R^{8'}$ are both H, $R^5$ is aminomethyl (i.e., —CH$_2$NH$_2$). In some embodiments wherein $R^8$ is —$C_1$-$C_6$alkyl and $R^{8'}$ is H, $R^5$ is —CH$_2$NH($C_1$-$C_6$alkyl). In some embodiments wherein $R^8$ and $R^{8'}$ are both —$C_1$-$C_6$alkyl, $R^5$ is —CH$_2$N($C_1$-$C_6$alkyl)($C_1$-$C_6$alkyl). In some embodiments wherein $R^8$ is —$C_0$-$C_6$alk-O$C_1$-$C_6$alkyl and $R^{8'}$ is H, $R^5$ is —CH$_2$NH(—$C_0$-$C_6$alk-O$C_1$-$C_6$alkyl). In some embodiments wherein $R^8$ and $R^{8'}$ are both —$C_0$-$C_6$alk-O$C_1$-$C_6$alkyl, $R^5$ is —CH$_2$N(—$C_0$-$C_6$alk-O$C_1$-$C_6$alkyl)(—$C_0$-$C_6$alk-O$C_1$-$C_6$alkyl).

In some embodiments, $R^5$ in the compounds of Formula I is —$C_0$-$C_6$alk-OH, for example, —$C_0$alk-OH, —$C_1$alk-OH, —$C_2$alk-OH, —$C_3$alk-OH, —$C_4$alk-OH, —$C_5$alk-OH, —$C_6$alk-OH, and the like. In some embodiments $R^5$ is —$C_1$alk-OH. In some embodiments, $R^5$ is hydroxymethyl (i.e., CH$_2$OH). In other embodiments, $R^5$ is hydroxyethyl (i.e., —CH$_2$CH$_2$OH).

In some embodiments, $R^5$ in the compounds of Formula I is —NR$^8$R$^{8'}$. Thus, in some embodiments wherein $R^8$ and $R^{8'}$ are both H, $R^5$ is amino (i.e., —NH$_2$). In some embodiments wherein $R^{8'}$ is —$C_1$-$C_6$alkyl and $R^{8'}$ is H, $R^5$ is —NH($C_1$-$C_6$alkyl). Thus, in some embodiments wherein $R^8$ is methyl and $R^{8'}$ is H, $R^5$ is methylamino (i.e., —NHCH$_3$). In some embodiments wherein $R^8$ and $R^{8'}$ are both —$C_1$-$C_6$alkyl, $R^5$ is —N(—$C_1$-$C_6$alkyl)(—$C_1$-$C_6$alkyl). In some embodiments wherein $R^8$ is —$C_0$-$C_6$alk-O$C_1$-$C_6$alkyl and $R^{8'}$ is H, $R^5$ is —NH(—$C_0$-$C_6$alk-O$C_1$-$C_6$alkyl). In some embodiments wherein $R^{8'}$ and $R^{8'}$ are both —$C_0$-$C_6$alk-O$C_1$-$C_6$alkyl, $R^5$ is —N(—$C_0$-$C_6$alk-O$C_1$-$C_6$alkyl)(—$C_0$-$C_6$alk-O$C_1$-$C_6$alkyl).

In some embodiments, $R^5$ in the compounds of Formula I is —N($R^9$)CN. In some embodiments wherein $R^9$ is —$C_1$-$C_6$alkyl, $R^5$ is —N($C_1$-$C_6$alkyl)CN. Thus, in some embodiments wherein $R^9$ is methyl, $R^5$ is —N(CH$_3$)CN. In some embodiments wherein $R^9$ is —$C_0$-$C_6$alk-$C_3$-$C_6$cycloalkyl, $R^5$ is —N(—$C_0$-$C_6$alk-$C_3$-$C_6$cycloalkyl)CN. In some embodiments wherein $R^9$ is H, $R^5$ is —NH—CN.

In some embodiments, $R^5$ in the compounds of Formula I is —O—$C_1$-$C_4$ alkyl, for example —O—$C_1$alkyl, —O—$C_2$alkyl, —O—$C_3$alkyl, —O—$C_4$alkyl.

In some embodiments, $R^5$ in the compounds of Formula I is —NR$^9$C(O)NR$^8$R$^{8'}$. In some embodiments wherein $R^9$ is H, $R^5$ is —NHC(O)NR$^8$R$^{8'}$. In some embodiments wherein $R^9$ is —$C_1$-$C_6$alkyl, $R^5$ is —N(—$C_1$-$C_6$alkyl)C(O)NR$^8$R$^{8'}$. In some embodiments wherein $R^9$ is $C_0$-$C_6$alk-$C_3$-$C_6$cycloalkyl, $R^5$ is —N($C_0$-$C_6$alk-$C_3$-$C_6$cycloalkyl)C(O)NR$^8$R$^{8'}$. In some embodiments wherein $R^{8'}$ is H, $R^5$ is —NR$^9$C(O)NHR$^{8'}$. In some embodiments wherein $R^{8'}$ is H and $R^{8'}$ is H, $R^5$ is —NR$^9$C(O)NH$_2$. Thus, in some embodiments wherein $R^9$ is H and $R^8$ and $R^{8'}$ are both H, $R^5$ is urea-1-yl (i.e., —NHC(O)NH$_2$). In some embodiments wherein $R^9$ is —$C_1$-$C_6$alkyl and $R^{8'}$ is H, $R^5$ is —NR$^9$C(O)NH($C_1$-$C_6$alkyl). In some embodiments wherein $R^8$ and $R^{8'}$ are both —$C_1$-$C_6$alkyl, $R^5$ is —NR$^9$C(O)N($C_1$-$C_6$alkyl)($C_1$-$C_6$alkyl). In some embodiments wherein $R^{8'}$ is —$C_0$-$C_6$alk-O$C_1$-$C_6$alkyl and $R^{8'}$ is H, $R^5$ is —NR$^9$C(O)NH(—$C_0$-$C_6$alk-O$C_1$-$C_6$alkyl). In some embodiments wherein $R^8$ and $R^{8'}$ are both —$C_0$-$C_6$alk-O$C_1$-$C_6$alkyl, $R^5$ is —NR$^9$C(O)N(—$C_0$-$C_6$alk-O$C_1$-$C_6$alkyl)(—$C_0$-$C_6$alk-O$C_1$-$C_6$alkyl).

In some embodiments, $R^5$ in the compounds of Formula I is —OC(O)NR$^8$R$^{8'}$. In some embodiments wherein $R^8$ is H, $R^5$ is —OC(O)NHR$^{8'}$. In some embodiments wherein $R^8$ is H and $R^{8'}$ is H, $R^5$ is —OC(O)NH$_2$. In some embodiments wherein $R^8$ is —$C_1$-$C_6$alkyl and $R^{8'}$ is H, $R^5$ is —OC(O)NH($C_1$-$C_6$alkyl). In some embodiments wherein $R^{8'}$ and $R^{8'}$ are both —$C_1$-$C_6$alkyl, $R^5$ is —OC(O)N($C_1$-$C_6$alkyl)($C_1$-$C_6$alkyl). In some embodiments wherein $R^{8'}$ is —$C_0$-$C_6$alk-O$C_1$-$C_6$alkyl and $R^{8'}$ is H, $R^5$ is —OC(O)NH(—$C_0$-$C_6$alk-O$C_1$-$C_6$alkyl). In some embodiments wherein $R^8$ and $R^{8'}$ are both —$C_0$-$C_6$alk-O$C_1$-$C_6$alkyl, $R^5$ is —OC(O)N(—$C_0$-$C_6$alk-O$C_1$-$C_6$alkyl)(—$C_0$-$C_6$alk-O$C_1$-$C_6$alkyl).

In some embodiments, $R^5$ in the compounds of Formula I is —NR$^9$C(O)OR$^{9a}$. In some embodiments wherein $R^9$ is H, $R^5$ is —NHC(O)OR$^{9a}$. In some embodiments wherein $R^9$ is —$C_1$-$C_6$alkyl, $R^5$ is —N(—$C_1$-$C_6$alkyl)C(O)OR$^{9a}$. In some embodiments wherein $R^9$ is $C_0$-$C_6$alk-$C_3$-$C_6$cycloalkyl, $R^5$ is —N($C_0$-$C_6$alk-$C_3$-$C_6$cycloalkyl)C(O)OR$^{9a}$. In some embodiments wherein $R^{9a}$ is —$C_1$-$C_6$alkyl, $R^5$ is —NR$^9$C(O)O—$C_1$-$C_6$alkyl. In some embodiments wherein $R^{9a}$ is —$C_0$-$C_6$alk-$C_3$-$C_6$cycloalkyl, $R^5$ is —NR$^9$C(O)O—$C_0$-$C_6$alk-$C_3$-$C_6$cycloalkyl. In some embodiments wherein $R^9$ is H and $R^{9a}$ is —$C_1$-$C_6$alkyl, $R^5$ is —NHC(O)O—$C_1$-$C_6$alkyl. Thus, in some embodiments wherein $R^9$ is H and $R^{9a}$ is methyl, $R^5$ is —NHC(O)OCH$_3$.

In embodiments of the disclosure wherein the compounds are of Formula I or Formula II, $R^6$ is —$C_1$-$C_6$alkyl or $C_0$-$C_6$alk-$C_3$-$C_6$cycloalkyl. In some embodiments, $R^6$ is —$C_1$-$C_6$alkyl, for example, methyl, ethyl, propyl, isopropyl, butyl, isobutyl, s-butyl, t-butyl, pentyl, and the like. Thus, in some embodiments, $R^6$ is methyl (i.e., —CH$_3$, or Me). In other embodiments, $R^6$ is —$C_0$-$C_6$alk-$C_3$-$C_6$cycloalkyl, for example, —$C_0$alk-$C_3$cycloalkyl, —$C_1$alk-$C_3$cycloalkyl, —$C_2$alk-$C_3$cycloalkyl, —$C_3$alk-$C_3$cycloalkyl, —$C_4$alk-$C_3$cycloalkyl, —$C_5$alk-$C_3$cycloalkyl, —$C_6$alk-$C_3$cycloalkyl, —$C_0$alk-$C_4$cycloalkyl, —$C_1$alk-$C_4$cycloalkyl, —$C_2$alk-$C_4$cycloalkyl, —$C_3$alk-$C_4$cycloalkyl, —$C_4$alk-$C_4$cycloalkyl, —$C_5$alk-$C_4$cycloalkyl, —$C_6$alk-$C_4$cycloalkyl, —$C_0$alk-$C_5$cycloalkyl, —$C_1$alk-$C_5$cycloalkyl, —$C_2$alk-$C_5$cycloalkyl, —$C_3$alk-$C_5$cycloalkyl, —$C_4$alk-$C_5$cycloalkyl, —$C_5$alk-$C_5$cycloalkyl, —$C_6$alk-$C_5$cycloalkyl, —$C_0$alk-$C_6$cycloalkyl, —$C_1$alk- $C_6$cycloalkyl, —$C_2$alk-$C_6$cycloalkyl, —$C_3$alk-$C_6$cycloalkyl, —$C_4$alk-$C_6$cycloalkyl, —$C_5$alk-$C_6$cycloalkyl, and —$C_6$alk-$C_6$cycloalkyl.

In embodiments of the disclosure wherein the compounds are of Formula I, $R^8$ and $R^{8'}$ are each independently H, $C_1$-$C_6$alkyl, or —$C_0$-$C_6$alk-O$C_1$-$C_6$alkyl, or $R^8$ and $R^{8'}$, together with the atom to which they are attached, form a $C_2$-$C_6$heterocycloalkyl ring or a $C_3$-$C_6$cycloalkyl ring.

In some aspects, $R^8$ and $R^{8'}$ in the compounds are of Formula I are each independently H, $C_1$-$C_6$alkyl (e.g., methyl, ethyl, propyl, isopropyl, butyl, isobutyl, s-butyl, t-butyl, pentyl, and the like), or —$C_0$-$C_6$alk-O$C_1$-$C_6$alkyl (e.g., —$C_0$alk-O—$C_1$alkyl, —$C_1$alk-O—$C_1$alkyl, —$C_2$alk-O—$C_1$alkyl, —$C_3$alk-O—$C_1$alkyl, —$C_4$alk-O—$C_1$alkyl, —$C_5$alk-O—$C_1$alkyl, —$C_6$alk-O—$C_1$alkyl, —$C_0$alk-O—$C_2$alkyl, —$C_1$alk-O—$C_2$alkyl, —$C_2$alk-O—$C_2$alkyl, —$C_3$alk-O—$C_2$alkyl, —$C_4$alk-O—$C_2$alkyl, —$C_6$alk-O—$C_2$alkyl, —$C_6$alk-O—$C_2$alkyl, —$C_0$alk-O—$C_3$alkyl, —$C_1$alk-O—$C_3$alkyl, —$C_2$alk-O—$C_3$alkyl, —$C_3$alk-O—$C_3$alkyl, —$C_4$alk-O—$C_3$alkyl, —$C_5$alk-O—$C_3$alkyl, —$C_6$alk-O—$C_3$alkyl, —$C_0$alk-O—$C_4$alkyl, —$C_1$alk-O—$C_4$alkyl, —$C_2$alk-O—$C_4$alkyl, —$C_3$alk-O—$C_4$alkyl, —$C_4$alk-O—$C_4$alkyl, —$C_5$alk-O—$C_4$alkyl, —$C_6$alk-O—$C_4$alkyl, —$C_0$alk-O—$C_5$alkyl, —$C_1$alk-O—$C_5$alkyl, —$C_2$alk-O—$C_5$alkyl, —$C_3$alk-O—$C_5$alkyl, —$C_4$alk-O—$C_5$alkyl, —$C_5$alk-O—$C_5$alkyl, —$C_6$alk-O—$C_5$alkyl, —$C_0$alk-O—$C_6$alkyl, —$C_1$alk-O—$C_6$alkyl, —$C_2$alk-O—$C_6$alkyl, —$C_3$alk-O—$C_6$alkyl, —$C_4$alk-O—$C_6$alkyl, —$C_5$alk-O—$C_6$alkyl, and —$C_0$alk-O—$C_6$alkyl). In some embodiments, $R^{8'}$ is $C_1$-$C_6$alkyl or —$C_0$-$C_6$alk-O$C_1$-$C_6$alkyl and $R^{8'}$ is H, $C_1$-$C_6$alkyl, or —$C_0$-$C_6$alk-O$C_1$-$C_6$alkyl.

In some embodiments, $R^{8'}$ in the compounds of Formula I is H or $C_1$-$C_6$alkyl. In some embodiments, $R^{8'}$ in the compounds of Formula I is H or $C_1$-$C_6$alkyl. In some embodiments, $R^1$ and $R^{8'}$ are each H. In other embodiments, $R^8$ and $R^{8'}$ are each independently $C_1$-$C_6$alkyl. In some aspects, $R^8$ is $C_1$-$C_6$alkyl and $R^{8'}$ is H.

In other aspects, $R^8$ and $R^{8'}$ in the compounds of Formula I are each independently —$C_0$-$C_6$alk-O$C_1$-$C_6$alkyl.

In other aspects, $R^8$ in the compounds of Formula I is —$C_0$-$C_6$alk-O$C_1$-$C_6$alkyl and $R^{8'}$ is H.

In yet other aspects, $R^8$ and $R^{8'}$ in the compounds of Formula I, together with the atom to which they are attached, form a $C_3$-$C_6$cycloalkyl ring, for example, cyclopropyl, cyclobutyl, cyclopentyl, or cyclohexyl, and the like, or a $C_2$-$C_6$heterocycloalkyl ring, for example, aziridinyl, azetidinyl, pyrrolidinyl, piperidinyl, and the like.

In embodiments of the disclosure wherein the compounds are of Formula I, $R^9$ is H, —$C_1$-$C_6$alkyl (e.g., methyl, ethyl, propyl, isopropyl, butyl, isobutyl, s-butyl, t-butyl, pentyl, and the like), or $C_0$-$C_6$alk-$C_3$-$C_6$cycloalkyl (e.g., —$C_0$alk-$C_3$cycloalkyl, —$C_1$alk-$C_3$cycloalkyl, —$C_2$alk-$C_3$cycloalkyl, —$C_3$alk-$C_3$cycloalkyl, —$C_4$alk-$C_3$cycloalkyl, —$C_5$alk-$C_3$cycloalkyl, —$C_6$alk-$C_3$cycloalkyl, —$C_0$alk-$C_4$cycloalkyl, —$C_1$alk-$C_4$cycloalkyl, —$C_2$alk-$C_4$cycloalkyl, —$C_3$alk-$C_4$cycloalkyl, —$C_4$alk-$C_4$cycloalkyl, —$C_5$alk-$C_4$cycloalkyl, —$C_6$alk-$C_4$cycloalkyl, —$C_0$alk-$C_5$cycloalkyl, —$C_1$alk-$C_5$cycloalkyl, —$C_2$alk-$C_5$cycloalkyl, —$C_3$alk-$C_5$cycloalkyl, —$C_4$alk-$C_5$cycloalkyl, —$C_5$alk-$C_5$cycloalkyl, —$C_6$alk-$C_5$cycloalkyl, —$C_0$alk-$C_6$cycloalkyl, —$C_1$alk-$C_6$cycloalkyl, —$C_2$alk-$C_6$cycloalkyl, —$C_3$alk-$C_6$cycloalkyl, —$C_4$alk-$C_6$cycloalkyl, —$C_5$alk-$C_6$cycloalkyl, and —$C_6$alk-$C_6$cycloalkyl).

In embodiments of the disclosure wherein the compounds are of Formula I, $R^{9a}$ is —$C_1$-$C_6$alkyl, or $C_0$-$C_6$alk-$C_3$-$C_6$cycloalkyl. In some embodiments, $R^{9a}$ is —$C_1$-$C_6$alkyl (e.g., methyl, ethyl, propyl, isopropyl, butyl, isobutyl, s-butyl, t-butyl, pentyl, and the like), or $C_0$-$C_6$alk-$C_3$-$C_6$cycloalkyl (e.g., —$C_0$alk-$C_3$cycloalkyl, —$C_1$alk-$C_3$cycloalkyl, —$C_2$alk-$C_3$cycloalkyl, —$C_3$alk-$C_3$cycloalkyl, —$C_4$alk-$C_3$cycloalkyl, —$C_5$alk-$C_3$cycloalkyl, —$C_6$alk-$C_3$cycloalkyl, —$C_0$alk-$C_4$cycloalkyl, —$C_1$alk-$C_4$cycloalkyl, —$C_2$alk-$C_4$cycloalkyl, —$C_3$alk-$C_4$cycloalkyl, —$C_4$alk-$C_4$cycloalkyl, —$C_5$alk-$C_4$cycloalkyl, —$C_6$alk-$C_4$cycloalkyl, —$C_0$alk-$C_5$cycloalkyl, —$C_1$alk-$C_5$cycloalkyl, —$C_2$alk-$C_5$cycloalkyl, —$C_3$alk-$C_5$cycloalkyl, —$C_4$alk-$C_5$cycloalkyl, —$C_5$alk-$C_5$cycloalkyl, —$C_6$alk-$C_5$cycloalkyl, —$C_0$alk-$C_6$cycloalkyl, —$C_1$alk-$C_6$cycloalkyl, —$C_2$alk-$C_6$cycloalkyl, —$C_3$alk-$C_6$cycloalkyl, —$C_4$alk-$C_6$cycloalkyl, —$C_6$alk-$C_6$cycloalkyl, and —$C_6$alk-$C_6$cycloalkyl).

In preferred embodiments of the compounds of Formula I or Formula II, $R^1$ is —$C_0$-$C_6$alk-$C_1$-$C_6$alkyl, —$C_0$-$C_6$alk-$C_1$-$C_6$haloalkyl, —$C_0$-$C_6$alk-C≡CH, —$C_0$-$C_6$alk-C≡C—$C_1$-$C_6$alkyl, —$C_0$-$C_6$alk-C≡C—$C_1$-$C_6$haloalkyl, —$C_0$-$C_6$alk-C≡C—$C_3$-$C_6$cycloalkyl, or —$C_1$-$C_6$alk-aryl.

More preferred embodiments of the compounds of Formula I or Formula II are those wherein $R^1$ is —CH(OH)—$C_1$-$C_6$alkyl, —CH(F)—$C_1$-$C_6$alkyl, —CH(NH$_2$)—$C_1$-$C_6$alkyl, —CH(Me)-$C_1$-$C_6$alkyl, —C(Me)(OH)—$C_1$-$C_6$alkyl, —CH(OH)—$C_1$-$C_6$ haloalkyl, —CH(F)—$C_1$-$C_6$ haloalkyl, —CH(NH$_2$)—$C_1$-$C_6$ haloalkyl, —CH(Me)-$C_1$-$C_6$ haloalkyl, —C(Me)(OH)—$C_1$-$C_6$ haloalkyl, —CH(OH)—C≡CH, —CH(F)—C≡CH, —CH(NH$_2$)—C≡CH, —CH(Me)-C≡CH, —C(Me)(OH)—C≡CH, —CH(OH)—C≡C—$C_1$-$C_6$alkyl, —CH(F)—C≡C—$C_1$-$C_6$alkyl, —CH(NH$_2$)—C≡C—$C_1$-$C_6$alkyl, —CH(Me)-C≡C—$C_1$-$C_6$alkyl, —C(Me)(OH)—C≡C—$C_1$-$C_6$alkyl, CH(OH)—C≡C—$C_1$-$C_6$haloalkyl, —CH(F)—C≡C—$C_1$-$C_6$haloalkyl, —CH(NH$_2$)—C≡C—$C_1$-$C_6$haloalkyl, —CH(Me)-C≡C—$C_1$-$C_6$haloalkyl, —C(Me)(OH)—C≡C—$C_1$-$C_6$haloalkyl, —CH(OH)—C≡C—$C_3$-$C_6$cycloalkyl, —CH(F)—C≡C—$C_3$-$C_6$cycloalkyl, —CH(NH$_2$)—C≡C—$C_3$-$C_6$cycloalkyl, —CH(Me)-C≡C—$C_3$-$C_6$cycloalkyl, —C(Me)(OH)—C≡C—$C_3$-$C_6$cycloalkyl, —CH(OH)-aryl, —CH(F)-aryl, —CH(NH$_2$)-aryl, —CH(Me)-aryl, or —C(Me)(OH)-aryl.

Most preferred embodiments of the compounds of Formula I or Formula II are those wherein $R^1$ is —CH(OH)—C≡C—CH$_3$, —CH(F)—C≡C—CH$_3$, —CH(NH$_2$)—C≡C—CH$_3$, —CH(Me)-C≡C—CH$_3$, —C(Me)(OH)—C≡C—CH$_3$, —CH(OH)—C≡C—CH$_3$, —CH(OH)—C≡C—CF$_3$, —CH(F)—C≡C—CF$_3$, —CH(NH$_2$)—C≡C—CF$_3$, —CH(Me)-C≡C—CF$_3$, —C(Me)(OH)—C≡C—CF$_3$, —CH(OH)—C≡C-cyclopropyl, —CH(F)—C≡C-cyclopropyl, —CH(NH$_2$)—C≡C-cyclopropyl, —CH(Me)-C≡C-cyclopropyl, —C(Me)(OH)—C≡C-cyclopropyl, —CH(OH)-4-chlorophenyl, —CH(OH)-3,4-dichlorophenyl, —CH(OH)-3,4-difluorophenyl, —CH(OH)-3-fluoro-4-chlorophenyl, —CH(OH)-3-chloro-4-fluorophenyl, —CH(F)-4-chlorophenyl, —CH(F)-3,4-dichlorophenyl, —CH(F)-3,4-difluorophenyl, —CH(F)-3-fluoro-4-chlorophenyl, —CH(F)-3-chloro-4-fluorophenyl, —CH(NH$_2$)-4-chlorophenyl, —CH(NH$_2$)-3,4-dichlorophenyl, —CH(NH$_2$)-3,4-difluorophenyl, —CH(NH$_2$)-3-fluoro-4-chlorophenyl, —CH(NH$_2$)-3-chloro-4-fluorophenyl, —CH(Me)-4-chlorophenyl, —CH(Me)-3,4-dichlorophenyl, —CH(Me)-3,4-difluorophenyl, —CH(Me)-3-fluoro-4-chlorophenyl, —CH(Me)-3-chloro-4-fluorophenyl, —C(Me)(OH)-4-chlorophenyl, —C(Me)(OH)-3,4-dichlorophenyl, —C(Me)(OH)-3,4- difluorophenyl, —C(Me)(OH)-3-fluoro-4-chlorophenyl, or —C(Me)(OH)-3-chloro-4-fluorophenyl Some aspects of the disclosure are directed to compounds of Formula IC and IIC:

IC
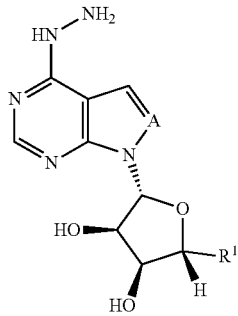

IIC
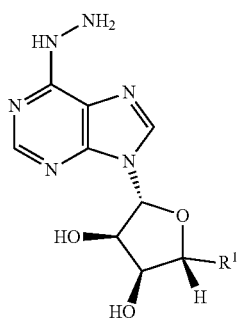

Some aspects of the disclosure are directed to compounds of Formula ID and IID:

ID
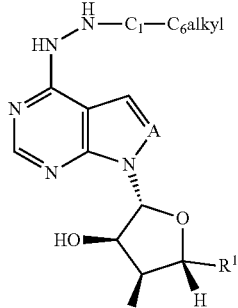

IID
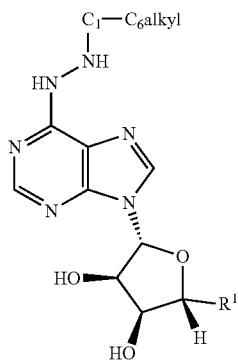

Some aspects of the disclosure are directed to compounds of Formula IE and IIE:

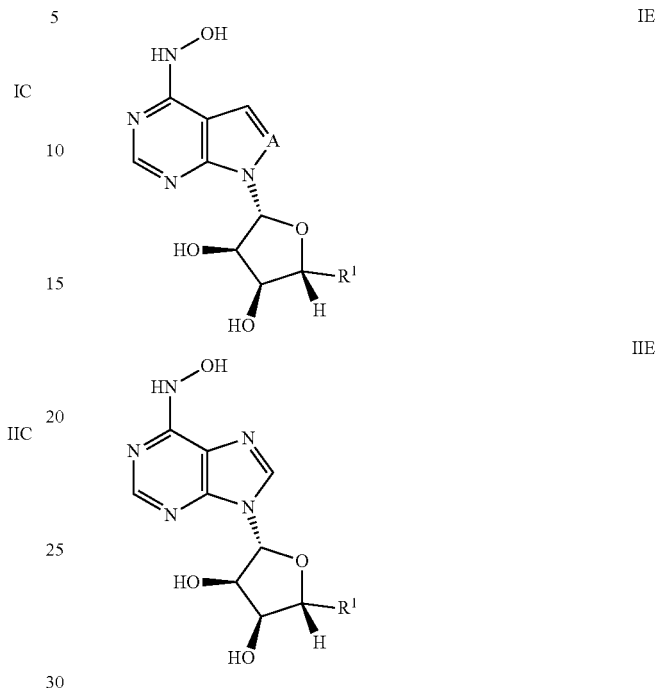

Some aspects of the disclosure are directed to compounds of Formula IF and IIF:

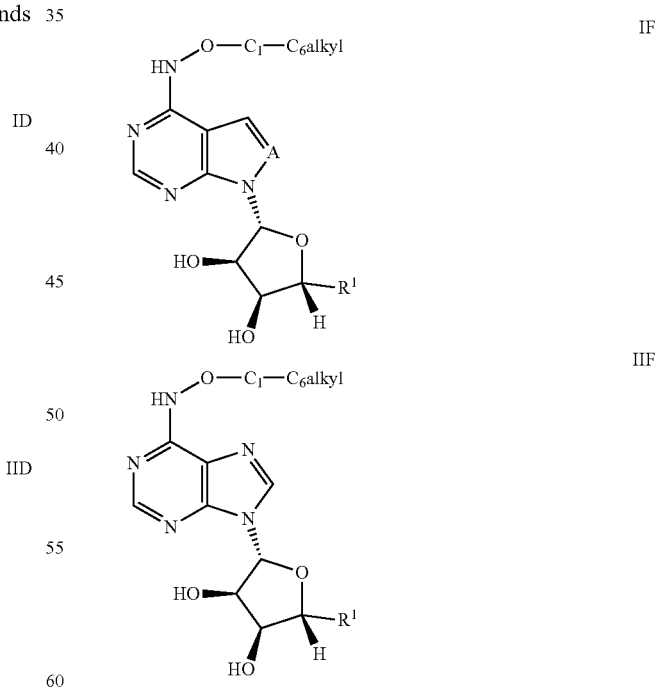

References to Formula I herein include subgenera of Formula I, for example, Formula IA. IA-1, IA-2, IA-3, IA-4, IB, IB-1, IB-2, IB-3, IB-4, IB-5, IB-6, IC, ID, IE, and IF. Similarly, references to Formula II herein include subgenera of Formula II, for example, Formula IIA, IIB, IIC, IID, IIE, IIF, IIG, IIG-1, IIG-2, IIG-3, and IIG-4.

Stereoisomers of compounds of Formula I and Formula II are also contemplated.

Pharmaceutically acceptable salts and solvates of the compounds of Formula I and Formula II are also within the scope of the disclosure.

Isotopic variants of the compounds of Formula I and Formula II are also contemplated by the present disclosure.

In some embodiments, the compounds of Formula I or Formula II are solvates. In preferred embodiments, the compounds of Formula I are ethanolates (i.e., ethanol solvates.). In other preferred embodiments, the compounds of Formula II are ethanolates.

In some aspects, the present disclosure is directed to compounds of Formula IB:

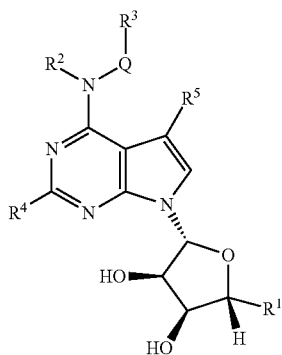

IB wherein Q is NH or O; $R^1$ is —$C_0$-$C_6$alk-heteroaryl or —$C_1$-$C_6$alk-aryl; $R^2$ is H; $R^3$ is H, —$C_1$-$C_6$alkyl, or —$C_1$-$C_6$haloalkyl; $R^4$ is H or —$C_1$-$C_6$alkyl, and $R^5$ is H, halo, or —$C_1$-$C_6$alkyl.

In some aspects, the present disclosure is directed to compounds of Formula IB-1

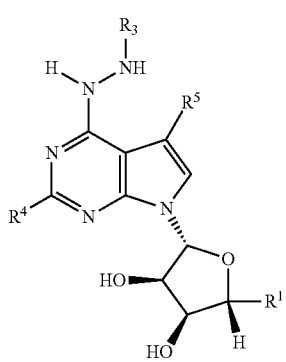

IB-1 wherein $R^1$ is —$C_0$-$C_6$alk-heteroaryl; $R^3$ is H, —$C_1$-$C_6$alkyl, or —$C_1$-$C_6$haloalkyl; $R^4$ is H or —$C_1$-$C_6$alkyl, and $R^5$ is H, halo, or —$C_1$-$C_6$alkyl.

In other aspects, the disclosure is directed to compounds of Formula IB-1 wherein $R^1$ is —$C_1$-$C_6$alk-aryl; $R^3$ is H, —$C_1$-$C_6$alkyl, or —$C_1$-$C_6$haloalkyl; $R^4$ is H or —$C_1$-$C_6$alkyl, and $R^5$ is H, halo, or —$C_1$-$C_6$alkyl.

Some preferred embodiments are compounds of Formula IB-2

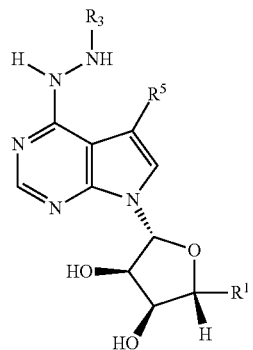

IB-2 wherein $R^1$ is 2-(2-amino-3-bromoquinolin-7-yl)ethyl, 2-(2-amino-3-chloroquinolin-7-yl)ethyl, 2-(2-((cyclopropylmethyl)amino)quinolin-7-yl)ethyl, 2-(2-(methylamino)quinolin-7-yl)ethyl, or 2-(2-aminoquinolin-7-yl)ethyl; $R^3$ is H or methyl; and $R^5$ is H or F.

Other preferred embodiments are compounds of Formula IB-2 wherein $R^1$ is —CH(OH)-aryl or —C(Me)(OH)-aryl; H; $R^3$ is H or —$C_1$-$C_6$alkyl; and $R^5$ is H or halo.

Other preferred embodiments are compounds of Formula IB-2 wherein $R^1$ is —CH(OH)-4-chlorophenyl, —CH(OH)-3,4-dichlorophenyl, —CH(OH)-3,4-difluorophenyl, —CH(OH)-3-fluoro-4-chlorophenyl, —CH(OH)-3-chloro-4-fluorophenyl, —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, CH(OH)-4-(trifluoromethyl)phenyl, —CH(OH)-3-fluoro-4-(trifluoromethyl)phenyl, —C(CF$_3$)(OH)-4-chlorophenyl, or —CH(OH)-3-methyl-4-chlorophenyl; $R^3$ is H or methyl; and $R^5$ is H or F.

Yet other preferred embodiments are compounds of Formula IB-2 wherein $R^1$ is —CH(OH)-4-chlorophenyl, —CH(OH)-3,4-dichlorophenyl, or —CH(OH)-4-(trifluoromethyl)phenyl; $R^3$ is H or methyl; and $R^5$ is H or F.

Other preferred embodiments are compounds of Formula IB-2 wherein $R^1$ is —C(Me)(OH)-3,4-dichlorophenyl or —CH(OH)-3,4-dichlorophenyl, $R^3$ is methyl; and $R^5$ is H.

In some aspects, the disclosure is directed to compounds of Formula IB-3

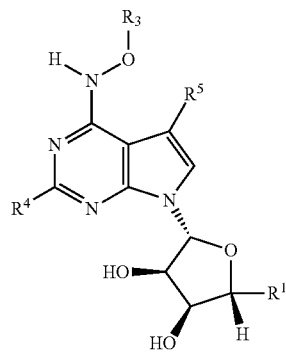

IB-3 wherein $R^1$ is —$C_0$-$C_6$alk-heteroaryl; $R^3$ is H, —$C_1$-$C_6$alkyl, or —$C_1$-$C_6$haloalkyl; $R^4$ is H or —$C_1$-$C_6$alkyl, and $R^5$ is H, halo, or —$C_1$-$C_6$alkyl.

In other aspects, the disclosure is directed to compounds of Formula IB-3 wherein $R^1$ is —$C_1$-$C_6$alk-aryl; $R^3$ is H, —$C_1$-$C_6$alkyl, or —$C_1$-$C_6$haloalkyl; $R^4$ is H or —$C_1$-$C_6$alkyl, and $R^5$ is H, halo, or —$C_1$-$C_6$alkyl.

Some preferred embodiments are compounds of Formula IB-4

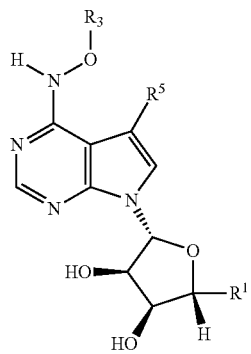

IB-4 wherein $R^1$ is 2-(2-amino-3-bromoquinolin-7-yl)ethyl, 2-(2-amino-3-chloroquinolin-7-yl)ethyl, 2-(2-((cyclopropylmethyl)amino)quinolin-7-yl)ethyl, 2-(2-(methylamino)quinolin-7-yl)ethyl, or 2-(2-aminoquinolin-7-yl)ethyl; $R^3$ is H or methyl; and $R^5$ is H or F.

Other preferred embodiments are compounds of Formula IB-4 wherein $R^1$ is —CH(OH)-aryl or —C(Me)(OH)-aryl; $R^3$ is H or —$C_1$-$C_6$alkyl; and $R^5$ is H or halo.

Other preferred embodiments are compounds of Formula IB-4 wherein $R^1$ is —CH(OH)-4-chlorophenyl, —CH(OH)-3,4-dichlorophenyl, —CH(OH)-3,4-difluorophenyl, —CH(OH)-3-fluoro-4-chlorophenyl, —CH(OH)-3-chloro-4-fluorophenyl, —CH(OH)-3-methyl-4-(trifluoromethyl)phenyl, —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, CH(OH)-4-(trifluoromethyl)phenyl, —CH(OH)-3-fluoro-4-(trifluoromethyl)phenyl, —C(CF$_3$)(OH)-4-chlorophenyl, or —CH(OH)-3-methyl-4-chlorophenyl; $R^3$ is H, methyl, or ethyl; and $R^5$ is H or F.

Yet other preferred embodiments are compounds of Formula IB-4 wherein $R^1$ is —CH(OH)-4-chlorophenyl, —CH(OH)-3,4-dichlorophenyl, or —CH(OH)-4-(trifluoromethyl)phenyl; $R^3$ is H or methyl; and $R^5$ is H or F.

Other preferred embodiments are compounds of Formula IB-4 wherein $R^1$ is —C(Me)(OH)-3,4-dichlorophenyl or —CH(OH)-3,4-dichlorophenyl, $R^3$ is methyl; and $R^5$ is H.

Other preferred embodiments are compounds of Formula IB-4 wherein $R^1$ is —CH(OH)-4-chlorophenyl, —CH(OH)-3,4-dichlorophenyl, —CH(OH)-3,4-difluorophenyl, —CH(OH)-3-fluoro-4-chlorophenyl, —CH(OH)-3-chloro-4-fluorophenyl, —CH(OH)-3-methyl-4-(trifluoromethyl)phenyl, —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, CH(OH)-4-(trifluoromethyl)phenyl, —CH(OH)-3-fluoro-4-(trifluoromethyl)phenyl, —C(CF$_3$)(OH)-4-chlorophenyl, or —CH(OH)-3-methyl-4-chlorophenyl; $R^3$ is —CH$_2$CF$_3$ or —CH$_2$CHF$_2$; and $R^5$ is H or F.

Other preferred embodiments are compounds of Formula IB-4 wherein $R^1$ is —CH(OH)-4-chlorophenyl, —CH(OH)-3,4-dichlorophenyl, —CH(OH)-3,4-difluorophenyl, —CH(OH)-3-fluoro-4-chlorophenyl, —CH(OH)-3-chloro-4-fluorophenyl, —CH(OH)-3-methyl-4-(trifluoromethyl)phenyl, —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, CH(OH)-4-(trifluoromethyl)phenyl, —CH(OH)-3-fluoro-4-(trifluoromethyl)phenyl, —C(CF$_3$)(OH)-4-chlorophenyl, or —CH(OH)-3-methyl-4-chlorophenyl; $R^3$ is H, methyl, ethyl. —CH$_2$CF$_3$, or —CH$_2$CHF$_2$; and $R^5$ is hydroxymethyl (i.e., CH$_2$OH), hydroxyethyl (i.e., —CH$_2$CH$_2$OH), or ethynyl.

Some preferred embodiments are compounds of Formula IB-5

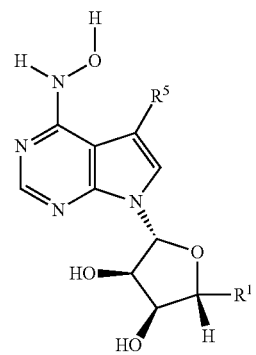

IB-5 wherein $R^1$ is $R^1$ is —CH(OH)-4-chlorophenyl, —CH(OH)-3,4-dichlorophenyl, —CH(OH)-3,4-difluorophenyl, —CH(OH)-3-fluoro-4-chlorophenyl, —CH(OH)-3-chloro-4-fluorophenyl, —C(Me)(OH)-4-chlorophenyl, or —C(Me)(OH)-3,4-dichlorophenyl, and $R^5$ is H or F.

Other preferred embodiments are compounds of Formula IB-6

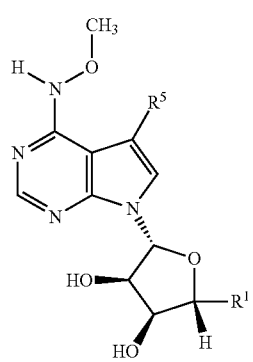

IB-6 wherein $R^1$—CH(OH)-3,4-dichlorophenyl, —CH(OH)-3-chloro-4-fluorophenyl, —C(Me)(OH)-3,4-dichlorophenyl, —CH(OH)-3-fluoro-4-(trifluoromethyl)phenyl, —CH(OH)-3-methyl-4-(trifluoromethyl)phenyl, or —CH(OH)-3-methyl-4-chlorophenyl; and $R^5$ is H.

In other aspects, the disclosure is directed to compounds of Formula II-G:

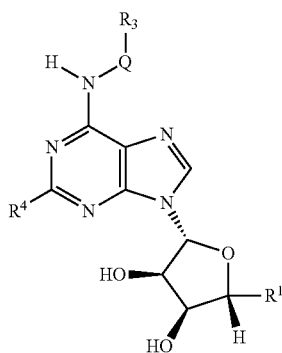

II-G wherein Q is NH or O, R is —C₀-C₆alk-heteroaryl or —C₁-C₆alk-aryl; R³ is H, —C₁-C₆alkyl, or —C₁-C₆haloalkyl; and R⁴ is H or —C₁-C₆alkyl.

Some preferred embodiments are compounds of Formula II-G-1

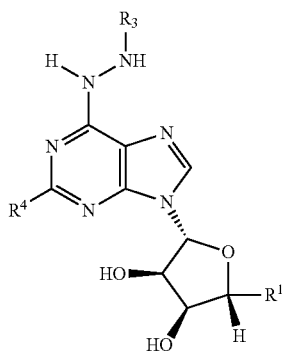

II-G-1 wherein R¹ is —C₀-C₆alk-heteroaryl; R³ is H, —C₁-C₆alkyl, or —C₁-C₆haloalkyl; and R⁴ is H or —C₁-C₆alkyl.

Other preferred embodiments are compounds of Formula II-G-1 wherein R¹ is 2-(2-amino-3-bromoquinolin-7-yl)ethyl, 2-(2-amino-3-chloroquinolin-7-yl)ethyl, 2-(2-((cyclopropylmethyl)amino)quinolin-7-yl)ethyl, 2-(2-(methylamino)quinolin-7-yl)ethyl, or 2-(2-aminoquinolin-7-yl)ethyl; R³ is H or methyl; and R⁴ is H.

Other preferred embodiments are compounds of Formula II-G-1 wherein R¹ is —C₁-C₆alk-aryl; R³ is H, —C₁-C₆alkyl, or —C₁-C₆haloalkyl; and R⁴ is H or —C₁-C₆alkyl.

Other preferred embodiments are compounds of Formula II-G-1 wherein R¹ is —CH(OH)-aryl or —C(Me)(OH)-aryl; R³ is H, —C₁-C₆alkyl, or —C₁-C₆haloalkyl; and R⁴ is H or —C₁-C₆alkyl.

Other preferred embodiments are compounds of Formula II-G-1 wherein R¹ is —CH(OH)-4-chlorophenyl, —CH(OH)-3,4-dichlorophenyl, —CH(OH)-3,4-difluorophenyl, —CH(OH)-3-fluoro-4-chlorophenyl, —CH(OH)-3-chloro-4-fluorophenyl, —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, CH(OH)-4-(trifluoromethyl)phenyl, —CH(OH)-3-fluoro-4-(trifluoromethyl)phenyl, —C(CF₃)(OH)-4-chlorophenyl, or —CH(OH)-3-methyl-4-chlorophenyl; R³ is H or methyl; and R⁴ is H or methyl.

In some aspects, the present disclosure is directed to compounds of Formula II-G-2

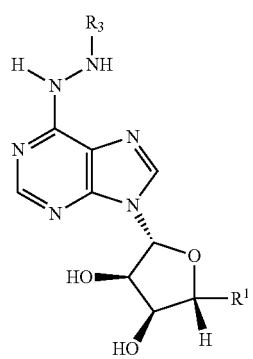

II-G-2 wherein R¹ is 2-(2-amino-3-bromoquinolin-7-yl)ethyl, 2-(2-amino-3-chloroquinolin-7-yl)ethyl, 2-(2-((cyclopropylmethyl)amino)quinolin-7-yl)ethyl, 2-(2-(methylamino)quinolin-7-yl)ethyl, or 2-(2-aminoquinolin-7-yl)ethyl; and R³ is H or methyl.

In other aspects, the present disclosure is directed to compounds of Formula II-G-2 wherein R¹ is —CH(OH)-4-chlorophenyl, and R³ is H or methyl.

In some aspects, the present disclosure is directed to compounds of Formula II-G-3

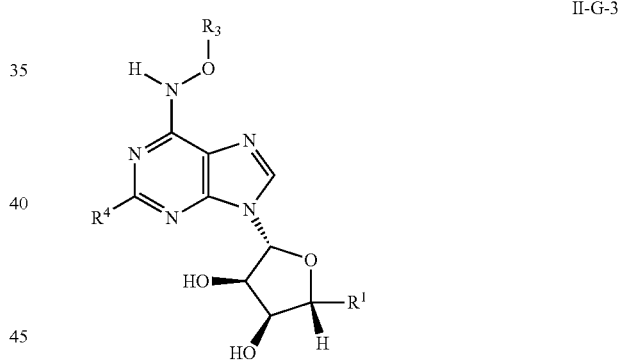

II-G-3 wherein R¹ is —C₀-C₆alk-heteroaryl; R³ is H, —C₁-C₆alkyl, or —C₁-C₆haloalkyl; and R⁴ is H or -C₁-C₆alkyl.

Some preferred embodiments are compounds of Formula II-G-3 wherein R¹ is 2-(2-amino-3-bromoquinolin-7-yl)ethyl, 2-(2-amino-3-chloroquinolin-7-yl)ethyl, 2-(2-((cyclopropylmethyl)amino)quinolin-7-yl)ethyl, 2-(2-(methylamino)quinolin-7-yl)ethyl, or 2-(2-aminoquinolin-7-yl)ethyl; R³ is H or methyl; and R⁴ is H.

Other preferred embodiments are compounds of Formula II-G-3 wherein R¹ is —C₁-C₆alk-aryl; R³ is H, —C₁-C₆alkyl, or —C₁-C₆haloalkyl; and R⁴ is H or —C₁-C₆alkyl.

Other preferred embodiments are compounds of Formula II-G-3 wherein R¹ is —CH(OH)-aryl or —C(Me)(OH)-aryl; R³ is H, —C₁-C₆alkyl, or —C₁-C₆haloalkyl; and R⁴ is H or —C₁-C₆alkyl.

Other preferred embodiments are compounds of Formula II-G-3 wherein R¹ is —CH(OH)-4-chlorophenyl, —CH(OH)-3,4-dichlorophenyl, —CH(OH)-3,4-difluorophenyl, —CH(OH)-3-fluoro-4-chlorophenyl, —CH(OH)-3-chloro-4-fluorophenyl, —C(Me)(OH)-4-chlorophenyl, —C(Me)

(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, CH(OH)-4-(trifluoromethyl)phenyl, —CH(OH)-3-fluoro-4-(trifluoromethyl)phenyl, —C(CF$_3$)(OH)-4-chlorophenyl, or —CH(OH)-3-methyl-4-chlorophenyl; R$^3$ is H, methyl, or ethyl; and R$^4$ is H or methyl.

In some aspects, the present disclosure is directed to compounds of Formula II-G-4

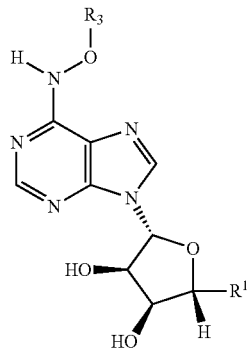

II-G-4 wherein R$^1$ is 2-(2-amino-3-bromoquinolin-7-yl)ethyl, 2-(2-amino-3-chloroquinolin-7-yl)ethyl, 2-(2-((cyclopropylmethyl)amino)quinolin-7-yl)ethyl, 2-(2-(methylamino)quinolin-7-yl)ethyl, or 2-(2-aminoquinolin-7-yl)ethyl; and R$^3$ is H or methyl.

In other aspects, the present disclosure is directed to compounds of Formula II-G-4 wherein R$^1$ is —CH(OH)-4-chlorophenyl, —CH(OH)-3,4-dichlorophenyl, —CH(OH)-3,4-difluorophenyl, —CH(OH)-3-fluoro-4-chlorophenyl, —CH(OH)-3-chloro-4-fluorophenyl, —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, CH(OH)-4-(trifluoromethyl)phenyl, —CH(OH)-3-fluoro-4-(trifluoromethyl)phenyl, —C(CF$_3$)(OH)-4-chlorophenyl, or —CH(OH)-3-methyl-4-chlorophenyl; and R$^3$ is H or methyl.

In yet other aspects, the present disclosure is directed to compounds of Formula II-G-4 wherein R$^1$ is —CH(OH)-4-chlorophenyl, and R$^3$ is H or methyl.

In some aspects, the present disclosure is directed to compounds of Formula IA:

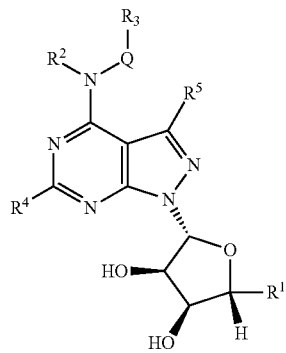

IA wherein Q is NH or O; R$^1$ is —C$_0$-C$_6$alk-heteroaryl or —C$_1$-C$_6$alk-aryl; R$^2$ is H; R$^3$ is H, —C$_1$-C$_6$alkyl, or —C$_1$-C$_6$haloalkyl; R$^4$ is H or —C$_1$-C$_6$alkyl, and R$^5$ is H, halo, or —C$_1$-C$_6$alkyl.

In some aspects, the present disclosure is directed to compounds of Formula IA-1

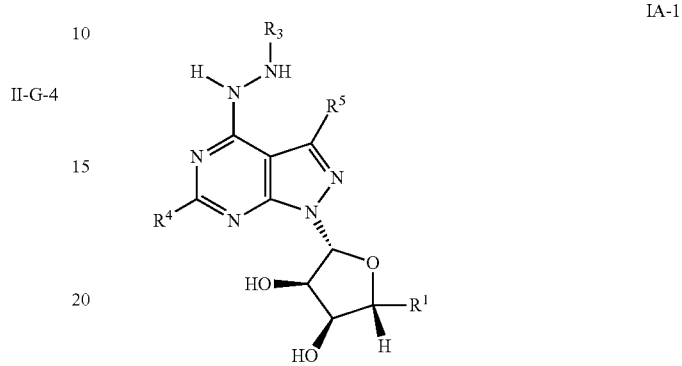

IA-1 wherein R$^1$ is —C$_0$-C$_6$alk-heteroaryl; R$^3$ is H, —C$_1$-C$_6$alkyl, or —C$_1$-C$_6$haloalkyl; R$^4$ is H or —C$_1$-C$_6$alkyl, and R$^5$ is H, halo, or —C$_1$-C$_6$alkyl.

In other aspects, the disclosure is directed to compounds of Formula IA-1 wherein R$^1$ is —C$_1$-C$_6$alk-aryl; R$^3$ is H, —C$_1$-C$_6$alkyl, or —C$_1$-C$_6$haloalkyl; R$^4$ is H or —C$_1$-C$_6$alkyl, and R$^5$ is H, halo, or —C$_1$-C$_6$alkyl.

Some preferred embodiments are compounds of Formula IA-2

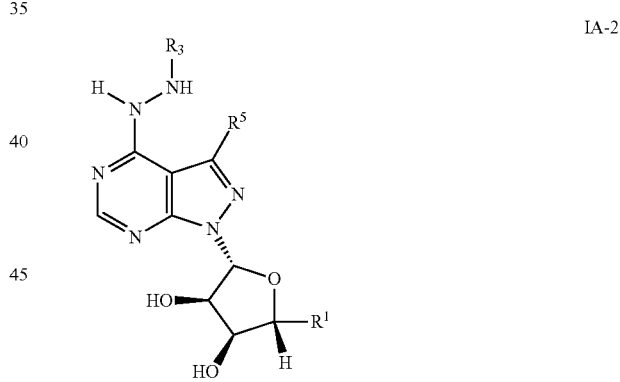

IA-2 wherein R$^1$ is 2-(2-amino-3-bromoquinolin-7-yl)ethyl, 2-(2-amino-3-chloroquinolin-7-yl)ethyl, 2-(2-((cyclopropylmethyl)amino)quinolin-7-yl)ethyl, 2-(2-(methylamino)quinolin-7-yl)ethyl, or 2-(2-aminoquinolin-7-yl)ethyl; R$^3$ is H or methyl; and R$^5$ is H or F.

Other preferred embodiments are compounds of Formula IA-2 wherein R$^1$ is —CH(OH)-aryl or —C(Me)(OH)-aryl; R$^3$ is H or —C$_1$-C$_6$alkyl; and R$^5$ is H or halo.

Other preferred embodiments are compounds of Formula IA-2 wherein R$^1$ is —CH(OH)-4-chlorophenyl, —CH(OH)-3,4-dichlorophenyl, —CH(OH)-3,4-difluorophenyl, —CH(OH)-3-fluoro-4-chlorophenyl, —CH(OH)-3-chloro-4-fluorophenyl, —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, CH(OH)-4-(trifluoromethyl)phenyl, —CH(OH)-3-fluoro-4-(trifluoromethyl)phenyl, —C(CF$_3$)

(OH)-4-chlorophenyl, or —CH(OH)-3-methyl-4-chlorophenyl; $R^3$ is H or methyl; and $R^5$ is H or F.

Yet other preferred embodiments are compounds of Formula IA-2 wherein $R^1$ is —CH(OH)-4-chlorophenyl, —CH(OH)-3,4-dichlorophenyl, or —CH(OH)-4-(trifluoromethyl)phenyl; $R^3$ is H or methyl; and $R^5$ is H or F.

In some aspects, the disclosure is directed to compounds of Formula IA-3

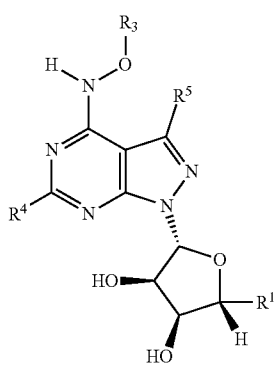

IA-3 wherein $R^1$ is —$C_0$-$C_6$alk-heteroaryl; $R^3$ is H, —$C_1$-$C_6$alkyl, or —$C_1$-$C_6$haloalkyl; $R^4$ is H or —$C_1$-$C_6$alkyl, and $R^5$ is H, halo, or —$C_1$-$C_6$alkyl.

In other aspects, the disclosure is directed to compounds of Formula IA-3 wherein $R^1$ is —$C_1$-$C_6$alk-aryl; $R^3$ is H, —$C_1$-$C_6$alkyl, or —$C_1$-$C_6$haloalkyl; $R^4$ is H or —$C_1$-$C_6$alkyl, and $R^5$ is H, halo, or —$C_1$-$C_6$alkyl.

Some preferred embodiments are compounds of Formula IA-4

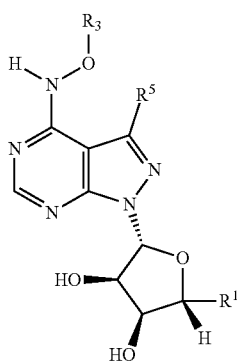

IA-4 wherein $R^1$ is 2-(2-amino-3-bromoquinolin-7-yl)ethyl, 2-(2-amino-3-chloroquinolin-7-yl)ethyl, 2-(2-((cyclopropylmethyl)amino)quinolin-7-yl)ethyl, 2-(2-(methylamino)quinolin-7-yl)ethyl, or 2-(2-aminoquinolin-7-yl)ethyl; $R^3$ is H or methyl; and $R^5$ is H or F.

Other preferred embodiments are compounds of Formula IA-4 wherein $R^1$ is —CH(OH)-aryl or —C(Me)(OH)-aryl; H; $R^3$ is H or —$C_1$-$C_6$alkyl; and $R^5$ is H or halo.

Other preferred embodiments are compounds of Formula IA-4 wherein $R^1$ is —CH(OH)-4-chlorophenyl, —CH(OH)-3,4-dichlorophenyl, —CH(OH)-3,4-difluorophenyl, —CH(OH)-3-fluoro-4-chlorophenyl, —CH(OH)-3-chloro-4-fluorophenyl, —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, CH(OH)-4-(trifluoromethyl)phenyl, —CH(OH)-3-fluoro-4-(trifluoromethyl)phenyl, —C(CF$_3$)(OH)-4-chlorophenyl, or —CH(OH)-3-methyl-4-chlorophenyl; $R^3$ is H or methyl; and $R^5$ is H or F.

Yet other preferred embodiments are compounds of Formula IA-4 wherein $R^1$ is —CH(OH)-4-chlorophenyl, —CH(OH)-3,4-dichlorophenyl, or —CH(OH)-4-(trifluoromethyl)phenyl; $R^3$ is H or methyl; and $R^5$ is H or F.

In some aspects, the present disclosure is directed to a crystalline form of (2S,3S,4R,5R)-2-[(1R)-1-(3,4-dichlorophenyl)-1-hydroxy-ethyl]-5-[(6Z)-6-methoxyimino-1H-purin-9-yl]tetrahydrofuran-3,4-diol (Example 92A).

A crystal form may be referred to herein as being characterized by graphical data "as shown in" or "as characterized by" a Figure. Such data include, for example, powder X-ray diffractograms (XRPD), Differential Scanning Calorimetry (DSC) thermograms, thermogravimetric analysis (TGA) profiles, and differential vapor sorption profiles (DVS). As is well-known in the art, the graphical data potentially provides additional technical information to further define the respective solid state form which can not necessarily be described by reference to numerical values or peak positions alone. Thus, the term "substantially as shown in" when referring to graphical data in a Figure herein means a pattern that is not necessarily identical to those depicted herein, but that falls within the limits of experimental error or deviations, when considered by one of ordinary skill in the art. The skilled person would readily be able to compare the graphical data in the Figures herein with graphical data generated for an unknown crystal form and confirm whether the two sets of graphical data are characterizing the same crystal form or two different crystal forms.

A solid, crystalline form may be referred to herein as "polymorphically pure" or as "substantially free of any other form." As used herein in this context, the expression "substantially free of any other forms" will be understood to mean that the solid form contains about 20% or less, about 10% or less, about 5% or less, about 2% or less, about 1% or less, or 0% of any other forms of the subject compound as measured, for example, by XRPD. Thus, a solid form of (2S,3S,4R,5R)-2-[(1R)-1-(3,4-dichlorophenyl)-1-hydroxyethyl]-5-[(6Z)-6-methoxyimino-1H-purin-9-yl]tetrahydrofuran-3,4-diol described herein as substantially free of any other solid forms would be understood to contain greater than about 80% (w/w), greater than about 90% (w/w), greater than about 95% (w/w), greater than about 98% (w/w), greater than about 99% (w/w), or about 100% of the subject solid form of (2S,3S,4R,5R)-2-[(1R)-1-(3,4-dichlorophenyl)-1-hydroxy-ethyl]-5-[(6Z)-6-methoxyimino-1H-purin-9-yl]tetrahydrofuran-3,4-diol. Accordingly, in some embodiments of the disclosure, the described solid form of (2S,3S,4R,5R)-2-[(1R)-1-(3,4-dichlorophenyl)-1-hydroxyethyl]-5-[(6Z)-6-methoxyimino-1H-purin-9-yl]tetrahydrofuran-3,4-diol may contain from about 1% to about 20% (w/w), from about 5% to about 20% (w/w), or from about 5% to about 10% (w/w) of one or more other solid forms of (2S,3S,4R,5R)-2-[(1R)-1-(3,4-dichlorophenyl)-1-hydroxyethyl]-5-[(6Z)-6-methoxyimino-1H-purin-9-yl]tetrahydrofuran-3,4-diol.

Figure 2:
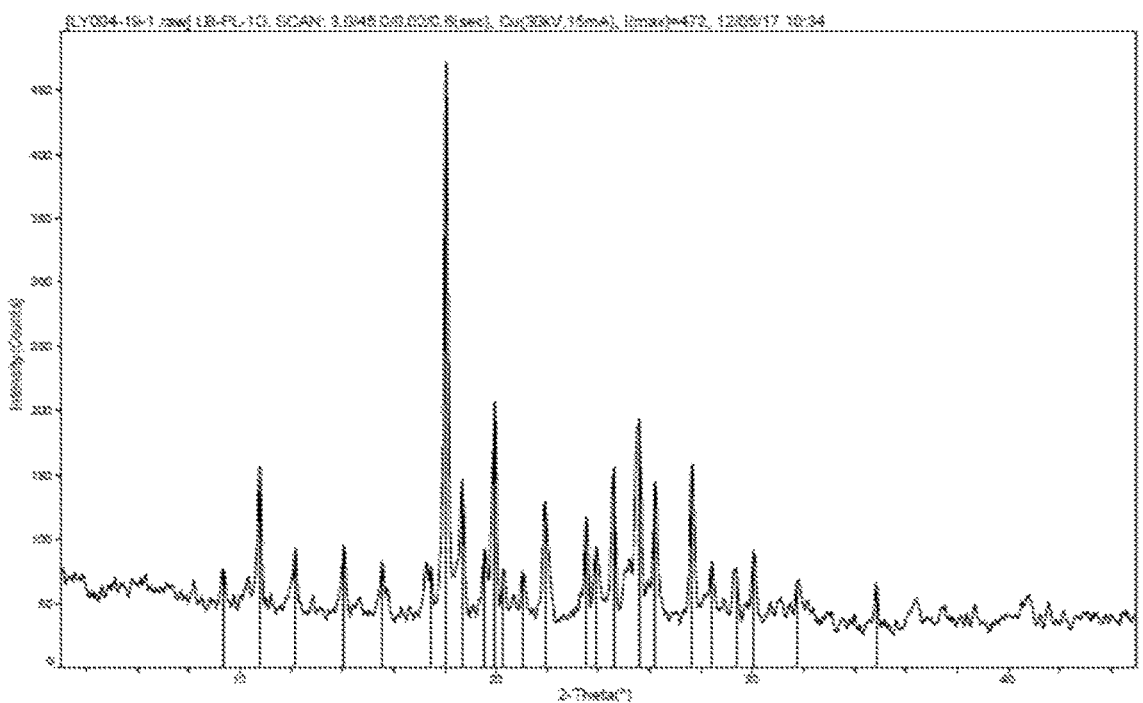
FIG. 2 is an XRPD scan of Example 92A.

In some aspects of the present disclosure, the solid form of (2S,3S,4R,5R)-2-[(1R)-1-(3,4-dichlorophenyl)-1-hydroxy-ethyl]-5-[(6Z)-6-methoxyimino-1H-purin-9-yl]tetrahydrofuran-3,4-diol is crystalline Form I of (2S,3S,4R,5R)-2-[(1R)-1-(3,4-dichlorophenyl)-1-hydroxy-ethyl]-5-[(6Z)-6-methoxyimino-1H-purin-9-yl]tetrahydrofuran-3,4-diol. In other aspects, the solid form is crystalline Form I of (2S, 3S,4R,5R)-2-[(1R)-1-(3,4-dichlorophenyl)-1-hydroxy-ethyl]-5-[(6Z)-6-methoxyimino-1H-purin-9-yl]tetrahydrofuran-3,4-diol substantially free of any other solid form of (2S,3S,4R,5R)-2-[(1R)-1-(3,4-dichlorophenyl)-1-hydroxy-ethyl]-5-[(6Z)-6-methoxyimino-1H-purin-9-yl]tetrahydrofuran-3,4-diol. Crystalline Form I of (2S,3S,4R,5R)-2-[(1R)-1-(3,4-dichlorophenyl)-1-hydroxy-ethyl]-5-[(6Z)-6-methoxyimino-1H-purin-9-yl]tetrahydrofuran-3,4-diol exhibits an XRPD substantially as shown in FIG. 2.

The XRPD of crystalline Form I of (2S,3S,4R,5R)-2-[(1R)-1-(3,4-dichlorophenyl)-1-hydroxy-ethyl]-5-[(6Z)-6-methoxyimino-1H-purin-9-yl]tetrahydrofuran-3,4-diol shown in FIG. 2 comprises reflection angles (degrees 2-theta±0.2 degrees 2-theta), line spacings (d Values), and relative intensities as shown in Table 6 (below).

In some embodiments of the present disclosure, crystalline Form I of (2S,3S,4R,5R)-2-[(1R)-1-(3,4-dichlorophenyl)-1-hydroxy-ethyl]-5-[(6Z)-6-methoxyimino-1H-purin-9-yl]tetrahydrofuran-3,4-diol is characterized by an XRPD pattern comprising a peak at one of the angles listed in Table 6. In other aspects, crystalline Form I of (2S,3S,4R,5R)-2-[(1R)-1-(3,4-dichlorophenyl)-1-hydroxy-ethyl]-5-[(6Z)-6-methoxyimino-1H-purin-9-yl]tetrahydrofuran-3,4-diol is characterized by an XRPD pattern comprising more than one peak at one of the angles listed in Table 6 below. In other aspects, crystalline Form I of (2S,3S,4R,5R)-2-[(1R)-1-(3,4-dichlorophenyl)-1-hydroxy-ethyl]-5-[(6Z)-6-methoxy-imino-1H-purin-9-yl]tetrahydrofuran-3,4-diol is characterized by an XRPD pattern comprising two peaks selected from the angles listed in Table 6 below. In other aspects, crystalline Form I of (2S,3S,4R,5R)-2-[(1R)-1-(3,4-dichlorophenyl)-1-hydroxy-ethyl]-5-[(6Z)-6-methoxyimino-1H-purin-9-yl]tetrahydrofuran-3,4-diol is characterized by an XRPD pattern comprising three peaks selected from the angles listed in Table 6 below. In other aspects, crystalline Form I of (2S,3S,4R,5R)-2-[(1R)-1-(3,4-dichlorophenyl)-1-hydroxy-ethyl]-5-[(6Z)-6-methoxyimino-1H-purin-9-yl]tetrahydrofuran-3,4-diol is characterized by an XRPD pattern comprising four peaks selected from the angles listed in Table 6 below. In other aspects, crystalline Form I of (2S,3S,4R,5R)-2-[(1R)-1-(3,4-dichlorophenyl)-1-hydroxy-ethyl]-5-[(6Z)-6-methoxyimino-1H-purin-9-yl]tetrahydrofuran-3,4-diol is characterized by an XRPD pattern comprising five peaks selected from the angles listed in Table 6 below. In other aspects, crystalline Form I of (2S,3S,4R,5R)-2-[(1R)-1-(3,4-dichlorophenyl)-1-hydroxy-ethyl]-5-[(6Z)-6-methoxyimino-1H-purin-9-yl]tetrahydrofuran-3,4-diol is characterized by an XRPD pattern comprising six peaks selected from the angles listed in Table 6 below. In other aspects, crystalline Form I of (2S,3S,4R,5R)-2-[(1R)-1-(3,4-dichlorophenyl)-1-hydroxy-ethyl]-5-[(6Z)-6-methoxyimino-1H-purin-9-yl]tetrahydrofuran-3,4-diol is characterized by an XRPD pattern comprising seven peaks selected from the angles listed in Table 6 below. In other aspects, crystalline Form I of (2S,3S,4R,5R)-2-[(1R)-1-(3,4-dichlorophenyl)-1-hydroxy-ethyl]-5-[(6Z)-6-methoxy-imino-1H-purin-9-yl]tetrahydrofuran-3,4-diol is characterized by an XRPD pattern comprising eight peaks selected from the angles listed in Table 6 below. In other aspects, crystalline Form I of (2S,3S,4R,5R)-2-[(1R)-1-(3,4-dichlorophenyl)-1-hydroxy-ethyl]-5-[(6Z)-6-methoxyimino-1H-purin-9-yl]tetrahydrofuran-3,4-diol is characterized by an XRPD pattern comprising nine peaks selected from the angles listed in Table 6 below. In other aspects, crystalline Form I of (2S,3S,4R,5R)-2-[(1R)-1-(3,4-dichlorophenyl)-1-hydroxy-ethyl]-5-[(6Z)-6-methoxyimino-1H-purin-9-yl]tetrahydrofuran-3,4-diol is characterized by an XRPD pattern comprising ten peaks selected from the angles listed in Table 6 below. In other aspects, crystalline Form I of (2S,3S,4R,5R)-2-[(1R)-1-(3,4-dichlorophenyl)-1-hydroxy-ethyl]-5-[(6Z)-6-methoxyimino-1H-purin-9-yl]tetrahydrofuran-3,4-diol is characterized by an XRPD pattern comprising more than ten peaks selected from the angles listed in Table 6 below.

Figure 3:
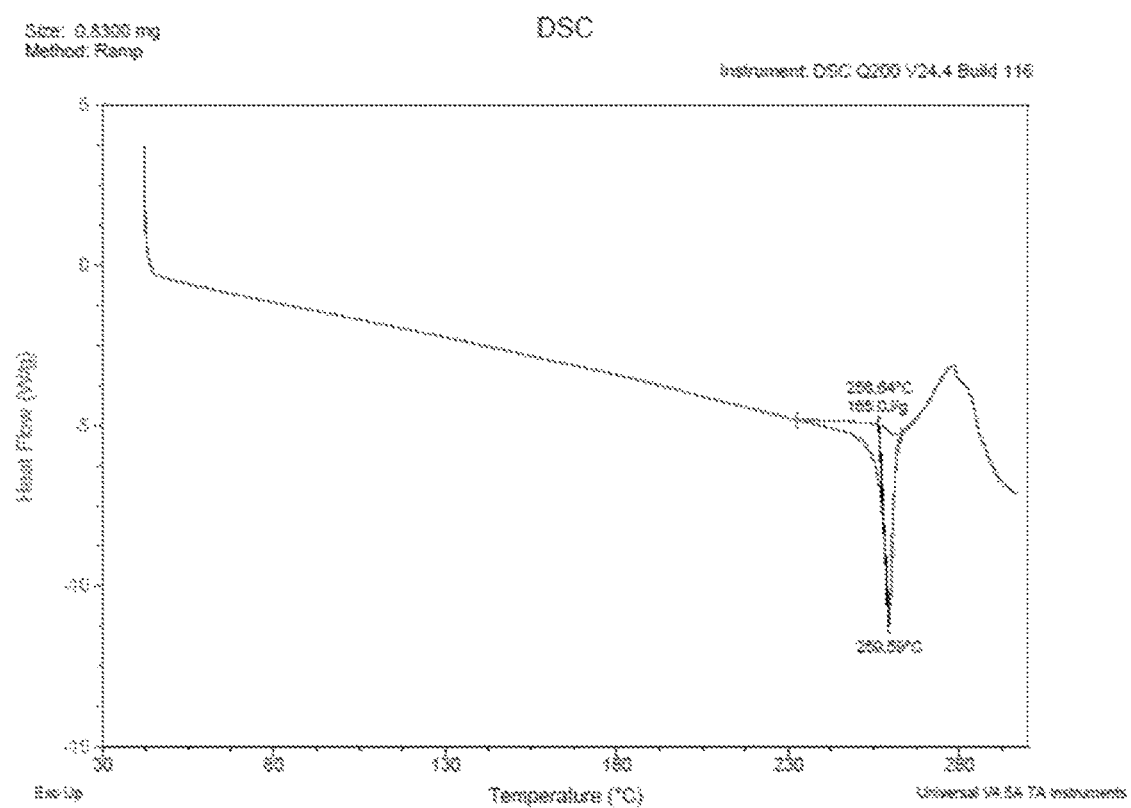
FIG. 3 is a Differential Scanning Calorimetry ("DSC") profile of Example 92A.

Crystalline Form I of (2S,3S,4R,5R)-2-[(1R)-1-(3,4-dichlorophenyl)-1-hydroxy-ethyl]-5-[(6Z)-6-methoxyimino-1H-purin-9-yl]tetrahydrofuran-3,4-diol can be characterized by a DSC thermogram substantially as shown in FIG. 3. As FIG. 3 shows, crystalline Form I of (2S,3S,4R,5R)-2-[(1R)-1-(3,4-dichlorophenyl)-1-hydroxy-ethyl]-5-[(6Z)-6-methoxyimino-1H-purin-9-yl]tetrahydrofuran-3,4-diol produced an endothermic peak at about 259.59° C. In some embodiments of the present disclosure, crystalline Form I of (2S,3S,4R,5R)-2-[(1R)-1-(3,4-dichlorophenyl)-1-hydroxy-ethyl]-5-[(6Z)-6-methoxyimino-1H-purin-9-yl]tetrahydrofuran-3,4-diol is characterized by a DSC thermogram comprising an endothermic peak at about 259° C.

Figure 4:
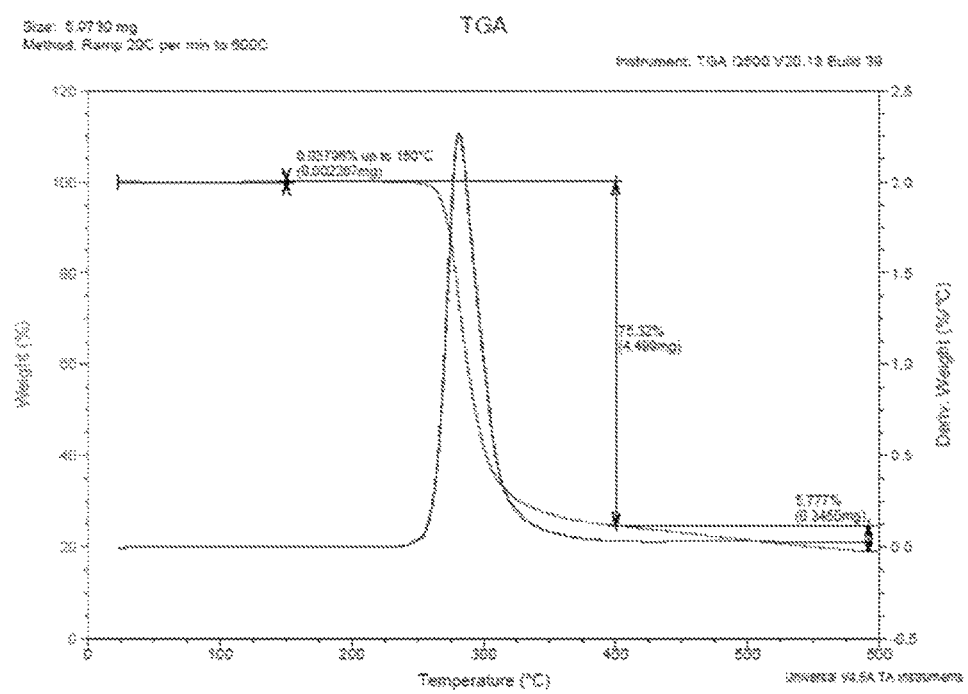
FIG. 4 is a thermogravimetric analysis ("TGA") scan of Example 92A.

Crystalline Form I of (2S,3S,4R,5R)-2-[(1R)-1-(3,4-dichlorophenyl)-1-hydroxy-ethyl]-5-[(6Z)-6-methoxyimino-1H-purin-9-yl]tetrahydrofuran-3,4-diol can be characterized by a TGA profile substantially as shown in FIG. 4.

Crystalline Form I of (2S,3S,4R,5R)-2-[(1R)-1-(3,4-dichlorophenyl)-1-hydroxy-ethyl]-5-[(6Z)-6-methoxyimino-1H-purin-9-yl]tetrahydrofuran-3,4-diol can be characterized by a DVS profile substantially as shown in FIG. 5.

In some embodiments of the present disclosure, crystalline Form I of (2S,3S,4R,5R)-2-[(1R)-1-(3,4-dichlorophenyl)-1-hydroxy-ethyl]-5-[(6Z)-6-methoxyimino-1H-purin-9-yl]tetrahydrofuran-3,4-diol is characterized by an XRPD pattern comprising peaks at three or more of the angles listed in Table 6 below, and a DSC thermogram comprising an endothermic peak at about 259° C.

The disclosure is also directed to compounds of Formula III or Formula IV. In some aspects, the disclosure is directed to compounds of Formula III:

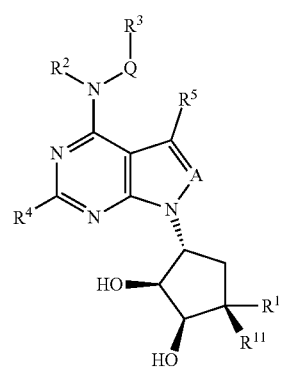

III

In other aspects, the disclosure is directed to compounds of Formula IV:

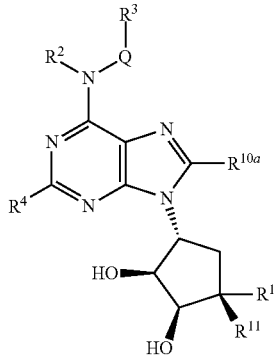

IV

According to the disclosure, A in Formula III is CH, CR$^{10}$, or N. In some aspects, A is N and the compounds of Formula III are of Formula IIIA:

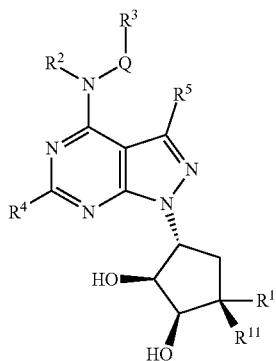

IIIA

In other aspects, A is CH and the compounds of Formula III are of Formula IIIB:

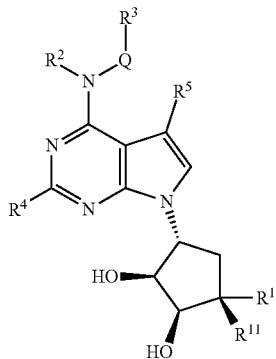

IIIB

In yet other aspects, A is CR$^{10}$ and the compounds of Formula III are of Formula IIIC:

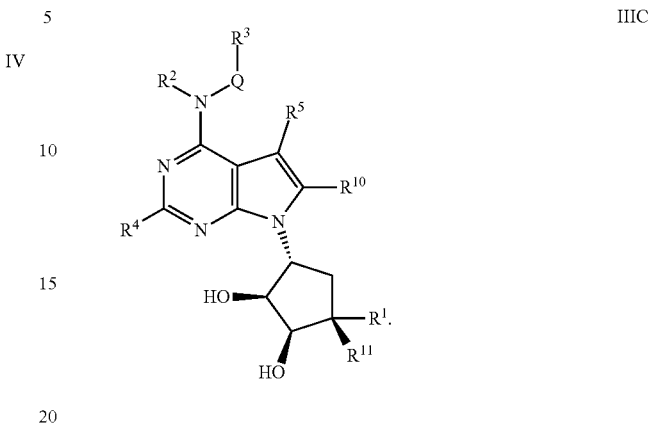

IIIC

According to the disclosure, Q in Formula III or Formula IV is NH, NR$^6$, or O. In some embodiments, Q is NH. In other embodiments, Q is O. In yet other embodiments, Q is NR$^6$.

According to the disclosure, R$^1$ in Formula III or Formula IV is —C$_0$-C$_6$alk-C$_3$-C$_6$cycloalkyl, —C$_0$-C$_6$alk-C$_3$-C$_6$halocycloalkyl, —C$_2$-C$_6$alkenyl, —C$_2$-C$_6$haloalkenyl, —C$_0$-C$_6$alk-C$_1$-C$_6$alkyl, —C$_0$-C$_6$alk-C$_1$-C$_6$haloalkyl, —C$_0$-C$_6$alk-C≡CH, —C$_0$-C$_6$alk-C≡C—C$_1$-C$_6$alkyl, —C$_0$-C$_6$alk-C≡C—C$_1$-C$_6$haloalkyl, —C$_0$-C$_6$alk-C≡C—C$_3$-C$_6$cycloalkyl, —C$_1$-C$_6$alk-aryl, —C$_1$-C$_6$alk-S—C$_1$-C$_6$alkyl, —C$_1$-C$_6$alk-S—C$_1$-C$_6$haloalkyl, —C$_1$-C$_6$alk-S—C$_3$-C$_6$cycloalkyl; —C$_1$-C$_6$alk-S—C$_3$-C$_6$halocycloalkyl; —C$_1$-C$_6$alk-O—C$_1$-C$_6$alkyl, —C$_1$-C$_6$alk-O—C$_3$-C$_6$cycloalkyl, —C$_1$-C$_6$alk-S—CH$_2$-aryl, —C$_1$-C$_6$alk-C(O)NH-aryl, —C$_0$-C$_6$alk-S-aryl, —C$_0$-C$_6$alk-S(O)aryl, —C$_0$-C$_6$alk-S(O)$_2$aryl, —C$_0$-C$_6$alk-Oaryl, —C$_0$-C$_6$alk-heteroaryl, —C$_1$-C$_6$alk-O-heteroaryl, —C$_1$-C$_6$alk-S-heteroaryl, or —C$_1$-C$_6$alk-NH-heteroaryl.

In some aspects, R$^1$ in Formula III or Formula IV is —C$_0$-C$_6$alk-C$_1$-C$_6$alkyl, —C$_0$-C$_6$alk-C$_1$-C$_6$haloalkyl, —C$_0$-C$_6$alk-C≡CH, —C$_0$-C$_6$alk-C≡C—C$_1$-C$_6$alkyl, —C$_0$-C$_6$alk-C≡C—C$_1$-C$_6$haloalkyl, —C$_0$-C$_6$alk-C≡C—C$_3$-C$_6$cycloalkyl, —C$_1$-C$_6$alk-aryl, —C$_0$-C$_6$alk-S-aryl, —C$_0$-C$_6$alk-S(O)aryl, —C$_0$-C$_6$alk-S(O)$_2$aryl, or —C$_0$-C$_6$alk-Oaryl.

In other aspects, R$^1$ in Formula III or Formula IV is —C$_0$-C$_6$alk-C$_3$-C$_6$cycloalkyl, for example, —C$_0$alk-C$_3$cycloalkyl, —C$_1$alk-C$_3$cycloalkyl, —C$_2$alk-C$_3$cycloalkyl, —C$_3$alk-C$_3$cycloalkyl, —C$_4$alk-C$_3$cycloalkyl, —C$_5$alk-C$_3$cycloalkyl, —C$_6$alk-C$_3$cycloalkyl, —C$_0$alk-C$_4$cycloalkyl, —C$_1$alk-C$_4$cycloalkyl, —C$_2$alk-C$_4$cycloalkyl, —C$_3$alk-C$_4$cycloalkyl, —C$_4$alk-C$_4$cycloalkyl, —C$_5$alk-C$_4$cycloalkyl, —C$_6$alk-C$_4$cycloalkyl, —C$_0$alk-C$_5$cycloalkyl, —C$_1$alk-C$_5$cycloalkyl, —C$_2$alk-C$_5$cycloalkyl, —C$_3$alk-C$_5$cycloalkyl, —C$_4$alk-C$_5$cycloalkyl, —C$_5$alk-C$_5$cycloalkyl, —C$_6$alk-C$_5$cycloalkyl, —C$_0$alk-C$_6$cycloalkyl, —C$_1$alk-C$_6$cycloalkyl, —C$_2$alk-C$_6$cycloalkyl, —C$_3$alk-C$_6$cycloalkyl, —C$_4$alk-C$_6$cycloalkyl, —C$_5$alk-C$_6$cycloalkyl, or —C$_6$alk-C$_6$cycloalkyl. Thus, in some aspects, R$^1$ is —CH$_2$-cyclopropyl.

In some aspects, R$^1$ in Formula III or Formula IV is —C$_0$-C$_6$alk-C$_3$-C$_6$halocycloalkyl, for example, —C$_0$alk-C$_3$halocycloalkyl, —C$_1$alk-C$_3$halocycloalkyl, —C$_2$alk-C$_3$halocycloalkyl, —C$_3$alk-C$_3$halocycloalkyl, —C$_4$alk- $C_3$halocycloalkyl, —$C_5$alk-$C_3$halocycloalkyl, —$C_6$alk-$C_3$halocycloalkyl, —$C_0$alk-$C_4$halocycloalkyl, —$C_1$alk-$C_4$halocycloalkyl, —$C_2$alk-$C_4$halocycloalkyl, —$C_3$alk-$C_4$halocycloalkyl, —$C_4$alk-$C_4$halocycloalkyl, —$C_5$alk-$C_4$halocycloalkyl, —$C_6$alk-$C_4$halocycloalkyl, —$C_0$alk-$C_5$halocycloalkyl, —$C_1$alk-$C_5$halocycloalkyl, —$C_2$alk-$C_5$halocycloalkyl, —$C_3$alk-$C_5$halocycloalkyl, —$C_4$alk-$C_5$halocycloalkyl, —$C_5$alk-$C_5$halocycloalkyl, —$C_6$alk-$C_5$halocycloalkyl, —$C_0$alk-$C_6$halocycloalkyl, —$C_1$alk-$C_6$halocycloalkyl, —$C_2$alk-$C_6$halocycloalkyl, —$C_3$alk-$C_6$halocycloalkyl, —$C_4$alk-$C_6$halocycloalkyl, —$C_5$alk-$C_6$halocycloalkyl, or —$C_6$alk-$C_6$halocycloalkyl.

In some aspects, $R^1$ in Formula III or Formula IV is —$C_2$-$C_6$alkenyl, for example, vinyl, allyl, and the like.

In some aspects, $R^1$ in Formula III or Formula IV is —$C_2$-$C_6$haloalkenyl, for example, —C(F)=CHMe, —C(F)=CH$_2$, and the like.

In some aspects, $R^1$ in Formula III or Formula IV is —$C_0$-$C_6$alk-$C_1$-$C_6$alkyl, for example, —$C_0$alk-$C_1$alkyl, —$C_1$alk-$C_1$alkyl, —$C_2$alk-$C_1$alkyl, —$C_6$alk-$C_1$alkyl, —$C_4$alk-$C_1$alkyl, —$C_5$alk-$C_1$alkyl, —$C_6$alk-$C_1$alkyl, —$C_0$alk-$C_2$alkyl, —$C_1$alk-$C_2$alkyl, —$C_2$alk-$C_2$alkyl, —$C_3$alk-$C_2$alkyl, —$C_4$alk-$C_2$alkyl, —$C_5$alk-$C_2$alkyl, —$C_6$alk-$C_2$alkyl, —$C_0$alk-$C_3$alkyl, —$C_1$alk-$C_3$alkyl, —$C_2$alk-$C_3$alkyl, —$C_3$alk-$C_3$alkyl, —$C_4$alk-$C_3$alkyl, —$C_5$alk-$C_3$alkyl, —$C_6$alk-$C_3$alkyl, —$C_0$alk-$C_4$alkyl, —$C_1$alk-$C_4$alkyl, —$C_2$alk-$C_4$alkyl, —$C_3$alk-$C_4$alkyl, —$C_4$alk-$C_4$alkyl, —$C_5$alk-$C_4$alkyl, —$C_6$alk-$C_4$alkyl, —$C_0$alk-$C_5$alkyl, —$C_1$alk-$C_5$alkyl, —$C_2$alk-$C_5$alkyl, —$C_3$alk-$C_5$alkyl, —$C_4$alk-$C_5$alkyl, —$C_5$alk-$C_5$alkyl, —$C_6$alk-$C_5$alkyl, —$C_0$alk-$C_6$alkyl, —$C_1$alk-$C_6$alkyl, —$C_2$alk-$C_6$alkyl, —$C_3$alk-$C_6$alkyl, —$C_4$alk-$C_6$alkyl, —$C_6$alk-$C_6$alkyl, —$C_6$alk-$C_6$alkyl, methyl, ethyl, propyl, isopropyl, butyl, isobutyl, s-butyl, t-butyl, pentyl, —CH(OH)—$C_1$-$C_6$alkyl, —CH(F)—$C_1$-$C_6$alkyl, —CH(NH$_2$)—$C_1$-$C_6$alkyl, —CH(Me)-$C_1$-$C_6$alkyl, —C(Me)(OH)—$C_1$-$C_6$alkyl, and the like.

In other aspects, $R^1$ in Formula III or Formula IV is —$C_0$-$C_6$alk-$C_1$-$C_6$haloalkyl, for example, —$C_0$alk-$C_1$haloalkyl, —$C_1$alk-$C_1$haloalkyl, —$C_2$alk-$C_1$haloalkyl, —$C_6$alk-$C_1$haloalkyl, —$C_4$alk-$C_1$haloalkyl, —$C_5$alk-$C_1$haloalkyl, —$C_0$alk-$C_1$haloalkyl, —$C_0$alk-$C_2$haloalkyl, —$C_1$alk-$C_2$haloalkyl, —$C_2$alk-$C_2$haloalkyl, —$C_3$alk-$C_2$haloalkyl, —$C_4$alk-$C_2$haloalkyl, —$C_5$alk-$C_2$haloalkyl, —$C_6$alk-$C_2$haloalkyl, —$C_0$alk-$C_3$haloalkyl, —$C_1$alk-$C_3$haloalkyl, —$C_2$alk-$C_3$haloalkyl, —$C_3$alk-$C_3$haloalkyl, —$C_4$alk-$C_3$haloalkyl, —$C_5$alk-$C_3$haloalkyl, —$C_6$alk-$C_3$haloalkyl, —$C_0$alk-$C_4$haloalkyl, —$C_1$alk-$C_4$haloalkyl, —$C_2$alk-$C_4$haloalkyl, —$C_3$alk-$C_4$haloalkyl, —$C_4$alk-$C_4$haloalkyl, —$C_5$alk-$C_4$haloalkyl, —$C_6$alk-$C_4$haloalkyl, —$C_0$alk-$C_5$haloalkyl, —$C_1$alk-$C_5$haloalkyl, —$C_2$alk-$C_5$haloalkyl, —$C_3$alk-$C_5$haloalkyl, —$C_4$alk-$C_5$haloalkyl, —$C_5$alk-$C_5$haloalkyl, —$C_6$alk-$C_5$haloalkyl, —$C_0$alk-$C_6$haloalkyl, —$C_1$alk-$C_6$haloalkyl, —$C_2$alk-$C_6$haloalkyl, —$C_3$alk-$C_6$haloalkyl, —$C_4$alk-$C_6$haloalkyl, —$C_5$alk-$C_6$haloalkyl, —$C_6$alk-$C_6$haloalkyl, fluoromethyl, fluoroethyl, fluoropropyl, fluorobutyl, fluoropentyl, chloromethyl, chloroethyl, chloropropyl, chlorobutyl, chloropentyl, bromomethyl, bromoethyl, bromopropyl, bromobutyl, bromopentyl, iodomethyl, iodoethyl, iodopropyl, iodobutyl, iodopentyl, —CH(OH)—$C_1$-$C_6$ haloalkyl, —CH(F)—$C_1$-$C_6$ haloalkyl, —CH(NH$_2$)—$C_1$-$C_6$ haloalkyl, —CH(Me)-$C_1$-$C_6$ haloalkyl, —C(Me)(OH)—$C_1$-$C_6$ haloalkyl, and the like.

In some aspects, $R^1$ in Formula III or Formula IV is —$C_0$-$C_6$alk-C≡CH, for example, —$C_0$alk-C≡CH, —$C_1$alk-C≡CH, —$C_2$alk-C≡CH, —$C_3$alk-C≡CH, —$C_4$alk-C≡CH, —$C_5$alk-C≡CH, —$C_6$alk-C≡CH, ethynyl, propargyl, —CH(OH)—C≡CH, —CH(F)—C≡CH, —CH(NH$_2$)—C≡CH, —CH(Me)-C≡CH, —C(Me)(OH)—C≡CH, and the like.

In some aspects, $R^1$ in Formula III or Formula IV is —$C_0$-$C_6$alk-C≡C—$C_1$-$C_6$alkyl, for example, —$C_0$alk-C≡C—$C_1$alkyl, —$C_1$alk-C≡C—$C_1$alkyl, —$C_2$alk-C≡C—$C_1$alkyl, —$C_3$alk-C≡C—$C_1$alkyl, —$C_4$alk-C≡C—$C_1$alkyl, —$C_5$alk-C≡C—$C_1$alkyl, —$C_6$alk-C≡C—$C_1$alkyl, —$C_0$alk-C≡C—$C_2$alkyl, —$C_1$alk-C≡C—$C_2$alkyl, —$C_2$alk-C≡C—$C_2$alkyl, —$C_3$alk-C≡C—$C_2$alkyl, —$C_4$alk-C≡C—$C_2$alkyl, —$C_5$alk-C≡C—$C_2$alkyl, —$C_6$alk-C≡C—$C_2$alkyl, —$C_0$alk-C≡C—$C_3$alkyl, —$C_1$alk-C≡C—$C_3$alkyl, —$C_2$alk-C≡C—$C_3$alkyl, —$C_3$alk-C≡C—$C_3$alkyl, —$C_4$alk-C≡C—$C_3$alkyl, —$C_5$alk-C≡C—$C_3$alkyl, —$C_6$alk-C≡C—$C_3$alkyl, —$C_0$alk-C≡C—$C_4$alkyl, —$C_1$alk-C≡C—$C_4$alkyl, —$C_2$alk-C≡C—$C_4$alkyl, —$C_3$alk-C≡C—$C_4$alkyl, —$C_4$alk-C≡C—$C_4$alkyl, —$C_5$alk-C≡C—$C_4$alkyl, —$C_6$alk-C≡C—$C_4$alkyl, —$C_0$alk-C≡C—$C_5$alkyl, —$C_1$alk-C≡C—$C_5$alkyl, —$C_2$alk-C≡C—$C_5$alkyl, —$C_3$alk-C≡C—$C_5$alkyl, —$C_4$alk-C≡C—$C_5$alkyl, —$C_5$alk-C≡C—$C_5$alkyl, —$C_6$alk-C≡C—$C_5$alkyl, —$C_0$alk-C≡C—$C_6$alkyl, —$C_1$alk-C≡C—$C_6$alkyl, —$C_2$alk-C≡C—$C_6$alkyl, —$C_3$alk-C≡C—$C_6$alkyl, —$C_4$alk-C≡C—$C_6$alkyl, —$C_5$alk-C≡C—$C_6$alkyl, —$C_0$alk-C≡C—$C_6$alkyl, propynyl, butynyl, —CH(OH)—C≡C—$C_1$-$C_6$alkyl, —CH(F)—C≡C—$C_1$-$C_6$alkyl, —CH(NH$_2$)—C≡C—$C_1$-$C_6$alkyl, —CH(Me)-C≡C—$C_1$-$C_6$alkyl, —C(Me)(OH)—C≡C—$C_1$-$C_6$alkyl, and the like. In some embodiments wherein —$C_0$-$C_6$alk-C≡C—$C_1$-$C_6$alkyl is —$C_0$-$C_6$alk-C≡C—CH$_3$, $R^1$ is —CH(OH)—C≡C—CH$_3$, —CH(F)—C≡C—CH$_3$, —CH(NH$_2$)—C≡C—CH$_3$, —CH(Me)-C≡C—CH$_3$, or —C(Me)(OH)—C≡C—CH$_3$. Thus, in some embodiments, $R^1$ is —CH(OH)—C≡C—CH$_3$.

In some aspects, $R^1$ in Formula III or Formula IV is —$C_0$-$C_6$alk-C≡C—$C_1$-$C_6$haloalkyl, for example, —$C_0$alk-C≡C—$C_1$haloalkyl, —$C_1$alk-C≡C—$C_1$haloalkyl, —$C_2$alk-C≡C—$C_1$haloalkyl, —$C_3$alk-C≡C—$C_1$haloalkyl, —$C_4$alk-C≡C—$C_1$haloalkyl, —$C_5$alk-C≡C—$C_1$haloalkyl, —$C_6$alk-C≡C—$C_1$haloalkyl, —$C_0$alk-C≡C—$C_2$haloalkyl, —$C_1$alk-C≡C—$C_2$haloalkyl, —$C_2$alk-C≡C—$C_2$haloalkyl, —$C_3$alk-C≡C—$C_2$haloalkyl, —$C_4$alk-C≡C—$C_2$haloalkyl, —$C_5$alk-C≡C—$C_2$haloalkyl, —$C_6$alk-C≡C—$C_2$haloalkyl, —$C_0$alk-C≡C—$C_3$haloalkyl, —$C_1$alk-C≡C—$C_3$haloalkyl, —$C_2$alk-C≡C—$C_3$haloalkyl, —$C_3$alk-C≡C—$C_3$haloalkyl, —$C_4$alk-C≡C—$C_3$haloalkyl, —$C_5$alk-C≡C—$C_3$haloalkyl, —$C_6$alk-C≡C—$C_3$haloalkyl, —$C_0$alk-C≡C—$C_4$haloalkyl, —$C_1$alk-C≡C—$C_4$haloalkyl, —$C_2$alk-C≡C—$C_4$haloalkyl, —$C_3$alk-C≡C—$C_4$haloalkyl, —$C_4$alk-C≡C—$C_4$haloalkyl, —$C_5$alk-C≡C—$C_4$haloalkyl, —$C_6$alk-C≡C—$C_4$haloalkyl, —$C_0$alk-C≡C—$C_5$haloalkyl, —$C_1$alk-C≡C—$C_5$haloalkyl, —$C_2$alk-C≡C—$C_5$haloalkyl, —$C_3$alk-C≡C—$C_5$haloalkyl, —$C_4$alk-C≡C—$C_5$haloalkyl, —$C_5$alk-C≡C—$C_5$haloalkyl, —$C_6$alk-C≡C—$C_5$haloalkyl, —$C_0$alk-C≡C—$C_6$haloalkyl, —$C_1$alk-C≡C—$C_6$haloalkyl, —$C_2$alk-C≡C—$C_6$haloalkyl, —$C_3$alk-C≡C—$C_6$haloalkyl, —$C_4$alk-C≡C—$C_6$haloalkyl, —$C_5$alk-C≡C—$C_6$haloalkyl, —$C_6$alk-C≡C—$C_6$haloalkyl, —CH(OH)—C≡C—$C_1$-$C_6$haloalkyl, —CH(F)—C≡C—$C_1$-$C_6$haloalkyl, —CH(NH$_2$)—C≡C—$C_1$-$C_6$haloalkyl, —CH(Me)-C≡C—$C_1$-$C_6$haloalkyl, —C(Me)(OH)—C≡C—$C_1$-$C_6$haloalkyl, and the like. In some embodiments wherein —$C_0$-$C_6$alk-C≡C—$C_1$-$C_6$haloalkyl is —$C_0$-$C_6$alk-C≡C—CF$_3$, $R^1$ is —CH(OH)—C≡C—CF$_3$, —CH(F)—C≡C—CF$_3$, —CH(NH$_2$)—C≡C—CF$_3$, —CH(Me)-C≡C—CF$_3$, —C(Me)(OH)—C≡C—CF$_3$, and the like. Thus, in some embodiments, $R^1$ is —CH(OH)—C≡C—CF$_3$.

In some aspects, $R^1$ in Formula III or Formula IV is —$C_0$-$C_6$alk-C≡C—$C_3$-$C_6$cycloalkyl, for example, —$C_0$alk-C≡C—$C_3$cycloalkyl, —$C_0$alk-C≡C—$C_4$cycloalkyl, —$C_0$alk-C≡C—$C_5$cycloalkyl, —$C_0$alk-C≡C—$C_6$cycloalkyl, —$C_1$alk-C≡C—$C_3$cycloalkyl, —$C_1$alk-C≡C—$C_4$cycloalkyl, —$C_1$alk-C≡C—$C_5$-cycloalkyl, —$C_1$alk-C≡C—$C_6$cycloalkyl, —$C_2$alk-C≡C—$C_3$cycloalkyl, —$C_2$alk-C≡C—$C_4$cycloalkyl, —$C_2$alk-C≡C—$C_5$cycloalkyl, —$C_2$alk-C≡C—$C_6$cycloalkyl, —$C_3$alk-C≡C—$C_3$cycloalkyl, —$C_3$alk-C≡C—$C_4$cycloalkyl, —$C_3$alk-C≡C—$C_5$cycloalkyl, —$C_3$alk-C≡C—$C_6$cycloalkyl, —$C_4$alk-C≡C—$C_3$cycloalkyl, —$C_4$alk-C≡C—$C_4$cycloalkyl, —$C_4$alk-C≡C—$C_5$cycloalkyl, —$C_4$alk-C≡C—$C_6$cycloalkyl, —$C_5$alk-C≡C—$C_3$cycloalkyl, —$C_5$alk-C≡C—$C_4$cycloalkyl, —$C_5$alk-C≡C—$C_5$cycloalkyl, —$C_5$alk-C≡C—$C_6$cycloalkyl, —$C_6$alk-C≡C—$C_3$cycloalkyl, —$C_6$alk-C≡C—$C_4$cycloalkyl, —$C_6$alk-C≡C—$C_5$cycloalkyl, —$C_6$alk-C≡C—$C_6$cycloalkyl, —CH(OH)—C≡C—$C_3$-$C_6$cycloalkyl, —CH(F)—C≡C—$C_3$-$C_6$cycloalkyl, —CH($NH_2$)—C≡C—$C_3$-$C_6$cycloalkyl, —CH(Me)-C≡C—$C_3$-$C_6$cycloalkyl, or —C(Me)(OH)—C≡C—$C_3$-$C_6$cycloalkyl. In some embodiments wherein —$C_0$-$C_6$alk-C≡C—$C_3$-$C_6$cycloalkyl is —$C_0$-$C_6$alk-C≡C-cyclopropyl, $R^1$ is —CH(OH)—C≡C-cyclopropyl, —CH(F)—C≡C-cyclopropyl, —CH($NH_2$)—C≡C-cyclopropyl, —CH(Me)-C≡C-cyclopropyl, —C(Me)(OH)—C≡C-cyclopropyl, and the like. Thus, in some embodiments, $R^1$ is —CH(OH)—C≡C-cyclopropyl.

In some aspects, $R^1$ in Formula III or Formula IV is —$C_1$-$C_6$alk-aryl, for example, —$C_1$alk-aryl, —$C_2$alk-aryl, —$C_3$alk-aryl, —$C_4$alk-aryl, —$C_5$alk-aryl, —$C_0$alk-aryl, —$CH_2$aryl, —CH(OH)-aryl, —CH(F)-aryl, —CH($NH_2$)-aryl, —CH(Me)-aryl, —C(Me)(OH)-aryl, and the like. In some embodiments wherein $R^1$ is —$C_1$-$C_6$alk-aryl, the -aryl is -4-chlorophenyl, -3,4-dichlorophenyl, -3,4-difluorophenyl, -3-fluoro-4-chlorophenyl, or -3-chloro-4-fluorophenyl. Thus in some embodiments, $R^1$ is —$CH_2$-difluorophenyl, —$CH_2$-3,4-difluorophenyl, —$CH_2$-4-chlorophenyl, —$CH_2$-3-chloro-4-fluorophenyl, —$CH_2$-4-chloro-3-fluorophenyl, —$CH_2$-dichlorophenyl, —$CH_2$-3,4-dichlorophenyl, —CH(OH)-4-chlorophenyl, —CH(OH)-3,4-dichlorophenyl, —CH(OH)-3,4-difluorophenyl, —CH(OH)-3-fluoro-4-chlorophenyl, —CH(OH)-3-chloro-4-fluorophenyl, —CH(F)-4-chlorophenyl, —CH(F)-3,4-dichlorophenyl, —CH(F)-3,4-difluorophenyl, —CH(F)-3-fluoro-4-chlorophenyl, —CH(F)-3-chloro-4-fluorophenyl, —CH($NH_2$)-4-chlorophenyl, —CH($NH_2$)-3,4-dichlorophenyl, —CH($NH_2$)-3,4-difluorophenyl, —CH($NH_2$)-3-fluoro-4-chlorophenyl, —CH($NH_2$)-3-chloro-4-fluorophenyl, —CH(Me)-4-chlorophenyl, —CH(Me)-3,4-dichlorophenyl, —CH(Me)-3,4-difluorophenyl, —CH(Me)-3-fluoro-4-chlorophenyl, —CH(Me)-3-chloro-4-fluorophenyl, —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, or —C(Me)(OH)-3-chloro-4-fluorophenyl.

In some aspects, $R^1$ in Formula III or Formula IV is —$C_1$-$C_6$alk-S—$C_1$-$C_6$alkyl, for example —$C_1$alk-S—$C_1$alkyl, —$C_2$alk-S—$C_1$alkyl, —$C_3$alk-S—$C_1$alkyl, —$C_4$alk-S—$C_1$alkyl, —$C_5$alk-S—$C_1$alkyl, —$C_6$alk-S—$C_1$alkyl, —$C_1$alk-S—$C_2$alkyl, —$C_2$alk-S—$C_2$alkyl, —$C_3$alk-S—$C_2$alkyl, —$C_4$alk-S—$C_2$alkyl, —$C_5$alk-S—$C_2$alkyl, —$C_6$alk-S—$C_2$alkyl, —$C_1$alk-S—$C_3$alkyl, —$C_2$alk-S—$C_3$alkyl, —$C_3$alk-S—$C_3$alkyl, —$C_4$alk-S—$C_3$alkyl, —$C_5$alk-S—$C_3$alkyl, —$C_6$alk-S—$C_3$alkyl, —$C_1$alk-S—$C_4$alkyl, —$C_2$alk-S—$C_4$alkyl, —$C_3$alk-S—$C_4$alkyl, —$C_4$alk-S—$C_4$alkyl, —$C_5$alk-S—$C_4$alkyl, —$C_6$alk-S—$C_4$alkyl, —$C_1$alk-S—$C_5$alkyl, —$C_2$alk-S—$C_5$alkyl, —$C_3$alk-S—$C_5$alkyl, —$C_4$alk-S—$C_5$alkyl, —$C_5$alk-S—$C_5$alkyl, —$C_6$alk-S—$C_5$alkyl, —$C_1$alk-S—$C_6$alkyl, —$C_2$alk-S—$C_6$alkyl, —$C_3$alk-S—$C_6$alkyl, —$C_4$alk-S—$C_6$alkyl, —$C_5$alk-S—$C_6$alkyl, —$C_6$alk-S—$C_6$alkyl, —$CH_2$S—$C_2$alkyl, —$CH_2$S—$C_3$alkyl, —$CH_2$S—$C_4$alkyl, —$CH_2$S—$C_5$alkyl, —$CH_2$S—$C_6$alkyl, and the like. Thus, in some aspects $R^1$ is —$CH_2$S—$C_1$alkyl. In some aspects, $R^1$ is —$CH_2$—S—$CH_3$.

In some aspects, $R^1$ in Formula III or Formula IV is —$C_1$-$C_6$alk-S—$C_1$-$C_6$haloalkyl, for example —$C_1$alk-S—$C_1$haloalkyl, —$C_2$alk-S—$C_1$haloalkyl, —$C_3$alk-S—$C_1$haloalkyl, —$C_4$alk-S—$C_1$haloalkyl, —$C_5$alk-S—$C_1$haloalkyl, —$C_6$alk-S—$C_1$haloalkyl, —$C_1$alk-S—$C_2$haloalkyl, —$C_2$alk-S—$C_2$haloalkyl, —$C_3$alk-S—$C_2$haloalkyl, —$C_4$alk-S—$C_2$haloalkyl, —$C_5$alk-S—$C_2$haloalkyl, —$C_6$alk-S—$C_2$haloalkyl, —$C_1$alk-S—$C_3$haloalkyl, —$C_2$alk-S—$C_3$haloalkyl, —$C_3$alk-S—$C_3$haloalkyl, —$C_4$alk-S—$C_3$haloalkyl, —$C_5$alk-S—$C_3$haloalkyl, —$C_6$alk-S—$C_3$haloalkyl, —$C_1$alk-S—$C_3$haloalkyl, —$C_2$alk-S—$C_4$haloalkyl, —$C_3$alk-S—$C_4$haloalkyl, —$C_4$alk-S—$C_4$haloalkyl, —$C_5$alk-S—$C_4$haloalkyl, —$C_6$alk-S—$C_4$haloalkyl, —$C_1$alk-S—$C_5$haloalkyl, —$C_2$alk-S—$C_5$haloalkyl, —$C_3$alk-S—$C_5$haloalkyl, —$C_4$alk-S—$C_5$haloalkyl, —$C_5$alk-S—$C_5$haloalkyl, —$C_1$alk-S—$C_5$haloalkyl, —$C_6$alk-S—$C_5$haloalkyl, —$C_2$alk-S—$C_6$haloalkyl, —$C_3$alk-S—$C_6$haloalkyl, —$C_4$alk-S—$C_6$haloalkyl, —$C_5$alk-S—$C_6$haloalkyl, —$C_6$alk-S—$C_6$haloalkyl, —$CH_2$S—$C_1$haloalkyl, —$CH_2$S—$C_2$haloalkyl, —$CH_2$S—$C_3$haloalkyl, —$CH_2$S—$C_4$haloalkyl, —$CH_2$S—$C_5$haloalkyl, and —$CH_2$S—$C_6$haloalkyl.

In some aspects, $R^1$ in Formula III or Formula IV is —$C_1$-$C_6$alk-S—$C_3$-$C_6$cycloalkyl, for example —$C_1$alk-S—$C_3$cycloalkyl, —$C_2$alk-S—$C_3$cycloalkyl, —$C_3$alk-S—$C_3$cycloalkyl, —$C_4$alk-S—$C_3$cycloalkyl, —$C_5$alk-S—$C_3$cycloalkyl, —$C_6$alk-S—$C_3$cycloalkyl, —$C_1$alk-S—$C_3$cycloalkyl, —$C_1$alk-S—$C_4$cycloalkyl, —$C_2$alk-S—$C_4$cycloalkyl, —$C_3$alk-S—$C_4$cycloalkyl, —$C_4$alk-S—$C_4$cycloalkyl, —$C_5$alk-S—$C_4$cycloalkyl, —$C_6$alk-S—$C_4$cycloalkyl, —$C_1$alk-S—$C_4$cycloalkyl, —$C_2$alk-S—$C_5$cycloalkyl, —$C_3$alk-S—$C_5$cycloalkyl, —$C_4$alk-S—$C_5$cycloalkyl, —$C_5$alk-S—$C_5$cycloalkyl, —$C_6$alk-S—$C_5$cycloalkyl, —$C_1$alk-S—$C_5$cycloalkyl, —$C_2$alk-S—$C_6$cycloalkyl, —$C_3$alk-S—$C_6$cycloalkyl, —$C_4$alk-S—$C_6$cycloalkyl, —$C_5$alk-S—$C_6$cycloalkyl, —$C_6$alk-S—$C_6$cycloalkyl, —$CH_2$S—$C_3$cycloalkyl, —$CH_2$S—$C_4$cycloalkyl, —$CH_2$S—$C_5$cycloalkyl, —$CH_2$S—$C_6$cycloalkyl, and the like.

In some aspects, $R^1$ in Formula III or Formula IV is —$C_1$-$C_6$alk-S—$C_3$-$C_6$halocycloalkyl, for example —$C_1$alk-S—$C_3$halocycloalkyl, —$C_2$alk-S—$C_3$halocycloalkyl, —$C_3$alk-S—$C_3$halocycloalkyl, —$C_4$alk-S—$C_3$halocycloalkyl, —$C_5$alk-S—$C_3$halocycloalkyl, —$C_6$alk-S—$C_3$halocycloalkyl, —$C_1$alk-S—$C_4$halocycloalkyl, —$C_2$alk-S—$C_4$halocycloalkyl, —$C_3$alk-S—$C_4$halocycloalkyl, —$C_4$alk-S—$C_4$halocycloalkyl, —$C_5$alk-S—$C_4$halocycloalkyl, —$C_6$alk-S—$C_4$halocycloalkyl, —$C_1$alk-S—$C_5$halocycloalkyl, —$C_2$alk-S—$C_5$halocycloalkyl, —$C_3$alk-S—$C_5$halocycloalkyl, —$C_4$alk-S—$C_5$halocycloalkyl, —$C_5$alk-S—$C_5$halocycloalkyl, —$C_6$alk-S—$C_5$halocycloalkyl, —$C_1$alk-S—$C_6$halocycloalkyl, —$C_2$alk-S—$C_6$halocycloalkyl, —$C_3$alk-S—$C_6$halocycloalkyl, —$C_4$alk-S—$C_6$halocycloalkyl, —$C_5$alk-S—$C_6$halocycloalkyl, —$C_6$alk-S—$C_6$halocycloalkyl, —$CH_2$S—$C_3$halocycloalkyl, —$CH_2$S—$C_4$halocycloalkyl, —$CH_2$S—$C_5$halocycloalkyl, —$CH_2$S—$C_6$halocycloalkyl, and the like.

In some aspects, $R^1$ in Formula III or Formula IV is —$C_1$-$C_6$alk-O—$C_1$-$C_6$alkyl, for example, —$C_1$alk-O—$C_1$alkyl, —$C_2$alk-O—$C_1$alkyl, —$C_3$alk-O—$C_1$alkyl, —C$_4$alk-O—C$_1$alkyl, —C$_5$alk-O—C$_1$alkyl, —C$_6$alk-O—C$_1$alkyl, —C$_1$alk-O—C$_2$alkyl, —C$_2$alk-O—C$_2$alkyl, —C$_3$alk-O—C$_2$alkyl, —C$_4$alk-O—C$_2$alkyl, —C$_5$alk-O—C$_2$alkyl, —C$_6$alk-O—C$_2$alkyl, —C$_1$alk-O—C$_3$alkyl, —C$_2$alk-O—C$_3$alkyl, —C$_3$alk-O—C$_3$alkyl, —C$_4$alk-O—C$_3$alkyl, —C$_5$alk-O—C$_3$alkyl, —C$_6$alk-O—C$_3$alkyl, —C$_1$alk-O—C$_4$alkyl, —C$_2$alk-O—C$_4$alkyl, —C$_3$alk-O—C$_4$alkyl, —C$_4$alk-O—C$_4$alkyl, —C$_5$alk-O—C$_4$alkyl, —C$_6$alk-O—C$_4$alkyl, —C$_1$alk-O—C$_5$alkyl, —C$_2$alk-O—C$_5$alkyl, —C$_3$alk-O—C$_5$alkyl, —C$_4$alk-O—C$_5$alkyl, —C$_5$alk-O—C$_5$alkyl, —C$_6$alk-O—C$_5$alkyl, —C$_1$alk-O—C$_6$alkyl, —C$_2$alk-O—C$_6$alkyl, —C$_3$alk-O—C$_6$alkyl, —C$_4$alk-O—C$_6$alkyl, —C$_6$alk-O—C$_6$alkyl, —C$_0$alk-O—C$_6$alkyl, —CH$_2$OC$_1$alkyl, —CH$_2$OC$_2$alkyl, —CH$_2$OC$_3$alkyl, —CH$_2$OC$_4$alkyl, —CH$_2$OC$_5$alkyl, —CH$_2$OC$_6$alkyl, and the like.

In some aspects, R$^1$ in Formula III or Formula IV is —C$_1$-C$_6$alk-O—C$_3$-C$_6$cycloalkyl, for example, —C$_1$alk-O—C$_3$cycloalkyl, —C$_2$alk-O—C$_3$cycloalkyl, —C$_3$alk-O—C$_3$cycloalkyl, —C$_4$alk-O—C$_3$cycloalkyl, —C$_5$alk-O—C$_3$cycloalkyl, —C$_6$alk-O—C$_3$cycloalkyl, —C$_1$alk-O—C$_4$cycloalkyl, —C$_2$alk-O—C$_4$cycloalkyl, —C$_3$alk-O—C$_4$cycloalkyl, —C$_4$alk-O—C$_4$cycloalkyl, —C$_5$alk-O—C$_4$cycloalkyl, —C$_6$alk-O—C$_4$cycloalkyl, —C$_1$alk-O—C$_5$cycloalkyl, —C$_2$alk-O—C$_5$cycloalkyl, —C$_3$alk-O—C$_5$cycloalkyl, —C$_4$alk-O—C$_5$cycloalkyl, —C$_5$alk-O—C$_5$cycloalkyl, —C$_6$alk-O—C$_5$cycloalkyl, —C$_1$alk-O—C$_6$cycloalkyl, —C$_2$alk-O—C$_6$cycloalkyl, —C$_3$alk-O—C$_6$cycloalkyl, —C$_4$alk-O—C$_6$cycloalkyl, —C$_5$alk-O—C$_6$cycloalkyl, —C$_6$alk-O—C$_6$cycloalkyl, —CH$_2$O—C$_6$cycloalkyl, —CH$_2$O—C$_5$cycloalkyl, —CH$_2$O—C$_4$cycloalkyl, —CH$_2$O—C$_3$cycloalkyl, —CH$_2$O—C$_6$cycloalkyl, and the like.

In some aspects, R$^1$ in Formula III or Formula IV is —C$_1$-C$_6$alk-SCH$_2$-aryl, for example —C$_1$alk-SCH$_2$-aryl, —C$_2$alk-SCH$_2$-aryl, —C$_3$alk-SCH$_2$-aryl, —C$_4$alk-SCH$_2$-aryl, —C$_5$alk-SCH$_2$-aryl, —C$_6$alk-SCH$_2$-aryl, —CH$_2$SCH$_2$-phenyl, —CH$_2$SCH$_2$-naphthyl, —CH$_2$SCH$_2$-fluorophenyl, —CH$_2$SCH$_2$-difluorophenyl, —CH$_2$SCH$_2$-fluoronaphthyl, —CH$_2$SCH$_2$-chlorophenyl, —CH$_2$SCH$_2$-bromophenyl, —CH$_2$SCH$_2$-iodophenyl, —CH$_2$SCH$_2$-methylphenyl, —CH$_2$SCH$_2$-4-chlorophenyl, —CH$_2$SCH$_2$-3,4-dichlorophenyl, —CH$_2$SCH$_2$-3,4-difluorophenyl, —CH$_2$SCH$_2$-3-fluoro-4-chlorophenyl, —CH$_2$SCH$_2$-3-chloro-4-fluorophenyl, and the like. Thus, in some aspects R$^1$ is —CH$_2$SCH$_2$-phenyl.

In some aspects, R$^1$ in Formula III or Formula IV is —C$_1$-C$_6$alkC(O)NH-aryl, for example, —C$_1$alk-C(O)NH-aryl, —C$_2$alk-C(O)NH-aryl, —C$_3$alk-C(O)NH-aryl, —C$_4$alk-C(O)NH-aryl, —C$_5$alk-C(O)NH-aryl, —C$_6$alk-C(O)NH-aryl, —CH$_2$C(O)NH-phenyl, —CH$_2$C(O)NH-naphthyl, —CH$_2$C(O)NH-fluorophenyl, —CH$_2$C(O)NH-difluorophenyl, —CH$_2$C(O)NH-fluoronaphthyl, —CH$_2$C(O)NH-chlorophenyl, —CH$_2$C(O)NH-bromophenyl, —CH$_2$C(O)NH-iodophenyl, —CH$_2$C(O)NH— methylphenyl, —CH$_2$C(O)NH-4-chlorophenyl, —CH$_2$C(O)NH-3,4-dichlorophenyl, —CH$_2$C(O)NH-3,4-difluorophenyl, —CH$_2$C(O)NH-3-fluoro-4-chlorophenyl, —CH$_2$C(O)NH-3-chloro-4-fluorophenyl and the like. Thus, in some aspects R$^1$ is —CH$_2$C(O)NH-phenyl.

In some aspects, R$^1$ in Formula III or Formula IV is —C$_0$-C$_6$alk-S-aryl, for example, —C$_0$alk-S-aryl, —C$_1$alk-S-aryl, —C$_2$alk-S-aryl, —C$_6$alk-S-aryl, —C$_4$alk-S-aryl, —C$_5$alk-S-aryl, —C$_0$alk-S-aryl, —S-phenyl, —S-naphthyl, —S-fluorophenyl, —S-difluorophenyl, —S-fluoronaphthyl, —S-chlorophenyl, —S-bromophenyl, —S-iodophenyl, —S-methylphenyl, and the like. In some aspects R$^1$ is —S-difluorophenyl. In some aspects R$^1$ is —S-3,4-difluorophenyl. In other aspects, R$^1$ is —S-chlorophenyl.

In other aspects, R$^1$ is —S-4-chlorophenyl. In other aspects, R$^1$ is —S-chlorofluorophenyl. In other aspects, R$^1$ is —S-3-chloro-4-fluorophenyl. In other aspects, R$^1$ is —S-4-chloro-3-fluorophenyl. In other aspects, R$^1$ is —S-dichlorophenyl. In other aspects, R$^1$ is —S-3,4-dichlorophenyl.

In some aspects, R$^1$ in Formula III or Formula IV is —C$_0$-C$_6$alk-S(O)aryl, for example, —C$_0$alk-S(O)aryl, —C$_1$alk-S(O)aryl, —C$_2$alk-S(O)aryl, —C$_3$alk-S(O)aryl, —C$_4$alk-S(O)aryl, —C$_5$alk-S(O)aryl, —C$_0$alk-S(O)aryl, —S(O)-phenyl, —S(O)-naphthyl, —S(O)-fluorophenyl, —S(O)— difluorophenyl, —S(O)-fluoronaphthyl, —S(O)-chlorophenyl, —S(O)-bromophenyl, —S(O)-iodophenyl, —S(O)-methylphenyl, and the like. In some aspects R$^1$ is —S(O)-difluorophenyl. In some aspects R$^1$ is —S(O)-3,4-difluorophenyl. In other aspects, R$^1$ is —S(O)-chlorophenyl. In other aspects, R$^1$ is —S(O)-4-chlorophenyl. In other aspects, R$^1$ is —S(O)-chlorofluorophenyl. In other aspects, R$^1$ is —S(O)-3-chloro-4-fluorophenyl. In other aspects, R$^1$ is —S(O)-4-chloro-3-fluorophenyl. In other aspects, R$^1$ is —S(O)-dichlorophenyl. In other aspects, R$^1$ is —S(O)-3,4-dichlorophenyl.

In some aspects, R$^1$ in Formula III or Formula IV is —C$_0$-C$_6$alk-S(O)$_2$aryl, for example, —C$_0$alk-S(O)$_2$aryl, —C$_1$alk-S(O)$_2$aryl, —C$_2$alk-S(O)$_2$aryl-C$_3$alk-S(O)$_2$aryl, —C$_4$alk-S(O)$_2$aryl, —C$_5$alk-S(O)$_2$aryl, —C$_6$alk-S(O)$_2$aryl, —S(O)$_2$-phenyl, —S(O)$_2$-naphthyl, —S(O)$_2$-fluorophenyl, —S(O)$_2$-difluorophenyl, —S(O)$_2$-fluoronaphthyl, —S(O)$_2$-chlorophenyl, —S(O)$_2$-bromophenyl, —S(O)$_2$-iodophenyl, —S(O)$_2$-methylphenyl, and the like. In some aspects R$^1$ is —S(O)$_2$-difluorophenyl. In some aspects R$^1$ is —S(O)$_2$-3,4-difluorophenyl. In other aspects, R$^1$ is —S(O)$_2$-chlorophenyl. In other aspects, R$^1$ is —S(O)$_2$-4-chlorophenyl. In other aspects, R$^1$ is —S(O)$_2$-chlorofluorophenyl. In other aspects, R$^1$ is —S(O)$_2$-3-chloro-4-fluorophenyl. In other aspects, R$^1$ is —S(O)$_2$-4-chloro-3-fluorophenyl. In other aspects, R$^1$ is —S(O)$_2$-dichlorophenyl. In other aspects, R$^1$ is —S(O)$_2$-3,4-dichlorophenyl.

In some aspects, R$^1$ in Formula III or Formula IV is —C$_0$-C$_6$alk-Oaryl, for example —C$_0$alk-Oaryl, —C$_1$alk-Oaryl, —C$_2$alk-Oaryl-C$_3$alk-Oaryl, —C$_4$alk-Oaryl, —C$_5$alk-Oaryl, —C$_0$alk-Oaryl, —O-phenyl, —O-naphthyl, —O-fluorophenyl, —O-difluorophenyl, —O-fluoronaphthyl, —O-chlorophenyl, —O-bromophenyl, —O-iodophenyl, —O-methylphenyl, and the like. In some aspects R$^1$ is —O— difluorophenyl. In some aspects R$^1$ is —O-3,4-difluorophenyl. In other aspects, R$^1$ is —O-chlorophenyl. In other aspects, R$^1$ is —O-4-chlorophenyl. In other aspects, R$^1$ is —O-chlorofluorophenyl. In other aspects, R$^1$ is —O-3-chloro-4-fluorophenyl. In other aspects, R$^1$ is —O-4-chloro-3-fluorophenyl. In other aspects, R$^1$ is —O-dichlorophenyl. In other aspects, R$^1$ is —O-3,4-dichlorophenyl.

In some aspects, R$^1$ in Formula III or Formula IV is —C$_0$-C$_6$alk-heteroaryl, for example, —C$_0$alk-heteroaryl, —C$_1$alk-heteroaryl, —C$_2$alk-heteroaryl, —C$_3$alk-heteroaryl, —C$_4$alk-heteroaryl, —C$_5$alk-heteroaryl, and —C$_0$alk-heteroaryl. In some aspects, R$^1$ is 2-(2-amino-3-bromoquinolin-7-yl)ethyl, 2-(2-amino-3-chloroquinolin-7-yl)ethyl, 2-(2-((cyclopropylmethyl)amino)quinolin-7-yl)ethyl, 2-(2-(methylamino)quinolin-7-yl)ethyl, or 2-(2-aminoquinolin-7-yl)ethyl.

In some aspects, R$^1$ in Formula III or Formula IV is —C$_1$-C$_6$alk-O-heteroaryl, for example, —C$_1$alk-O-heteroaryl, —C$_2$alk-O-heteroaryl, —C$_3$alk-O-heteroaryl, —C₄alk-O-heteroaryl, —C₅alk-O-heteroaryl, and —C₆alk-O-heteroaryl. In some aspects, R¹ is 2-amino-3-bromoquinolin-7-yl)oxy)methyl.

In some aspects, R¹ in Formula III or Formula IV is —C₁-C₆alk-S-heteroaryl, for example, —C₁alk-S-heteroaryl, —C₂alk-S-heteroaryl, —C₃alk-S-heteroaryl, —C₄alk-S-heteroaryl, —C₅alk-S-heteroaryl, and —C₆alk-S-heteroaryl. In some aspects, R¹ is 2-amino-3-bromoquinolin-7-yl)thio)methyl.

In some aspects, R¹ in Formula III or Formula IV is —C₁-C₆alk-NH-heteroaryl, for example, —C₁alk-NH-heteroaryl, —C₂alk-NH-heteroaryl, —C₃alk-NH-heteroaryl, —C₄alk-NH-heteroaryl, —C₅alk-NH-heteroaryl, and —C₆alk-NH-heteroaryl. In some aspects, R¹ is 2-amino-3-bromoquinolin-7-yl)amino)methyl.

In some aspects of Formula III or Formula IV, R² is H, —C₁-C₆alkyl, —C₁-C₆haloalkyl, or —C₀-C₆alk-C₃-C₆cycloalkyl. Thus, in some embodiments, R² is H.

It will be apparent that when R² is H, the compounds of Formula III or Formula IV may exist in equivalent, tautomeric forms. Thus, when R² is H, compounds of Formula III may be represented by either of the following equivalent structures:

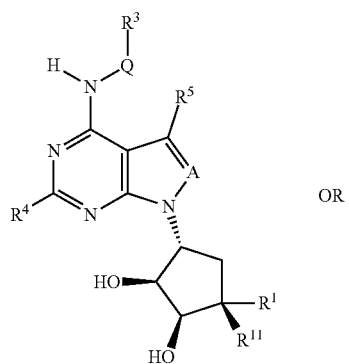

OR

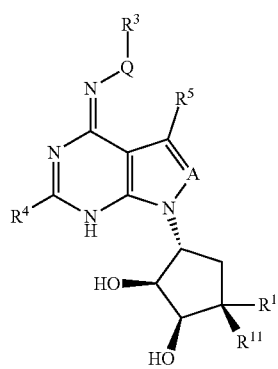

Similarly, when R² is H, compounds of Formula IV may be represented by the following equivalent structures:

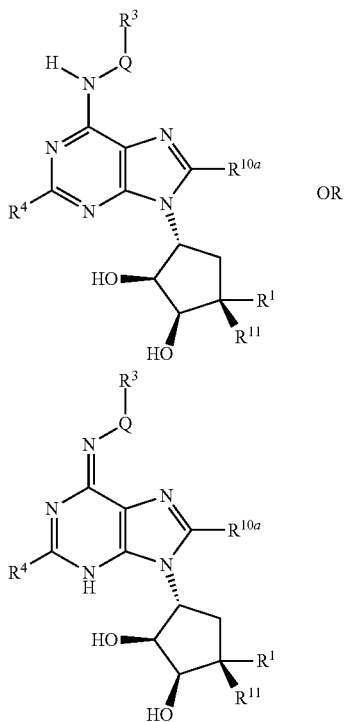

It will be apparent that in some tautomeric forms of the compounds of Formula III or Formula IV, geometric isomerism in the exocyclic carbon-nitrogen double bond can result in E- and Z-isomers, as shown below:

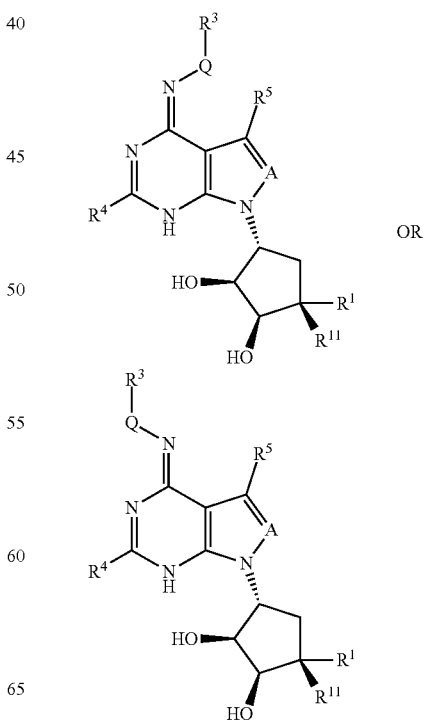

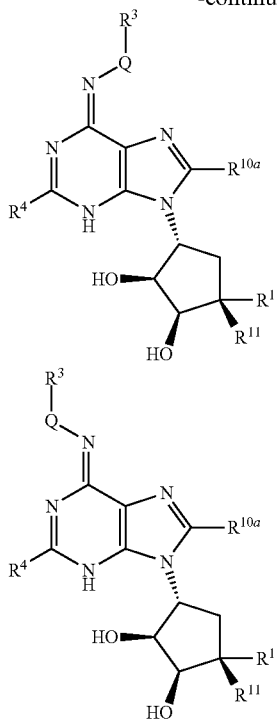

The compounds of Formula III or Formula IV described and claimed herein are meant to encompass both E- and Z-geometric isomers. The depiction of a particular geometric isomer is not intended to be limiting.

In some embodiments, $R^2$ in Formula III or Formula IV is —$C_1$-$C_6$alkyl, for example, methyl, ethyl, propyl, isopropyl, butyl, isobutyl, s-butyl, t-butyl, pentyl, and the like. Thus, in some embodiments, $R^2$ is methyl (i.e., —$CH_3$, or Me).

In some aspects, $R^2$ in Formula III or Formula IV is —$C_1$-$C_6$haloalkyl, for example, —$CF_3$ or —$CHF_2$ and the like.

In some aspects, $R^2$ in Formula III or Formula IV is —$C_0$-$C_6$alk-$C_3$-$C_6$cycloalkyl, for example, —$C_0$alk-$C_3$cycloalkyl, —$C_1$alk-$C_3$cycloalkyl, —$C_2$alk-$C_3$cycloalkyl, —$C_3$alk-$C_3$cycloalkyl, —$C_4$alk-$C_3$cycloalkyl, —$C_5$alk-$C_3$cycloalkyl, —$C_6$alk-$C_3$cycloalkyl, —$C_0$alk-$C_4$cycloalkyl, —$C_1$alk-$C_4$cycloalkyl, —$C_2$alk-$C_4$cycloalkyl, —$C_3$alk-$C_4$cycloalkyl, —$C_4$alk-$C_4$cycloalkyl, —$C_5$alk-$C_4$cycloalkyl, —$C_6$alk-$C_4$cycloalkyl, —$C_0$alk-$C_5$cycloalkyl, —$C_1$alk-$C_5$cycloalkyl, —$C_2$alk-$C_5$cycloalkyl, —$C_3$alk-$C_5$cycloalkyl, —$C_4$alk-$C_5$cycloalkyl, —$C_5$alk-$C_5$cycloalkyl, —$C_6$alk-$C_5$cycloalkyl, —$C_0$alk-$C_6$cycloalkyl, —$C_1$alk-$C_6$cycloalkyl, —$C_2$alk-$C_6$cycloalkyl, —$C_3$alk-$C_6$cycloalkyl, —$C_4$alk-$C_6$cycloalkyl, —$C_5$alk-$C_6$cycloalkyl, —$C_6$cycloalkyl, or —$C_6$alk-$C_6$cycloalkyl. In some aspects wherein $R^2$ is —$C_0$-$C_6$alk-$C_3$-$C_6$cycloalkyl, the cycloalkyl is unsubstituted. In other aspects wherein $R^2$ is —$C_0$-$C_6$alk-$C_3$-$C_6$cycloalkyl, the cycloalkyl is substituted with one, two, or three R substituents independently selected from $C_1$-$C_6$alkyl, (e.g., methyl, ethyl, propyl, isopropyl, butyl), —$OC_1$-$C_6$alkyl (e.g., —Omethyl, —Oethyl, —Opropyl, —Oisopropyl, —Obutyl), and halo (e.g., F or $C_1$).

In some aspects of Formula III or Formula IV, $R^3$ is H, —$C_1$-$C_6$alkyl, —$C_1$-$C_6$haloalkyl, —$C_0$-$C_6$alk-$C_3$-$C_6$cycloalkyl, —$C(O)R^7$, —$C(O)OR^7$, or —$C(O)NR^{8a}R^{8b}$. Thus, in some embodiments, $R^3$ is H.

In some aspects, $R^3$ in Formula III or Formula IV is —$C_1$-$C_6$alkyl, for example, methyl, ethyl, propyl, isopropyl, butyl, isobutyl, s-butyl, t-butyl, pentyl, and the like. Thus, in some embodiments, $R^3$ is methyl. In other embodiments, $R^3$ is ethyl.

In some aspects, $R^3$ in Formula III or Formula IV is —$C_1$-$C_6$haloalkyl, for example, —$CF_3$, —$CH_2CF_3$, —$CH_2CHF_2$ or —$CHF_2$ and the like.

In some aspects, $R^3$ in Formula III or Formula IV is —$C_0$-$C_6$alk-$C_3$-$C_6$cycloalkyl, for example, —$C_0$alk-$C_3$cycloalkyl, —$C_1$alk-$C_3$cycloalkyl, —$C_2$alk-$C_3$cycloalkyl, —$C_3$alk-$C_3$cycloalkyl, —$C_4$alk-$C_3$cycloalkyl, —$C_5$alk-$C_3$cycloalkyl, —$C_6$alk-$C_3$cycloalkyl, —$C_0$alk-$C_4$cycloalkyl, —$C_1$alk-$C_4$cycloalkyl, —$C_2$alk-$C_4$cycloalkyl, —$C_3$alk-$C_4$cycloalkyl, —$C_4$alk-$C_4$cycloalkyl, —$C_5$alk-$C_4$cycloalkyl, —$C_6$alk-$C_4$cycloalkyl, —$C_0$alk-$C_5$cycloalkyl, —$C_1$alk-$C_5$cycloalkyl, —$C_2$alk-$C_5$cycloalkyl, —$C_3$alk-$C_5$cycloalkyl, —$C_4$alk-$C_5$cycloalkyl, —$C_5$alk-$C_5$cycloalkyl, —$C_6$alk-$C_5$cycloalkyl, —$C_0$alk-$C_6$cycloalkyl, —$C_1$alk-$C_6$cycloalkyl, —$C_2$alk-$C_6$cycloalkyl, —$C_3$alk-$C_6$cycloalkyl, —$C_4$alk-$C_6$cycloalkyl, —$C_5$alk-$C_6$cycloalkyl, —$C_6$cycloalkyl, —$C_6$alk-$C_6$cycloalkyl. In some aspects wherein $R^3$ is —$C_0$-$C_6$alk-$C_3$-$C_6$cycloalkyl, the cycloalkyl is unsubstituted. In other aspects wherein $R^3$ is —$C_0$-$C_6$alk-$C_3$-$C_6$cycloalkyl, the cycloalkyl is substituted with one, two, or three R substituents independently selected from $C_1$-$C_6$alkyl, (e.g., methyl, ethyl, propyl, isopropyl, butyl), —$OC_1$-$C_6$alkyl (e.g., —Omethyl, —Oethyl, —Opropyl, —Oisopropyl, —Obutyl), and halo (e.g., F or $C_1$).

In some aspects, $R^3$ in Formula III or Formula IV is —$C(O)R$ or —$C(O)OR^7$. In these embodiments, $R^7$ is H, $C_1$-$C_6$alkyl, or $C_0$-$C_6$alk-$C_3$-$C_6$cycloalkyl.

In some aspects, $R^7$ in Formula III or Formula IV is H, $C_1$-$C_6$alkyl, or $C_0$-$C_6$alk-$C_3$-$C_6$cycloalkyl. Thus, in some aspects, $R^7$ is H.

In other aspects, $R^7$ in Formula III or Formula IV is $C_1$-$C_6$alkyl, for example, methyl, ethyl, propyl, isopropyl, butyl, isobutyl, s-butyl, t-butyl, pentyl, and the like. Thus, in some embodiments, $R^7$ is methyl.

In some aspects, $R^7$ in Formula III or Formula IV is —$C_0$-$C_6$alk-$C_3$-$C_6$cycloalkyl, for example, —$C_0$alk-$C_3$cycloalkyl, —$C_1$alk-$C_3$cycloalkyl, —$C_2$alk-$C_3$cycloalkyl, —$C_3$alk-$C_3$cycloalkyl, —$C_4$alk-$C_3$cycloalkyl, —$C_5$alk-$C_3$cycloalkyl, —$C_6$alk-$C_3$cycloalkyl, —$C_0$alk-$C_4$cycloalkyl, —$C_1$alk-$C_4$cycloalkyl, —$C_2$alk-$C_4$cycloalkyl, —$C_3$alk-$C_4$cycloalkyl, —$C_4$alk-$C_4$cycloalkyl, —$C_5$alk-$C_4$cycloalkyl, —$C_6$alk-$C_4$cycloalkyl, —$C_0$alk-$C_5$cycloalkyl, —$C_1$alk-$C_5$cycloalkyl, —$C_2$alk-$C_5$cycloalkyl, —$C_3$alk-$C_5$cycloalkyl, —$C_4$alk-$C_5$cycloalkyl, —$C_5$alk-$C_5$cycloalkyl, —$C_6$alk-$C_5$cycloalkyl, —$C_0$alk-$C_6$cycloalkyl, —$C_1$alk-$C_6$cycloalkyl, —$C_2$alk-$C_6$cycloalkyl, —$C_3$alk-$C_6$cycloalkyl, —$C_4$alk-$C_6$cycloalkyl, —$C_5$alk-$C_6$cycloalkyl, —$C_6$cycloalkyl, and —$C_6$alk-$C_6$cycloalkyl.

In some aspects, $R^3$ in Formula III or Formula IV is —$C(O)R$. In some embodiments wherein $R^7$ is —$C_1$-$C_6$alkyl, $R^3$ is —$C(O)C_1$-$C_6$alkyl. Thus, in some embodiments wherein $R^7$ is methyl, $R^3$ is acetyl (i.e., —$C(O)CH_3$).

In some aspects, $R^3$ in Formula III or Formula IV is —$C(O)OR^7$. In some embodiments wherein $R^7$ is —$C_1$-$C_6$alkyl, $R^3$ is —$C(O)OC_1$-$C_6$alkyl. Thus, in some embodiments wherein $R^7$ is methyl, $R^3$ is —$C(O)OCH_3$.

In some aspects, $R^3$ in Formula III or Formula IV is or —C(O)NR$^{8a}$R$^{8b}$.

In some aspects, $R^{8a}$ and $R^{8b}$ in Formula III or Formula IV are each independently H, $C_1$-$C_6$alkyl (e.g., methyl, ethyl, propyl, isopropyl, butyl, isobutyl, s-butyl, t-butyl, pentyl, and the like), or —$C_0$-$C_6$alk-O—$C_1$-$C_6$alkyl (e.g., —$C_0$alk-O—$C_1$alkyl, —$C_1$alk-O—$C_1$alkyl, —$C_2$alk-O—$C_1$alkyl, —$C_3$alk-O—$C_1$alkyl, —$C_4$alk-O—$C_1$alkyl, —$C_5$alk-O—$C_1$alkyl, —$C_0$alk-O—$C_1$alkyl, —$C_0$alk-O—$C_2$alkyl, —$C_1$alk-O—$C_2$alkyl, —$C_2$alk-O—$C_2$alkyl, —$C_3$alk-O—$C_2$alkyl, —$C_4$alk-O—$C_2$alkyl, —$C_5$alk-O—$C_2$alkyl, —$C_6$alk-O—$C_2$alkyl, —$C_0$alk-O—$C_3$alkyl, —$C_1$alk-O—$C_3$alkyl, —$C_2$alk-O—$C_3$alkyl, —$C_3$alk-O—$C_3$alkyl, —$C_4$alk-O—$C_3$alkyl, —$C_5$alk-O—$C_3$alkyl, —$C_6$alk-O—$C_3$alkyl, —$C_0$alk-O—$C_4$alkyl, —$C_1$alk-O—$C_4$alkyl, —$C_2$alk-O—$C_4$alkyl, —$C_3$alk-O—$C_4$alkyl, —$C_4$alk-O—$C_4$alkyl, —$C_5$alk-O—$C_4$alkyl, —$C_6$alk-O—$C_4$alkyl, —$C_0$alk-O—$C_5$alkyl, —$C_1$alk-O—$C_5$alkyl, —$C_2$alk-O—$C_5$alkyl, —$C_3$alk-O—$C_5$alkyl, —$C_4$alk-O—$C_5$alkyl, —$C_6$alk-O—$C_5$alkyl, —$C_6$alk-O—$C_5$alkyl, —$C_0$alk-O—$C_6$alkyl, —$C_1$alk-O—$C_6$alkyl, —$C_2$alk-O—$C_6$alkyl, —$C_3$alk-O—$C_6$alkyl, —$C_4$alk-O—$C_6$alkyl, —$C_5$alk-O—$C_6$alkyl, —$C_6$alk-O—$C_6$alkyl). In some embodiments, $R^{8a}$ is $C_1$-$C_6$alkyl or —$C_0$-$C_6$alk-O$C_1$-$C_6$alkyl and $R^{8b}$ is H, $C_1$-$C_6$alkyl, and —$C_0$-$C_6$alk-O$C_1$-$C_6$alkyl.

In some embodiments, $R^{8a}$ in Formula III or Formula IV is H or $C_1$-$C_6$alkyl. In some embodiments, $R^{8b}$ is H or $C_1$-$C_6$alkyl. In some embodiments, $R^{8a}$ and $R^{8b}$ are each H. In other embodiments, $R^{8a}$ and $R^{8b}$ are each independently $C_1$-$C_6$alkyl. In some aspects, $R^{8a}$ is $C_1$-$C_6$alkyl and $R^{8b}$ is H.

In other aspects, $R^{8a}$ and $R^{8b}$ in Formula III or Formula IV are each independently —$C_0$-$C_6$alk-O$C_1$-$C_6$alkyl.

In other aspects, $R^{8a}$ in Formula III or Formula IV is —$C_0$-$C_6$alk-O$C_1$-$C_6$alkyl and $R^{8b}$ is H.

In yet other aspects, $R^{8a}$ and $R^{8b}$ in Formula III or Formula IV, together with the atom to which they are attached, form a $C_2$-$C_6$heterocycloalkyl ring, for example, aziridinyl, azetidinyl, pyrrolidinyl, piperidinyl, and the like.

In some aspects of Formula III or Formula IV, $R^4$ is H, halo, —$C_1$-$C_6$alkyl, or NH$_2$. Thus in some embodiments, $R^4$ is H. In other embodiments, $R^4$ is halo, for example F, Cl, Br, or I, with —Cl being preferred. In other embodiments, $R^4$ is —$C_1$-$C_6$alkyl, for example, methyl, ethyl, propyl, isopropyl, butyl, isobutyl, s-butyl, t-butyl, pentyl, and the like. In yet other embodiments, $R^4$ is NH$_2$.

In some aspects of Formula III, $R^5$ is H, halo, CN, —$C_1$-$C_6$alkyl, —$C_2$-$C_4$alkenyl, —$C_2$-$C_4$haloalkenyl, $C_2$-$C_4$cyanoalkenyl, —$C_0$-$C_6$alk-C≡CH, —$C_0$-$C_6$alk-C≡C—$C_1$-$C_6$alkyl, —$C_1$-$C_4$haloalkyl, —$C_2$-$C_6$heterocycloalkyl, oxo-substituted-$C_2$-$C_6$heterocycloalkyl, —$C_3$-$C_6$cycloalkyl, —CHO, —C(O)R$^9$, —CR$^8$R$^{8'}$CN, —CH$_2$NR$^8$R$^{8'}$, —$C_0$-$C_6$alk-OH, —NR$^8$R$^{8'}$, —NH—CN, —N(R$^9$)CN, —O—$C_1$-$C_4$alkyl, —NR$^9$CONR$^8$R$^{8'}$, —OCONR$^8$R$^{8'}$, or —NR$^9$C(O)OR$^{9a}$.

In some embodiments of Formula III, $R^5$ is H.

In some embodiments of Formula III, $R^5$ is halo, for example, F, Cl, Br, or I. Thus, in some embodiments, $R^5$ is F.

In some embodiments of Formula III, $R^5$ is CN.

In other embodiments of Formula III, $R^5$ is —$C_1$-$C_6$alkyl, for example, methyl, ethyl, propyl, isopropyl, butyl, isobutyl, s-butyl, t-butyl, pentyl, and the like. Thus, in some aspects, $R^5$ is methyl.

In some aspects, $R^5$ in Formula III is —$C_2$-$C_4$alkenyl, for example, vinyl, allyl, and the like. Thus, in some embodiments, $R^5$ is vinyl (—CH═CH$_2$).

In some aspects, $R^5$ in Formula III is —$C_2$-$C_4$haloalkenyl, for example, —C(F)═CH$_2$, C(CF$_3$)═CH$_2$, and the like. Thus, in some embodiments, R is —C(F)═CH$_2$.

In other aspects, $R^5$ in Formula III is —$C_2$-$C_4$cyanoalkenyl, for example, —C(CN)═CH$_2$, —CH═CHCN, and the like. Thus, in some embodiments, $R^5$ is —C(CN)═CH$_2$.

In other embodiments, $R^5$ in Formula III is —$C_0$-$C_6$alk-C≡CH, for example, —$C_0$alk-C≡CH, —$C_1$alk-C≡CH, —$C_2$alk-C≡CH, —$C_6$alk-C≡CH, —$C_4$alk-C≡CH, —$C_5$alk-C≡CH, —$C_0$alk-C≡CH, ethynyl, propargyl, and the like. Thus, in some embodiments, $R^5$ is ethynyl (—C≡CH).

In some aspects, $R^5$ in Formula III is —$C_0$-$C_6$alk-C≡C—$C_1$-$C_6$alkyl, for example, —$C_0$alk-C≡C—$C_1$alkyl, —$C_1$alk-C≡C—$C_1$alkyl, —$C_2$alk-C≡C—$C_1$alkyl, —$C_6$alk-C≡C—$C_1$alkyl, —$C_4$alk-C≡C—$C_1$alkyl, —$C_5$alk-C≡C—$C_1$alkyl, —$C_0$alk-C≡C—$C_1$alkyl, —$C_0$alk-C≡C—$C_2$alkyl, —$C_1$alk-C≡C—$C_2$alkyl, —$C_2$alk-C≡C—$C_2$alkyl, —$C_3$alk-C≡C—$C_2$alkyl, —$C_4$alk-C≡C—$C_2$alkyl, —$C_5$alk-C≡C—$C_2$alkyl, —$C_0$alk-C≡C—$C_2$alkyl, —$C_0$alk-C≡C—$C_3$alkyl, —$C_1$alk-C≡C—$C_3$alkyl, —$C_2$alk-C≡C—$C_3$alkyl, —$C_3$alk-C≡C—$C_3$alkyl, —$C_4$alk-C≡C—$C_3$alkyl, —$C_5$alk-C≡C—$C_3$alkyl, —$C_0$alk-C≡C—$C_3$alkyl, —$C_0$alk-C≡C—$C_4$alkyl, —$C_1$alk-C≡C—$C_4$alkyl, —$C_2$alk-C≡C—$C_4$alkyl, —$C_3$alk-C≡C—$C_4$alkyl, —$C_4$alk-C≡C—$C_4$alkyl, —$C_5$alk-C≡C—$C_4$alkyl, —$C_6$alk-C≡C—$C_4$alkyl, —$C_0$alk-C≡C—$C_5$alkyl, —$C_1$alk-C≡C—$C_5$alkyl, —$C_2$alk-C≡C—$C_5$alkyl, —$C_3$alk-C≡C—$C_5$alkyl, —$C_4$alk-C≡C—$C_5$alkyl, —$C_5$alk-C≡C—$C_5$alkyl, —$C_0$alk-C≡C—$C_5$alkyl, —$C_0$alk-C≡C—$C_6$alkyl, —$C_1$alk-C≡C—$C_6$alkyl, —$C_2$alk-C≡C—$C_6$alkyl, —$C_3$alk-C≡C—$C_6$alkyl, —$C_4$alk-C≡C—$C_6$alkyl, —$C_5$alk-C≡C—$C_6$alkyl, or —$C_0$alk-C—$C_1$-$C_6$alkyl.

In some embodiments, $R^5$ in Formula III is —$C_1$-$C_4$haloalkyl, for example, —CF$_3$ or —CHF$_2$.

In some embodiments, $R^5$ in Formula III is —$C_2$-$C_6$heterocycloalkyl, for example $C_2$heterocycloalkyl, $C_3$heterocycloalkyl, $C_4$ heterocycloalkyl, $C_5$ heterocycloalkyl, and $C_6$ heterocycloalkyl, including azepanyl, aziridinyl, azetidinyl, pyrrolidinyl, dioxolanyl, imidazolidinyl, pyrazolidinyl, piperazinyl, piperidinyl, dioxanyl, morpholinyl, dithianyl, thiomorpholinyl, oxazepanyl, oxiranyl, oxetanyl, tetrahydrofuranyl, tetrahydropyranyl, piperazinyl, and the like. Thus, in some embodiments, $R^5$ is 2-oxiranyl. In other embodiments, $R^5$ is 1-azetidinyl.

In some embodiments, $R^5$ in Formula III is oxo-substituted-$C_2$-$C_6$heterocycloalkyl, for example, oxo-substituted-$C_2$heterocycloalkyl, oxo-substituted-$C_3$heterocycloalkyl, oxo-substituted-$C_4$heterocycloalkyl, oxo-substituted-$C_5$heterocycloalkyl, oxo-substituted-$C_6$heterocycloalkyl, including aziridinonyl, azetidinonyl, pyrrolidinonyl, dioxolanonyl, imidazolidinonyl, pyrazolidinonyl, piperazinonyl, piperidinonyl, dioxanonyl, dithianonyl, thiomorpholinonyl, oxazepanonyl, oxiranonyl, oxetanonyl, quinuclidinonyl, tetrahydrofuranonyl, tetrahydropyranonyl, piperazinonyl, and the like. Thus, in some embodiments, $R^5$ is azetidin-2-one-1-yl.

In some embodiments, $R^5$ in Formula III is —$C_3$-$C_6$cycloalkyl, for example —$C_3$cycloalkyl, —$C_4$cycloalkyl, —$C_5$cycloalkyl, —$C_6$cycloalkyl, and the like. In some embodiments, $R^5$ is —$C_3$cycloalkyl. Thus, in some embodiments, $R^5$ is cyclopropyl.

In other embodiments, $R^5$ in Formula III is —C(O)R$^9$. In some embodiments wherein R$^9$ is $C_1$-$C_6$alkyl, $R^5$ is —C(O)$C_1$-$C_6$alkyl. Thus, in some embodiments wherein R$^9$ is methyl, $R^5$ is acetyl (i.e., —C(O)CH$_3$). In some embodiments wherein R$^9$ is $C_0$-$C_6$alk-$C_3$-$C_6$cycloalkyl, $R^5$ is —C(O)C$_0$-C$_6$alk-C$_3$-C$_6$cycloalkyl. In some embodiments wherein R$^9$ is H, R$^5$ is —CHO.

In some embodiments, R$^5$ in Formula III is —CR$^8$R$^{8'}$CN. Thus, in some embodiments wherein R$^8$ and R$^{8'}$ are both H, R$^5$ in Formula III is cyanomethyl (i.e., —CH$_2$CN). In some embodiments wherein R$^{8'}$ is —C$_1$-C$_6$alkyl and R$^{8'}$ is H, R$^5$ is —CH(—C$_1$-C$_6$alkyl)CN. In some embodiments wherein R$^8$ and R$^{8'}$ are both —C$_1$-C$_6$alkyl, R$^5$ is —C(C$_1$-C$_6$alkyl)(C$_1$-C$_6$alkyl)CN. In some embodiments wherein R$^8$ is —C$_0$-C$_6$alk-OC$_1$-C$_6$alkyl and R$^{8'}$ is H, R$^5$ is —CH(—C$_0$-C$_6$alk-OC$_1$-C$_6$alkyl)CN. In some embodiments wherein R$^8$ and R$^{8'}$ are both —C$_0$-C$_6$alk-OC$_1$-C$_6$alkyl, R$^5$ is —C(—C$_0$-C$_6$alk-OC$_1$-C$_6$alkyl)(—C$_0$-C$_6$alk-OC$_1$-C$_6$alkyl)CN.

In some embodiments, R$^5$ in Formula III is CH$_2$NR$^8$R$^{8'}$. Thus, in some embodiments wherein R$^8$ and R$^{8'}$ are both H, R$^5$ in Formula III is aminomethyl (i.e., —CH$_2$NH$_2$). In some embodiments wherein R$^8$ is —C$_1$-C$_6$alkyl and R$^{8'}$ is H, R$^5$ is —CH$_2$NH(C$_1$-C$_6$alkyl). In some embodiments wherein R$^8$ and R$^{8'}$ are both —C$_1$-C$_6$alkyl, R$^5$ is —CH$_2$NH(C$_1$-C$_6$alkyl)(C$_1$-C$_6$alkyl). In some embodiments wherein R$^{8'}$ is —C$_0$-C$_6$alk-OC$_1$-C$_6$alkyl and R$^{8'}$ is H, R$^5$ is —CH$_2$NH(—C$_0$-C$_6$alk-OC$_1$-C$_6$alkyl). In some embodiments wherein R$^8$ and R$^{8'}$ are both —C$_0$-C$_6$alk-OC$_1$-C$_6$alkyl, R$^5$ is —CH$_2$NH(—C$_0$-C$_6$alk-OC$_1$-C$_6$alkyl)(—C$_0$-C$_6$alk-OC$_1$-C$_6$alkyl).

In some embodiments, R$^5$ in Formula III is —C$_0$-C$_6$alk-OH, for example, —C$_0$alk-OH, —C$_1$alk-OH, —C$_2$alk-OH, —C$_3$alk-OH, —C$_4$alk-OH, —C$_5$alk-OH, —C$_6$alk-OH, and the like. In some embodiments R$^5$ is —C$_1$alk-OH. In some embodiments, R$^5$ is hydroxymethyl (i.e., CH$_2$OH).

In some embodiments, R$^5$ in Formula III is —NR$^8$R$^{8'}$. Thus, in some embodiments wherein R$^8$ and R$^{8'}$ are both H, R$^5$ is amino (i.e., —NH$_2$). In some embodiments wherein R$^8$ is —C$_1$-C$_6$alkyl and R$^{8'}$ is H, R$^5$ is —NH(C$_1$-C$_6$alkyl). Thus, in some embodiments wherein R$^8$ is methyl and R$^{8'}$ is H, R$^5$ is methylamino (i.e., —NHCH$_3$). In some embodiments wherein R$^8$ and R$^{8'}$ are both —C$_1$-C$_6$alkyl, R$^5$ is —N(—C$_1$-C$_6$alkyl)(—C$_1$-C$_6$alkyl). In some embodiments wherein R$^8$ is —C$_0$-C$_6$alk-OC$_1$-C$_6$alkyl and R$^{8'}$ is H, R$^5$ is —NH(—C$_0$-C$_6$alk-OC$_1$-C$_6$alkyl). In some embodiments wherein R$^8$ and R$^{8'}$ are both —C$_0$-C$_6$alk-OC$_1$-C$_6$alkyl, R$^5$ is —N(—C$_0$-C$_6$alk-OC$_1$-C$_6$alkyl)(—C$_0$-C$_6$alk-OC$_1$-C$_6$alkyl).

In some embodiments, R$^5$ in Formula III is —N(R$^9$)CN. In some embodiments wherein R$^9$ is —C$_1$-C$_6$alkyl, R$^5$ is —N(C$_1$-C$_6$alkyl)CN. Thus, in some embodiments wherein R$^9$ is methyl, R$^5$ is —N(CH$_3$)CN. In some embodiments wherein R$^9$ is —C$_0$-C$_6$alk-C$_3$-C$_6$cycloalkyl, R$^5$ is —N(—C$_0$-C$_6$alk-C$_3$-C$_6$cycloalkyl)CN. In some embodiments wherein R$^9$ is H, R$^5$ is —NH—CN.

In some embodiments, R$^5$ in Formula III is —O—C$_1$-C$_4$alkyl, for example —O—C$_1$alkyl, —O—C$_2$alkyl, —O—C$_3$alkyl, and —O—C$_4$alkyl.

In some embodiments, R$^5$ in Formula III is —NR$^9$C(O)NR$^8$R$^{8'}$. In some embodiments wherein R$^9$ is H, R$^5$ in Formula III is —NHC(O)NR$^8$R$^{8'}$. In some embodiments wherein R$^9$ is —C$_1$-C$_6$alkyl, R$^5$ is —N(—C$_1$-C$_6$alkyl)C(O)NR$^8$R$^{8'}$. In some embodiments wherein R$^9$ is C$_0$-C$_6$alk-C$_3$-C$_6$cycloalkyl, R$^5$ is —N(C$_0$-C$_6$alk-C$_3$-C$_6$cycloalkyl)C(O)NR$^8$R$^{8'}$. In some embodiments wherein R$^{8'}$ is H, R$^5$ is —NR$^9$C(O)NHR$^{8'}$. In some embodiments wherein R$^{8'}$ is H and R$^{8'}$ is H, R$^5$ is —NR$^9$C(O)NH$_2$. Thus, in some embodiments wherein R$^9$ is H and R$^8$ and R$^{8'}$ are both H, R$^5$ is urea-1-yl (i.e., —NHC(O)NH$_2$). In some embodiments wherein R$^9$ is —C$_1$-C$_6$alkyl and R$^{8'}$ is H, R$^5$ is —NR$^9$C(O)NH(C$_1$-C$_6$alkyl). In some embodiments wherein R$^8$ and R$^{8'}$ are both —C$_1$-C$_6$alkyl, R$^5$ is —NR$^9$C(O)N(C$_1$-C$_6$alkyl)(C$_1$-C$_6$alkyl). In some embodiments wherein R is —C$_0$-C$_6$alk-O—C$_1$-C$_6$alkyl and R$^{8'}$ is H, R$^5$ is —NR$^9$C(O)NH(C$_0$-C$_6$alk-O—C$_1$-C$_6$alkyl). In some embodiments wherein R$^{8'}$ and R$^{8'}$ are both —C$_0$-C$_6$alk-O—C$_1$-C$_6$alkyl, R$^5$ is —NR$^9$C(O)N(C$_0$-C$_6$alk-O—C$_1$-C$_6$alkyl)(C$_0$-C$_6$alk-O—C$_1$-C$_6$alkyl).

In some embodiments, R$^5$ in Formula III is —OC(O)NR$^8$R$^{8'}$. In some embodiments wherein R$^{8'}$ is H, R$^5$ is —OC(O)NHR$^{8'}$. In some embodiments wherein R$^8$ is H and R$^{8'}$ is H, R$^5$ is —OC(O)NH$_2$. In some embodiments wherein R$^8$ is —C$_1$-C$_6$alkyl and R$^{8'}$ is H, R$^5$ is —OC(O)NH(C$_1$-C$_6$alkyl). In some embodiments wherein R$^8$ and R$^{8'}$ are both —C$_1$-C$_6$alkyl, R$^5$ is —OC(O)N(C$_1$-C$_6$alkyl)(C$_1$-C$_6$alkyl). In some embodiments wherein R$^{8'}$ is —C$_0$-C$_6$alk-O—C$_1$-C$_6$alkyl and R$^{8'}$ is H, R$^5$ is —OC(O)NH(C$_0$-C$_6$alk-O—C$_1$-C$_6$alkyl). In some embodiments wherein R$^8$ and R$^{8'}$ are both —C$_0$-C$_6$alk-O—C$_1$-C$_6$alkyl, R$^5$ is —OC(O)N(C$_0$-C$_6$alk-O—C$_1$-C$_6$alkyl)(C$_0$-C$_6$alk-O—C$_1$-C$_6$alkyl).

In some embodiments, R$^5$ in Formula III is —NR$^9$C(O)OR$^{9a}$. In some embodiments wherein R$^9$ is H, R$^5$ is —NHC(O)OR$^{9a}$. In some embodiments wherein R$^9$ is —C$_1$-C$_6$alkyl, R$^5$ is —N(—C$_1$-C$_6$alkyl)C(O)OR$^{9a}$. In some embodiments wherein R$^9$ is C$_0$-C$_6$alk-C$_3$-C$_6$cycloalkyl, R$^5$ is —NC$_0$-C$_6$alk-C$_3$-C$_6$cycloalkyl)C(O)OR$^{9a}$. In some embodiments wherein R$^{9a}$ is —C$_1$-C$_6$alkyl, R$^5$ is —NR$^9$C(O)O—C$_1$-C$_6$alkyl. In some embodiments wherein R$^{9a}$ is —C$_0$-C$_6$alk-C$_3$-C$_6$cycloalkyl, R is —NR$^9$C(O)O—C$_0$-C$_6$alk-C$_3$-C$_6$cycloalkyl. In some embodiments wherein R$^9$ is H and R$^{9a}$ is —C$_1$-C$_6$alkyl, R$^5$ is —NHC(O)O—C$_1$-C$_6$alkyl. Thus, in some embodiments wherein R$^9$ is H and R$^{9a}$ is methyl, R$^5$ is —NHC(O)OCH$_3$.

In some aspects of Formula III, R$^8$ and R$^{8'}$ are each independently H, C$_1$-C$_6$alkyl, or —C$_0$-C$_6$alk-OC$_1$-C$_6$alkyl, or R$^8$ and R$^{8'}$, together with the atom to which they are attached, form a C$_3$-C$_6$cycloalkyl ring or a C$_2$-C$_6$heterocycloalkyl ring.

In some aspects of Formula III, R$^8$ and R$^{8'}$ are each independently H, C$_1$-C$_6$alkyl (e.g., methyl, ethyl, propyl, isopropyl, butyl, isobutyl, s-butyl, t-butyl, pentyl, and the like), or —C$_0$-C$_6$alk-OC$_1$-C$_6$alkyl, (for example, —C$_0$alk-O—C$_1$alkyl, —C$_1$alk-O—C$_1$alkyl, —C$_2$alk-O—C$_1$alkyl, —C$_6$alk-O—C$_1$alkyl, —C$_4$alk-O—C$_1$alkyl, —C$_5$alk-O—C$_1$alkyl, —C$_0$alk-O—C$_1$alkyl, —C$_0$alk-O—C$_2$alkyl, —C$_1$alk-O—C$_2$alkyl, —C$_2$alk-O—C$_2$alkyl, —C$_3$alk-O—C$_2$alkyl, —C$_4$alk-O—C$_2$alkyl, —C$_5$alk-O—C$_2$alkyl, —C$_6$alk-O—C$_2$alkyl, —C$_0$alk-O—C$_3$alkyl, —C$_1$alk-O—C$_3$alkyl, —C$_2$alk-O—C$_3$alkyl, —C$_3$alk-O—C$_3$alkyl, —C$_4$alk-O—C$_3$alkyl, —C$_5$alk-O—C$_3$alkyl, —C$_6$alk-O—C$_3$alkyl, —C$_0$alk-O—C$_4$alkyl, —C$_1$alk-O—C$_4$alkyl, —C$_2$alk-O—C$_4$alkyl, —C$_3$alk-O—C$_4$alkyl, —C$_4$alk-O—C$_4$alkyl, —C$_5$alk-O—C$_4$alkyl, —C$_6$alk-O—C$_4$alkyl, —C$_0$alk-O—C$_5$alkyl, —C$_1$alk-O—C$_5$alkyl, —C$_2$alk-O—C$_5$alkyl, —C$_3$alk-O—C$_5$alkyl, —C$_4$alk-O—C$_5$alkyl, —C$_5$alk-O—C$_5$alkyl, —C$_6$alk-O—C$_5$alkyl, —C$_0$alk-O—C$_6$alkyl, —C$_1$alk-O—C$_6$alkyl, —C$_2$alk-O—C$_6$alkyl, —C$_3$alk-O—C$_6$alkyl, —C$_4$alk-O—C$_6$alkyl, —C$_5$alk-O—C$_6$alkyl, and -C$_6$alk-O—C$_6$alkyl). In some embodiments, R$^8$ is C$_1$-C$_6$alkyl or —C$_0$-C$_6$alk-OC$_1$-C$_6$alkyl and R$^{8'}$ is H, C$_1$-C$_6$alkyl, or —C$_0$-C$_6$alk-OC$_1$-C$_6$alkyl.

In some embodiments of Formula III, R$^8$ is H or C$_1$-C$_6$alkyl. In some embodiments, R$^{8'}$ is H or C$_1$-C$_6$alkyl. In some embodiments, R$^8$ and R$^{8'}$ are each H. In other embodiments, R$^8$ and R$^{8'}$ are each independently C$_1$-C$_6$alkyl. In some aspects, R$^8$ is C$_1$-C$_6$alkyl and R$^{8'}$ is H.

In other aspects of Formula III, R$^8$ and R$^{8'}$ are each independently —C$_0$-C$_6$alk-OC$_1$-C$_6$alkyl.

In other aspects of Formula III, R$^{8'}$ is —C$_0$-C$_6$alk-OC$_1$-C$_6$alkyl and R$^{8'}$ is H.

In yet other aspects of Formula III, $R^8$ and $R^{8'}$, together with the atom to which they are attached, form a $C_2$-$C_6$cycloalkyl ring, for example, cyclopropyl, cyclobutyl, cyclopentyl, or cyclohexyl, and the like, or a $C_2$-$C_6$heterocycloalkyl ring, for example, aziridinyl, azetidinyl, pyrrolidinyl, piperidinyl, and the like.

In some aspects of Formula III, $R^9$ is H, —$C_1$-$C_6$alkyl (e.g., methyl, ethyl, propyl, isopropyl, butyl, isobutyl, s-butyl, t-butyl, pentyl, and the like), or $C_0$-$C_6$alk-$C_3$-$C_6$cycloalkyl (e.g., —$C_0$alk-$C_3$cycloalkyl, —$C_1$alk-$C_3$cycloalkyl, —$C_2$alk-$C_3$cycloalkyl, —$C_3$alk-$C_3$cycloalkyl, —$C_4$alk-$C_3$cycloalkyl, —$C_5$alk-$C_3$cycloalkyl, —$C_6$alk-$C_3$cycloalkyl, —$C_0$alk-$C_4$cycloalkyl, —$C_1$alk-$C_4$cycloalkyl, —$C_2$alk-$C_4$cycloalkyl, —$C_3$alk-$C_4$cycloalkyl, —$C_4$alk-$C_4$cycloalkyl, —$C_5$alk-$C_4$cycloalkyl, —$C_6$alk-$C_4$cycloalkyl, —$C_0$alk $C_5$cycloalkyl, —$C_1$alk-$C_5$cycloalkyl, —$C_2$alk-$C_5$cycloalkyl, —$C_3$alk-$C_5$cycloalkyl, —$C_4$alk-$C_5$cycloalkyl, —$C_5$alk-$C_5$cycloalkyl, —$C_6$alk-$C_5$cycloalkyl, —$C_0$alk-$C_6$cycloalkyl, —$C_1$alk-$C_6$cycloalkyl, —$C_2$alk-$C_6$cycloalkyl, —$C_3$alk-$C_6$cycloalkyl, —$C_4$alk-$C_6$cycloalkyl, —$C_6$alk-$C_6$cycloalkyl, and —$C_6$alk-$C_6$cycloalkyl).

In some aspects of Formula III, $R^{9a}$ is —$C_1$-$C_6$alkyl, or $C_0$-$C_6$alk-$C_3$-$C_6$cycloalkyl.

In some embodiments, $R^{9a}$ in Formula III is —$C_1$-$C_6$alkyl (e.g., methyl, ethyl, propyl, isopropyl, butyl, isobutyl, s-butyl, t-butyl, pentyl, and the like), or $C_0$-$C_6$alk-$C_3$-$C_6$cycloalkyl (e.g., —$C_0$alk-$C_3$cycloalkyl, —$C_1$alk-$C_3$cycloalkyl, —$C_2$alk-$C_3$cycloalkyl, —$C_3$alk-$C_3$cycloalkyl, —$C_4$alk-$C_3$cycloalkyl, —$C_5$alk-$C_3$cycloalkyl, —$C_6$alk-$C_3$cycloalkyl, —$C_0$alk-$C_4$cycloalkyl, —$C_1$alk-$C_4$cycloalkyl, —$C_2$alk-$C_4$cycloalkyl, —$C_3$alk-$C_4$cycloalkyl, —$C_4$alk-$C_4$cycloalkyl, —$C_5$alk-$C_4$cycloalkyl, —$C_6$alk-$C_4$cycloalkyl, —$C_0$alk-$C_5$cycloalkyl, —$C_1$alk-$C_5$cycloalkyl, —$C_2$alk-$C_5$cycloalkyl, —$C_3$alk-$C_5$cycloalkyl, —$C_4$alk-$C_5$cycloalkyl, —$C_5$alk-$C_5$cycloalkyl, —$C_6$alk-$C_5$cycloalkyl, —$C_0$alk-$C_6$cycloalkyl, —$C_1$alk-$C_6$cycloalkyl, —$C_2$alk-$C_6$cycloalkyl, —$C_3$alk-$C_6$cycloalkyl, —$C_4$alk-$C_6$cycloalkyl, —$C_6$alk-$C_6$cycloalkyl, and —$C_6$alk-$C_6$cycloalkyl).

In some aspects of Formula III and Formula IV, $R^6$ is $C_1$-$C_6$alkyl or $C_0$-$C_6$alk-$C_3$-$C_6$cycloalkyl. In some embodiments, $R^6$ is —$C_1$-$C_6$alkyl, for example, methyl, ethyl, propyl, isopropyl, butyl, isobutyl, s-butyl, t-butyl, pentyl, and the like. Thus, in some embodiments, $R^6$ is methyl (i.e., —$CH_3$, or Me). In other embodiments, $R^6$ is —$C_0$-$C_6$alk-$C_3$-$C_6$cycloalkyl, for example, —$C_0$alk-$C_3$cycloalkyl, —$C_1$alk-$C_3$cycloalkyl, —$C_2$alk-$C_3$cycloalkyl, —$C_3$alk-$C_3$cycloalkyl, —$C_4$alk-$C_3$cycloalkyl, —$C_5$alk-$C_3$cycloalkyl, —$C_6$alk-$C_3$cycloalkyl, —$C_0$alk-$C_4$cycloalkyl, —$C_1$alk-$C_4$cycloalkyl, —$C_2$alk-$C_4$cycloalkyl, —$C_3$alk-$C_4$cycloalkyl, —$C_4$alk-$C_4$cycloalkyl, —$C_6$alk-$C_4$cycloalkyl, —$C_0$alk-$C_5$cycloalkyl, —$C_1$alk-$C_5$cycloalkyl, —$C_2$alk-$C_5$cycloalkyl, —$C_3$alk-$C_5$cycloalkyl, —$C_4$alk-$C_5$cycloalkyl, —$C_5$alk-$C_5$cycloalkyl, —$C_0$alk-$C_5$cycloalkyl, —$C_1$alk-$C_6$cycloalkyl, —$C_3$alk-$C_6$cycloalkyl, —$C_5$alk-$C_6$cycloalkyl, —$C_6$cycloalkyl, In some aspects of Formula III and Formula IV, $R^{11}$ is H, —$C_1$-$C_6$alkyl, —$C_1$-$C_6$haloalkyl, —$C_0$-$C_6$alk-$C_3$-$C_6$cycloalkyl, —$C_0$-$C_6$alk-$C_3$-$C_6$halocycloalkyl, —$C_0$-$C_6$alk-OH, —$C_0$-$C_6$alk-$NH_2$, —$C_0$-$C_6$alk-NH—$C_1$-$C_6$alkyl, —$C_0$-$C_6$alk-N($C_1$-$C_6$alkyl)-$C_1$-$C_6$alkyl, —$C_0$-$C_6$alk-NH—$C_3$-$C_6$cycloalkyl, —$C_0$-$C_6$alk-N($C_1$-$C_6$alkyl)-$C_3$-$C_6$cycloalkyl; or $R^{11}$ and $R^1$, together with the atom to which they are attached, form a $C_3$-$C_6$cycloalkyl ring or a heterocycloalkyl ring.

In some embodiments, $R^{11}$ in Formula III and Formula IV is H.

In some embodiments, $R^{11}$ in Formula III and Formula IV is —$C_1$-$C_6$alkyl, for example, methyl, ethyl, propyl, isopropyl, butyl, isobutyl, s-butyl, t-butyl, pentyl, and the like.

In some embodiments, $R^{11}$ in Formula III and Formula IV is —$C_1$-$C_6$haloalkyl, for example, $C_1$haloalkyl, $C_2$haloalkyl, $C_3$haloalkyl, $C_4$haloalkyl, $C_5$haloalkyl, or $C_6$haloalkyl.

In some aspects, $R^{11}$ in Formula III and Formula IV is —$C_0$-$C_6$alk-$C_3$-$C_6$cycloalkyl, for example —$C_0$alk-$C_3$cycloalkyl, —$C_1$alk-$C_3$cycloalkyl, —$C_2$alk-$C_3$cycloalkyl, —$C_3$alk-$C_3$cycloalkyl, —$C_4$alk-$C_3$cycloalkyl, —$C_5$alk-$C_3$cycloalkyl, —$C_6$alk-$C_3$cycloalkyl, —$C_0$alk-$C_4$cycloalkyl, —$C_1$alk-$C_4$cycloalkyl, —$C_2$alk-$C_4$cycloalkyl, —$C_3$alk-$C_4$cycloalkyl, —$C_4$alk-$C_4$cycloalkyl, —$C_6$alk-$C_4$cycloalkyl, —$C_0$alk-$C_5$cycloalkyl, —$C_1$alk-$C_5$cycloalkyl, —$C_2$alk-$C_5$cycloalkyl, —$C_3$alk-$C_5$cycloalkyl, —$C_4$alk-$C_5$cycloalkyl, —$C_5$alk-$C_5$cycloalkyl, —$C_6$alk-$C_5$cycloalkyl, —$C_0$alk-$C_6$cycloalkyl, —$C_1$alk-$C_6$cycloalkyl, —$C_2$alk-$C_6$cycloalkyl, —$C_3$alk-$C_6$cycloalkyl, —$C_4$alk-$C_6$cycloalkyl, —$C_5$alk-$C_6$cycloalkyl, and —$C_6$alk-$C_6$cycloalkyl. In some embodiments, $R^{11}$ is —$C_1$alk-$C_3$cycloalkyl. Thus, in some embodiments, $R^{11}$ is —$CH_2$-cyclopropyl.

In some aspects, $R^{11}$ in Formula III and Formula IV is —$C_0$-$C_6$alk-$C_3$-$C_6$halocycloalkyl, for example —$C_0$alk-$C_3$halocycloalkyl, —$C_1$alk-$C_3$halocycloalkyl, —$C_2$alk-$C_3$halocycloalkyl, —$C_3$alk-$C_3$halocycloalkyl, —$C_4$alk-$C_3$halocycloalkyl, —$C_5$alk-$C_3$halocycloalkyl, —$C_6$alk-$C_3$halocycloalkyl, —$C_0$alk-$C_4$halocycloalkyl, —$C_1$alk-$C_4$halocycloalkyl, —$C_2$alk-$C_4$halocycloalkyl, —$C_3$alk-$C_4$halocycloalkyl, —$C_4$alk-$C_4$halocycloalkyl, —$C_5$alk-$C_4$halocycloalkyl, —$C_6$alk-$C_4$halocycloalkyl, —$C_0$alk-$C_5$halocycloalkyl, —$C_1$alk-$C_5$halocycloalkyl, —$C_2$alk-$C_5$halocycloalkyl, —$C_3$alk-$C_5$halocycloalkyl, —$C_4$alk-$C_5$halocycloalkyl, —$C_5$alk-$C_5$halocycloalkyl, —$C_6$alk-$C_5$halocycloalkyl, —$C_0$alk-$C_6$halocycloalkyl, —$C_1$alk-$C_6$halocycloalkyl, —$C_2$alk-$C_6$halocycloalkyl, —$C_3$alk-$C_6$halocycloalkyl, —$C_4$alk-$C_6$halocycloalkyl, —$C_5$alk-$C_6$halocycloalkyl, and —$C_6$alk-$C_6$halocycloalkyl.

In some aspects, $R^{11}$ in Formula III and Formula IV is —$C_0$-$C_6$alk-OH, for example, —$C_0$alk-OH (i.e., —OH), —$C_1$alk-OH, —$C_2$alk-OH, —$C_3$alk-OH, —$C_4$alk-OH, —$C_5$alk-OH, —$C_6$alk-OH, and the like. In some embodiments, $R^{11}$ is —$C_1$alk-OH. Thus, in some embodiments, $R^{11}$ is hydroxymethyl (i.e., —$CH_2$OH).

In some aspects, $R^{11}$ in Formula III and Formula IV is —$C_0$-$C_6$alk-$NH_2$, for example, —$C_0$alk-$NH_2$ (i.e., —$NH_2$), —$C_1$alk-$NH_2$, —$C_2$alk-$NH_2$, —$C_3$alk-$NH_2$, —$C_4$alk-$NH_2$, —$C_5$alk-$NH_2$, —$C_6$alk-$NH_2$, and the like. In some embodiments, $R^{11}$ is —$C_1$alk-$NH_2$. Thus, in some embodiments, $R^{11}$ is aminomethyl (i.e., —$CH_2NH_2$).

In some aspects, $R^{11}$ in Formula III and Formula IV is —$C_0$-$C_6$alk-NH—$C_1$-$C_6$alkyl, for example, —$C_0$alk-NH—$C_1$alkyl, —$C_1$alk-NH—$C_1$alkyl, —$C_2$alk-NH—$C_1$alkyl, —$C_3$alk-NH—$C_1$alkyl, —$C_4$alk-NH—$C_1$alkyl, —$C_6$alk-NH—$C_1$alkyl, —$C_6$alk-NH—$C_1$alkyl, —$C_0$alk-NH—$C_2$alkyl, —$C_1$alk-NH—$C_2$alkyl, —$C_2$alk-NH—$C_2$alkyl, —$C_3$alk-NH—$C_2$alkyl, —$C_4$alk-NH—$C_2$alkyl, —$C_5$alk- NH—C$_2$alkyl, —C$_6$alk-NH—C$_2$alkyl, —C$_0$alk-NH—C$_3$alkyl, —C$_1$alk-NH—C$_3$alkyl, —C$_2$alk-NH—C$_3$alkyl, —C$_3$alk-NH—C$_3$alkyl, —C$_4$alk-NH—C$_3$alkyl, —C$_5$alk-NH—C$_3$alkyl, —C$_6$alk-NH—C$_3$alkyl, —C$_0$alk-NH—C$_4$alkyl, —C$_1$alk-NH—C$_4$alkyl, —C$_2$alk-NH—C$_4$alkyl, —C$_3$alk-NH—C$_4$alkyl, —C$_4$alk-NH—C$_4$alkyl, —C$_5$alk-NH—C$_4$alkyl, —C$_6$alk-NH—C$_4$alkyl, —C$_0$alk-NH—C$_5$alkyl, —C$_1$alk-NH—C$_5$alkyl, —C$_2$alk-NH—C$_5$alkyl, —C$_3$alk-NH—C$_5$alkyl, —C$_4$alk-NH—C$_5$alkyl, —C$_5$alk-NH—C$_5$alkyl, —C$_6$alk-NH—C$_5$alkyl, —C$_0$alk-NH—C$_6$alkyl, —C$_1$alk-NH—C$_6$alkyl, —C$_2$alk-NH—C$_6$alkyl, —C$_3$alk-NH—C$_6$alkyl, —C$_4$alk-NH—C$_6$alkyl, —C$_5$alk-NH—C$_6$alkyl, and —C$_6$alk-NH—C$_6$alkyl.

In some aspects, $R^{11}$ in Formula III and Formula IV is —C$_0$-C$_6$alk-N(C$_1$-C$_6$alkyl)-C$_1$-C$_6$alkyl, for example, —C$_0$alk-N(C$_1$-C$_6$alkyl)-C$_1$alkyl, —C$_1$alk-N(C$_1$-C$_6$alkyl)-C$_1$alkyl, —C$_2$alk-N(C$_1$-C$_6$alkyl)-C$_1$alkyl, —C$_3$alk-N(C$_1$-C$_6$alkyl)-C$_1$alkyl, —C$_4$alk-N(C$_1$-C$_6$alkyl)-C$_1$alkyl, —C$_5$alk-N(C$_1$-C$_6$alkyl)-C$_1$alkyl, —C$_6$alk-N(C$_1$-C$_6$alkyl)-C$_1$alkyl, —C$_0$alk-N(C$_1$-C$_6$alkyl)-C$_2$alkyl, —C$_1$alk-N(C$_1$-C$_6$alkyl)-C$_2$alkyl, —C$_2$alk-N(C$_1$-C$_6$alkyl)-C$_2$alkyl, —C$_3$alk-N(C$_1$-C$_6$alkyl)-C$_2$alkyl, —C$_4$alk-N(C$_1$-C$_6$alkyl)-C$_2$alkyl, —C$_5$alk-N(C$_1$-C$_6$alkyl)-C$_2$alkyl, —C$_6$alk-N(C$_1$-C$_6$alkyl)-C$_2$alkyl, —C$_0$alk-N(C$_1$-C$_6$alkyl)-C$_3$alkyl, —C$_1$alk-N(C$_1$-C$_6$alkyl)-C$_3$alkyl, —C$_2$alk-N(C$_1$-C$_6$alkyl)-C$_3$alkyl, —C$_3$alk-N(C$_1$-C$_6$alkyl)-C$_3$alkyl, —C$_4$alk-N(C$_1$-C$_6$alkyl)-C$_3$alkyl, —C$_5$alk-N(C$_1$-C$_6$alkyl)-C$_3$alkyl, —C$_6$alk-N(C$_1$-C$_6$alkyl)-C$_3$alkyl, —C$_0$alk-N(C$_1$-C$_6$alkyl)-C$_4$alkyl, —C$_1$alk-N(C$_1$-C$_6$alkyl)-C$_4$alkyl, —C$_2$alk-N(C$_1$-C$_6$alkyl)-C$_4$alkyl, —C$_3$alk-N(C$_1$-C$_6$alkyl)-C$_4$alkyl, —C$_4$alk-N(C$_1$-C$_6$alkyl)-C$_4$alkyl, —C$_5$alk-N(C$_1$-C$_6$alkyl)-C$_4$alkyl, —C$_6$alk-N(C$_1$-C$_6$alkyl)-C$_4$alkyl, —C$_0$alk-N(C$_1$-C$_6$alkyl)-C$_5$alkyl, —C$_1$alk-N(C$_1$-C$_6$alkyl)-C$_5$alkyl, —C$_2$alk-N(C$_1$-C$_6$alkyl)-C$_5$alkyl, —C$_3$alk-N(C$_1$-C$_6$alkyl)-C$_5$alkyl, —C$_4$alk-N(C$_1$-C$_6$alkyl)-C$_5$alkyl, —C$_5$alk-N(C$_1$-C$_6$alkyl)-C$_5$alkyl, —C$_6$alk-N(C$_1$-C$_6$alkyl)-C$_5$alkyl, —C$_0$alk-N(C$_1$-C$_6$alkyl)-C$_6$alkyl, —C$_1$alk-N(C$_1$-C$_6$alkyl)-C$_6$alkyl, —C$_2$alk-N(C$_1$-C$_6$alkyl)-C$_6$alkyl, —C$_3$alk-N(C$_1$-C$_6$alkyl)-C$_6$alkyl, —C$_4$alk-N(C$_1$-C$_6$alkyl)-C$_6$alkyl, —C$_5$alk-N(C$_1$-C$_6$alkyl)-C$_6$alkyl, —C$_6$alk-N(C$_1$-C$_6$alkyl)-C$_6$alkyl and the like.

In some aspects, $R^{11}$ in Formula III and Formula IV is —C$_0$-C$_6$alk-NH—C$_3$-C$_6$cycloalkyl, for example, —C$_0$alk-NH—C$_3$cycloalkyl, —C$_1$alk-NH—C$_3$cycloalkyl, —C$_2$alk-NH—C$_3$cycloalkyl, —C$_3$alk-NH—C$_3$cycloalkyl, —C$_4$alk-NH—C$_3$cycloalkyl, —C$_5$alk-NH—C$_3$cycloalkyl, —C$_6$alk-NH—C$_3$cycloalkyl, —C$_0$alk-NH—C$_4$cycloalkyl, —C$_1$alk-NH—C$_4$cycloalkyl, —C$_2$alk-NH—C$_4$cycloalkyl, —C$_3$alk-NH—C$_4$cycloalkyl, —C$_4$alk-NH—C$_4$cycloalkyl, —C$_5$alk-NH—C$_4$cycloalkyl, —C$_6$alk-NH—C$_4$cycloalkyl, —C$_0$alk-NH—C$_5$cycloalkyl, —C$_1$alk-NH—C$_5$cycloalkyl, —C$_2$alk-NH—C$_5$cycloalkyl, —C$_3$alk-NH—C$_5$cycloalkyl, —C$_4$alk-NH—C$_5$cycloalkyl, —C$_5$alk-NH—C$_5$cycloalkyl, —C$_6$alk-NH—C$_5$cycloalkyl, —C$_0$alk-NH—C$_6$cycloalkyl, —C$_1$alk-NH—C$_6$cycloalkyl, —C$_2$alk-NH—C$_6$cycloalkyl, —C$_3$alk-NH—C$_6$cycloalkyl, —C$_4$alk-NH—C$_6$cycloalkyl, —C$_5$alk-NH—C$_6$cycloalkyl, —C$_6$alk-NH—C$_6$cycloalkyl, and the like.

In some aspects, $R^{11}$ in Formula III and Formula IV is —C$_0$-C$_6$alk-N(C$_1$-C$_6$alkyl)-C$_3$-C$_6$cycloalkyl, for example, —C$_0$alk-N(C$_1$-C$_6$alkyl)-C$_3$cycloalkyl, —C$_1$alk-N(C$_1$-C$_6$alkyl)-C$_3$cycloalkyl, —C$_2$alk-N(C$_1$-C$_6$alkyl)-C$_3$cycloalkyl, —C$_3$alk-N(C$_1$-C$_6$alkyl)-C$_3$cycloalkyl, —C$_4$alk-N(C$_1$-C$_6$alkyl)-C$_3$cycloalkyl, —C$_5$alk-N(C$_1$-C$_6$alkyl)-C$_3$cycloalkyl, —C$_6$alk-N(C$_1$-C$_6$alkyl)-C$_3$cycloalkyl, —C$_0$alk-N(C$_1$-C$_6$alkyl)-C$_4$cycloalkyl, —C$_1$alk-N(C$_1$-C$_6$alkyl)-C$_4$cycloalkyl, —C$_2$alk-N(C$_1$-C$_6$alkyl)-C$_4$cycloalkyl, —C$_3$alk-N(C$_1$-C$_6$alkyl)-C$_4$cycloalkyl, —C$_4$alk-N(C$_1$-C$_6$alkyl)-C$_4$cycloalkyl, —C$_5$alk-N(C$_1$-C$_6$alkyl)-C$_4$cycloalkyl, —C$_6$alk-N(C$_1$-C$_6$alkyl)-C$_4$cycloalkyl, —C$_0$alk-N(C$_1$-C$_6$alkyl)-C$_5$cycloalkyl, —C$_1$alk-N(C$_1$-C$_6$alkyl)-C$_5$cycloalkyl, —C$_2$alk-N(C$_1$-C$_6$alkyl)-C$_5$cycloalkyl, —C$_3$alk-N(C$_1$-C$_6$alkyl)-C$_5$cycloalkyl, —C$_4$alk-N(C$_1$-C$_6$alkyl)-C$_5$cycloalkyl, —C$_5$alk-N(C$_1$-C$_6$alkyl)-C$_5$cycloalkyl, —C$_6$alk-N(C$_1$-C$_6$alkyl)-C$_5$cycloalkyl, —C$_0$alk-N(C$_1$-C$_6$alkyl)-C$_6$cycloalkyl, —C$_1$alk-N(C$_1$-C$_6$alkyl)-C$_6$cycloalkyl, —C$_2$alk-N(C$_1$-C$_6$alkyl)-C$_6$cycloalkyl, —C$_3$alk-N(C$_1$-C$_6$alkyl)-C$_6$cycloalkyl, —C$_4$alk-N(C$_1$-C$_6$alkyl)-C$_6$cycloalkyl, —C$_5$alk-N(C$_1$-C$_6$alkyl)-C$_6$cycloalkyl, —C$_6$alk-N(C$_1$-C$_6$alkyl)-C$_6$cycloalkyl, and the like.

In some aspects of Formula III and Formula IV, $R^{11}$ and $R^1$, together with the atom to which they are attached, form a C$_3$-C$_6$cycloalkyl ring or a heterocycloalkyl ring.

In some aspects of Formula III, $R^{10}$ is -halo or —C$_1$-C$_6$alkyl. Thus in some embodiments of the compound of Formula III, $R^1$ is halo (e.g., —F, —Cl, —Br, or —I). Thus, in some embodiments of the compound of Formula III, $R^{10}$ is —F. In other embodiments of the compound of Formula III, $R^{10}$ is —Cl.

In other aspects of Formula III, $R^{10}$ is —C$_1$-C$_6$alkyl (e.g., methyl, ethyl, propyl, isopropyl, butyl, isobutyl, s-butyl, t-butyl, pentyl, and the like). Thus in some embodiments of Formula III, $R^{11}$ is methyl (i.e., —CH$_3$, or Me).

In some aspects of Formula IV, $R^{10a}$ is H, halo, or —C$_1$-C$_6$alkyl. Thus in some embodiments of the compounds of Formula IV, $R^{10a}$ is H. In other embodiments of the compound of Formula IV, $R^{10a}$ is halo, for example, —F, —Cl, —Br, or —I. Thus, in some embodiments, $R^{10a}$ is —F. In yet other embodiments of the compound of Formula IV, $R^{10a}$ is —Cl. In other embodiments of the compounds of Formula IV, $R^{10a}$ is —C$_1$-C$_6$alkyl, for example, methyl, ethyl, propyl, isopropyl, butyl, isobutyl, s-butyl, t-butyl, pentyl, and the like. Thus, in some embodiments, $R^{10a}$ is methyl (i.e., —CH$_3$, or Me).

In preferred embodiments of the compounds of Formula III or Formula IV, $R^1$ is —C$_0$-C$_6$alk-C$_1$-C$_6$alkyl, —C$_0$-C$_6$alk-C$_1$-C$_6$haloalkyl, —C$_0$-C$_6$alk-C≡CH, —C$_0$-C$_6$alk-C≡C—C$_1$-C$_6$alkyl, —C$_0$-C$_6$alk-C≡C—C$_1$-C$_6$haloalkyl, —C$_0$-C$_6$alk-C≡C—C$_3$-C$_6$cycloalkyl, —C$_1$-C$_6$alk-aryl, —C$_0$-C$_6$alk-S-aryl, —C$_0$-C$_6$alk-S(O)-aryl, —C$_0$-C$_6$alk-S(O)$_2$-aryl, or —C$_0$-C$_6$alk-O-aryl.

More preferred embodiments of the compounds of Formula III or Formula IV are those wherein $R^1$ is —CH(OH)—C$_1$-C$_6$alkyl, —CH(F)—C$_1$-C$_6$alkyl, —CH(NH$_2$)—C$_1$-C$_6$alkyl, —CH(Me)-C$_1$-C$_6$alkyl, —C(Me)(OH)—C$_1$-C$_6$alkyl, —CH(OH)—C$_1$-C$_6$ haloalkyl, —CH(F)—C$_1$-C$_6$ haloalkyl, —CH(NH$_2$)—C$_1$-C$_6$ haloalkyl, —CH(Me)-C$_1$-C$_6$ haloalkyl, —C(Me)(OH)—C$_1$-C$_6$ haloalkyl, —CH(OH)—C≡CH, —CH(F)—C≡CH, —CH(NH$_2$)—C≡CH, —CH(Me)-C≡CH, —C(Me)(OH)—C≡CH, —CH(OH)—C≡C—C$_1$-C$_6$alkyl, —CH(F)—C≡C—C$_1$-C$_6$alkyl, —CH(NH$_2$)—C≡C—C$_1$-C$_6$alkyl, —CH(Me)-C≡C—C$_1$-C$_6$alkyl, —C(Me)(OH)—C≡C—C$_1$-C$_6$alkyl, —CH(OH)—C≡C—C$_1$-C$_6$haloalkyl, —CH(F)—C≡C—C$_1$-C$_6$haloalkyl, —CH(NH$_2$)—C≡C—C$_1$-C$_6$haloalkyl, —CH(Me)-C≡C—C$_1$-C$_6$haloalkyl, —C(Me)(OH)—C≡C—C$_1$-C$_6$haloalkyl, —CH(OH)—C≡C—C$_3$-C$_6$cycloalkyl, —CH(F)—C≡C—C$_3$-C$_6$cycloalkyl, —CH(NH$_2$)—C≡C—C$_3$-C$_6$cycloalkyl, —CH(Me)-C≡C—C$_3$-C$_6$cycloalkyl, —C(Me)(OH)—C≡C—C$_3$-C$_6$cycloalkyl, —CH$_2$-aryl, —CH(OH)-aryl, —CH(F)-aryl, —CH(NH₂)-aryl, —CH(Me)-aryl, —C(Me)(OH)-aryl, —S-aryl, —S(O)-aryl, —S(O)₂-aryl, or —O-aryl.

Most preferred embodiments of the compounds of Formula III or Formula IV are those wherein R¹ is —CH(OH)—C≡C—CH₃, —CH(F)—C≡C—CH₃, —CH(NH₂)—C≡C—CH₃, —CH(Me)-C≡C—CH₃, or —C(Me)(OH)—C≡C—CH₃, —CH(OH)—C≡C—CH₃, —CH(OH)—C≡C—CF₃, —CH(F)—C≡C—CF₃, —CH(NH₂)—C≡C—CF₃, —CH(Me)-C≡C—CF₃, or —C(Me)(OH)—C≡C—CF₃, —CH(OH)—C≡C-cyclopropyl, —CH(F)—C≡C-cyclopropyl, —CH(NH₂)—C≡C-cyclopropyl, —CH(Me)-C≡C-cyclopropyl, or —C(Me)(OH)—C—C-cyclopropyl, —CH₂-4-chlorophenyl, —CH₂-3,4-dichlorophenyl, —CH₂-3,4-difluorophenyl, —CH₂-3-fluoro-4-chlorophenyl, —CH₂-3-chloro-4-fluorophenyl, —CH(OH)-4-chlorophenyl, —CH(OH)-3,4-dichlorophenyl, —CH(OH)-3,4-difluorophenyl, —CH(OH)-3-fluoro-4-chlorophenyl, —CH(OH)-3-chloro-4-fluorophenyl, —CH(F)-aryl-4-chlorophenyl, —CH(F)-3,4-dichlorophenyl, —CH(F)-3,4-difluorophenyl, —CH(F)-3-fluoro-4-chlorophenyl, —CH(F)-3-chloro-4-fluorophenyl, —CH(NH₂)-aryl-4-chlorophenyl, —CH(NH₂)-3,4-dichlorophenyl, —CH(NH₂)-3,4-difluorophenyl, —CH(NH₂)-3-fluoro-4-chlorophenyl, —CH(NH₂)-3-chloro-4-fluorophenyl, —CH(Me)-aryl-4-chlorophenyl, —CH(Me)-3,4-dichlorophenyl, —CH(Me)-3,4-difluorophenyl, —CH(Me)-3-fluoro-4-chlorophenyl, —CH(Me)-3-chloro-4-fluorophenyl, —C(Me)(OH)-aryl-4-chlorophenyl, —C(Me)(OH)-3,4-dichlorophenyl, —C(Me)(OH)-3,4-difluorophenyl, —C(Me)(OH)-3-fluoro-4-chlorophenyl, or —C(Me)(OH)-3-chloro-4-fluorophenyl, —S-4-chlorophenyl, —S-3,4-dichlorophenyl, —S-3,4-difluorophenyl, —S-3-fluoro-4-chlorophenyl, or —S-3-chloro-4-fluorophenyl, —S(O)-4-chlorophenyl, —S(O)-3,4-dichlorophenyl, —S(O)-3,4-difluorophenyl, —S(O)-3-fluoro-4-chlorophenyl, or —S(O)-3-chloro-4-fluorophenyl, —S(O)₂-4-chlorophenyl, —S(O)₂-3,4-dichlorophenyl, —S(O)₂-3,4-difluorophenyl, —S(O)₂-3-fluoro-4-chlorophenyl, or —S(O)₂-3-chloro-4-fluorophenyl, —O-4-chlorophenyl, —O-3,4-dichlorophenyl, —O-3,4-difluorophenyl, —O-3-fluoro-4-chlorophenyl, or —O-3-chloro-4-fluorophenyl.

In some preferred embodiments, R¹ is ((cyclopropylmethyl)amino)quinolin-7-yl-ethyl, 2-(methylamino)quinolin-7-yl)ethyl, 2-(2-aminoquinolin-7-yl)ethyl, 2-(2-amino-3-chloroquinolin-7-yl)ethyl, R¹ is —CH(OH)-4-chlorophenyl, —CH(OH)-3,4-difluorophenyl, —CH(OH)-3,4-dichlorophenyl, or —C(Me)(OH)-3,4-dichlorophenyl.

Some aspects of the disclosure are directed to compounds of Formula IIID or IVD:

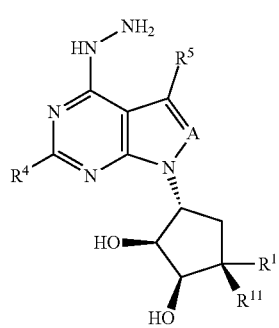

IIID

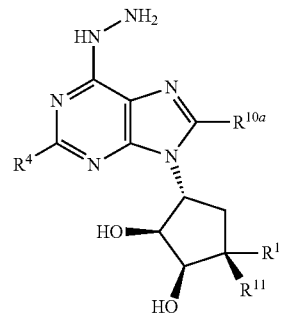

IVD

In some embodiments, the disclosure is directed to compounds of Formula IIID, wherein A is CH, R¹ is —C₁-C₆alkaryl, R⁴ is H, R⁵ is H or F, and R¹¹ is H. In some embodiments, the compounds of Formula IIID are those wherein A is CH, R¹ is —CH(OH)-4-chlorophenyl, —CH(OH)-3,4-difluorophenyl, —CH(OH)-3,4-dichlorophenyl, or —C(Me)(OH)-3,4-dichlorophenyl, R⁴ is H, R⁵ is H or F, and R¹¹ is H.

Some aspects of the disclosure are directed to compounds of Formula IIIE or IVE:

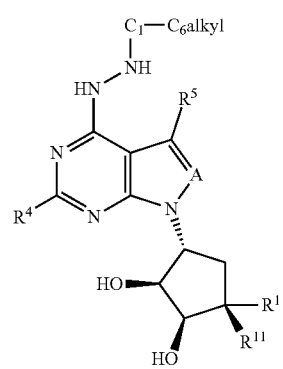

IIIE

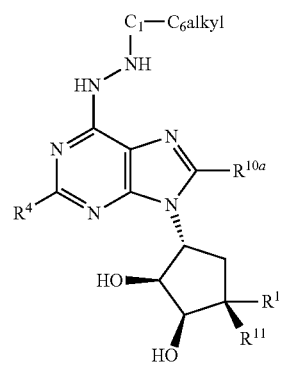

IVE

In some embodiments, the compounds of Formula IIIE are those wherein A is CH, R¹ is —C₀-C₆alk-heteroaryl, R⁴ is H, R⁵ is H, R¹¹ is H, and —C₁-C₆alkyl is methyl. In some embodiments, the compounds of Formula IIIE are those wherein A is CH, R¹ is ((cyclopropylmethyl)amino)quinolin-7-yl-ethyl, 2-(methylamino)quinolin-7-yl)ethyl, 2-(2-aminoquinolin-7-yl)ethyl, or 2-(2-amino-3-chloroquinolin-7-yl)ethyl; R⁴ is H, R⁵ is H, R¹¹ is H, and —C₁-C₆alkyl is methyl.

Some aspects of the disclosure are directed to compounds of Formula IIIF or IVF:

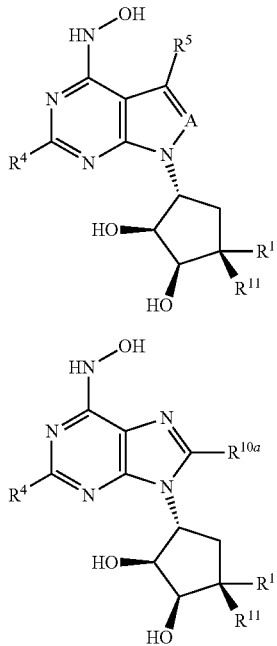

In some embodiments, the disclosure is directed to compounds of Formula IIIF, wherein A is CH, $R^1$ is —$C_1$-$C_6$alk-aryl or —$C_0$-$C_6$alk-heteroaryl, $R^4$ is H, $R^5$ is H, and $R^{11}$ is H. In some embodiments, the compounds of Formula IIIF are those wherein A is CH, $R^1$ is —$C_1$-$C_6$alk-aryl, $R^4$ is H, $R^5$ is H or F, and $R^{11}$ is H. In some embodiments, the compounds of Formula IIIF are those wherein A is CH, $R^1$ is —CH(OH)-4-chlorophenyl, —CH(OH)-3,4-difluorophenyl, —CH(OH)-3,4-dichlorophenyl, or —C(Me)(OH)-3,4-dichlorophenyl; $R^4$ is H, $R^5$ is H or F, and $R^{11}$ is H. In some embodiments, the compounds of Formula IIIF are those wherein A is CH, $R^1$ is —$C_0$-$C_6$alk-heteroaryl, $R^4$ is H, $R^5$ is H or F, and $R^{11}$ is H. In some embodiments, the compounds of Formula IIIF are those wherein A is CH, R is ((cyclopropylmethyl)amino)quinolin-7-yl-ethyl, 2-(methylamino)quinolin-7-yl)ethyl, 2-(2-aminoquinolin-7-yl)ethyl, or 2-(2-amino-3-chloroquinolin-7-yl)ethyl, $R^4$ is H, $R^5$ is H or F, and $R^{11}$ is H.

Some aspects of the disclosure are directed to compounds of Formula IIIG or IVG:

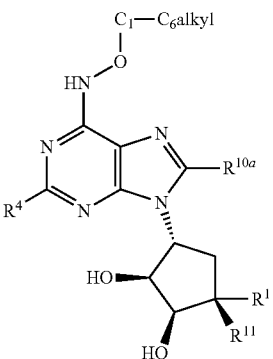

In some embodiments, the disclosure is directed to compounds of Formula IIIG, wherein A is CH, $R^1$ is —$C_1$-$C_6$alk-aryl or —$C_0$-$C_6$alk-heteroaryl, $R^4$ is H, R is H, $R^{11}$ is H, and —$C_1$-$C_6$alkyl is methyl. In some embodiments, the compounds of Formula IIIG are those wherein A is CH, $R^1$ is —$C_1$-$C_6$alk-aryl, $R^4$ is H, $R^5$ is H, $R^{11}$ is H, and —$C_1$-$C_6$alkyl is methyl. In some embodiments, the compounds of Formula IIIG are those wherein A is CH, $R^1$ is —CH(OH)-4-chlorophenyl, —CH(OH)-3,4-difluorophenyl, —CH(OH)-3,4-dichlorophenyl, or —C(Me)(OH)-3,4-dichlorophenyl; $R^4$ is H, $R^5$ is H, $R^{11}$ is H, and —$C_1$-$C_6$alkyl is methyl. In some embodiments, the compounds of Formula IIIG are those wherein A is CH, $R^1$ is —$C_0$-$C_6$alk-heteroaryl, $R^4$ is H, $R^5$ is H, $R^{11}$ is H, and —$C_1$-$C_6$alkyl is methyl.

In some embodiments, the compounds of Formula IIIG are those wherein A is CH, $R^1$ is ((cyclopropylmethyl)amino)quinolin-7-yl-ethyl, 2-(methylamino)quinolin-7-yl) ethyl, 2-(2-aminoquinolin-7-yl)ethyl, or 2-(2-amino-3-chloroquinolin-7-yl)ethyl; $R^4$ is H, $R^5$ is H, $R^{11}$ is H, and —$C_1$-$C_6$alkyl is methyl.

Some aspects of the disclosure are directed to compounds of Formula IIIH or IVH:

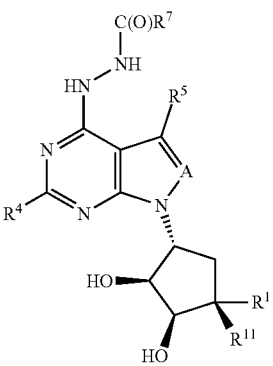

IVH

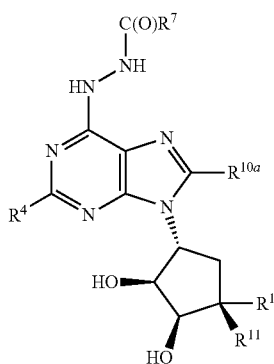

Some aspects of the disclosure are directed to compounds of Formula IIIB

IIIB

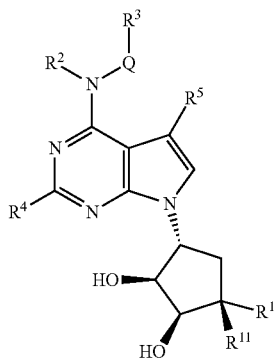

wherein Q is NH, $R^1$ is —$C_1$-$C_6$alk-aryl or —$C_0$-$C_6$alk-heteroaryl, $R^2$ is methyl, $R^3$ is H, $R^4$ is H, $R^5$ is H, and $R^{11}$ is H. In some embodiments, the compounds of Formula IIIB are those wherein Q is NH, $R^1$ is —$C_1$-$C_6$alk-aryl, $R^2$ is methyl, $R^3$ is H, $R^4$ is H, $R^5$ is H, and $R^{11}$ is H. In some embodiments, the compounds of Formula IIIB are those wherein Q is NH, $R^1$ is —CH(OH)-4-chlorophenyl, —CH(OH)-3,4-difluorophenyl, —CH(OH)-3,4-dichlorophenyl, or —C(Me)(OH)-3,4-dichlorophenyl; $R^2$ is methyl, $R^3$ is H, $R^4$ is H, $R^5$ is H, and $R^{11}$ is H. In some embodiments, the compounds of Formula IIIB are those wherein Q is NH, $R^1$ is —$C_0$-$C_6$alk-heteroaryl, $R^2$ is methyl, $R^3$ is H, $R^4$ is H, $R^5$ is H, and $R^{11}$ is H. In some embodiments, the compounds of Formula IIIB are those wherein Q is NH, $R^1$ is ((cyclopropylmethyl)amino)quinolin-7-yl-ethyl, 2-(methylamino)quinolin-7-yl)ethyl, 2-(2-aminoquinolin-7-yl)ethyl, or 2-(2-amino-3-chloroquinolin-7-yl)ethyl; $R^2$ is methyl, $R^3$ is H, $R^4$ is H, $R^5$ is H, and $R^{11}$ is H.

Stereoisomers of compounds of Formula III or Formula IV are also contemplated.

Pharmaceutically acceptable salts and solvates of the compounds of Formula III or Formula IV are also within the scope of the disclosure.

The disclosure is also directed to compounds of Formula V or Formula VI, as well as pharmaceutically acceptable salts of compounds of Formula V and of Formula VI. In some aspects, the disclosure is directed to compounds and salts of Formula V:

V

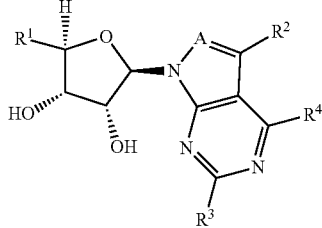

In other aspects, the disclosure is directed to compounds and salts of Formula VI:

VI

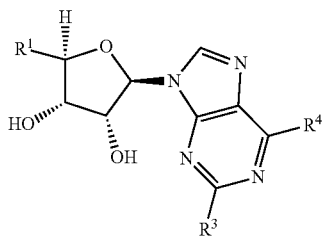

According to the disclosure, A in Formula V is N or CH. In some aspects, A is N and the compounds of Formula V are of Formula VA:

VA

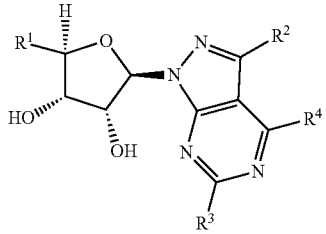

In some aspects, A is CH and the compounds of Formula V are of Formula VB:

VB

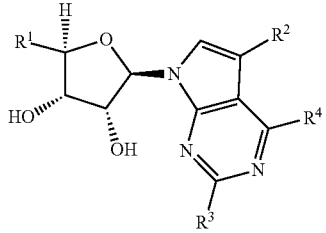

According to the disclosure, $R^1$ in Formula V or Formula VI is —$C_1$-$C_6$alk-aryl, —$C_1$-$C_6$alk-heteroaryl, —$C_1$-$C_6$alk-C≡CH, —$C_1$-$C_6$alk-C≡C—$C_1$-$C_6$alkyl, —$C_1$-$C_6$alk-C≡C—$C_1$-$C_6$haloalkyl, or —$C_1$-$C_6$alk-C≡C—$C_3$-$C_6$cycloalkyl.

In some aspects, $R^1$ in Formula V or Formula VI is —$C_1$-$C_6$alk-aryl, for example, —$C_1$alk-aryl, —$C_2$alk-aryl, —$C_3$alk-aryl, —$C_4$alk-aryl, —$C_5$alk-aryl, —$C_6$alk-aryl, —$CH_2$aryl, —CH(OH)-aryl, —CH(F)-aryl, —CH($NH_2$)-aryl, —CH(Me)-aryl, —C(Me)(OH)-aryl, —CH($CH_2$OH)- aryl and the like. In some embodiments the -aryl is -4-chlorophenyl, -3,4-dichlorophenyl, -3,4-difluorophenyl, -3-fluoro-4-chlorophenyl, 3-methyl-4-chlorophenyl, 3-fluoro-4-trifluoromethylphenyl, 4-trifluoromethylphenyl, 3-methyl-4-trifluoromethylphenyl, or -3-chloro-4-fluorophenyl.

Thus in some embodiments, $R^1$ in Formula V or Formula VI is —$CH_2$-aryl, for example, —$CH_2$-difluorophenyl, —$CH_2$-3,4-difluorophenyl, —$CH_2$-4-chlorophenyl, —$CH_2$-3-chloro-4-fluorophenyl, —$CH_2$-4-chloro-3-fluorophenyl, —$CH_2$-dichlorophenyl, —$CH_2$-3,4-dichlorophenyl, —$CH_2$-3-methyl-4-chlorophenyl, —$CH_2$-3-fluoro-4-trifluoromethylphenyl, —$CH_2$-4-trifluoromethylphenyl, —$CH_2$-3-methyl-4-trifluoromethylphenyl, or —$CH_2$-3-chloro-4-fluorophenyl.

In other embodiments, $R^1$ in Formula V or Formula VI is CH(OH)-aryl, for example, —CH(OH)-4-chlorophenyl, —CH(OH)-3,4-dichlorophenyl, —CH(OH)-3,4-difluorophenyl, —CH(OH)-3-fluoro-4-chlorophenyl, —CH(OH)-3-chloro-4-fluorophenyl, —CH(OH)-3-methyl-4-chlorophenyl, —CH(OH)-3-fluoro-4-trifluoromethylphenyl, —CH(OH)-4-trifluoromethylphenyl, —CH(OH)-3-methyl-4-trifluoromethylphenyl, or —CH(OH)-3-chloro-4-fluorophenyl.

In other embodiments, $R^1$ in Formula V or Formula VI is —CH(halo)-aryl, for example, —CH(F)-4-chlorophenyl, —CH(F)-3,4-dichlorophenyl, —CH(F)-3,4-difluorophenyl, —CH(F)-3-fluoro-4-chlorophenyl, —CH(F)-3-chloro-4-fluorophenyl, —CH(F)-3-methyl-4-chlorophenyl, —CH(F)-3-fluoro-4-trifluoromethylphenyl, —CH(F)-4-trifluoromethylphenyl, —CH(F)-3-methyl-4-trifluoromethylphenyl, or —CH(F)-3-chloro-4-fluorophenyl.

In other embodiments, $R^1$ in Formula V or Formula VI is —CH($NH_2$)-aryl, for example, —CH($NH_2$)-4-chlorophenyl, —CH($NH_2$)-3,4-dichlorophenyl, —CH($NH_2$)-3,4-difluorophenyl, —CH($NH_2$)-3-fluoro-4-chlorophenyl, —CH($NH_2$)-3-chloro-4-fluorophenyl, —CH($NH_2$)-3-methyl-4-chlorophenyl, —CH($NH_2$)-3-fluoro-4-trifluoromethylphenyl, —CH($NH_2$)-4-trifluoromethylphenyl, —CH($NH_2$)-3-methyl-4-trifluoromethylphenyl, or —CH($NH_2$)-3-chloro-4-fluorophenyl.

In other embodiments, $R^1$ in Formula V or Formula VI is —CH(Me)-aryl, for example, —CH(Me)-4-chlorophenyl, —CH(Me)-3,4-dichlorophenyl, —CH(Me)-3,4-difluorophenyl, —CH(Me)-3-fluoro-4-chlorophenyl, —CH(Me)-3-chloro-4-fluorophenyl, —CH(Me)-3-methyl-4-chlorophenyl, —CH(Me)-3-fluoro-4-trifluoromethylphenyl, —CH(Me)-4-trifluoromethylphenyl, —CH(Me)-3-methyl-4-trifluoromethylphenyl, or —CH(Me)-3-chloro-4-fluorophenyl.

In other embodiments, $R^1$ in Formula V or Formula VI is —C(Me)(OH)-aryl, for example, —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, —CH(Me)(OH)-3-methyl-4-chlorophenyl, —CH(Me)(OH)-3-fluoro-4-trifluoromethylphenyl, —CH(Me)(OH)-4-trifluoromethylphenyl, —CH(Me)(OH)-3-methyl-4-trifluoromethylphenyl, or —CH(Me)(OH)-3-chloro-4-fluorophenyl.

In other embodiments, $R^1$ in Formula V or Formula VI is —CH($CH_2$OH)-aryl, for example, —CH($CH_2$OH)-4-chlorophenyl, —CH($CH_2$OH)-3,4-dichlorophenyl, —CH($CH_2$OH)-3,4-difluorophenyl, —CH($CH_2$OH)-3-fluoro-4-chlorophenyl, —CH($CH_2$OH)-3-chloro-4-fluorophenyl, —CH($CH_2$OH)-3-methyl-4-chlorophenyl, —CH($CH_2$OH)-3-fluoro-4-trifluoromethylphenyl, —CH($CH_2$OH)-4-trifluoromethylphenyl, —CH($CH_2$OH)-3-methyl-4-trifluoromethylphenyl, or —CH($CH_2$OH)-3-chloro-4-fluorophenyl.

In some aspects, $R^1$ in Formula V or Formula VI is —$C_1$-$C_6$alk-heteroaryl, for example, —$C_1$alk-heteroaryl, —$C_2$alk-heteroaryl, —$C_3$alk-heteroaryl, —$C_4$alk-heteroaryl, —$C_5$alk-heteroaryl, —$C_6$alk-heteroaryl, —$CH_2$heteroaryl, —CH(OH)-heteroaryl, —CH(F)-heteroaryl, —CH($NH_2$)-heteroaryl, —CH(Me)-heteroaryl, —C(Me)(OH)-heteroaryl, —CH($CH_2$OH)-heteroaryl and the like. In some embodiments the -heteroaryl is 5-chlorothiophen-2-yl, and $R^1$ is —$CH_2$-5-chlorothiophen-2-yl, —CH(OH)-5-chlorothiophen-2-yl, —CH(F)-5-chlorothiophen-2-yl, —CH($NH_2$)-5-chlorothiophen-2-yl, —CH(Me)-5-chlorothiophen-2-yl, —C(Me)(OH)-5-chlorothiophen-2-yl, or —CH($CH_2$OH)-5-chlorothiophen-2-yl.

In some aspects, $R^1$ in Formula V or Formula VI is —$C_1$-$C_6$alk-C≡CH, for example, —$C_1$alk-C≡CH, —$C_2$alk-C≡CH, —$C_3$alk-C≡CH, —$C_4$alk-C≡CH, —$C_5$alk-C≡CH, —$C_6$alk-C≡CH, ethynyl, propargyl, —CH(OH)—C≡CH, —CH(F)—C≡CH, —CH($NH_2$)—C≡CH, —CH(Me)-C≡CH, —C(Me)(OH)—C—CH, —CH($CH_2$OH)—C≡CH and the like.

In some aspects, $R^1$ in Formula V or Formula VI is —$C_1$-$C_6$alk-C≡C—$C_1$-$C_6$alkyl, for example, —$C_1$alk-C≡C—$C_1$alkyl, —$C_2$alk-C≡C—$C_1$alkyl, —$C_3$alk-C≡C—$C_1$alkyl, —$C_4$alk-C≡C—$C_1$alkyl, —$C_5$alk-C≡C—$C_1$alkyl, —$C_6$alk-C≡C—$C_1$alkyl, —$C_1$alk-C≡C—$C_2$alkyl, —$C_2$alk-C≡C—$C_2$alkyl, —$C_3$alk-C≡C—$C_2$alkyl, —$C_4$alk-C≡C—$C_2$alkyl, —$C_5$alk-C≡C—$C_2$alkyl, —$C_6$alk-C≡C—$C_2$alkyl, —$C_1$alk-C≡C—$C_3$alkyl, —$C_2$alk-C≡C—$C_3$alkyl, —$C_3$alk-C≡C—$C_3$alkyl, —$C_4$alk-C≡C—$C_3$alkyl, —$C_5$alk-C≡C—$C_3$alkyl, —$C_6$alk-C≡C—$C_3$alkyl, —$C_1$alk-C≡C—$C_4$alkyl, —$C_2$alk-C≡C—$C_4$alkyl, —$C_3$alk-C≡C—$C_4$alkyl, —$C_4$alk-C≡C—$C_4$alkyl, —$C_5$alk-C≡C—$C_4$alkyl, —$C_6$alk-C≡C—$C_4$alkyl, —$C_1$alk-C≡C—$C_5$alkyl, —$C_2$alk-C≡C—$C_5$alkyl, —$C_3$alk-C≡C—$C_5$alkyl, —$C_4$alk-C≡C—$C_5$alkyl, —$C_5$alk-C≡C—$C_5$alkyl, —$C_6$alk-C≡C—$C_5$alkyl, —$C_1$alk-C≡C—$C_6$alkyl, —$C_2$alk-C≡C—$C_6$alkyl, —$C_3$alk-C≡C—$C_6$alkyl, —$C_4$alk-C≡C—$C_6$alkyl, —$C_5$alk-C≡C—$C_6$alkyl, —$C_6$alk-C≡C—$C_6$alkyl, propynyl, butynyl, —CH(OH)—C≡C—$C_1$-$C_6$alkyl, —CH(F)—C≡C—$C_1$-$C_6$alkyl, —CH($NH_2$)—C≡C—$C_1$-$C_6$alkyl, —CH(Me)-C≡C—$C_1$-$C_6$alkyl, —C(Me)(OH)—C≡C—$C_1$-$C_6$alkyl, —CH($CH_2$OH)—C≡C—$C_1$-$C_6$alkyl, and the like. In some embodiments wherein —$C_1$-$C_6$alk-C≡C—$C_1$-$C_6$alkyl is —$C_1$-$C_6$alk-C≡C—$CH_3$, $R^1$ is —CH(OH)—C≡C—$CH_3$, —CH(F)—C≡C—$CH_3$, —CH($NH_2$)—C≡C—$CH_3$, —CH(Me)-C≡C—$CH_3$, or —C(Me)(OH)—C≡C—$CH_3$, —CH($CH_2$OH)—C≡C—$CH_3$. In some embodiments, $R^1$ is —CH(OH)—C≡C—$CH_3$.

In other embodiments, $R^1$ is —CH(F)—C≡C—$CH_3$. In yet other embodiments, $R^1$ is —CH($NH_2$)—C≡C—$CH_3$. In some embodiments, $R^1$ is —CH(Me)-C≡C—$CH_3$. In other embodiments, $R^1$ is —CH(OH)(Me)-C—C≡C—$CH_3$. In yet other embodiments, $R^1$ is —CH($CH_2$H)(Me)-C≡C—$CH_3$.

In some aspects, $R^1$ in Formula V or Formula VI is —$C_1$-$C_6$alk-C≡C—$C_1$-$C_6$haloalkyl, for example, —$C_1$alk-C≡C—$C_1$haloalkyl, —$C_2$alk-C≡C—$C_1$haloalkyl, —$C_3$alk-C≡C—$C_1$haloalkyl, —$C_4$alk-C≡C—$C_1$haloalkyl, —$C_5$alk-C≡C—$C_1$haloalkyl, —$C_6$alk-C≡C—$C_1$haloalkyl, —$C_1$alk-C≡C—$C_2$haloalkyl, —$C_2$alk-C≡C—$C_2$haloalkyl, —$C_3$alk-C≡C—$C_2$haloalkyl, —$C_4$alk-C≡C—$C_2$haloalkyl, —$C_5$alk-C≡C—$C_2$haloalkyl, —$C_6$alk-C≡C—$C_2$haloalkyl, —$C_1$alk-C≡C—$C_3$haloalkyl, —$C_2$alk-C≡C—$C_3$haloalkyl, —$C_3$alk-C≡C—$C_3$haloalkyl, —$C_4$alk-C≡C—$C_3$haloalkyl, —$C_5$alk-C≡C—$C_3$haloalkyl, —$C_6$alk-C≡C—$C_3$haloalkyl, —$C_1$alk-C≡C—$C_4$haloalkyl, —$C_2$alk-C≡C—$C_4$haloalkyl, —$C_3$alk-C≡C—$C_4$haloalkyl, —$C_4$alk-C≡C—$C_4$haloalkyl, —$C_5$alk- C≡C—C₄haloalkyl, —C₆alk-C≡C—C₄haloalkyl, —C₁alk-C≡C—C₅haloalkyl, —C₂alk-C≡C—C₅haloalkyl, —C₃alk-C≡C—C₅haloalkyl, —C₄alk-C≡C—C₅haloalkyl, —C₅alk-C≡C—C₅haloalkyl, —C₆alk-C≡C—C₅haloalkyl, —C₁alk-C≡C—C₆haloalkyl, —C₂alk-C≡C—C₆haloalkyl, —C₃alk-C≡C—C₆haloalkyl, —C₄alk-C≡C—C₆haloalkyl, —C₅alk-C≡C—C₆haloalkyl, —C₆alk-C≡C—C₆haloalkyl, —CH(OH)—C≡C—C₁-C₆haloalkyl, —CH(F)—C≡C—C₁-C₆haloalkyl, —CH(NH₂)—C≡C—C₁-C₆haloalkyl, —CH(Me)-C≡C—C₁-C₆haloalkyl, —C(Me)(OH)—C≡C—C₁-C₆haloalkyl, —C(Me)(CH₂OH)—C≡C—C₁-C₆haloalkyl, and the like. In some embodiments wherein —C₁-C₆alk-C≡C—C₁-C₆haloalkyl is —C₁-C₆alk-C≡C—CF₃, $R^1$ is —CH(OH)—C≡C—CF₃, —CH(F)—C≡C—CF₃, —CH(NH₂)—C≡C—CF₃, —CH(Me)-C≡C—CF₃, —C(Me)(OH)—C≡C—CF₃, —C(Me)(CH₂OH)—C≡C—CF₃, and the like. Thus, in some embodiments, $R^1$ is —CH(OH)—C≡C—CF₃.

In some aspects, $R^1$ in Formula V or Formula VI is —C₁-C₆alk-C≡C—C₃-C₆cycloalkyl, for example, C₁alk-C≡C—C₃cycloalkyl, —C₁alk-C≡C—C₄cycloalkyl, —C₁alk-C≡C—C₅-cycloalkyl, —C₁alk-C≡C—C₆cycloalkyl, —C₂alk-C≡C—C₃cycloalkyl, —C₂alk-C≡C—C₄cycloalkyl, —C₂alk-C≡C—C₅cycloalkyl, —C₂alk-C≡C—C₆cycloalkyl, —C₃alk-C≡C—C₃cycloalkyl, —C₃alk-C≡C—C₄cycloalkyl, —C₃alk-C≡C—C₅cycloalkyl, —C₃alk-C≡C—C₆cycloalkyl, —C₄alk-C≡C—C₃cycloalkyl, —C₄alk-C≡C—C₄cycloalkyl, —C₄alk-C≡C—C₅cycloalkyl, —C₄alk-C≡C—C₆cycloalkyl, —C₅alk-C≡C—C₃cycloalkyl, —C₅alk-C≡C—C₄cycloalkyl, —C₅alk-C≡C—C₅cycloalkyl, —C₅alk-C≡C—C₆cycloalkyl, —C₆alk-C≡C—C₃cycloalkyl, —C₆alk-C≡C—C₄cycloalkyl, —C₆alk-C≡C—C₅cycloalkyl, —C₆alk-C≡C—C₆cycloalkyl, —CH(OH)—C≡C—C₃-C₆cycloalkyl, —CH(F)—C≡C—C₃-C₆cycloalkyl, —CH(NH₂)—C≡C—C₃-C₆cycloalkyl, —CH(Me)-C≡C—C₃-C₆cycloalkyl, —C(Me)(OH)—C≡C—C₃-C₆cycloalkyl, or —C(Me)(CH₂OH)—C≡C—C₃-C₆cycloalkyl. In some embodiments wherein —C₁-C₆alk-C≡C—C₃-C₆cycloalkyl is —C₁-C₆alk-C≡C-cyclopropyl, $R^1$ is —CH(OH)—C≡C-cyclopropyl, —CH(F)—C≡C-cyclopropyl, —CH(NH₂)—C≡C-cyclopropyl, —CH(Me)-C≡C-cyclopropyl, —C(Me)(OH)—C≡C-cyclopropyl, —C(Me)(CH₂OH)—C≡C-cyclopropyl, and the like. Thus, in some embodiments, $R^1$ is —CH(OH)—C≡C-cyclopropyl.

In compounds of the present disclosure that are compounds of Formula V, $R^2$ is H or halo.

Thus, in some embodiments, $R^2$ in Formula V is H.

In other embodiments, $R^2$ in Formula V is halo, for example F, Cl, Br, or I. In some embodiments, $R^2$ is F.

In compounds of the present disclosure of Formula V or Formula VI, $R^3$ is H, halo, —C₁-C₆alkyl, or NH₂. Thus in some embodiments, $R^3$ is H. In other embodiments, $R^3$ is halo, for example F, Cl, Br, or I, with —Cl being preferred. In other embodiments, $R^3$ is —C₁-C₆alkyl, for example, methyl, ethyl, propyl, isopropyl, butyl, isobutyl, s-butyl, t-butyl, pentyl, and the like. Thus, in some embodiments, $R^3$ is methyl (Me). In yet other embodiments, $R^3$ is NH₂.

In compounds of the present disclosure of Formula V or Formula VI, $R^4$ is NH₂ or CH₃. In some embodiments, $R^4$ is N12. In other embodiments, $R^4$ is CH₃.

Preferred embodiments of the compounds of Formula V are those in which $R^1$ is —CH(OH)-aryl, —CH(Me)-aryl, —C(Me)(OH)-aryl, —CH(CH₂OH)-aryl, —C(Me)(OH)-heteroaryl, or —CH(OH)—C≡C—C₃-C₆cycloalkyl; $R^2$ is H or F; $R^3$ is H, and $R^4$ is NH₂.

Particularly preferred embodiments of the compounds of Formula V are those wherein $R^1$ is —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, —CH(Me)(OH)-3-methyl-4-chlorophenyl, —CH(Me)(OH)-3-fluoro-4-trifluoromethylphenyl, —CH(Me)(OH)-4-trifluoromethylphenyl, —CH(Me)(OH)-3-methyl-4-trifluoromethylphenyl, —CH(Me)(OH)-3-chloro-4-fluorophenyl, —CH(Me)-4-chlorophenyl, —CH(CH₂OH)-4-chlorophenyl, —C(Me)(OH)-5-chlorothiophen-2-yl, or —CH(OH)—C≡C-cyclopropyl; R2 is H or F; $R^3$ is H; and $R^4$ is NH₂.

Preferred embodiments of the compounds of Formula VI are those in which $R^1$ is —CH(OH)-aryl, —CH(Me)-aryl, —C(Me)(OH)-aryl, —CH(CH₂OH)-aryl, —C(Me)(OH)-heteroaryl, or —CH(OH)—C≡C—C₃-C₆cycloalkyl; $R^3$ is H; and $R^4$ is NH₂.

Particularly preferred embodiments of the compounds of Formula VI are those wherein $R^1$ is —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, —CH(Me)(OH)-3-methyl-4-chlorophenyl, —CH(Me)(OH)-3-fluoro-4-trifluoromethylphenyl, —CH(Me)(OH)-4-trifluoromethylphenyl, —CH(Me)(OH)-3-methyl-4-trifluoromethylphenyl, —CH(Me)(OH)-3-chloro-4-fluorophenyl, —CH(Me)-4-chlorophenyl, —CH(CH₂OH)-4-chlorophenyl, —C(Me)(OH)-5-chlorothiophen-2-yl, or —CH(OH)—C≡C-cyclopropyl; $R^3$ is H; and $R^4$ is NH₂.

In some aspects, the present disclosure is directed to compounds of formula VA-1

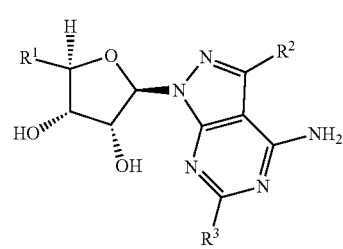

VA-1 wherein $R^1$ is —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, —CH(Me)(OH)-3-methyl-4-chlorophenyl, —CH(Me)(OH)-3-fluoro-4-trifluoromethylphenyl, —CH(Me)(OH)-4-trifluoromethylphenyl, —CH(Me)(OH)-3-methyl-4-trifluoromethylphenyl, —CH(Me)(OH)-3-chloro-4-fluorophenyl, —CH(Me)-4-chlorophenyl, —CH(CH₂OH)-4-chlorophenyl, —C(Me)(OH)-5-chlorothiophen-2-yl, or —CH(OH)—C≡C-cyclopropyl; and $R^2$ is H or F.

In some aspects, the present disclosure is directed to compounds of formula VA-2

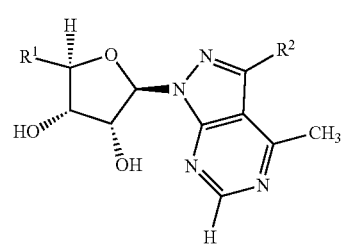

VA-2 wherein $R^1$ is —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, —C(Me)

(OH)-3-chloro-4-fluorophenyl, —CH(Me)(OH)-3-methyl-4-chlorophenyl, —CH(Me)(OH)-3-fluoro-4-trifluoromethylphenyl, —CH(Me)(OH)-4-trifluoromethylphenyl, —CH(Me)(OH)-3-methyl-4-trifluoromethylphenyl, —CH(Me)(OH)-3-chloro-4-fluorophenyl, —CH(Me)-4-chlorophenyl, —CH(CH$_2$OH)-4-chlorophenyl, —C(Me)(OH)-5-chlorothiophen-2-yl, or —CH(OH)—C≡C-cyclopropyl; and R$^2$ is H or F.

In other aspects, the present disclosure is directed to compounds of formula VB-1

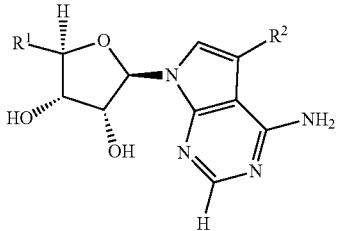

VB-1 wherein R$^1$ is —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, —CH(Me)(OH)-3-methyl-4-chlorophenyl, —CH(Me)(OH)-3-fluoro-4-trifluoromethylphenyl, —CH(Me)(OH)-4-trifluoromethylphenyl, —CH(Me)(OH)-3-methyl-4-trifluoromethylphenyl, —CH(Me)(OH)-3-chloro-4-fluorophenyl, —CH(Me)-4-chlorophenyl, —CH(CH$_2$OH)-4-chlorophenyl, —C(Me)(OH)-5-chlorothiophen-2-yl, or —CH(OH)—C≡C-cyclopropyl; and R$^2$ is H or F.

In some embodiments, the compounds of formula VB-1 are those wherein R$^1$ is —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, —CH(Me)(OH)-3-methyl-4-chlorophenyl, —CH(Me)(OH)-3-fluoro-4-trifluoromethylphenyl, —CH(Me)(OH)-4-trifluoromethylphenyl, —CH(Me)(OH)-3-methyl-4-trifluoromethylphenyl, —CH(Me)(OH)-3-chloro-4-fluorophenyl, —CH(Me)-4-chlorophenyl, —CH(CH$_2$OH)-4-chlorophenyl, —C(Me)(OH)-5-chlorothiophen-2-yl, or —CH(OH)—C≡C-cyclopropyl; and R$^2$ is F.

In some embodiments, the compounds of formula VB-1 are those wherein R$^1$ is —C(Me)(OH)-3-chloro-4-fluorophenyl, —CH(Me)(OH)-3-methyl-4-chlorophenyl, —CH(Me)(OH)-3-fluoro-4-trifluoromethylphenyl, —CH(Me)(OH)-4-trifluoromethylphenyl, —CH(Me)(OH)-3-methyl-4-trifluoromethylphenyl, —CH(Me)(OH)-3-chloro-4-fluorophenyl, —CH(Me)-4-chlorophenyl, —CH(CH$_2$OH)-4-chlorophenyl, —C(Me)(OH)-5-chlorothiophen-2-yl, or —CH(OH)—C≡C-cyclopropyl; and R$^2$ is H or F.

In other aspects, the present disclosure is directed to compounds of formula VB-2

VB-2 wherein R$^1$ is —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, —CH(Me)(OH)-3-methyl-4-chlorophenyl, —CH(Me)(OH)-3-fluoro-4-trifluoromethylphenyl, —CH(Me)(OH)-4-trifluoromethylphenyl, —CH(Me)(OH)-3-methyl-4-trifluoromethylphenyl, —CH(Me)(OH)-3-chloro-4-fluorophenyl, —CH(Me)-4-chlorophenyl, —CH(CH$_2$OH)-4-chlorophenyl, —C(Me)(OH)-5-chlorothiophen-2-yl, or —CH(OH)—C≡C-cyclopropyl; and R$^2$ is H or F.

In some embodiments, the compounds of formula VB-2 are those wherein R$^1$ is —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, —CH(Me)(OH)-3-methyl-4-chlorophenyl, —CH(Me)(OH)-3-fluoro-4-trifluoromethylphenyl, —CH(Me)(OH)-4-trifluoromethylphenyl, —CH(Me)(OH)-3-methyl-4-trifluoromethylphenyl, —CH(Me)(OH)-3-chloro-4-fluorophenyl, —CH(Me)-4-chlorophenyl, —CH(CH$_2$OH)-4-chlorophenyl, —C(Me)(OH)-5-chlorothiophen-2-yl, or —CH(OH)—C≡C-cyclopropyl; and R$^2$ is F.

In other embodiments, the compounds of formula VB-2 are those wherein R$^1$ is —C(Me)(OH)-3,4-difluorophenyl, —C(Me)(OH)-3-fluoro-4-chlorophenyl, —C(Me)(OH)-3-chloro-4-fluorophenyl, —CH(Me)(OH)-3-methyl-4-chlorophenyl, —CH(Me)(OH)-3-fluoro-4-trifluoromethylphenyl, —CH(Me)(OH)-4-trifluoromethylphenyl, —CH(Me)(OH)-3-methyl-4-trifluoromethylphenyl, —CH(Me)(OH)-3-chloro-4-fluorophenyl, —CH(Me)-4-chlorophenyl, —CH(CH$_2$OH)-4-chlorophenyl, —C(Me)(OH)-5-chlorothiophen-2-yl, or —CH(OH)—C≡C-cyclopropyl; and R$^2$ is H.

In yet other aspects, the present disclosure is directed to compounds of formula VI-A-1

VI-A-1 wherein R$^1$ is —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, —CH(Me)(OH)-3-methyl-4-chlorophenyl, —CH(Me)(OH)-3-fluoro-4-trifluoromethylphenyl, —CH(Me)(OH)-4-trifluoromethylphenyl, —CH(Me)(OH)-3-methyl-4-trifluoromethylphenyl, —CH(Me)(OH)-3-chloro-4-fluorophenyl, —CH(Me)-4-chlorophenyl, —CH(CH$_2$OH)-4-chlorophenyl, —C(Me)(OH)-5-chlorothiophen-2-yl, or —CH(OH)—C≡C-cyclopropyl.

In yet other aspects, the present disclosure is directed to compounds of formula VI-A-2

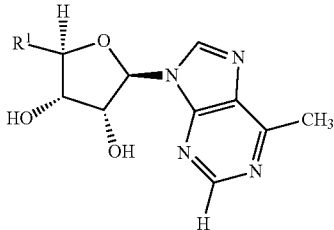

VI-A-2 wherein R¹ is —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, —CH(Me)(OH)-3-methyl-4-chlorophenyl, —CH(Me)(OH)-3-fluoro-4-trifluoromethylphenyl, —CH(Me)(OH)-4-trifluoromethylphenyl, —CH(Me)(OH)-3-methyl-4-trifluoromethylphenyl, —CH(Me)(OH)-3-chloro-4-fluorophenyl, —CH(Me)-4-chlorophenyl, —CH(CH₂OH)-4-chlorophenyl, —C(Me)(OH)-5-chlorothiophen-2-yl, or —CH(OH)—C≡C-cyclopropyl.

Stereoisomers of compounds of Formula V and Formula VI are also contemplated.

Pharmaceutically acceptable salts and solvates of the compounds of Formula V and Formula VI are also within the scope of the disclosure.

The oximes of the present disclosure, i.e., the compounds of Formula I or II, wherein Q=O, and R¹, R², R³, R⁴, R⁵ have the values described above,

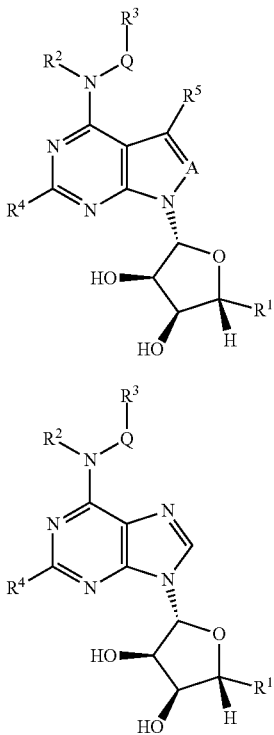

I

II can be converted under physiological conditions, or by methods known to those skilled in the art, into the corresponding amino compounds, shown below.

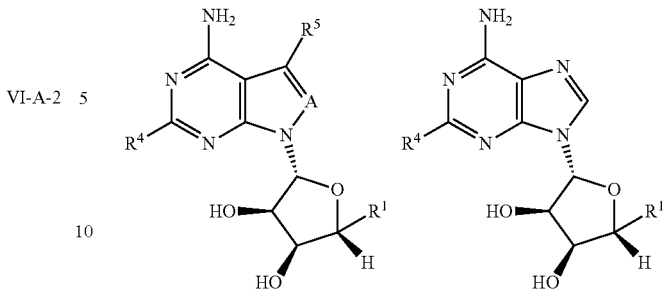

Thus, the amino compounds corresponding to oximes of Formula I or II, as well as the amino compounds corresponding to the oxime-containing subgenera of Formula I or II, described herein, are also encompassed by the disclosure. Subgenera of these amino compounds, corresponding to oxime containing subgenera of IA. IA-3, IA-4, IB, IB-3, IB-4, IB-5, IB-6, IE, and IF, IIA, IIB, IIE, IIF, IIG, IIG-3, and IIG-4 described herein, are also encompassed by the present disclosure. The individual amino compounds corresponding to the oximes set forth in Table A below are also encompassed by the disclosure.

Pharmaceutical Compositions and Methods of Administration

The subject pharmaceutical compositions are typically formulated to provide a therapeutically effective amount of a compound of the present disclosure as the active ingredient, or a pharmaceutically acceptable salt, ester, prodrug, solvate, hydrate or derivative thereof. Where desired, the pharmaceutical compositions contain pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The subject pharmaceutical compositions can be administered alone or in combination with one or more other agents, which are also typically administered in the form of pharmaceutical compositions. Where desired, the one or more compounds of the invention and other agent(s) may be mixed into a preparation or both components may be formulated into separate preparations to use them in combination separately or at the same time.

In some embodiments, the concentration of one or more compounds provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11% 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% (or a number in the range defined by and including any two numbers above) w/w, w/v or v/v.

In some embodiments, the concentration of one or more compounds of the invention is greater than 90%, 80%, 70%, 60%, 50%, 40%, 30%, 20%, 19.75%, 19.50%, 19.25%, 19%, 18.75%, 18.50%, 18.25% 18%, 17.75%, 17.50%, 17.25% 17%, 16.75%, 16.50%, 16.25%, 16%, 15.75%, 15.50%, 15.25% 15%, 14.75%, 14.50%, 14.25% 14%, 13.75%, 13.50%, 13.25%, 13%, 12.75%, 12.50%, 12.25%, 12%, 11.75%, 11.50%, 11.25% 11%, 10.75%, 10.50%, 10.25% 10%, 9.75%, 9.50%, 9.25%, 9%, 8.75%, 8.50%, 8.25% 8%, 7.75%, 7.50%, 7.25%, 7%, 6.75%, 6.50%, 6.25%, 6%, 5.75%, 5.50%, 5.25%, 5%, 4.75%, 4.50%, 4.25%, 4%, 3.75%, 3.50%, 3.25%, 3%, 2.75%, 2.50%, 2.25%, 2%, 1.75%, 1.50%, 1.25%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% (or a number in the range defined by and including any two numbers above) w/w, w/v, or v/v.

In some embodiments, the concentration of one or more compounds of the invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of one or more compounds of the invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more compounds of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g (or a number in the range defined by and including any two numbers above).

In some embodiments, the amount of one or more compounds of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g (or a number in the range defined by and including any two numbers above).

In some embodiments, the amount of one or more compounds of the invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. An exemplary dosage is 10 to 30 mg per day. The exact dosage will depend upon the route of administration, the form in which the compound is administered, the subject to be treated, the body weight of the subject to be treated, and the preference and experience of the attending physician.

A pharmaceutical composition of the invention typically contains an active ingredient (i.e., a compound of the disclosure) of the present invention or a pharmaceutically acceptable salt and/or coordination complex thereof, and one or more pharmaceutically acceptable excipients, carriers, including but not limited to inert solid diluents and fillers, diluents, sterile aqueous solution and various organic solvents, permeation enhancers, solubilizers and adjuvants.

Described below are non-limiting exemplary pharmaceutical compositions and methods for preparing the same.

Pharmaceutical Compositions for Oral Administration.

In some embodiments, the invention provides a pharmaceutical composition for oral administration containing a compound of the invention, and a pharmaceutical excipient suitable for oral administration.

In some embodiments, the invention provides a solid pharmaceutical composition for oral administration containing: (i) an effective amount of a compound of the invention; optionally (ii) an effective amount of a second agent; and (iii) a pharmaceutical excipient suitable for oral administration. In some embodiments, the composition further contains: (iv) an effective amount of a third agent.

In some embodiments, the pharmaceutical composition may be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This invention further encompasses anhydrous pharmaceutical compositions and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions.

Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof, carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof, polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-1Ooleate, Tween 40, Tween 60, sucrose monostearate, sucrose mono laurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present invention and to minimize precipitation of the compound of the present invention. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof, and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a subject using conventional techniques, such as distillation or evaporation. Thus, if present, the solubilizer can be in a weight ratio of 10%, 25‰, 50%), 100‰, or up to about 200%> by weight, based on the combined weight of the drug, and other excipients. If desired, very small amounts of solubilizer may also be used, such as 5%>, 2%>, 1%) or even less. Typically, the solubilizer may be present in an amount of about 1%> to about 100%, more typically about 5%> to about 25%> by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical Compositions for Injection.

In some embodiments, the invention provides a pharmaceutical composition for injection containing a compound of the present invention and a pharmaceutical excipient suitable for injection. Components and amounts of agents in the compositions are as described herein.

The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Topical (e.g. Transdermal) Delivery.

In some embodiments, the invention provides a pharmaceutical composition for transdermal delivery containing a compound of the present invention and a pharmaceutical excipient suitable for transdermal delivery.

Compositions of the present invention can be formulated into preparations in solid, semisolid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation.

Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of a compound of the present invention in controlled amounts, either with or without another agent.

The construction and use of transdermal patches for the delivery of pharmaceutical agents is well known in the art. See, e.g., U.S. Pat. Nos. 5,023,252, 4,992,445 and 5,001, 139. Such patches may be constructed for continuous, pulsatile, or on demand delivery of pharmaceutical agents.

Pharmaceutical Compositions for Inhalation.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

Other Pharmaceutical Compositions.

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins., 2000; Martindale, The Extra Pharmacopoeia, Thirty-Second Edition (The Pharmaceutical Press, London, 1999); all of which are incorporated by reference herein in their entirety.

Administration of the compounds or pharmaceutical composition of the present invention can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g. transdermal application), rectal administration, via local delivery by catheter or stent or through inhalation. Compounds can also be administered intraadiposally or intrathecally.

The amount of the compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g. by dividing such larger doses into several small doses for administration throughout the day.

In some embodiments, a compound of the invention is administered in a single dose.

Typically, such administration will be by injection, e.g., intravenous injection, in order to introduce the agent quickly. However, other routes may be used as appropriate. A single dose of a compound of the invention may also be used for treatment of an acute condition.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the compounds of the invention may continue as long as necessary. In some embodiments, a compound of the invention is administered for more than 1, 2, 3, 4, 5, 6, 7, 14, or 28 days. In some embodiments, a compound of the invention is administered for less than 28, 14, 7, 6, 5, 4, 3, 2, or 1 day. In some embodiments, a compound of the invention is administered chronically on an ongoing basis, e.g., for the treatment of chronic effects.

An effective amount of a compound of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

The compositions of the invention may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds of the invention may slow or inhibit the migration and proliferation of smooth muscle cells in the arterial wall which contribute to restenosis. A compound of the invention may be administered, for example, by local delivery from the struts of a stent, from a stent graft, from grafts, or from the cover or sheath of a stent. In some embodiments, a compound of the invention is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly (ether-ester) copolymers (e.g. PEO-PLLA); polydimethylsiloxane, poly(ethylene-vinylacetate), acrylate-based polymers or copolymers (e.g. polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. Compounds of the invention may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the invention in a suitable solvent, followed by evaporation of the solvent. Excess drug on the surface of the stent may be removed via an additional brief solvent wash. In yet other embodiments, compounds of the invention may be covalently linked to a stent or graft. A covalent linker may be used which degrades in vivo, leading to the release of the compound of the invention. Any bio-labile linkage may be used for such a purpose, such as ester, amide or anhydride linkages. Compounds of the invention may additionally be administered intravascularly from a balloon used during angioplasty. Extravascular administration of the compounds via the pericard or via advential application of formulations of the invention may also be performed to decrease restenosis.

A variety of stent devices which may be used as described are disclosed, for example, in the following references, all of which are hereby incorporated by reference: U.S. Pat. Nos. 5,451,233; 5,040,548; 5,061,273; 5,496,346; 5,292,331; 5,674,278; 3,657,744; 4,739,762; 5,195,984; 5,292,331; 5,674,278; 5,879,382; 6,344,053.

The compounds of the invention may be administered in dosages. It is known in the art that due to intersubject variability in compound pharmacokinetics, individualization of dosing regimen is necessary for optimal therapy. Dosing for a compound of the invention may be found by routine experimentation in light of the instant disclosure.

When a compound of the invention is administered in a composition that comprises one or more agents, and the agent has a shorter half-life than the compound of the invention unit dose forms of the agent and the compound of the invention may be adjusted accordingly.

The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compound in sterile aqueous solutions, for example, aqueous propylene glycol or dextrose solutions. Such dosage forms can be suitably buffered, if desired.

Methods of Use

The method typically comprises administering to a subject a therapeutically effective amount of a compound of the invention. The therapeutically effective amount of the subject combination of compounds may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of proliferation or downregulation of activity of a target protein. The specific dose will vary depending on the particular compounds chosen, the dosing regimen to be followed, whether it is administered in combination with other compounds, timing of administration, the tissue to which it is administered, and the physical delivery system in which it is carried.

As used herein, the term "$IC_{50}$" refers to the half maximal inhibitory concentration of an inhibitor in inhibiting biological or biochemical function. This quantitative measure indicates how much of a particular inhibitor is needed to inhibit a given biological process (or component of a process, i.e. an enzyme, cell, cell receptor or microorganism) by half. In other words, it is the half maximal (50%) inhibitory concentration (IC) of a substance (50% IC, or IC50). EC50 refers to the plasma concentration required for obtaining 50%> of a maximum effect in vivo.

In some embodiments, the subject methods utilize a PRMT5 inhibitor with an IC50 value of about or less than a predetermined value, as ascertained in an in vitro assay. In some embodiments, the PRMT5 inhibitor inhibits PRMT5 a with an IC50 value of about 1 nM or less, 2 nM or less, 5 nM or less, 7 nM or less, 10 nM or less, 20 nM or less, 30 nM or less, 40 nM or less, 50 nM or less, 60 nM or less, 70 nM or less, 80 nM or less, 90 nM or less, 100 nM or less, 120 nM or less, 140 nM or less, 150 nM or less, 160 nM or less, 170 nM or less, 180 nM or less, 190 nM or less, 200 nM or less, 225 nM or less, 250 nM or less, 275 nM or less, 300 nM or less, 325 nM or less, 350 nM or less, 375 nM or less, 400 nM or less, 425 nM or less, 450 nM or less, 475 nM or less, 500 nM or less, 550 nM or less, 600 nM or less, 650 nM or less, 700 nM or less, 750 nM or less, 800 nM or less, 850 nM or less, 900 nM or less, 950 nM or less, 1 µM or less, 1.1 µM or less, 1.2 µM or less, 1.3 µM or less, 1.4 µM or less, 1.5 µM or less, 1.6 µM or less, 1.7 µM or less, 1.8 µM or less, 1.9 µM or less, 2 µM or less, 5 µM or less, 10 µM or less, 15 µM or less, 20 µM or less, 25 µM or less, 30 µM or less, 40 µM or less, 50 µM, 60 µM, 70 µM, 80 µM, 90 µM, 100 µM, 200 µM, 300 µM, 400 µM, or 500 µM, or less, (or a number in the range defined by and including any two numbers above).

In some embodiments, the PRMT5 inhibitor selectively inhibits PRMT5 a with an IC50 value that is at least 2, 3, 4, 5, 6, 7, 8, 9, 10, 15, 20, 25, 30, 35, 40, 45, 50, 100, or 1000 times less (or a number in the range defined by and including any two numbers above) than its IC50 value against one, two, or three other PRMTs.

In some embodiments, the PRMT5 inhibitor selectively inhibits PRMT5 a with an IC50 value that is less than about 1 nM, 2 nM, 5 nM, 7 nM, 10 nM, 20 nM, 30 nM, 40 nM, 50 nM, 60 nM, 70 nM, 80 nM, 90 nM, 100 nM, 120 nM, 140 nM, 150 nM, 160 nM, 170 nM, 180 nM, 190 nM, 200 nM, 225 nM, 250 nM, 275 nM, 300 nM, 325 nM, 350 nM, 375 nM, 400 nM, 425 nM, 450 nM, 475 nM, 500 nM, 550 nM, 600 nM, 650 nM, 700 nM, 750 nM, 800 nM, 850 nM, 900 nM, 950 nM, 1 µM, 1.1 µM, 1.2 µM, 1.3 µM, 1.4 µM, 1.5 µM, 1.6 µM, 1.7 µM, 1.8 µM, 1.9 µM, 2 µM, 5 µM, 10 µM, M, 20 µM, 25 µM, 30 µM, 40 µM, 50 µM, 60 µM, 70 µM, 80 µM, 90 µM, 100 µM, 200 µM, 300 µM, 400 µM, or 500 µM (or in the range defined by and including any two numbers above), and said IC50 value is at least 2, 3, 4, 5, 6, 7, 8, 9, 10, 15, 20, 25, 30, 35, 40, 45, 50, 100, or 1000 times less (or a number in the range defined by and including any two numbers above) than its IC50 value against one, two or three other PRMTs.

The subject methods are useful for treating a disease condition associated with PRMT. Any disease condition that results directly or indirectly from an abnormal activity or expression level of PRMT5 can be an intended disease condition.

Different disease conditions associated with PRMTS have been reported. PRMTS has been implicated, for example, in a variety of human cancers as well as a number of hemoglobinopathies.

Non-limiting examples of such conditions include but are not limited to Acanthoma, Acinic cell carcinoma, Acoustic neuroma, Acral lentiginous melanoma, Acrospiroma, Acute eosinophilic leukemia, Acute lymphoblastic leukemia, Acute lymphocytic leukemia, Acute megakaryoblastic leukemia, Acute monocytic leukemia, Acute myeloblasts leukemia with maturation, Acute myeloid dendritic cell leukemia, Acute myeloid leukemia, Acute myelogenous leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epidermoid cancer, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Head and Neck Cancer, Head and neck cancer, Heart cancer, Hemoglobinopathies such as b-thalassemia and sickle cell disease (SCD), Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mastocytosis, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplasia Disease, Myelodysplasia Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, or any combination thereof.

In some embodiments, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

In some embodiments, said method is for treating a disease selected from breast cancer, lung cancer, pancreatic cancer, prostate cancer, colon cancer, ovarian cancer, uterine cancer, cervical cancer, leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), myelodysplastic syndrome (MDS), epidermoid cancer, or hemoglobinopathies such as b-thalassemia and sickle cell disease (SCD).

In other embodiments, said method is for treating a disease selected from breast cancer, lung cancer, pancreatic cancer, prostate cancer, colon cancer, ovarian cancer, uterine cancer, or cervical cancer.

In other embodiments, said method is for treating a disease selected from leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), myelodysplastic syndrome (MDS), epidermoid cancer, or hemoglobinopathies such as b-thalassemia and sickle cell disease (SCD).

In yet other embodiments, said method is for treating a disease selected from CDKN2A deleted cancers; 9P deleted cancers; MTAP deleted cancers; glioblastoma, NSCLC, head and neck cancer, bladder cancer, or hepatocellular carcinoma.

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

Compounds of the disclosure can be prepared, for example, by reference to the following schemes.

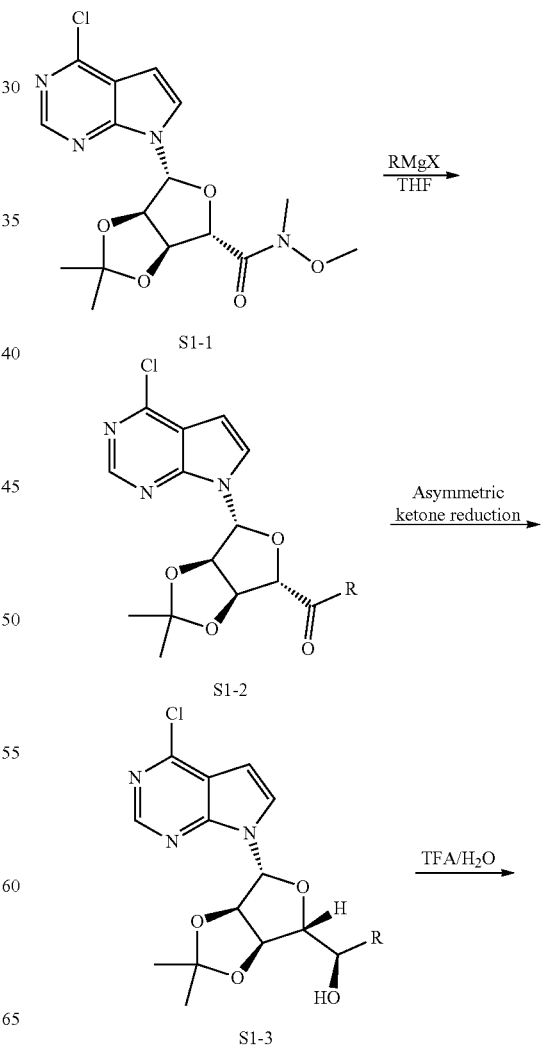

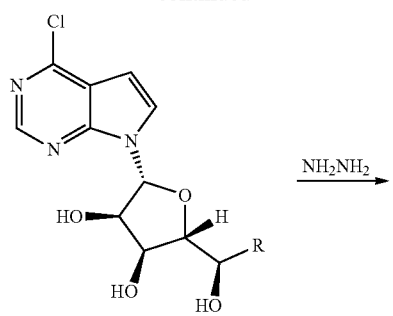
S1-4
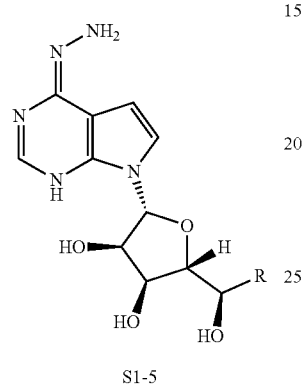
S1-5
Scheme 2
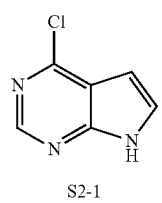 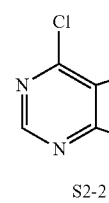 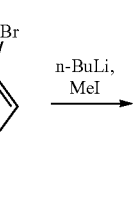
S2-1    S2-2    S2-3
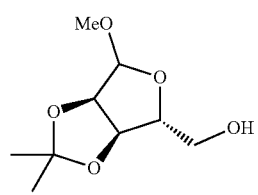
S2-4
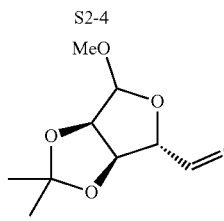 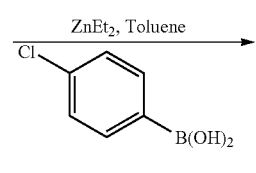
S2-5    S2-6
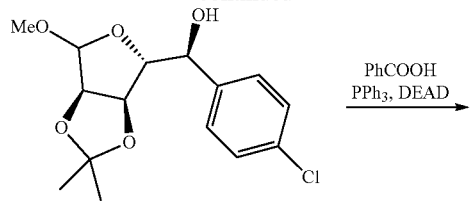
S2-7
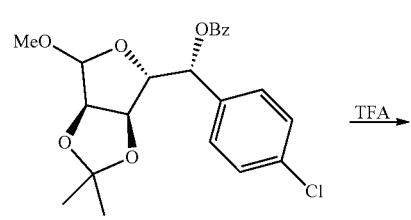
S2-8
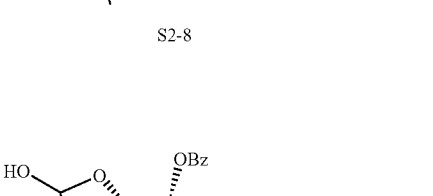
S2-9
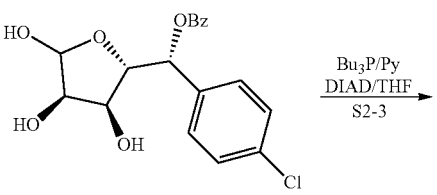
S2-10
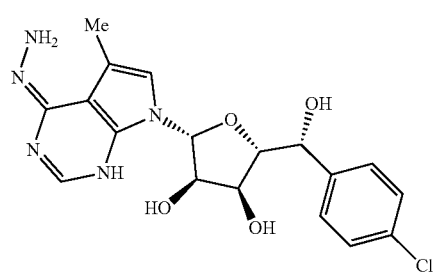
Ex. 22

Scheme 3
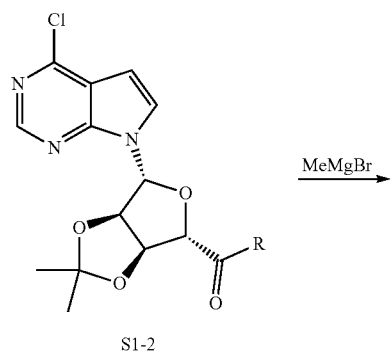
S1-2
MeMgBr →
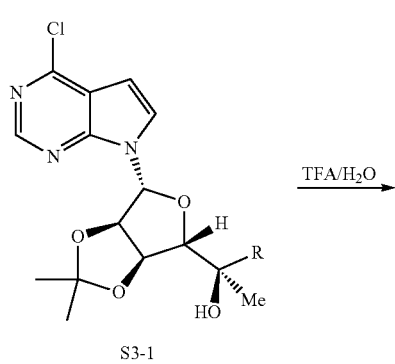
S3-1
TFA/H₂O →
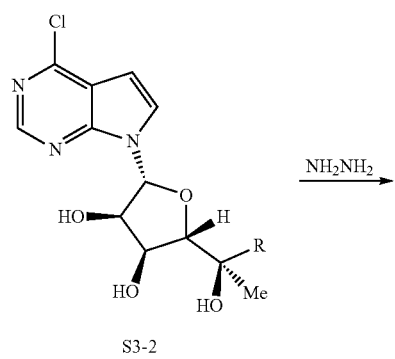
S3-2
NH₂NH₂ →
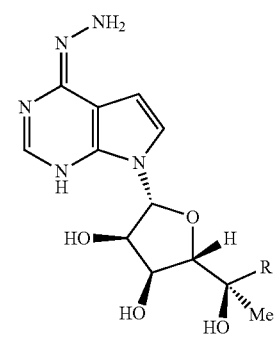
S3-3
Scheme 4
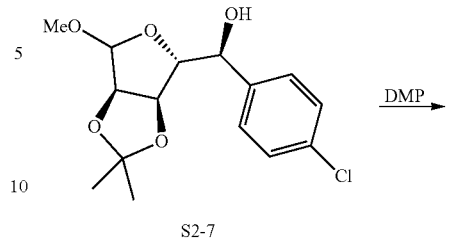
S2-7
DMP →
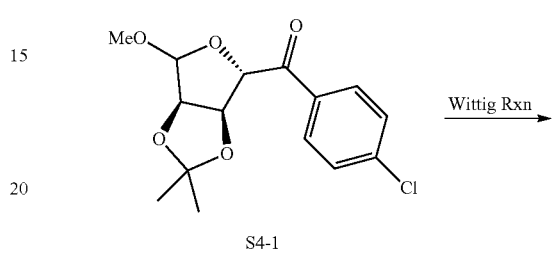
S4-1
Wittig Rxn →
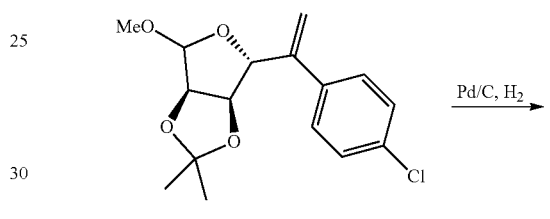
S4-2
Pd/C, H₂ →
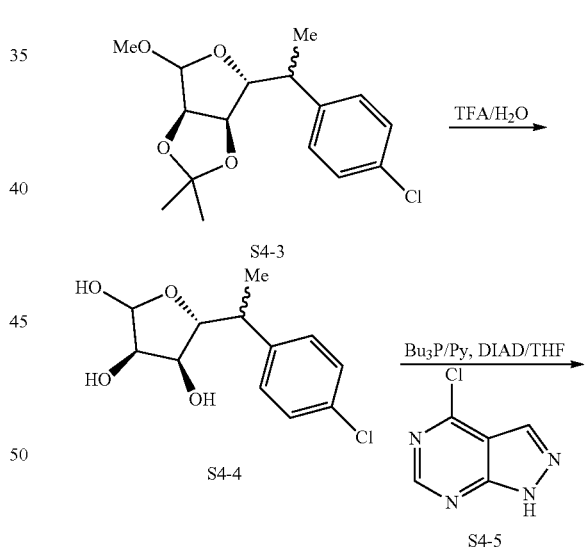
S4-3
TFA/H₂O →
S4-4
Bu₃P/Py, DIAD/THF
S4-5
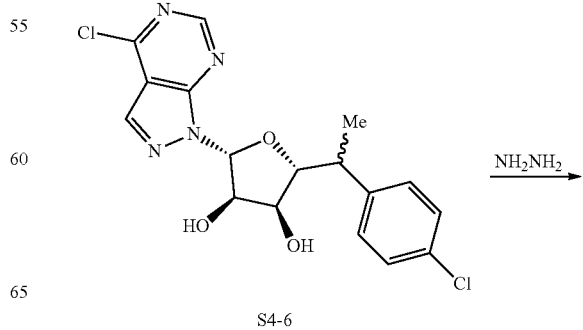
S4-6
NH₂NH₂ →

97
-continued
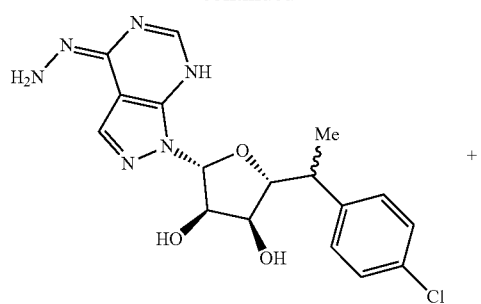
Ex. 6
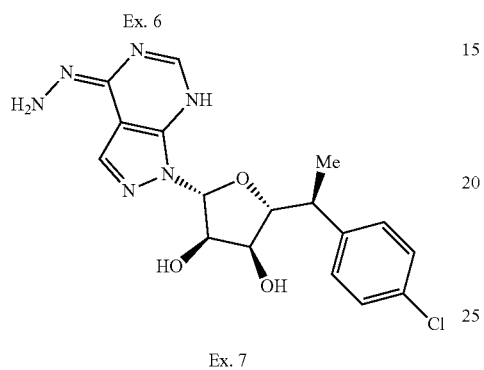
Ex. 7
Scheme 1-B
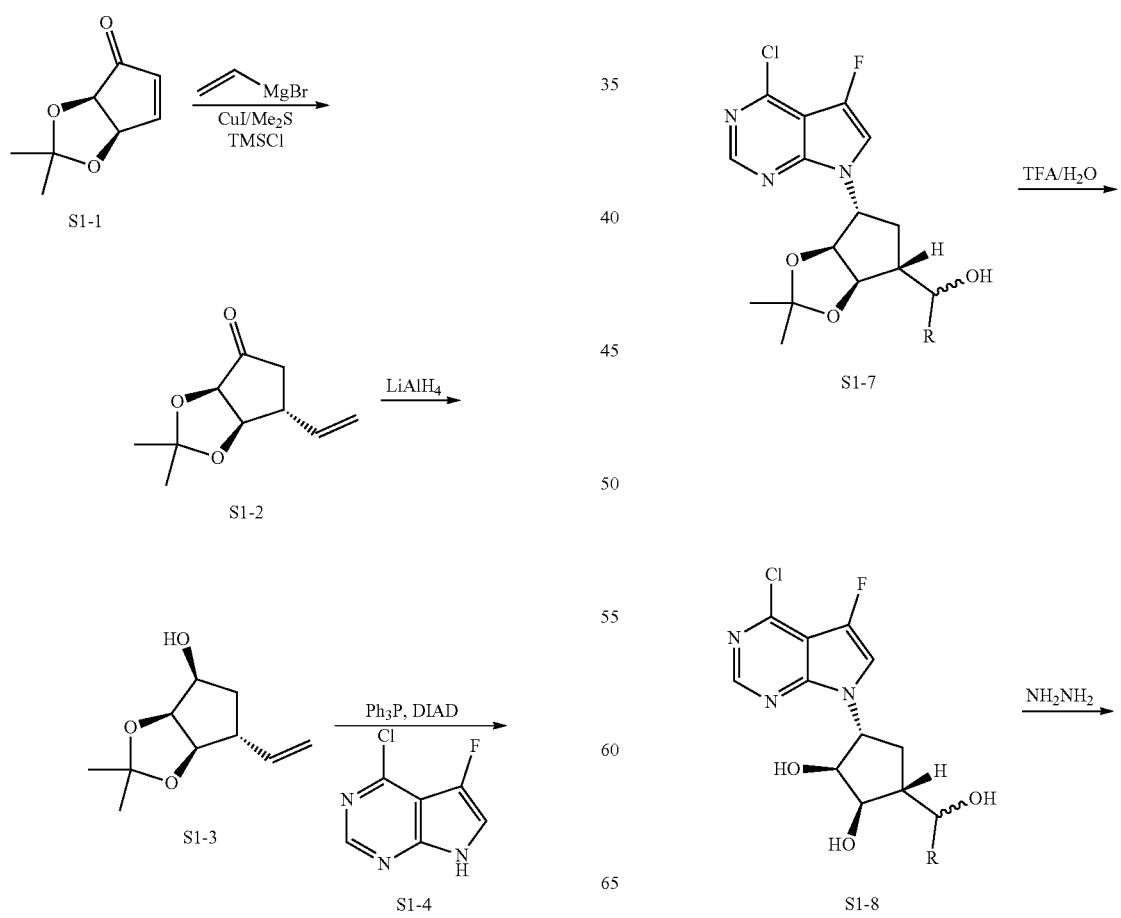
98
-continued
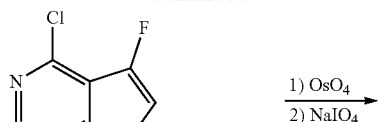
S1-5
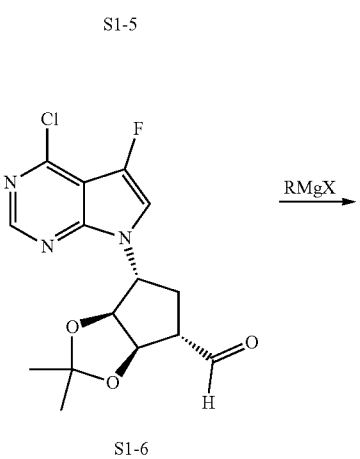

-continued
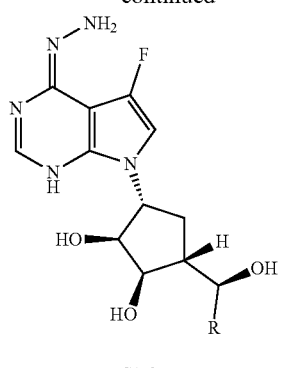
S1-9a
+
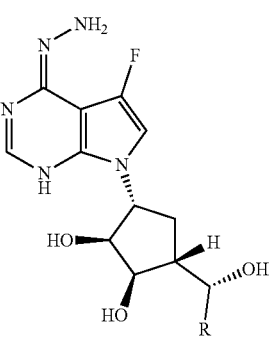
S1-9b
Scheme 2-B
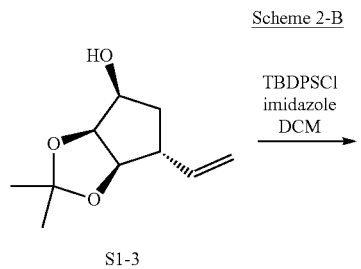
S1-3
TBDPSCl
imidazole
DCM
→
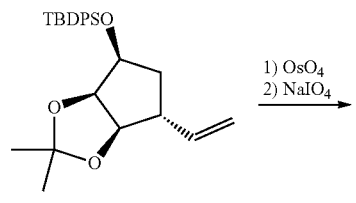
S2-1
1) OsO$_4$
2) NaIO$_4$
→
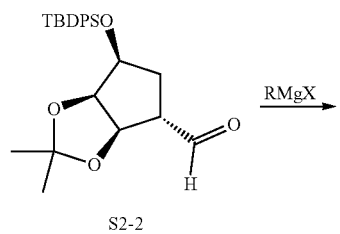
S2-2
RMgX
→
-continued
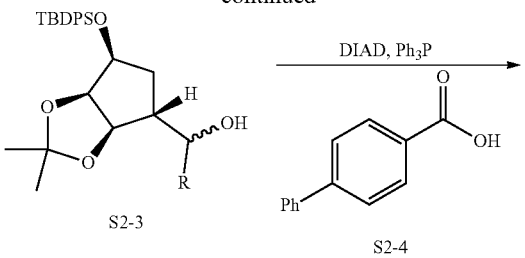
S2-3        S2-4
DIAD, Ph$_3$P
→
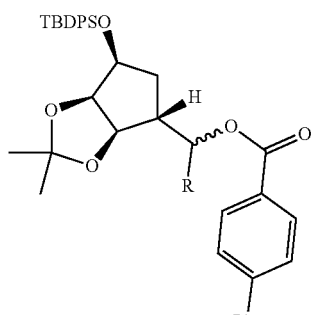
S2-5
1. TBAF
2. Tf$_2$O, Py, DCM
→
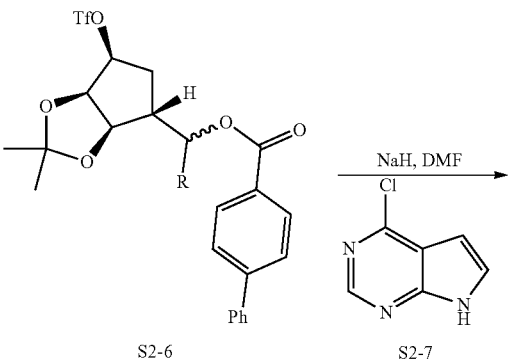
S2-6        S2-7
NaH, DMF
→
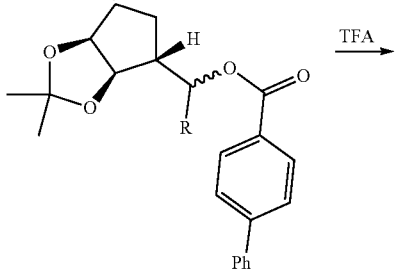
S2-8
TFA
→

101
-continued
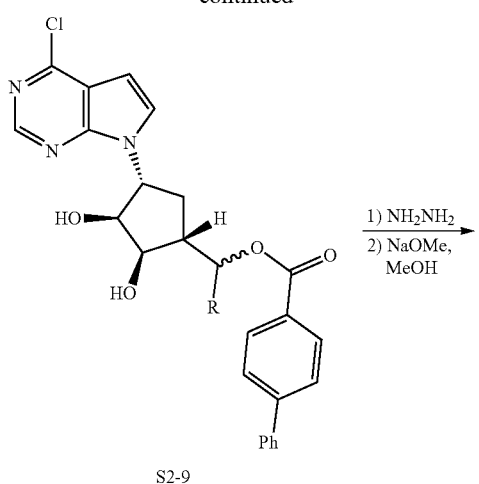
S2-9
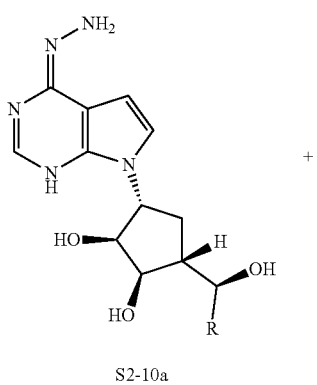
S2-10a
+
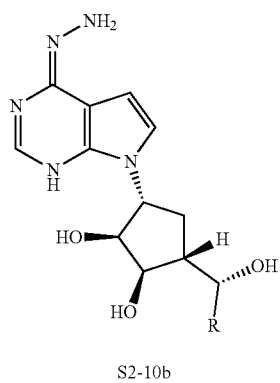
S2-10b
Scheme 3-B
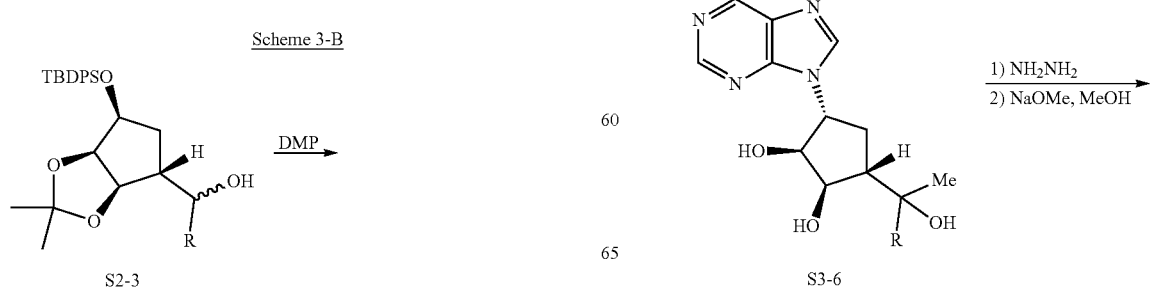

-continued
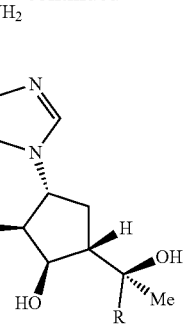
S3-7a
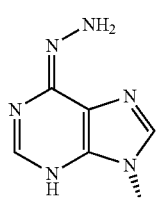
S3-7b
Scheme 4-B
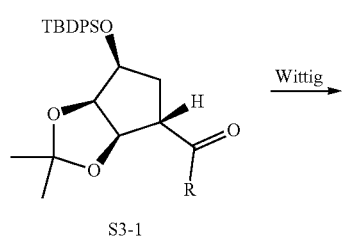
S3-1
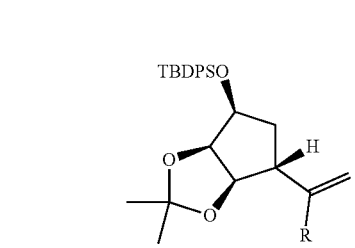
S4-2
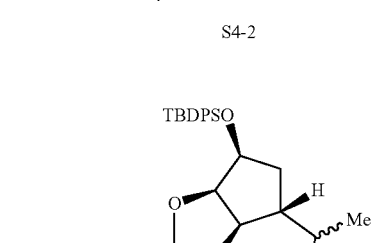
S4-3
-continued
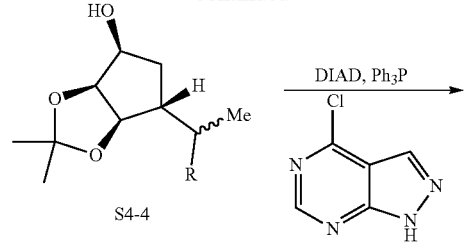
S4-4  S4-5
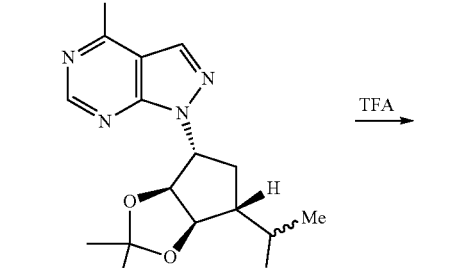
S4-6
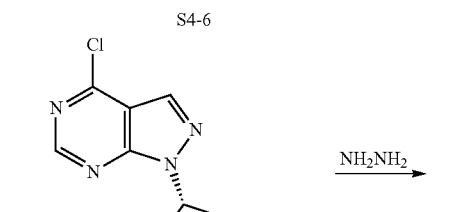
S4-7
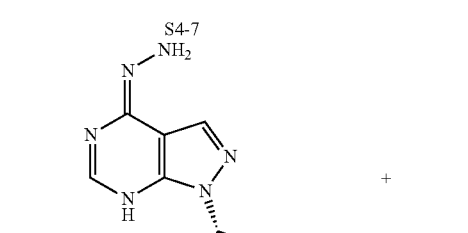
S4-8a
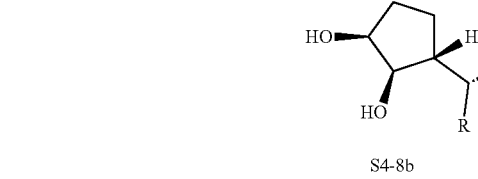
S4-8b

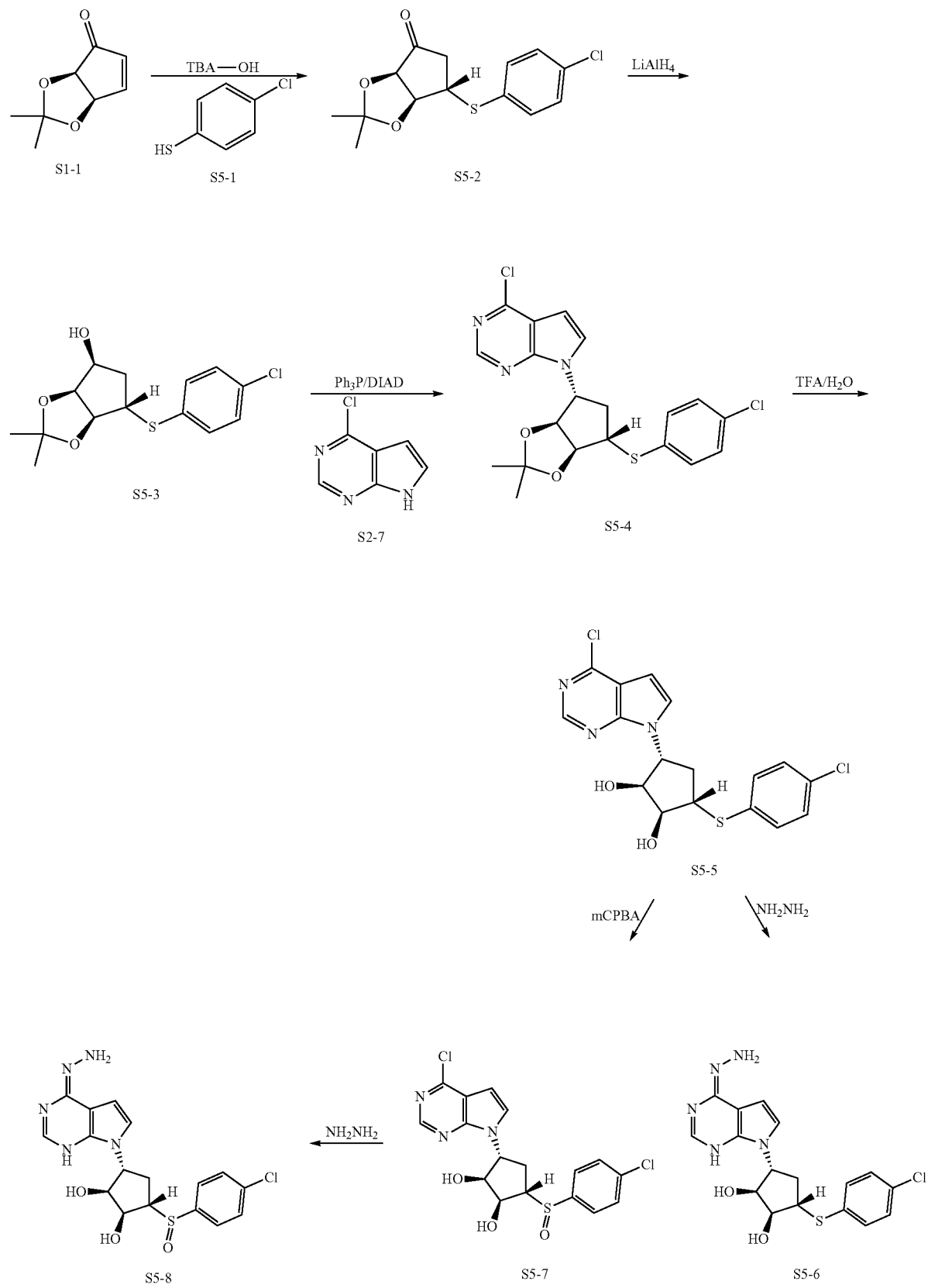

Scheme 1-C
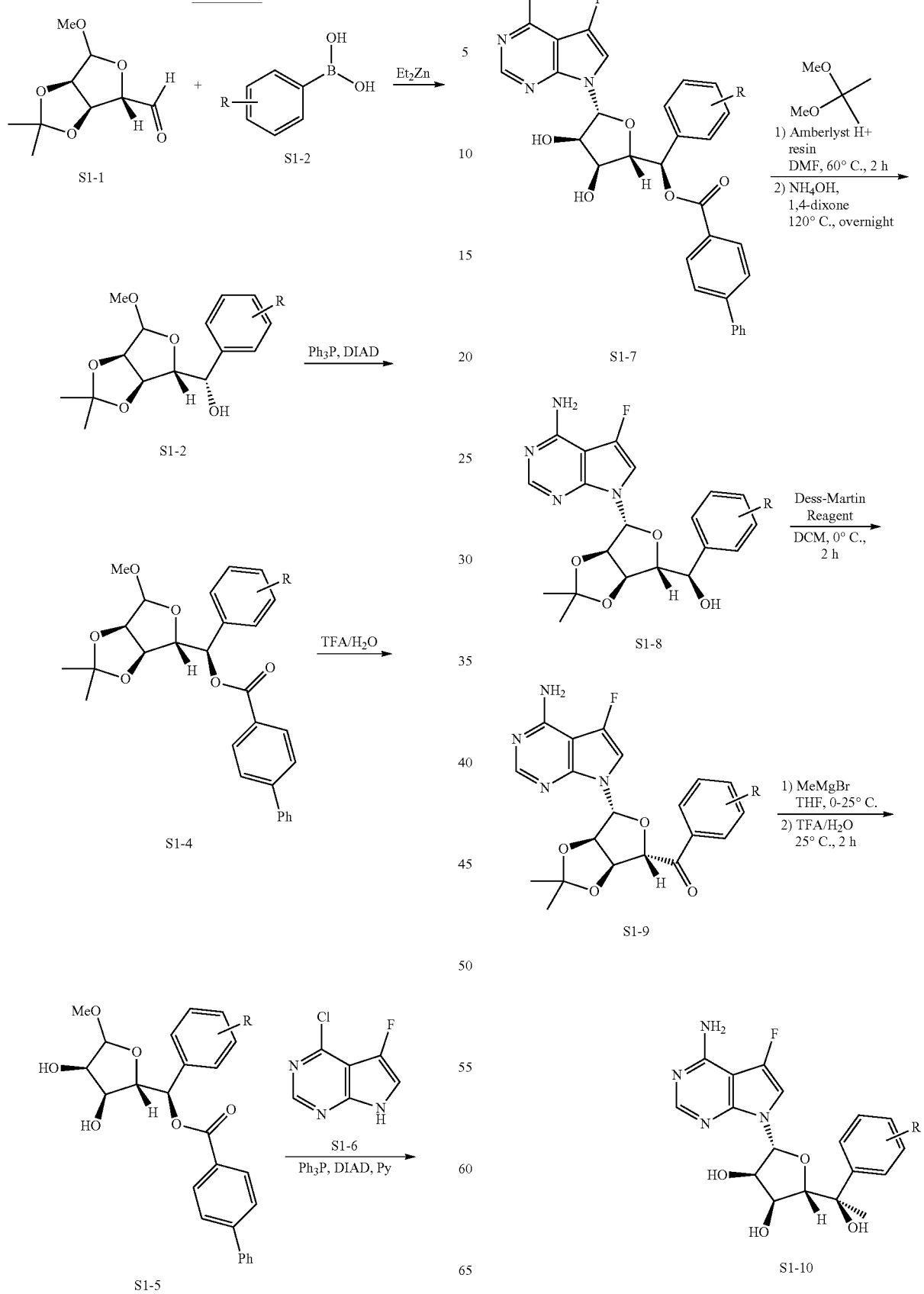

Scheme 2-C
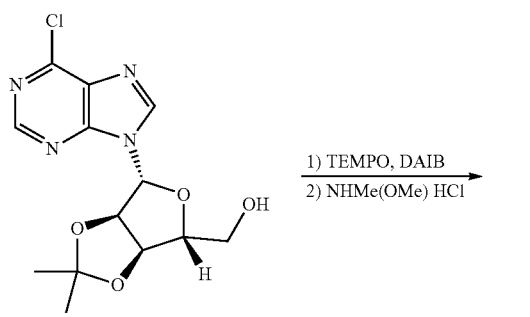
S2-1
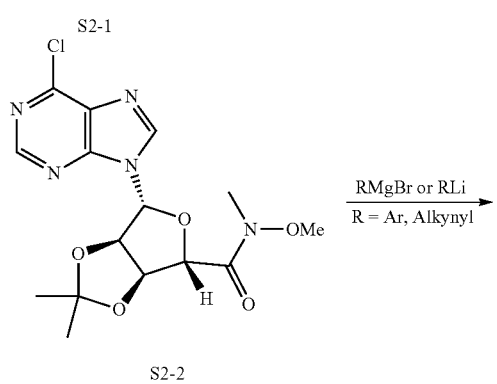
S2-2
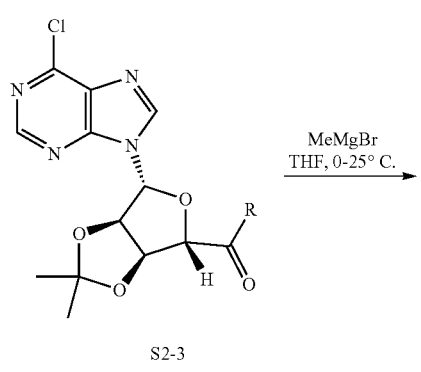
S2-3
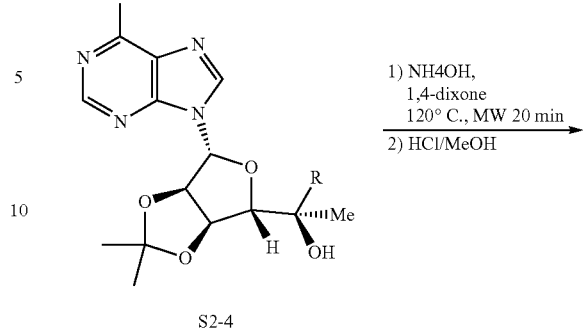
S2-4
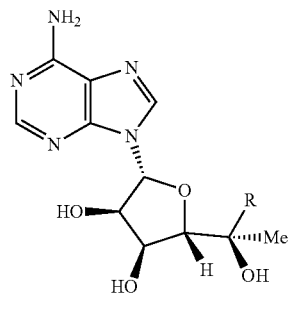
S2-5
Compounds of the disclosure of Formula I and Formula II include, for example, the compounds identified in Table A.
TABLE A
| Ex. # | Structures | MW | Chemical Name |
|---|---|---|---|
| 1 | 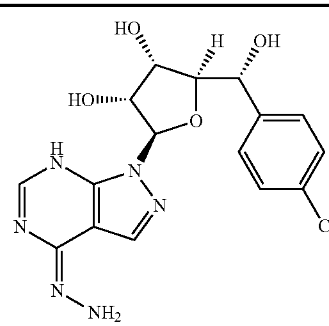 | 392.8 | (2R,3S,4R,5R)-2-((R)-(4-chlorophenyl)(hydroxy)methyl)-5-(4-hydrazineylidene-4,7-dihydro-1H-pyrazolo[3,4-d]pyrimidin-1-yl)tetrahydrofuran-3,4-diol |

TABLE A-continued

| Ex. # | Structures | MW | Chemical Name |
|---|---|---|---|
| 2 | 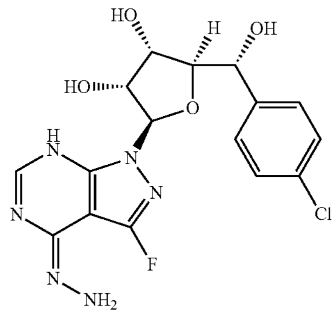 [SMILES: N/N=c1/nc[nH]c2c1c(F)nn2[C@@H]1O[C@H]([C@H](O)c2ccc(Cl)cc2)[C@@H](O)[C@H]1O] | 410.8 | (2R,3S,4R,5R)-2-((R)-(4-chlorophenyl)(hydroxy)methyl)-5-(3-fluoro-4-hydrazineylidene-4,7-dihydro-1H-pyrazolo[3,4-d]pyrimidin-1-yl)tetrahydrofuran-3,4-diol |
| 3 | 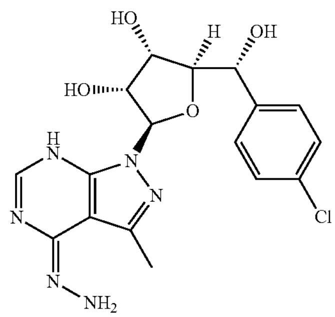 [SMILES: Cc1nn([C@@H]2O[C@H]([C@H](O)c3ccc(Cl)cc3)[C@@H](O)[C@H]2O)c2[nH]cn/c(=N/N)c12] | 406.8 | (2R,3S,4R,5R)-2-((R)-(4-chlorophenyl)(hydroxy)methyl)-5-(4-hydrazineylidene-3-methyl-4,7-dihydro-1H-pyrazolo[3,4-d]pyrimidin-1-yl)tetrahydrofuran-3,4-diol |
| 4 | 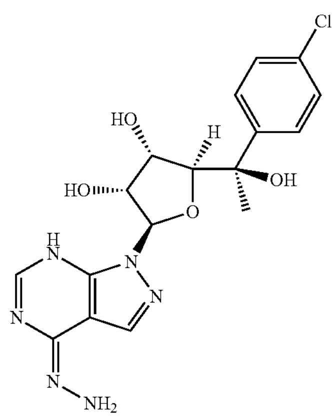 [SMILES: C[C@@](O)(c1ccc(Cl)cc1)[C@H]1O[C@@H](n2ncc3/c(=N\N)nc[nH]c32)[C@H](O)[C@@H]1O] | 406.8 | (2S,3S,4R,5R)-2-((R)-1-(4-chlorophenyl)-1-hydroxyethyl)-5-(4-hydrazineylidene-4,7-dihydro-1H-pyrazolo[3,4-d]pyrimidin-1-yl)tetrahydrofuran-3,4-diol |
| 5 | 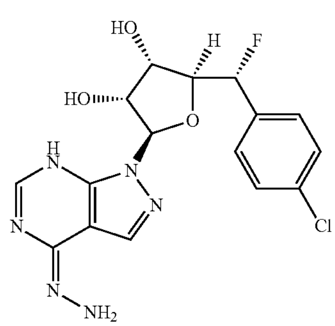 [SMILES: N/N=c1/nc[nH]c2c1cnn2[C@@H]1O[C@H]([C@H](F)c2ccc(Cl)cc2)[C@@H](O)[C@H]1O] | 394.8 | (2S,3S,4R,5R)-2-((R)-(4-chlorophenyl)fluoromethyl)-5-(4-hydrazineylidene-4,7-dihydro-1H-pyrazolo[3,4-d]pyrimidin-1-yl)tetrahydrofuran-3,4-diol |

TABLE A-continued

| Ex. # | Structures | MW | Chemical Name |
|---|---|---|---|
| 6 | 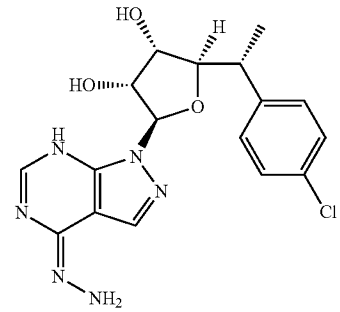 [SMILES: C[C@H](c1ccc(Cl)cc1)[C@H]1O[C@@H](n2ncc3/c(=N\N)nc[nH]c32)[C@H](O)[C@@H]1O] | 390.8 | (2R,3S,4R,5R)-2-((R)-1-(4-chlorophenyl)ethyl)-5-(4-hydrazineylidene-4,7-dihydro-1H-pyrazolo[3,4-d]pyrimidin-1-yl)tetrahydrofuran-3,4-diol |
| 7 | 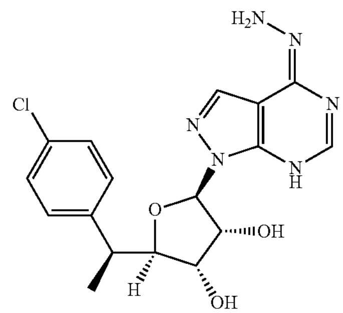 [SMILES: C[C@@H](c1ccc(Cl)cc1)[C@H]1O[C@@H](n2ncc3/c(=N\N)nc[nH]c32)[C@H](O)[C@@H]1O] | 390.8 | (2R,3S,4R,5R)-2-((S)-1-(4-chlorophenyl)ethyl)-5-(4-hydrazineylidene-4,7-dihydro-1H-pyrazolo[3,4-d]pyrimidin-1-yl)tetrahydrofuran-3,4-diol |
| 8 | 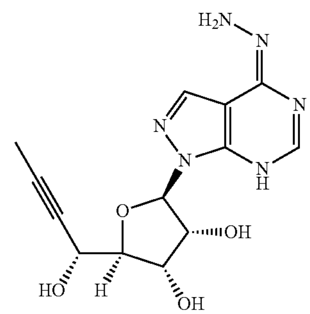 [SMILES: CC#C[C@@H](O)[C@H]1O[C@@H](n2ncc3/c(=N\N)nc[nH]c32)[C@H](O)[C@@H]1O] | 320.3 | (2R,3R,4S,5R)-2-(4-hydrazineylidene-4,7-dihydro-1H-pyrazolo[3,4-d]pyrimidin-1-yl)-5-((R)-1-hydroxybut-2-yn-1-yl)tetrahydrofuran-3,4-diol |
| 9 | 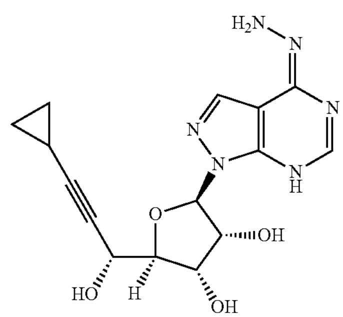 [SMILES: N/N=c1/nc[nH]c2c1cnn2[C@@H]1O[C@H]([C@H](O)C#CC2CC2)[C@@H](O)[C@H]1O] | 346.3 | (2R,3S,4R,5R)-2-((R)-3-cyclopropyl-1-hydroxyprop-2-yn-1-yl)-5-(4-hydrazineylidene-4,7-dihydro-1H-pyrazolo[3,4-d]pyrimidin-1-yl)tetrahydrofuran-3,4-diol |
| 10 | 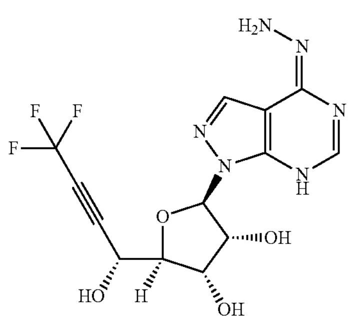 [SMILES: N/N=c1/nc[nH]c2c1cnn2[C@@H]1O[C@H]([C@H](O)C#CC(F)(F)F)[C@@H](O)[C@H]1O] | 374.3 | (2R,3R,4S,5R)-2-(4-hydrazineylidene-4,7-dihydro-1H-pyrazolo[3,4-d]pyrimidin-1-yl)-5-((R)-4,4,4-trifluoro-1-hydroxybut-2-yn-1-yl)tetrahydrofuran-3,4-diol |

TABLE A-continued

| Ex. # | Structures | MW | Chemical Name |
|---|---|---|---|
| 11 | 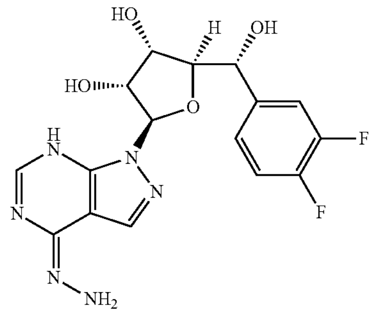 [SMILES: N/N=c1/nc[nH]c2c1cnn2[C@@H]1O[C@H]([C@H](O)c2ccc(F)c(F)c2)[C@@H](O)[C@H]1O] | 394.3 | (2R,3S,4R,5R)-2-((R)-(3,4-difluorophenyl)(hydroxy)methyl)-5-(4-hydrazineylidene-4,7-dihydro-1H-pyrazolo[3,4-d]pyrimidin-1-yl)tetrahydrofuran-3,4-diol |
| 12 | 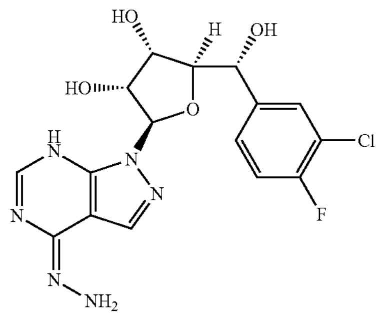 [SMILES: N/N=c1/nc[nH]c2c1cnn2[C@@H]1O[C@H]([C@H](O)c2ccc(F)c(Cl)c2)[C@@H](O)[C@H]1O] | 410.8 | (2R,3S,4R,5R)-2-((R)-(3-chloro-4-fluorophenyl)(hydroxy)methyl)-5-(4-hydrazineylidene-4,7-dihydro-1H-pyrazolo[3,4-d]pyrimidin-1-yl)tetrahydrofuran-3,4-diol |
| 13 | 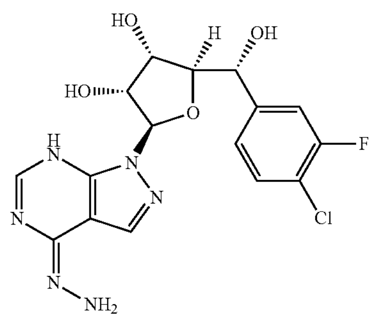 [SMILES: N/N=c1/nc[nH]c2c1cnn2[C@@H]1O[C@H]([C@H](O)c2ccc(Cl)c(F)c2)[C@@H](O)[C@H]1O] | 410.8 | (2R,3S,4R,5R)-2-((R)-(4-chloro-3-fluorophenyl)(hydroxy)methyl)-5-(4-hydrazineylidene-4,7-dihydro-1H-pyrazolo[3,4-d]pyrimidin-1-yl)tetrahydrofuran-3,4-diol |
| 14 | 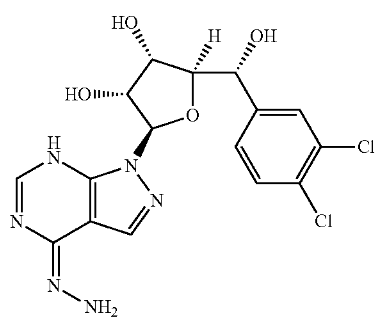 [SMILES: N/N=c1/nc[nH]c2c1cnn2[C@@H]1O[C@H]([C@H](O)c2ccc(Cl)c(Cl)c2)[C@@H](O)[C@H]1O] | 427.2 | (2R,3S,4R,5R)-2-((R)-(3,4-dichlorophenyl)(hydroxy)methyl)-5-(4-hydrazineylidene-4,7-dihydro-1H-pyrazolo[3,4-d]pyrimidin-1-yl)tetrahydrofuran-3,4-diol |
| 15 | 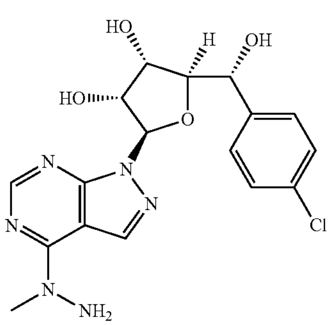 [SMILES: CN(N)c1ncnc2c1cnn2[C@@H]1O[C@H]([C@H](O)c2ccc(Cl)cc2)[C@@H](O)[C@H]1O] | 406.8 | (2R,3S,4R,5R)-2-((R)-(4-chlorophenyl)(hydroxy)methyl)-5-(4-(1-methylhydrazineyl)-1H-pyrazolo[3,4-d]pyrimidin-1-yl)tetrahydrofuran-3,4-diol |

TABLE A-continued

| Ex. # | Structures | MW | Chemical Name |
|---|---|---|---|
| 16 | 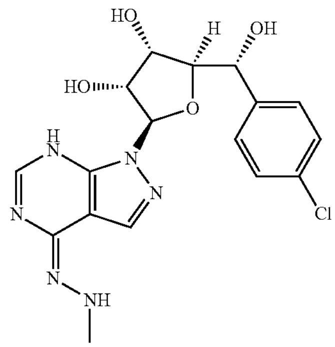 [SMILES: CN/N=c1/nc[nH]c2c1cnn2[C@@H]1O[C@H]([C@H](O)c2ccc(Cl)cc2)[C@@H](O)[C@H]1O] | 406.8 | (2R,3S,4R,5R)-2-((R)-(4-chlorophenyl)(hydroxy)methyl)-5-(4-(2-methylhydrazineylidene)-4,7-dihydro-1H-pyrazolo[3,4-d]pyrimidin-1-yl)tetrahydrofuran-3,4-diol |
| 17 | 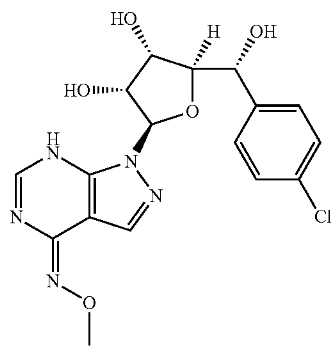 [SMILES: CO/N=c1/nc[nH]c2c1cnn2[C@@H]1O[C@H]([C@H](O)c2ccc(Cl)cc2)[C@@H](O)[C@H]1O] | 407.8 | 1-((2R,3R,4S,5R)-5-((R)-(4-chlorophenyl)(hydroxy)methyl)-3,4-dihydroxytetrahydrofuran-2-yl)-1,7-dihydro-4H-pyrazolo[3,4-d]pyrimidin-4-one O-methyl oxime |
| 18 | 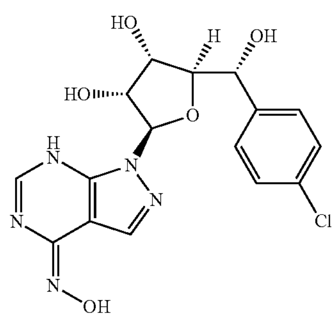 [SMILES: O/N=c1/nc[nH]c2c1cnn2[C@@H]1O[C@H]([C@H](O)c2ccc(Cl)cc2)[C@@H](O)[C@H]1O] | 393.8 | 1-((2R,3R,4S,5R)-5-((R)-(4-chlorophenyl)(hydroxy)methyl)-3,4-dihydroxytetrahydrofuran-2-yl)-1,7-dihydro-4H-pyrazolo[3,4-d]pyrimidin-4-one oxime |
| 19 | 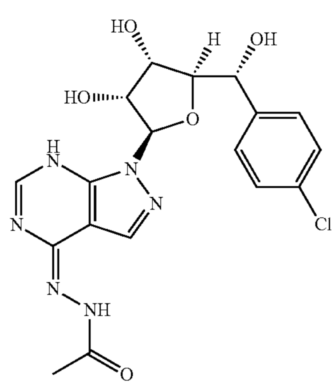 [SMILES: CC(=O)N/N=c1/nc[nH]c2c1cnn2[C@@H]1O[C@H]([C@H](O)c2ccc(Cl)cc2)[C@@H](O)[C@H]1O] | 434.8 | N'-1-((2R,3R,4S,5R)-5-((R)-(4-chlorophenyl)(hydroxy)methyl)-3,4-dihydroxytetrahydrofuran-2-yl)-1,7-dihydro-4H-pyrazolo[3,4-d]pyrimidin-4-ylidene)acetohydrazide |

TABLE A-continued

| Ex. # | Structures | MW | Chemical Name |
|---|---|---|---|
| 20 | 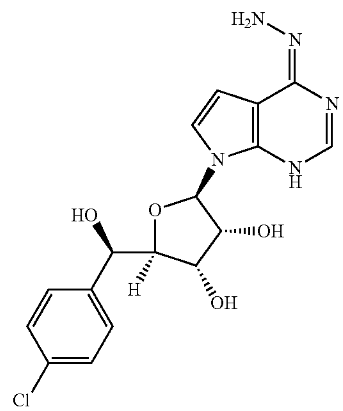 [SMILES: N/N=c1/nc[nH]c2c1ccn2[C@@H]1O[C@H]([C@H](O)c2ccc(Cl)cc2)[C@@H](O)[C@H]1O] | 391.8 | (2R,3S,4R,5R)-2-((R)-(4-chlorophenyl)(hydroxy)methyl)-5-(4-hydrazineylidene-1,4-dihydro-7H-pyrrolo[2,3-d]pyrimidin-7-yl)tetrahydrofuran-3,4-diol |
| 21 | 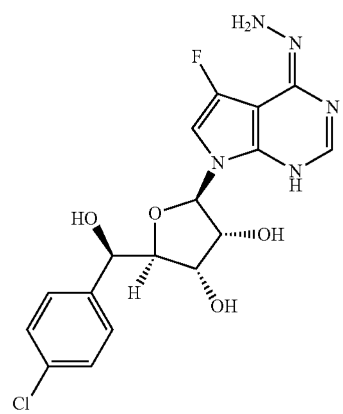 [SMILES: N/N=c1/nc[nH]c2c1c(F)cn2[C@@H]1O[C@H]([C@H](O)c2ccc(Cl)cc2)[C@@H](O)[C@H]1O] | 409.8 | (2R,3S,4R,5R)-2-((R)-(4-chlorophenyl)(hydroxy)methyl)-5-(5-fluoro-4-hydrazineylidene-1,4-dihydro-7H-pyrrolo[2,3-d]pyrimidin-7-yl)tetrahydrofuran-3,4-diol |
| 22 | 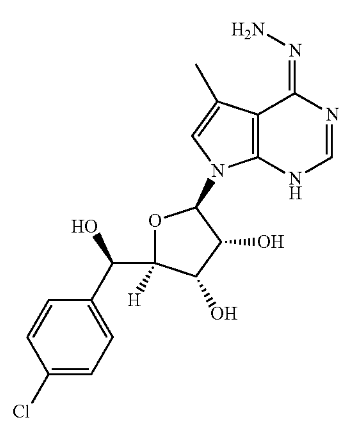 [SMILES: Cc1cn([C@@H]2O[C@H]([C@H](O)c3ccc(Cl)cc3)[C@@H](O)[C@H]2O)c2[nH]cn/c(=N/N)c12] | 405.8 | (2R,3S,4R,5R)-2-((R)-(4-chlorophenyl)(hydroxy)methyl)-5-(4-hydrazineylidene-5-methyl-1,4-dihydro-7H-pyrrolo[2,3-d]pyrimidin-7-yl)tetrahydrofuran-3,4-diol |

TABLE A-continued

| Ex. # | Structures | MW | Chemical Name |
|---|---|---|---|
| 23 | 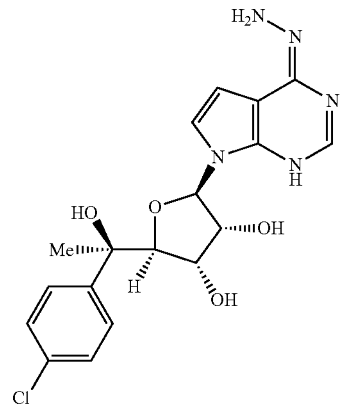 [SMILES: C[C@@](O)(c1ccc(Cl)cc1)[C@H]1O[C@@H](n2ccc3/c(=N\N)nc[nH]c32)[C@H](O)[C@@H]1O] | 405.8 | (2S,3S,4R,5R)-2-((R)-1-(4-chlorophenyl)-1-hydroxyethyl)-5-(4-hydrazineylidene-1,4-dihydro-7H-pyrrolo[2,3-d]pyrimidin-7-yl)tetrahydrofuran-3,4-diol |
| 24 | 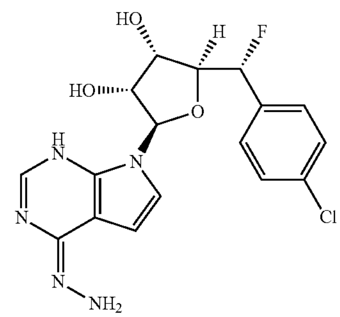 [SMILES: N/N=c1/nc[nH]c2c1ccn2[C@@H]1O[C@H]([C@H](F)c2ccc(Cl)cc2)[C@@H](O)[C@H]1O] | 393.8 | (2S,3S,4R,5R)-2-((R)-(4-chlorophenyl)fluoromethyl)-5-(4-hydrazineylidene-1,4-dihydro-7H-pyrrolo[2,3-d]pyrimidin-7-yl)tetrahydrofuran-3,4-diol |
| 25 | 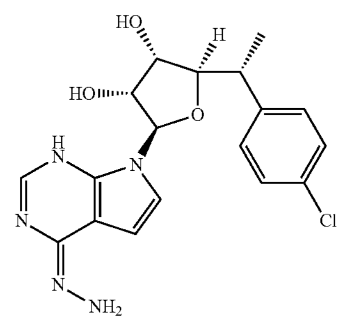 [SMILES: C[C@H](c1ccc(Cl)cc1)[C@H]1O[C@@H](n2ccc3/c(=N\N)nc[nH]c32)[C@H](O)[C@@H]1O] | 389.8 | (2R,3S,4R,5R)-2-((R)-1-(4-chlorophenyl)ethyl)-5-(4-hydrazineylidene-1,4-dihydro-7H-pyrrolo[2,3-d]pyrimidin-7-yl)tetrahydrofuran-3,4-diol |
| 26 | 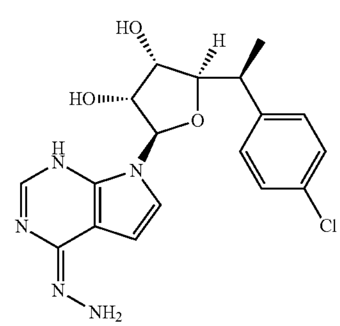 [SMILES: C[C@@H](c1ccc(Cl)cc1)[C@H]1O[C@@H](n2ccc3/c(=N\N)nc[nH]c32)[C@H](O)[C@@H]1O] | 389.8 | (2R,3S,4R,5R)-2-((S)-1-(4-chlorophenyl)ethyl)-5-(4-hydrazineylidene-1,4-dihydro-7H-pyrrolo[2,3-d]pyrimidin-7-yl)tetrahydrofuran-3,4-diol |

TABLE A-continued

| Ex. # | Structures | MW | Chemical Name |
|---|---|---|---|
| 27 | 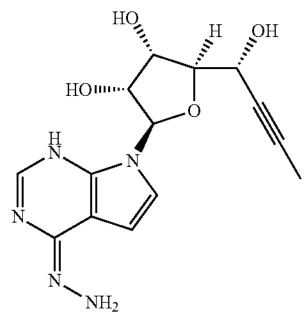 [SMILES: CC#C[C@@H](O)[C@H]1O[C@@H](n2ccc3/c(=N\N)nc[nH]c32)[C@H](O)[C@@H]1O] | 319.3 | (2R,3R,4S,5R)-2-(4-hydrazineylidene-1,4-dihydro-7H-pyrrolo[2,3-d]pyrimidin-7-yl)-5-((R)-1-hydroxybut-2-yn-1-yl)tetrahydrofuran-3,4-diol |
| 28 | 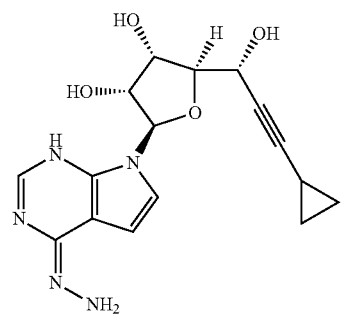 | 345.4 | (2R,3S,4R,5R)-2-((R)-3-cyclopropyl-1-hydroxyprop-2-yn-1-yl)-5-(4-hydrazineylidene-1,4-dihydro-7H-pyrrolo[2,3-d]pyrimidin-7-yl)tetrahydrofuran-3,4-diol |
| 29 | 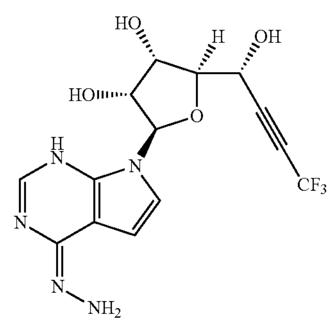 [SMILES: N/N=c1/nc[nH]c2c1ccn2[C@@H]1O[C@H]([C@H](O)C#CC(F)(F)F)[C@@H](O)[C@H]1O] | 373.3 | (2R,3R,4S,5R)-2-(4-hydrazineylidene-1,4-dihydro-7H-pyrrolo[2,3-d]pyrimidin-7-yl)-5-((R)-4,4,4-trifluoro-1-hydroxybut-2-yn-1-yl)tetrahydrofuran-3,4-diol |
| 30 | 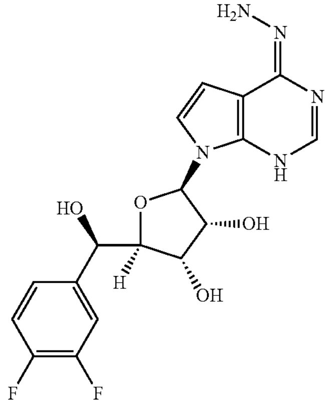 [SMILES: N/N=c1/nc[nH]c2c1ccn2[C@@H]1O[C@H]([C@H](O)c2ccc(F)c(F)c2)[C@@H](O)[C@H]1O] | 393.4 | (2R,3S,4R,5R)-2-((R)-(3,4-difluorophenyl)(hydroxy)methyl)-5-(4-hydrazineylidene-1,4-dihydro-7H-pyrrolo[2,3-d]pyrimidin-7-yl)tetrahydrofuran-3,4-diol |

TABLE A-continued

| Ex. # | Structures | MW | Chemical Name |
|---|---|---|---|
| 31 | 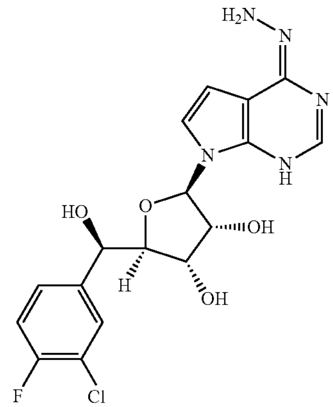 [SMILES: N/N=c1/nc[nH]c2c1ccn2[C@@H]1O[C@H]([C@H](O)c2ccc(F)c(Cl)c2)[C@@H](O)[C@H]1O] | 409.8 | (2R,3S,4R,5R)-2-((R)-(3-chloro-4-fluorophenyl)(hydroxy)methyl)-5-(4-hydrazineylidene-1,4-dihydro-7H-pyrrolo[2,3-d]pyrimidin-7-yl)tetrahydrofuran-3,4-diol |
| 32 | 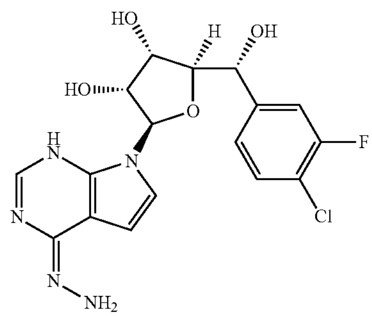 | 409.8 | (2R,3S,4R,5R)-2-((R)-(4-chloro-3-fluorophenyl)(hydroxy)methyl)-5-(4-hydrazineylidene-1,4-dihydro-7H-pyrrolo[2,3-d]pyrimidin-7-yl)tetrahydrofuran-3,4-diol |
| 33 | 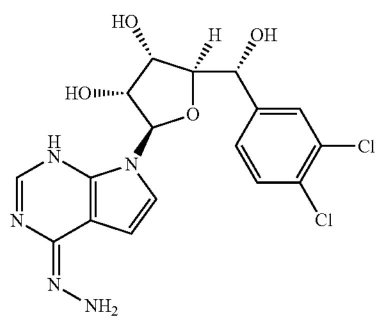 | 426.3 | (2R,3S,4R,5R)-2-((R)-(3,4-dichlorophenyl)(hydroxy)methyl)-5-(4-hydrazineylidene-1,4-dihydro-7H-pyrrolo[2,3-d]pyrimidin-7-yl)tetrahydrofuran-3,4-diol |
| 34 | 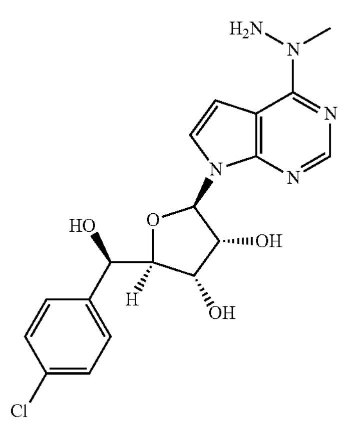 [SMILES: CN(N)c1ncnc2c1ccn2[C@@H]1O[C@H]([C@H](O)c2ccc(Cl)cc2)[C@@H](O)[C@H]1O] | 405.8 | (2R,3S,4R,5R)-2-((R)-(4-chlorophenyl)(hydroxy)methyl)-5-(4-(1-methylhydrazineyl)-7H-pyrrolo[2,3-d]pyrimidin-7-yl)tetrahydrofuran-3,4-diol |

TABLE A-continued

| Ex. # | Structures | MW | Chemical Name |
|---|---|---|---|
| 35 | 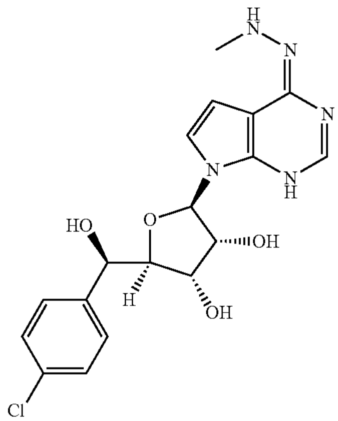 [SMILES: CN/N=c1/nc[nH]c2c1ccn2[C@@H]1O[C@H]([C@H](O)c2ccc(Cl)cc2)[C@@H](O)[C@H]1O] | 405.8 | (2R,3S,4R,5R)-2-((R)-(4-chlorophenyl)(hydroxy)methyl)-5-(4-(2-methylhydrazineylidene)-1,4-dihydro-7H-pyrrolo[2,3-d]pyrimidin-7-yl)tetrahydrofuran-3,4-diol |
| 36 | 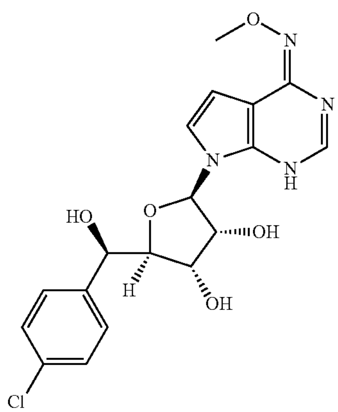 [SMILES: CO/N=c1/nc[nH]c2c1ccn2[C@@H]1O[C@H]([C@H](O)c2ccc(Cl)cc2)[C@@H](O)[C@H]1O] | 406.8 | 7-((2R,3R,4S,5R)-5-((R)-(4-chlorophenyl)(hydroxy)methyl)-3,4-dihydroxytetrahydrofuran-2-yl)-1,7-dihydro-4H-pyrrolo[2,3-d]pyrimidin-4-one O-methyl oxime |
| 37 | 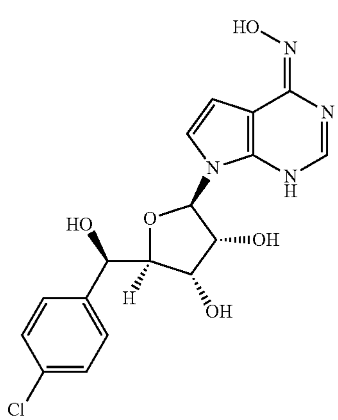 [SMILES: O/N=c1/nc[nH]c2c1ccn2[C@@H]1O[C@H]([C@H](O)c2ccc(Cl)cc2)[C@@H](O)[C@H]1O] | 392.8 | 7-((2R,3R,4S,5R)-5-((R)-(4-chlorophenyl)(hydroxy)methyl)-3,4-dihydroxytetrahydrofuran-2-yl)-1,7-dihydro-4H-pyrrolo[2,3-d]pyrimidin-4-one oxime |

TABLE A-continued

| Ex. # | Structures | MW | Chemical Name |
|---|---|---|---|
| 38 | 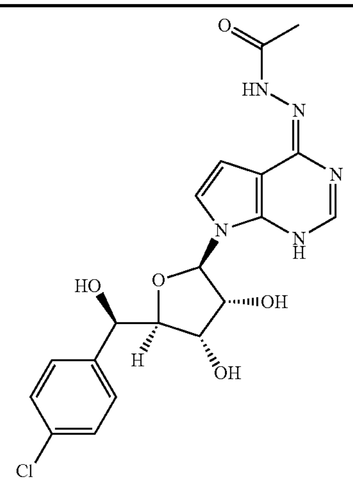 | 433.8 | N'-(7-((2R,3R,4S,5R)-5-((R)-(4-chlorophenyl)(hydroxy)methyl)-3,4-dihydroxytetrahydrofuran-2-yl)-1,7-dihydro-4H-pyrrolo[2,3-d]pyrimidin-4-ylidene)acetohydrazide |
| 39 | 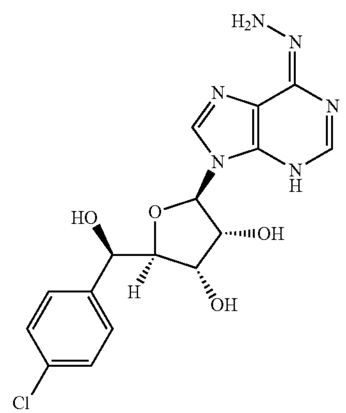 [SMILES: N/N=c1/nc[nH]c2c1ncn2[C@@H]1O[C@H]([C@H](O)c2ccc(Cl)cc2)[C@@H](O)[C@H]1O] | 392.8 | (2R,3S,4R,5R)-2-((R)-(4-chlorophenyl)(hydroxy)methyl)-5-(6-hydrazineylidene-3,6-dihydro-9H-purin-9-yl)tetrahydrofuran-3,4-diol |
| 40 | 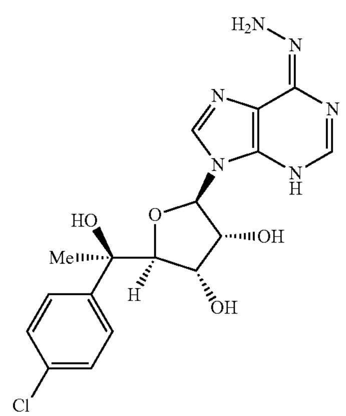 [SMILES: C[C@@](O)(c1ccc(Cl)cc1)[C@H]1O[C@@H](n2cnc3/c(=N\N)nc[nH]c32)[C@H](O)[C@@H]1O] | 406.8 | (2S,3S,4R,5R)-2-((R)-1-(4-chlorophenyl)-1-hydroxyethyl)-5-(6-hydrazineylidene-3,6-dihydro-9H-purin-9-yl)tetrahydrofuran-3,4-diol |
| 41 | 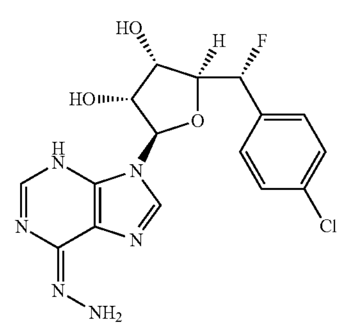 [SMILES: N/N=c1/nc[nH]c2c1ncn2[C@@H]1O[C@H]([C@H](F)c2ccc(Cl)cc2)[C@@H](O)[C@H]1O] | 394.8 | (2S,3S,4R,5R)-2-((R)-(4-chlorophenyl)fluoromethyl)-5-(6-hydrazineylidene-3,6-dihydro-9H-purin-9-yl)tetrahydrofuran-3,4-diol |

TABLE A-continued

| Ex. # | Structures | MW | Chemical Name |
|---|---|---|---|
| 42 | 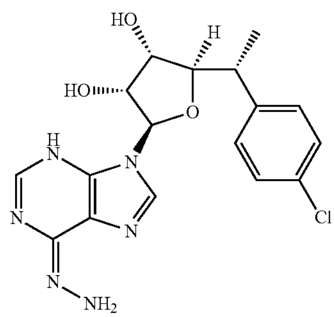 [SMILES: C[C@H](c1ccc(Cl)cc1)[C@H]1O[C@@H](n2cnc3/c(=N\N)nc[nH]c32)[C@H](O)[C@@H]1O] | 390.8 | (2R,3S,4R,5R)-2-((R)-1-(4-chlorophenyl)ethyl)-5-(6-hydrazineylidene-3,6-dihydro-9H-purin-9-yl)tetrahydrofuran-3,4-diol |
| 43 | 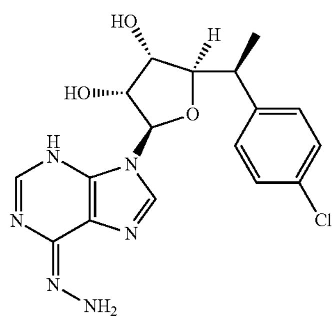 [SMILES: C[C@@H](c1ccc(Cl)cc1)[C@H]1O[C@@H](n2cnc3/c(=N\N)nc[nH]c32)[C@H](O)[C@@H]1O] | 390.8 | (2R,3S,4R,5R)-2-((S)-1-(4-chlorophenyl)ethyl)-5-(6-hydrazineylidene-3,6-dihydro-9H-purin-9-yl)tetrahydrofuran-3,4-diol |
| 44 | 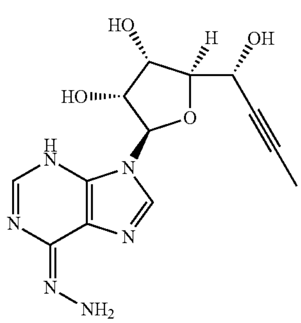 [SMILES: CC#C[C@@H](O)[C@H]1O[C@@H](n2cnc3/c(=N\N)nc[nH]c32)[C@H](O)[C@@H]1O] | 320.3 | (2R,3R,4S,5R)-2-(6-hydrazineylidene-3,6-dihydro-9H-purin-9-yl)-5-((R)-1-hydroxybut-2-yn-1-yl)tetrahydrofuran-3,4-diol |
| 45 | 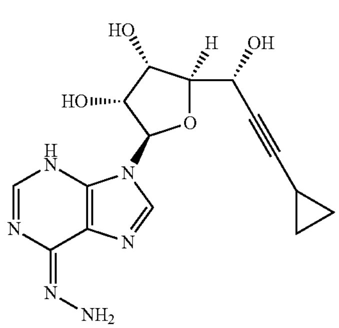 [SMILES: N/N=c1/nc[nH]c2c1ncn2[C@@H]1O[C@H]([C@H](O)C#CC2CC2)[C@@H](O)[C@H]1O] | 346.3 | (2R,3S,4R,5R)-2-((R)-3-cyclopropyl-1-hydroxyprop-2-yn-1-yl)-5-(6-hydrazineylidene-3,6-dihydro-9H-purin-9-yl)tetrahydrofuran-3,4-diol |

TABLE A-continued

| Ex. # | Structures | MW | Chemical Name |
|---|---|---|---|
| 46 | 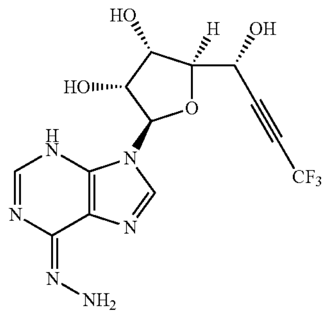 [SMILES: N/N=c1/nc[nH]c2c1ncn2[C@@H]1O[C@H]([C@H](O)C#CC(F)(F)F)[C@@H](O)[C@H]1O] | 374.3 | (2R,3R,4S,5R)-2-(-6-hydrazineylidene-3,6-dihydro-9H-purin-9-yl)-5-((R)-4,4,4-trifluoro-1-hydroxybut-2-yn-1-yl)tetrahydrofuran-3,4-diol |
| 47 | 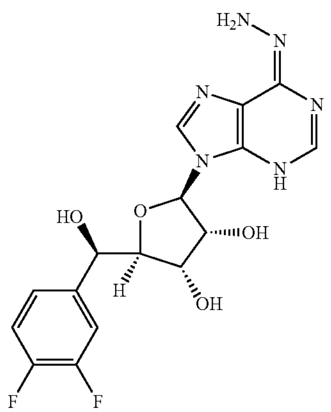 [SMILES: N/N=c1/nc[nH]c2c1ncn2[C@@H]1O[C@H]([C@H](O)c2ccc(F)c(F)c2)[C@@H](O)[C@H]1O] | 394.3 | (2R,3S,4R,5R)-2-((R)-(3,4-difluorophenyl)(hydroxy)methyl)-5-(6-hydrazineylidene-3,6-dihydro-9H-purin-9-yl)tetrahydrofuran-3,4-diol |
| 48 | 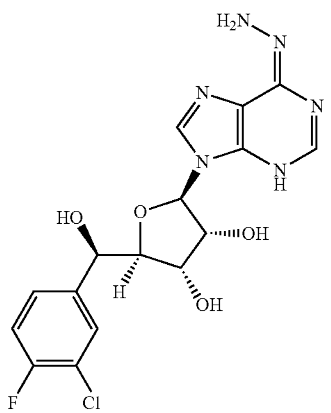 [SMILES: N/N=c1/nc[nH]c2c1ncn2[C@@H]1O[C@H]([C@H](O)c2ccc(F)c(Cl)c2)[C@@H](O)[C@H]1O] | 410.8 | (2R,3S,4R,5R)-2-((R)-(3-chloro-4-fluorophenyl)(hydroxy)methyl)-5-(6-hydrazineylidene-3,6-dihydro-9H-purin-9-yl)tetrahydrofuran-3,4-diol |
| 49 | 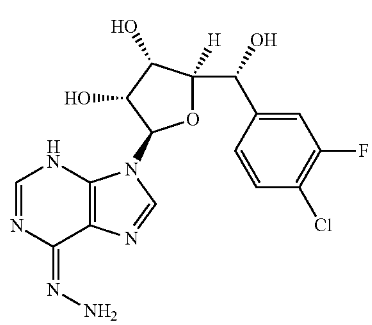 [SMILES: N/N=c1/nc[nH]c2c1ncn2[C@@H]1O[C@H]([C@H](O)c2ccc(Cl)c(F)c2)[C@@H](O)[C@H]1O] | 410.8 | (2R,3S,4R,5R)-2-((R)-(4-chloro-3-fluorophenyl)(hydroxy)methyl)-5-(6-hydrazineylidene,36-dihydro-9H-purin-9-yl)tetrahydrofuran-3,4-diol |

TABLE A-continued

| Ex. # | Structures | MW | Chemical Name |
|---|---|---|---|
| 50 | 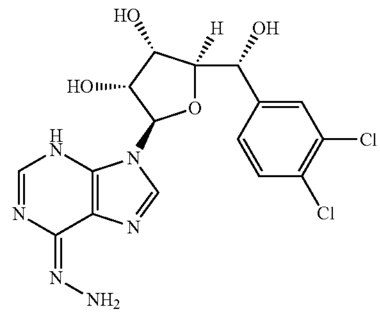 [SMILES: N/N=c1/nc[nH]c2c1ncn2[C@@H]1O[C@H]([C@H](O)c2ccc(Cl)c(Cl)c2)[C@@H](O)[C@H]1O] | 427.2 | (2R,3S,4R,5R)-2-((R)-(3,4-dichlorophenyl)(hydroxy)methyl)-5-(6-hydrazineylidene-3,6-dihydro-9H-purin-9-yl)tetrahydrofuran-3,4-diol |
| 51 | 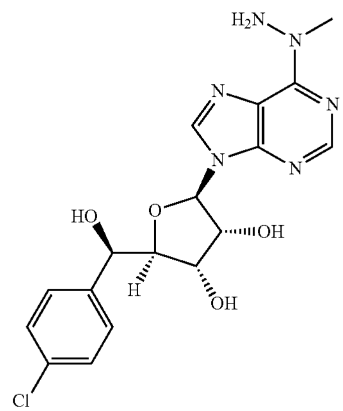 [SMILES: CN(N)c1ncnc2c1ncn2[C@@H]1O[C@H]([C@H](O)c2ccc(Cl)cc2)[C@@H](O)[C@H]1O] | 406.8 | (2R,3S,4R,5R)-2-((R)-(4-chlorophenyl)(hydroxy)methyl)-5-(6-(1-methylhydrazineyl)-9H-purin-9-yl)tetrahydrofuran-3,4-diol |
| 52 | 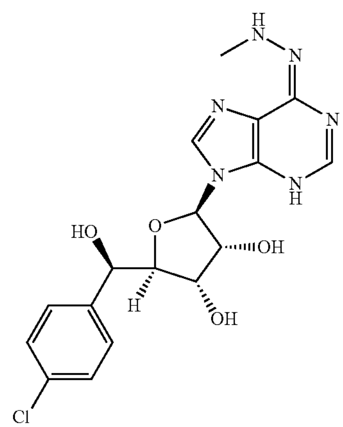 [SMILES: CN/N=c1/nc[nH]c2c1ncn2[C@@H]1O[C@H]([C@H](O)c2ccc(Cl)cc2)[C@@H](O)[C@H]1O] | 406.8 | (2R,3S,4R,5R)-2-((R)-(4-chlorophenyl)(hydroxy)methyl)-5-(6-(2-methylhydrazineylidene)-3,6-dihydro-9H-purin-9-yl)tetrahydrofuran-3,4-diol |
| 53 | 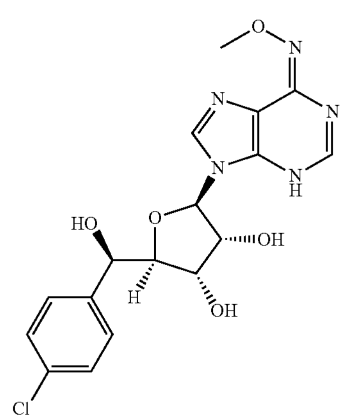 [SMILES: CO/N=c1/nc[nH]c2c1ncn2[C@@H]1O[C@H]([C@H](O)c2ccc(Cl)cc2)[C@@H](O)[C@H]1O] | 407.8 | 9-((2R,3R,4S,5R)-5-((R)-(4-chlorophenyl)(hydroxy)methyl)-3,4-dihydroxytetrahydrofuran-2-yl)-3,9-dihydro-6H-purin-6-one O-methyl oxime |

TABLE A-continued

| Ex. # | Structures | MW | Chemical Name |
|---|---|---|---|
| 54 | 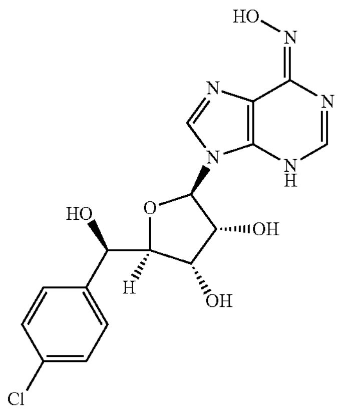 [SMILES: O/N=c1/nc[nH]c2c1ncn2[C@@H]1O[C@H]([C@H](O)c2ccc(Cl)cc2)[C@@H](O)[C@H]1O] | 393.8 | 9-((2R,3R,4S,5R)-5-((R)-(4-chlorophenyl)(hydroxy)methyl)-3,4-dihydroxytetrahydrofuran-2-yl)-3,9-dihydro-6H-purin-6-one oxime |
| 55 | 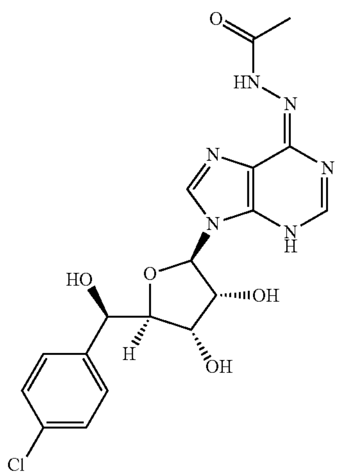 [SMILES: CC(=O)N/N=c1/nc[nH]c2c1ncn2[C@@H]1O[C@H]([C@H](O)c2ccc(Cl)cc2)[C@@H](O)[C@H]1O] | 434.8 | N'-(9-((2R,3R,4S,5R)-5-((R)-(4-chlorophenyl)(hydroxy)methyl)-3,4-dihydroxytetrahydrofuran-2-yl)-3,9-dihydro-6H-purin-6-ylidene)acetohydrazide |
| 56 | 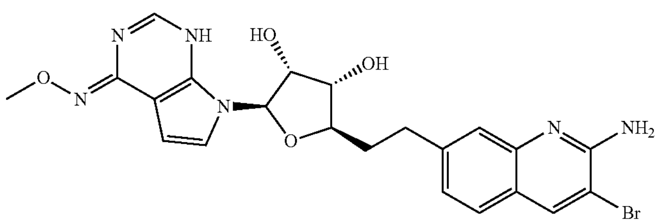 [SMILES: CO/N=c1\nc[nH]c2c1ccn2[C@@H]1O[C@H](CCc2ccc3cc(Br)c(N)nc3c2)[C@@H](O)[C@H]1O] | 515.4 | -7-((2R,3R,4S,5R)-5-(2-(2-amino-3-bromoquinolin-7-yl)ethyl)-3,4-dihydroxytetrahydrofuran-2-yl)-1,7-dihydro-4H-pyrrolo[2,3-d]pyrimidin-4-one O-methyl oxime |
| 57 | 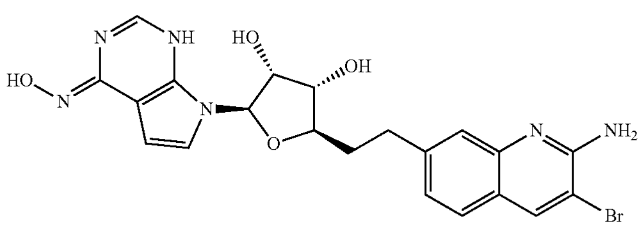 [SMILES: Nc1nc2cc(CC[C@H]3O[C@@H](n4ccc5/c(=N/O)nc[nH]c54)[C@H](O)[C@@H]3O)ccc2cc1Br] | 501.3 | 7-((2R,3R,4S,5R)-5-(2-(2-amino-3-bromoquinolin-7-yl)ethyl)-3,4-dihydroxytetrahydrofuran-2-yl)-1,7-dihydro-4H-pyrrolo[2,3-d]pyrimidin-4-one oxime |

TABLE A-continued

| Ex. # | Structures | MW | Chemical Name |
|---|---|---|---|
| 59 | 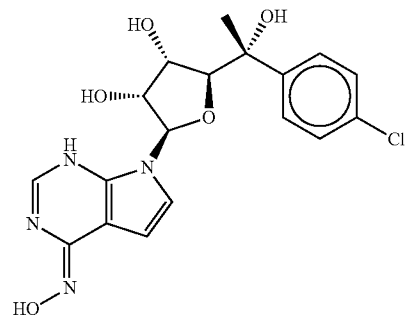 | 406.8 | 7-((2R,3R,4S,5S)-5-((R)-1-(4-chlorophenyl)-1-hydroxyethyl)-3,4-dihydroxytetrahydrofuran-2-yl)-1,7-dihydro-4H-pyrrolo[2,3-d]pyrimidin-4-one oxime |
| 60 | 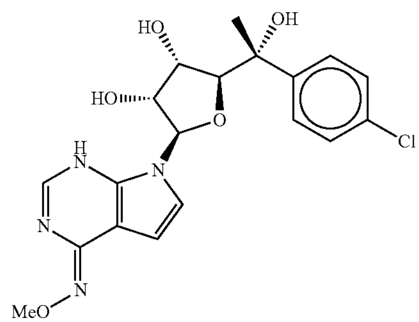 | 420.9 | 7-((2R,3R,4S,5S)-5-((R)-1-(4-chlorophenyl)-1-hydroxyethyl)-3,4-dihydroxytetrahydrofuran-2-yl)-1,7-dihydro-4H-pyrrolo[2,3-d]pyrimidin-4-one O-methyl oxime |
| 61 | 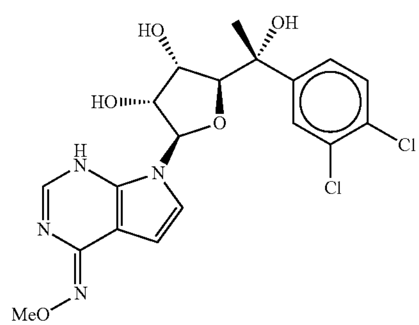 | 455.3 | 7-((2R,3R,4S,5S)-5-((R)-1-(3,4-dichlorophenyl)-1-hydroxyethyl)-3,4-dihydroxytetrahydrofuran-2-yl)-1,7-dihydro-4H-pyrrolo[2,3-d]pyrimidin-4-one O-methyl oxime |
| 62 | 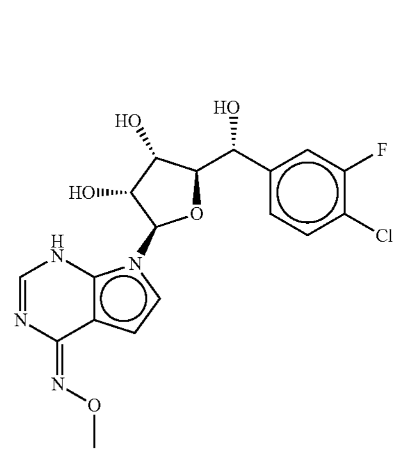 | 424.8 | 7-((2R,3R,4S,5R)-5-((R)-(4-chloro-3-fluorophenyl)(hydroxy)methyl)-3,4-dihydroxytetrahydrofuran-2-yl)-1,7-dihydro-4H-pyrrolo[2,3-d]pyrimidin-4-one O-methyl oxime |

TABLE A-continued

| Ex. # | Structures | MW | Chemical Name |
|---|---|---|---|
| 63 | 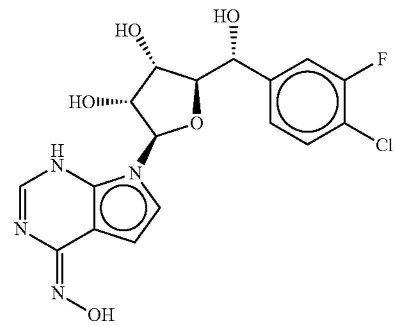 | 410.8 | 7-((2R,3R,4S,5R)-5-((R)-(4-chloro-3-fluorophenyl)(hydroxy)methyl)-3,4-dihydroxytetrahydrofuran-2-yl)-1,7-dihydro-4H-pyrrolo[2,3-d]pyrimidin-4-one oxime |
| 64 | 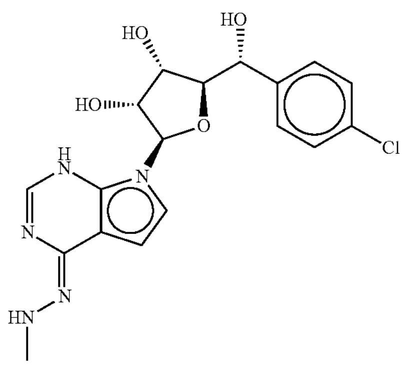 | 405.8 | (2R,3S,4R,5R)-2-((R)-(4-chlorophenyl)(hydroxy)methyl)-5-((Z)-4-(2-methylhydrazineylidene)-1,4-dihydro-7H-pyrrolo[2,3-d]pyrimidin-7-yl)tetrahydrofuran-3,4-diol |
| 65 | 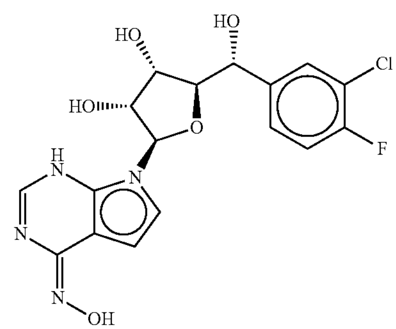 | 410.8 | 7-((2R,3R,4S,5R)-5-((R)-(3-chloro-4-fluorophenyl)(hydroxy)methyl)-3,4-dihydroxytetrahydrofuran-2-yl)-1,7-dihydro-4H-pyrrolo[2,3-d]pyrimidin-4-one oxime |
| 66 | 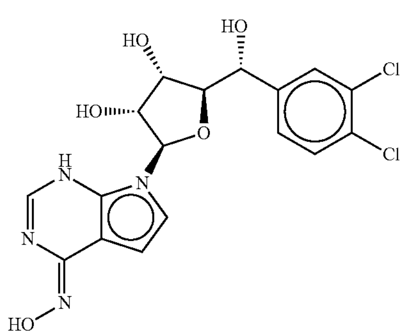 | 427.2 | 7-((2R,3R,4S,5R)-5-((R)-(3,4-dichlorophenyl)(hydroxy)methyl)-3,4-dihydroxytetrahydrofuran-2-yl)-1,7-dihydro-4H-pyrrolo[2,3-d]pyrimidin-4-one oxime |

TABLE A-continued

| Ex. # | Structures | MW | Chemical Name |
|---|---|---|---|
| 67 | 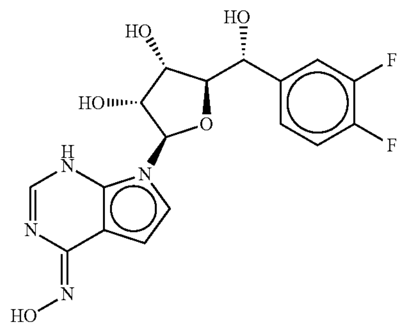 | 394.3 | 7-((2R,3R,4S,5R)-5-((R)-(3,4-difluorophenyl)(hydroxy)methyl)-3,4-dihydroxytetrahydrofuran-2-yl)-1,7-dihydro-4H-pyrrolo[2,3-d]pyrimidin-4-one oxime |
| 68 | 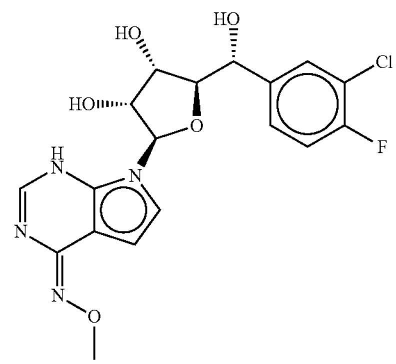 | 424.8 | 7-((2R,3R,4S,5R)-5-((R)-(3-chloro-4-fluorophenyl)(hydroxy)methyl)-3,4-dihydroxytetrahydrofuran-2-yl)-1,7-dihydro-4H-pyrrolo[2,3-d]pyrimidin-4-one O-methyl oxime |
| 69 | 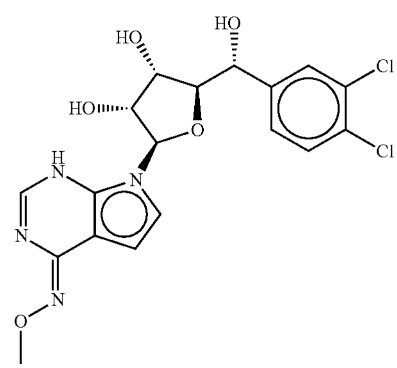 | 441.3 | 7-((2R,3R,4S,5R)-5-((R)-(3,4-dichlorophenyl)(hydroxy)methyl)-3,4-dihydroxytetrahydrofuran-2-yl)-1,7-dihydro-4H-pyrrolo[2,3-d]pyrimidin-4-one O-methyl oxime |
| 70 | 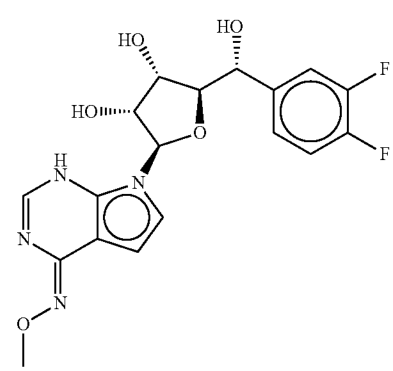 | 408.4 | 7-((2R,3R,4S,5R)-5-((R)-(3,4-difluorophenyl)(hydroxy)methyl)-3,4-dihydroxytetrahydrofuran-2-yl)-1,7-dihydro-4H-pyrrolo[2,3-d]pyrimidin-4-one O-methyl oxime |

TABLE A-continued

| Ex. # | Structures | MW | Chemical Name |
|---|---|---|---|
| 71 | 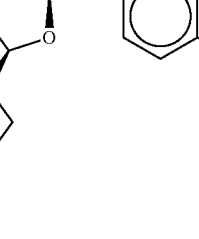 | 406.8 | 7-((2R,3R,4S,5R)-5-((R)-(4-chlorophenyl)(hydroxy)methyl)-3,4-dihydroxytetrahydrofuran-2-yl)-2-methyl-1,7-dihydro-4H-pyrrolo[2,3-d]pyrimidin-4-one oxime |
| 72 | 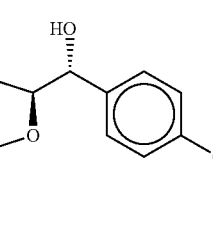 | 410.8 | 7-((2R,3R,4S,5R)-5-((R)-(4-chlorophenyl)(hydroxy)methyl)-3,4-dihydroxytetrahydrofuran-2-yl)-5-fluoro-1,7-dihydro-4H-pyrrolo[2,3-d]pyrimidin-4-one oxime |
| 73 | 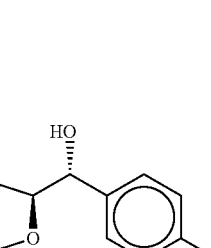 | 409.8 | (2R,3S,4R,5R)-2-((R)-(4-chlorophenyl)(hydroxy)methyl)-5-(5-fluoro-4-hydrazineylidene-1,4-dihydro-7H-pyrrolo[2,3-d]pyrimidin-7-yl)tetrahydrofuran-3,4-diol |
| 74 | 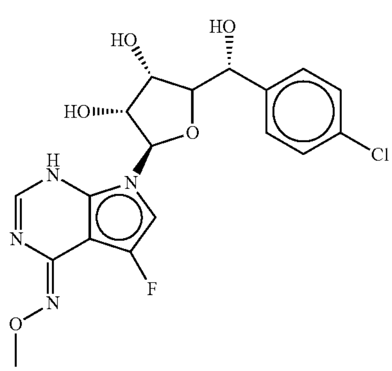 | 424.8 | 7-((2R,3R,4S)-5-((R)-(4-chlorophenyl)(hydroxy)methyl)-3,4-dihydroxytetrahydrofuran-2-yl)-5-fluoro-1,7-dihydro-4H-pyrrolo[2,3-d]pyrimidin-4-one O-methyl oxime |

TABLE A-continued

| Ex. # | Structures | MW | Chemical Name |
|---|---|---|---|
| 75 | 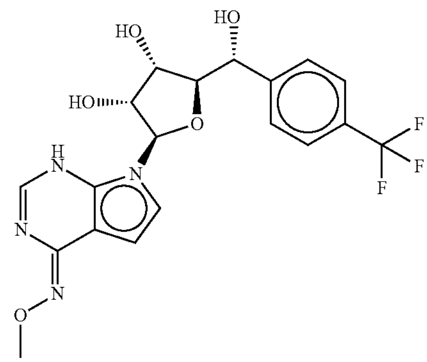 | 440.4 | 7-((2R,3R,4S,5R)-3,4-dihydroxy-5-((R)-hydroxy(4-(trifluoromethyl)phenyl)methyl)tetrahydrofuran-2-yl)-1,7-dihydro-4H-pyrrolo[2,3-d]pyrimidin-4-one O-methyl oxime |
| 76 | 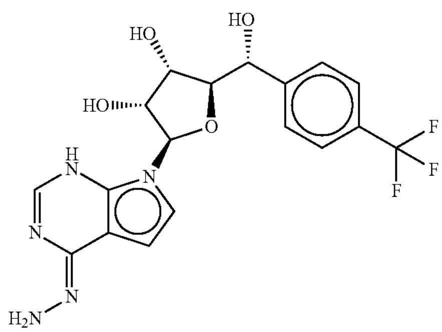 | 425.4 | (2R,3R,4S,5R)-2-(4-hydrazineylidene-1,4-dihydro-7H-pyrrolo[2,3-d]pyrimidin-7-yl)-5-((R)-hydroxy(4-(trifluoromethyl)phenyl)methyl)tetrahydrofuran-3,4-diol |
| 77 | 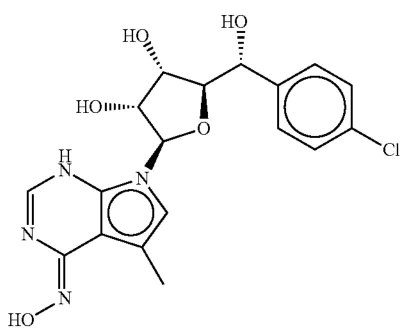 | 406.8 | 7-((2R,3R,4S,5R)-5-((R)-(4-chlorophenyl)(hydroxy)methyl)-3,4-dihydroxytetrahydrofuran-2-yl)-5-methyl-1,7-dihydro-4H-pyrrolo[2,3-d]pyrimidin-4-one oxime |
| 78 | 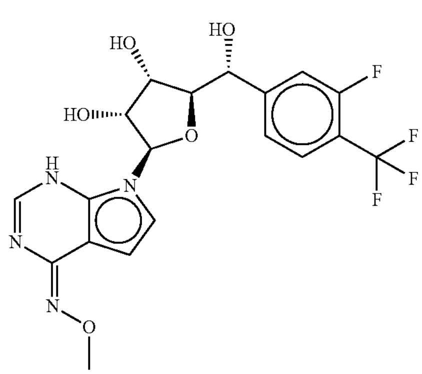 | 458.4 | 7-((2R,3R,4S,5R)-5-((R)-(3-fluoro-4-(trifluoromethyl)phenyl)(hydroxy)methyl)-3,4-dihydroxytetrahydrofuran-2-yl)-1,7-dihydro-4H-pyrrolo[2,3-d]pyrimidin-4-one O-methyl oxime |

TABLE A-continued

| Ex. # | Structures | MW | Chemical Name |
| --- | --- | --- | --- |
| 79 | 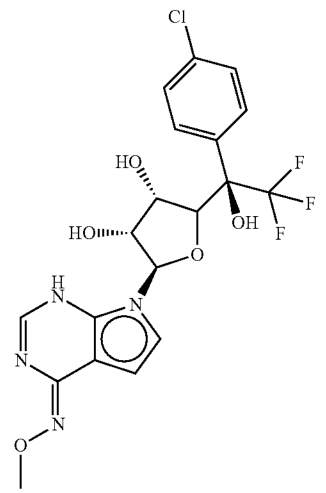 | 475.8 | 7-((2R,3R,4S)-5-((R)-1-(4-chlorophenyl)-2,2,2-trifluoro-1-hydroxyethyl)-3,4-dihydroxytetrahydrofuran-2-yl)-1,7-dihydro-4H-pyrrolo[2,3-d]pyrimidin-4-one O-methyl oxime |
| 80 | 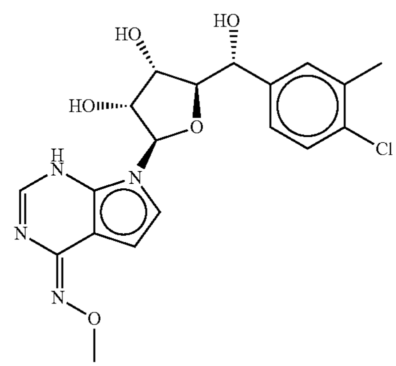 | 420.9 | 7-((2R,3R,4S,5R)-5-((R)-(4-chloro-3-methylphenyl)(hydroxy)methyl)-3,4-dihydroxytetrahydrofuran-2-yl)-1,7-dihydro-4H-pyrrolo[2,3-d]pyrimidin-4-one O-methyl oxime |
| 81 | 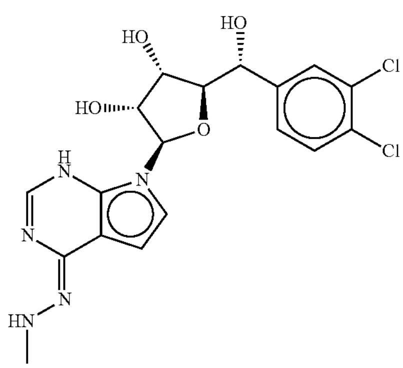 | 440.3 | (2R,3S,4R,5R)-2-((R)-(3,4-dichlorophenyl)(hydroxy)methyl)-5-((Z)-4-(2-methylhydrazineylidene)-1,4-dihydro-7H-pyrrolo[2,3-d]pyrimidin-7-yl)tetrahydrofuran-3,4-diol |
| 82 | 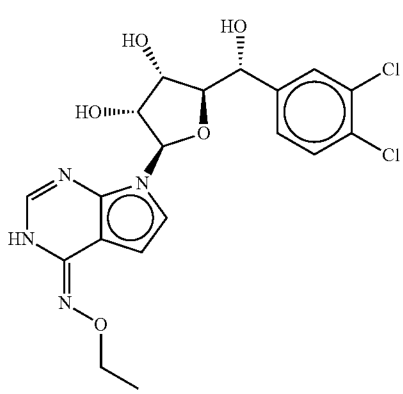 | 455.3 | 7-((2R,3R,4S,5R)-5-((R)-(3,4-dichlorophenyl)(hydroxy)methyl)-3,4-dihydroxytetrahydrofuran-2-yl)-3,7-dihydro-4H-pyrrolo[2,3-d]pyrimidin-4-one O-ethyl oxime |

TABLE A-continued

| Ex. # | Structures | MW | Chemical Name |
|---|---|---|---|
| 83 | 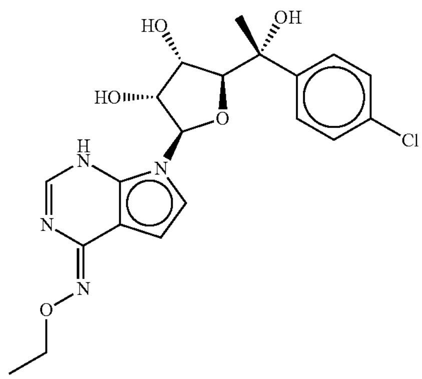 | 434.9 | 7-((2R,3R,4S)-5-((R)-1-(4-chlorophenyl)-1-hydroxyethyl)-3,4-dihydroxytetrahydrofuran-2-yl)-1,7-dihydro-4H-pyrrolo[2,3-d]pyrimidin-4-one O-ethyl oxime |
| 84 | 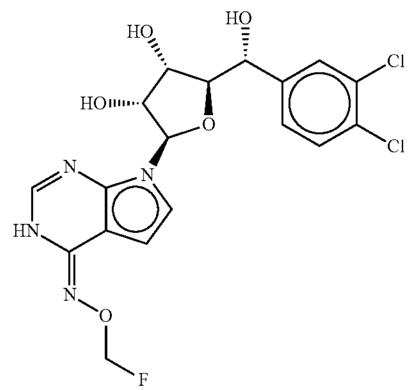 | 459.3 | 7-((2R,3R,4S,5R)-5-((R)-(3,4-dichlorophenyl)(hydroxy)methyl)-3,4-dihydroxytetrahydrofuran-2-yl)-3,7-dihydro-4H-pyrrolo[2,3-d]pyrimidin-4-one O-fluoromethyl oxime |
| 85 | 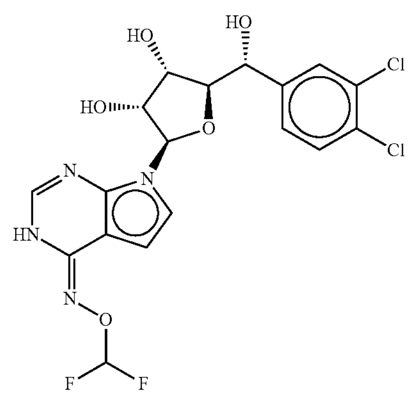 | 477.2 | 7-((2R,3R,4S,5R)-5-((R)-(3,4-dichlorophenyl)(hydroxy)methyl)-3,4-dihydroxytetrahydrofuran-2-yl)-3,7-dihydro-4H-pyrrolo[2,3-d]pyrimidin-4-one O-difluoromethyl oxime |
| 86 | 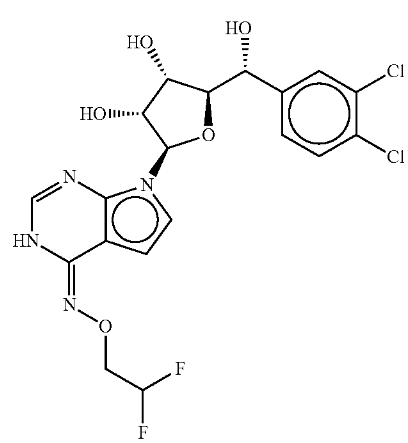 | 491.3 | 7-((2R,3R,4S,5R)-5-((R)-(3,4-dichlorophenyl)(hydroxy)methyl)-3,4-dihydroxytetrahydrofuran-2-yl)-3,7-dihydro-4H-pyrrolo[2,3-d]pyrimidin-4-one O-(2,2-difluoroethyl)oxime |

TABLE A-continued

| Ex. # | Structures | MW | Chemical Name |
|---|---|---|---|
| 87 | 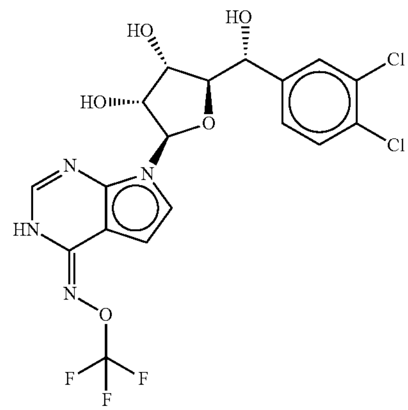 | 495.2 | 7-((2R,3R,4S,5R)-5-((R)-(3,4-dichlorophenyl)(hydroxy)methyl)-3,4-dihydroxytetrahydrofuran-2-yl)-3,7-dihydro-4H-pyrrolo[2,3-d]pyrimidin-4-one O-trifluoromethyl oxime |
| 88 | 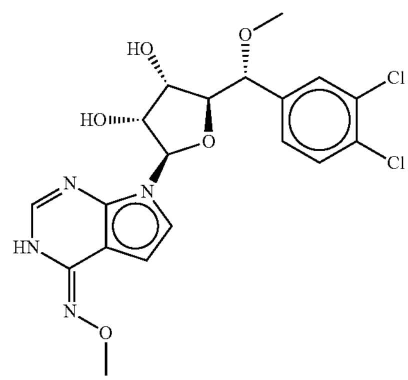 | 455.3 | 7-((2R,3R,4S,5S)-5-((R)-(3,4-dichlorophenyl)(methoxy)methyl)-3,4-dihydroxytetrahydrofuran-2-yl)-3,7-dihydro-4H-pyrrolo[2,3-d]pyrimidin-4-one O-methyl oxime |
| 89 | 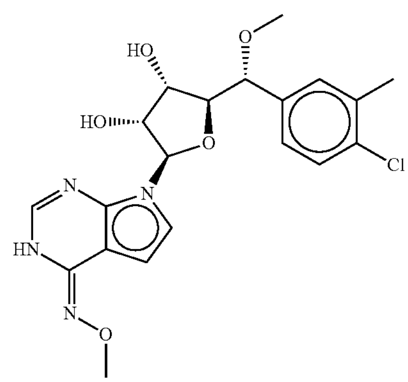 | 434.9 | 7-((2R,3R,4S,5S)-5-((R)-(4-chloro-3-methylphenyl)(methoxy)methyl)-3,4-dihydroxytetrahydrofuran-2-yl)-3,7-dihydro-4H-pyrrolo[2,3-d]pyrimidin-4-one O-methyl oxime |
| 90 | 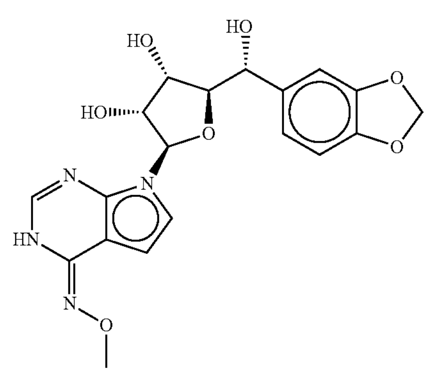 | 416.4 | 7-((2R,3R,4S,5R)-5-((R)-benzo[d][1,3]dioxol-5-yl(hydroxy)methyl)-3,4-dihydroxytetrahydrofuran-2-yl)-3,7-dihydro-4H-pyrrolo[2,3-d]pyrimidin-4-one O-methyl oxime |

TABLE A-continued

| Ex. # | Structures | MW | Chemical Name |
|---|---|---|---|
| 91 | 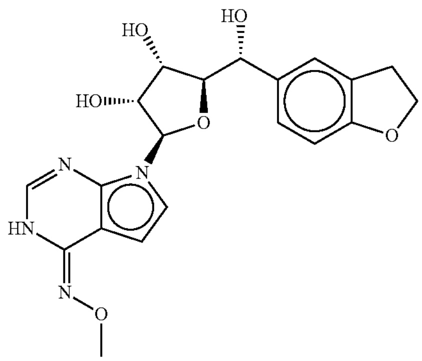 | 414.4 | 7-((2R,3R,4S,5R)-5-((R)-(2,3-dihydrobenzofuran-5-yl)(hydroxy)methyl)-3,4-dihydroxytetrahydrofuran-2-yl)-3,7-dihydro-4H-pyrrolo[2,3-d]pyrimidin-4-one O-methyl oxime |
| 92 | 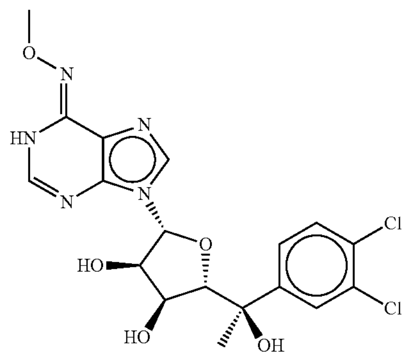 | 456.28 | (Z)-9-((2R,3R,4S,5S)-5-((R)-1-(3,4-dichlorophenyl)-1-hydroxyethyl)-3,4-dihydroxytetrahydrofuran-2-yl)-1,9-dihydro-6H-purin-6-one O-methyl oxime |
| 93 | 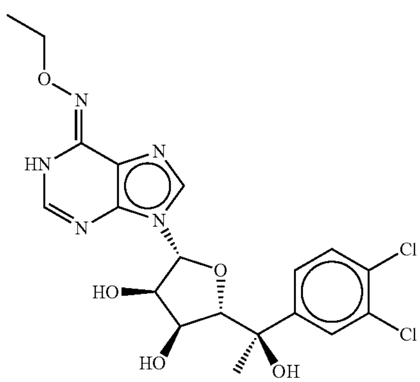 | 470.31 | (Z)-9-((2R,3R,4S,5S)-5-((R)-1-(3,4-dichlorophenyl)-1-hydroxyethyl)-3,4-dihydroxytetrahydrofuran-2-yl)-1,9-dihydro-6H-purin-6-one O-ethyl oxime |
| 94 | 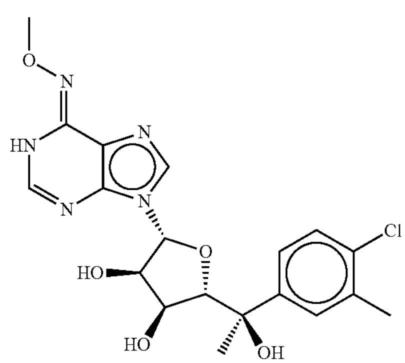 | 435.86 | (Z)-9-((2R,3R,4S,5S)-5-((R)-1-(4-chloro-3-methylphenyl)-1-hydroxyethyl)-3,4-dihydroxytetrahydrofuran-2-yl)-1,9-dihydro-6H-purin-6-one O-methyl oxime |

TABLE A-continued

| Ex. # | Structures | MW | Chemical Name |
|---|---|---|---|
| 95 | 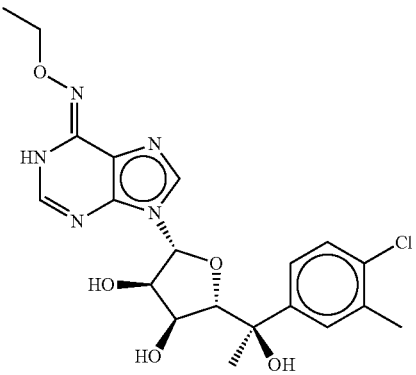 | 449.89 | (Z)-9-((2R,3R,4S,5S)-5-((R)-1-(4-chloro-3-methylphenyl)-1-hydroxyethyl)-3,4-dihydroxytetrahydrofuran-2-yl)-1,9-dihydro-6H-purin-6-one O-ethyl oxime |
| 96 | 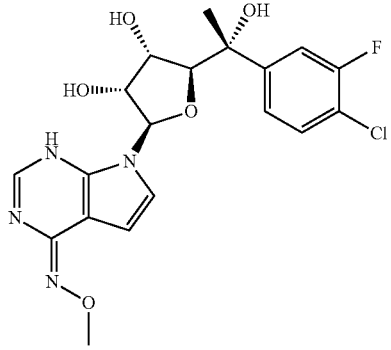 [SMILES: CO/N=c1/nc[nH]c2c1ccn2[C@@H]1O[C@H]([C@](C)(O)c2ccc(Cl)c(F)c2)[C@@H](O)[C@H]1O] | 438.84 | (E)-7-((2R,3R,4S,5S)-5-((R)-1-(4-chloro-3-fluorophenyl)-1-hydroxyethyl)-3,4-dihydroxytetrahydrofuran-2-yl)-1,5,6,7-tetrahydro-4H-pyrrolo[2,3-d]pyrimidin-4-one O-methyl oxime |
| 97 | 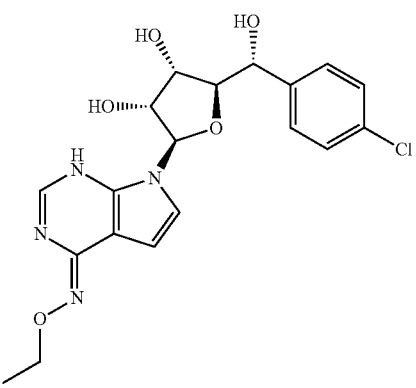 [SMILES: CCO/N=c1\nc[nH]c2c1ccn2[C@@H]1O[C@H]([C@H](O)c2ccc(Cl)cc2)[C@@H](O)[C@H]1O] | 420.85 | (Z)-7-((2R,3R,4S,5R)-5-((R)-(4-chlorophenyl)(hydroxy)methyl)-3,4-dihydroxytetrahydrofuran-2-yl)-1,7-dihydro-4H-pyrrolo[2,3-d]pyrimidin-4-one O-ethyl oxime |
| 98 | 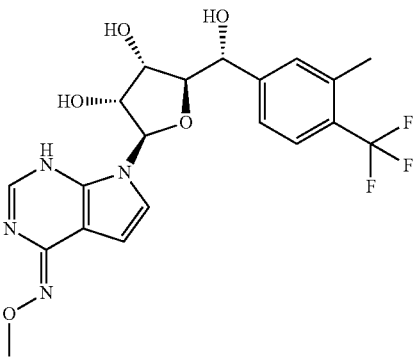 [SMILES: CO/N=c1\nc[nH]c2c1ccn2[C@@H]1O[C@H]([C@H](O)c2ccc(C(F)(F)F)c(C)c2)[C@@H](O)[C@H]1O] | 454.4 | (Z)-7-((2R,3R,4S,5R)-3,4-dihydroxy-5-((R)-hydroxy(3-ethyl-4-(trifluoromethyl)phenyl)methyl)tetrahydrofuran-2-yl)-1,7-dihydro-4H-pyrrolo[2,3-d]pyrimidin-4-one O-methyl oxime |

TABLE A-continued

| Ex. # | Structures | MW | Chemical Name |
|---|---|---|---|
| 99 | 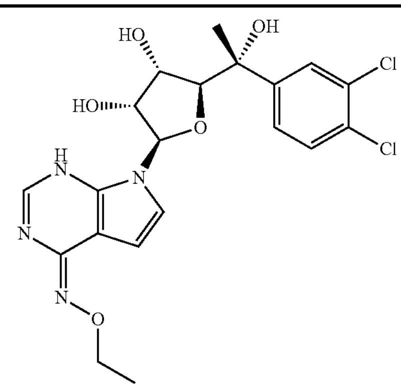 | 469.32 | (E)-7-((2R,3R,4S,5S)-5-((R)-1-(3,4-dichlorophenyl)-1-hydroxyethyl)-3,4-dihydroxytetrahydrofuran-2-yl)-1,7-dihydro-4H-pyrrolo[2,3-d]pyrimidin-4-one O-ethyl oxime |
| 100 | 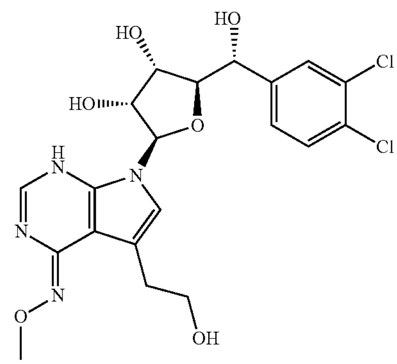 [SMILES: CO/N=c1\nc[nH]c2c1c(CCO)cn2[C@@H]1O[C@H]([C@H](O)c2ccc(Cl)c(Cl)c2)[C@@H](O)[C@H]1O] | 485.32 | (Z)-7-((2R,3R,4S,5R)-5-((R)-(3,4-dichlorophenyl)(hydroxy)methyl)-3,4-dihydroxytetrahydrofuran-2-yl)-5-(2-hydroxyethyl)-1,5-dihydro-4H-7l4-pyrrolo[2,3-d]pyrimidin-4-one O-methyl oxime |
| 101 | 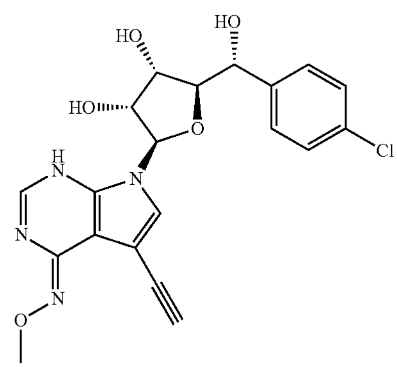 [SMILES: C#Cc1cn([C@@H]2O[C@H]([C@H](O)c3ccc(Cl)cc3)[C@@H](O)[C@H]2O)c2[nH]cn/c(=N\OC)c12] | 430.84 | (Z)-7-((2R,3R,4S,5R)-5-((R)-(4-chlorophenyl)(hydroxy)methyl)-3,4-dihydroxytetrahydrofuran-2-yl)-5-ethynyl-1,7-dihydro-4H-pyrrolo[2,3-d]pyrimidin-4-one O-methyl oxime |
| 102 | 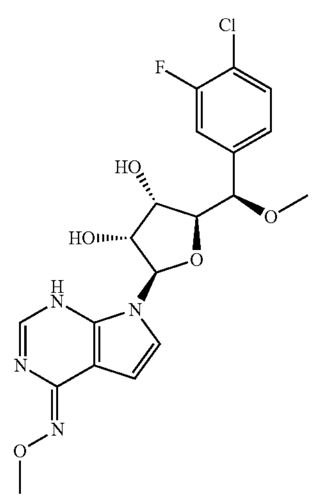 [SMILES: CO/N=c1\nc[nH]c2c1ccn2[C@@H]1O[C@H]([C@H](OC)c2ccc(Cl)c(F)c2)[C@@H](O)[C@H]1O] | 438.84 | (Z)-7-((2R,3R,4S,5S)-5-((R)-(4-chloro-3-fluorophenyl)(methoxy)methyl)-3,4-dihydroxytetrahydrofuran-2-yl)-1,7-dihydro-4H-pyrrolo[2,3-d]pyrimidin-4-one O-methyl oxime |

TABLE A-continued

| Ex. # | Structures | MW | Chemical Name |
|---|---|---|---|
| 103 | 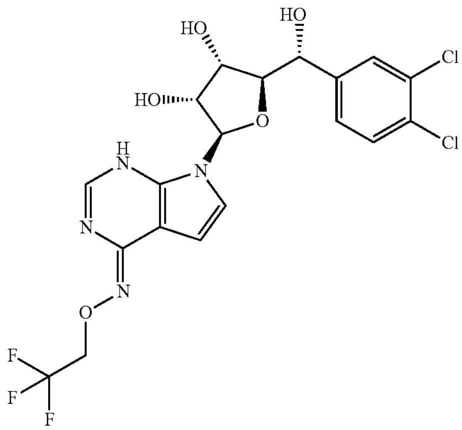 [SMILES: O[C@@H]1[C@H](O)[C@@H]([C@H](O)c2ccc(Cl)c(Cl)c2)O[C@H]1n1ccc2/c(=N/OCC(F)(F)F)nc[nH]c21] | 509.26 | (Z)-7-((2R,3R,4S,5R)-5-((R)-(3,4-dichlorophenyl)(hydroxy)methyl)-3,4-dihydroxytetrahydrofuran-2-yl)-1,4a,7,7a-tetrahydro-4H-pyrrolo[2,3-d]pyrimidin-4-one O-(2,2,2-trifluoroethyl)oxime |
| 104 | 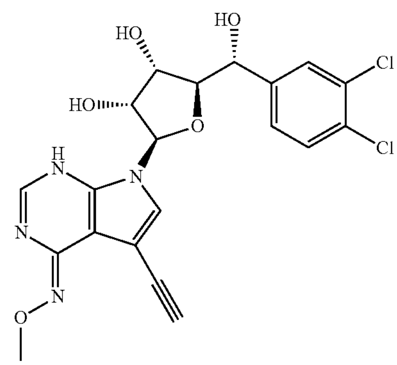 [SMILES: C#Cc1cn([C@@H]2O[C@H]([C@H](O)c3ccc(Cl)c(Cl)c3)[C@@H](O)[C@H]2O)c2[nH]cn/c(=N\OC)c12] | 465.29 | (Z)-7-((2R,3R,4S,5R)-5-((R)-(3,4-dichlorophenyl)(hydroxy)methyl)-3,4-dihydroxytetrahydrofuran-2-yl)-5-ethynyl-1,5-dihydro-4H-7l4-pyrrolo[2,3-d]pyrimidin-4-one O-methyl oxime |
| 105 | 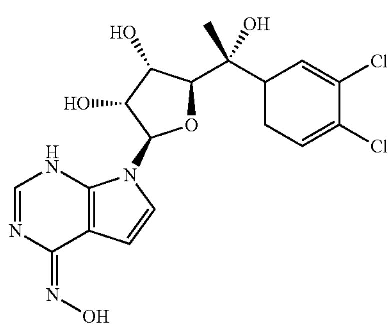 [SMILES: C[C@@](O)(C1C=C(Cl)C(Cl)=CC1)[C@H]1O[C@@H](n2ccc3/c(=N\O)nc[nH]c32)[C@H](O)[C@@H]1O] | 441.27 | (E)-7-((2R,3R,4S,5S)-5-((1R)-1-(3,4-dichlorocyclohexa-2,4-dien-1-yl)-1-hydroxyethyl)-3,4-dihydroxytetrahydrofuran-2-yl)-1,7-dihydro-4H-pyrrolo[2,3-d]pyrimidin-4-one oxime |
| 106 | 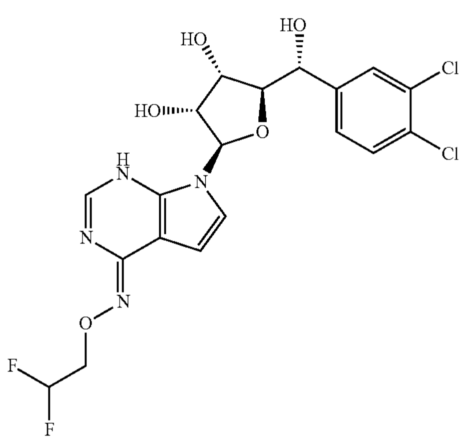 [SMILES: O[C@@H]1[C@H](O)[C@@H]([C@H](O)c2ccc(Cl)c(Cl)c2)O[C@H]1n1ccc2/c(=N/OCC(F)F)nc[nH]c21] | 491.27 | (Z)-7-((2R,3R,4S,5R)-5-((R)-(3,4-dichlorophenyl)(hydroxy)methyl)-3,4-dihydroxytetrahydrofuran-2-yl)-1,4a,7,7a-tetrahydro-4H-pyrrolo[2,3-d]pyrimidin-4-one O-(2,2-difluoroethyl)oxime |

TABLE A-continued

| Ex. # | Structures | MW | Chemical Name |
|---|---|---|---|
| 107 | 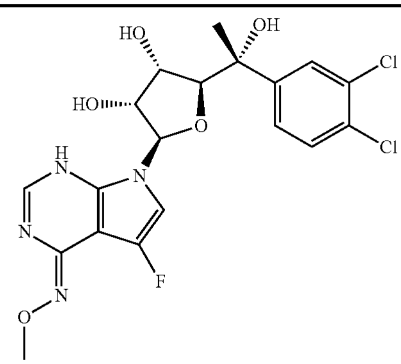 | 473.28 | (Z)-7-((2R,3R,4S,5S)-5-((R)-1-(3,4-dichlorophenyl)-1-hydroxyethyl)-3,4-dihydroxytetrahydrofuran-2-yl)-5-fluoro-1,7-dihydro-4H-pyrrolo[2,3-d]pyrimidin-4-one O-methyl oxime |
| 108 | 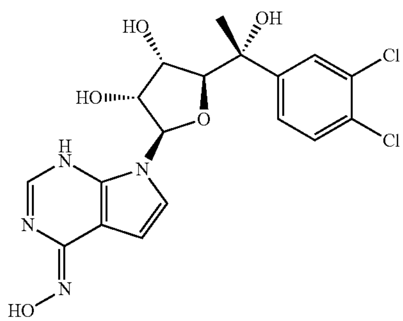 [SMILES: C[C@@](O)(c1ccc(Cl)c(Cl)c1)[C@H]1O[C@@H](n2ccc3/c(=N/O)nc[nH]c32)[C@H](O)[C@@H]1O] | 422.25 | (Z)-9-((2R,3R,4S,5S)-5-((R)-1-(3,4-dichlorophenyl)-1-hydroxyethyl)-3,4-dihydroxytetrahydrofuran-2-yl)-3,9-dihydro-6H-purin-6-one oxime |

Compounds of the disclosure of Formula III and Formula IV include, for example, the compounds identified in Table B.

TABLE B

| Ex. No. | Structure | MW | Chemical Name |
|---|---|---|---|
| 1-B | 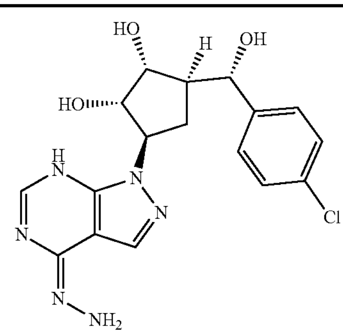 | 390.828 | (1S,2R,3R(5R))-3-((S)-(4-chlorophenyl)(hydroxy)methyl)-5-((E)-4-hydrazineylidene-4,7-dihydro-1H-pyrazolo[3,4-d]pyrimidin-1-yl)cyclopentane-1,2-diol |
| 2-B | 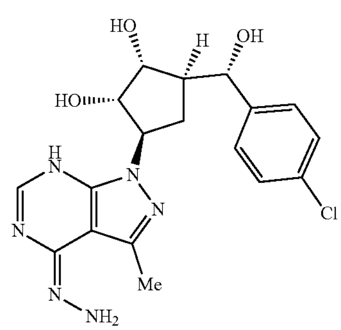 [SMILES: Cc1nn([C@@H]2C[C@H]([C@H](O)c3ccc(Cl)cc3)[C@@H](O)[C@H]2O)c2[nH]cn/c(=N/N)c12] | 404.855 | (1S,2R,3R,5R)-3-((S)-(4-chlorophenyl)(hydroxy)methyl)-5-((E)-4-hydrazineylidene-3-methyl-4,7-dihydro-1H-pyrazolo[3,4-d]pyrimidin-1-yl)cyclopentane-1,2-diol |

TABLE B-continued

| Ex. No. | Structure | MW | Chemical Name |
|---|---|---|---|
| 3-B | 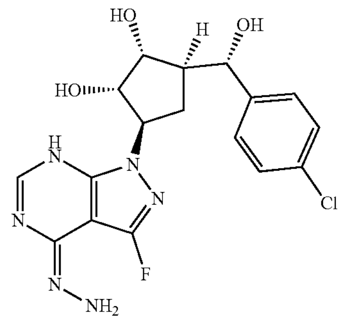 [SMILES: N/N=c1/nc[nH]c2c1c(F)nn2[C@@H]1C[C@H]([C@H](O)c2ccc(Cl)cc2)[C@@H](O)[C@H]1O] | 408.8184 | (1S,2R,3R,5R)-3-((S)-(4-chlorophenyl)(hydroxy)methyl)-5-((E)-3-fluoro-4-hydrazineylidene-4,7-dihydro-1H-pyrazolo[3,4-d]pyrimidin-1-yl)cyclopentane-1,2-diol |
| 4-B | 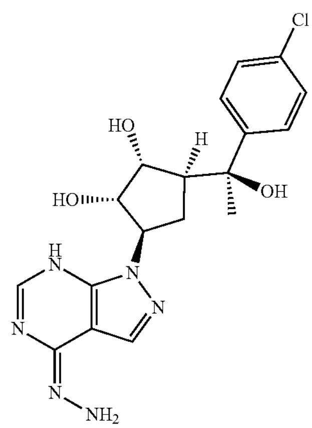 [SMILES: C[C@@](O)(c1ccc(Cl)cc1)[C@H]1C[C@@H](n2ncc3/c(=N\N)nc[nH]c32)[C@H](O)[C@@H]1O] | 404.855 | (1S,2R,3S,5R)-3-((S)-1-(4-chlorophenyl)-1-hydroxyethyl)-5-((E)-4-hydrazineylidene-4,7-dihydro-1H-pyrazolo[3,4-d]pyrimidin-1-yl)cyclopentane-1,2-diol |
| 5-B | 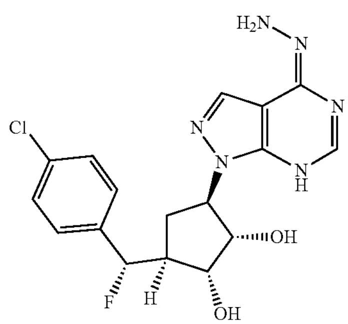 [SMILES: N/N=c1/nc[nH]c2c1cnn2[C@@H]1C[C@H]([C@H](F)c2ccc(Cl)cc2)[C@@H](O)[C@H]1O] | 392.8194 | (1S,2R,3S,5R)-3-((S)-(4-chlorophenyl)fluoromethyl)-5-((E)-4-hydrazineylidene-4,7-dihydro-1H-pyrazolo[3,4-d]pyrimidin-1-yl)cyclopentane-1,2-diol |
| 6-B | 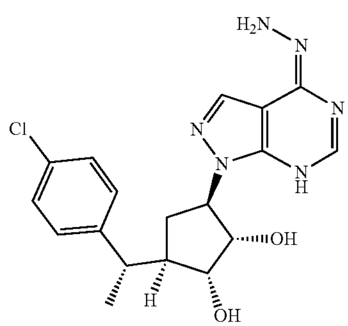 [SMILES: C[C@H](c1ccc(Cl)cc1)[C@H]1C[C@@H](n2ncc3/c(=N\N)nc[nH]c32)[C@H](O)[C@@H]1O] | 388.856 | (1S,2R,3R,5R)-3-((S)-1-(4-chlorophenyl)ethyl)-5-((E)-4-hydrazineylidene-4,7-dihydro-1H-pyrazolo[3,4-d]pyrimidin-1-yl)cyclopentane-1,2-diol |

TABLE B-continued

| Ex. No. | Structure | MW | Chemical Name |
|---|---|---|---|
| 7-B | 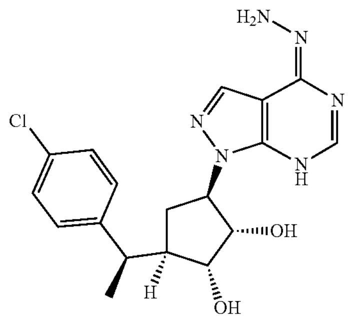 [SMILES: C[C@@H](c1ccc(Cl)cc1)[C@H]1C[C@@H](n2ncc3/c(=N\N)nc[nH]c32)[C@H](O)[C@@H]1O] | 388.856 | (1S,2R,3R,5R)-3-((R)-1-(4-chlorophenyl)ethyl)-5-((E)-4-hydrazineylidene-4,7-dihydro-1H-pyrazolo[3,4-d]pyrimidin-1-yl)cyclopentane-1,2-diol |
| 8-B | 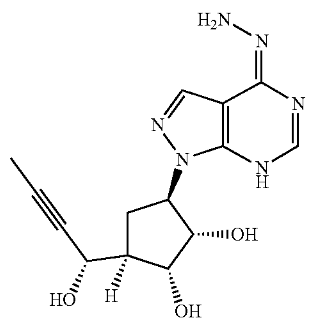 [SMILES: CC#C[C@@H](O)[C@H]1C[C@@H](n2ncc3/c(=N\N)nc[nH]c32)[C@H](O)[C@@H]1O] | 318.337 | (1R,2S,3R,5R)-3-((E)-4-hydrazineylidene-4,7-dihydro-1H-pyrazolo[3,4-d]pyrimidin-1-yl)-5-((S)-1-hydroxybut-2-yn-1-yl)cyclopentane-1,2-diol |
| 9-B | 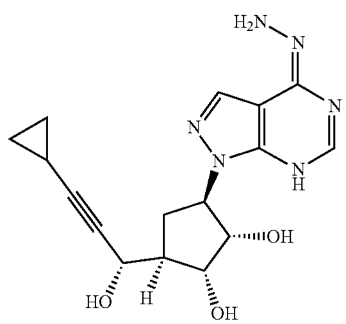 [SMILES: N/N=c1/nc[nH]c2c1cnn2[C@@H]1C[C@H]([C@H](O)C#CC2CC2)[C@@H](O)[C@H]1O] | 344.375 | (1S,2R,3R,5R)-3-((S)-3-cyclopropyl-1-hydroxyprop-2-yn-1-yl)-5-((E)-4-hydrazineylidene-4,7-dihydro-1H-pyrazolo[3,4-d]pyrimidin-1-yl)cyclopentane-1,2-diol |
| 10-B | 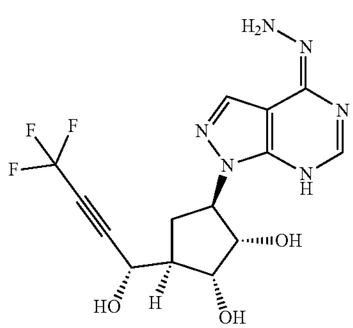 [SMILES: N/N=c1/nc[nH]c2c1cnn2[C@@H]1C[C@H]([C@H](O)C#CC(F)(F)F)[C@@H](O)[C@H]1O] | 372.3082 | (1R,2S,3R,5R)-3-((E)-4-hydrazineylidene-4,7-dihydro-1H-pyrazolo[3,4-d]pyrimidin-1-yl)-5-((S)-4,4,4-trifluoro-1-hydroxybut-2-yn-1-yl)cyclopentane-1,2-diol |

TABLE B-continued

| Ex. No. | Structure | MW | Chemical Name |
|---|---|---|---|
| 11-B | 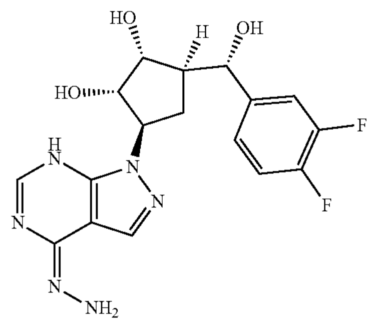 [SMILES: N/N=c1/nc[nH]c2c1cnn2[C@@H]1C[C@H]([C@H](O)c2ccc(F)c(F)c2)[C@@H](O)[C@H]1O] | 392.3668 | (1S,2R,3R,5R)-3-((S)-(3,4-difluorophenyl)(hydroxy)methyl)-5-((E)-4-hydrazineylidene-4,7-dihydro-1H-pyrazolo[3,4-d]pyrimidin-1-yl)cyclopentane-1,2-diol |
| 12-B | 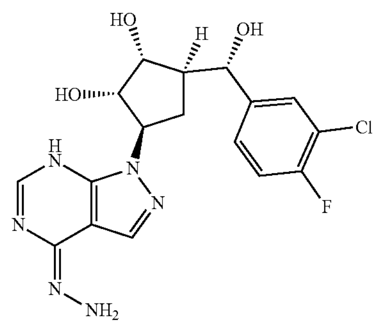 [SMILES: N/N=c1/nc[nH]c2c1cnn2[C@@H]1C[C@H]([C@H](O)c2ccc(F)c(Cl)c2)[C@@H](O)[C@H]1O] | 408.8184 | (1S,2R,3R,5R)-3-((S)-(3-chloro-4-fluorophenyl)(hydroxy)methyl)-5-((E)-4-hydrazineylidene-4,7-dihydro-1H-pyrazolo[3,4-d]pyrimidin-1-yl)cyclopentane-1,2-diol |
| 13-B | 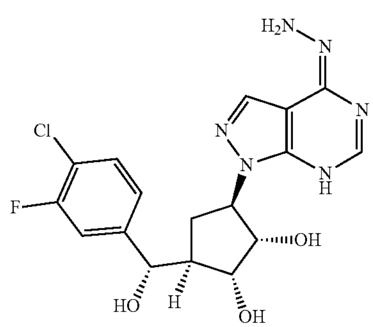 [SMILES: N/N=c1/nc[nH]c2c1cnn2[C@@H]1C[C@H]([C@H](O)c2ccc(Cl)c(F)c2)[C@@H](O)[C@H]1O] | 408.8184 | (1S,2R,3R,5R)-3-((S)-(4-chloro-3-fluorophenyl)(hydroxy)methyl)-5-((E)-4-hydrazineylidene-4,7-dihydro-1H-pyrazolo[3,4-d]pyrimidin-1-yl)cyclopentane-1,2-diol |
| 14-B | 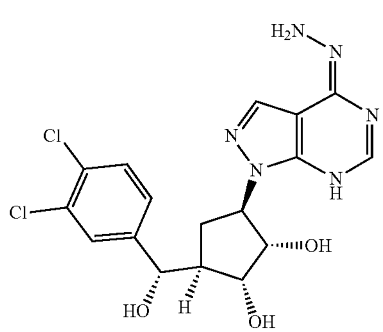 [SMILES: N/N=c1/nc[nH]c2c1cnn2[C@@H]1C[C@H]([C@H](O)c2ccc(Cl)c(Cl)c2)[C@@H](O)[C@H]1O] | 425.27 | (1S,2R,3R,5R)-3-((S)-(3,4-dichlorophenyl)(hydroxy)methyl)-5-((E)-4-hydrazineylidene-4,7-dihydro-1H-pyrazolo[3,4-d]pyrimidin-1-yl)cyclopentane-1,2-diol |

TABLE B-continued

| Ex. No. | Structure | MW | Chemical Name |
|---|---|---|---|
| 15-B | 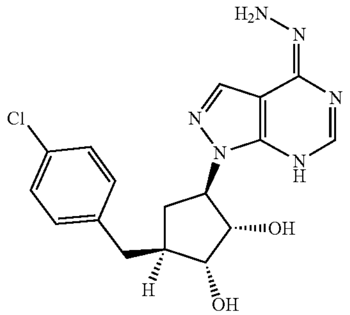 [SMILES: N/N=c1/nc[nH]c2c1cnn2[C@@H]1C[C@H](Cc2ccc(Cl)cc2)[C@@H](O)[C@H]1O] | 374.829 | (1S,2R,3S,5R)-3-(4-chlorobenzyl)-5-((E)-4-hydrazineylidene-4,7-dihydro-1H-pyrazolo[3,4-d]pyrimidin-1-yl)cyclopentane-1,2-diol |
| 16-B | 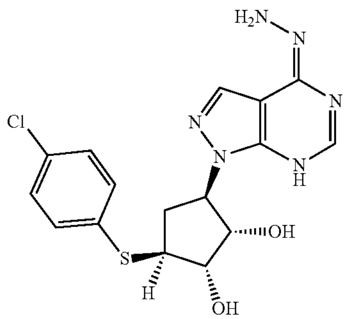 | 392.862 | (1S,2S,3S,5R)-3-((4-chlorophenyl)thio)-5-((E)-4-hydrazineylidene-4,7-dihydro-1H-pyrazolo[3,4-d]pyrimidin-1-yl)cyclopentane-1,2-diol |
| 17-B | 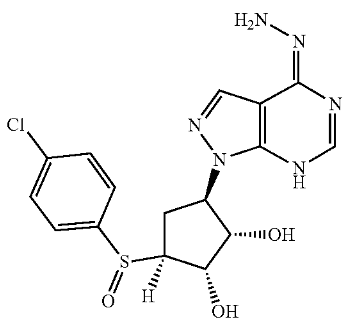 [SMILES: N/N=c1/nc[nH]c2c1cnn2[C@@H]1C[C@H](S(=O)c2ccc(Cl)cc2)[C@@H](O)[C@H]1O] | 408.861 | (1S,2S,3S,5R)-3-((4-chlorophenyl)sulfinyl)-5-((E)-4-hydrazineylidene-4,7-dihydro-1H-pyrazolo[3,4-d]pyrimidin-1-yl)cyclopentane-1,2-diol |
| 18-B | 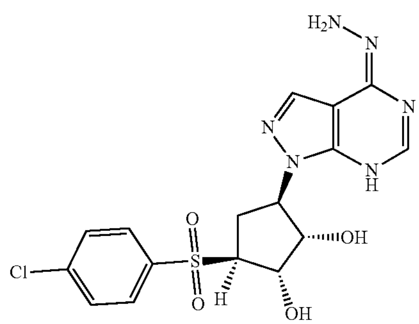 [SMILES: N/N=c1/nc[nH]c2c1cnn2[C@@H]1C[C@H](S(=O)(=O)c2ccc(Cl)cc2)[C@@H](O)[C@H]1O] | 424.86 | (1S,2S,3S,5R)-3-((4-chlorophenyl)sulfonyl)-5-((E)-4-hydrazineylidene-4,7-dihydro-1H-pyrazolo[3,4-d]pyrimidin-1-yl)cyclopentane-1,2-diol |
| 19-B | 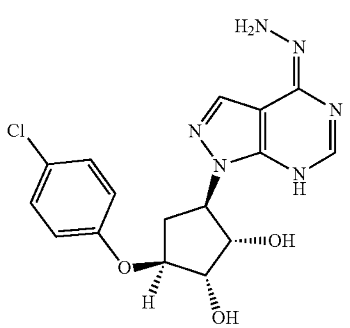 [SMILES: N/N=c1/nc[nH]c2c1cnn2[C@@H]1C[C@H](Oc2ccc(Cl)cc2)[C@@H](O)[C@H]1O] | 376.801 | (1S,2S,3S,5R)-3-(4-chlorophenoxy)-5-((E)-4-hydrazineylidene-4,7-dihydro-1H-pyrazolo[3,4-d]pyrimidin-1-yl)cyclopentane-1,2-diol |

TABLE B-continued

| Ex. No. | Structure | MW | Chemical Name |
|---|---|---|---|
| 20-B | 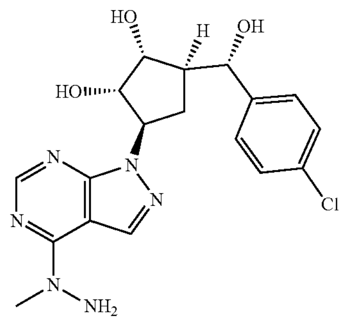 [SMILES: CN(N)c1ncnc2c1cnn2[C@@H]1C[C@H]([C@H](O)c2ccc(Cl)cc2)[C@@H](O)[C@H]1O] | 404.855 | (1S,2R,3R,5R)-3-((S)-(4-chlorophenyl)(hydroxy)methyl)-5-(4-(1-methylhydrazineyl)-1H-pyrazolo[3,4-d]pyrimidin-1-yl)cyclopentane-1,2-diol |
| 21-B | 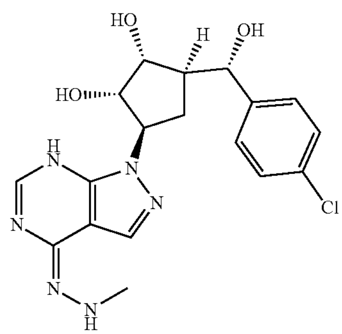 [SMILES: CN/N=c1/nc[nH]c2c1cnn2[C@@H]1C[C@H]([C@H](O)c2ccc(Cl)cc2)[C@@H](O)[C@H]1O] | 404.855 | (1S,2R,3R,5R)-3-((S)-(4-chlorophenyl)(hydroxy)methyl)-5-((E)-4-(2-methylhydrazineylidene)-4,7-dihydro-1H-pyrazolo[3,4-d]pyrimidin-1-yl)cyclopentane-1,2-diol |
| 22-B | 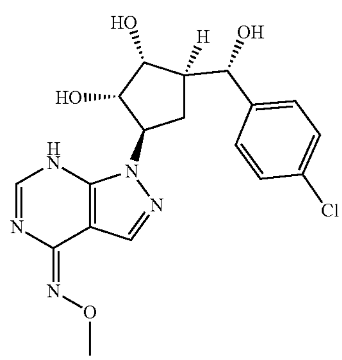 [SMILES: CO/N=c1/nc[nH]c2c1cnn2[C@@H]1C[C@H]([C@H](O)c2ccc(Cl)cc2)[C@@H](O)[C@H]1O] | 405.839 | (E)-1-((1R,2S,3R,4R)-4-((S)-(4-chlorophenyl)(hydroxy)methyl)-2,3-dihydroxycyclopentyl)-1,7-dihydro-4H-pyrazolo[3,4-d]pyrimidin-4-one O-methyl oxime |
| 23-B | 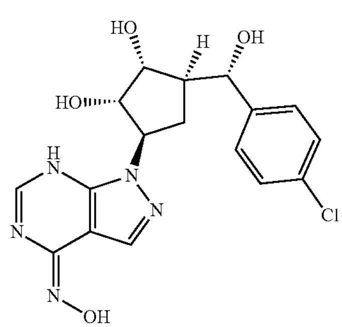 [SMILES: O/N=c1/nc[nH]c2c1cnn2[C@@H]1C[C@H]([C@H](O)c2ccc(Cl)cc2)[C@@H](O)[C@H]1O] | 391.812 | (E)-1-((1R,2S,3R,4R)-4-((S)-(4-chlorophenyl)(hydroxy)methyl)-2,3-dihydroxycyclopentyl)-1,7-dihydro-4H-pyrazolo[3,4-d]pyrimidin-4-one oxime |

TABLE B-continued

| Ex. No. | Structure | MW | Chemical Name |
|---|---|---|---|
| 24-B | 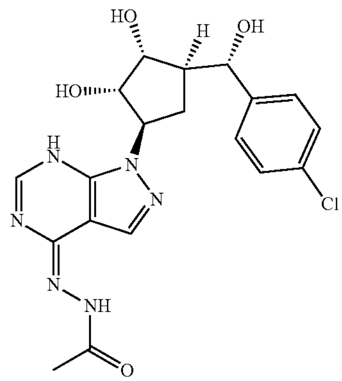 [SMILES: CC(=O)N/N=c1/nc[nH]c2c1cnn2[C@@H]1C[C@H]([C@H](O)c2ccc(Cl)cc2)[C@@H](O)[C@H]1O] | 432.865 | N'-((E)-1-((1R,2S,3R,4R)-4-((S)-(4-chlorophenyl)(hydroxy)methyl)-2,3-dihydroxycyclopentyl)-1,7-dihydro-4H-pyrazolo[3,4-d]pyrimidin-4-ylidene)acetohydrazide |
| 25-B | 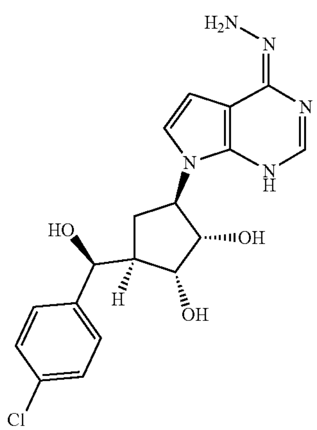 [SMILES: N/N=c1/nc[nH]c2c1ccn2[C@@H]1C[C@H]([C@H](O)c2ccc(Cl)cc2)[C@@H](O)[C@H]1O] | 389.84 | (1S,2R,3R,5R)-3-((S)-(4-chlorophenyl)(hydroxy)methyl)-5-((E)-4-hydrazineylidene-1,4-dihydro-7H-pyrrolo[2,3-d]pyrimidin-7-yl)cyclopentane-1,2-diol |
| 26-B | 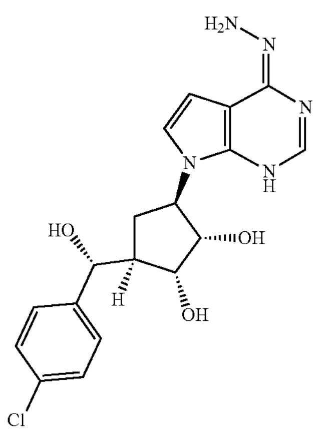 [SMILES: N/N=c1/nc[nH]c2c1ccn2[C@@H]1C[C@H]([C@@H](O)c2ccc(Cl)cc2)[C@@H](O)[C@H]1O] | 389.84 | (1S,2R,3R,5R)-3-((R)-(4-chlorophenyl)(hydroxy)methyl)-5-((E)-4-hydrazineylidene-1,4-dihydro-7H-pyrrolo[2,3-d]pyrimidin-7-yl)cyclopentane-1,2-diol |
| 27-B | 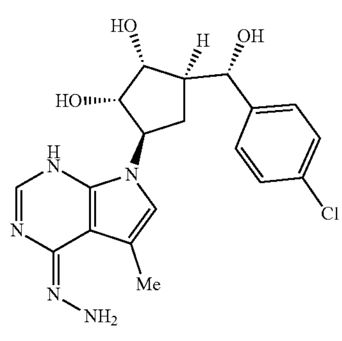 [SMILES: Cc1cn([C@@H]2C[C@H]([C@H](O)c3ccc(Cl)cc3)[C@@H](O)[C@H]2O)c2[nH]cn/c(=N/N)c12] | 403.867 | (1S,2R,3R,5R)-3-((S)-(4-chlorophenyl)(hydroxy)methyl)-5-((E)-4-hydrazineylidene-5-methyl-1,4-dihydro-7H-pyrrolo[2,3-d]pyrimidin-7-yl)cyclopentane-1,2-diol |

TABLE B-continued

| Ex. No. | Structure | MW | Chemical Name |
|---|---|---|---|
| 28-B | 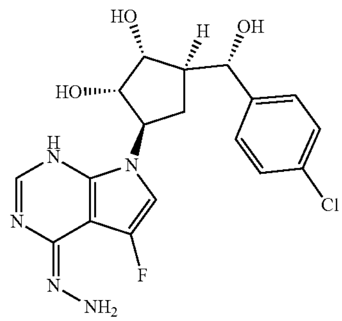 [SMILES: N/N=c1/nc[nH]c2c1c(F)cn2[C@@H]1C[C@H]([C@H](O)c2ccc(Cl)cc2)[C@@H](O)[C@H]1O] | 407.8304 | (1S,2R,3R,5R)-3-((S)-(4-chlorophenyl)(hydroxy)methyl)-5-((E)-5-fluoro-4-hydrazineylidene-1,4-dihydro-7H-pyrrolo[2,3-d]pyrimidin-7-yl)cyclopentane-1,2-diol |
| 29-B | 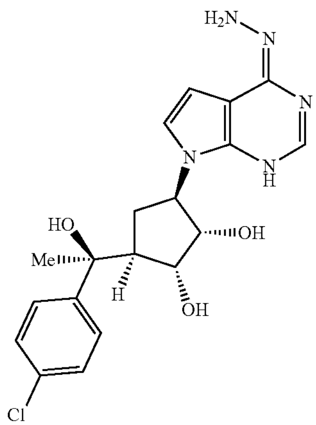 [SMILES: C[C@@](O)(c1ccc(Cl)cc1)[C@H]1C[C@@H](n2ccc3/c(=N\N)nc[nH]c32)[C@H](O)[C@@H]1O] | 403.867 | (1S,2R,3S,5R)-3-((S)-1-(4-chlorophenyl)-1-hydroxyethyl)-5-((E)-4-hydrazineylidene-1,4-dihydro-7H-pyrrolo[2,3-d]pyrimidin-7-yl)cyclopentane-1,2-diol |
| 30-B | 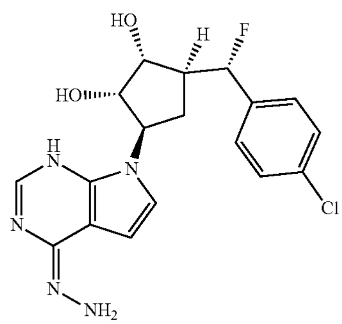 | 391.8314 | (1S,2R,3S,5R)-3-((S)-(4-chlorophenyl)fluoromethyl)-5-((E)-4-hydrazineylidene-1,4-dihydro-7H-pyrrolo[2,3-d]pyrimidin-7-yl)cyclopentane-1,2-diol |
| 31-B | 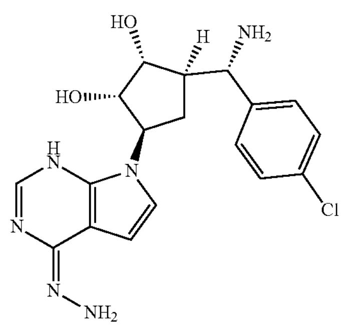 [SMILES: N/N=c1/nc[nH]c2c1ccn2[C@@H]1C[C@H]([C@H](N)c2ccc(Cl)cc2)[C@@H](O)[C@H]1O] | 388.856 | (1S,2R,3R,5R)-3-((S)-amino(4-chlorophenyl)methyl)-5-((E)-4-hydrazineylidene-1,4-dihydro-7H-pyrrolo[2,3-d]pyrimidin-7-yl)cyclopentane-1,2-diol |

TABLE B-continued

| Ex. No. | Structure | MW | Chemical Name |
|---|---|---|---|
| 32-B | 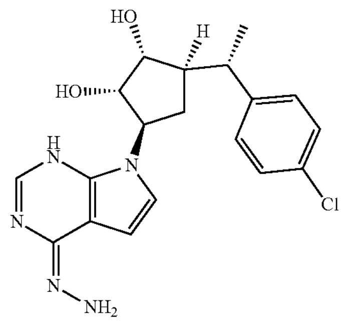 [SMILES: C[C@H](c1ccc(Cl)cc1)[C@H]1C[C@@H](n2ccc3/c(=N\N)nc[nH]c32)[C@H](O)[C@@H]1O] | 387.868 | (1S,2R,3R,5R)-3-((S)-1-(4-chlorophenyl)ethyl)-5-((E)-4-hydrazineylidene-1,4-dihydro-7H-pyrrolo[2,3-d]pyrimidin-7-yl)cyclopentane-1,2-diol |
| 33-B | 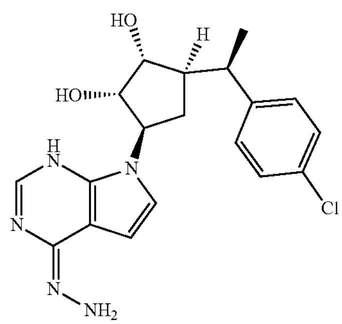 [SMILES: C[C@@H](c1ccc(Cl)cc1)[C@H]1C[C@@H](n2ccc3/c(=N\N)nc[nH]c32)[C@H](O)[C@@H]1O] | 387.868 | (1S,2R,3R,5R)-3-((R)-1-(4-chlorophenyl)ethyl)-5-((E)-4-hydrazineylidene-1,4-dihydro-7H-pyrrolo[2,3-d]pyrimidin-7-yl)cyclopentane-1,2-diol |
| 34-B | 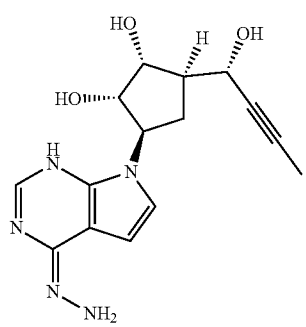 [SMILES: CC#C[C@@H](O)[C@H]1C[C@@H](n2ccc3/c(=N\N)nc[nH]c32)[C@H](O)[C@@H]1O] | 317.349 | (1R,2S,3R,5R)-3-((E)-4-hydrazineylidene-1,4-dihydro-7H-pyrrolo[2,3-d]pyrimidin-7-yl)-5-((S)-1-hydroxybut-2-yn-1-yl)cyclopentane-1,2-diol |
| 35-B | 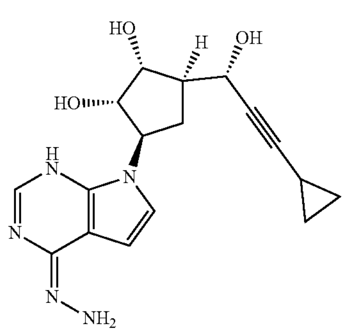 [SMILES: N/N=c1/nc[nH]c2c1ccn2[C@@H]1C[C@H]([C@H](O)C#CC2CC2)[C@@H](O)[C@H]1O] | 343.387 | (1S,2R,3R,5R)-3-((S)-3-cyclopropyl-1-hydroxyprop-2-yn-1-yl)-5-((E)-4-hydrazineylidene-1,4-dihydro-7H-pyrrolo[2,3-d]pyrimidin-7-yl)cyclopentane-1,2-diol |

TABLE B-continued

| Ex. No. | Structure | MW | Chemical Name |
|---|---|---|---|
| 36-B | 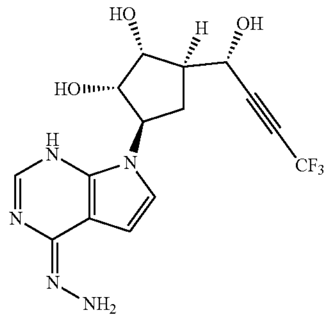 [SMILES: N/N=c1/nc[nH]c2c1ccn2[C@@H]1C[C@H]([C@H](O)C#CC(F)(F)F)[C@@H](O)[C@H]1O] | 371.3202 | (1R,2S,3R,5R)-3-((E)-4-hydrazineylidene-1,4-dihydro-7H-pyrrolo[2,3-d]pyrimidin-7-yl)-5-((S)-4,4,4-trifluoro-1-hydroxybut-2-yn-1-yl)cyclopentane-1,2-diol |
| 37-B | 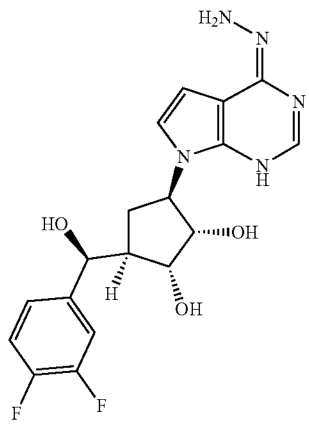 [SMILES: N/N=c1/nc[nH]c2c1ccn2[C@@H]1C[C@H]([C@H](O)c2ccc(F)c(F)c2)[C@@H](O)[C@H]1O] | 391.3788 | (1S,2R,3R,5R)-3-((S)-(3,4-difluorophenyl)(hydroxy)methyl)-5-((E)-4-hydrazineylidene-1,4-dihydro-7H-pyrrolo[2,3-d]pyrimidin-7-yl)cyclopentane-1,2-diol |
| 38-B | 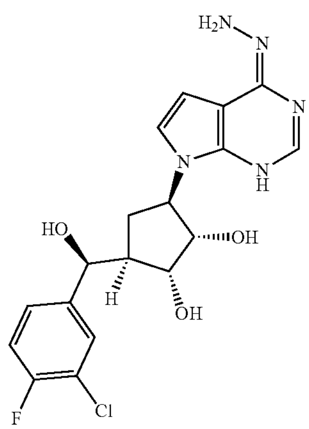 [SMILES: N/N=c1/nc[nH]c2c1ccn2[C@@H]1C[C@H]([C@H](O)c2ccc(F)c(Cl)c2)[C@@H](O)[C@H]1O] | 407.8304 | (1S,2R,3R,5R)-3-((S)-(3-chloro-4-fluorophenyl)(hydroxy)methyl)-5-((E)-4-hydrazineylidene-1,4-dihydro-7H-pyrrolo[2,3-d]pyrimidin-7-yl)cyclopentane-1,2-diol |
| 39-B | 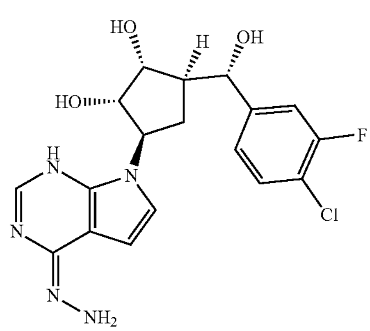 [SMILES: N/N=c1/nc[nH]c2c1ccn2[C@@H]1C[C@H]([C@H](O)c2ccc(Cl)c(F)c2)[C@@H](O)[C@H]1O] | 407.8304 | (1S,2R,3R,5R)-3-((S)-(4-chloro-3-fluorophenyl)(hydroxy)methyl)-5-((E)-4-hydrazineylidene-1,4-dihydro-7H-pyrrolo[2,3-d]pyrimidin-7-yl)cyclopentane-1,2-diol |

TABLE B-continued

| Ex. No. | Structure | MW | Chemical Name |
|---|---|---|---|
| 40-B | 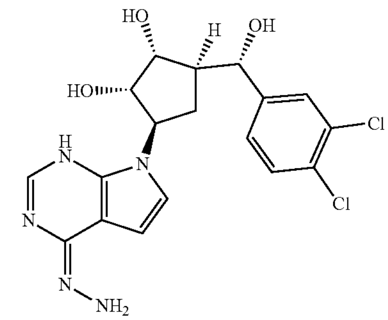 [SMILES: N/N=c1/nc[nH]c2c1ccn2[C@@H]1C[C@H]([C@H](O)c2ccc(Cl)c(Cl)c2)[C@@H](O)[C@H]1O] | 424.282 | (1S,2R,3R,5R)-3-((S)-(3,4-dichlorophenyl)(hydroxy)methyl)-5-((E)-4-hydrazineylidene-1,4-dihydro-7H-pyrrolo[2,3-d]pyrimidin-7-yl)cyclopentane-1,2-diol |
| 41-B | 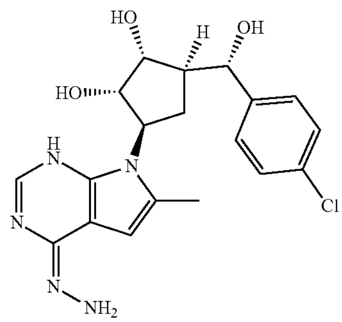 [SMILES: Cc1cc2/c(=N\N)nc[nH]c2n1[C@@H]1C[C@H]([C@H](O)c2ccc(Cl)cc2)[C@@H](O)[C@H]1O] | 403.867 | (1S,2R,3R,5R)-3-((S)-(4-chlorophenyl)(hydroxy)methyl)-5-((E)-4-hydrazineylidene-6-methyl-1,4-dihydro-7H-pyrrolo[2,3-d]pyrimidin-7-yl)cyclopentane-1,2-diol |
| 42-B | 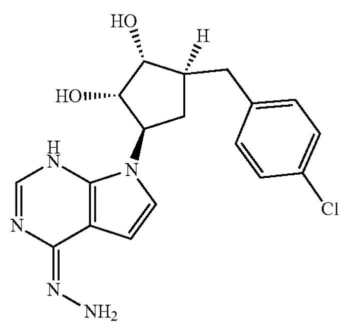 [SMILES: N/N=c1/nc[nH]c2c1ccn2[C@@H]1C[C@H](Cc2ccc(Cl)cc2)[C@@H](O)[C@H]1O] | 373.841 | (1S,2R,3S,5R)-3-(4-chlorobenzyl)-5-((E)-4-hydrazineylidene-1,4-dihydro-7H-pyrrolo[2,3-d]pyrimidin-7-yl)cyclopentane-1,2-diol |
| 43-B | 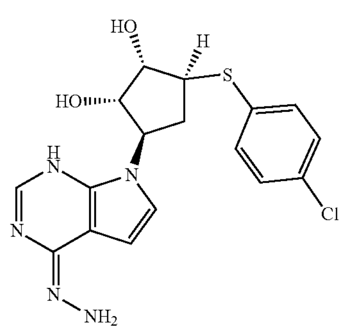 | 391.874 | (1S,2S,3S,5R)-3-((4-chlorophenyl)thio)-5-((E)-4-hydrazineylidene-1,4-dihydro-7H-pyrrolo[2,3-d]pyrimidin-7-yl)cyclopentane-1,2-diol |

TABLE B-continued

| Ex. No. | Structure | MW | Chemical Name |
|---|---|---|---|
| 44-B | 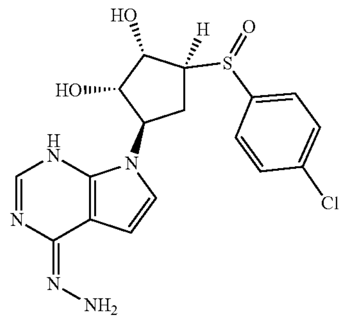 [SMILES: N/N=c1/nc[nH]c2c1ccn2[C@@H]1C[C@H](S(=O)c2ccc(Cl)cc2)[C@@H](O)[C@H]1O] | 407.873 | (1S,2S,3S,5R)-3-((4-chlorophenyl)sulfinyl)-5-((E)-4-hydrazineylidene-1,4-dihydro-7H-pyrrolo[2,3-d]pyrimidin-7-yl)cyclopentane-1,2-diol |
| 45-B | 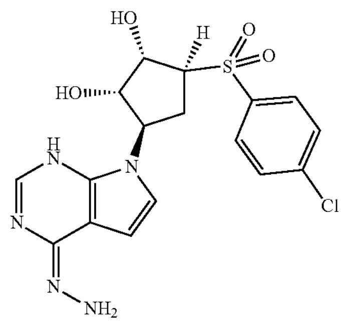 [SMILES: N/N=c1/nc[nH]c2c1ccn2[C@@H]1C[C@H](S(=O)(=O)c2ccc(Cl)cc2)[C@@H](O)[C@H]1O] | 423.872 | (1S,2S,3S,5R)-3-((4-chlorophenyl)sulfonyl)-5-((E)-4-hydrazineylidene-1,4-dihydro-7H-pyrrolo[2,3-d]pyrimidin-7-yl)cyclopentane-1,2-diol |
| 46-B | 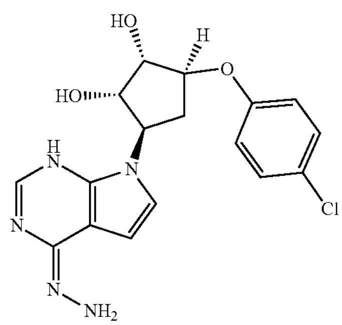 [SMILES: N/N=c1/nc[nH]c2c1ccn2[C@@H]1C[C@H](Oc2ccc(Cl)cc2)[C@@H](O)[C@H]1O] | 375.813 | (1S,2S,3S,5R)-3-(4-chlorophenoxy)-5-((E)-4-hydrazineylidene-1,4-dihydro-7H-pyrrolo[2,3-d]pyrimidin-7-yl)cyclopentane-1,2-diol |
| 47-B | 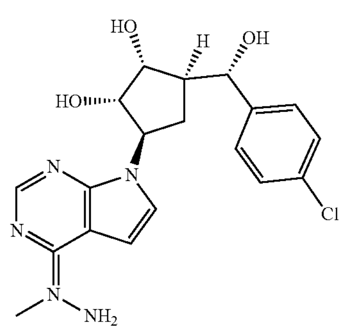 | 403.867 | (1S,2R,3R,5R)-3-((S)-(4-chlorophenyl)(hydroxy)methyl)-5-(4-(1-methylhydrazineyl)-7H-pyrrolo[2,3-d]pyrimidin-7-yl)cyclopentane-1,2-diol |

TABLE B-continued

| Ex. No. | Structure | MW | Chemical Name |
|---|---|---|---|
| 48-B | 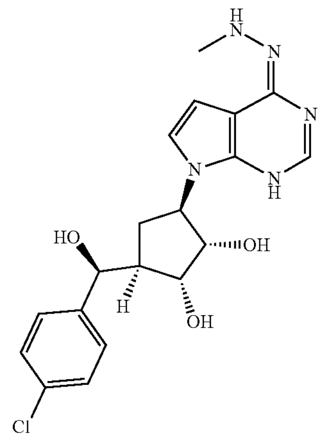 [SMILES: CN/N=c1/nc[nH]c2c1ccn2[C@@H]1C[C@H]([C@H](O)c2ccc(Cl)cc2)[C@@H](O)[C@H]1O] | 403.867 | (1S,2R,3R,5R)-3-((S)-(4-chlorophenyl)(hydroxy)methyl)-5-((E)-4-(2-methylhydrazineylidene)-1,4-dihydro-7H-pyrrolo[2,3-d]pyrimidin-7-yl)cyclopentane-1,2-diol |
| 49-B | 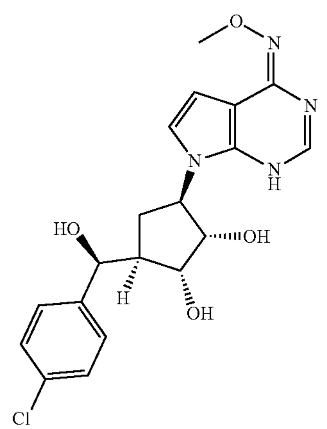 [SMILES: CO/N=c1/nc[nH]c2c1ccn2[C@@H]1C[C@H]([C@H](O)c2ccc(Cl)cc2)[C@@H](O)[C@H]1O] | 404.851 | (E)-7-((1R,2S,3R,4R)-4-((S)-(4-chlorophenyl)(hydroxy)methyl)-2,3-dihydroxycyclopentyl)-1,7-dihydro-4H-pyrrolo[2,3-d]pyrimidin-4-one O-methyl oxime |
| 50-B | 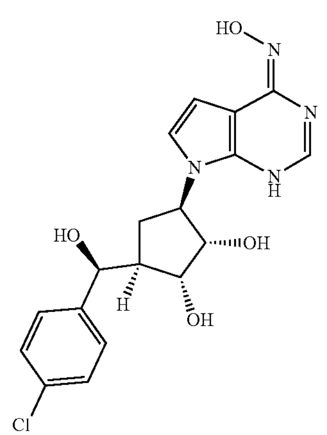 [SMILES: O/N=c1/nc[nH]c2c1ccn2[C@@H]1C[C@H]([C@H](O)c2ccc(Cl)cc2)[C@@H](O)[C@H]1O] | 390.824 | (E)-7-((1R,2S,3R,4R)-4-((S)-(4-chlorophenyl)(hydroxy)methyl)-2,3-dihydroxycyclopentyl)-1,7-dihydro-4H-pyrrolo[2,3-d]pyrimidin-4-one oxime |

TABLE B-continued

| Ex. No. | Structure | MW | Chemical Name |
|---|---|---|---|
| 51-B | 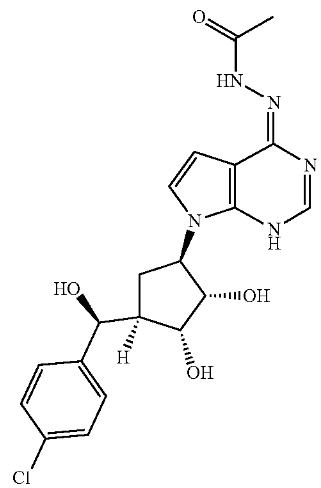 [SMILES: CC(=O)N/N=c1/nc[nH]c2c1ccn2[C@@H]1C[C@H]([C@H](O)c2ccc(Cl)cc2)[C@@H](O)[C@H]1O] | 431.877 | N'-((E)-7-((1R,2S,3R,4R)-4-((S)-(4-chlorophenyl)(hydroxy)methyl)-2,3-dihydroxycyclopentyl)-1,7-dihydro-4H-pyrrolo[2,3-d]pyrimidin-4-ylidene)acetohydrazide |
| 52-B | 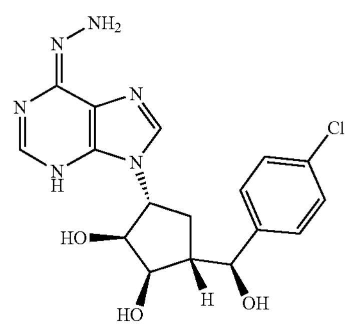 [SMILES: N/N=c1/nc[nH]c2c1ncn2[C@@H]1C[C@H]([C@H](O)c2ccc(Cl)cc2)[C@@H](O)[C@H]1O] | 390.828 | (1S,2R,3R,5R)-3-((S)-(4-chlorophenyl)(hydroxy)methyl)-5-((E)-6-hydrazineylidene-3,6-dihydro-9H-purin-9-yl)cyclopentane-1,2-diol |
| 53-B | 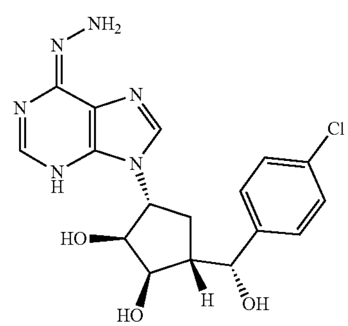 [SMILES: N/N=c1/nc[nH]c2c1ncn2[C@@H]1C[C@H]([C@@H](O)c2ccc(Cl)cc2)[C@@H](O)[C@H]1O] | 390.828 | (1S,2R,3R,5R)-3-((R)-(4-chlorophenyl)(hydroxy)methyl)-5-((E)-6-hydrazineylidene-3,6-dihydro-9H-purin-9-yl)cyclopentane-1,2-diol |
| 54-B | 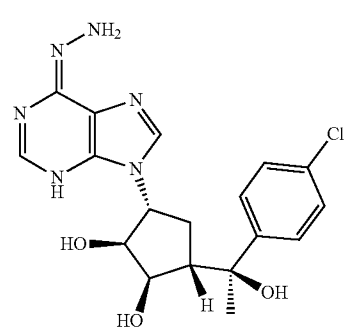 [SMILES: C[C@@](O)(c1ccc(Cl)cc1)[C@H]1C[C@@H](n2cnc3/c(=N\N)nc[nH]c32)[C@H](O)[C@@H]1O] | 404.855 | (1S,2R,3S,5R)-3-((S)-1-(4-chlorophenyl)-1-hydroxyethyl)-5-((E)-6-hydrazineylidene-3,6-dihydro-9H-purin-9-yl)cyclopentane-1,2-diol |

TABLE B-continued

| Ex. No. | Structure | MW | Chemical Name |
|---|---|---|---|
| 55-B | 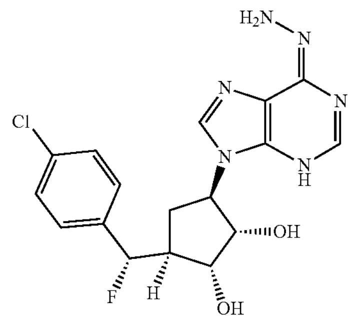 | 392.8194 | (1S,2R,3S,5R)-3-((S)-(4-chlorophenyl)fluoromethyl)-5-((E)-6-hydrazineylidene-3,6-dihydro-9H-purin-9-yl)cyclopentane-1,2-diol |
| 56-B | 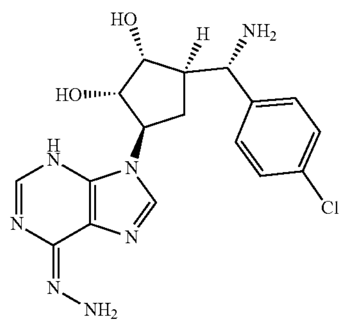 [SMILES: N/N=c1/nc[nH]c2c1ncn2[C@@H]1C[C@H]([C@H](N)c2ccc(Cl)cc2)[C@@H](O)[C@H]1O] | 389.844 | (1S,2R,3R,5R)-3-((S)-amino(4-chlorophenyl)methyl)-5-((E)-6-hydrazineylidene-3,6-dihydro-9H-purin-9-yl)cyclopentane-1,2-diol |
| 57-B | 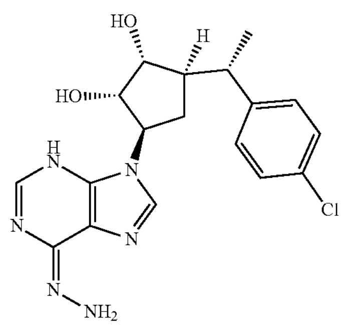 [SMILES: C[C@H](c1ccc(Cl)cc1)[C@H]1C[C@@H](n2cnc3/c(=N\N)nc[nH]c32)[C@H](O)[C@@H]1O] | 388.856 | (1S,2R,3R,5R)-3-((S)-1-(4-chlorophenyl)ethyl)-5-((E)-6-hydrazineylidene-3,6-dihydro-9H-purin-9-yl)cyclopentane-1,2-diol |
| 58-B | 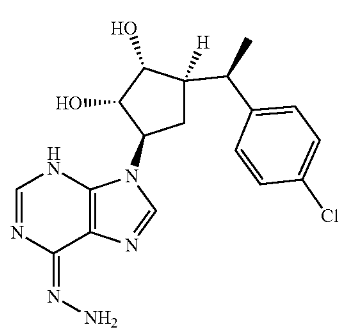 [SMILES: C[C@@H](c1ccc(Cl)cc1)[C@H]1C[C@@H](n2cnc3/c(=N\N)nc[nH]c32)[C@H](O)[C@@H]1O] | 388.856 | (1S,2R,3R,5R)-3-((R)-1-(4-chlorophenyl)ethyl)-5-((E)-6-hydrazineylidene-3,6-dihydro-9H-purin-9-yl)cyclopentane-1,2-diol |

TABLE B-continued

| Ex. No. | Structure | MW | Chemical Name |
|---|---|---|---|
| 59-B | 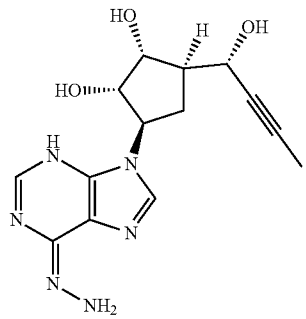 [SMILES: CC#C[C@@H](O)[C@H]1C[C@@H](n2cnc3/c(=N\N)nc[nH]c32)[C@H](O)[C@@H]1O] | 318.337 | (1R,2S,3R,5R)-3-((E)-6-hydrazineylidene-3,6-dihydro-9H-purin-9-yl)-5-((S)-1-hydroxybut-2-yn-1-yl)cyclopentane-1,2-diol |
| 60-B | 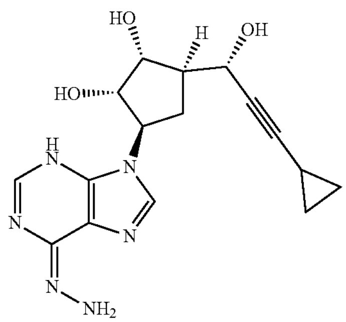 [SMILES: N/N=c1/nc[nH]c2c1ncn2[C@@H]1C[C@H]([C@H](O)C#CC2CC2)[C@@H](O)[C@H]1O] | 344.375 | (1S,2R,3R,5R)-3-((S)-3-cyclopropyl-1-hydroxyprop-2-yn-1-yl)-5-((E)-6-hydrazineylidene-3,6-dihydro-9H-purin-9-yl)cyclopentane-1,2-diol |
| 61-B | 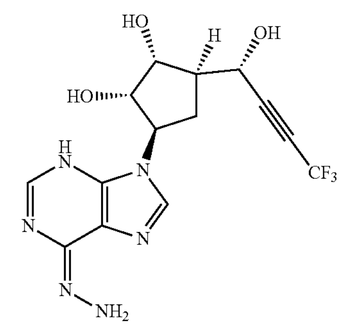 [SMILES: N/N=c1/nc[nH]c2c1ncn2[C@@H]1C[C@H]([C@H](O)C#CC(F)(F)F)[C@@H](O)[C@H]1O] | 372.3082 | (1R,2S,3R,5R)-3-((E)-6-hydrazineylidene-3,6-dihydro-9H-purin-9-yl)-5-((S)-4,4,4-trifluoro-1-hydroxybut-2-yn-1-yl)cyclopentane-1,2-diol |
| 62-B | 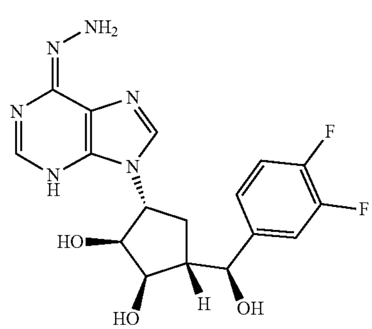 [SMILES: N/N=c1/nc[nH]c2c1ncn2[C@@H]1C[C@H]([C@H](O)c2ccc(F)c(F)c2)[C@@H](O)[C@H]1O] | 392.3668 | (1S,2R,3R,5R)-3-((S)-(3,4-difluorophenyl)(hydroxy)methyl)-5-((E)-6-hydrazineylidene-3,6-dihydro-9H-purin-9-yl)cyclopentane-1,2-diol |

TABLE B-continued

| Ex. No. | Structure | MW | Chemical Name |
|---|---|---|---|
| 63-B | 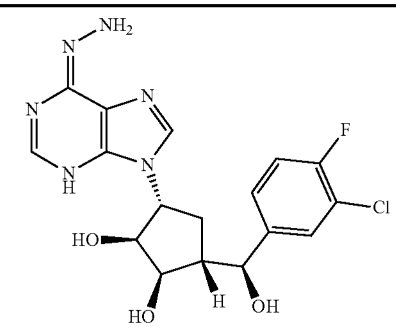 | 408.8184 | (1S,2R,3R,5R)-3-((S)-(3-chloro-4-fluorophenyl)(hydroxy)methyl)-5-((E)-6-hydrazineylidene-3,6-dihydro-9H-purin-9-yl)cyclopentane-1,2-diol |
| 64-B | 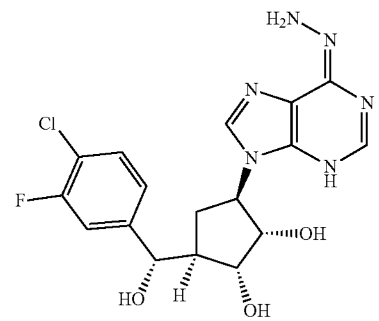 [SMILES: N/N=c1/nc[nH]c2c1ncn2[C@@H]1C[C@H]([C@H](O)c2ccc(Cl)c(F)c2)[C@@H](O)[C@H]1O] | 408.8184 | (1S,2R,3R,5R)-3-((S)-(4-chloro-3-fluorophenyl)(hydroxy)methyl)-5-((E)-6-hydrazineylidene-3,6-dihydro-9H-purin-9-yl)cyclopentane-1,2-diol |
| 65-B | 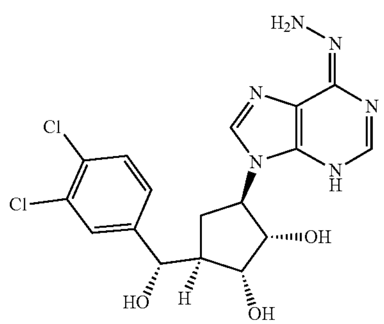 [SMILES: N/N=c1/nc[nH]c2c1ncn2[C@@H]1C[C@H]([C@H](O)c2ccc(Cl)c(Cl)c2)[C@@H](O)[C@H]1O] | 425.27 | (1S,2R,3R,5R)-3-((S)-(3,4-dichlorophenyl)(hydroxy)methyl)-5-((E)-6-hydrazineylidene-3,6-dihydro-9H-purin-9-yl)cyclopentane-1,2-diol |
| 66-B | 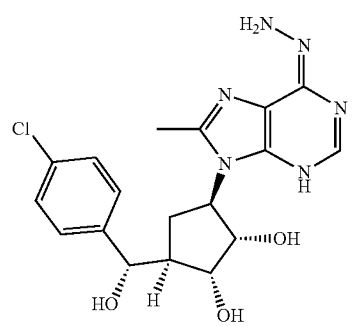 [SMILES: Cc1nc2/c(=N\N)nc[nH]c2n1[C@@H]1C[C@H]([C@H](O)c2ccc(Cl)cc2)[C@@H](O)[C@H]1O] | 404.855 | (1S,2R,3R,5R)-3-((S)-(4-chlorophenyl)(hydroxy)methyl)-5-((E)-6-hydrazineylidene-8-methyl-3,6-dihydro-9H-purin-9-yl)cyclopentane-1,2-diol |
| 67-B | 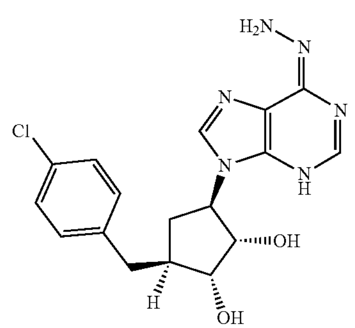 [SMILES: N/N=c1/nc[nH]c2c1ncn2[C@@H]1C[C@H](Cc2ccc(Cl)cc2)[C@@H](O)[C@H]1O] | 374.829 | (1S,2R,3S,5R)-3-(4-chlorobenzyl)-5-((E)-6-hydrazineylidene-3,6-dihydro-9H-purin-9-yl)cyclopentane-1,2-diol |

TABLE B-continued

| Ex. No. | Structure | MW | Chemical Name |
|---|---|---|---|
| 68-B | 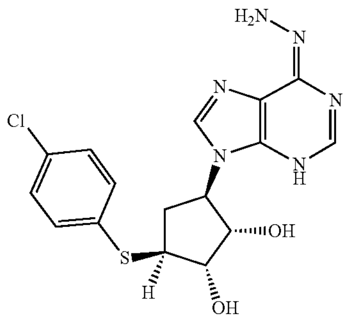 | 392.862 | (1S,2S,3S,5R)-3-((4-chlorophenyl)thio)-5-((E)-6-hydrazineylidene-3,6-dihydro-9H-purin-9-yl)cyclopentane-1,2-diol |
| 69-B | 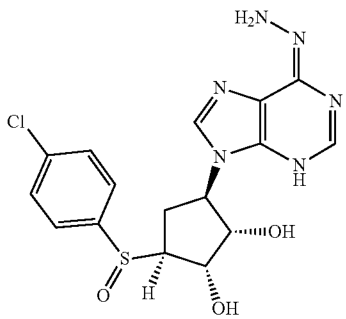 [SMILES: N/N=c1/nc[nH]c2c1ncn2[C@@H]1C[C@H](S(=O)c2ccc(Cl)cc2)[C@@H](O)[C@H]1O] | 408.861 | (1S,2S,3S,5R)-3-((4-chlorophenyl)sulfinyl)-5-((E)-6-hydrazineylidene-3,6-dihydro-9H-purin-9-yl)cyclopentane-1,2-diol |
| 70-B | 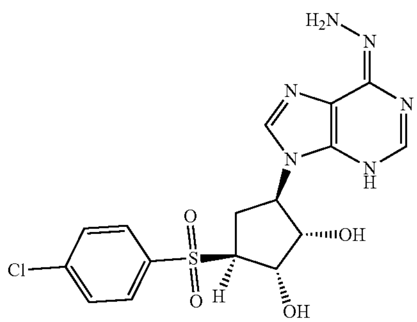 [SMILES: N/N=c1/nc[nH]c2c1ncn2[C@@H]1C[C@H](S(=O)(=O)c2ccc(Cl)cc2)[C@@H](O)[C@H]1O] | 424.86 | (1S,2S,3S,5R)-3-((4-chlorophenyl)sulfonyl)-5-((E)-6-hydrazineylidene-3,6-dihydro-9H-purin-9-yl)cyclopentane-1,2-diol |
| 71-B | 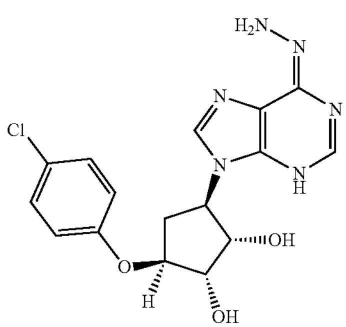 [SMILES: N/N=c1/nc[nH]c2c1ncn2[C@@H]1C[C@H](Oc2ccc(Cl)cc2)[C@@H](O)[C@H]1O] | 376.801 | (1S,2S,3S,5R)-3-(4-chlorophenoxy)-5-((E)-6-hydrazineylidene-3,6-dihydro-9H-purin-9-yl)cyclopentane-1,2-diol |

TABLE B-continued

| Ex. No. | Structure | MW | Chemical Name |
|---|---|---|---|
| 72-B | 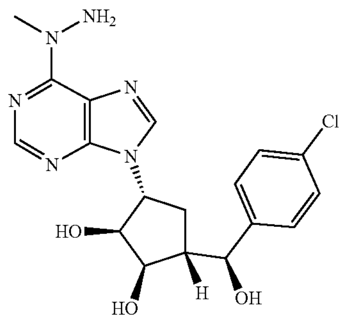 [SMILES: CN(N)c1ncnc2c1ncn2[C@@H]1C[C@H]([C@H](O)c2ccc(Cl)cc2)[C@@H](O)[C@H]1O] | 404.855 | (1S,2R,3R,5R)-3-((S)-(4-chlorophenyl)(hydroxy)methyl)-5-(6-(1-methylhydrazineyl)-9H-purin-9-yl)cyclopentane-1,2-diol |
| 73-B | 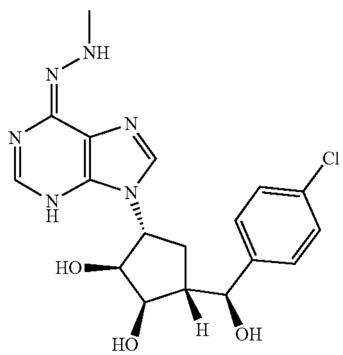 [SMILES: CN/N=c1/nc[nH]c2c1ncn2[C@@H]1C[C@H]([C@H](O)c2ccc(Cl)cc2)[C@@H](O)[C@H]1O] | 404.855 | (1S,2R,3R,5R)-3-((S)-(4-chlorophenyl)(hydroxy)methyl)-5-((E)-6-(2-methylhydrazineylidene)-3,6-dihydro-9H-purin-9-yl)cyclopentane-1,2-diol |
| 74-B | 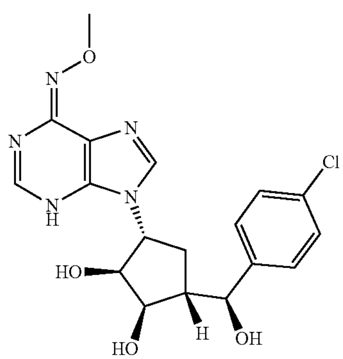 [SMILES: CO/N=c1/nc[nH]c2c1ncn2[C@@H]1C[C@H]([C@H](O)c2ccc(Cl)cc2)[C@@H](O)[C@H]1O] | 405.839 | (E)-9-((1R,2S,3R,4R)-4-((S)-(4-chlorophenyl)(hydroxy)methyl)-2,3-dihydroxycyclopentyl)-3,9-dihydro-6H-purin-6-one O-methyl oxime |
| 75-B | 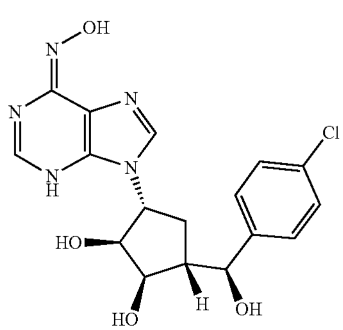 [SMILES: O/N=c1/nc[nH]c2c1ncn2[C@@H]1C[C@H]([C@H](O)c2ccc(Cl)cc2)[C@@H](O)[C@H]1O] | 391.812 | (E)-9-((1R,2S,3R,4R)-4-((S)-(4-chlorophenyl)(hydroxy)methyl)-2,3-dihydroxycyclopentyl)-3,9-dihydro-6H-purin-6-one oxime |

TABLE B-continued

| Ex. No. | Structure | MW | Chemical Name |
|---|---|---|---|
| 76-B | 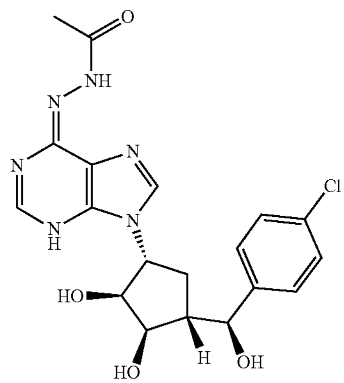 [SMILES: CC(=O)N/N=c1/nc[nH]c2c1ncn2[C@@H]1C[C@H]([C@H](O)c2ccc(Cl)cc2)[C@@H](O)[C@H]1O] | 432.865 | N'-((E)-9-((1R,2S,3R,4R)-4-((S)-(4-chlorophenyl)(hydroxy)methyl)-2,3-dihydroxycyclopentyl)-3,9-dihydro-6H-purin-6-ylidene)acetohydrazide |
| 77-B | 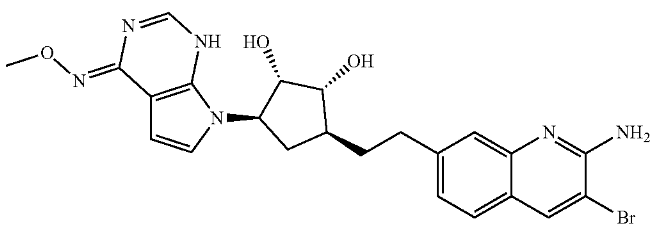 [SMILES: CO/N=c1\nc[nH]c2c1ccn2[C@@H]1C[C@H](CCc2ccc3cc(Br)c(N)nc3c2)[C@@H](O)[C@H]1O] | 513.40 | (Z)-7-((1R,2S,3R,4S)-4-(2-(2-amino-3-bromoquinolin-7-yl)ethyl)-2,3-dihydroxycyclopentyl)-1,7-dihydro-4H-pyrrolo[2,3-d]pyrimidin-4-one O-methyl oxime |
| 78-B | 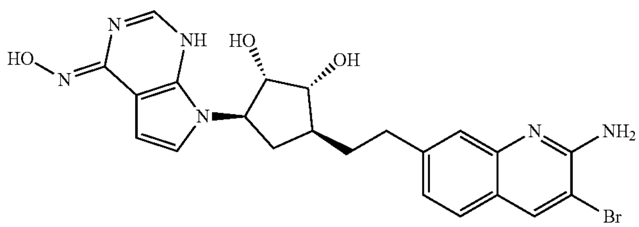 [SMILES: Nc1nc2cc(CC[C@H]3C[C@@H](n4ccc5/c(=N/O)nc[nH]c54)[C@H](O)[C@@H]3O)ccc2cc1Br] | 499.37 | (Z)-7-((1R,2S,3R,4S)-4-(2-(2-amino-3-bromoquinolin-7-yl)ethyl)-2,3-dihydroxycyclopentyl)-1,7-dihydro-4H-pyrrolo[2,3-d]pyrimidin-4-one oxime |
| 79-B | 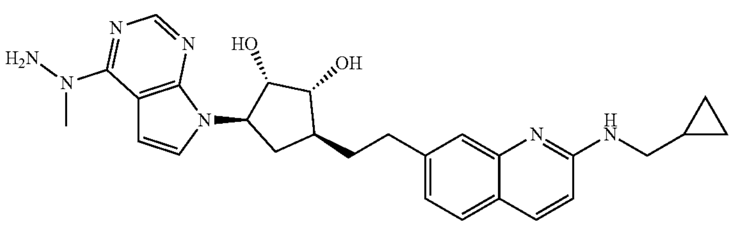 [SMILES: CN(N)c1ncnc2c1ccn2[C@@H]1C[C@H](CCc2ccc3ccc(NCC4CC4)nc3c2)[C@@H](O)[C@H]1O] | 487.61 | (1S,2R,3S,5R)-3-(2-(2-((cyclopropylmethyl)amino)quinolin-7-yl)ethyl)-5-(4-(1-methylhydrazineyl)-7H-pyrrolo[2,3-d]pyrimidin-7-yl)cyclopentane-1,2-diol |
| 80-B | 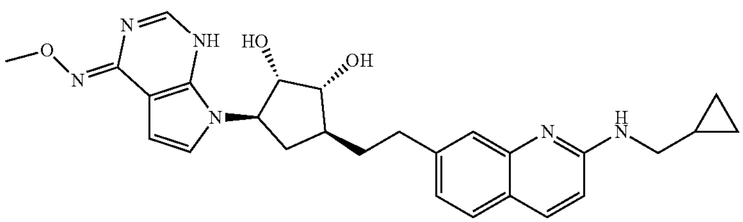 [SMILES: CO/N=c1\nc[nH]c2c1ccn2[C@@H]1C[C@H](CCc2ccc3ccc(NCC4CC4)nc3c2)[C@@H](O)[C@H]1O] | 488.59 | (Z)-7-((1R,2S,3R,4S)-4-(2-(2-((cyclopropylmethyl)amino)quinolin-7-yl)ethyl)-2,3-dihydroxycyclopentyl)-1,7-dihydro-4H-pyrrolo[2,3-d]pyrimidin-4-one O-methyl oxime |
| 81-B | 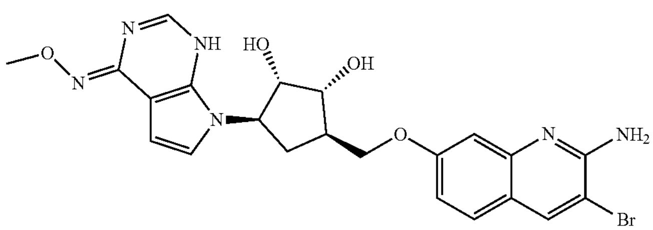 | 515.37 | (Z)-7-((1R,2S,3R,4R)-4-(((2-amino-3-bromoquinolin-7-yl)oxy)methyl)-2,3-dihydroxycyclopentyl)-1,7-dihydro-4H-pyrrolo[2,3-d]pyrimidin-4-one O-methyl oxime |

TABLE B-continued

| Ex. No. | Structure | MW | Chemical Name |
|---|---|---|---|
| 82-B | 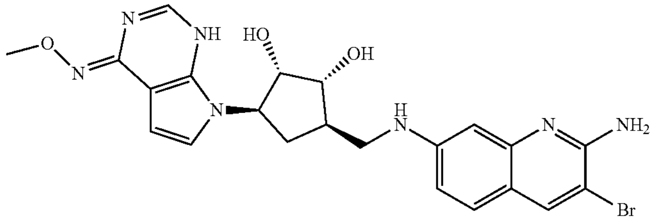 | 514.38 | (Z)-7-((1R,2S,3R,4R)-4-(((2-amino-3-bromoquinolin-7-yl)amino)methyl)-2,3-dihydroxycyclopentyl)-1,7-dihydro-4H-pyrrolo[2,3-d]pyrimidin-4-one O-methyl oxime |
| 83-B | 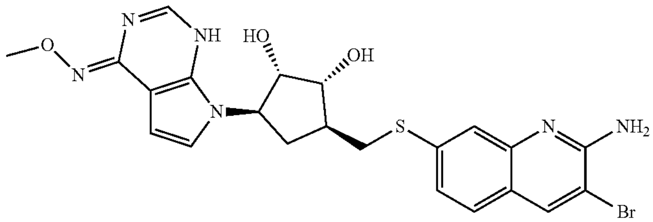 [SMILES: CO/N=c1\nc[nH]c2c1ccn2[C@@H]1C[C@H](COc2ccc3cc(Br)c(N)nc3c2)[C@@H](O)[C@H]1O] | 531.43 | (Z)-7-((1R,2S,3R,4S)-4-(((2-amino-3-bromoquinolin-7-yl)thio)methyl)-2,3-dihydroxycyclopentyl)-1,7-dihydro-4H-pyrrolo[2,3-d]pyrimidin-4-one O-methyl oxime |
| 84-B | 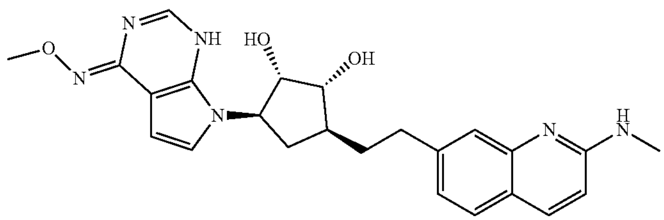 | 448.53 | (Z)-7-((1R,2S,3R,4S)-2,3-dihydroxy-4-(2-(2-(methylamino)quinolin-7-yl)ethyl)cyclopentyl)-1,7-dihydro-4H-pyrrolo[2,3-d]pyrimidin-4-one O-methyl oxime |
| 85-B | 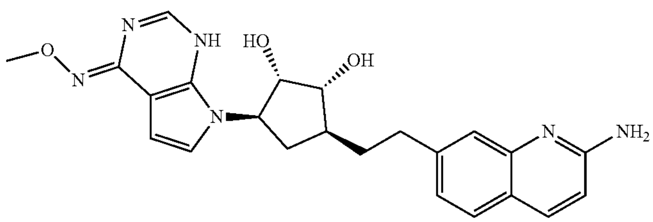 [SMILES: CO/N=c1\nc[nH]c2c1ccn2[C@@H]1C[C@H](CCc2ccc3ccc(N)nc3c2)[C@@H](O)[C@H]1O] | 434.5 | (Z)-7-((1R,2S,3R,4S)-4-(2-(2-aminoquinolin-7-yl)ethyl)-2,3-dihydroxycyclopentyl)-1,7-dihydro-4H-pyrrolo[2,3-d]pyrimidin-4-one O-methyl oxime |
| 86-B | 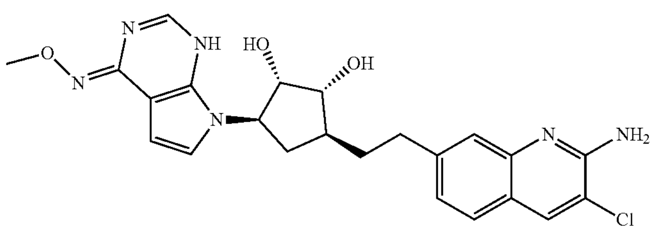 [SMILES: CO/N=c1\nc[nH]c2c1ccn2[C@@H]1C[C@H](CCc2ccc3cc(Cl)c(N)nc3c2)[C@@H](O)[C@H]1O] | 468.94 | (Z)-7-((1R,2S,3R,4S)-4-(2-(2-amino-3-chloroquinolin-7-yl)ethyl)-2,3-dihydroxycyclopentyl)-1,7-dihydro-4H-pyrrolo[2,3-d]pyrimidin-4-one O-methyl oxime |
| 87-B | 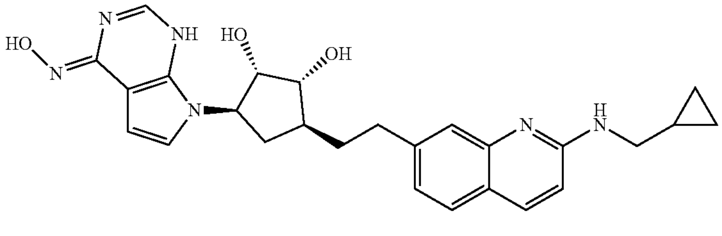 [SMILES: O/N=c1\nc[nH]c2c1ccn2[C@@H]1C[C@H](CCc2ccc3ccc(NCC4CC4)nc3c2)[C@@H](O)[C@H]1O] | 474.57 | (Z)-7-((1R,2S,3R,4S)-4-(2-(2-((cyclopropylmethyl)amino)quinolin-7-yl)ethyl)-2,3-dihydroxycyclopentyl)-1,7-dihydro-4H-pyrrolo[2,3-d]pyrimidin-4-one oxime |

TABLE B-continued

| Ex. No. | Structure | MW | Chemical Name |
|---|---|---|---|
| 88-B | 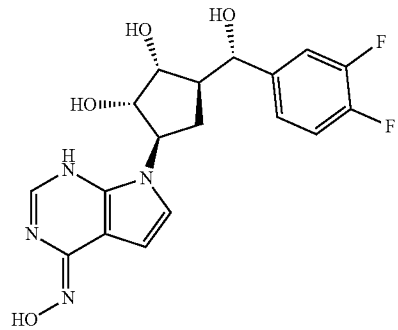 [SMILES: O/N=c1\nc[nH]c2c1ccn2[C@@H]1C[C@H]([C@H](O)c2ccc(F)c(F)c2)[C@@H](O)[C@H]1O] | 392.36 | (Z)-7-((1R,2S,3R,4R)-4-((S)-(3,4-difluorophenyl)(hydroxy)methyl)-2,3-dihydroxycyclopentyl)-1,7-dihydro-4H-pyrrolo[2,3-d]pyrimidin-4-one oxime |
| 89-B | 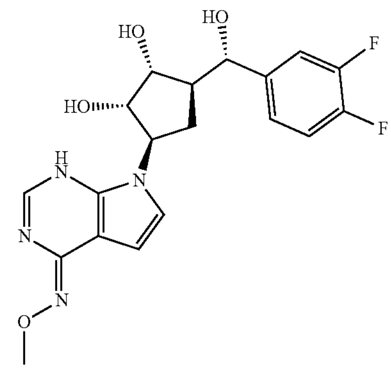 [SMILES: CO/N=c1\nc[nH]c2c1ccn2[C@@H]1C[C@H]([C@H](O)c2ccc(F)c(F)c2)[C@@H](O)[C@H]1O] | 406.38 | (Z)-7-((1R,2S,3R,4R)-4-((S)-(3,4-difluorophenyl)(hydroxy)methyl)-2,3-dihydroxycyclopentyl)-1,7-dihydro-4H-pyrrolo[2,3-d]pyrimidin-4-one O-methyl oxime |
| 90-B | 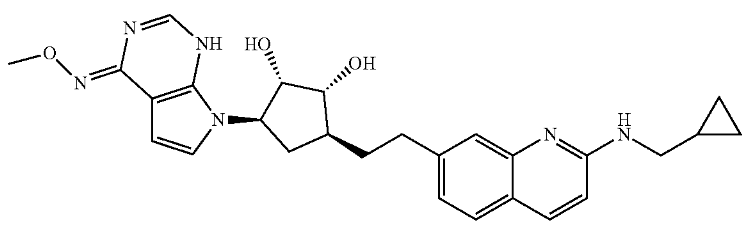 [SMILES: CO/N=c1\nc[nH]c2c1ccn2[C@@H]1C[C@H](CCc2ccc3ccc(NCC4CC4)nc3c2)[C@@H](O)[C@H]1O] | 488.58 | (Z)-7-((1R,2S,3R,4S)-4-(2-(2-((cyclopropylmethyl)amino)quinolin-7-yl)ethyl)-2,3-dihydroxycyclopentyl)-1,7-dihydro-4H-pyrrolo[2,3-d]pyrimidin-4-one O-methyl oxime |
| 91-B | 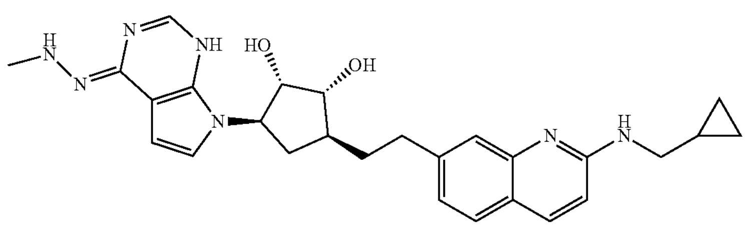 [SMILES: CN/N=c1\nc[nH]c2c1ccn2[C@@H]1C[C@H](CCc2ccc3ccc(NCC4CC4)nc3c2)[C@@H](O)[C@H]1O] | 487.6 | (1S,2R,3S,5R)-3-(2-(2-((cyclopropylmethyl)amino)quinolin-7-yl)ethyl)-5-((Z)-4-(2-methylhydrazineylidene)-1,4-dihydro-7H-pyrrolo[2,3-d]pyrimidin-7-yl)cyclopentane-1,2-diol |
| 92-B | 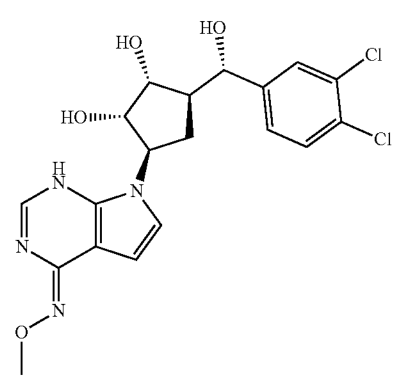 [SMILES: CO/N=c1\nc[nH]c2c1ccn2[C@@H]1C[C@H]([C@H](O)c2ccc(Cl)c(Cl)c2)[C@@H](O)[C@H]1O] | 439.29 | (Z)-7-((1R,2S,3R,4R)-4-((S)-(3,4-dichlorophenyl)(hydroxy)methyl)-2,3-dihydroxycyclopentyl)-1,7-dihydro-4H-pyrrolo[2,3-d]pyrimidin-4-one O-methyl oxime |

TABLE B-continued

| Ex. No. | Structure | MW | Chemical Name |
|---|---|---|---|
| 93-B | 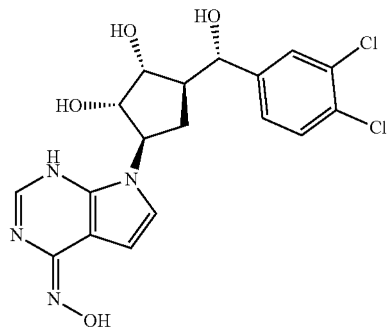 [SMILES: O/N=c1/nc[nH]c2c1ccn2[C@@H]1C[C@H]([C@H](O)c2ccc(Cl)c(Cl)c2)[C@@H](O)[C@H]1O] | 425.27 | (E)-7-((1R,2S,3R,4R)-4-((S)-(3,4-dichlorophenyl)(hydroxy)methyl)-2,3-dihydroxycyclopentyl)-1,7-dihydro-4H-pyrrolo[2,3-d]pyrimidin-4-one oxime |
| 94-B | 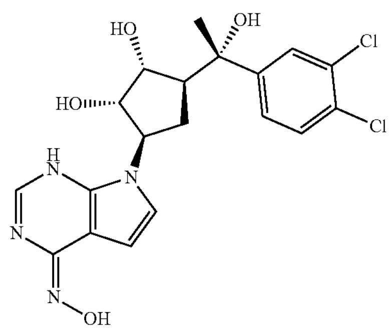 [SMILES: C[C@@](O)(c1ccc(Cl)c(Cl)c1)[C@H]1C[C@@H](n2ccc3/c(=N\O)nc[nH]c32)[C@H](O)[C@@H]1O] | 439.29 | (E)-7-((1R,2S,3R,4S)-4-((S)-1-(3,4-dichlorophenyl)-1-hydroxyethyl)-2,3-dihydroxycyclopentyl)-1,7-dihydro-4H-pyrrolo[2,3-d]pyrimidin-4-one oxime |

Compounds of the disclosure of Formula V and Formula VI include, for example, the compounds identified in Table C.

TABLE C

| Ex. No. | Structure | MW | Chemical Name |
|---|---|---|---|
| 1-C | 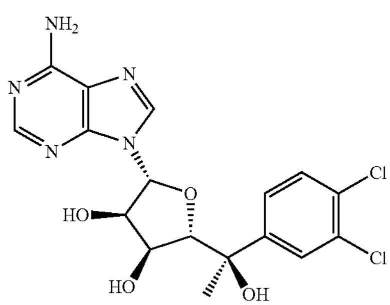 [SMILES: C[C@@](O)(c1ccc(Cl)c(Cl)c1)[C@H]1O[C@@H](n2cnc3c(N)ncnc32)[C@H](O)[C@@H]1O] | 426.254 | (2R,3R,4S,5S)-2-(6-amino-9H-purin-9-yl)-5-((R)-1-(3,4-dichlorophenyl)-1-hydroxyethyl)tetrahydrofuran-3,4-diol |
| 2-C | 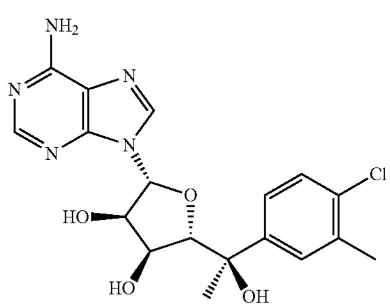 [SMILES: Cc1cc([C@@](C)(O)[C@H]2O[C@@H](n3cnc4c(N)ncnc43)[C@H](O)[C@@H]2O)ccc1Cl] | 405.839 | (2R,3R,4S,5S)-2-(6-amino-9H-purin-9-yl)-5-((R)-1-(4-chloro-3-methylphenyl)-1-hydroxyethyl)tetrahydrofuran-3,4-diol |

TABLE C-continued

| Ex. No. | Structure | MW | Chemical Name |
|---|---|---|---|
| 3-C | 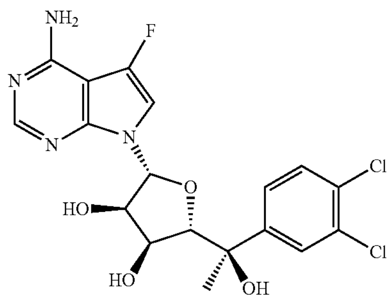 [SMILES: C[C@@](O)(c1ccc(Cl)c(Cl)c1)[C@H]1O[C@@H](n2cc(F)c3c(N)ncnc32)[C@H](O)[C@@H]1O] | 443.256 | (2R,3R,4S,5S)-2-(4-amino-5-fluoro-7H-pyrrolo[2,3-d]pyrimidin-7-yl)-5-((R)-1-(3,4-dichlorophenyl)-1-hydroxyethyl)tetrahydrofuran-3,4-diol |
| 4-C | 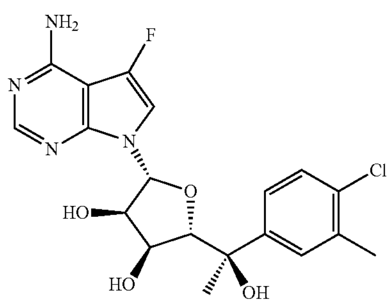 [SMILES: Cc1cc([C@@](C)(O)[C@H]2O[C@@H](n3cc(F)c4c(N)ncnc43)[C@H](O)[C@@H]2O)ccc1Cl] | 422.841 | (2R,3R,4S,5S)-2-(4-amino-5-fluoro-7H-pyrrolo[2,3-d]pyrimidin-7-yl)-5-((R)-1-(4-chloro-3-methylphenyl)-1-hydroxyethyl)tetrahydrofuran-3,4-diol |
| 5-C | 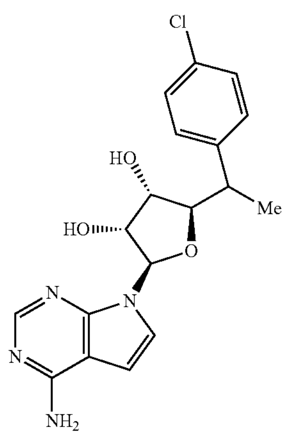 [SMILES: CC(c1ccc(Cl)cc1)[C@H]1O[C@@H](n2ccc3c(N)ncnc32)[C@H](O)[C@@H]1O] | 405.839 | (2R,3R,4S,5S)-2-(4-amino-7H-pyrrolo[2,3-d]pyrimidin-7-yl)-5-(1-(4-chlorophenyl)ethyl)tetrahydrofuran-3,4-diol |
| 6-C | R or S | 405.839 | (2R,3R,4S,5S)-2-(4-amino-7H-pyrrolo[2,3-d]pyrimidin-7-yl)-5-(1-(4-chlorophenyl)ethyl)tetrahydrofuran-3,4-diol |

TABLE C-continued

| Ex. No. | Structure | MW | Chemical Name |
|---|---|---|---|
| 7-C | 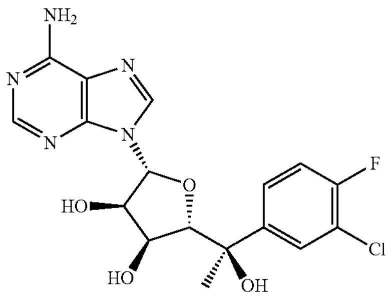 [SMILES: C[C@@](O)(c1ccc(F)c(Cl)c1)[C@H]1O[C@@H](n2cnc3c(N)ncnc32)[C@H](O)[C@@H]1O] | 4090802 | (2R,3R,4S,5S)-2-(6-amino-9H-purin-9-yl)-5-((R)-1-(3-chloro-4-fluorophenyl)-1-hydroxyethyl)tetrahydrofuran-3,4-diol |
| 8-C | 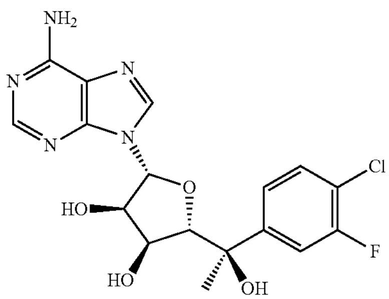 [SMILES: C[C@@](O)(c1ccc(Cl)c(F)c1)[C@H]1O[C@@H](n2cnc3c(N)ncnc32)[C@H](O)[C@@H]1O] | 409.802 | (2R,3R,4S,5S)-2-(6-amino-9H-purin-9-yl)-5-((R)-1-(4-chloro-3-fluorophenyl)-1-hydroxyethyl)tetrahydrofuran-3,4-diol |
| 9-C | 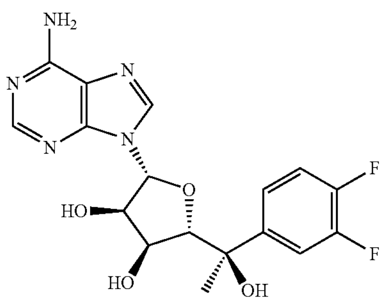 [SMILES: C[C@@](O)(c1ccc(F)c(F)c1)[C@H]1O[C@@H](n2cnc3c(N)ncnc32)[C@H](O)[C@@H]1O] | 393.351 | (2R,3R,4S,5S)-2-(6-amino-9H-purin-9-yl)-5-((R)-1-(3,4-difluorophenyl)-1-hydroxyethyl)tetrahydrofuran-3,4-diol |
| 10-C | 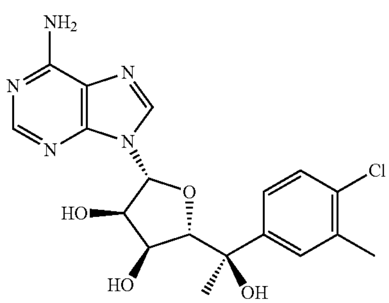 [SMILES: Cc1cc([C@@](C)(O)[C@H]2O[C@@H](n3cnc4c(N)ncnc43)[C@H](O)[C@@H]2O)ccc1Cl] | 405.839 | (2R,3R,4S,5S)-2-(6-amino-9H-purin-9-yl)-5-((R)-1-(4-chloro-3-methylphenyl)-1-hydroxyethyl)tetrahydrofuran-3,4-diol |
| 11-C | 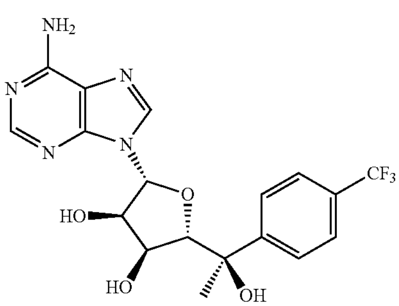 [SMILES: C[C@@](O)(c1ccc(C(F)(F)F)cc1)[C@H]1O[C@@H](n2cnc3c(N)ncnc32)[C@H](O)[C@@H]1O] | 425.368 | (2R,3R,4S,5S)-2-(6-amino-9H-purin-9-yl)-5-((R)-1-hydroxy-1-(4-(trifluoromethyl)phenyl)ethyl)tetrahydrofuran-3,4-diol |

TABLE C-continued

| Ex. No. | Structure | MW | Chemical Name |
|---|---|---|---|
| 12-C | 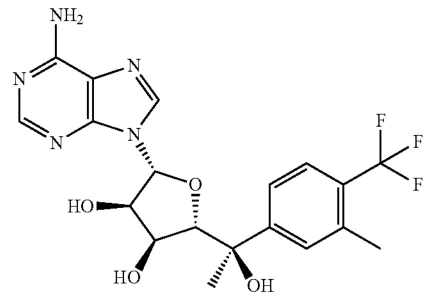 [SMILES: Cc1cc([C@@](C)(O)[C@H]2O[C@@H](n3cnc4c(N)ncnc43)[C@H](O)[C@@H]2O)ccc1C(F)(F)F] | 439.395 | (2R,3R,4S,5S)-2-(6-amino-9H-purin-9-yl)-5-((R)-1-hydroxy-1-(3-methyl-4-(trifluoromethyl)phenyl)ethyl)tetrahydrofuran-3,4-diol |
| 13-C | 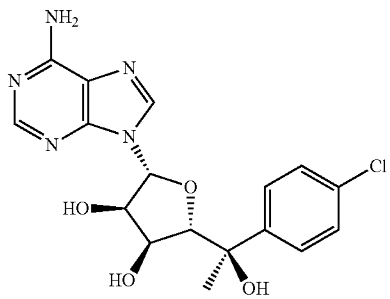 [SMILES: C[C@@](O)(c1ccc(Cl)cc1)[C@H]1O[C@@H](n2cnc3c(N)ncnc32)[C@H](O)[C@@H]1O] | 391.812 | (2R,3R,4S,5S)-2-(6-amino-9H-purin-9-yl)-5-((R)-1-(4-chlorophenyl)-1-hydroxyethyl)tetrahydrofuran-3,4-diol |
| 14-C | 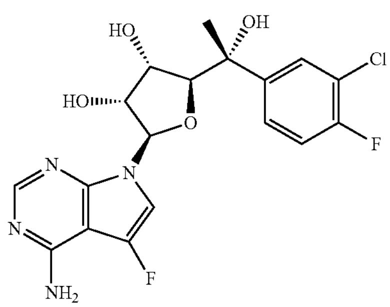 | 426.805 | (2R,3R,4S,5S)-2-(4-amino-5-fluoro-7H-pyrrolo[2,3-d]pyrimidin-7-yl)-5-((R)-1-(3-chloro-4-fluorophenyl)-1-hydroxyethyl)tetrahydrofuran-3,4-diol |
| 15-C | 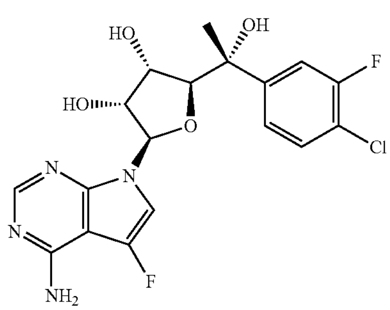 [SMILES: C[C@@](O)(c1ccc(F)c(Cl)c1)[C@H]1O[C@@H](n2cc(F)c3c(N)ncnc32)[C@H](O)[C@@H]1O] | 426.805 | (2R,3R,4S,5S)-2-(4-amino-5-fluoro-7H-pyrrolo[2,3-d]pyrimidin-7-yl)-5-((R)-1-(4-chloro-3-fluorophenyl)-1-hydroxyethyl)tetrahydrofuran-3,4-diol |
| 16-C | 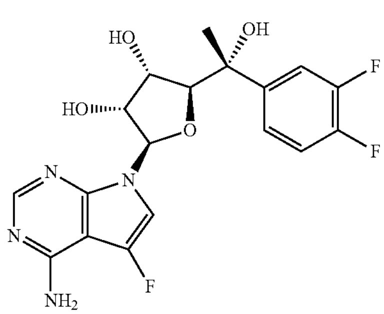 [SMILES: C[C@@](O)(c1ccc(F)c(F)c1)[C@H]1O[C@@H](n2cc(F)c3c(N)ncnc32)[C@H](O)[C@@H]1O] | 410.353 | (2R,3R,4S,5S)-2-(4-amino-5-fluoro-7H-pyrrolo[2,3-d]pyrimidin-7-yl)-5-((R)-1-(3,4-difluorophenyl)-1-hydroxyethyl)tetrahydrofuran-3,4-diol |

TABLE C-continued

| Ex. No. | Structure | MW | Chemical Name |
|---|---|---|---|
| 17-C | 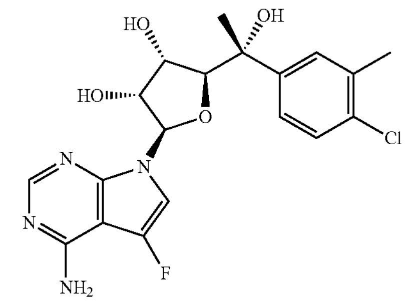 [SMILES: Cc1cc([C@@](C)(O)[C@H]2O[C@@H](n3cc(F)c4c(N)ncnc43)[C@H](O)[C@@H]2O)ccc1Cl] | 422.841 | (2R,3R,4S,5S)-2-(4-amino-5-fluoro-7H-pyrrolo[2,3-d]pyrimidin-7-yl)-5-((R)-1-(4-chloro-3-methylphenyl)-1-hydroxyethyl)tetrahydrofuran-3,4-diol |
| 18-C | 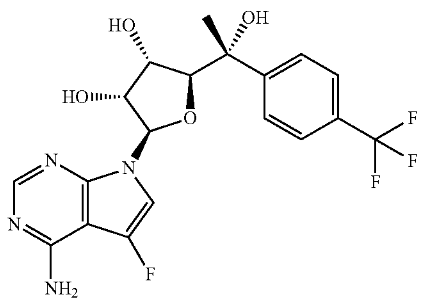 [SMILES: C[C@@](O)(c1ccc(C(F)(F)F)cc1)[C@H]1O[C@@H](n2cc(F)c3c(N)ncnc32)[C@H](O)[C@@H]1O] | 442.371 | (2R,3R,4S,5S)-2-(4-amino-5-fluoro-7H-pyrrolo[2,3-d]pyrimidin-7-yl)-5-((R)-1-hydroxy-1-(4-(trifluoromethyl)phenyl)ethyl)tetrahydrofuran-3,4-diol |
| 19-C | 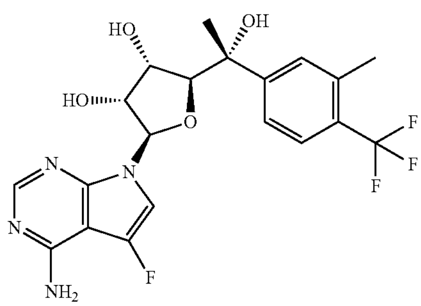 [SMILES: Cc1cc([C@@](C)(O)[C@H]2O[C@@H](n3cc(F)c4c(N)ncnc43)[C@H](O)[C@@H]2O)ccc1C(F)(F)F] | 456.398 | (2R,3R,4S,5S)-2-(4-amino-5-fluoro-7H-pyrrolo[2,3-d]pyrimidin-7-yl)-5-((R)-1-hydroxy-1-(3-methyl-4-(trifluoromethyl)phenyl)ethyl)tetrahydrofuran-3,4-diol |
| 20-C | 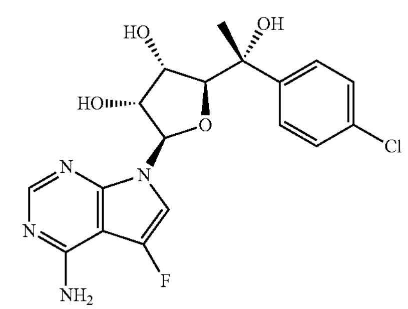 [SMILES: C[C@@](O)(c1ccc(Cl)cc1)[C@H]1O[C@@H](n2cc(F)c3c(N)ncnc32)[C@H](O)[C@@H]1O] | 408.814 | (2R,3R,4S,5S)-2-(4-amino-5-fluoro-7H-pyrrolo[2,3-d]pyrimidin-7-yl)-5-((R)-1-(4-chlorophenyl)-1-hydroxyethyl)tetrahydrofuran-3,4-diol |
| 21-C | 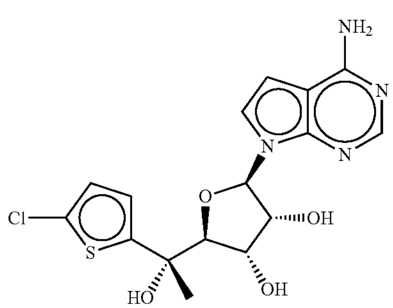 | 396.846 | (2R,3R,4S,5S)-2-(4-amino-7H-pyrrolo[2,3-d]pyrimidin-7-yl)-5-((R)-1-(5-chlorothiophen-2-yl)-1-hydroxyethyl)tetrahydrofuran-3,4-diol |

TABLE C-continued

| Ex. No. | Structure | MW | Chemical Name |
|---|---|---|---|
| 22-C | 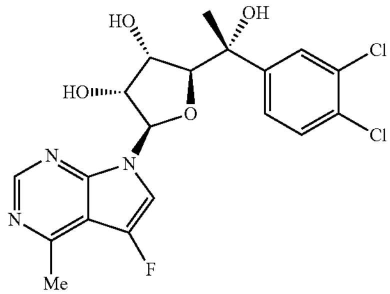 [SMILES: Cc1ncnc2c1c(F)cn2[C@@H]1O[C@H]([C@](C)(O)c2ccc(Cl)c(Cl)c2)[C@@H](O)[C@H]1O] | 442.268403 | (2S,3S,4R,5R)-2-((R)-1-(3,4-dichlorophenyl)-1-hydroxyethyl)-5-(5-fluoro-4-methyl-7H-pyrrolo[2,3-d]pyrimidin-7-yl)tetrahydrofuran-3,4-diol |
| 23-C | 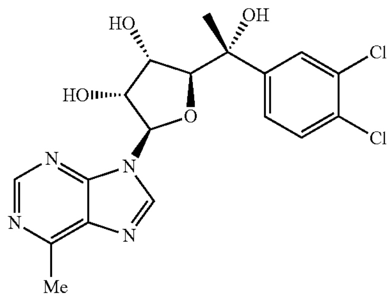 [SMILES: Cc1ncnc2c1ncn2[C@@H]1O[C@H]([C@](C)(O)c2ccc(Cl)c(Cl)c2)[C@@H](O)[C@H]1O] | 425.266 | (2S,3S,4R,5R)-2-((R)-1-(3,4-dichlorophenyl)-1-hydroxyethyl)-5-(6-methyl-9H-purin-9-yl)tetrahydrofuran-3,4-diol |

EXPERIMENTAL PROCEDURES

Synthesis of [(R)-[(2S,3S,4R,5R)-5-(4-chloropyrrolo[2,3-d]pyrimidin-7-yl)-3,4-dihydroxy-tetrahydrofuran-2-yl]-[4-(trifluoromethyl)phenyl]methyl] 4-phenylbenzoate (Int-1)

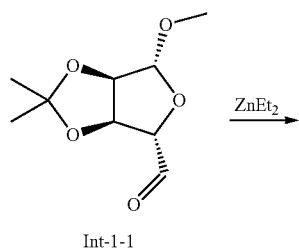

Int-1-1

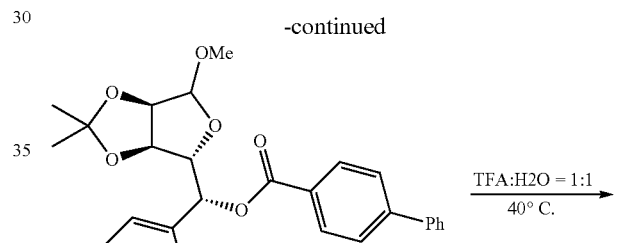

Int-1-3

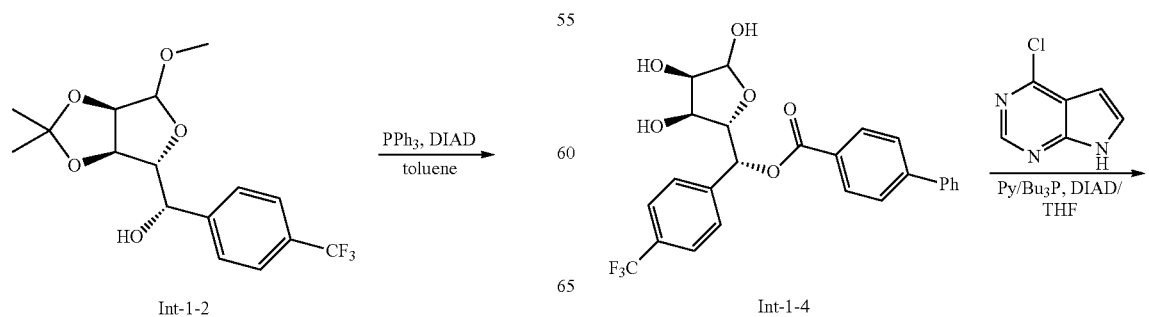

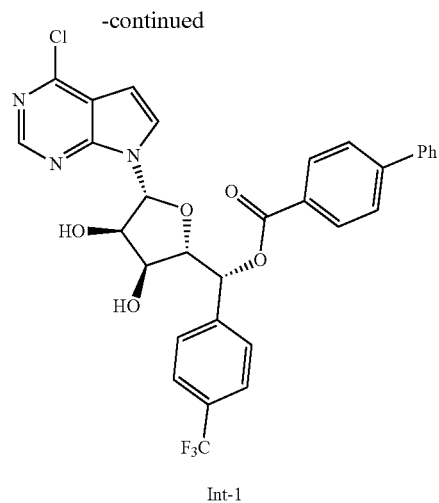

Int-1

Step 1. Preparation of (S)-[(3aR,4R,6R,6aR)-4-methoxy-2,2-dimethyl-3a,4,6,6a-tetrahydrofuro[3,4-d][1,3]dioxol-6-yl]-(4-chlorophenyl)methanol (Int-1-2)

To a solution of [4-(trifluoromethyl)phenyl]boronic acid (10 g, 52.65 mmol) in toluene (100 mL) was added diethylzine (157.95 mL, 157.95 mmol) at 25° C. The reaction mixture was stirred at 60° C. for 1 h. Then, (3aR,4R,6S,6aR)-4-methoxy-2,2-dimethyl-3a,4,6,6a-tetrahydrofuro[3,4-d][1,3]dioxole-6-carbaldehyde (Int-1-1) (10.65 g, 52.65 mmol) was added to the mixture and stirred at 60° C. for 3 hh. LCMS showed the reaction was completed and no Int-1-1 was left. The reaction was quenched with water and filtered. The mixture was concentrated in vacuum to give crude product, which was purified on a silica gel column (PE:EA=10:1 to 4:1) to afford (S)-[(3aR,4R,6R,6aR)-4-methoxy-2,2-dimethyl-3a,4,6,6a-tetrahydrofuro[3,4-d][1,3]dioxol-6-yl]-(4-chlorophenyl)methanol (Int-1-2) (4.7 g, 14.2 mmol, 26.9% yield) as white solid. $^1$H NMR (400 MHz, CDCl$_3$) δ 7.63 (d, J=8.0 Hz, 2H), 7.49 (d, J=8.0 Hz, 2H), 4.96 (s, 1H), 4.93 (d, J=6.0 Hz, 1H), 4.77-4.80 (m, 1H), 4.71 (d, J=3.6 Hz, 1H), 4.68 (d, J=6.0 Hz, 1H), 4.12 (d, J=9.6 Hz, 1H), 3.37 (s, 3H), 1.47 (s, 3H), 1.33 (s, 3H).

Step 2. Preparation of [(R)-[(3aR,4R,6R,6aR)-4-methoxy-2,2-dimethyl-3a,4,6,6a-tetrahydrofuro[3,4-d][1,3]dioxol-6-yl]-[4-(trifluoromethyl)phenyl]methyl]4-phenylbenzoate(Int-1-3)

To a solution of (S)-[(3aR,4R,6R,6aR)-4-methoxy-2,2-dimethyl-3a,4,6,6a-tetrahydrofuro[3,4-d][1,3]dioxol-6-yl]-[4-(trifluoromethyl)phenyl]methanol (Int-1-2) (4.7 g, 12.9 mmol) in toluene (50 mL) was added triphenylphosphine (5 g, 19.4 mmol) and 4-biphenylcarboxylic acid (3.85 g, 19.4 mmol), then DIAD (3.83 mL, 19.4 mmol) was added at 0° C. The reaction mixture was stirred at room temperature for 3 h. TLC (PE:EA=5:1) showed the reaction was completed. The solvent was concentrated under reduced pressure. The residue was purified on a silica gel column (PE:EA=50:1 to PE:EA=30:1) to give [(R)-[(3aR,4R,6R,6aR)-4-methoxy-2,2-dimethyl-3a,4,6,6a-tetrahydrofuro[3,4-d][1,3]dioxol-6-yl]-[4-(trifluoromethyl)phenyl]methyl] 4-phenylbenzoate (Int-1-3) (5.7 g, 10.6 mmol, 81.6% yield) as a white solid. $^1$H NMR (400 MHz, DMSO-d6) δ 8.13 (d, J=8.0 Hz, 2H), 7.86 (d, J=8.4 Hz, 2H), 7.74-7.78 (m, 6H), 7.52 (t, J=7.2 Hz, 2H), 7.44 (t, J=7.2 Hz, 1H), 5.97 (d, J=8.0 Hz, 1H), 5.03 (d, J=5.2 Hz, 1H), 4.94 (s, 1H), 4.69-4.72 (m, 2H), 3.15 (s, 3H), 1.40 (s, 3H), 1.27 (s, 3H).

Step 3. Preparation of [(R)-[4-(trifluoromethyl)phenyl]-[(2S,3S,4R)-3,4,5-trihydroxytetrahydrofuran-2-yl]methyl]4-phenylbenzoate(Int-1-4)

A solution of [(R)-[(3aR,4R,6R,6aR)-4-methoxy-2,2-dimethyl-3a,4,6,6a-tetrahydrofuro[3,4-d][1,3]dioxol-6-yl]-[4-(trifluoromethyl)phenyl]methyl] 4-phenylbenzoate (5.7 g, 10.6 mmol) in TFA (114 mL, 1.54 mol) and water (114 mL) was stirred at 40° C. for 18 hh. LCMS showed the reaction was completed. The solvent was concentrated under reduced pressure, and the residue was washed with NaHCO$_3$ aqueous, extracted with EA. The combined organic layers were washed with brine, dried over anhydrous Na$_2$SO$_4$. The solvent was concentrated under reduced pressure and purified by silica gel column chromatography (PE:EA=10:1 to PE:EA=2:1) to give impure product (7.2 g) which was purified again by reversed-phase combi-flash eluting with H$_2$O:CH$_3$CN from 90:10 to 5:95 to give [(R)-[4-(trifluoromethyl)phenyl]-[(2S,3S,4R)-3,4,5-trihydroxytetrahydrofuran-2-yl]methyl] 4-phenylbenzoate (Int-1-4) (4.35 g, 8.99 mmol, 85.0% yield) as a white solid. $^1$H NMR (400 MHz, DMSO-d6+D$_2$O) δ 8.16 (d, J=8.0 Hz, 2H), 7.86 (d, J=8.0 Hz, 2H), 7.69-7.77 (m, 6H), 7.53 (t, J=7.6 Hz, 2H), 7.45 (t, J=7.2 Hz, 1H), 6.05 (d, J=6.0 Hz, 1H), 4.99 (s, 1H), 4.22 (t, J=7.2 Hz, 1H), 4.15 (d, J=6.0 Hz, 1H), 3.70 (d, J=4.4 Hz, 1H), 4.06 (d, J=4.4 Hz, 1H), 2.76 (s, 3H).

Step 4. Preparation of [(R)-[(2S,3S,4R,5R)-5-(4-chloropyrrolo[2,3-d]pyrimidin-7-yl)-3,4-dihydroxy-tetrahydrofuran-2-yl]-[4-(trifluoromethyl)phenyl]methyl] 4-phenylbenzoate (Int-1)

To a solution of 4-Chloro-7H-pyrrolo[2,3-d]pyrimidine (0.32 g, 2.1 mmol) and pyridine (0.17 mL, 2.1 mmol) in dry THF (10 mL) was added tributylphosphane (1.03 mL, 4.13 mmol) and DIAD (0.85 mL, 4.34 mmol) at 30° C. [(R)-[4-(trifluoromethyl)phenyl]-[(2S,3S,4R)-3,4,5-trihydroxytetrahydrofuran-2-yl]methyl] 4-phenylbenzoate (1 g, 2.1 mmol) in dry THF (10 mL) was added in one portion. The reaction mixture was stirred at 30° C. for 1 h. LCMS showed the reaction was completed. The crude product was purified by prep-HPLC (0.1% TFA) eluting with H$_2$O:CH$_3$CN from 90:10 to 5:95 to give [(R)-[(2S,3S,4R,5R)-5-(4-chloropyrrolo[2,3-d]pyrimidin-7-yl)-3,4-dihydroxy-tetrahydrofuran-2-yl]-[4-(trifluoromethyl)phenyl]methyl] 4-phenylbenzoate (Int-1) (330 mg, 0.53 mmol, 25.7% yield) as pale yellow solid. LCMS [M+H]: 610.3.

Synthesis of (R)-((2S,3S,4R,5R)-5-(6-chloro-9H-purin-9-yl)-3,4-dihydroxytetrahydrofuran-2-yl)(4-chlorophenyl)methyl [1,1'-biphenyl]-4-carboxylate (Int-2)

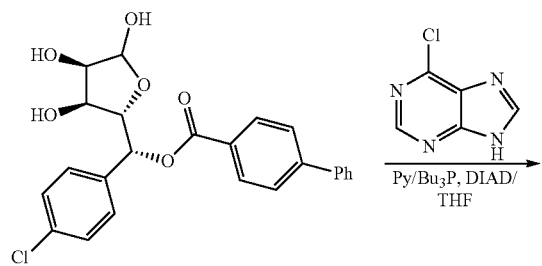

Int-2

Step 1. Preparation of (1R)-(4-chlorophenyl)((2S,3S,4R)-3,4,5-trihydroxytetrahydrofuran-2-yl)methyl [1,1'-biphenyl]-4-carboxylate (Int-2-1)

Int-2-1 was prepared similar to that of Int-1-4 except substituting [4-(trifluoromethyl)phenyl]boronic acid with (4-chlorophenyl)boronic acid.

Step 2. Preparation of (R)-((2S,3S,4R,5R)-5-(6-chloro-9H-purin-9-yl)-3,4-dihydroxytetrahydrofuran-2-yl)(4-chlorophenyl)methyl [1,1'-biphenyl]-4-carboxylate (Int-2)

To a mixture of 6-Chloropurine (1.6 g, 10.6 mmol) in THF (40.0 mL) was added pyridine (0.8 mL, 10.6 mmol), tributyl phosphine (5.2 mL, 21.1 mmol) and DIAD (4.6 mL, 23.2 mmol). The mixture was cooled with ice-bath and [(R)-(4-chlorophenyl)-[(2S,3S,4R)-3,4,5-trihydroxy tetrahydrofuran-2-yl]methyl]4-phenylbenzoate (Int-2-1) (5.0 g, 10.6 mmol) in THF (30.0 mL) was added. The mixture was stirred at 25° C. for 2 h. The solvent was removed and the residue was purified by reversed phase combi-flash eluting with CH$_3$CN/H$_2$O (neutral condition) from 30/70 to 70/30 to give [(R)-(4-chlorophenyl)-[(2S,3S,4R,5R)-5-(6-chloropurin-9-yl)-3,4-dihydroxy-tetrahydrofuran-2-yl]methyl] 4-phenylbenzoate (2.6 g, 4.22 mmol, 40.0% yield) as yellow solid. LCMS: no MS signal. $^1$H NMR (400 MHz, DMSO-d6): δ 8.75 (s, 1H), 8.54 (s, 1H), 8.20 (d, J=4.4 Hz, 2H), 7.87 (d, J=4.4 Hz, 2H), 7.77 (d, J=4.0 Hz, 2H), 7.50-7.55 (m, 2H), 7.43-7.47 (m, 3H), 7.29 (d, J=4.0 Hz, 2H), 6.25 (d, J=5.2 Hz, 1H), 6.04 (d, J=5.6 Hz, 1H), 5.69 (d, J=6.0 Hz, 1H), 5.57 (d, J=5.2 Hz, 1H), 4.91-4.96 (m, 1H), 4.47-4.50 (m, 1H), 4.41-4.44 (m, 1H). $^1$H NMR (400 MHz, DMSO-d6+D$_2$O): δ 8.67 (s, 1H), 8.51 (s, 1H), 8.11 (d, J=4.4 Hz, 2H), 7.86 (d, J=8.4 Hz, 2H), 7.77 (d, J=7.6 Hz, 2H), 7.52-7.56 (m, 2H), 7.43-7.49 (m, 3H), 7.27 (d, J=8.4 Hz, 2H), 6.23 (d, J=4.4 Hz, 1H), 6.04 (d, J=5.2 Hz, 1H), 4.96 (t, J=4.8 Hz, 1H), 4.54 (t, J=4.8 Hz, 1H), 4.51 (t, J=4.8 Hz, 1H).

Synthesis of (R)-(4-chloro-3-fluorophenyl)((3aR,4R,6R,6aR)-6-(4-chloro-7H-pyrrolo[2,3-d]pyrimidin-7-yl)-2,2-dimethyltetrahydrofuro[3[(R)-(4-chlorophenyl)-[(2R,3R,4R)-3,4,5-triacetoxytetra-hydrofuran-2-yl]methyl] 4-phenylbenzoate,4-d][1,3]dioxol-4-yl) methanol (Int-3)

Diisobutylalumanylium; hydride (DIBAL, 1.08 mL, 1.08 mmol) (1M in toluene) was added a solution of [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-(4-chloro-3-fluoro-phenyl)methanone (Int-3-1) (245.mg, 0.54 mmol) in Toluene (5 mL) at −78° C. The resulting mixture was stirred at −78° C. for 1 h. TLC showed small amount of remaining starting material, major desired product and small amount (more polar spot) wrong epimer. This was warmed up to room temperature, stirred for another 30 min, then cooled to 0° C. EtOAc was added, then the reaction mixture was poured into ice cold sat. aq. Rocher's salt. The aq. layer was extracted with EtOAc and the combined organic layers were washed with brine, dried over Na$_2$SO$_4$, filtered and concentrated. The residue was purified on a 20 g column which was eluted with 0-50% of EA/hexane to recover 20 mg starting ketone (8%); and to give (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(4-chloro-3-fluoro-phenyl)methanol (Int-3) (163 mg, 0.359 mmol, 66.2% yield) as a white foamy solid.

Synthesis of [(R)-(4-chlorophenyl)-[(2R,3R,4R,5R)-3,4-diacetoxy-5-(4-chloro-5-fluoro-pyrrolo[2,3-d]pyrimidin-7-yl)tetrahydrofuran-2-yl]methyl] 4-phenylbenzoate (Int-4)

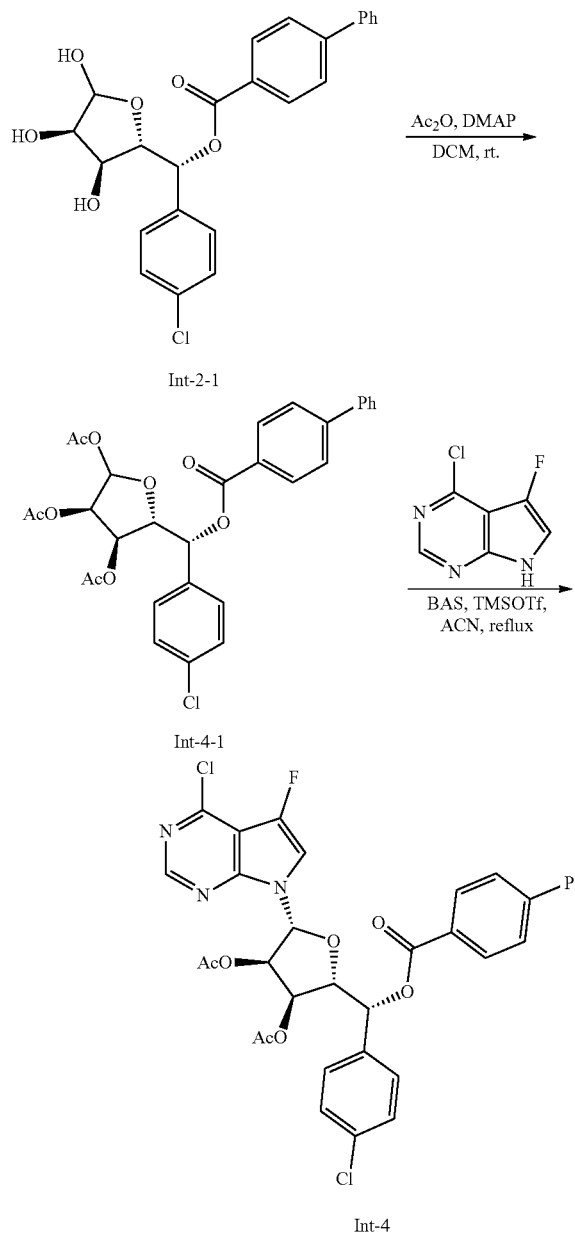

Step 1. Preparation of [(R)-(4-chlorophenyl)-[(2R,3R,4R)-3,4,5-triacetoxytetra-hydrofuran-2-yl]methyl] 4-phenylbenzoate (Int-4-1)

To a solution of [(R)-(4-chlorophenyl)-[(2S,3S,4R)-3,4,5-trihydroxytetrahydrofuran-2-yl]methyl] 4-phenylbenzoate (Int-2-1) (4.0 g, 8.17 mmol) in pyridine (50 mL) was added DMAP (200.0 mg, 1.62 mmol), followed by acetic anhydride (3.86 mL, 40.7 mmol). The mixture was added at 23° C. for 16 h. After the reaction was complete, the solvent was removed under vacuum. The residue was purified by silica gel column chromatography (PE:EtOAc=4:1) to afford (3.6 g, 5.86 mmol, 71.8% yield) as white solid. LCMS [M+H]: 589.2.

Step 2. Preparation of [(R)-(4-chlorophenyl)-[(2R,3R,4R,5R)-3,4-diacetoxy-5-(4-chloro-5-fluoro-pyrrolo[2,3-d]pyrimidin-7-yl)tetrahydrofuran-2-yl]methyl] 4-phenylbenzoate (Int-4)

To a solution of 4-chloro-5-fluoro-7H-pyrrolo[2,3-d]pyrimidine (600.0 mg, 3.46 mmol) in dry MeCN (30 mL) was added N,O-Bis(trimethylsilyl)acetamide (1 mL, 4.09 mmol). The mixture was stirred at 23° C. for 15 min. Then [(R)-(4-chlorophenyl)-[(2R,3R,4R)-3,4,5-triacetoxytetrahydrofuran-2-yl]methyl] 4-phenylbenzoate (Int-4-1) (2.15 g, 3.49 mmol) was added, followed by TMSOTf (1.0 mL, 5.53 mmol). The mixture was stirred at 82° C. for 16 h. After the reaction was complete, the solvent was removed in vacuo. The residue was purified by silica gel column chromatography (PE:EtOAc=3:1) to afford [(R)-(4-chlorophenyl)-[(2R,3R,4R,5R)-3,4-diacetoxy-5-(4-chloro-5-fluoro-pyrrolo[2,3-d]pyrimidin-7-yl)tetrahydrofuran-2-yl]methyl] 4-phenylbenzoate (Int-4) (300 mg, 0.385 mmol, 11% yield) as white solid. LCMS [M+H]: 680.3.

Example 20. 7-[(2R,3R,4S,5R)-5-[(R)-(4-chlorophenyl)-hydroxy-methyl]-3,4-dihydroxy-tetrahydro-furan-2-yl]-1H-pyrrolo[2,3-d]pyrimidin-4-one hydrazone (20)

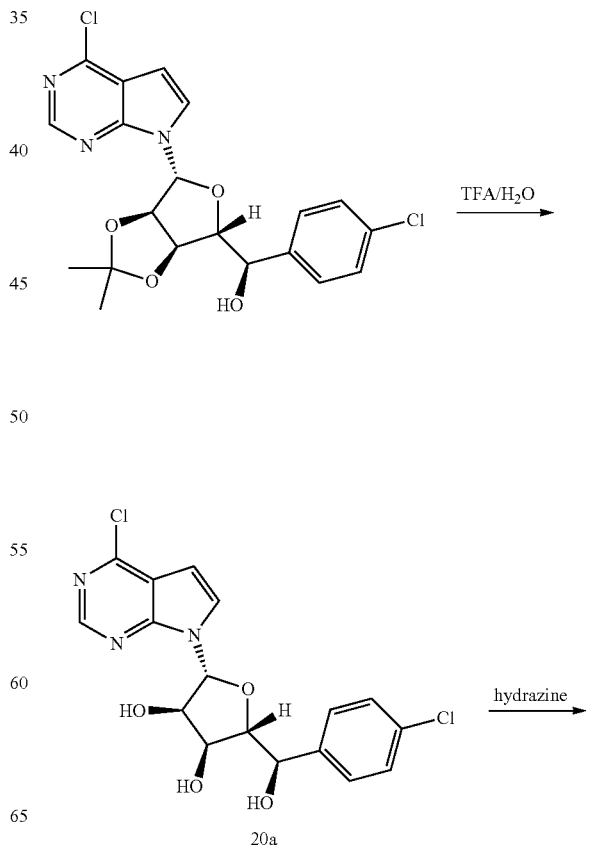

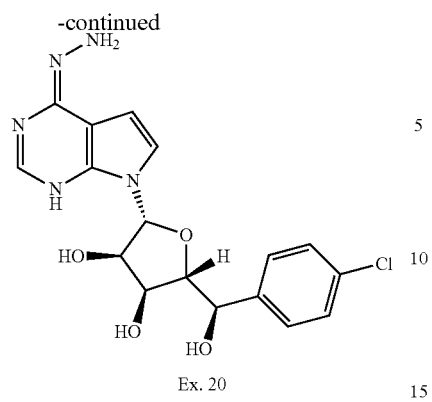

Ex. 20 a) (2R,3S,4R,5R)-2-[(R)-(4-chlorophenyl)-hydroxy-methyl]-5-(4-chloropyrrolo[2,3-d]pyrimidin-7-yl)tetrahydrofuran-3,4-diol (20a)

A 50 mL RBF and septum containing (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(4-chlorophenyl)methanol (Ref. PCT Int. Appl., 2016178870) (455.mg, 1.04 mmol,) was charged with a RT mixture of 2,2,2-trifluoroacetic acid (2.5 mL, 32.45 mmol) and Water (2.5 mL), sonicated for 10 s, blanketed with Ar, and stirred at RT for 2 h. The reaction mixture was concentrated under reduced pressure to remove the water and most of the TFA. The reaction was then diluted in MeOH (20 mL), and quenched with Amberlyst IRA-67 until a neutral pH was obtained. The mixture was then filtered through a cotton plug, rinsed with additional MeOH and DCM, and concentrated under reduced pressure to light brown foam. The crude product was purified by FCC (40 g SiO2, 3→4% MeOH in DCM, wet-loaded in DCM) to yield (2R,3S,4R,5R)-2-[(R)-(4-chlorophenyl)-hydroxy-methyl]-5-(4-chloropyrrolo[2,3-d]pyrimidin-7-yl)tetrahydrofuran-3,4-diol (20a) (128 mg, 0.31 mmol, 30.0% yield) as a white powder. Rf=0.26 (3% MeOH in DCM). LCMS (ESI) m/z calcd for [M+H]+ $C_{17}H_{16}C_{12}N_3O_4$: 396.051. Found: 396.0. $^1$H NMR (400 MHz, DMSO-d$_6$) δ 8.67 (s, 1H), 8.02 (d, J=3.8 Hz, 1H), 7.44-7.32 (m, 4H), 6.79 (d, J=3.7 Hz, 1H), 6.19 (d, J=7.7 Hz, 1H), 6.02 (d, J=4.1 Hz, 1H), 5.39 (s, 1H), 5.21 (d, J=4.0 Hz, 1H), 4.80 (t, J=4.1 Hz, 1H), 4.58 (s, 1H), 4.12 (t, J=3.3 Hz, 1H), 4.00 (dd, J=5.3, 1.3 Hz, 1H). $^1$H NMR of (400 MHz, DMSO-d$_6$+D$_2$O) δ 8.66-8.60 (m, 1H), 7.96-7.87 (m, 1H), 7.42-7.29 (m, 4H), 6.76 (t, J=3.1 Hz, 1H), 6.15 (dd, J=7.6, 3.5 Hz, 1H), 4.76 (t, J=3.9 Hz, 1H), 4.55 (t, J=6.5 Hz, 1H), 4.11 (d, J=5.1 Hz, 1H), 4.01 (dd, J=5.1, 1.1 Hz, 1H).

b) Synthesis of 7-[(2R,3R,4S,5R)-5-[(R)-(4-chlorophenyl)-hydroxy-methyl]-3,4-dihydroxy-tetrahydrofuran-2-yl]-1H-pyrrolo[2,3-d]pyrimidin-4-one hydrazine (20)

A 4 mL vial with septum containing (2R,3S,4R,5R)-2-[(R)-(4-chlorophenyl)-hydroxy-methyl]-5-(4-chloropyrrolo[2,3-d]pyrimidin-7-yl)tetrahydrofuran-3,4-diol (20a) (122.mg, 0.3100 mmol, ~9% 6-methoxy impurity) in IPA (0.6000 mL) was sparged with Ar for 1 min, then charged with hydrazine solution, 1 μM in THF (1.2 mL, 1.2 mmol). The vial was heated at 50° C. for 2 h, then stirred at rt for 16 h. The reaction mixture was dry loaded on Celite and purified by FCC (12 g SiO2, 20→100% of 1:15:85 NH4OH:MeOH:DCM in DCM). Desired fractions were combined, charged with 0.5 mL of 1 μM hydrazine in THF, stirred at RT for 5 min, and concentrated under reduced pressure to yield 7-[(2R,3R,4S,5R)-5-[(R)-(4-chlorophenyl)-hydroxy-methyl]-3,4-dihydroxy-tetrahydrofuran-2-yl]-1H-pyrrolo[2,3-d]pyrimidin-4-one hydrazone (20) (107.5 mg, 0.2661 mmol, 86.4% yield) as a white solid. Rf=0.2 (1:15:85 NH4OH:MeOH:DCM). LCMS (ESI) m/z calcd for [M+H]+ $C_{17}H_{19}ClN_5O_4$: 392.112. Found: 392.1. $^1$H NMR (400 MHz, DMSO-d$_6$) δ 8.75 (s, 1H), 8.13 (s, 1H), 7.47-7.34 (m, 4H), 7.32 (d, J=3.6 Hz, 1H), 6.69 (d, J=3.5 Hz, 2H), 5.92 (d, J=7.9 Hz, 1H), 5.23 (d, J=7.1 Hz, 1H), 5.04 (d, J=3.8 Hz, 1H), 4.81 (t, J=3.9 Hz, 1H), 4.62 (td, J=7.4, 4.8 Hz, 1H), 4.52 (s, 2H), 4.04-3.97 (m, 2H). $^1$H NMR (400 MHz, DMSO-d$_6$+D$_2$O) δ 8.12 (s, 1H), 7.45-7.33 (m, 4H), 7.30 (d, J=3.6 Hz, 1H), 6.79-6.56 (m, 1H), 5.91 (d, J=7.9 Hz, 1H), 4.79 (d, J=4.3 Hz, 1H), 4.59 (dd, J=7.9, 5.0 Hz, 1H), 4.00 (d, J=4.5 Hz, 2H).

Example 36 (2R,3S,4R,5R)-2-[(R)-(4-chlorophenyl)-hydroxy-methyl]-5-(-4-methoxyimino-1H-pyrrolo[2,3-d]pyrimidin-7-yl]tetrahydrofuran-3,4-diol (36)

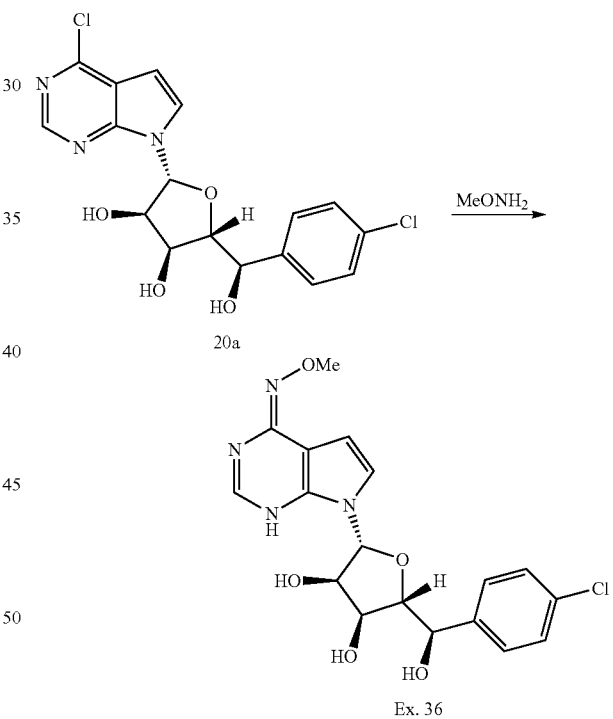

Ex. 36

A 4 mL vial containing a mixture of (R)-[(3aR,4R,6R,6aR)-2,2-dimethyl-4-(4-methylpyrrolo[2,3-d]pyrimidin-7-yl)-3a,4,6,6a-tetrahydrofuro[3,4-d][1,3]dioxol-6-yl]-(4-chlorophenyl)methanol (20a) (21.mg, 0.050 mmol) and O-Methylhydroxylamine hydrochloride (22.mg, 0.26 mmol) in 1,4-Dioxane (0.4 mL) and IPA (0.2 mL) was charged with Triethylamine (0.04 mL, 0.29 mmol). The vial was blanketed with Ar, sealed, and heated at 100° C. for 10 h. TLC showed consumption of SM. The mixture was concentrated under reduced pressure and purified by FCC (4 g SiO$_2$, 5→20% MeOH in DCM, wet-loaded in DCM+eluent). Fractions containing product were concentrated under reduced pressure and heat (50° C.) to yield (2R,3S,4R,5R)-2-[(R)-(4-chlorophenyl)-hydroxy-methyl]-5-(4-methoxy-imino-1H-pyrrolo[2,3-d]pyrimidin-7-yl]tetrahydrofuran-3,4-diol (36) (20.4 mg, 0.0466 mmol, 88% yield) as a yellow/tan powder. Rf=0.4 (10% MeOH in DCM). LCMS (ESI) m/z calcd for [M+H]+ $C_{18}H_{20}ClN_4O_5$: 407.112. Found: 407.0. $^1$H NMR (400 MHz, DMSO-$d_6$) δ 10.71 (s, 1H), 8.11 (s, 1H), 7.66-7.52 (m, 1H), 7.44-7.33 (m, 4H), 6.68 (s, 1H), 6.03 (d, J=7.7 Hz, 1H), 4.77 (d, J=5.3 Hz, 1H), 4.50 (dd, J=7.8, 4.9 Hz, 1H), 4.08 (d, J=4.9 Hz, 1H), 3.97 (dd, J=5.3, 1.2 Hz, 1H), 3.82 (s, 3H), 3.76 (m, 2H), 3.07 (m, 1H).

Example 37. 7-[(2R,3R,4S,5R)-5-[(R)-(4-chlorophenyl)-hydroxy-methyl]-3,4-dihydroxy-tetrahydrofuran-2-yl]-1H-pyrrolo[2,3-d]pyrimidin-4-one oxime hydrochloride (37)

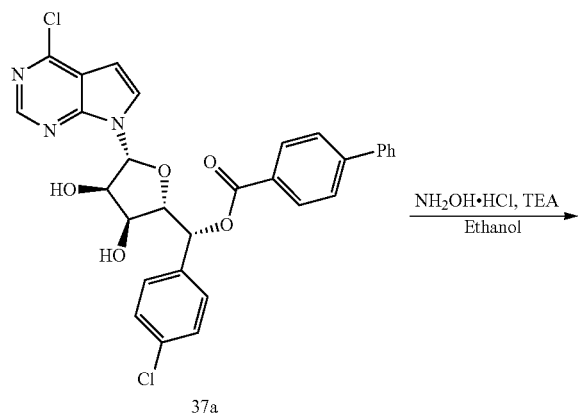

Ex. 37 a) Preparation of [(R)-(4-chlorophenyl)-[(2S,3S,4R,5R)-5-(4-chloropyrrolo[2,3-d]pyrimidin-7-yl)-3,4-dihydroxy-tetrahydrofuran-2-yl]methyl] 4-phenylbenzoate (37a)

Compound 37a was prepared similar to that of Int-1 except substituting [4-(trifluoromethyl)phenyl]boronic acid with (4-chlorophenyl)boronic acid.

b) Preparation of 7-[(2R,3R,4S,5R)-5-[(R)-(4-chlorophenyl)-hydroxy-methyl]-3,4-dihydroxy-tetrahydrofuran-2-yl]-1H-pyrrolo[2,3-d]pyrimidin-4-one oxime hydrochloride (37)

To a solution of [(R)-(4-chlorophenyl)-[(2S,3S,4R,5R)-5-(4-chloropyrrolo[2,3-d]pyrimidin-7-yl)-3,4-dihydroxy-tetrahydrofuran-2-yl]methyl] 4-phenylbenzoate (500 mg, 0.65 mmol) in ethanol (10 mL) was added hydroxylamine hydrochloride (37a) (904.14 mg, 13.01 mmol) and TEA (2.26 mL, 16.26 mmol). The reaction mixture was heated to 90° C. and stirred for 5 hh. LCMS showed the reaction was completed. The solvent was concentrated under reduced pressure, and the residue was purified by prep-HPLC (0.1% TFA) eluting with $H_2O:CH_3CN$ from 95:5 to 5:95 to give [(R)-(4-chlorophenyl)-[(2S,3S,4R,5R)-3,4-dihydroxy-5-(4-hydroxy-imino-1H-pyrrolo[2,3-d]pyrimidin-7-yl]tetrahydrofuran-2-yl]methyl] 4-phenylbenzoate (146 mg, 0.25 mmol, 39.17% yield) and impure 7-[(2R,3R,4S,5R)-5-[(R)-(4-chlorophenyl)-hydroxy-methyl]-3,4-dihydroxy-tetrahydrofuran-2-yl]-1H-pyrrolo[2,3-d]pyrimidin-4-one oxime which was further purified by prep-TLC (DCM:MeOH=5:1). The product was dissolved in 1 μM HCl, filtered and lyophilized to afford 7-[(2R,3R,4S,5R)-5-[(R)-(4-chlorophenyl)-hydroxy-methyl]-3,4-dihydroxy-tetrahydrofuran-2-yl]-1H-pyrrolo[2,3-d]pyrimidin-4-one oxime hydrochloride (37) (59.4 mg, 0.14 mmol, 20.88% yield) as pale yellow solid. LCMS [M+H]: 393.3. $^1$H NMR (400 MHz, DMSO-d6) δ 8.28 (s, 1H), 7.75 (d, J=3.6 Hz, 1H), 7.35-7.42 (m, 4H), 7.01-7.03 (m, 1H), 6.11 (d, J=7.6 Hz, 1H), 4.77 (d, J=5.2 Hz, 1H), 4.49 (m, 1H), 4.13 (d, J=4.8 Hz, 1H), 3.99 (d, J=5.6 Hz, 1H). $^1$H NMR (400 MHz, DMSO-d6+$D_2O$) δ 8.33 (s, 1H), 7.75 (d, J=3.6 Hz, 1H), 7.35-7.42 (m, 4H), 6.91 (d, J=3.6 Hz, 1H), 6.12 (d, J=7.2 Hz, 1H), 4.77 (d, J=5.2 Hz, 1H), 4.50 (m, 1H), 4.14 (d, J=4.8 Hz, 1H), 4.02 (d, J=5.2 Hz, 1H).

Example 39. (2R,3S,4R,5R)-2-[(R)-(4-chlorophenyl)-hydroxy-methyl]-5-(6-hydrazinopurin-9-yl)tetrahydrofuran-3,4-diol; 2,2,2-trifluoroacetic Acid (39)

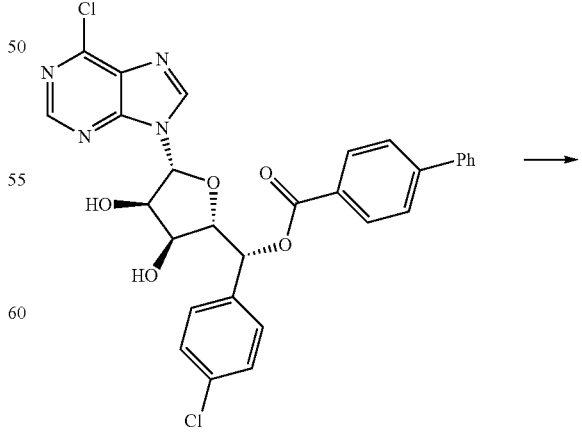

Int-2

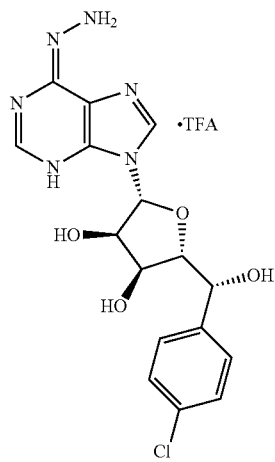

Ex. 39

To a solution of [(R)-(4-chlorophenyl)-[(2S,3S,4R,5R)-5-(6-chloropurin-9-yl)-3,4-dihydroxy-tetrahydrofuran-2-yl]methyl] 4-phenylbenzoate (Int-2) (150 mg, 0.23 mmol) in ethanol (2 mL) was added hydrazine hydrate (2 mL) and stirred at 25° C. for 1 h. LCMS showed the reaction was completed. The solution was purified by prep-HPLC (0.1% TFA) eluting with $H_2O:CH_3CN$ from 85:15 to 5:95 to give (2R,3S,4R,5R)-2-[(R)-(4-chlorophenyl)-hydroxy-methyl]-5-(6-hydrazinopurin-9-yl) tetrahydrofuran-3,4-diol; 2,2,2-trifluoroacetic acid (39) (43.1 mg, 0.083 mmol, 36.28% yield) as white solid. LCMS [M+H]: 393.3. $^1$H NMR (400 MHz, DMSO-d6) δ 8.57 (s, 1H), 8.47 (s, 1H), 7.34-7.42 (m, 4H), 6.29 (s, 1H), 5.94 (d, J=7.6 Hz, 1H), 5.46 (s, 1H), 5.22 (s, 1H), 4.85 (d, J=5.2 Hz, 1H), 4.72-4.77 (m, 1H), 4.13 (d, J=5.2 Hz, 1H), 4.06 (d, J=4.4 Hz, 1H). H NMR (400 MHz, DMSO-d6+$D_2O$) δ 8.56 (s, 1H), 8.48 (s, 1H), 7.35-7.42 (m, 4H), 5.95 (d, J=7.6 Hz, 1H), 4.85 (d, J=4.8 Hz, 1H), 4.72-4.77 (m, 1H), 4.14 (d, J=5.2 Hz, 1H), 4.09 (d, J=4.8 Hz, 1H).

Example 52. (2R,3S,4R,5R)-2-[(R)-(4-chlorophenyl)-hydroxy-methyl]-5-[6-(methylhydrazono)-3H-purin-9-yl]tetrahydrofuran-3,4-diol; 2,2,2-trifluoroacetic Acid (52)

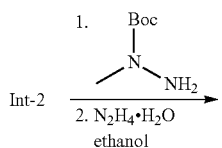

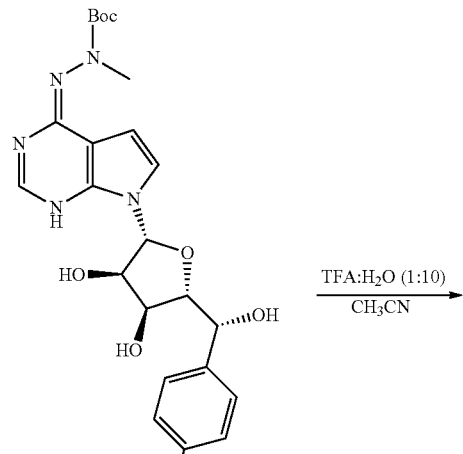

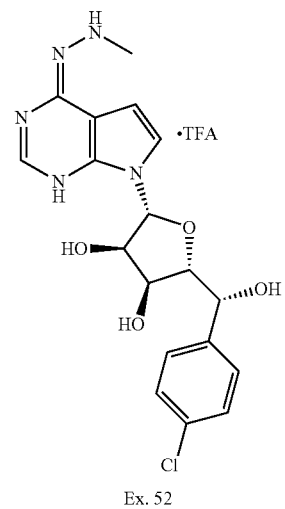

Ex. 52 a) Preparation of tert-butyl-2-(9-((2R,3R,4S,5R)-5-((R)-(4-chlorophenyl)(hydroxy)methyl)-3,4-dihydroxytetrahydrofuran-2-yl)-3H-purin-6(9H)-ylidene)-1-methylhydrazinecarboxylate (52a)

To a solution of (R)-((2S,3S,4R,5R)-5-(6-chloro-9H-purin-9-yl)-3,4-dihydroxytetrahydrofuran-2-yl) (4-chlorophenyl)methyl [1,1'-biphenyl]-4-carboxylate (Int-2) (375 mg, 0.65 mmol) in ethanol (2 mL) was added tert-butyl 1-methylhydrazinecarboxylate (2 mL). The reaction mixture was heated to 90° C. and stirred for 12 hh. LCMS showed the reaction was completed. The reaction mixture was cooled to rt. Hydrazine hydrate (2 mL) was added and stirred at 25° C. for 1.5 hh. LCMS showed the reaction was completed. The solvent was concentrated under reduced pressure to give crude product which was purified by silica gel column chromatography (DCM to DCM:$CH_3CN$=10:1 to DCM:$CH_3OH$=10:1) to give tert-butyl-2-(9-((2R,3R,4S,5R)-5-((R)-(4-chlorophenyl)(hydroxy)methyl)-3,4-dihydroxytetrahydrofuran-2-yl)-3H-purin-6(9H)-ylidene)-1-methylhydrazinecarboxylate (52a) (300 mg, 88% purity, 80% yield) as solid. LCMS [M+H]: 507.3.

b) Preparation of (2R,3S,4R,5R)-2-[(R)-(4-chlorophenyl)-hydroxy-methyl]-5-[6-(methylhydrazono)-3H-purin-9-yl]tetrahydrofuran-3,4-diol; 2,2,2-trifluoroacetic Acid (52)

To a solution of tert-butyl N-[[9-[(2R,3R,4S,5R)-5-[(R)-(4-chlorophenyl)-hydroxy-methyl]-3,4-dihydroxy-tetrahydrofuran-2-yl]-3H-purin-6-ylidene]amino]-N-methyl-carbamate (52a) (150 mg, 0.26 mmol) in MeCN (1 mL) and water (5 mL) was added 2,2,2-trifluoroacetic acid (0.5 mL). The reaction mixture was stirred at 25° C. for 18 h. LCMS showed the reaction was completed. The solution was purified by prep-HPLC (0.1% TFA) eluting with H₂O:CH₃CN from 85:15 to 5:95 to give (2R,3S,4R,5R)-2-[(R)-(4-chlorophenyl)-hydroxy-methyl]-5-[6-(methylhydrazono)-3H-purin-9-yl]tetrahydrofuran-3,4-diol; 2,2,2-trifluoroacetic acid (52) (30 mg, 0.0556 mmol, 21.36% yield) as white solid. LCMS [M+H]: 407.3. ¹H NMR (400 MHz, DMSO-d6) δ 8.61 (s, 1H), 8.45 (s, 1H), 7.34-7.42 (m, 4H), 6.22 (s, 1H), 5.94 (d, J=7.6 Hz, 1H), 5.47 (s, 1H), 5.24 (s, 1H), 4.84 (d, J=5.2 Hz, 1H), 4.71-4.73 (m, 1H), 4.14 (d, J=4.8 Hz, 1H), 4.06 (d, J=4.4 Hz, 1H), 2.76 (s, 3H). ¹H NMR (400 MHz, DMSO-d6+D₂O) δ 8.62 (s, 1H), 8.47 (s, 1H), 7.34-7.42 (m, 4H), 5.95 (d, J=7.6 Hz, 1H), 4.84 (d, J=5.2 Hz, 1H), 4.71-4.73 (m, 1H), 4.14 (d, J=5.2 Hz, 1H), 4.07 (d, J=5.2 Hz, 1H), 2.77 (s, 3H).

Example 53. (2R,3S,4R,5R)-2-[(R)-(4-chlorophenyl)-hydroxy-methyl]-5-[6-methoxyimino-3H-purin-9-yl]tetrahydrofuran-3,4-diol trifluoroacetic Acid Salt (53)

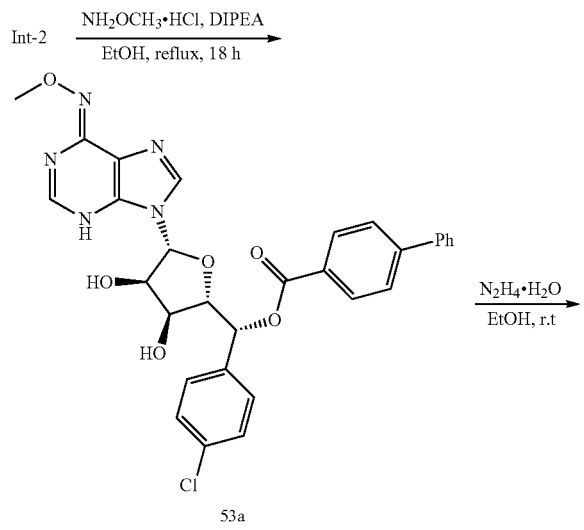

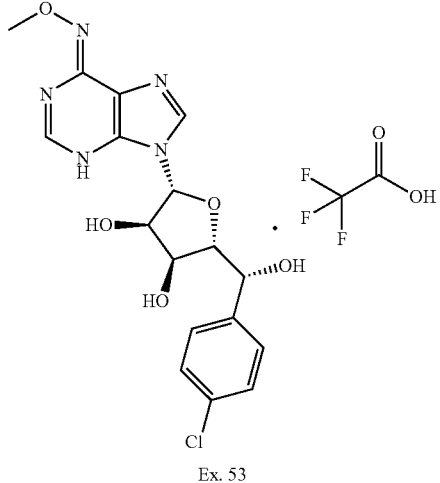

Ex. 53 a) Preparation of [(R)-(4-chlorophenyl)-[(2S,3S,4R,5R)-3,4-dihydroxy-5-[6-methoxyimino-3H-purin-9-yl]tetrahydrofuran-2-yl]methyl]-4-phenylbenzoate (53a)

To a solution of [(R)-(4-chlorophenyl)-[(2S,3S,4R,5R)-5-(6-chloropurin-9-yl)-3,4-dihydroxy-tetrahydrofuran-2-yl]methyl] 4-phenylbenzoate (Int-2) (100.0 mg, 0.16 mmol) in ethanol (4.0 mL), DIPEA (0.9 mL, 5.65 mmol) and methoxyammonium chloride (404.3 mg, 4.84 mmol) was added in portions. The mixture was stirred at 80° C. for 24 hh. LCMS showed the starting material was consumed completely. The mixture was used directly for the next step without further purification. LCMS [M+H]: 588.1.

b) Preparation of (2R,3S,4R,5R)-2-[(R)-(4-chlorophenyl)-hydroxy-methyl]-5-[6-methoxyimino-3H-purin-9-yl]tetrahydrofuran-3,4-diol trifluoroacetic Acid Salt (53)

To the reaction mixture of last step (containing [(R)-(4-chlorophenyl)-[(2S,3S,4R,5R)-3,4-dihydroxy-5-[6-methoxyimino-3H-purin-9-yl]tetrahydrofuran-2-yl]methyl]-4-phenylbenzoate (53a), hydrazine hydrate (3.0 mL, 61.73 mmol) was added. The mixture was stirred at 25° C. for 16 h. LCMS showed the starting material was consumed completely. The mixture was purified by prep-HPLC eluting with CH₃CN/H₂O (0.1% TFA contained) from 5/95 to 95/5 to give (2R,3S,4R,5R)-2-[(R)-(4-chlorophenyl)-hydroxy-methyl]-5-[6-methoxyimino-3H-purin -9-yl]tetrahydrofuran-3,4-diol (53, TFA salt, 22.0 mg, 0.04 mmol, 24.8% yield) as white solid. LCMS [M+H]: 408.1. ¹H NMR (400 MHz, DMSO-d6): δ 8.19 (s, 1H), 7.80 (s, 1H), 7.36-7.42 (m, 4H), 5.78 (d, J=7.6 Hz, 1H), 4.81 (d, J=5.2 Hz, 1H), 4.62-4.65 (m, 1H), 4.08 (d, J=5.2 Hz, 1H), 4.01 (d, J=5.2 Hz, 1H), 3.77 (s, 3H). ¹H NMR (400 MHz, DMSO-d6+D₂O): δ 8.19 (s, 1H), 7.84 (s, 1H), 7.36-7.42 (m, 4H), 5.79 (d, J=7.6 Hz, 1H), 4.82 (d, J=4.8 Hz, 1H), 4.63 (m, 1H), 4.09 (d, J=5.2 Hz, 1H), 4.04 (d, J=5.2 Hz, 1H), 3.77 (s, 3H).

Example 54. 9-[(2R,3R,4S,5R)-5-[(R)-(4-chlorophenyl)-hydroxy-methyl]-3,4-dihydroxy-tetrahydrofuran-2-yl]-3H-purin-6-one oxime trifluoroacetic Acid Salt (54)

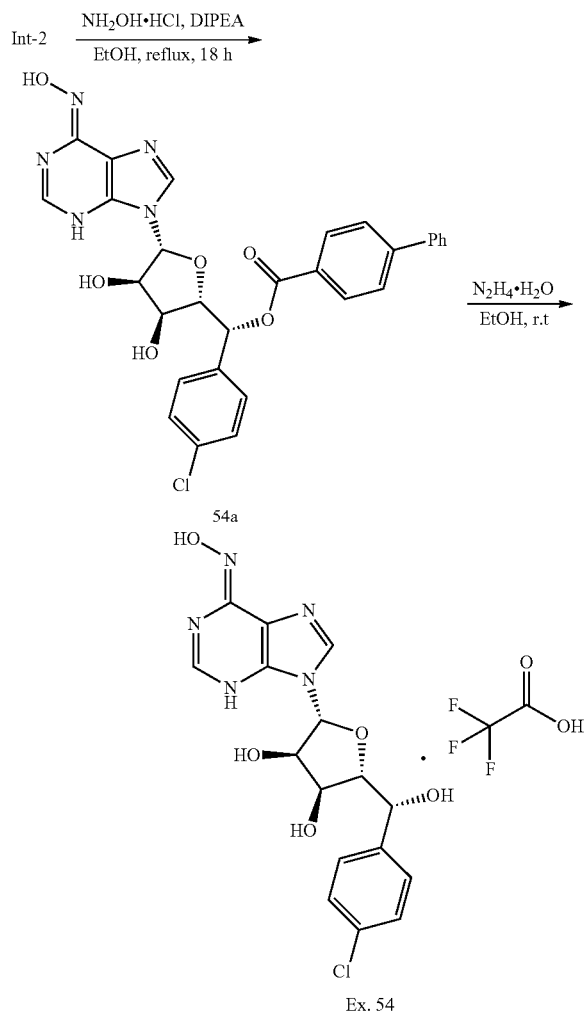

Ex. 54 a) Preparation of [(R)-(4-chlorophenyl)-[(2S,3S,4R,5R)-3,4-dihydroxy-5-[6-hydroxyimino-3H-purin-9-yl]tetrahydrofuran-2-yl]methyl]-4-phenylbenzoate (54a)

To a solution of [(R)-(4-chlorophenyl)-[(2S,3S,4R,5R)-5-(6-chloropurin-9-yl)-3,4-dihydroxy -tetrahydrofuran-2-yl]methyl] 4-phenylbenzoate (200.0 mg, 0.32 mmol) in ethanol (2.0 mL) was added DIPEA (0.4 mL, 2.58 mmol) and hydroxylamine hydrochloride (134.5 mg, 1.94 mmol). The mixture was stirred at 80° C. for 4 hh. LCMS showed the starting material was consumed completely and 30% desired product was detected in 254 nm. The mixture was used directly in the next step without further purification. LCMS [M+H]: 574.3.

b) Preparation of 9-[(2R,3R,4S,5R)-5-[(R)-(4-chlorophenyl)-hydroxy-methyl]-3,4-dihydroxy-tetrahydrofuran-2-yl]-3H-purin-6-one oxime trifluoroacetic Acid Salt (54)

To the reaction mixture of last step (containing [(R)-(4-chlorophenyl)-[(2S,3S,4R,5R)-3,4-dihydroxy-5-[6-hydroxyimino-3H-purin-9-yl]tetrahydrofuran-2-yl]methyl]-4-phenylbenzoate (54a), hydrazine hydrate (2.0 mL, 41.15 mmol) was added, the mixture was stirred at 25° C. for 16 h. LCMS showed the starting material was consumed completely. The mixture was purified by prep-HPLC eluting with $CH_3CN/H_2O$ (0.1% TFA contained) from 5/95 to 95/5 to give 9-[(2R,3R,4S,5R)-5-[(R)-(4-chlorophenyl)-hydroxy-methyl]-3,4-dihydroxy-tetrahydrofuran-2-yl]-3H-purin-6-one oxime (54, TFA salt, 11.0 mg, 0.02 mmol, 22% yield) as white solid. LCMS [M+H]: 394.3. $^1$H NMR (400 MHz, DMSO-d6): δ 8.31 (s, 1H), 8.02 (s, 1H), 7.35-7.43 (m, 4H), 5.83 (d, J=7.6 Hz, 1H), 4.82 (d, J=4.8 Hz, 1H), 4.65-4.68 (m, 1H), 4.09 (d, J=4.8 Hz, 1H), 4.03 (d, J=4.8 Hz, 1H). $^1$H NMR (400 MHz, DMSO-d6+$D_2O$): δ 8.30 (s, 1H), 8.05 (s, 1H), 7.36-7.43 (m, 4H), 5.84 (d, J=7.6 Hz, 1H), 4.83 (d, J=4.8 Hz, 1H), 4.66 (m, 1H), 4.11 (d, J=4.8 Hz, 1H), 4.07 (d, J=4.8 Hz, 1H).

Example 59. 7-((2R,3R,4S)-5-((R)-1-(4-chlorophenyl)-1-hydroxyethyl)-3,4-dihydroxytetrahydrofuran-2-yl)-1,7-dihydro-4H-pyrrolo[2,3-d]pyrimidin-4-one oxime hydrochloride (59)

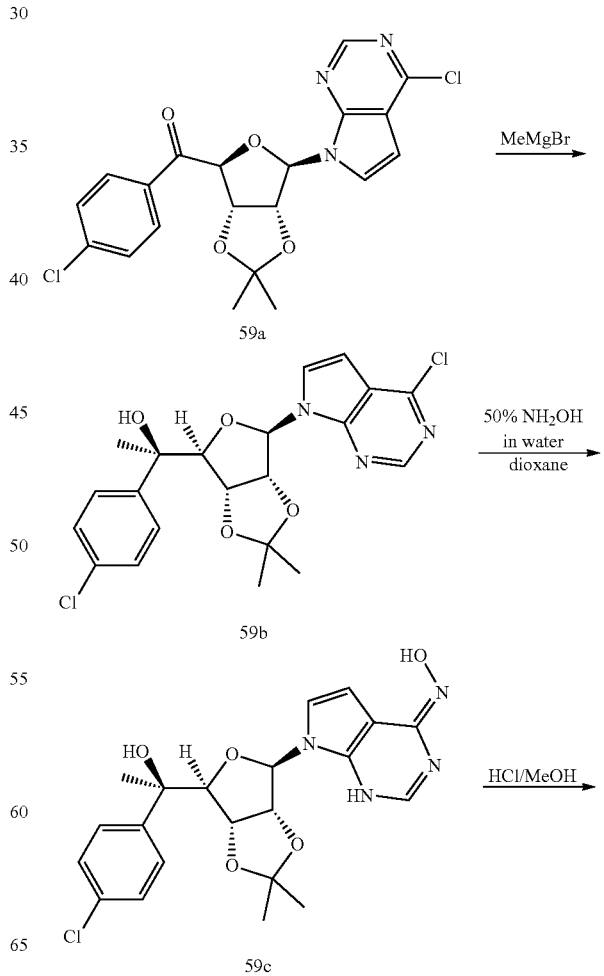

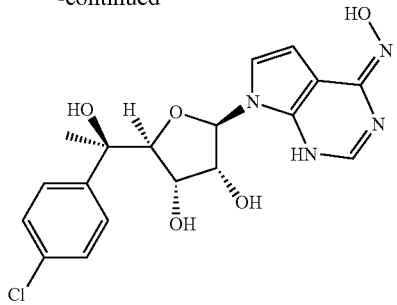

Ex. 59 a) Preparation of (R)-1-((3aR,4S,6R,6aR)-6-(4-chloro-7H-pyrrolo[2,3-d]pyrimidin-7-yl)-2,2-dimethyltetrahydrofuro[3,4-d][1,3]dioxol-4-yl)-1-(4-chlorophenyl)ethan-1-ol (59b)

A mixture of compound 59a (300 mg, 691 umol, 1 eq.) in THF (3 mL) was degassed and purged with N2 for 3 times, and then the mixture was cooled to 0° C. MeMgBr (3 μM, 460.54 uL, 2 eq.) was added at 0° C., then the solution was stirred at 0° C. for 2 h under N$_2$ atmosphere. LC-MS showed compound 59a was consumed completely and one main peak with desired MS was detected. The reaction was quenched by sat. aq. NH$_4$Cl (5 mL), and extracted with EtOAc (5 mL*3), and the organic phase was concentrated in vacuo. The residue was purified by Prep-TLC (SiO$_2$, Petroleum ether:Ethyl acetate=5:1). Compound 59b (160 mg, crude) was obtained as a white solid. LCMS: (M+H$^+$): 450.0; TLC (Petroleum ether:Ethyl acetate=5:1) R$_f$=0.28.

b) Preparation of 7-((3aR,4R,6S,6aR)-6-((R)-1-(4-chlorophenyl)-1-hydroxyethyl)-2,2-dimethyltetrahydrofuro[3,4-d][1,3]dioxol-4-yl)-1,7-dihydro-4H-pyrrolo[2,3-d]pyrimidin-4-one oxime (59c)

To a solution of compound 59b (0.16 g, 355 umol, 1 eq.) in dioxane (5 mL) was added hydroxylamine (555 mg, 8.40 mmol, 0.5 mL, 23.6 eq.). The mixture was stirred at 120° C. for 12 h. LC-MS showed compound 59b was consumed completely and one main peak with desired MS was detected. The reaction was concentrated in vacuo. No purification. The crude product compound 59c (158 mg, crude) was used into the next step without further purification as a white solid. LCMS: (M–H$^+$): 447.0;

c) Preparation of 7-((2R,3R,4S,5S)-5-((R)-1-(4-chlorophenyl)-1-hydroxyethyl)-3,4-dihydroxytetrahydrofuran-2-yl)-1,7-dihydro-4H-pyrrolo[2,3-d]pyrimidin-4-one oxime (59)

A solution of compound 59c(158 mg, 354 umol, 1 eq.) in HCl/MeOH (4 μM, 3 mL, 34 eq.) was stirred at 25° C. for 2 h. LC-MS showed compound 59c was consumed completely and one main peak with desired MS was detected. The mixture was concentrated in vacuo. The residue was purified by prep-HPLC (HCl condition). Compound 59 (130 mg, 292. umol, 83% yield, 99.65% purity, HCl salt) was obtained as a white solid. $^1$H NMR (400 MHz, DMSO-d6) δ=8.29 (s, 1H), 7.77 (br d, J=3.1 Hz, 1H), 7.54 (d, J=8.8 Hz, 2H), 7.40 (d, J=8.8 Hz, 2H), 6.90 (br d, J=3.9 Hz, 1H), 6.10 (d, J=7.9 Hz, 1H), 4.37 (dd, J=5.0, 7.7 Hz, 1H), 4.06 (s, 1H), 3.71 (d, J=5.3 Hz, 1H), 1.42 (s, 3H); $^1$H NMR (400 MHz, DMSO-d6+D$_2$O) δ=8.33 (s, 1H), 7.79 (d, J=3.5 Hz, 1H), 7.54 (d, J=8.8 Hz, 2H), 7.40 (d, J=8.3 Hz, 2H), 6.88 (d, J=3.5 Hz, 1H), 6.12 (d, J=7.9 Hz, 1H), 4.38 (dd, J=5.3, 7.9 Hz, 1H), 4.07 (s, 1H), 3.72 (d, J=4.8 Hz, 1H), 1.42 (s, 3H); LCMS: (M+H$^+$): 407.0;

Example 60. 7-((2R,3R,4S)-5-((R)-1-(4-chlorophenyl)-1-hydroxyethyl)-3,4-dihydroxytetrahydrofuran-2-yl)-1,7-dihydro-4H-pyrrolo[2,3-d]pyrimidin-4-one O-methyl oxime (60)

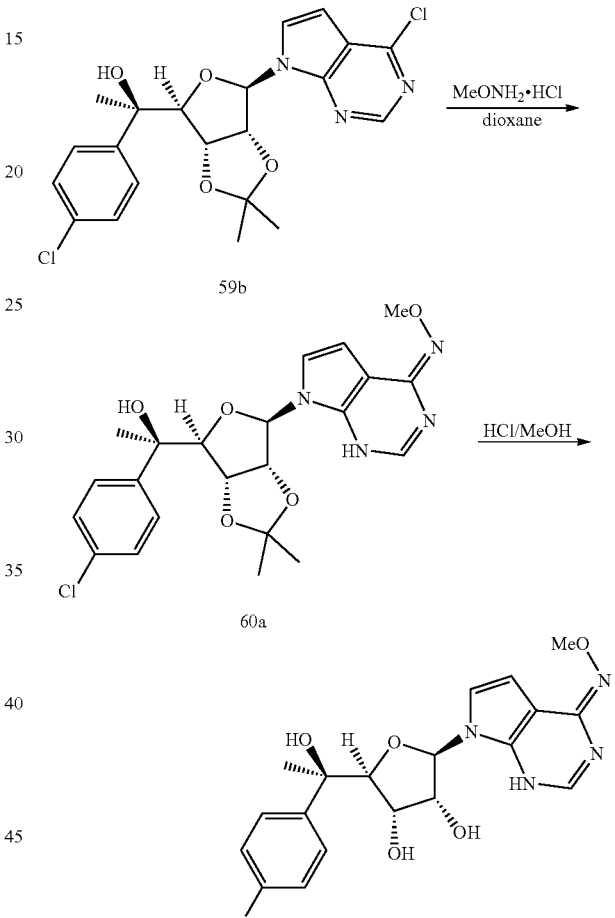

Ex. 60 a) Preparation of 7-((3aR,4R,6S,6aR)-6-((R)-1-(4-chlorophenyl)-1-hydroxyethyl)-2,2-dimethyltetrahydrofuro[3,4-d][1,3]dioxol-4-yl)-1,7-dihydro-4H-pyrrolo[2,3-d]pyrimidin-4-one O-methyl oxime (60a)

To a solution of compound 59b (30 mg, 66.32 umol, 1 eq.) in dioxane (6 mL) was added K$_2$CO$_3$ (274.99 mg, 1.99 mmol, 30 eq.) and O-methylhydroxylamine hydrochloride (110.78 mg, 1.33 mmol, 100.71 uL, 20 eq.). The mixture was stirred at 100° C. for 12 h in a sealed tube. LC-MS showed compound 59b was consumed completely and one main peak with desired MS was detected. The reaction was filtered and the filtrate was concentrated in vacuo. No purification. The crude product compound 60a (30 mg, crude) was used into the next step without further purification as a yellow oil. LCMS: (M+H⁺): 461.0;

b) Preparation of 7-((2R,3R,4S)-5-((R)-1-(4-chlorophenyl)-1-hydroxyethyl)-3,4-dihydroxytetrahydrofuran-2-yl)-1,7-dihydro-4H-pyrrolo[2,3-d]pyrimidin-4-one O-methyl oxime (60)

To a solution of compound 60a (30 mg, 65 umol, 1 eq.) in MeOH (1 mL) was added HCl/MeOH (4 μM, 1 mL, 61 eq.). The mixture was stirred at 25° C. for 1 h. LC-MS showed compound 60a was consumed completely and one main peak with desired MS was detected. The reaction was concentrated in vacuo at 25° C. The residue was purified by prep-HPLC. Ex. 60 (4.8 mg, 9.9 umol, 15% yield, 94.67% purity, HCl salt) was obtained as a white solid. ¹H NMR (400 MHz, DMSO-d6)=8.24 (s, 1H), 7.70 (br d, J=3.3 Hz, 1H), 7.55 (d, J=8.6 Hz, 2H), 7.40 (d, J=8.6 Hz, 2H), 6.82 (br d, J=2.9 Hz, 1H), 6.06 (d, J=7.7 Hz, 1H), 4.41 (dd, J=5.1, 7.7 Hz, 1H), 4.08 (s, 1H), 3.86 (s, 3H), 3.72 (br d, J=5.1 Hz, 1H); ¹H NMR (400 MHz, DMSO-d6+D₂O) δ=8.26 (s, 1H), 7.70 (d, J=3.7 Hz, 1H), 7.52 (d, J=8.6 Hz, 2H), 7.38 (d, J=8.6 Hz, 2H), 6.77 (d, J=3.5 Hz, 1H), 6.06 (d, J=7.9 Hz, 1H), 4.38 (dd, J=5.2, 7.8 Hz, 1H), 4.06 (s, 1H), 3.84 (s, 3H), 3.70 (d, J=5.3 Hz, 1H); LCMS: (M+H⁺): 421.1.

Example 61. 7-((2R,3R,4S,5S)-5-((R)-1-(3,4-dichlorophenyl)-1-hydroxyethyl)-3,4-dihydroxytetrahydrofuran-2-yl)-1,7-dihydro-4H-pyrrolo[2,3-d]pyrimidin-4-one O-methyl oxime (61)

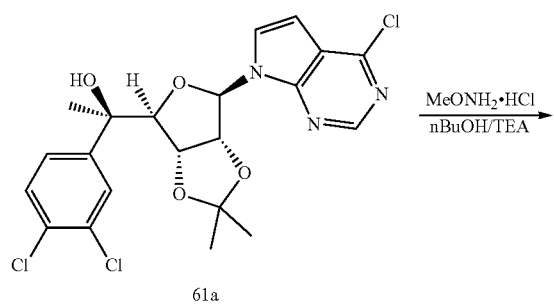

61a

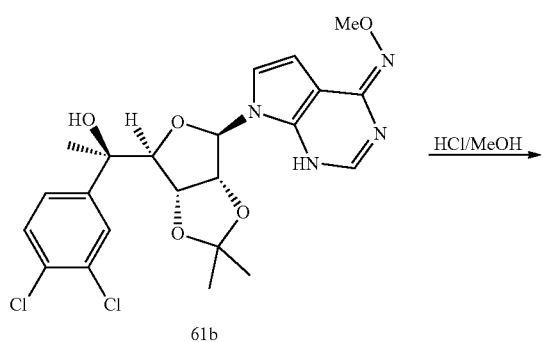

61b

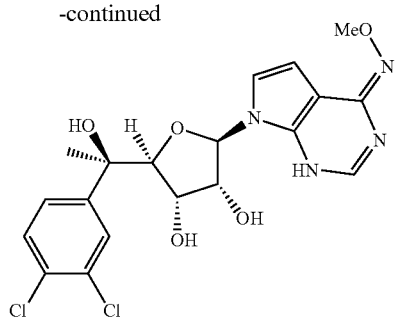

Ex. 61 a) Preparation of ((1R)-1-[(3aR,4R,6S,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-1-(3,4-dichlorophenyl)ethanol (61a)

Compound 61a was prepared following the procedure of (4-chloro-3-fluorophenyl)((3aS,4S,6R,6aR)-6-(4-chloro-7H-pyrrolo[2,3-d]pyrimidin-7-yl)-2,2-dimethyltetrahydrofuro[3,4-d][1,3]dioxol-4-yl)methanone (59b) except for substituting (4-chlorophenyl)((3aS,4S,6R,6aR)-6-(4-chloro-7H-pyrrolo[2,3-d]pyrimidin-7-yl)-2,2-dimethyltetrahydrofuro[3,4-d][1,3]dioxol-4-yl)methanone (59a) with (3,4-dichlorophenyl)((3aS,4S,6R,6aR)-6-(4-chloro-7H-pyrrolo[2,3-d]pyrimidin-7-yl)-2,2-dimethyltetrahydrofuro[3,4-d][1,3]dioxol-4-yl)methanone.

b) Preparation of 7-((3aR,4R,6S,6aR)-6-((R)-1-(3,4-dichlorophenyl)-1-hydroxyethyl)-2,2-dimethyltetrahydrofuro[3,4-d][1,3]dioxol-4-yl)-1,7-dihydro-4H-pyrrolo[2,3-d]pyrimidin-4-one O-methyl oxime (61b)

A mixture of ((1R)-1-[(3aR,4R,6S,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-1-(3,4-dichlorophenyl)ethanol (61a) (450.mg, 0.7900 mmol), O-Methylhydroxylamine hydrochloride (347 mg, 3.95 mmol), and Triethylamine; TEA (0.67 mL, 4.73 mmol) in 1-Butanol (6 mL) was stirred in a sealed tube at 110° C. for 20 h. The reaction mixture was diluted with EtOAc and filtered. The filtrates were concentrated and purified on a 24 g column, which was eluted with 0-30% EA/DCM to give (1R)-1-[(3aR,4R,6S,6aR)-4-[(4E)-4-methoxyimino-1H-pyrrolo[2,3-d]pyrimidin-7-yl]-2,2-dimethyl-3a,4,6,6a-tetrahydrofuro[3,4-d][1,3]dioxol-6-yl]-1-(3,4-dichlorophenyl)ethanol (61b) (175 mg, 0.35 mmol, 44.8% yield).

c) Preparation of 7-((2R,3R,4S,5S)-5-((R)-1-(3,4-dichlorophenyl)-1-hydroxyethyl)-3,4-dihydroxytetrahydrofuran-2-yl)-1,7-dihydro-4H-pyrrolo[2,3-d]pyrimidin-4-one O-methyl oxime (61)

To a solution of (1R)-1-[(3aR,4R,6S,6aR)-4-[(4E)-4-methoxyimino-1H-pyrrolo[2,3-d]pyrimidin-7-yl]-2,2-dimethyl-3a,4,6,6a-tetrahydrofuro[3,4-d][1,3]dioxol-6-yl]-1-(3,4-dichlorophenyl)ethanol (61b) (175.mg, 0.35 mmol) in Methanol (5 mL) was added Hydrochloric acid (0.5 mL, 5.8 mmol) and stirred at room temperature for 3 h. The reaction was concentrated, the crude was treated with saturated NaHCO₃, extracted with ethyl acetate and the layers separated. The ethyl acetate layer was washed with water, brine, dried over sodium sulfate, filtered and concentrated. The crude was purified by silica gel chromatography on a 12 g Agela column using 0-30% EtOAc in DCM to give the product as free base, which was treated with 1M HCl and concentrated to give (2S,3S,4R,5R)-2-[(1R)-1-(3,4-dichlorophenyl)-1-hydroxy-ethyl]-5-[4-methoxyimino-1H-pyrrolo[2,3-d]pyrimidin-7-yl]tetrahydrofuran-3,4-diol hydrochloride (61) (130 mg, 0.264 mmol, 74.8% yield) as a light yellow solid. $^1$H NMR (400 MHz, DMSO-d6+D$_2$O) δ 8.04 (s, 1H), 7.58-7.45 (m, 4H), 6.58 (d, J=3.6 Hz, 1H), 5.94 (d, J=7.2 Hz, 1H), 4.38 (m, 1H), 4.07 (s, 1H), 3.78 (s, 3H), 3.70 (d, J=5.2 Hz, 1H), 1.40 (S, 3H). LCMS [M+H]: 455.0/457.0.

Example 62. 7-((2R,3R,4S,5R)-5-((R)-(4-chloro-3-fluorophenyl)(hydroxy)methyl)-3,4-dihydroxytetrahydrofuran-2-yl)-1,7-dihydro-4H-pyrrolo[2,3-d]pyrimidin-4-one O-methyl oxime (62)

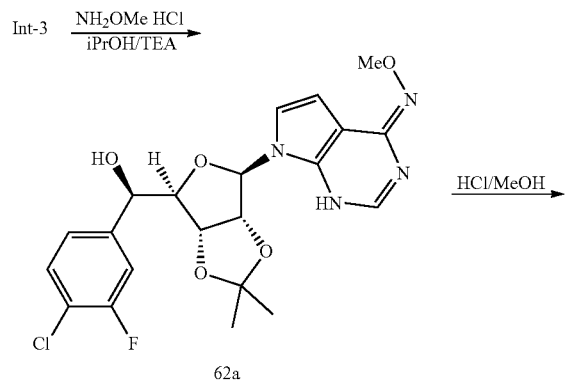

Ex. 62 a) Preparation of 7-((3aR,4R,6S,6aR)-6-((R)-1-(4-chloro-3-fluorophenyl)-1-hydroxyethyl)-2,2-dimethyltetrahydrofuro[3,4-d][1,3]dioxol-4-yl)-1,7-dihydro-4H-pyrrolo[2,3-d]pyrimidin-4-one O-methyl oxime (62a)

A mixture of (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(4-chloro-3-fluoro-phenyl)methanol (Int-3) (70.mg, 0.1500 mmol), O-Methylhydroxylamine hydrochloride (40.6 mg, 0.46 mmol) and Triethylamine; TEA (0.05 mL, 0.39 mmol) in IPA (1.5 mL) was heated at 110° C. Reaction was completed in 2 h by TLC (1:1 hexane/EA, product Rf~0.3). The reaction mixture was diluted with EtOAc, filtered, concentrated, and the residue was purified on a 12 g column, eluted with 0-100 EA/hexane to give (R)-[(3aR,4R,6R,6aR)-4-[(4E)-4-methoxyimino-1H-pyrrolo[2,3-d]pyrimidin-7-yl]-2,2-dimethyl-3a,4,6,6a-tetrahydrofuro[3,4-d][1,3]dioxol-6-yl]-(4-chloro-3-fluoro-phenyl)methanol (62a) (37 mg, 0.080 mmol, 52% yield) as an off white solid.

b) Preparation of 7-((2R,3R,4S,5R)-5-((R)-(4-chloro-3-fluorophenyl)(hydroxy)methyl)-3,4-dihydroxytetrahydrofuran-2-yl)-1,7-dihydro-4H-pyrrolo[2,3-d]pyrimidin-4-one O-methyl oxime (62)

A solution of (R)-[(3aR,4R,6R,6aR)-4-[4-(methoxyamino)pyrrolo[2,3-d]pyrimidin-7-yl]-2,2-dimethyl-3a,4,6,6a-tetrahydrofuro[3,4-d][1,3]dioxol-6-yl]-(4-chloro-3-fluoro-phenyl)methanol (62a) (37.mg, 0.080 mmol) in pre-mixed TFA (0.9 mL, 12 mmol) and water (0.10 mL) was stirred at RT for 30 min. TLC showed most st.m. was consumed and a new spot was formed (10:1 DCM/MeOH, Rf~0.4). The reaction mixture was concentrated and the residue was purified by C18 5.5 g column. The product fractions were combined, concentrated, and was re-dissolved in MeOH. A few drops of 1N HCl (aq.) was added and the mixture was concentrated to give 22 mg of compound 62 as an off-white solid. 19F NMR showed TFA was replaced. This was HCl salt. $^1$H NMR (400 MHz, DMSO-d6+D$_2$O) δ 8.05 (br s, 1H), 7.58-7.45 (m, 4H), 6.60 (br s, 1H), 6.02 (d, J=8 Hz, 1H), 4.49 (m, 1H), 4.07 (d, J=4 Hz, 1H), 3.97 (m, 1H), 3.81 (s, 3H).

Example 63. 7-((2R,3R,4S,5R)-5-((R)-(4-chloro-3-fluorophenyl)(hydroxy)methyl)-3,4-dihydroxytetrahydrofuran-2-yl)-1,7-dihydro-4H-pyrrolo[2,3-d]pyrimidin-4-one oxime (63)

Example 63 was prepared following the same procedures of Example 62 except for substituting NH$_2$OMe.HCl with NH$_2$OH.HCl. $^1$H NMR (400 MHz, DMSO-d6+D$_2$O) δ 8.28 (s, 1H), 7.69 (br s, 1H), 7.49 (dd, J=8.8 Hz, 1H), 7.33 (d, J=8 Hz, 1H), 7.23 (m, 1H), 6.79 (d, J=4 Hz, 1H), 6.08 (d, J=8 Hz, 1H), 4.75 (d, J=4 Hz, 1H), 4.46 (dd, J=8, 4 Hz, 1H), 4.09 (m, 1H), 4.00 (m, 1H). LCMS [M+H]: 411.1/413.1.

Example 64. (2R,3S,4R,5R)-2-[(R)-(4-chlorophenyl)-hydroxy-methyl]-5-[4-(methylhydrazono)-1H-pyrrolo[2,3-d]pyrimidin-7-yl]tetrahydrofuran-3,4-diol hydrochloride (64)

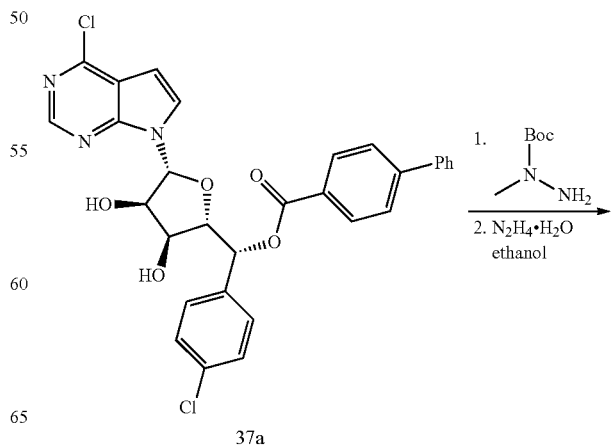

37a

241

-continued

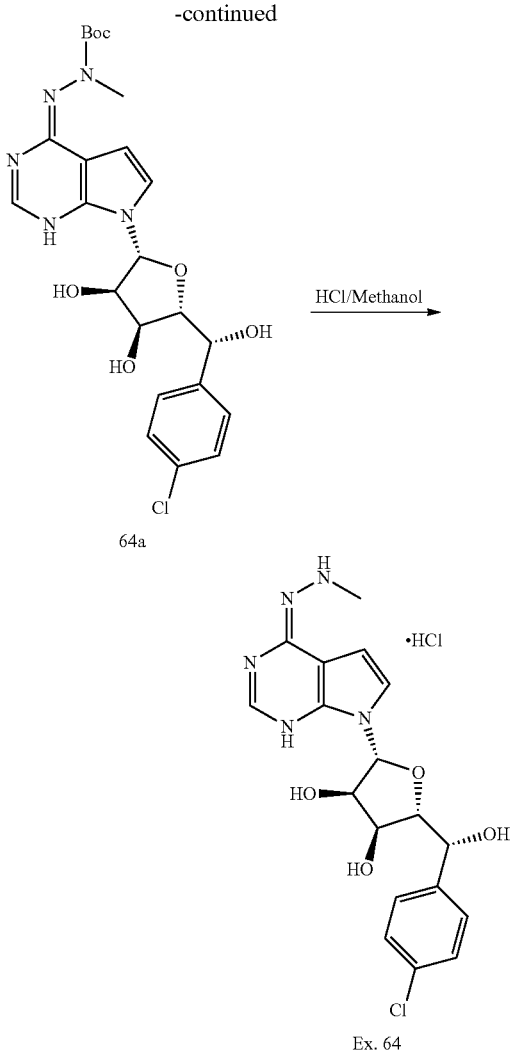

64a

Ex. 64 a) Preparation of tert-butyl N-[7-[(2R,3R,4S,5R)-5-[(R)-(4-chlorophenyl)-hydroxy-methyl]-3,4-dihydroxy-tetrahydrofuran-2-yl]-1H-pyrrolo[2,3-d]pyrimidin-4-ylidene]amino-N-methyl-carbamate (64a)

To a solution of [(R)-(4-chlorophenyl)-[(2S,3S,4R,5R)-5-(4-chloropyrrolo[2,3-d]pyrimidin-7-yl)-3,4-dihydroxy-tetrahydrofuran-2-yl]methyl] 4-phenylbenzoate (37a) (300 mg, 0.39 mmol) in ethanol (2 mL) was added 1-Boc-1-methyl-hydrazine (2 mL, 13.48 mmol). The reaction mixture was heated to 90° C. and stirred for 18 hh. LCMS showed the reaction was complete. The reaction mixture was cold to 25° C., and hydrazine hydrate (2 mL) was added and stirred for 1 h. LCMS showed the reaction was completed. The solvent was concentrated under reduced pressure, the residue was washed with water, extracted with EA. The combined organic layers were washed with brine, dried over anhydrous Na₂SO₄, concentrated under reduced pressure to give crude tert-butyl N-[7-[(2R,3R,4S,5R)-5-[(R)-(4-chlorophenyl)-hydroxy-methyl]-3,4-dihydroxy-tetrahydrofuran-2-yl]-1H-pyrrolo[2,3-d]pyrimidin-4-ylidene]amino-N-methyl-carbamate (64a) (2 g, 0.23 mmol, 81.37% yield) which was used in the next step without further purification. LCMS [M+H]: 506.3.

b) Preparation of (2R,3S,4R,5R)-2-[(R)-(4-chlorophenyl)-hydroxy-methyl]-5-[4-(methylhydrazono)-1H-pyrrolo[2,3-d]pyrimidin-7-yl]tetrahydrofuran-3,4-diol hydrochloride (64)

To a solution of tert-butyl N-[7-[(2R,3R,4S,5R)-5-[(R)-(4-chlorophenyl)-hydroxy-methyl]-3,4-dihydroxy-tetrahydrofuran-2-yl]-1H-pyrrolo[2,3-d]pyrimidin-4-ylidene]amino-N-methyl-carbamate (64a) (2 g, 0.24 mmol) in methanol (5 mL) was added HCl/MeOH (4 mol/L, 5 mL). The reaction mixture was heated to 90° C. and stirred for 2 h. LCMS showed the reaction was completed. The solvent was concentrated under reduced pressure, and the residue was purified by prep-HPLC (0.1% TFA) twice eluting with H₂O:CH₃CN from 95:5 to 5:95 to give (2R,3S,4R,5R)-2-[(R)-(4-chlorophenyl)-hydroxy-methyl]-5-[(4Z)-4-(methylhydrazono)-1H-pyrrolo[2,3-d]pyrimidin-7-yl]tetrahydrofuran-3,4-diol hydrochloride (64) (40 mg, 0.088 mmol, 37.02% yield) as white solid. LCMS [M+H]: 406.2. ¹H NMR (400 MHz, DMSO-d6) δ 10.90 (s, 1H), 8.28 (s, 1H), 7.72 (s, 1H), 7.35-7.42 (m, 4H), 6.88 (d, J=3.2 Hz, 1H), 6.10 (d, J=7.6 Hz, 1H), 6.00 (s, 1H), 5.31 (s, 1H), 5.15 (s, 1H), 4.77 (d, J=4.8 Hz, 1H), 4.49-4.52 (m, 1H), 4.11 (d, J=4.4 Hz, 1H), 4.00 (d, J=5.2 Hz, 1H), 2.67 (s, 3H). ¹H NMR (400 MHz, DMSO-d6+D₂O) δ 8.30 (s, 1H), 7.73 (d, J=3.2 Hz, 1H), 7.35-7.42 (m, 4H), 6.89 (d, J=3.6 Hz, 1H), 6.11 (d, J=7.6 Hz, 1H), 4.77 (d, J=5.2 Hz, 1H), 4.48-4.52 (m, 1H), 4.12 (d, J=4.8 Hz, 1H), 4.01 (d, J=4.4 Hz, 1H), 2.67 (s, 3H).

Example 65. 7-((2R,3R,4S,5R)-5-((R)-(3-chloro-4-fluorophenyl)(hydroxy)methyl)-3,4-dihydroxytetrahydrofuran-2-yl)-1,7-dihydro-4H-pyrrolo[2,3-d]pyrimidin-4-one oxime (65)

Example 65 was prepared following similar procedures as those for Example 63 except for substituting [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-(4-chloro-3-fluoro-phenyl)methanone (Int-3-1) with [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-(3-chloro-4-fluoro-phenyl)methanone. ¹H NMR (400 MHz, DMSO-d₆) δ 8.30 (s, 1H), 7.77 (d, J=3.7 Hz, 1H), 7.55 (dd, J=7.3, 1.9 Hz, 1H), 7.44-7.31 (m, 2H), 6.89 (d, J=3.6 Hz, 1H), 6.10 (d, J=7.5 Hz, 1H), 4.78 (d, J=5.6 Hz, 1H), 4.48 (dd, J=7.6, 4.9 Hz, 1H), 4.12 (dd, J=4.9, 1.5 Hz, 1H), 3.98 (dd, J=5.7, 1.4 Hz, 1H).

Example 66. 7-((2R,3R,4S,5R)-5-((R)-(3,4-dichlorophenyl)(hydroxy)methyl)-3,4-dihydroxytetrahydrofuran-2-yl)-1,7-dihydro-4H-pyrrolo[2,3-d]pyrimidin-4-one oxime (66)

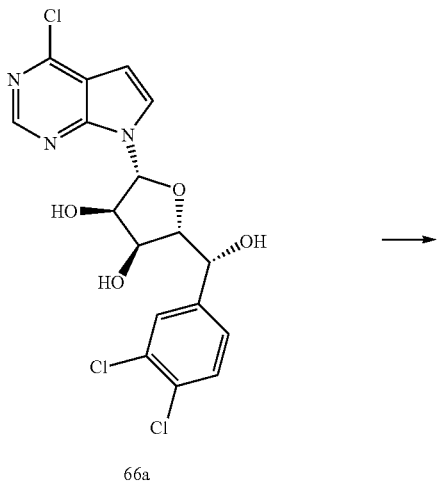

66a

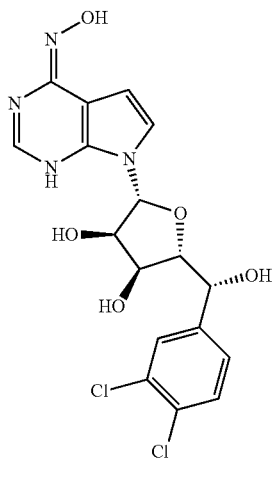

Ex. 66 a) Preparation of (2R,3S,4R,5R)-2-[(R)-(3,4-dichlorophenyl)-hydroxy-methyl]-5-(4-chloropyrrolo[2,3-d]pyrimidin-7-yl)tetrahydrofuran-3,4-diol (66a)

Compound 66a was prepared following a similar procedure as that of compound 20a except substituting (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(4-chlorophenyl)methanol with (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(3,4-dichlorophenyl)methanol.

b) Preparation of 7-((2R,3R,4S,5R)-5-((R)-(3,4-dichlorophenyl)(hydroxy)methyl)-3,4-dihydroxytetrahydrofuran-2-yl)-1,7-dihydro-4H-pyrrolo[2,3-d]pyrimidin-4-one oxime (66)

A 4 mL vial with septum containing (2R,3R,4S,5R)-2-(4-chloro-7H-pyrrolo[2,3-d]pyrimidin-7-yl)-5-((R)-(3,4-dichlorophenyl)(hydroxy)methyl)tetrahydrofuran-3,4-diol (66a) (56.5 mg, 0.130 mmol) and hydroxylamine; hydrochloride (45 mg, 0.65 mmol) was charged with IPA (2 mL) and then sparged with Ar for 1 min. The vial was then charged with Triethylamine; TEA (0.4 mL, 2.87 mmol) and heated at 100° C. for 5 h. The reaction mixture was concentrated under reduced pressure and purified by FCC (20 g C18, 5-35% MeCN in $H_2O$, wet-loaded in $H_2O$ with TFA). Fractions containing product were combined and concentrated under reduced pressure. This material was further purified by FCC (30 g C18, 5-35% MeCN in $H_2O$, wet-loaded in $H_2O$+DMSO). Fractions containing only product by HPLC were combined, concentrated under reduced pressure, and repeatedly co-evaporated with 1 N $HCl(a_q)$ and MeOH to remove TFA and yield the HCl salt of 7-((2R,3R,4S,5R)-5-((R)-(3,4-dichlorophenyl)(hydroxy)methyl)-3,4-dihydroxytetrahydrofuran-2-yl)-1,7-dihydro-4H-pyrrolo[2,3-d]pyrimidin-4-one oxime (66) (20. mg, 0.043 mmol, 33% yield) as a yellow solid. LRMS (ESI) m/z calcd for [M+H]+ $C_{17}H_{17}Cl_2N_4O_5$: 427.06/429.05. Found: 427.1/429.1; $^1$H NMR (600 MHz, DMSO-$d_6$) δ 13.57 (s, 1H), 12.90 (s, 1H), 10.96 (s, 1H), 8.27 (s, 1H), 7.73 (s, 1H), 7.60 (d, J=1.9 Hz, 1H), 7.57 (d, J=8.3 Hz, 1H), 7.38 (dd, J=8.4, 2.0 Hz, 1H), 6.85 (d, J=3.6 Hz, 1H), 6.09 (d, J=7.5 Hz, 2H), 5.31 (s, 2H), 4.79 (d, J=5.5 Hz, 1H), 4.49 (dd, J=7.5, 5.0 Hz, 1H), 4.11 (dd, J=4.9, 1.6 Hz, 1H), 3.99 (dd, J=5.6, 1.6 Hz, 1H).

Example 67. 7-((2R,3R,4S,5R)-5-((R)-(3,4-difluorophenyl)(hydroxy)methyl)-3,4-dihydroxytetrahydrofuran-2-yl)-1,7-dihydro-4H-pyrrolo[2,3-d]pyrimidin-4-one oxime (67)

Example 67 was prepared following similar procedures as those for Example 66 except for substituting (2R,3R,4S,5R)-2-(4-chloro-7H-pyrrolo[2,3-d]pyrimidin-7-yl)-5-((R)-(3,4-dichlorophenyl)(hydroxy)methyl)tetrahydrofuran-3,4-diol with (2R,3R,4S,5R)-2-(4-chloro-7H-pyrrolo[2,3-d]pyrimidin-7-yl)-5-((R)-(3,4-difluorophenyl)(hydroxy)methyl)tetrahydrofuran-3,4-diol. LRMS (ESI) m/z calcd for [M+H]$^+$ $C_{17}H_{17}F_2N_4O_5$: 395.12. Found: 395.1; $^1$H NMR (400 MHz, DMSO-$d_6$) δ 13.60 (s, 1H), 13.00 (s, 1H), 10.97 (s, 1H), 8.28 (s, 1H), 7.75 (d, J=3.9 Hz, 1H), 7.46-7.31 (m, 2H), 7.27-7.21 (m, 1H), 6.85 (d, J=3.6 Hz, 1H), 6.20-5.92 (m, 2H), 5.35 (s, 2H), 4.77 (d, J=5.5 Hz, 1H), 4.48 (dd, J=7.7, 5.0 Hz, 1H), 4.11 (dd, J=4.9, 1.4 Hz, 1H), 3.99 (dd, J=5.5, 1.4 Hz, 1H).

Example 68. 7-((2R,3R,4S,5R)-5-((R)-(3-chloro-4-fluorophenyl)(hydroxy)methyl)-3,4-dihydroxytetrahydrofuran-2-yl)-1,7-dihydro-4H-pyrrolo[2,3-d]pyrimidin-4-one O-methyl oxime (68)

Example 68 was prepared following similar procedures as those for Example 62 except for substituting Int-3 with (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(3-chloro-4-fluorophenyl)methanol. $^1$H NMR (400 MHz, Methanol-$d_4$) δ 8.15 (s, 1H), 7.62-7.48 (m, 2H), 7.43-7.29 (m, 1H), 7.20 (t, J=8.8 Hz, 1H), 6.67 (d, J=3.7 Hz, 1H), 6.15 (d, J=6.8 Hz, 1H), 4.60 (dd, J=4.9, 6.8 Hz, 1H), 4.29-4.19 (m, 2H), 3.94 (s, 3H).

Example 69. 7-((2R,3R,4S,5R)-5-((R)-(3,4-dichlorophenyl)(hydroxy)methyl)-3,4-dihydroxytetrahydrofuran-2-yl)-1,7-dihydro-4H-pyrrolo[2,3-d]pyrimidin-4-one O-methyl oxime hydrochloride (69)

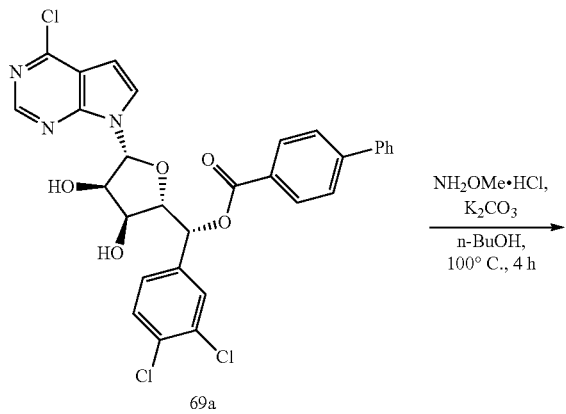

69a

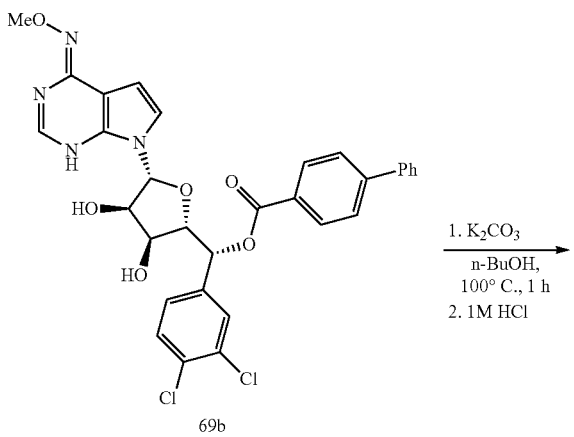

69b

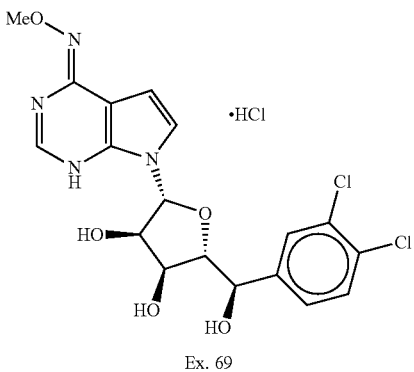

Ex. 69 a) Preparation of [(R)-[(2S,3S,4R,5R)-5-(4-chloropyrrolo[2,3-d]pyrimidin-7-yl)-3,4-dihydroxy-tetrahydrofuran-2-yl]-(3,4-dichlorophenyl)methyl] 4-phenylbenzoate (69a)

Compound 69a was prepared similar to that of Int-1 except substituting [4-(trifluoromethyl)phenyl]boronic acid with (3,4-dichlorophenyl)boronic acid.

b) Preparation of [(R)-(3,4-dichlorophenyl)-[(2S,3S,4R,5R)-3,4-dihydroxy-5-[4-methoxyimino-1H-pyrrolo[2,3-d]pyrimidin-7-yl]tetrahydrofuran-2-yl]methyl] 4-phenylbenzoate (69b)

To a solution of [(R)-[(2S,3S,4R,5R)-5-(4-chloropyrrolo[2,3-d]pyrimidin-7-yl)-3,4-dihydroxy-tetrahydrofuran-2-yl]-(3,4-dichlorophenyl)methyl] 4-phenylbenzoate (69a) (10 g, 13.1 mmol) in 1-butanol (200 mL) was added methoxyammonium chloride (7.66 g, 91.7 mmol) and $K_2CO_3$ (18.07 g, 131 mmol). The reaction mixture was stirred at 100° C. for 4 hh. LCMS showed the reaction was completed. The solvent was concentrated under reduced pressure, and the residue was washed with water, extracted with EtOAc, dried over anhydrous $Na_2SO_4$. The solvent was removed in vacuum to give crude [(R)-(3,4-dichlorophenyl)-[(2S,3S,4R,5R)-3,4-dihydroxy-5-[4-methoxyimino-1H-pyrrolo[2,3-d]pyrimidin-7-yl]tetrahydrofuran-2-yl]methyl] 4-phenylbenzoate (10 g, 8.05 mmol, 61.4% yield) as oil (69b). LCMS [M+H]:621.3.

c) Preparation of (2R,3S,4R,5R)-2-[(R)-(3,4-dichlorophenyl)-hydroxy-methyl]-5-[(4Z)-4-methoxy-imino-1H-pyrrolo[2,3-d]pyrimidin-7-yl]tetrahydrofuran-3,4-diol hydrochloride (69)

To a solution of [(R)-(3,4-dichlorophenyl)-[(2S,3S,4R,5R)-3,4-dihydroxy-5-[4-methoxyimino-1H-pyrrolo[2,3-d]pyrimidin-7-yl]tetrahydrofuran-2-yl]methyl] 4-phenylbenzoate (69a) (10 g, 8.05 mmol) in 1-butanol (100 mL) was added potassium carbonate (1.67 g, 12.1 mmol). The reaction mixture was stirred at 100° C. for 1.5 h. LCMS showed the reaction was completed. HCl aqueous (1M) was added to adjust pH=7.0, and the solvent was concentrated under reduced pressure. The residue was dissolved in DMSO, filtered. The filtrate was purified by reversed-phase combi-flash to give the impure product (5.5 g). The impure product was further purified by recrystallization (the material was suspended in the hot methanol and then filtered after the mixture was cooled to room temperature) from $CH_3OH$ to afford pure (2R,3S,4R,5R)-2-[(R)-(3,4-dichlorophenyl)-hydroxy-methyl]-5-[4-methoxyimino-1H-pyrrolo[2,3-d]pyrimidin-7-yl]tetrahydrofuran-3,4-diol (2.4 g, 5.40 mmol, 67% yield, free base) as a pale yellow solid. Mp. 131.3° C. The mother liquid was purified by prep-HPLC (0.1% TFA) eluting with $H_2O$:$CH_3CN$ from 90:10 to 5:95 to give crude TFA salt which was dissolved in 1M HCl and lyophilized to give (2R,3 S,4R,5R)-2-[(R)-(3,4-dichlorophenyl)-hydroxy-methyl]-5-[4-methoxyimino-1H-pyrrolo[2,3-d]pyrimidin-7-yl]tetrahydrofuran-3,4-diol hydrochloride (69) (1.1 g, 2.19 mmol, 27.2% yield). Mp. 131.3° C.; LCMS [M+H]:441.3. H NMR (400 MHz, DMSO-d6) δ 10.95 (d, J=3.2 Hz, 1H), 10.64 (s, 0.5H), 8.17 (s, 0.5H), 7.56-7.62 (m, 4H), 7.47 (d, J=4.0 Hz, 1H), 7.36-7.40 (m, 2H), 7.18 (d, J=3.6 Hz, 1H), 6.59 (d, J=3.6 Hz, 0.6H), 6.25 (d, J=3.2 Hz, 1H), 6.14 (d, J=4.4 Hz, 1H), 6.02 (d, J=7.2 Hz, 0.6H), 5.86 (d, J=7.6 Hz, 1H), 5.21-5.24 (m, 1.6H), 5.08 (d, J=4.4 Hz, 0.6H), 5.05 (d, J=4.0 Hz, 1H), 4.81 (t, J=4.8 Hz, 0.7H), 4.76 (t, J=4.8 Hz, 1H), 4.56 (b, 0.7H), 4.40-4.45 (m, 1H), 4.02-4.06 (m, 1.8H), 3.99 (d, J=4.8 Hz, 0.7H), 3.93 (d, J=4.8 Hz, 1H), 3.75 (s, 2H), 3.72 (s, 3H). H NMR (400 MHz, DMSO-d6+$D_2O$) δ 8.20 (b, 1H), 7.56-7.62 (m, 3.7H), 7.49 (s, 1H), 7.36-7.40 (m, 1.8H), 7.17 (d, J=3.2 Hz, 1H), 6.59 (d, J=3.6 Hz, 1H), 6.26 (d, J=3.2 Hz, 1H), 6.04 (b, 0.6H), 5.86 (d, J=7.6 Hz, 1H), 4.81 (d, J=4.8 Hz, 0.7H), 4.75 (d, J=5.2 Hz, 1H), 4.56

(b, 1H), 4.43 (dd, J=7.6 Hz, J=5.2 Hz, 1H), 4.02-4.06 (m, 1.8H), 3.99 (d, J=4.8 Hz, 0.7H), 3.93 (d, J=4.0 Hz, 1H), 3.75 (m, 2H), 3.72 (s, 3H).

Example 70. 7-((2R,3R,4S,5R)-5-((R)-(3,4-difluorophenyl)(hydroxy)methyl)-3,4-dihydroxytetrahydrofuran-2-yl)-1,7-dihydro-4H-pyrrolo[2,3-d]pyrimidin-4-one O-methyl oxime (70)

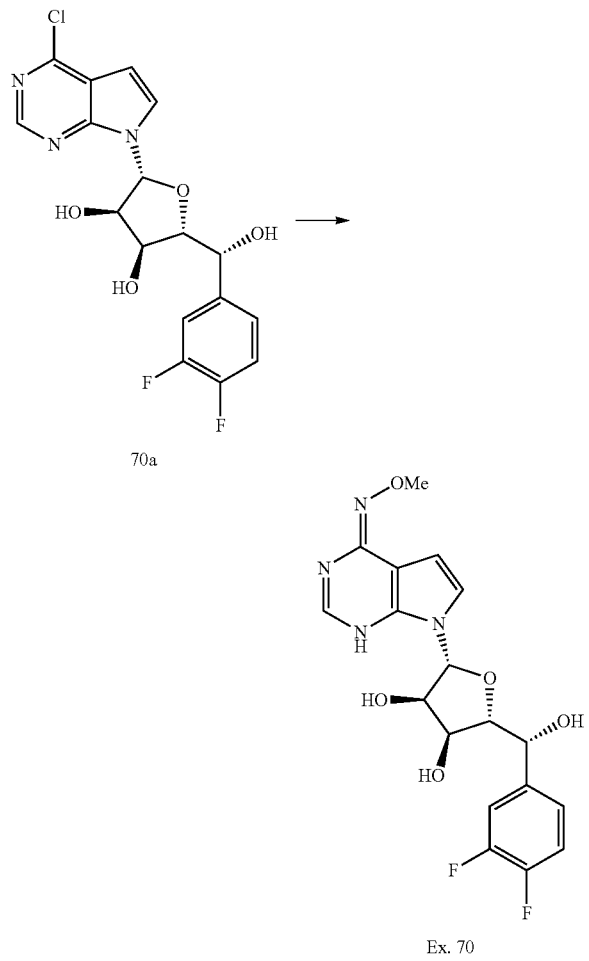

a) Preparation of (2R,3S,4R,5R)-2-[(R)-(3,4-dichlorophenyl)-hydroxy-methyl]-5-(4-chloropyrrolo[2,3-d]pyrimidin-7-yl)tetrahydrofuran-3,4-diol (70a)

Compound 70a was prepared following a similar procedure as that of compound 20a except substituting (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(4-chlorophenyl)methanol with (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(3,4-difluorophenyl)methanol.

b) Preparation of 7-((2R,3R,4S,5R)-5-((R)-(3,4-difluorophenyl)(hydroxy)methyl)-3,4-dihydroxytetrahydrofuran-2-yl)-1,7-dihydro-4H-pyrrolo[2,3-d]pyrimidin-4-one O-methyl oxime (70)

A 2 mL microwave vial with septum containing a solution of (2R,3R,4S,5R)-2-(4-chloro-7H-pyrrolo[2,3-d]pyrimidin-7-yl)-5-((R)-(3,4-difluorophenyl)(hydroxy)methyl)tetrahydrofuran-3,4-diol (70a) (50.3 mg, 0.130 mmol) and O-methylhydroxylamine hydrochloride (76 mg, 0.91 mmol) in IPA (0.5 mL) and N-ethyl-N-isopropyl-propan-2-amine (0.4 mL, 2.3 mmol) was sparged with Ar for 2 min, then heated in a microwave reactor for 1 h at 120° C. TLC showed minimal conversion of product. The vial was then heated conventionally at 110° C. for 2 d. The mixture was charged with IPA (1.5 mL), then O-methylhydroxylamine hydrochloride (90.mg, 1.02 mmol), and N-ethyl-N-isopropyl-propan-2-amine (0.3 mL, 1.72 mmol). The vial was blanketed with Ar, then heated at 110° C. for 3 d. The reaction mixture was concentrated under reduced pressure and heat (50° C.), then attempted purification by FCC (30 g C18, 5→25% MeCN in $H_2O$, wet-loaded in $H_2O$+DMSO). Fractions containing product by HPLC were combined, concentrated, neutralized with Amberlite IRA-67 resin, filtered, and repurified by FCC (12 g $SiO_2$, 0→4% MeOH in DCM, wet-loaded in eluent). Fraction containing pure product were combined, concentrated under reduced pressure, and twice co-evaporated with 1N $HCl_{(aq)}$ and methanol to yield the HCl salt of (Z)-7-((2R,3R,4S,5R)-5-((R)-(3,4-difluorophenyl)(hydroxy)methyl)-3,4-dihydroxytetrahydrofuran-2-yl)-1,7-dihydro-4H-pyrrolo[2,3-d]pyrimidin-4-one O-methyl oxime (70) (17.9 mg, 0.0398 mmol, 31.5% yield) as an off-white powder. Rf=0.20 (6% MeOH in DCM); LRMS (ESI) m/z calcd for [M+H]$^+$ $C_{18}H_{19}F_2N_4O_5$: 409.13. Found: 409.2; $^1$H NMR (400 MHz, DMSO-d$_6$+D$_2$O) δ 8.18 (s, 1H), 7.66 (s, 1H), 7.46-7.31 (m, 2H), 7.28-7.19 (m, 1H), 6.71 (s, 1H), 6.06 (d, J=7.6 Hz, 1H), 4.77 (d, J=5.4 Hz, 1H), 4.48 (dd, J=7.7, 5.0 Hz, 1H), 4.09 (dd, J=5.0, 1.4 Hz, 1H), 3.98 (dd, J=5.3, 1.3 Hz, 1H), 3.84 (s, 3H).

Example 71. 7-((2R,3R,4S,5R)-5-((R)-(4-chlorophenyl)(hydroxy)methyl)-3,4-dihydroxytetrahydrofuran-2-yl)-2-methyl-1,7-dihydro-4H-pyrrolo[2,3-d]pyrimidin-4-one oxime (71)

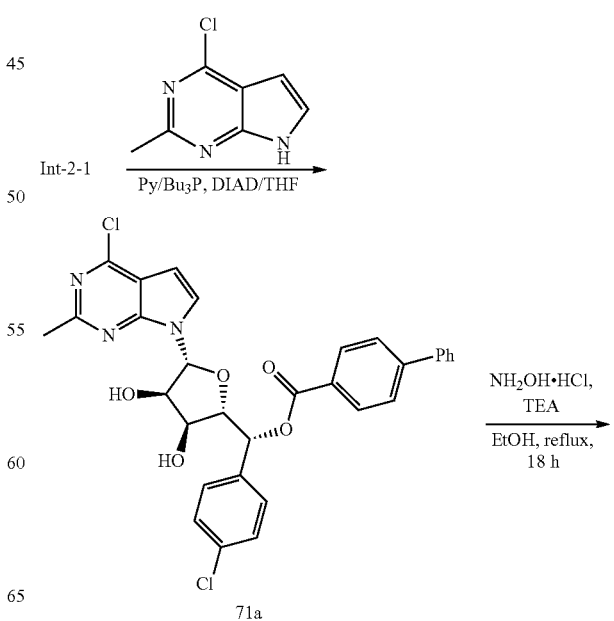

-continued

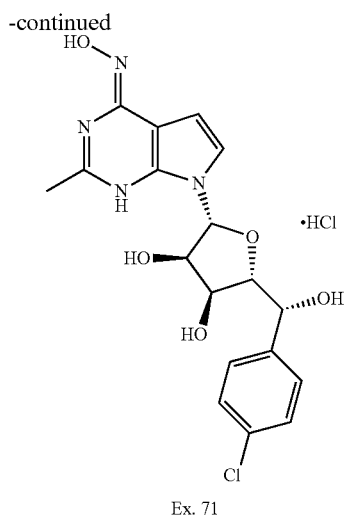

Ex. 71 a) Preparation of [(R)-[(2S,3S,4R,5R)-5-(4-chloro-2-methyl-pyrrolo [2,3-d]pyrimidin-7-yl)-3,4-dihydroxy-tetrahydrofuran-2-yl]-(4-chlorophenyl)methyl]4-phenylbenzoate (71a)

To a solution of 4-chloro-2-methyl-7H-pyrrolo[2,3-d]pyrimidine (190.08 mg, 1.11 mmol) and pyridine (0.09 mL, 1.11 mmol) in dry THF (5 mL) was added tributylphosphane (0.56 mL, 2.22 mmol) and DIAD (0.46 mL, 2.33 mmol) at 30° C. Then [(R)-(4-chlorophenyl)-[(2S,3S,4R)-3,4,5-trihydroxytetrahydrofuran-2-yl]methyl]4-phenylbenzoate (Int-2-1) (500 mg, 1.11 mmol) in dry THF (10 mL) was added in one portion. The reaction mixture was stirred at 30° C. for 1 h. LCMS showed the reaction was completed. The solution was purified by prep-HPLC (0.1% TFA) eluting with H$_2$O: CH$_3$CN from 90:10 to 5:95 to give [(R)-[(2S,3S,4R,5R)-5-(4-chloro-2-methyl-pyrrolo [2,3-d]pyrimidin-7-yl)-3,4-dihydroxy-tetrahydrofuran-2-yl]-(4-chlorophenyl)methyl]4-phenylbenzoate (71a) (140 mg, 0.2324 mmol, 20.907% yield) as pale yellow solid. LCMS [M+H]: 590.3.

b) Preparation of 7-((2R,3R,4S,5R)-5-((R)-(4-chlorophenyl)(hydroxy)methyl)-3,4-dihydroxytetrahydrofuran-2-yl)-2-methyl-1,7-dihydro-4H-pyrrolo[2,3-d]pyrimidin-4-one oxime (71)

To a solution of [(R)-[(2S,3S,4R,5R)-5-(4-chloro-2-methyl-pyrrolo[2,3-d]pyrimidin-7-yl)-3,4-dihydroxy-tetrahydrofuran-2-yl]-(4-chlorophenyl)methyl] 4-phenylbenzoate (71a) (210 mg, 0.36 mmol) in ethanol (5 mL) was added hydroxylamine hydrochloride (0.22 mL, 7.11 mmol) and TEA (1.07 g, 10.67 mmol). The reaction mixture was heated to 90° C. and stirred for 18 hh. The reaction mixture was concentrated under reduced pressure. The residue was washed with water, extracted with EtOAc. The combined organic layers were washed with brine, dried over anhydrous Na$_2$SO$_4$. The solvent was concentrated under reduced pressure to give impure product, which was purified by prep-HPLC (0.1% TFA) eluting with H$_2$O:CH$_3$CN from 95:5 to 5:95. The product was dissolved in 1M HCl, lyophilized to give 7-[(2R,3R,4S,5R)-5-[(R)-(4-chlorophenyl)-hydroxy-methyl]-3,4-dihydroxy-tetrahydrofuran-2-yl]-2-methyl-1H-pyrrolo[2,3-d]pyrimidin-4-one oxime hydrochloride (71) (21.3 mg, 0.0471 mmol, 13.2% yield) as yellow solid. LCMS [M+H]: 407.3. $^1$H NMR (400 MHz, DMSO-d6) δ 11.11 (s, 1H), 7.65 (d, J=2.8 Hz, 1H), 7.35-7.41 (m, 4H), 6.90 (d, J=3.2 Hz, 1H), 6.06 (d, J=7.2 Hz, 1H), 4.76 (d, J=5.2 Hz, 1H), 4.48-4.51 (m, 1H), 4.11 (d, J=4.4 Hz, 1H), 3.97 (d, J=5.2 Hz, 1H), 2.60 (s, 3H). $^1$H NMR (400 MHz, DMSO-d6+D$_2$O) δ 7.65 (d, J=3.6 Hz, 1H), 7.35-7.41 (m, 4H), 6.82 (d, J=3.6 Hz, 1H), 6.07 (d, J=8.0 Hz, 1H), 4.75 (d, J=5.2 Hz, 1H), 4.49-4.51 (m, 1H), 4.12 (d, J=5.2 Hz, 1H), 3.99 (d, J=5.2 Hz, 1H), 2.61 (s, 3H).

Example 72. 7-((2R,3R,4S,5R)-5-((R)-(4-chlorophenyl)(hydroxy)methyl)-3,4-dihydroxytetrahydrofuran-2-yl)-5-fluoro-1,7-dihydro-4H-pyrrolo[2,3-d]pyrimidin-4-one oxime (72)

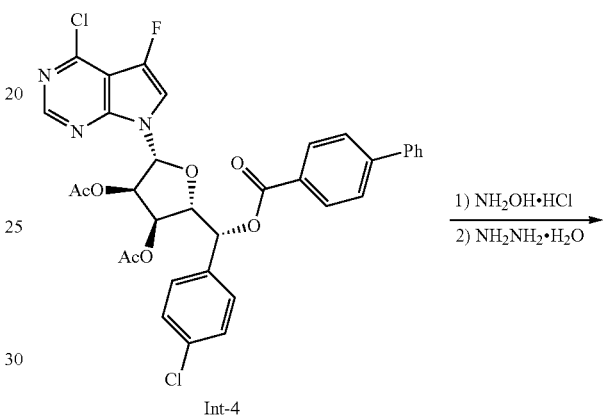

Int-4

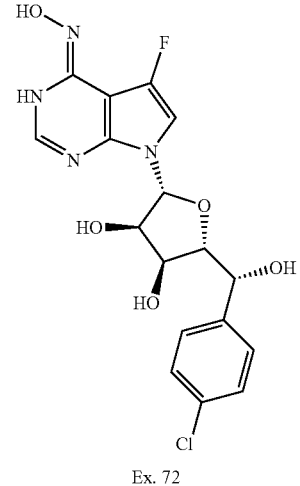

Ex. 72

To a solution of [(R)-(4-chlorophenyl)-[(2R,3R,4R,5R)-3,4-diacetoxy-5-(4-chloro-5-fluoro-pyrrolo [2,3-d]pyrimidin-7-yl)tetrahydrofuran-2-yl]methyl] 4-phenylbenzoate (Int-4) (185.0 mg, 0.24 mmol) in ethanol (5 mL) was added hydroxylamine hydrochloride (135.0 mg, 1.93 mmol) and triethylamine (0.4 mL, 2.87 mmol). The mixture was heated to reflux and stirred for 3 hh. LCMS showed the material was consumed, but the protection groups were remained. The solvent was removed in vacuo, and the residue was dissolved in 1,4-dioxane (2 mL). Then hydrazine hydrate (1.01 mL, 20.58 mmol) was added. The mixture was stirred at 24° C. for 16 hh. LCMS showed the benzoate was removed. The mixture was diluted by EtOAc (25 mL), dried over anhydrous Na$_2$SO$_4$, filtered, concentrated in vacuo. The residue was purified by prep-HPLC (0.1% TFA eluting with H₂O:CH₃CN from 90:10 to 5:95), then 0.05 mL of conc. HCl was added. The mixture was lyophilized to afford 7-[(2R,3R,4S,5R)-5-[(R)-(4-chlorophenyl)-hydroxy-methyl]-3,4-dihydroxy-tetrahydrofuran-2-yl]-5-fluoro-1H-pyrrolo[2,3-d]pyrimidin-4-one oxime hydrochloride (72) (17.5 mg, 0.037 mmol, 15.5% yield) as white solid. ¹H NMR (400 MHz, DMSO-d₆) δ 8.14 (s, 1H), 7.63 (s, 1H), 7.36-7.42 (m, 4H), 6.10 (d, J=7.2 Hz, 1H), 4.76-4.77 (m, 1H), 4.38-4.41 (m, 1H), 4.09-4.11 (m, 1H), 3.96-3.97 (m, 1H). LCMS [M+H]: m/z 411.2.

Example 73. (2R,3S,4R,5R)-2-((R)-(4-chlorophenyl)(hydroxy)methyl)-5-(5-fluoro-4-hydraziney-lidene-1,4-dihydro-7H-pyrrolo[2,3-d]pyrimidin-7-yl)tetrahydrofuran-3,4-diol (73)

To a solution of [(R)-(4-chlorophenyl)-[(2R,3R,4R,5R)-3,4-diacetoxy-5-(4-chloro-5-fluoro-pyrrolo[2,3-d]pyrimidin-7-yl)tetrahydrofuran-2-yl]methyl] 4-phenylbenzoate (Int-4) (68.97 mg, 0.09 mmol) in 1,4-dioxane (2 mL) was added hydrazine monohydrate (9 μL, 0.29 mmol). The mixture was stirred at 24° C. for 1 h. LCMS showed the material was consumed, but biphenyl was remained. More hydrazine monohydrate (2 mL, 64 mmol) was added, and the mixture was stirred at 24° C. for 1 h. LCMS show the reaction was complete and EtOAc (5 mL) was added. The mixture was dried over Na₂SO₄, and filtered. The filtrate was concentrated in vacuo. The residue was purified by prep-HPLC (0.1% TFA) eluting with H₂O:CH₃CN from 90:10 to 5:95, then 0.1 mL of conc. HCl was added and the resulting mixture was lyophilized to afford 7-[(2R,3R,4S,5R)-5-[(R)-(4-chlorophenyl)-hydroxy-methyl]-3,4-dihydroxy-tetrahydrofuran-2-yl]-5-fluoro-1H-pyrrolo[2,3-d]pyrimidin-4-one hydrazone hydrochloride (73) (12 mg, 0.0248 mmol, 28% yield) as a white solid. ¹H NMR (400 MHz, DMSO-d₆) δ 8.39 (s, 1H), 7.70 (s, 1H), 7.30-7.45 (m, 4H), 6.16 (d, J=7.2 Hz, 1H), 4.76-4.77 (m, 1H), 4.43-4.46 (m, 1H), 4.09-4.11 (m, 1H), 3.96-3.97 (m, 1H). LCMS [M+H]: 416.1.

Example 74. 7-((2R,3R,4S)-5-((R)-(4-chlorophenyl)(hydroxy)methyl)-3,4-dihydroxytetrahydrofuran-2-yl)-5-fluoro-1,7-dihydro-4H-pyrrolo[2,3-d]pyrimidin-4-one O-methyl oxime (74)

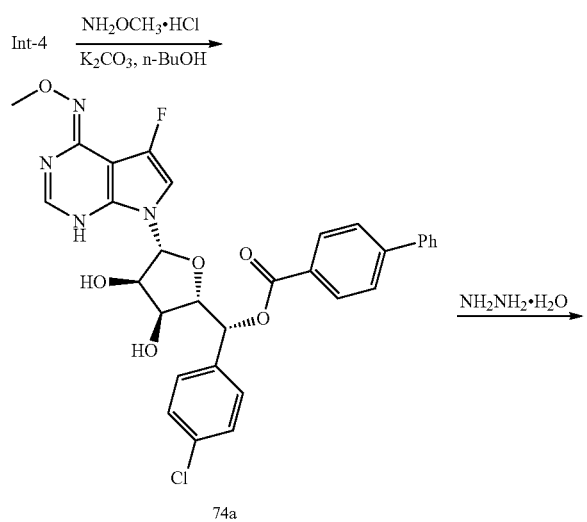

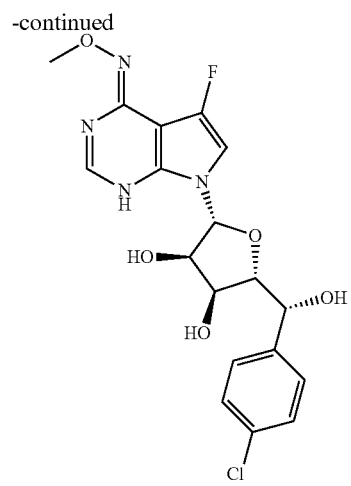

Ex. 74 a) Preparation of [(R)-(4-chlorophenyl)-[(2R,3R,4R,5R)-3,4-diacetoxy-5-[5-fluoro-4-(methoxyamino)pyrrolo[2,3-d]pyrimidin-7-yl]tetrahydrofuran-2-yl]methyl] 4-phenylbenzoate (74a)

To a solution of [(R)-(4-chlorophenyl)-[(2R,3R,4R,5R)-3,4-diacetoxy-5-(4-chloro-5-fluoro-pyrrolo[2,3-d]pyrimidin-7-yl)tetrahydrofuran-2-yl]methyl] 4-phenylbenzoate (Int-4) (120 mg, 0.17 mmol) in 1-butanol (5 mL) was added methoxyammonium chloride (120 mg, 1.42 mmol) and potassium carbonate (120.0 mg, 0.86 mmol). The mixture was stirred at 100° C. for 4.5 h. The mixture was diluted with EtOAc (40 mL), washed with brine (20 mL), dried over Na₂SO₄ and filtered. The filtrate was concentrated in vacuo to afford [(R)-(4-chlorophenyl)-[(2R,3R,4R,5R)-3,4-diacetoxy-5-[5-fluoro-4-(methoxyamino)pyrrolo[2,3-d]pyrimidin-7-yl]tetrahydrofuran-2-yl]methyl] 4-phenylbenzoate (74a) (105 mg, 0.090 mmol, 51.8% yield) as yellow solid, which used in the next step without further purification. LCMS [M+H]: m/z 689.3.

b) Preparation of (2R,3S,4R,5R)-2-[(R)-(4-chlorophenyl)-hydroxy-methyl]-5-[(4Z)-5-fluoro-4-methoxyimino-1H-pyrrolo[2,3-d]pyrimidin-7-yl]tetrahydrofuran-3,4-diol hydrochloride (74)

To a solution of [(R)-(4-chlorophenyl)-[(2R,3R,4R,5R)-3,4-diacetoxy-5-[5-fluoro-4-(methoxyamino)pyrrolo[2,3-d]pyrimidin-7-yl]tetrahydrofuran-2-yl]methyl] 4-phenylbenzoate (74a) (159 mg, 0.15 mmol) in ethanol (2 mL) was added hydrazine hydrate (1 mL, 20.6 mmol). The mixture was stirred at 24° C. for 2 hh. The mixture was diluted with EtOAc (30 mL), washed with brine (25 mL), dried over Na₂SO₄ and filtered. The filtrate was concentrated in vacuo. The residue was first purified prep-TLC, then further purified by prep-HPLC (0.1% TFA) eluting with H₂O:CH₃CN from 90:10 to 5:95. The product was treated with 1N HCl to afford (2R,3 S,4R,5R)-2-[(R)-(4-chlorophenyl)-hydroxy-methyl]-5-[(4Z)-5-fluoro-4-methoxyimino-1H-pyrrolo[2,3-d]pyrimidin-7-yl]tetrahydrofuran-3,4-diol hydrochloride (74) (7 mg, 0.015 mmol, 9.8% yield) as white solid. ¹H NMR (400 MHz, DMSO-d6) δ 7.58 (s, 1H), 7.35-7.41 (m, 4H), 7.21 (s, 1H), 5.94 (d, J=6.8 Hz, 1H), 4.71-4.73 (m, 1H), 4.33-4.37 (m, 1H), 3.99-4.05 (m, 1H), 3.90-3.92 (m, 1H), 3.74 (s, 3H). LCMS [M+H]: m/z 411.2.

Example 75. 7-((2R,3R,4S,5R)-3,4-dihydroxy-5-((R)-hydroxy(4-(trifluoromethyl)phenyl)methyl)tetrahydrofuran-2-yl)-1,7-dihydro-4H-pyrrolo[2,3-d]pyrimidin-4-one O-methyl oxime (75)

Example 75 was prepared following the similar procedures as those of Example 74 except substituting Int-4 with Int-1. LCMS [M+H]: 441.3. $^1$H NMR (400 MHz, DMSO-d$_6$) δ 8.26 (s, 1H), 7.72 (d, J=2.4 Hz, 1H), 7.60-7.68 (m, 4H), 6.84 (s, 1H), 6.09 (d, J=8.0 Hz, 1H), 4.88 (d, J=5.2 Hz, 1H), 4.50-4.54 (m, 1H), 4.13 (d, J=4.8 Hz, 1H), 4.03 (d, J=4.8 Hz, 1H), 3.86 (s, 3H). $^1$H NMR (400 MHz, DMSO-d$_6$+D$_2$O) δ 8.30 (s, 1H), 7.72 (d, J=3.6 Hz, 1H), 7.61-7.69 (m, 4H), 6.79 (d, J=3.6 Hz, 1H), 6.11 (d, J=8.0 Hz, 1H), 4.87 (d, J=5.2 Hz, 1H), 4.50-4.54 (m, 1H), 4.13 (d, J=4.8 Hz, 1H), 4.05 (d, J=5.2 Hz, 1H), 3.87 (s, 3H).

Example 76. (2R,3R,4S,5R)-2-((Z)-4-hydrazinylidene-1,4-dihydro-7H-pyrrolo[2,3-d]pyrimidin-7-yl)-5-((R)-hydroxy(4-(trifluoromethyl)phenyl)methyl)tetrahydrofuran-3,4-diol (76)

Example 76 was prepared following the similar procedures as those of Example 73 except substituting Int-4 with Int-1. LCMS [M+H]: 426.4. $^1$H NMR (400 MHz, DMSO-d$_6$) δ 11.13 (s, 1H), 8.31 (s, 1H), 7.72 (d, J=3.6 Hz, 1H), 7.61-7.68 (m, 4H), 6.97 (d, J=3.2 Hz, 1H), 6.11 (d, J=7.6 Hz, 1H), 4.88 (d, J=5.2 Hz, 1H), 4.52-4.56 (m, 1H), 4.14 (d, J=4.8 Hz, 1H), 4.03 (d, J=5.2 Hz, 1H). $^1$H NMR (400 MHz, DMSO-d$_6$+D$_2$O) δ 8.32 (s, 1H), 7.61-7.72 (m, 5H), 6.93 (d, J=3.6 Hz, 1H), 6.12 (d, J=7.6 Hz, 1H), 4.87 (d, J=5.2 Hz, 1H), 4.52-4.56 (m, 1H), 4.13 (d, J=4.8 Hz, 1H), 4.05 (d, J=5.6 Hz, 1H).

Example 77. 7-((2R,3R,4S,5R)-5-((R)-(4-chlorophenyl)(hydroxy)methyl)-3,4-dihydroxytetrahydrofuran-2-yl)-5-methyl-1,7-dihydro-4H-pyrrolo[2,3-d]pyrimidin-4-one oxime (77)

Example 77 was prepared following the similar procedures as those of Example 37 except for substituting 4-chloro-7H-pyrrolo[2,3-d]pyrimidine with 4-chloro-5-methyl-7H-pyrrolo[2,3-d]pyrimidine. LCMS [M+H]: 407.1. $^1$H NMR (400 MHz, DMSO-d6): δ 13.55 (s, 1H), 11.02 (s, 1H), 8.26 (s, 1H), 7.36-7.44 (m, 5H), 6.07 (d, J=7.2 Hz, 1H), 4.76 (d, J=5.2 Hz, 1H), 4.38-4.42 (m, 1H), 4.08 (d, J=4.8 Hz, 1H), 3.99 (d, J=4.0 Hz, 1H), 2.37 (s, 3H). $^1$H NMR (400 MHz, DMSO-d6+D$_2$O): δ 8.29 (s, 1H), 7.36-7.43 (m, 5H), 6.08 (d, J=7.2 Hz, 1H), 4.76 (d, J=5.2 Hz, 1H), 4.39-4.43 (m, 1H), 4.08 (d, J=4.8 Hz, 1H), 4.01 (d, J=4.0 Hz, 1H), 2.37 (s, 3H).

Example 78. 7-((2R,3R,4S,5R)-5-((R)-(3-fluoro-4-(trifluoromethyl)phenyl)(hydroxy)methyl)-3,4-dihydroxytetrahydrofuran-2-yl)-1,7-dihydro-4H-pyrrolo[2,3-d]pyrimidin-4-one O-methyl oxime (78)

Example 78 was prepared following the same procedure as Example 75 except for substituting (4-(trifluoromethyl)phenyl)boronic acid with (3-fluoro-4-(trifluoromethyl)phenyl)boronic acid. LCMS [M+H]: 459.2. $^1$H NMR (400 MHz, DMSO-d6+D$_2$O): δ 8.13 (s, 1H), 7.73 (t, J=7.6 Hz, 1H), 7.59 (d, J=3.4 Hz, 1H), 7.48-7.44 (m, 2H), 6.66 (d, J=3.2 Hz, 1H), 6.05 (d, J=7.4 Hz, 1H), 4.88 (d, J=4.8 Hz, 1H), 4.52-4.49 (m, 1H), 4.11-4.10 (m, 1H), 4.05-4.04 (m, 1H), 3.83 (s, 3H).

Example 79. 7-((2R,3R,4S)-5-((R)-1-(4-chlorophenyl)-2,2,2-trifluoro-1-hydroxyethyl)-3,4-dihydroxytetrahydrofuran-2-yl)-1,7-dihydro-4H-pyrrolo[2,3-d]pyrimidin-4-one O-methyl oxime (79)

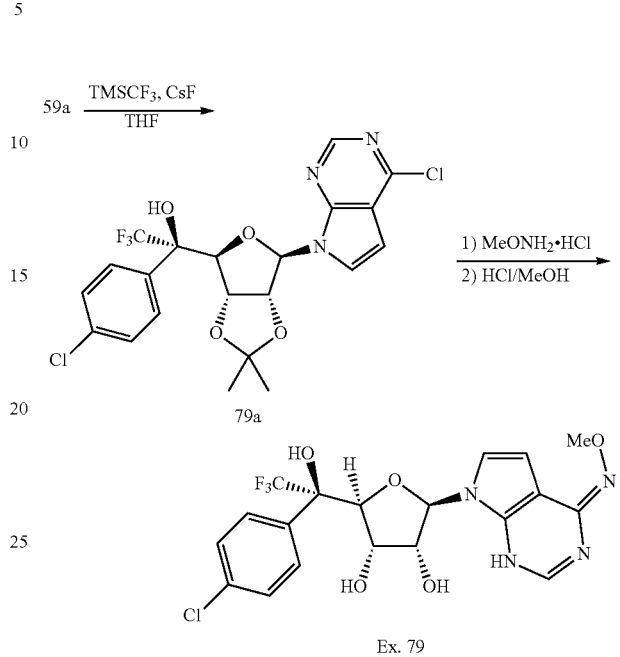

Ex. 79 a) Preparation of (R)-1-((3aR,4S,6R,6aR)-6-(4-chloro-7H-pyrrolo[2,3-d]pyrimidin-7-yl)-2,2-dimethyltetrahydrofuro[3,4-d][1,3]dioxol-4-yl)-1-(4-chlorophenyl)-2,2,2-trifluoroethan-1-ol (79a)

To a solution of compound 59a (50 mg, 115.14 umol, 1 eq.) in THF (2 mL) was added CsF (87.45 mg, 575.68 umol, 5 eq.), TMSCF3 (32.74 mg, 230.27 umol, 2 eq.). The mixture was stirred at −20° C. for 3 h. LC-MS showed compound 4 was consumed completely and one main peak with desired MS was detected. The reaction was quenched by H$_2$O (4 mL), and extracted with EtOAc (4 mL*3), and the organic phase was concentrated in vacuo. The residue was purified by prep-TLC (SiO2, Petroleum ether:Ethyl acetate=5:1). Compound 79a (10 mg) was obtained as a white solid (and 8 mg of the diastereomer). 1H NMR (400 MHz, CHLOROFORM-d) δ=8.63 (s, 1H), 8.07 (s, 1H), 7.65-7.53 (m, 2H), 7.36 (d, J=8.3 Hz, 2H), 7.26-7.20 (m, 1H), 6.57 (d, J=3.5 Hz, 1H), 5.78 (d, J=5.0 Hz, 1H), 5.09-4.90 (m, 2H), 4.48 (br d, J=6.4 Hz, 1H), 1.48 (s, 3H), 1.09-1.04 (m, 3H); LCMS: (M+H$^+$): 503.9, 505.9; TLC (Petroleum ether:Ethyl acetate=5:1) Rf=0.43.

b) Preparation of 7-((2R,3R,4S)-5-((R)-1-(4-chlorophenyl)-2,2,2-trifluoro-1-hydroxyethyl)-3,4-dihydroxytetrahydrofuran-2-yl)-1,7-dihydro-4H-pyrrolo[2,3-d]pyrimidin-4-one O-methyl oxime (79)

Example 79 was prepared using the similar procedures as those of Example 60 except for substituting (R)-1-((3aR,4S,6R,6aR)-6-(4-chloro-7H-pyrrolo[2,3-d]pyrimidin-7-yl)-2,2-dimethyltetrahydrofuro[3,4-d][1,3]dioxol-4-yl)-1-(4-chlorophenyl)ethan-1-ol (59b) with (R)-1-((3aR,4S,6R,6aR)-6-(4-chloro-7H-pyrrolo[2,3-d]pyrimidin-7-yl)-2,2-dimethyltetrahydrofuro[3,4-d][1,3]dioxol-4-yl)-1-(4-chlorophenyl)-

2,2,2-trifluoroethan-1-ol (79a). ¹H NMR (400 MHz, DMSO-d6) δ=8.20 (s, 1H), 7.67 (d, J=8.4 Hz, 2H), 7.59 (br d, J=3.1 Hz, 1H), 7.55 (d, J=8.6 Hz, 2H), 6.71 (br d, J=3.1 Hz, 1H), 5.97 (d, J=8.2 Hz, 1H), 4.66 (s, 1H), 4.47 (br dd, J=5.5, 7.9 Hz, 1H), 3.84 (s, 3H), 3.60 (d, J=5.5 Hz, 1H); ¹H NMR (400 MHz, DMSO-d6+D₂O) δ=8.22 (s, 1H), 7.65 (d, J=8.8 Hz, 2H), 7.60 (d, J=3.5 Hz, 1H), 7.55 (d, J=8.8 Hz, 2H), 6.69 (d, J=3.5 Hz, 1H), 5.97 (d, J=8.2 Hz, 1H), 4.65 (s, 1H), 4.45 (dd, J=5.4, 8.0 Hz, 1H), 3.84 (s, 3H); LCMS: (M+H⁺): 475.0; HPLC purity: 97.36%;

Example 80. 7-((2R,3R,4S,5R)-5-((R)-(4-chloro-3-methylphenyl)(hydroxy)methyl)-3,4-dihydroxytetrahydrofuran-2-yl)-1,7-dihydro-4H-pyrrolo[2,3-d]pyrimidin-4-one O-methyl oxime (80)

Example 80 was prepared following the same procedure as Example 75 except for substituting (4-(trifluoromethyl)phenyl)boronic acid with (3-methyl-4-(trifluoromethyl)phenyl)boronic acid. LCMS [M+H]: 421.3; ¹H NMR (400 MHz, DMSO-d6+D₂O) δ 8.08 (s, 1H), 7.49 (d, J=3.4 Hz, 1H), 7.32-7.30 (m, 2H), 7.19 (d, J=8.2 Hz, 1H), 6.64 (d, J=3.5 Hz, 1H), 6.00 (d, J=7.6 Hz, 1H), 4.70 (d, J=4.8 Hz, 1H), 4.48-4.45 (m, 1H), 4.08-4.07 (m, 1H), 4.01-3.99 (m, 1H), 3.80 (s, 3H), 2.26 (s, 3H).

Example 81. (2R,3S,4R,5R)-2-((R)-(3,4-dichlorophenyl)(hydroxy)methyl)-5-(4-(2-methylhydrazineylidene)-1,4-dihydro-7H-pyrrolo[2,3-d]pyrimidin-7-yl)tetrahydrofuran-3,4-diol (81)

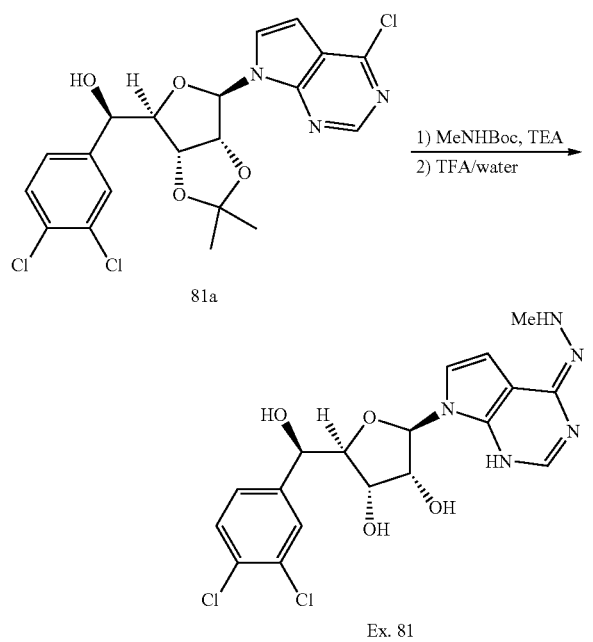

Ex. 81 a) Preparation of (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(3,4-dichlorophenyl)methanol (81a)

Compound 81a was prepared following the same procedure as that of Int-3 except for substituting [(3aR,4R,6S,6aS)-4-(4-chloropyrrolo[2,3-d]pyrimidin-7-yl)-2,2-dim-ethyl-3a,4,6,6a-tetrahydrofuro[3,4-d][1,3]dioxol-6-yl]-(4-chloro-3-fluoro-phenyl)methanone (Int-3-1) with [(3aR,4R,6S,6aS)-4-(4-chloropyrrolo[2,3-d]pyrimidin-7-yl)-2,2-dimethyl-3a,4,6,6a-tetrahydrofuro[3,4-d][1,3]dioxol-6-yl]-(3,4-dichlorophenyl)methanone.

b) Preparation of (2R,3S,4R,5R)-2-((R)-(3,4-dichlorophenyl)(hydroxy)methyl)-5-(4-(2-methylhydrazineylidene)-1,4-dihydro-7H-pyrrolo[2,3-d]pyrimidin-7-yl)tetrahydrofuran-3,4-diol (81)

A microwave tube containing a mixture of (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(3,4-dichlorophenyl)methanol (81a) (110.mg, 0.2300 mmol) was charged with 1-Boc-1-methylhydrazine (0.5 mL, 3.27 mmol) and Triethylamine; TEA (120.51 uL, 0.8600 mmol). Then, it was blanketed with N₂, heated at 95° C. After 24 h LCMS showed 1:1 ratio between the final compound and the starting material. The reaction was purged with N₂ and stirred for another 21 h at 95° C. LCMS showed 2:1 ratio. Another equiv of Et₃N and 3.7 equiv of 1-Boc-1-methylhydrazine were added and the reaction was stirred for 30 min at 95° C. in the microwave. LCMS showed the same ratio as before so the reaction was stirred at 100° C. for another 3 h. This time the ratio was 2.5:1 so the reaction was stirred for another 16 h at 100° C. Although there still remained some starting material, the crude was concentrated and treated with 1.5 mL of a 9:1 (TFA:water) solution for 2 h (LCMS showed no more starting material). The crude was concentrated, dissolved in DMSO, loaded onto a 30 g C₁₈ column and purified using H₂O/ACN (2 min 5% AcCN then ramp up for 5 min until 40%, then 8 min at 40% and finally ramp up to 80%) to give (2R,3S,4R,5R)-2-[(R)-(3,4-dichlorophenyl)-hydroxy-methyl]-5-[4-(methylhydrazono)-1H-pyrrolo[2,3-d]pyrimidin-7-yl]tetrahydrofuran-3,4-diol TFA salt (81) (48 mg, 0.095 mmol, 41% yield). ¹H NMR (400 MHz, Methanol-d₄) δ 8.22 (s, 1H), 7.64 (d, J=3.8 Hz, 1H), 7.57 (d, J=1.9 Hz, 1H), 7.47 (d, J=8.3 Hz, 1H), 7.34 (dd, J=2.0, 8.3 Hz, 1H), 6.84 (d, J=3.8 Hz, 1H), 6.23 (d, J=6.4 Hz, 1H), 4.59 (dd, J=5.2, 6.4 Hz, 1H), 4.26 (dd, J=2.9, 5.2 Hz, 1H), 4.23 (t, J=3.2 Hz, 1H), 2.78 (s, 3H).

Example 82. 7-((2R,3R,4S,5R)-5-((R)-(3,4-dichlorophenyl)(hydroxy)methyl)-3,4-dihydroxytetrahydrofuran-2-yl)-3,7-dihydro-4H-pyrrolo[2,3-d]pyrimidin-4-one O-ethyl oxime (82)

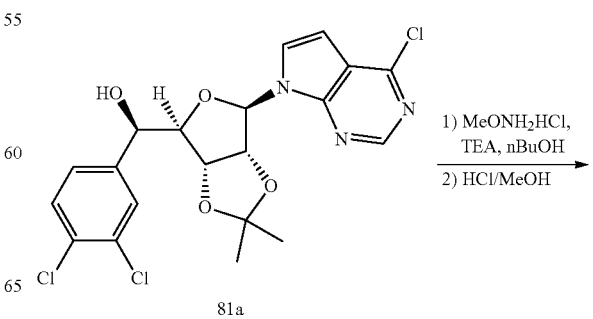

-continued

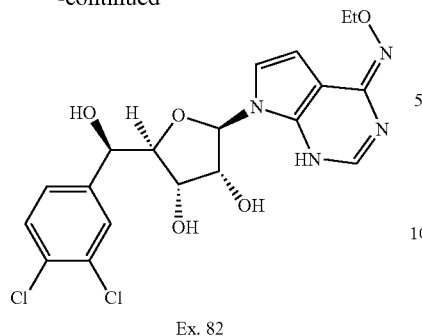

Ex. 82

To a solution of (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(3,4-dichlorophenyl)methanol (81a) (102.mg, 0.22 mmol) in 1-Butanol (1 mL) was added the Triethylamine; TEA (0.18 mL, 1.3 mmol) and ethoxyamine hydrochloride (108.95 mg, 1.08 mmol). The reaction was sparged with nitrogen and heated in an oil bath for 16 h at 110° C. The reaction mixture was concentrated and the crude was dissolved in 1 mL of methanol and treated with few drops of conc HCl. The reaction was stirred for 2 h, concentrated, the crude redissolved back in 1 mL of MeOH and 1 mL of water, treated with Amberlite IRA 67 and stirred for 30 mins. The reaction mixture was filtered, concentrated and the crude purified by silica gel chromatography using 4 g Agela column and gradient of 0-10% MeOH in DCM. The product was treated with 1N HCl to give (2R,3S,4R,5R)-2-[(R)-(3,4-dichlorophenyl)-hydroxymethyl]-5-[4-ethoxyimino-3H-pyrrolo[2,3-d]pyrimidin-7-yl]tetrahydrofuran-3,4-diol hydrochloride (82) (9 mg, 0.02 mmol, 9% yield). $^1$H NMR (400 MHz, DMSO-d$_6$) δ 8.15 (d, J=7.7 Hz, 1H), 7.68-7.53 (m, 4H), 7.38 (dd, J=2.0, 8.4 Hz, 1H), 6.69 (s, 1H), 6.05 (d, J=7.5 Hz, 1H), 4.79 (d, J=5.4 Hz, 1H), 4.50 (dd, J=4.9, 7.6 Hz, 1H), 4.13-3.94 (m, 4H), 1.30 (t, J=7.0 Hz, 3H).

Example 83. 7-((2R,3R,4S)-5-((R)-1-(4-chlorophenyl)-1-hydroxyethyl)-3,4-dihydroxytetrahydrofuran-2-yl)-1,7-dihydro-4H-pyrrolo[2,3-d]pyrimidin-4-one O-ethyl oxime (83)

Example 83 was prepared following the same procedure as Example 60 except for substituting MeONH$_2$.HCl with EtONH$_2$.HCl. $^1$H NMR (400 MHz, DMSO-d6) δ=8.22 (br s, 1H), 7.67 (br s, 1H), 7.55 (d, J=8.6 Hz, 2H), 7.40 (d, J=8.6 Hz, 2H), 6.76 (br s, 1H), 6.04 (br d, J=7.9 Hz, 1H), 4.47-4.38 (m, 1H), 4.09-4.03 (m, 3H), 3.71 (br d, J=5.1 Hz, 1H), 1.42 (s, 3H), 1.31 (t, J=6.9 Hz, 3H); $^1$H NMR (400 MHz, DMSO-d6+D$_2$O) δ=8.20 (s, 1H), 7.64 (d, J=3.3 Hz, 1H), 7.52 (d, J=8.6 Hz, 2H), 7.39 (d, J=8.6 Hz, 2H), 6.70 (d, J=3.7 Hz, 1H), 6.02 (d, J=7.7 Hz, 1H), 4.41 (dd, J=5.1, 7.9 Hz, 1H), 4.07-4.01 (m, 3H), 3.70 (br d, J=5.3 Hz, 1H), 1.40 (s, 3H), 1.29 (t, J=6.9 Hz, 3H); LCMS: (M+H$^+$): 435.1

Example 92. (2S,3S,4R,5R)-2-[(1R)-1-(3,4-dichlorophenyl)-1-hydroxy-ethyl]-5-[(6Z)-6-methoxyimino-1H-purin-9-yl]tetrahydrofuran-3,4-diol (92)

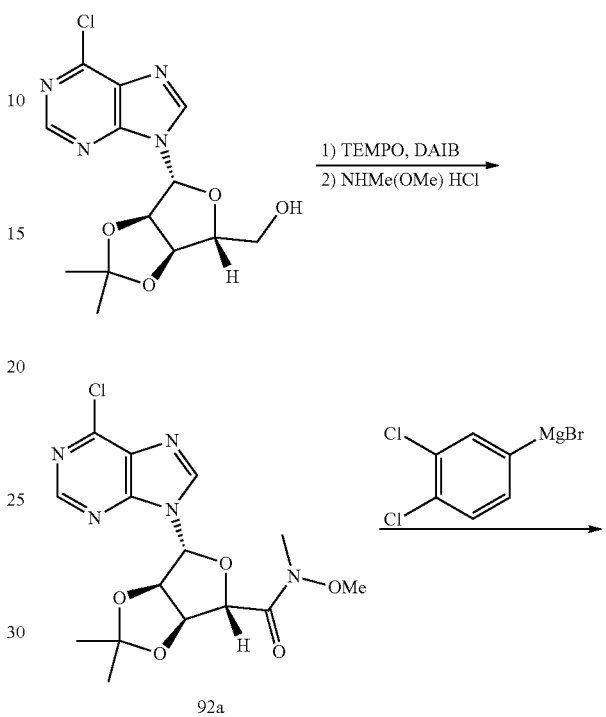

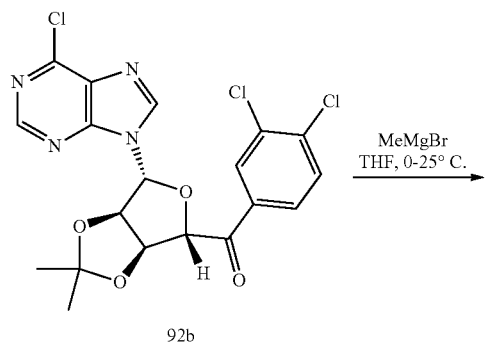

92b

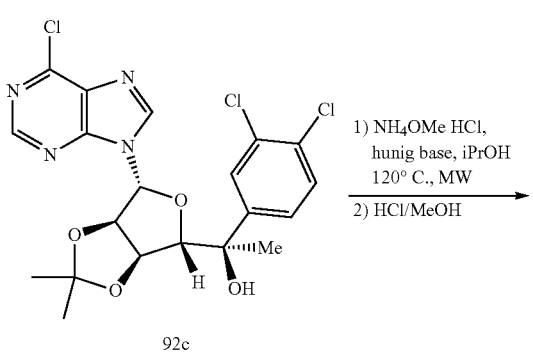

92c

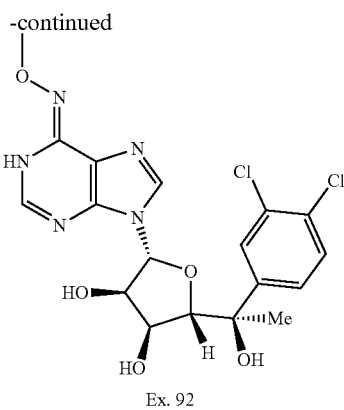

Ex. 92 a) Synthesis of (3aR,4R,6S,6aS)-4-(6-chloropurin-9-yl)-N-methoxy-N,2,2-trimethyl-3a,4,6,6a-tetrahydrofuro[3,4-d][1,3]dioxole-6-carboxamide (92a)

A mixture of 6-Chloro-9-(2,3-O-isopropylidene-beta-D-ribofuranosyl)-9H-purine (5.g, 14.69 mmol) in MeCN (15 mL) and Water (15 mL) was cooled to 0° C. (Diacetoxyiodo)benzene (10.4 g, 32.32 mmol) and TEMPO (462 mg, 2.94 mmol) was added portionwise. The resulting mixture was stirred at RT overnight. TLC (9:1 DCM/MeOH) showed completion of the reaction.

The solid was filtered and quickly rinsed with EtOAc to give (3aR,4R,6S,6aS)-4-(6-chloropurin-9-yl)-2,2-dimethyl-3a,4,6,6a-tetrahydrofuro[3,4-d][1,3]dioxole-6-carboxylic acid (2.68 g, 7.87 mmol, 53.5% yield) as an off-white solid. The aq. layer of the filtrates was extracted with EtOAc and the combined organic layers were washed with sat. aq. sodium thiosulfate, water, brine, dried over sodium sulfate, filtered and concentrated to give (3aR,4R,6S,6aS)-4-(6-chloropurin-9-yl)-2,2-dimethyl-3a,4,6,6a-tetrahydrofuro[3,4-d][1,3]dioxole-6-carboxylic acid (6.7 g, 7.9 mmol, 54% yield) as a brown solid, estimated to be ~40% purity based on TLC N-ethyl-N-isopropyl-propan-2-amine (2.74 mL, 15.73 mmol) was added to a solution of (3aR,4R,6S,6aS)-4-(6-chloropurin-9-yl)-2,2-dimethyl-3a,4,6,6a-tetrahydrofuro[3,4-d][1,3]dioxole-6-carboxylic acid (2.68 g, 7.87 mmol) and 1-PROPANEPHOSPHONIC ACID CYCLIC ANHYDRIDE (8.mL, 15.73 mmol) in Ethyl acetate (30 mL) at 0 C. Note that the patent procedure missed the base. The reaction doesn't proceed without base, typically TEA or hunig base. The resultion solution was stirred at RT for 1 hr. TLC showed the completion of the reaction (9:1 DCM/MeOH).

The reaction was poured into ice-cold water, the aq. layer was extracted with EtOAc 3×. Note that the product was difficult to extract under strong acidic conditions. The combined organic layers were washed with sat. aq. NaHCO₃, water, brine, dried over sodium sulfate, filtered and concentrated. The crude product was purified on a 40 g column to give (3aR,4R,6S,6aS)-4-(6-chloropurin-9-yl)-N-methoxy-N,2,2-trimethyl-3a,4,6,6a-tetrahydrofuro[3,4-d][1,3]dioxole-6-carboxamide (92a) (1.72 g, 4.48 mmol, 57.0% yield) as a white foamy solid.

The impure portion of acid was converted to the Weinreb amide following the same procedure as shown above to give another 3.6 g of the product, which made the total yield of these two steps over 80%.

b) Synthesis of [(3aR,4R,6S,6aS)-4-(6-chloropurin-9-yl)-2,2-dimethyl-3a,4,6,6a-tetrahydrofuro[3,4-d][1,3]dioxol-6-yl]-(3,4-dichlorophenyl)methanone (92b)

To an ice-cold solution of (3aR,4R,6S,6aS)-4-(6-chloropurin-9-yl)-N-methoxy-N,2,2-trimethyl-3a,4,6,6a-tetrahydrofuro[3,4-d][1,3]dioxole-6-carboxamide (92a)(1.72 g, 4.48 mmol) in THE (30 mL) was added a solution of (3,4-Dichlorophenyl)magnesium bromide, 0.50 μM in 2-MeTHF (17.93 mL, 8.96 mmol) dropwise. The resulting mixture was warmed to rt, stirred for 2 hr. LCMS showed the completion of the reaction. The reaction mixture was poured onto ice-cold sat. aq. NH₄Cl solution, which was extracted with EtOAc. The organic layer was washed with brine, dried over Na₂SO₄, filtered and concentrated. The crude product was purified on a 20 g column, which was eluted with 0-50% EA/hexane to give [(3aR,4R,6S,6aS)-4-(6-chloropurin-9-yl)-2,2-dimethyl-3a,4,6,6a-tetrahydrofuro[3,4-d][1,3]dioxol-6-yl]-(3,4-dichlorophenyl)methanone (92b) (1.82 g, 3.87 mmol, 86.5% yield) as a light yellow solid. LCMS (M+H⁺) 469/471/473 c) Synthesis of (1R)-1-[(3aR,4R,6S,6aR)-4-(6-chloropurin-9-yl)-2,2-dimethyl-3a,4,6,6a-tetrahydrofuro[3,4-d][1,3]dioxol-6-yl]-1-(3,4-dichlorophenyl)ethanol (92c)

To an ice-cold solution of [(3aR,4R,6S,6aS)-4-(6-chloropurin-9-yl)-2,2-dimethyl-3a,4,6,6a-tetrahydrofuro[3,4-d][1,3]dioxol-6-yl]-(3,4-dichlorophenyl)methanone (92b) (1.82 g, 3.87 mmol) in THF (30 mL) was added a solution of bromo(methyl)magnesium (3 μM, 2.42 mL, 7.75 mmol) dropwise. The resulting mixture was warmed to rt, stirred for 2 hr. LCMS showed the completion of the reaction. The reaction mixture was poured onto ice-cold sat. aq. NH₄Cl solution, which was extracted with EtOAc. The organic layer was washed with brine, dried over Na₂SO₄, filtered and concentrated. The crude product was purified on a 20 g column, which was eluted with 0-50% EA/hexane to give (1R)-1-[(3aR,4R,6S,6aR)-4-(6-chloropurin-9-yl)-2,2-dimethyl-3a,4,6,6a-tetrahydrofuro[3,4-d][1,3]dioxol-6-yl]-1-(3,4-dichlorophenyl)ethanol (92c) (1.5 g, 3.1 mmol, 80% yield) as a light yellow solid and (1S)-1-[(3aR,4R,6S,6aR)-4-(6-chloropurin-9-yl)-2,2-dimethyl-3a,4,6,6a-tetrahydrofuro[3,4-d][1,3]dioxol-6-yl]-1-(3,4-dichlorophenyl)ethanol (171 mg, 0.352 mmol, 9% yield) as a yellow foamy solid. LCMS (M+H⁺) 475/477/479.

d) Synthesis of (2S,3S,4R,5R)-2-[(1R)-1-(3,4-dichlorophenyl)-1-hydroxy-ethyl]-5-[(6Z)-6-methoxyimino-1H-purin-9-yl]tetrahydrofuran-3,4-diol hydrochloride (Ex. 92)

A mixture of N-ethyl-N-isopropyl-propan-2-amine (0.14 mL, 0.8200 mmol), 0-Methylhydroxylamine hydrochloride (72.39 mg, 0.8200 mmol), (1R)-1-[(3aR,4R,6S,6aR)-4-(6-chloropurin-9-yl)-2,2-dimethyl-3a,4,6,6a-tetrahydrofuro[3,4-d][1,3]dioxol-6-yl]-1-(3,4-dichlorophenyl)ethanol (92c) (200.mg, 0.4100 mmol) in IPA (5 mL) was purged with N₂, sealed and irradiated with MW at 120 C for 20 min. LCMS showed the consumption of the st.m. The reaction mixture was diluted with DCM and water. The aq. layer was extracted with DCM several times until not floating yellow solids visible. All organic layers were combined, dried over Na₂SO₄, filtered and concentrated to give crude (1R)-1-[(3aR,4R,6S,6aR)-4-[(6Z)-6-methoxyimino-1H-purin-9-yl]-2,2-dimethyl-3a,4,6,6a-tetrahydrofuro[3,4-d][1,3]dioxol-6-yl]-1-(3,4-dichlorophenyl)ethanol (200 mg, 0.4029 mmol, 98% yield) as a light yellow solid A mixture of (1R)-1-[(3aR,4R,6S,6aR)-4-[(6Z)-6-methoxyimino-1H-purin-9-yl]-2,2-dimethyl-3a,4,6,6a-tetrahydrofuro[3,4-d][1,3]dioxol-6-yl]-1-(3,4-dichlorophenyl)ethanol (200.mg, 0.4000 mmol) and HCl (0.16 mL, 2.16 mmol) in Methanol (2 mL) (pre-mixed) was stirred at RT overnight. White precipitate was formed, filtered and dried to give (2S,3S,4R,5R)-2-[(1R)-1-(3,4-dichlorophenyl)-1-hydroxy-ethyl]-5-[(6Z)-6-methoxyimino-1H-purin-9-yl]tetrahydrofuran-3,4-diol hydrochloride (Ex. 92) (148 mg, 0.29 mmol, 72% yield). HPLC 97% pure; LCMS 456.0/458.0; $^1$H NMR (400 MHz, CD$_3$OD) δ 7.75 (d, J=2.0 Hz, 1H), 7.53-7.45 (m, 2H), 6.05 (d, J=6.8 Hz), 4.67 (dd, J=6.8, 5.2 Hz, 1H), 4.32 (d, J=2.0 Hz, 1H), 4.00 (m, 1H), 3.98 (s, 3H), 1.58 (s, 3H).

Example 92A. (2S,3S,4R,5R)-2-[(1R)-1-(3,4-dichlorophenyl)-1-hydroxy-ethyl]-5-[(6Z)-6-methoxyimino-1H-purin-9-yl]tetrahydrofuran-3,4-diol, free base crystals (92A)

9.5 g of (2S,3S,4R,5R)-2-[(1R)-1-(3,4-dichlorophenyl)-1-hydroxy-ethyl]-5-[(6Z)-6-methoxyimino-1H-purin-9-yl] tetrahydrofuran-3,4-diol, white solid, with 99.0% purity was suspended in deionized water (30.0 mL) and stirred at 100° C. for 2 h, cooled, filtered, dried in vacuum to give 92A (8.3 g) as a white crystalline solid, m.p. 238.5° C.

Example 93. (2S,3S,4R,5R)-2-[(1R)-Example 931-(3,4-dichlorophenyl)-1-hydroxy-ethyl]-5-[(6Z)-6-ethoxyimino-1H-purin-9-yl]tetrahydrofuran-3,4-diol (93)

Example 93 was prepared following the similar procedures as Ex. 92 except for substituting O-Methylhydroxylamine hydrochloride with O-Ethylhydroxylamine hydrochloride. $^1$H NMR (400 MHz, DMSO-d$_6$+D$_2$O) δ 8.45 (s, 1H), 8.09 (s, 1H), 7.77-7.78 (m, 1H), 7.61-7.63 (m, 1H), 7.51-7.54 (m, 1H), 5.88-5.90 (m, 1H), 4.47-4.50 (m, 1H), 4.18-4.19 (m, 1H), 4.04-4.09 (q, 2H), 3.72-3.73 (m, 1H), 1.45 (s, 3H), 1.27-1.30 (t, 3H).

Example 94. (2S,3S,4R,5R)-2-[(1R)-1-(4-chloro-3-methylphenyl)-1-hydroxy-ethyl]-5-[(6Z)-6-methoxyimino-1H-purin-9-yl]tetrahydrofuran-3,4-diol (94)

Example 94 (HCl salt) was prepared following the similar procedures as Ex. 92 except for substituting 3,4-dichlorophenylmagnesium bromide with 4-chloro-3-methylphenylmagnesium bromide. $^1$H NMR (600 MHz, Methanol-d4) δ 8.76 (s, 1H), 8.31 (s, 1H), 7.48 (d, J=2.1 Hz, 1H), 7.39-7.29 (m, 2H), 6.10 (d, J=6.9 Hz, 1H), 4.68 (dd, J=5.2, 6.9 Hz, 1H), 4.34 (d, J=1.9 Hz, 1H), 4.03 (dd, J=1.9, 5.2 Hz, 1H), 4.01 (s, 3H), 2.40 (s, 3H), 1.58 (s, 3H).

Example 95. (2S,3S,4R,5R)-2-[(1R)-1-(4-chloro-3-methylphenyl)-1-hydroxy-ethyl]-5-[(6Z)-6-ethoxyimino-1H-purin-9-yl]tetrahydrofuran-3,4-diol (95)

Example 95 (HCl salt) was prepared following the similar procedures as Ex. 94 except for substituting O-Methylhydroxylamine hydrochloride with O-Ethylhydroxylamine hydrochloride. $^1$H NMR (600 MHz, Methanol-d$_4$) δ 8.76 (s, 1H), 8.36 (s, 1H), 7.49 (d, J=2.1 Hz, 1H), 7.40-7.32 (m, 2H), 6.12 (d, J=6.9 Hz, 1H), 4.68 (dd, J=5.2, 6.9 Hz, 1H), 4.34 (d, J=1.9 Hz, 1H), 4.25 (q, J=7.0 Hz, 2H), 4.03 (dd, J=1.9, 5.2 Hz, 1H), 2.40 (s, 3H), 1.58 (s, 3H), 1.45 (t, J=7.0 Hz, 3H).

Example 96. 7-((2R,3R,4S,5S)-5-((R)-1-(4-chloro-3-fluorophenyl)-1-hydroxyethyl)-3,4-dihydroxytetrahydrofuran-2-yl)-1,5,6,7-tetrahydro-4H-pyrrolo[2,3-d]pyrimidin-4-one O-methyl oxime (96)

Example 96 (TFA salt) was prepared similarly to that of Ex. 60. $^1$H NMR (400 MHz, Methanol-d4) δ 8.24 (s, 1H), 7.68 (d, J=3.7 Hz, 1H), 7.51-7.43 (m, 2H), 7.35 (dd, J=2.0, 8.5 Hz, 1H), 6.73 (d, J=3.6 Hz, 1H), 6.16 (d, J=7.5 Hz, 1H), 4.60 (dd, J=5.3, 7.5 Hz, 1H), 4.24 (d, J=1.5 Hz, 1H), 4.00-3.90 (m, 4H), 1.55 (s, 3H).

Example 97. 7-((2R,3R,4S,5R)-5-((R)-(4-chlorophenyl)(hydroxy)methyl)-3,4-dihydroxytetrahydrofuran-2-yl)-1,7-dihydro-4H-pyrrolo[2,3-d]pyrimidin-4-one O-ethyl oxime (97)

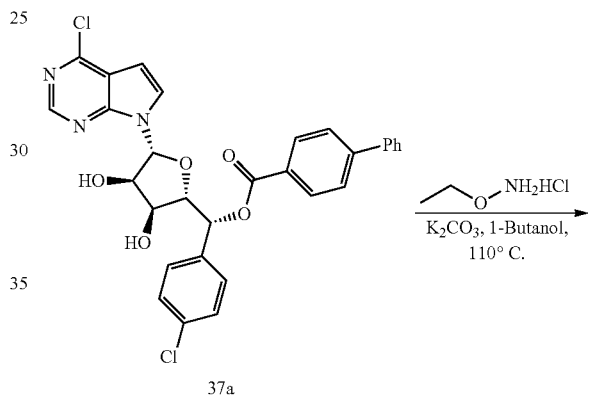

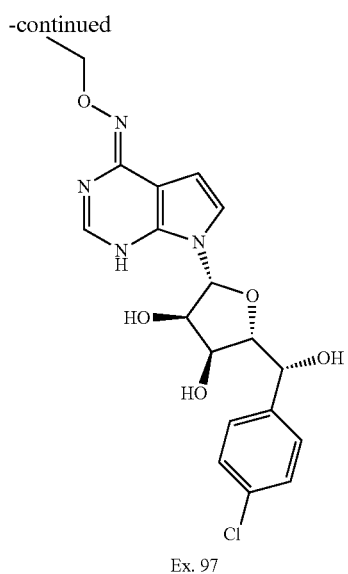

Ex. 97 a) Synthesis of [(R)-(4-chlorophenyl)-[(2S,3S,4R,5R)-5-[(4Z)-4-ethoxyimino-1H-pyrrolo[2,3-d]pyrimidin-7-yl]-3,4-dihydroxy-tetrahydrofuran-2-yl]methyl] 4-phenylbenzoate (97a)

To a solution of [(R)-(4-chlorophenyl)-[(2S,3S,4R,5R)-5-(4-chloropyrrolo[2,3-d]pyrimidin-7-yl)-3,4-dihydroxy-tetrahydrofuran-2-yl]methyl] 4-phenylbenzoate (37a) (390.0 mg, 0.68 mmol) in 1-Butanol (20.0 mL) was added Ethoxyamine hydrochloride (330.0 mg, 3.38 mmol) and Triethylamine (0.8 mL, 5.41 mmol). The reaction mixture was stirred at 110° C. for 120 h. The reaction mixture was concentrated to give crude which was purified by silica gel column chromatography (EA:PE=5:1 to 1:1) to give [(R)-(4-chlorophenyl)-[(2S,3S,4R,5R)-5-[(4Z)-4-ethoxyimino-1H-pyrrolo[2,3-d] pyrimidin-7-yl]-3,4-dihydroxy-tetrahydrofuran-2-yl]methyl] 4-phenylbenzoate (97a) (40.0 mg, 0.07 mmol, 9.6% yield) as a yellow solid. LCMS [M+H]: 601.4.

b) Synthesis of (2R,3S,4R,5R)-2-[(R)-(4-chlorophenyl)-hydroxy-methyl]-5-[(4Z)-4-ethoxyimino-1H-pyrrolo[2,3-d]-pyrimidin-7-yl]tetrahydrofuran-3,4-diol hydrochloride (97)

To a mixture of Hydrazine hydrate (1.0 mL, 20.58 mmol) and Ethanol (1.0 mL) was added [(R) -(4-chlorophenyl)-[(2S,3S,4R,5R)-5-[(4Z)-4-ethoxyimino-1H-pyrrolo[2,3-d] pyrimidin-7-yl]-3,4-dihydroxy-tetrahydrofuran-2-yl] methyl] 4-phenylbenzoate (97a) (40.0 mg, 0.07 mmol). The reaction mixture was stirred at 30° C. for 2 h. The mixture reaction was concentrated to give crude product which was purified by prep-HPLC, eluted with $CH_3CN$ in $H_2O$ (0.1% TFA) from 10.0% to 95.0% to obtain (2R,3S,4R,5R)-2-[(R)-(4-chlorophenyl)-hydroxy-methyl]-5-[(4Z)-4-ethoxyimino-1H-pyrrolo[2,3-d]-pyrimidin-7-yl]tetrahydrofuran-3,4-diol hydrochloride (97) (15.9 mg, 0.03 mmol, 51.6% yield) as a white solid. LCMS [M+H]: 421.2. $^1$H NMR (400 MHz, DMSO-$d_6$): δ 8.05 (s, 1H), 7.57 (s, 1H), 7.35-7.42 (m, 4H), 6.71 (s, 1H), 6.03 (d, J=8.0 Hz, 1H), 4.77 (d, J=4.0 Hz, 1H), 4.49-4.52 (m, 1H), 4.09 (d, J=4 Hz, 1H), 4.01-4.07 (m, 2H), 3.97-3.99 (m, 1H), 1.28-1.32 (m, 3H). $^1$H NMR (400 MHz, DMSO-$d_6$+$D_2O$): δ 8.20 (s, 1H), 7.62 (s, 1H), 7.36-7.42 (m, 4H), 6.74 (s, 1H), 6.06 (d, J=8.0 Hz, 1H), 4.77 (d, J=4.0 Hz, 1H), 4.49-4.52 (m, 1H), 4.10 (d, J=4 Hz, 1H), 4.04-4.07 (m, 2H), 4.00-4.01 (d, J=4.0 Hz, 1H), 1.29-1.33 (m, 3H).

Example 98. 7-((2R,3R,4S,5R)-3,4-dihydroxy-5-((R)-hydroxy(3-methyl-4-(trifluoromethyl)phenyl)methyl)tetrahydrofuran-2-yl)-1,7-dihydro-4H-pyrrolo[2,3-d]pyrimidin-4-one O-methyl oxime (98)

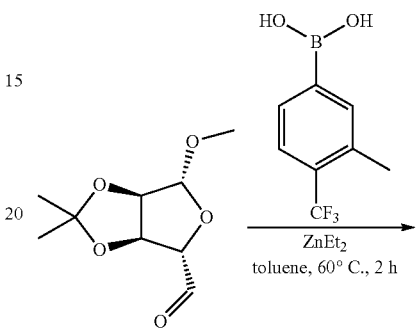

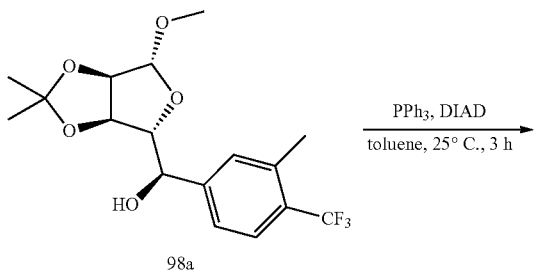

98a

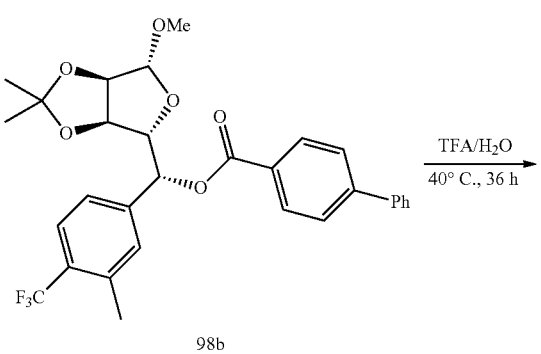

98b

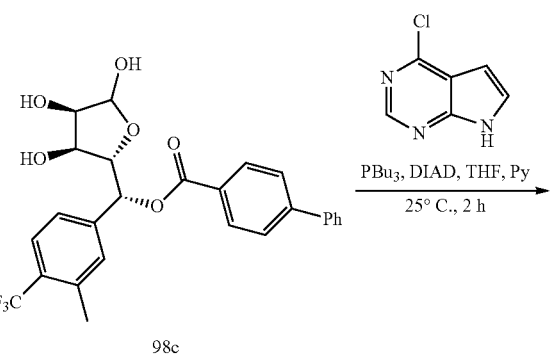

98c

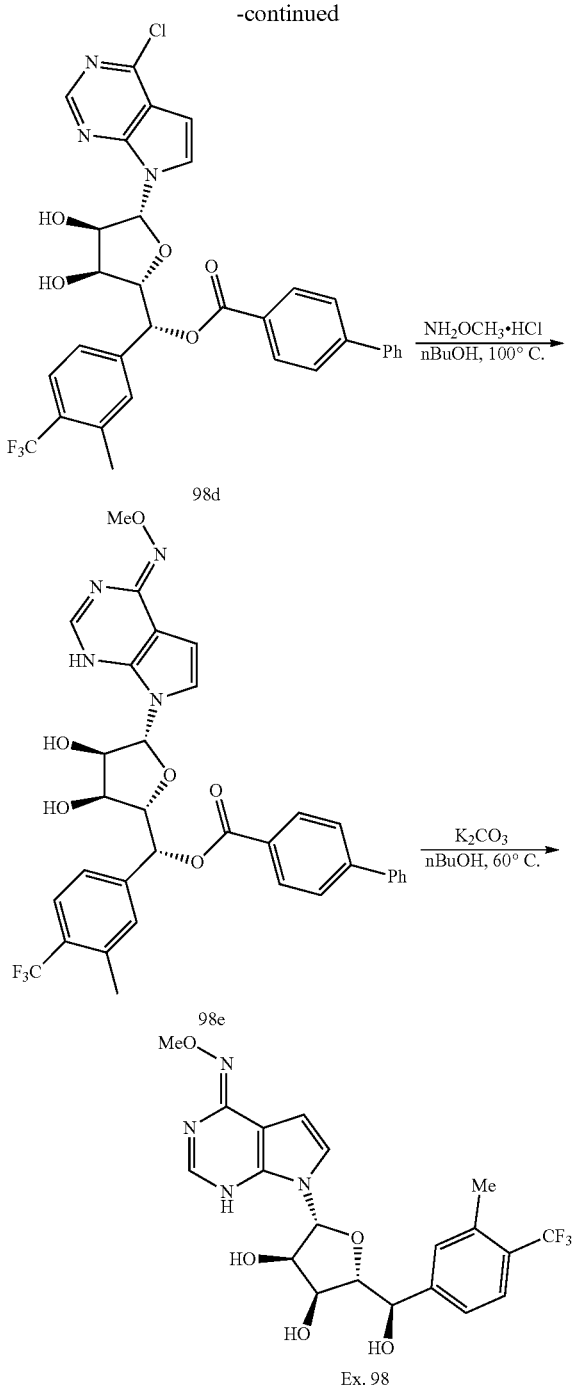

a) Synthesis of (S)-[(3aR,4R,6R,6aR)-4-methoxy-2,
2-dimethyl -3a,4,6,6a-tetrahydrofuro[3,4-d][1,3]
dioxol-6-yl]-[3-methyl-4-(trifluoromethyl)phenyl]
methanol (98a)

To a solution of [3-methyl-4-(trifluoromethyl)phenyl]boronic acid (484.1 mg, 2.37 mmol) in Toluene (10.0 mL), Diethylzine (3.6 mL, 7.12 mmol) was added slowly at 25° C. The mixture was stirred at 60° C. for 1 h. (3aR,4R,6S,6aR)-4-methoxy-2,2-dimethyl-3a,4,6,6a-tetrahydrofuro[3,4-d][1,3]dioxole-6-carbaldehyde (400.0 mg, 1.98 mmol) in Toluene (6.0 mL) was added slowly at 60° C. The mixture was stirred at 60° C. for 2 h. TLC (PE:EA=5:1) showed the reaction was completed. Water (4.0 mL) was added to quench the reaction. The mixture was filtered. The filtrate was concentrated and purified by reversed-phase combi-flash, eluted with CH$_3$CN in H$_2$O (neutral condition) from 5.0% to 85.0% to give (S)-[(3aR,4R,6R,6aR)-4-methoxy-2,2-dimethyl -3a,4,6,6a-tetrahydrofuro[3,4-d][1,3]dioxol-6-yl]-[3-methyl-4-(trifluoromethyl)phenyl]methanol (98a) (350.0 mg, 0.96 mmol, 48.6% yield) as a white solid. $^1$H NMR (400 MHz, DMSO-d$_6$): δ 7.64 (d, J=8.0 Hz, 1H), 7.45 (s, 1H), 7.39 (d, J=8.0 Hz, 1H), 5.38 (d, J=5.6 Hz, 1H), 4.96 (s, 1H), 4.48-4.56 (m, 3H), 4.19 (d, J=8.4 Hz, 1H), 3.32 (s, 3H), 2.45 (s, 3H), 1.34 (s, 3H), 1.17 (s, 3H). 19F NMR (376 MHz, DMSO-d$_6$): δ −59.99 (s, 3 F).

b) Synthesis of [(R)-[(3aR,4R,6R,6aR)-4-methoxy-2,2-dimethyl-3a,4,6,6a-tetrahydrofuro[3,4-d][1,3]dioxol-6-yl]-[3-methyl-4-(trifluoromethyl)phenyl]methyl]-4-phenylbenzoate(98b)

To a mixture of (S)-[(3aR,4R,6R,6aR)-4-methoxy-2,2-dimethyl-3a,4,6,6a-tetrahydrofuro[3,4-d][1,3]dioxol-6-yl]-[3-methyl-4-(trifluoromethyl)phenyl]methanol(98a)(3200.0 mg, 8.83 mmol), 4-phenylbenzoic acid (2625.9 mg, 13.25 mmol) and Triphenylphosphine (3474.6 mg, 13.25 mmol) in Toluene (50.0 mL) was added DIAD (2.6 mL, 13.25 mmol) at 0° C. The mixture was stirred at 25° C. for 3 h. The mixture was concentrated and purified by reversed-phase combi-flash, eluted with CH$_3$CN in H$_2$O (neutral) from 5.0% to 95.0% to give [(R)-[(3aR,4R,6R,6aR)-4-methoxy-2,2-dimethyl-3a,4,6,6a-tetrahydrofuro[3,4-d][1,3]dioxol-6-yl]-[3-methyl-4-(trifluoromethyl)phenyl]methyl]-4-phenylbenzoate (98b) (2700.0 mg, 4.98 mmol, 56.4% yield) as a white solid. $^1$H NMR (400 MHz, DMSO-d$_6$): δ 8.12 (d, J=8.0 Hz, 2H), 7.86 (d, J=8.0 Hz, 2H), 7.52 (d, J=8.0 Hz, 2H), 7.70 (d, J=8.0 Hz, 1H), 7.62 (s, 1H), 7.50-7.56 (m, 3H), 7.45 (d, J=7.6 Hz, 1H), 5.90 (d, J=8.4 Hz, 1H), 5.01 (d, J=6.0 Hz, 1H), 4.93 (s, 1H), 4.67-4.71 (m, 2H), 3.15 (s, 3H), 2.47 (s, 3H), 1.40 (s, 3H), 1.27 (s, 3H). $^{19}$F NMR (376 MHz, DMSO-d6): δ −60.22 (s, 3F).

c) Synthesis of [(R)-[3-methyl-4-(trifluoromethyl)phenyl]-[(2S,3S,4R,5R)-3,4,5-trihydroxytetrahydrofuran-2-yl]methyl] 4-phenylbenzoate (98c)

A mixture of [(R)-[(3aR,4R,6R,6aR)-4-methoxy-2,2-dimethyl-3a,4,6,6a-tetrahydrofuro[3,4-d][1,3] dioxol-6-yl]-[3-methyl-4-(trifluoromethyl)phenyl]methyl] 4-phenylbenzoate (98b) (2700.0 mg, 4.98 mmol) in water (30.0 mL, 1664.8 mmol) and TFA (30.0 mL, 405.19 mmol) was heated to 40° C. and stirred for 36 h. LCMS showed the reaction was completed. The mixture was concentrated and purified by reversed-phase combi-flash, eluted with CH$_3$CN in H$_2$O (neutral) from 5.0% to 95.0% to give [(R)-[3-methyl-4-(trifluoromethyl)phenyl]-[(2S,3S,4R,5R)-3,4,5-trihydroxytetrahydrofuran-2-yl]methyl] 4-phenylbenzoate (98c) (1600.0 mg, 3.28 mmol, 65.8% yield) as white solid. LCMS [M−H]: 487.1.

d) Synthesis of [(R)-[(2S,3S,4R,5R)-5-(4-chloropyrrolo[2,3-d]pyrimidin-7-yl)-3,4-dihydroxy-tetrahydrofuran-2-yl]-[3-methyl-4-(trifluoromethyl)phenyl]methyl] 4-phenylbenzoate (98d)

To a solution of 4-Chloro-7H-pyrrolo[2,3-d]pyrimidine (380.4 mg, 2.48 mmol) in dry THF (60.0 mL) was added Pyridine (0.2 mL, 2.48 mmol), Tributylphosphane (1.2 mL, 4.95 mmol) and DIAD (1.1 mL, 5.45 mmol) at 25° C. [(R)-[3-methyl-4-(trifluoromethyl)phenyl]-[(2S,3S,4R,5R)-3,4,5-trihydroxytetrahydrofuran-2-yl]methyl] 4-phenylbenzoate (98c) (1210.0 mg, 2.48 mmol)) in dry THF (20.0 mL) was added at once. The reaction mixture was stirred at 25° C. for 2 h. LCMS showed the reaction was completed. The reaction mixture was purified by reversed-phase combi-flash, eluted with CH$_3$CN in H$_2$O (neutral condition) from 10.0% to 95.0% to afford [(R)-[(2S,3S,4R,5R)-5-(4-chloro-pyrrolo[2,3-d]pyrimidin-7-yl)-3,4-dihydroxy-tetrahydro-furan-2-yl]-[3-methyl-4-(trifluoromethyl)phenyl]methyl] 4-phenylbenzoate (98d) (1070.0 mg, 1.71 mmol, 69.2% yield) as a pale yellow solid. LCMS [M+H]: 624.3.

e) Synthesis of [(R)-[(2S,3S,4R,5R)-3,4-dihydroxy-5-[(4Z)-4-methoxyimino-1H-pyrrolo[2,3-d]pyrimidin-7-yl]tetrahydrofuran-2-yl]-[3-methyl-4-(trifluoromethyl)phenyl]methyl] 4-phenylbenzoate (98e)

To a solution of [(R)-[(2S,3S,4R,5R)-5-(4-chloropyrrolo[2,3-d]pyrimidin-7-yl)-3,4-dihydroxy-tetra hydrofuran-2-yl]-[3-methyl-4-(trifluoromethyl)phenyl]methyl] 4-phenyl-benzoate (98d) (520.0 mg, 0.83 mmol) in 1-Butanol (20.0 mL), Potassium carbonate (921.4 mg, 6.67 mmol) and Methoxy ammonium chloride (348.0 mg, 4.17 mmol) was added. The mixture was stirred at 100° C. for 6 h. LCMS showed the reaction was completed. The mixture was filtered and concentrated to give crude product which was used for the next step directly.

f) Synthesis of (2R,3S,4R,5R)-2-[(R)-hydroxy-[3-methyl-4-(trifluoromethyl)phenyl]methyl]-5-[(4Z)-4-methoxyimino-1H-pyrrolo[2,3-d]pyrimidin-7-yl]tetrahydrofuran-3,4-diol hydrochloride (98)

To a solution of [(R)-[(2S,3S,4R,5R)-3,4-dihydroxy-5-[(4Z)-4-methoxyimino-1H-pyrrolo[2,3-d] pyrimidin-7-yl]tetrahydrofuran-2-yl]-[3-methyl-4-(trifluoromethyl)phenyl]methyl] 4-phenylbenzoate (98e) (520.0 mg, 0.60 mmol) in 1-Butanol (30.0 mL), Potassium carbonate (249.4 mg, 1.80 mmol) was added. The mixture was stirred at 60° C. for 2 h. LCMS showed the reaction was completed. The mixture was filtered and washed with EA (50.0 mL). The combined filtrate was concentrated and acidified with 1 μM HCl to pH 2 and purified by prep-HPLC, eluted with CH$_3$CN in H$_2$O (0.1% TFA) from 5.0% to 95.0% to give the solution of the desired product. 5 drops con. HCl was added to the solution and the solution was lyophilized to give (2R,3S,4R,5R)-2-[(R)-hydroxy-[3-methyl-4-(trifluoromethyl)phenyl]methyl]-5-[(4Z)-4-methoxyimino-1H-pyrrolo[2,3-d]pyrimidin-7-yl]tetrahydrofuran-3,4-diol hydrochloride (98) (79.4 mg, 0.16 mmol, 26.8% yield) as a yellow solid. $^1$H NMR (400 MHz, DMSO-d$_6$): δ 8.13 (s, 1H), 7.75-7.62 (m, 2H), 7.45 (s, 1H), 7.40 (d, J=8.0 Hz, 1H), 6.67 (s, 1H), 6.05 (d, J=7.2 Hz, 1H), 4.82 (d, J=5.2 Hz, 1H), 4.49-4.53 (m, 1H), 4.10 (d, J=4.8 Hz, 1H), 4.04 (d, J=4.8 Hz, 1H), 3.83 (s, 3H), 2.41 (s, 3H). $^1$H NMR (400 MHz, DMSO-d6+D$_2$O). δ 8.13 (s, 1H), 7.62 (d, J=7.6 Hz, 1H), 7.53 (d, J=3.6 Hz, 1H), 7.39-7.43 (m, 2H), 6.64 (d, J=3.6 Hz, 1H), 6.05 (d, J=7.6 Hz, 1H), 4.82 (d, J=4.8 Hz, 1H), 4.49-4.53 (m, 1H), 4.11 (d, J=5.2 Hz, 1H), 4.07 (d, J=4.8 Hz, 1H), 3.83 (s, 3H), 2.41 (s, 3H). $^{19}$F NMR (376 MHz, DMSO-d$_6$): δ −59.93 (s, 3F).

Example 99. 7-((2R,3R,4S,5S)-5-((R)-1-(3,4-dichlorophenyl)-1-hydroxyethyl)-3,4-dihydroxytetrahydrofuran-2-yl)-1,7-dihydro-4H-pyrrolo[2,3-d]pyrimidin-4-one O-ethyl oxime (99)

Example 99 was prepared similarly to that of Example 60. $^1$H NMR (400 MHz, DMSO-d$_6$): δ 8.14 (br s, 1H), 7.77 (d, J=1.2 Hz, 1H), 7.62-7.51 (m, 3H), 6.67 (br s, 1H), 6.01 (br s, 1H), 4.42 (br s, 1H), 4.10 (d, J=0.8 Hz, 1H), 4.04 (m, 2H), 3.71 (d, J=3.2 Hz, 1H), 1.44 (s, 3H), 1.30 (t, J=4.8 Hz, 3H).

Example 100. 7-((2R,3R,4S,5R)-5-((R)-(3,4-dichlorophenyl)(hydroxy)methyl)-3,4-dihydroxytetrahydrofuran-2-yl)-5-(2-hydroxyethyl)-1,5-dihydro-4H-7l4-pyrrolo[2,3-d]pyrimidin-4-one O-methyl oxime (100)

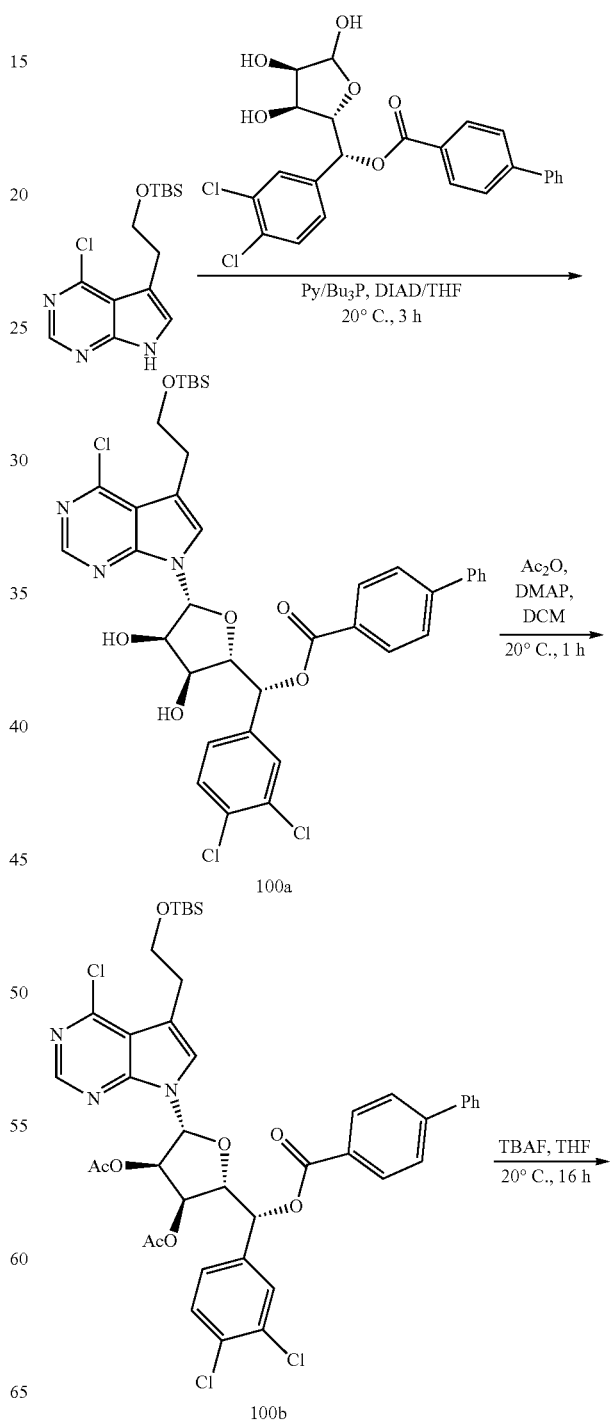

269
-continued

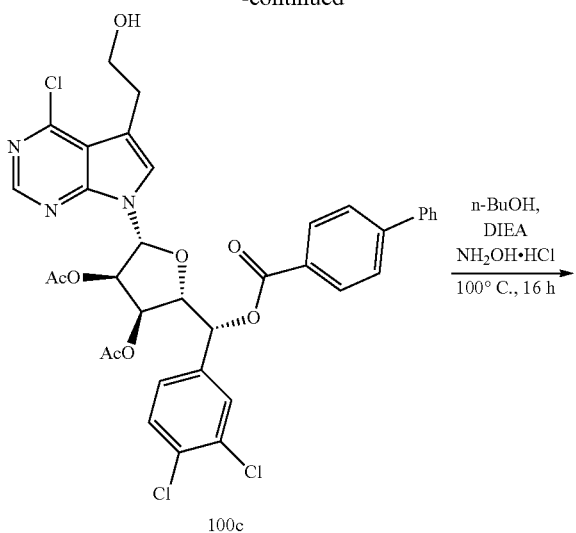

100c n-BuOH, DIEA
NH₂OH·HCl
―――――――→
100° C., 16 h

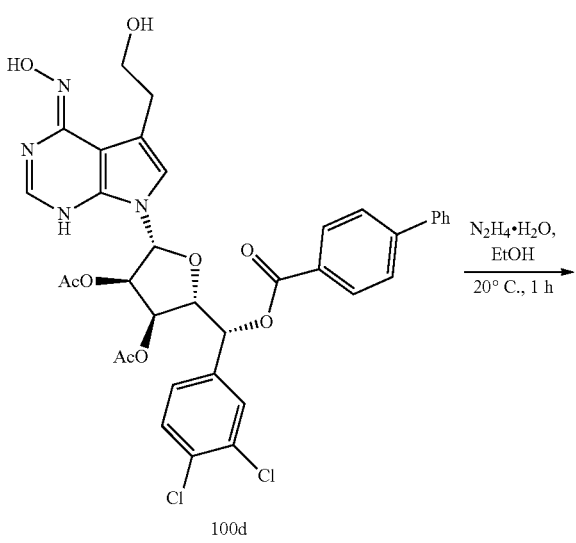

100d

N₂H₄·H₂O, EtOH
―――――→
20° C., 1 h

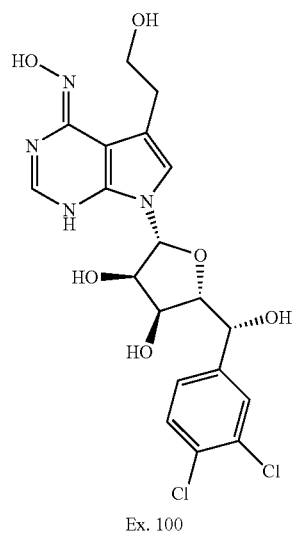

Ex. 100

270 a) Synthesis of [(R)-[(2S,3S,4R,5R)-5-[5-[2-[tert-butyl(dimethyl)silyl]oxyethyl]-4-chloro-pyrrolo[2,3-d]pyrimidin-7-yl]-3,4-dihydroxy-tetrahydrofuran-2-yl]-(3,4-dichlorophenyl)methyl] 4-phenylbenzoate (100a)

To a solution of [(R)-(3,4-dichlorophenyl)-[(2S,3S,4R)-3,4,5-trihydroxytetrahydrofuran-2-yl]methyl] 4-phenylbenzoate (2.00 g, 4.21 mmol) in THF (35.0 mL) was added PBu₃ (2.1 mL, 8.42 mmol), pyridine (0.3 mL, 4.21 mmol), DIAD (1.6 mL, 8.42 mmol) and tert-butyl-[2-(4-chloro-7H-pyrrolo[2,3-d]pyrimidin-5-yl)ethoxy]-dimethyl-silane (1.31 g, 4.21 mmol) under N₂. The mixture was stirred at 20° C. for 3 h. The solvent was removed in vacuum to give crude product which was purified by silica chromatography (PE:EA=10:1 to 3:1 to give the [(R)-[(2S,3S,4R,5R)-5-[5-[2-[tert-butyl(dimethyl)silyl]oxyethyl]-4-chloro-pyrrolo[2,3-d]pyrimidin-7-yl]-3,4-dihydroxy-tetrahydrofuran-2-yl]-(3,4-dichlorophenyl)methyl] 4-phenylbenzoate (100a) (1.20 g, 1.56 mmol, 37.1% yield) as a yellow solid. LCMS [M+H]: 768.2.

b) Synthesis of [(R)-[(2R,3R,4R,5R)-3,4-diacetoxy-5-[5-[2-[tert-butyl(dimethyl)silyl]oxyethyl]-4-chloro-pyrrolo[2,3-d]pyrimidin-7-yl]tetrahydrofuran-2-yl]-(3,4-dichlorophenyl)methyl] 4-phenylbenzoate (100b)

To a solution of [(R)-[(2S,3S,4R,5R)-5-[5-[2-[tert-butyl(dimethyl)silyl]oxyethyl]-4-chloro-pyrrolo [2,3-d]pyrimidin-7-yl]-3,4-dihydroxy-tetrahydrofuran-2-yl]-(3,4-dichlorophenyl)methyl]4-phenylbenzoate (100a) (1.20 g, 1.56 mmol) in DCM (15.0 mL) was added Pyridine (0.6 mL, 7.80 mmol), DMAP (19.0 mg, 0.16 mmol) and Ac₂O (0.80 g, 7.80 mmol). The mixture was stirred at 20° C. for 1 h. The solvent was removed in vacuum and EA (100.0 mL) was added. The mixture was washed with NH₄Cl solution (50.0 mL), brine (50.0 mL), dried over Na₂SO₄, concentrated in vacuum to give [(R)-[(2R,3R,4R,5R)-3,4-diacetoxy-5-[5-[2-[tert-butyl(dimethyl)silyl]oxyethyl]-4-chloro-pyrrolo[2,3-d]pyrimidin-7-yl]tetrahydrofuran-2-yl]-(3,4-dichlorophenyl)methyl] 4-phenylbenzoate (100b) (1.20 g, 1.40 mmol, 90.1% yield) as a white solid. LCMS [M+H]: 852.2.

c) Synthesis of [(R)-[(2R,3R,4R,5R)-3,4-diacetoxy-5-[4-chloro-5-(2-hydroxyethyl)pyrrolo[2,3-d]pyrimidin-7-yl]tetrahydrofuran-2-yl]-(3,4-dichlorophenyl)methyl]4-phenylbenzoate (100c)

To a solution of [(R)-[(2R,3R,4R,5R)-3,4-diacetoxy-5-[5-[2-[tert-butyl(dimethyl)silyl]oxyethyl]-4-chloro-pyrrolo[2,3-d]pyrimidin-7-yl]tetrahydrofuran-2-yl]-(3,4-dichlorophenyl)methyl]4-phenylbenzoate (100b) (1.20 g, 1.41 mmol) in THF (10.0 mL) was added TBAF (0.5 mL, 4.0 μM, 2.11 mmol). The mixture was stirred at 20° C. for 16 h. The solvent was removed in vacuum and the residue was purified by silica chromatography (PE:EA=10:1 to 2:1 to give [(R)-[(2R,3R,4R,5R)-3,4-diacetoxy-5-[4-chloro-5-(2-hydroxyethyl)pyrrolo[2,3-d]pyrimidin-7-yl]tetrahydrofuran-2-yl]-(3,4-dichlorophenyl)methyl] 4-phenylbenzoate (100c) (0.80 g, 1.08 mmol, 76.9% yield) as a gray solid. LCMS [M+H]: 738.1.

d) Synthesis of [(R)-(3,4-dichlorophenyl)-[(2S,3S,4R,5R) -3,4-dihydroxy-5-[(4Z)-5-(2-hydroxyethyl)-4-methoxyimino-1H-pyrrolo[2,3-d]pyrimidin-7-yl]tetrahydrofuran-2-yl]methyl] 4-phenylbenzoate (100d)

To a solution of [(R)-[(2R,3R,4R,5R)-3,4-diacetoxy-5-[4-chloro-5-(2-hydroxyethyl)pyrrolo[2,3-d]-pyrimidin-7-yl]

tetrahydrofuran-2-yl]-(3,4-dichlorophenyl)methyl] 4-phenylbenzoate (100c) (0.30 g, 0.41 mmol) in 1-Butanol (6.0 mL) was added DIEA (1.31 g, 10.15 mmol) and O-Methylhydroxylamine hydrochloride (0.68 g, 8.12 mmol). The mixture was stirred at 100° C. for 16 h. The solvent was removed in vacuum to give crude product which was purified by prep-HPLC, eluted with MeCN in H₂O (0.1% TFA) from 5.0% to 80.0%1 to give [(R)-(3,4-dichlorophenyl)-[(2S,3S,4R,5R)-3,4-dihydroxy-5-[(4Z)-5-(2-hydroxyethyl)-4-methoxyimino-1H-pyrrolo[2,3-d]pyrimidin-7-yl]tetrahydrofuran-2-yl]methyl] 4-phenylbenzoate (100d) (40.0 mg, 0.06 mmol, 14.8% yield) as a white solid. LCMS [M+H]: 735.1.

e) Synthesis of (2R,3S,4R,5R)-2-[(R)-(3,4-dichlorophenyl)-hydroxy-methyl]-5-[(4Z)-5-(2-hydroxyethyl)-4-methoxyimino-1H-pyrrolo[2,3-d]pyrimidin-7-yl]tetrahydrofuran-3,4-diol (100)

To a solution of [(R)-(3,4-dichlorophenyl)-[(2S,3S,4R,5R)-3,4-dihydroxy-5-[(4Z)-5-(2-hydroxyethyl)-4-methoxyimino-1H-pyrrolo[2,3-d]pyrimidin-7-yl]tetrahydrofuran-2-yl]methyl]4-phenylbenzoate (100d) (40.0 mg, 0.06 mmol) in Ethanol (2.0 mL) was added N₂H₄.H₂O (15.0 mg, 0.30 mmol). The mixture was stirred at 20° C. for 1 h. The solvent was removed in vacuum to give crude product which was purified by prep-HPLC, eluted with MeCN in H₂O (0.1% TFA) from 10.0% to 70.0% to afford (2R,3S,4R,5R)-2-[(R)-(3,4-dichlorophenyl)-hydroxy-methyl]-5-[(4Z)-5-(2-hydroxyethyl)-4-methoxyimino-1H-pyrrolo[2,3-d]pyrimidin-7-yl]tetrahydrofuran-3,4-diol (Ex. 100) (2.5 mg, 0.005 mmol, 8.4% yield) as a white solid. LCMS [M+H]: 485.3.
¹H NMR (400 MHz, DMSO-d₆): δ 10.87 (s, 1H), 7.59-7.55 (m, 2H), 7.43 (s, 1H), 7.37 (d, J=9.0 Hz, 1H), 6.90 (s, 1H), 6.11 (d, J=4.2 Hz, 1H), 5.81 (d, J=7.5 Hz, 1H), 5.19 (d, J=6.8 Hz, 1H), 5.06 (d, J=3.8 Hz, 1H), 4.75-4.73 (m, 1H), 4.60-4.57 (m, 1H), 4.37-4.36 (m, 1H), 4.02 (brs, 1H), 3.91-3.90 (m, 1H), 3.71 (s, 3H), 3.64-3.59 (m, 2H), 2.75 (t, J=7.0 Hz, 2H).

Example 101. 7-((2R,3R,4S,5R)-5-((R)-(4-chlorophenyl)(hydroxy)methyl)-3,4-dihydroxytetrahydrofuran-2-yl)-5-ethynyl-1,7-dihydro-4H-pyrrolo[2,3-d]pyrimidin-4-one O-methyl oxime (101)

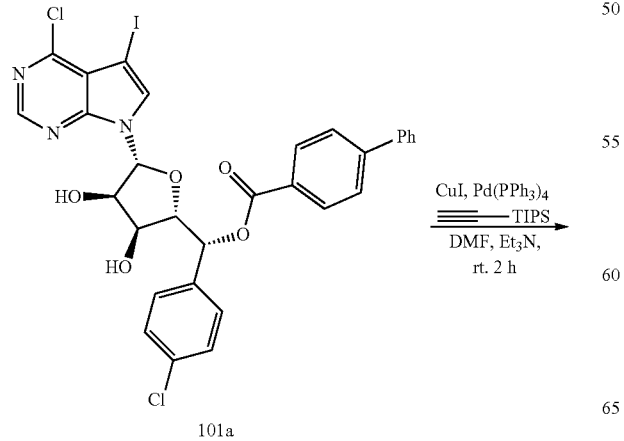

101a

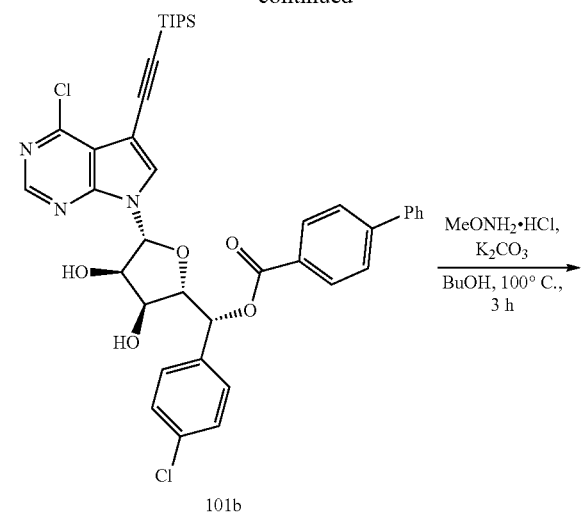

101b

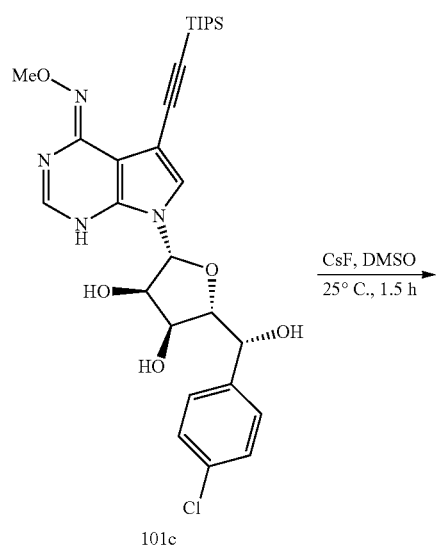

101c

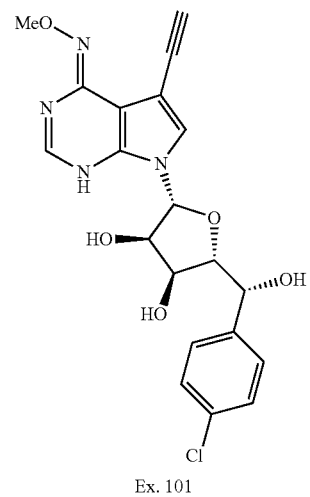

Ex. 101 a) Preparation of [(R)-[(2S,3S,4R,5R)-5-(4-chloro-5-iodo-pyrrolo[2,3-d]pyrimidin-7-yl)-3,4-dihydroxy-tetrahydrofuran-2-yl]-(4-chlorophenyl)methyl] 4-phenylbenzoate (101a)

Compound 101a was prepared similarly to that of Int-2 except for substituting 6-chloropurine with 4-chloro-5-iodo-7H-pyrrolo[2,3-d]pyrimidine.

b) Synthesis of [(R)-(4-chlorophenyl)-[(2S,3S,4R,5R)-5-[4-chloro-5-(2-triisopropylsilylethynyl)pyrrolo[2,3-d]pyrimidin-7-yl]-3,4-dihydroxy-tetrahydrofuran-2-yl]methyl] 4-phenylbenzoate (101b)

To a solution of [(R)-[(2S,3 S,4R,5R)-5-(4-chloro-5-iodo-pyrrolo[2,3-d]pyrimidin-7-yl)-3,4-dihydroxy-tetrahydrofuran-2-yl]-(4-chlorophenyl)methyl] 4-phenylbenzoate (101a) (3.00 g, 3.42 mmol), Pd(PPh$_3$)$_4$ (197.4 mg, 0.17 mmol) and CuI (65.1 mg, 0.34 mmol) in DMF (30.00 mL) was added (Triisopropylsilyl)acetylene (1.15 mL, 5.13 mmol) and TEA (1.42 mL, 10.25 mmol) under N$_2$. The reaction mixture was stirred at 25° C. for 18 h under N$_2$. LCMS showed the reaction was completed. The solution was filtered and the filtrate was poured into water, extracted with EA (100.0 mL×3). The organic layers were washed with brine (50.0 mL×3), dried over anhydrous Na$_2$SO$_4$, filtered and concentrated in vacuum to give crude product which was purified by silica gel column chromatography (PE:EA=10:1 to PE:EA=2:1) to give [(R)-(4-chlorophenyl)-[(2S,3S,4R,5R)-5-[4-chloro-5-(2-triisopropylsilylethynyl)pyrrolo[2,3-d]pyrimidin-7-yl]-3,4-dihydroxy-tetrahydrofuran-2-yl]methyl]4-phenylbenzoate (101b) (1.94 g, 2.31 mmol, 67.5% yield) as a white solid. LCMS [M+H]:756.4.

c) Synthesis of (2R,3S,4R,5R)-2-[(R)-(4-chlorophenyl)-hydroxy-methyl]-5-[(4Z)-4-methoxyimino-5-(2-tri-isopropylsilylethynyl)-1H-pyrrolo[2,3-d]pyrimidin-7-yl]tetrahydrofuran-3,4-diol(101c)

To a solution of [(R)-(4-chlorophenyl)-[(2S,3S,4R,5R)-5-[4-chloro-5-(2-triisopropylsilylethynyl) pyrrolo[2,3-d]pyrimidin-7-yl]-3,4-dihydroxy-tetrahydrofuran-2-yl]methyl] 4-phenylbenzoate (101b) (0.90 g, 0.95 mmol) in 1-Butanol (10.00 mL) was added Methoxyammonium chloride (0.40 g, 4.76 mmol) and K$_2$CO$_3$ (1.18 g, 8.56 mmol). The reaction mixture was stirred at 100° C. for 3 h. LCMS showed the reaction was completed. The reaction mixture was adjusted to pH=7.0 and purified by reversed-phase combi-flash (neutral condition), eluted with MeCN in H$_2$O from 10.0% to 95.0% to give (2R,3S,4R,5R)-2-[(R)-(4-chlorophenyl)-hydroxy-methyl]-5-[(4Z)-4-methoxyimino-5-(2-tri-isopropyl silylethynyl)-1H-pyrrolo[2,3-d]pyrimidin-7-yl]tetrahydrofuran-3,4-diol (101c) (214.0 mg, 0.33 mmol, 34.5% yield) as a white solid. LCMS [M+H]:587.4.

d) Synthesis of (2R,3S,4R,5R)-2-[(R)-(4-chlorophenyl)-hydroxy-methyl]-5-[(4Z)-5-ethynyl-4-methoxyimino-1H-pyrrolo[2,3-d]pyrimidin-7-yl]tetrahydrofuran-3,4-diol (101)

To a solution of (2R,3S,4R,5R)-2-[(R)-(4-chlorophenyl)-hydroxy-methyl]-5-[(4Z)-4-methoxyimino-5-(2-triisopropylsilylethynyl)-1H-pyrrolo[2,3-d]pyrimidin-7-yl]tetrahydrofuran-3,4-diol (101c) (214.0 mg, 0.36 mmol) in DMSO (5.00 mL) and Methanol (0.10 mL) was added CsF (54.3 mg, 0.36 mmol) under N$_2$. The reaction mixture was stirred at 25° C. for 1.5 h. LCMS showed the reaction was completed. The reaction mixture was filtered and the filtrate was purified by prep-HPLC, eluted with MeCN in H$_2$O (0.1% NH$_3$.H$_2$O) from 10.0% to 95.0% to give crude product (95.0 mg, HPLC: 95.6%), the crude product was purified by prep-TLC (DCM:CH$_3$OH=10:1) to give 105.0 mg of crude product and further purified by reversed-phase combi-flash, eluted with MeCN in H$_2$O (neutral condition) from 10.0% to 95.0% to give crude product (95.0 mg, HPLC:95.6%) to give (2R,3 S,4R,5R)-2-[(R)-(4-chlorophenyl)-hydroxy-methyl]-5-[(4Z)-5-ethynyl-4-methoxyimino-1H-pyrrolo[2,3-d]pyrimidin-7-yl]tetrahydrofuran-3,4-diol (Ex. 101) (55.0 mg, 0.13 mmol, 35.7% yield) as a white solid. LCMS [M+H]:431.3. $^1$H NMR (400 MHz, DMSO-d$_6$) δ 11.02 (d, J=3.2 Hz, 1H), 7.50 (s, 1H), 7.47 (d, J=3.6 Hz, 1H), 7.36-7.42 (m, 4H), 6.00 (d, J=4.4 Hz, 1H), 5.85 (d, J=7.6 Hz, 1H), 5.25 (d, J=6.8 Hz, 1H), 5.01 (d, J=4.4 Hz, 1H), 4.76 (t, J=4.4 Hz, 1H), 4.37-4.42 (m, 1H), 4.02 (t, J=4.0 Hz, 1H), 3.94 (d, J=4.4 Hz, 1H), 3.90 (s, 1H), 3.73 (s, 3H). $^1$H NMR (400 MHz, DMSO-d$_6$+D$_2$O) δ 7.51 (s, 1H), 7.46 (s, 1H), 7.37-7.42 (m, 4H), 5.85 (d, J=7.6 Hz, 1H), 4.76 (d, J=4.4 Hz, 1H), 4.38-4.41 (m, 1H), 4.03 (d, J=4.8 Hz, 1H), 3.97 (d, J=4.8 Hz, 1H), 3.87 (s, 1H), 3.74 (s, 3H).

Example 102. 7-((2R,3R,4S,5S)-5-((R)-(4-chloro-3-fluorophenyl)(methoxy)methyl)-3,4-dihydroxytetrahydrofuran-2-yl)-1,7-dihydro-4H-pyrrolo[2,3-d]pyrimidin-4-one O-methyl oxime (102)

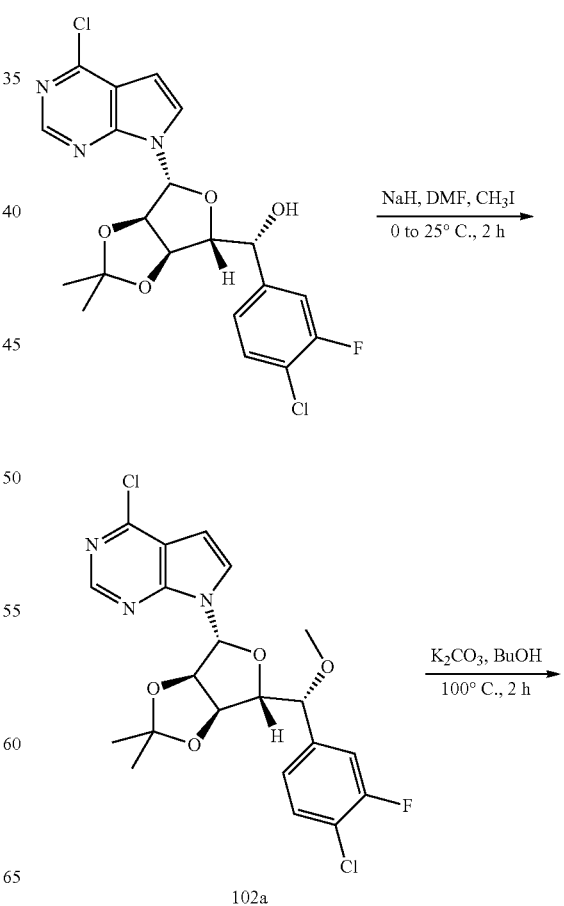

102a

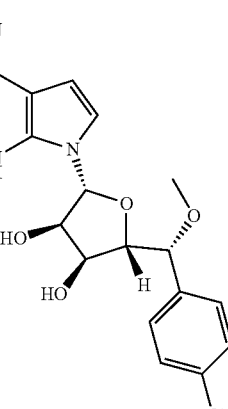

Ex. 102 a) Synthesis of 7-[(3aR,4R,6R,6aR)-6-[(4-chloro-3-fluoro-phenyl)-methoxy-methyl]-2,2-dimethyl-3a,4,6,6a-tetrahydrofuro[3,4-d][1,3]dioxol-4-yl]-4-chloro-pyrrolo[2,3-d]pyrimidine (102a)

To a solution of (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(4-chloro-3-fluoro-phenyl)methanol (800.0 mg, 1.76 mmol) in DMF (12.0 mL) was added iodomethane (299.9 mg, 2.11 mmol), then added sodium hydride (105.66 mg, 2.64 mmol) at 0° C., then the mixture warmed to 25° C. naturally and stirred at 25° C. for 2 h. LCMS showed the reaction was completed. The reaction mixture was added NH$_4$Cl aqueous (20.00 mL), EA (150.00 mL). The reaction mixture was washed with H$_2$O (30.00 mL×4), dried over Na$_2$SO$_4$, filtered and concentrated in vacuum to give crude product which was purified by silica gel column chromatography (PE:EA=12:1) to give 7-[(3aR,4R,6R,6aR)-6-[(4-chloro-3-fluoro-phenyl)-methoxy-methyl]-2,2-dimethyl-3a,4,6,6a-tetrahydrofuro[3,4-d][1,3]dioxol-4-yl]-4-chloro-pyrrolo[2,3-d]pyrimidine (102a) (690.0 mg, 1.47 mmol, 83.7% yield). LCMS [M+H]: 468.3.

b) Synthesis of compound (2S,3S,4R,5R)-2-[(R)-(4-chloro-3-fluoro-phenyl)-methoxy-methyl]-5-[(4Z)-4-methoxyimino-1H-pyrrolo[2,3-d]pyrimidin-7-yl]tetrahydrofuran-3,4-diol hydrochloride (102)

To a solution of 7-[(3aR,4R,6R,6aR)-6-[(R)-(4-chloro-3-fluoro-phenyl)-methoxy-methyl]-2,2-dimethyl-3a,4,6,6a-tetrahydrofuro[3,4-d][1,3]dioxol-4-yl]-4-chloro-pyrrolo[2,3-d]pyrimidine (102a) (250.0 mg, 0.53 mmol) in 1-butanol (8.0 mL) was added O-Methylhydroxylamine hydrochloride (222.9 mg, 2.67 mmol), K$_2$CO$_3$ (589.35 mg, 4.27 mmol). The reaction mixture was stirred at 100° C. for 2 h. LCMS showed the reaction was completed. The reaction mixture was sent to pre-HPLC to give (2S,3S,4R,5R)-2-[(R)-(4-chloro-3-fluoro-phenyl)-methoxy-methyl]-5-[(4Z)-4-methoxyimino-1H-pyrrolo[2,3-d]pyrimidin-7-yl]tetrahydrofuran-3,4-diol hydrochloride (Ex. 102) (120.0 mg, 0.25 mmol, 47.1% yield) as a white solid. LCMS [M+H]: 439.1. H NMR (400 MHz, DMSO-d$_6$+D$_2$O): δ 8.21 (s, 1H), 7.53-7.57 (m, 2H), 7.31-7.34 (m, 1H), 7.20-7.22 (m, 1H), 6.73-6.74 (m, 1H), 6.07-6.09 (m, 1H), 4.46-4.51 (m, 2H), 4.14-4.15 (m, 1H), 3.99-4.00 (m, 1H), 3.85 (s, 3H), 3.24 (s, 3H).

Example 103. 7-((2R,3R,4S,5R)-5-((R)-(3,4-dichlorophenyl)(hydroxy)methyl)-3,4-dihydroxytetrahydrofuran-2-yl)-1,4a,7,7a-tetrahydro-4H-pyrrolo[2,3-d]pyrimidin-4-one O-(2,2,2-trifluoroethyl) oxime (103)

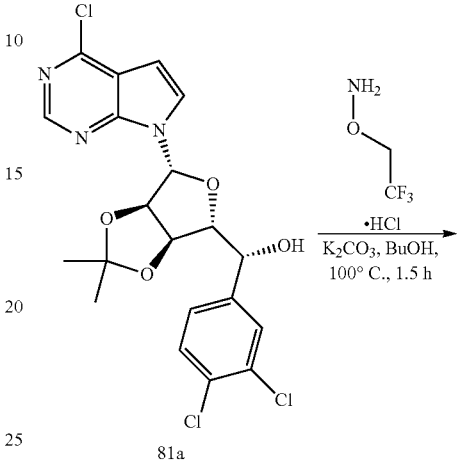

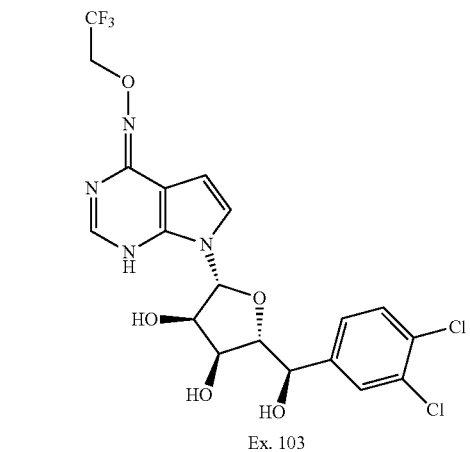

Ex. 103

To a solution of (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]-(3,4-dichlorophenyl)methanol (81a) (199.6 mg, 0.42 mmol) in 1-Butanol (16.0 mL), Potassium carbonate (351.6 mg, 2.54 mmol) was added. The mixture was stirred at 100° C. for 1.5 h. LCMS showed the reaction was completed. The mixture was filtered and concentrated. The residue was purified by prep-HPLC, eluted with CH$_3$CN in H$_2$O (0.1% TFA) from 5.0% to 95.0% to give the TFA salt of the desired product (132.1 mg). The TFA salt was dissolved in CH$_3$CN (3.0 mL) and was added 1 μM HCl aq. (4.0 mL). The solution was concentrated and lyophilized to give (2R,3S,4R,5R)-2-[(R)-(3,4-dichlorophenyl)-hydroxy-methyl]-5-[(4Z)-4-(2,2,2-trifluoroethoxyimino)-1H-pyrrolo[2,3-d]pyrimidin-7-yl]tetrahydrofuran-3,4-diol hydrochloride (Ex. 103) (107.4 mg, 0.20 mmol, 46.4% yield) as an off-white solid. LCMS [M+H]: 509.1. $^1$H NMR (400 MHz, DMSO-d$_6$): δ 7.70 (s, 1H), 7.60 (d, J=1.6 Hz, 1H), 7.57 (d, J=8.4 Hz, 1H), 7.36-7.39 (m, 1H), 7.32 (d, J=3.2 Hz, 1H), 6.41 (s, 1H), 5.93 (d, J=7.6 Hz, 1H), 4.77 (d, J=5.2 Hz, 1H), 4.55 (q, J=9.2 Hz, 2H), 4.43-4.46 (m, 1H), 4.06 (d, J=4.8 Hz, 1H), 3.94 (d, J=4.8 Hz, 1H). $^1$H NMR (400 MHz, DMSO-d6+D$_2$O): δ 7.67 (s, 1H), 7.56-7.59 (m, 2H), 7.36-7.39 (m, 1H), 7.22 (d, J=3.2 Hz, 1H), 6.39 (d, J=3.2 Hz, 1H), 5.90 (d, J=7.2 Hz, 1H), 4.76 (d, J=5.2 Hz, 1H), 4.43-4.54 (m, 3H), 4.07 (d, J=4.8 Hz, 1H), 3.97 (d, J=5.2 Hz, 1H). $^{19}$F NMR (376 MHz, DMSO-d$_6$): δ −71.85 (s, 3F).

Example 104. 7-((2R,3R,4S,5R)-5-((R)-(3,4-dichlorophenyl)(hydroxy)methyl)-3,4-dihydroxytetrahydrofuran-2-yl)-5-ethynyl-1,5-dihydro-4H-7l4-pyrrolo[2,3-d]pyrimidin-4-one O-methyl oxime (104)

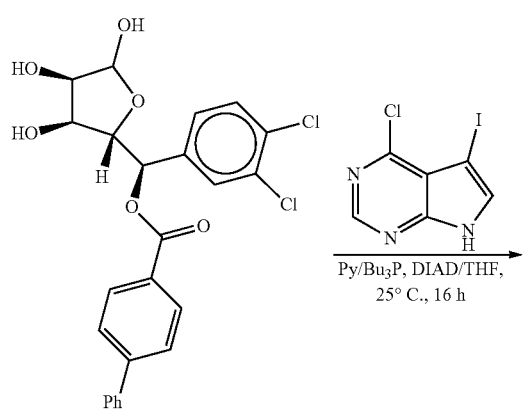

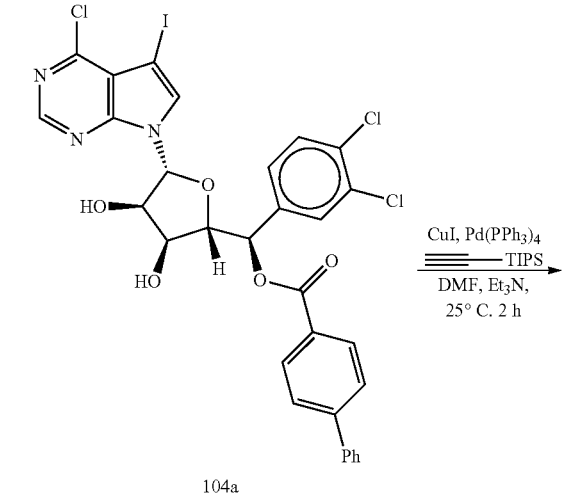

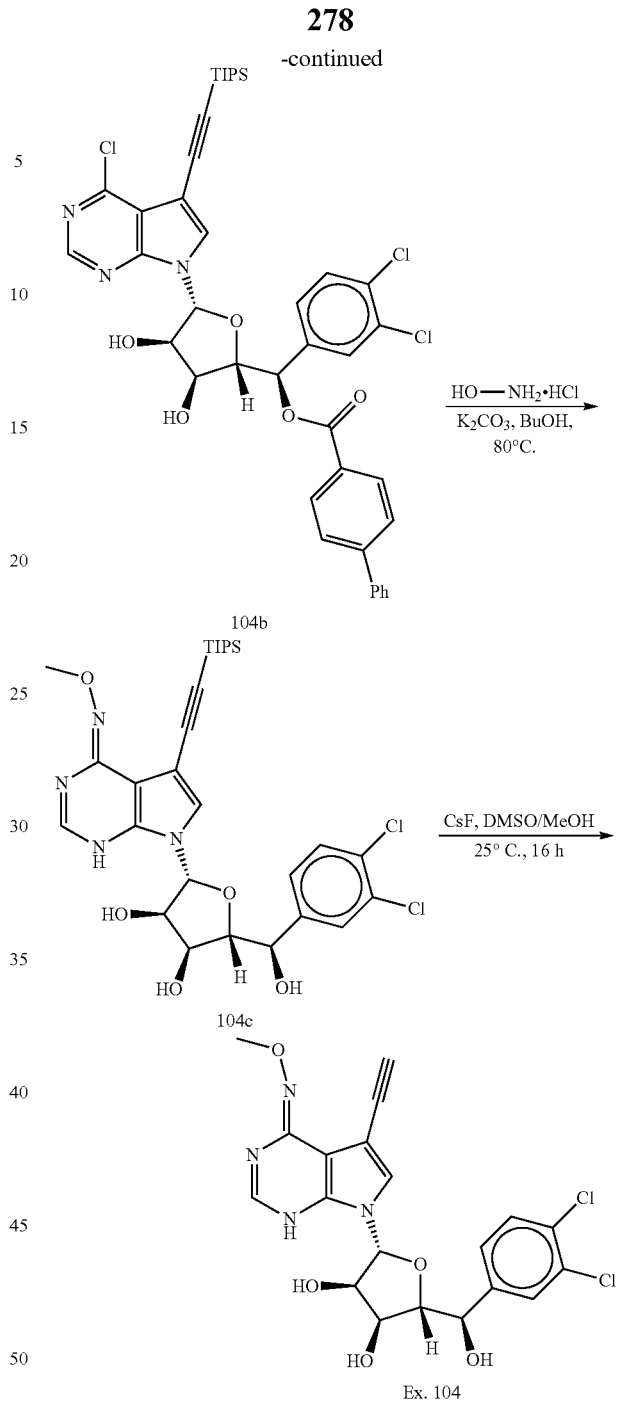

a) Synthesis of [(R)-[(2S,3S,4R,5R) -5-(4-chloro-5-iodo-pyrrolo[2,3-d]pyrimidin-7-yl)-3,4-dihydroxy-tetrahydrofuran-2-yl]-(3,4-dichloro -phenyl)methyl] 4-phenylbenzoate (104a)

To a solution of 4-chloro-5-iodo-7H-pyrrolo[2,3-d]pyrimidine (1.76 g, 6.31 mmol) in THF (20.0 mL) was added Pyridine (0.5 mL, 6.31 mmol), Diisopropyl azodicarboxylate (2.68 mL, 13.25 mmol), followed by Tributylphosphine (3.2 mL, 12.62 mmol). [(R)-(3,4-dichlorophenyl)-[(2S,3S, 4R,5R) -3,4,5-trihydroxytetrahydrofuran-2-yl]methyl]-4-phenyl -benzoate (3.0 g, 6.31 mmol) was added all at once at 25° C. The reaction mixture was stirred at 25° C. for 16 h under N₂. The solvent was removed in vacuum and the residue was purified by prep-HPLC to give [(R)-[(2S,3S, 4R,5R) -5-(4-chloro-5-iodo-pyrrolo[2,3-d]pyrimidin-7-yl)-3,4-dihydroxy-tetrahydrofuran-2-yl]-(3,4-dichloro-phenyl) methyl] 4-phenylbenzoate (104a) (2.80 g, 2.81 mmol, 44.6% yield) as a pale yellow solid. LCMS [M+H]: 736.2 b) Synthesis of [(R)-[(2S,3S,4R,5R)-5-[4-chloro-5-(2-triisopropylsilylethynyl)pyrrolo[2,3-d]pyrimidin-7-yl]-3,4-dihydroxy-tetrahydrofuran-2-yl]-(3,4-dichlorophenyl)methyl]4-phenylbenzoate (104b)

To a solution of [(R)-[(2S,3 S,4R,5R)-5-(4-chloro-5-iodo-pyrrolo[2,3-d]pyrimidin-7-yl)-3,4-dihydroxy-tetrahydrofuran-2-yl]-(3,4-dichlorophenyl)methyl]-4-phenylbenzoate (104a) (1.5 g, 2.04 mmol) in DMF (20.0 mL) was added TEA (0.62 g, 6.11 mmol), CuI (0.04 g, 0.20 mmol) and ethynyl(triisopropyl)silane (0.56 g, 3.05 mmol), Pd(PPh₃)₄ (0.12 g, 0.10 mmol). The reaction mixture was stirred at 25° C. for 2 h under N₂. LCMS showed the reaction was completed and no SM was left. The reaction mixture was diluted with EA (150.0 mL) and washed with water (100.0 mL×3) and brine (100 mL×3). The organic layer was dried over anhydrous Na₂SO₄, filtered and concentrated in vacuum to give crude product, which was purified by silica gel column chromatography (EA:PE=50:1 to 20:1) to give [(R)-[(2S,3S,4R,5R)-5-[4-chloro-5-(2-triisopropylsilylethynyl)pyrrolo[2,3-d]pyrimidin-7-yl]-3,4-dihydroxy-tetrahydrofuran-2-yl]-(3,4-dichloro phenyl)methyl]4-phenylbenzoate (104b) (1.0 g, 1.26 mmol, 62.1% yield) as a yellow oil. LCMS [M+H]: 790.0.

c) Synthesis of (2R,3S,4R,5R)-2-[(R)-(3,4-dichloro-phenyl)-hydroxy-methyl]-5-[(4Z)-4-methoxyimino-5-(2-triisopropylsilylethynyl)-1H-pyrrolo[2,3-d]pyrimidin-7-yl]tetrahydrofuran-3,4-diol (104c)

To a solution of [(R)-[(2S,3S,4R,5R)-5-[4-chloro-5-(2-triisopropylsilylethynyl)pyrrolo[2,3-d]pyrimidin-7-yl]-3,4-dihydroxy-tetrahydrofuran-2-yl]-(3,4-dichlorophenyl) methyl]4-phenylbenzoate (104b) (1.0 g, 1.26 mmol) in 1-Butanol (20.0 mL) was added O-Methylhydroxylamine hydrochloride (0.56 g, 6.32 mmol) and K₂CO₃ (1.4 g, 10.11 mmol). The reaction mixture was stirred at 80° C. for 6 h. The reaction was monitored by TLC (PE:EA=1:1, R_f=0.4), it showed the reaction was completed. The reaction mixture was filtered and concentrated in vacuum to give (2R,3S,4R, 5R)-2-[(R)-(3,4-dichlorophenyl)-hydroxy-methyl]-5-[(4Z)-4-methoxyimino-5-(2-triisopropylsilylethynyl)-1H-pyrrolo [2,3-d]pyrimidin-7-yl]tetrahydrofuran-3,4-diol (104c) (1.25 g, 0.80 mmol, 63.6% yield) as a pale yellow solid.

d) Synthesis of (2R,3S,4R,5R)-2-[(R)-(3,4-dichloro-phenyl)-hydroxy-methyl]-5-[(4Z)-5-ethynyl-4-methoxyimino-1H-pyrrolo[2,3-d]pyrimidin-7-yl] tetrahydrofuran-3,4-diol (Ex. 104)

To a solution of (2R,3S,4R,5R)-2-[(R)-(3,4-dichlorophenyl)-hydroxy-methyl]-5-[(4Z)-4-methoxyimino-5-(2-triisopropylsilylethynyl)-1H-pyrrolo[2,3-d]pyrimidin-7-yl]tetrahydrofuran-3,4-diol (104c) (1.25 g, 0.80 mmol) in DMSO (20.0 mL) and Methanol (0.10 mL) was added CsF (122.18 mg, 0.80 mmol). The reaction mixture was stirred at 25° C. for 16 h. LCMS showed the reaction was completed. The reaction mixture was filtered and concentrated in vacuum to give crude product which was purified by prep-HPLC, eluted with CH₃CN in H₂O (0.1% NH₃.H₂O) from 10.0% to 95.0%) to obtain (2R,3S,4R,5R)-2-[(R)-(3,4-dichlorophenyl)-hydroxy-methyl]-5-[(4Z)-5-ethynyl -4-methoxyimino-1H-pyrrolo[2,3-d]pyrimidin-7-yl]tetrahydrofuran-3,4-diol (Ex. 104) (130.0 mg, 0.26 mmol, 32.2% yield) as a pale yellow solid. LCMS [M+H]: 465.3. ¹H NMR (400 MHz, DMSO-d₆): δ 11.03 (s, 1H), 7.61-7.62 (m, 1H), 7.57-7.59 (m, 2H), 7.48-7.52 (m, 1H), 7.37-7.39 (m, 1H), 6.13-6.14 (m, 1H), 5.84-5.86 (d, J=7.6 Hz, 1H), 5.28-5.30 (d, J=6.4 Hz, 1H), 5.08-5.09 (d, J=3.6 Hz, 1H), 4.77-4.78 (m, 1H), 3.36-4.40 (m, 1H), 4.02 (m, 1H), 3.93-3.94 (m, 1H), 3.91 (s, 1H), 3.73 (s, 3H). ¹H NMR (400 MHz, DMSO-d₆+D₂O): δ 7.61 (m, 1H), 7.57-7.60 (d, J=8.4 Hz, 1H), 7.50 (m, 2H), 7.37-7.39 (m, 1H), 5.84-5.86 (d, J=7.2 Hz, 1H), 4.76-4.78 (d, J=9.2 Hz, 1H), 4.37-4.40 (m, 1H), 4.02-4.03 (m, 1H), 3.94-3.96 (m, 1H), 3.89 (s, 1H), 3.74 (s, 3H).

Example 105. 7-((2R,3R,4S,5S)-5-((1R)-1-(3,4-dichlorocyclohexa-2,4-dien-1-yl)-1-hydroxyethyl)-3,4-dihydroxytetrahydrofuran-2-yl)-1,7-dihydro-4H-pyrrolo[2,3-d]pyrimidin-4-one oxime (105)

Example 105 (TFA salt) was prepared similarly to that of Ex. 61. ¹H NMR (600 MHz, Methanol-d₄) δ 8.27 (s, 1H), 7.73 (dd, J=2.9, 10.1 Hz, 2H), 7.51 (d, J=8.4 Hz, 1H), 7.45 (dd, J=2.1, 8.4 Hz, 1H), 6.77 (d, J=3.7 Hz, 1H), 6.20 (d, J=7.2 Hz, 1H), 4.57 (dd, J=5.3, 7.2 Hz, 1H), 4.23 (d, J=1.8 Hz, 1H), 3.97 (dd, J=1.8, 5.3 Hz, 1H), 1.56 (s, 3H).

Example 106. 7-((2R,3R,4S,5R)-5-((R)-(3,4-dichlorophenyl)(hydroxy)methyl)-3,4-dihydroxytetrahydrofuran-2-yl)-1,4a,7,7a-tetrahydro-4H-pyrrolo[2,3-d]pyrimidin-4-one 0-(2,2-difluoroethyl) oxime (106)

Example 106 was prepared similarly to that of Ex. 66. LCMS [M+H]:491.2. ¹H NMR (400 MHz, DMSO-d₆+D₂O) δ 7.85 (s, 1H), 7.56-7.61 (m, 2H), 7.36-7.39 (m, 2H), 6.51 (d, J=3.2 Hz, 1H), 6.16-6.46 (m, 1H), 5.96 (d, J=7.6 Hz, 1H), 4.77 (d, J=5.2 Hz, 1H), 4.45-4.48 (m, 1H), 4.18-4.26 (m, 2H), 4.07 (d, J=4.8 Hz, 1H) 3.97 (d, J=4.8 Hz, 1H). ¹⁹FNMR (376 MHz, DMSO-d6) δ -125.497 (s, 2F).

Example 107. 7-((2R,3R,4S,5S)-5-((R)-1-(3,4-dichlorophenyl)-1-hydroxyethyl)-3,4-dihydroxytetrahydrofuran-2-yl)-5-fluoro-1,7-dihydro-4H-pyrrolo[2, 3-d]pyrimidin-4-one O-methyl oxime (107)

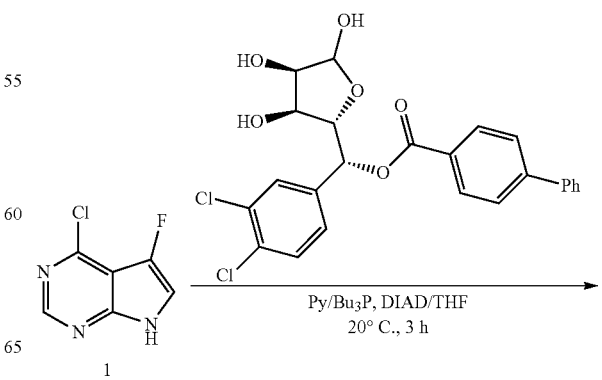

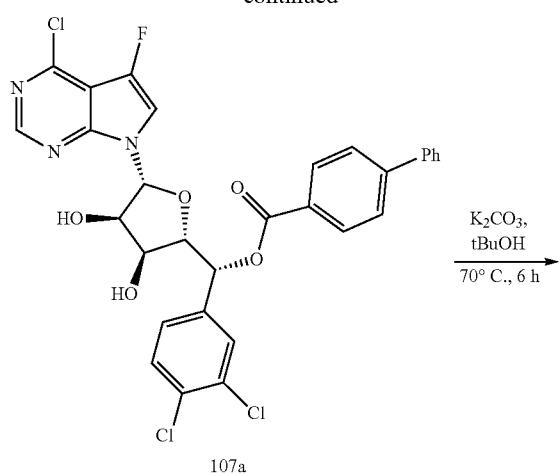
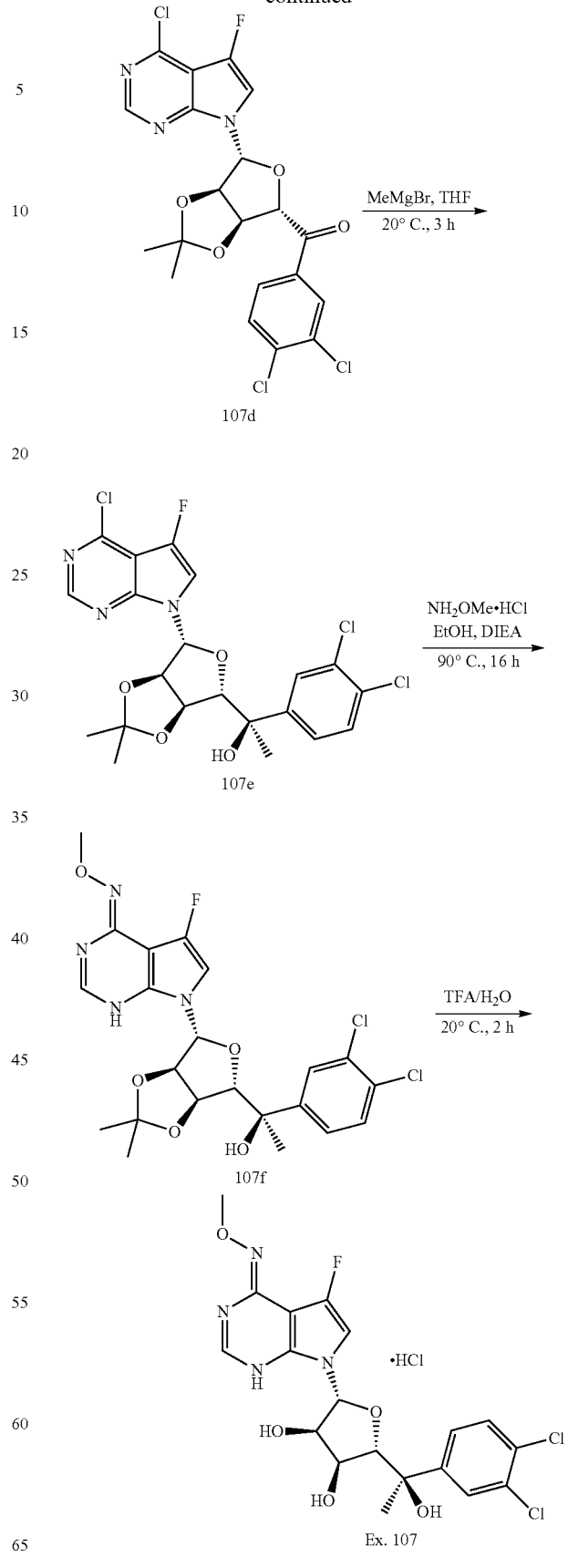

a) Synthesis of [(R)-[(2S,3S,4R,5R) -5-(4-chloro-5-fluoro-pyrrolo[2,3-d]pyrimidin-7-yl)-3,4-dihydroxy-tetrahydrofuran-2-yl]-(3,4-dichlorophenyl)methyl] 4-phenylbenzoate (107a)

To a solution of 4-chloro-5-fluoro-7H-pyrrolo[2,3-d]pyrimidine (1.08 g, 6.31 mmol), pyridine (0.5 mL, 6.31 mmol), PBu$_3$ (3.1 mL, 12.62 mmol) in THF (35.0 mL) was quickly added DIAD (2.4 mL, 12.62 mmol) and [(R)-(3,4-dichlorophenyl)-[(2S,3S,4R)-3,4,5-trihydroxytetrahydrofuran-2-yl]-methyl] 4-phenylbenzoate (3.00 g, 6.31 mmol) in THF at 0° C. under N$_2$. The mixture was stirred at 20° C. for 3 h. The solvent was removed in vacuum. The residue was purified by reversed-phase combi-flash, eluted with MeCN in H$_2$O from 20.0% to 80.0% to give [(R)-[(2S,3S,4R,5R) -5-(4-chloro-5-fluoro-pyrrolo[2,3-d]pyrimidin-7-yl)-3,4-dihydroxy-tetrahydrofuran-2-yl]-(3,4-dichlorophenyl)methyl] 4-phenylbenzoate (107a) (2.50 g, 3.97 mmol, 62.9% yield) as a light yellow solid. LCMS [M+H]: 628.1.

b) Synthesis of (2R,3R,4S,5R)-2-(4-chloro-5-fluoro-pyrrolo[2,3-d]pyrimidin-7-yl)-5-[(R)-(3,4dichloro-phenyl)-hydroxy-methyl]tetrahydrofuran-3,4-diol (107b)

To a solution of [(R)-[(2S,3S,4R,5R)-5-(4-chloro-5-fluoro-pyrrolo[2,3-d]pyrimidin-7-yl)-3,4-dihydroxy-tetrahydrofuran-2-yl]-(3,4-dichlorophenyl)methyl] 4-phenylbenzoate (107a) (1.50 g, 2.39 mmol) in tert-butanol (20.0 mL) was added K$_2$CO$_3$ (1.97 g, 14.31 mmol) under N$_2$. The mixture was stirred at 70° C. for 6 h. The solvent was removed in vacuum to give crude product which was purified by reversed-phase combi-flash, eluted with CH$_3$CN in H$_2$O (neutral condition) from 10.0% to 85.0% to afford (2R,3R,4S,5R)-2-(4-chloro-5-fluoro-pyrrolo[2,3-d]pyrimidin-7-yl)-5-[(R)-(3,4-dichlorophenyl)-hydroxy-methyl]tetrahydrofuran-3,4-diol (107b) (0.75 g, 1.67 mmol, 70.1% yield) as a yellow solid. LCMS [M+H]: 448.1.

c) Synthesis of (R)-[(3aR,4R,6R,6aR)-4-(4-chloro-5-fluoro-pyrrolo[2,3-d]pyrimidin-7-yl)-2,2-dimethyl-3a,4,6,6a-tetrahydrofuro[3,4-d][1,3]dioxol-6-yl]-(3,4-dichlorophenyl)methanol (107c))

To a solution of (2R,3R,4S,5R)-2-(4-chloro-5-fluoro-pyrrolo[2,3-d]pyrimidin-7-yl)-5-[(R)-(3,4-dichlorophenyl)-hydroxy-methyl]tetrahydrofuran-3,4-diol (107b) (0.53 g, 1.18 mmol) in DMF (5.0 mL) was added amberlyst H+ resin (0.53 g) and 2,2-Dimethoxypropane (1.84 g, 17.72 mmol) under N$_2$. The mixture was stirred at 60° C. for 3 h. The solvent was removed in vacuum to give crude product which was purified by silica chromatography (PE:EA=10:1 to 2:1) to give (R)-[(3aR,4R,6R,6aR)-4-(4-chloro-5-fluoro-pyrrolo[2,3-d]pyrimidin-7-yl)-2,2-dimethyl-3a,4,6,6a-tetrahydrofuro[3,4-d][1,3]dioxol-6-yl]-(3,4-dichlorophenyl)methanol (107c) (0.23 g, 0.47 mmol, 39.8% yield) as a yellow solid. LCMS [M+H]: 488.1.

d) Synthesis of [(3aR,4R,6S,6aS)-4-(4-chloro-5-fluoro-pyrrolo[2,3-d]pyrimidin-7-yl)-2,2-dimethyl-3a,4,6,6a-tetrahydrofuro[3,4-d][1,3]dioxol-6-yl]-(3,4-dichlorophenyl)methanone (107d)

To a solution of (R)-[(3aR,4R,6R,6aR)-4-(4-chloro-5-fluoro-pyrrolo[2,3-d]pyrimidin-7-yl)-2,2-dimethyl-3a,4,6,6a-tetrahydrofuro[3,4-d][1,3]dioxol-6-yl]-(3,4-dichlorophenyl)methanol (107c) (230.0 mg, 0.47 mmol) in DCM (5.0 mL) was added Dess-Martin periodinane (499.0 mg, 1.18 mmol) under N$_2$. The mixture was stirred at 20° C. for 16 h. The solvent was removed in vacuum to give the crude product, which was purified by silica chromatography (PE: EA=10:1 to 2:1) to give [(3aR,4R,6S,6aS)-4-(4-chloro-5-fluoro-pyrrolo[2,3-d]pyrimidin-7-yl)-2,2-dimethyl-3a,4,6,6a-tetrahydrofuro[3,4-d][1,3]dioxol-6-yl]-(3,4-dichlorophenyl)methanone (107d) (200.0 mg, 0.41 mmol, 87.3% yield) as a yellow solid. LCMS [M+H]: 486.1.

e) Synthesis of (1R)-1-[(3aR,4R,6S,6aR) -4-(4-chloro-5-fluoro-pyrrolo[2,3-d]pyrimidin-7-yl)-2,2-dimethyl-3a,4,6,6a-tetrahydrofuro[3,4-d][1,3]dioxol-6-yl]-1-(3,4-dichlorophenyl)ethanol (107e)

To a solution of [(3aR,4R,6S,6aS)-4-(4-chloro-5-fluoro-pyrrolo[2,3-d]pyrimidin-7-yl)-2,2-dimethyl-3a,4,6,6a-tetrahydrofuro[3,4-d][1,3]dioxol-6-yl]-(3,4-dichlorophenyl)methanone (107d) (200.0 mg, 0.41 mmol) in THF (2.0 mL) was added MeMgBr (0.4 mL, 1.23 mmol) under N$_2$. The mixture was stirred at 20° C. for 3 h. The reaction was quenched with sat. aq. NH$_4$Cl and extracted with EA. The organic layers were dried with Na$_2$SO$_4$ and filtered. The filtrates were concentrated in vacuum to give the crude product, which was purified by silica chromatography (PE: EA=10:1 to 2:1) to afford (1R)-1-[(3aR,4R,6S,6aR) -4-(4-chloro-5-fluoro-pyrrolo[2,3-d]pyrimidin-7-yl)-2,2-dimethyl-3a,4,6,6a-tetrahydrofuro[3,4-d][1,3]dioxol-6-yl]-1-(3,4-dichlorophenyl)ethanol (107e) (70.0 mg, 0.14 mmol, 33.9% yield) as a yellow solid. LCMS [M+H]: 502.1.

f) Synthesis of (1R)-1-[(3aR,4R,6S,6aR)-4-[(4Z)-5-fluoro-4-methoxyimino-1H-pyrrolo[2,3-d]pyrimidin-7-yl]-2,2-dimethyl-3a,4,6,6a-tetrahydrofuro[3,4-d][1,3]dioxol-6-yl]-1-(3,4-dichlorophenyl)ethanol (107f)

To a solution of (1R)-1-[(3aR,4R,6S,6aR)-4-(4-chloro-5-fluoro-pyrrolo[2,3-d]pyrimidin-7-yl)-2,2-dimethyl-3a,4,6,6a-tetrahydrofuro[3,4-d][1,3]dioxol-6-yl]-1-(3,4-dichlorophenyl)ethanol (107e) (70.0 mg, 0.14 mmol) in Ethanol (3.0 mL) was added O-Methylhydroxylamine hydrochloride (69.7 mg, 0.84 mmol) and DIEA (143.9 mg, 1.11 mmol). The reaction mixture was stirred at 90° C. for 16 h. The solvent was removed in vacuum to give crude product which was purified by reversed-phase combi-flash, eluted with MeCN in H$_2$O from 10.0% to 70.0% to give (1R)-1-[(3aR,4R,6S,6aR)-4-[(4Z)-5-fluoro-4-methoxyimino-1H-pyrrolo[2,3-d]pyrimidin-7-yl]-2,2-dimethyl-3a,4,6,6a-tetrahydrofuro[3,4-d][1,3]dioxol-6-yl]-1-(3,4-dichlorophenyl)ethanol (107f) (40.0 mg, 0.08 mmol, 55.9% yield) as a gray solid. LCMS [M+H]: 513.1.

g) Synthesis of (2S,3S,4R,5R)-2-[(1R)-1-(3,4-dichlorophenyl)-1-hydroxy-ethyl]-5-[(4Z)-5-fluoro-4-methoxyimino-1H-pyrrolo[2,3-d]pyrimidin-7-yl]tetrahydrofuran-3,4-diol hydrochloride (Ex. 107)

A mixture of (1R)-1-[(3aR,4R,6S,6aR)-4-[(4Z)-5-fluoro-4-methoxyimino-1H-pyrrolo[2,3-d] pyrimidin-7-yl]-2,2-dimethyl-3a,4,6,6a-tetrahydrofuro[3,4-d][1,3]dioxol-6-yl]-1-

(3,4-dichlorophenyl)ethanol (107f) (40.0 mg, 0.08 mmol) in Water (1.0 mL) and TFA (0.5 mL, 6.73 mmol) was stirred at 20° C. for 2 h. The solvent was removed in vacuum to give the crude product, which was purified by prep-HPLC, eluted with MeCN in $H_2O$ (0.1% TFA) from 5.0% to 80.0%. The fractions were combined and 5 drops of 1M HCl were added, then lyophilized to afford (2S,3S,4R,5R)-2-[(1R)-1-(3,4-dichlorophenyl)-1-hydroxy-ethyl]-5-[(4Z)-5-fluoro-4-methoxyimino-1H-pyrrolo[2,3-d]pyrimidin-7-yl]tetrahydrofuran-3,4-diol hydrochloride (Ex. 107) (9.5 mg, 0.018 mmol, 23.8% yield) as a white solid. LCMS [M+H]: 473.1. $^1$H NMR (400 MHz, DMSO-$d_6$+$D_2O$) δ 7.73-7.70 (m, 2H), 7.61 (d, J=8.4 Hz, 1H), 7.49 (d, J=8.4 Hz, 1H), 7.23 (s, 1H), 5.93 (d, J=7.7 Hz, 1H), 4.28-4.25 (m, 1H), 4.04 (brs, 1H), 3.77 (s, 3H), 3.69 (d, J=5.1 Hz, 1H), 1.44 (s, 3H). $^{19}$FNMR (377 MHz, DMSO-$d_6$) δ−163.6 (s, 1F)

Example 108. 9-((2R,3R,4S,5S)-5-((R)-1-(3,4-dichlorophenyl)-1-hydroxyethyl)-3,4-dihydroxytetrahydrofuran-2-yl)-3,9-dihydro-6H-purin-6-one oxime (108)

Example 108 was prepared similarly to that of Ex. 92. LCMS [M+H]: 442.2. $^1$H NMR (400 MHz, DMSO-$d_6$): δ 8.92 (s, 1H), 8.33 (s, 1H), 8.07 (s, 1H), 7.79 (d, J=2.0 Hz, 1H), 7.61-7.63 (m, 1H), 7.52-7.55 (m, 1H), 5.87 (d, J=7.6 Hz, 1H), 4.50-4.54 (m, 1H), 4.19 (s, 1H), 3.70 (d, J=4.8 Hz, 1H), 1.44 (s, 3H). $^1$H NMR (400 MHz, DMSO-$d_6$+$D_2O$): S 8.37 (s, 1H), 8.12 (s, 1H), 7.77 (d, J=2.0 Hz, 1H), 7.61-7.63 (m, 1H), 7.51-7.54 (m, 1H), 5.89 (d, J=7.6 Hz, 1H), 4.49-4.53 (m, 1H), 4.18 (s, 1H), 3.72 (d, J=4.8 Hz, 1H), 1.45 (s, 3H).

X-Ray Crystal Structure of Example 69

Compound of Example 69 was recrystallized from ethanol. Crystals suitable for X-ray diffraction studies were obtained as clear colorless prisms. A clear colourless block-like specimen of C20H24Cl2N4O6, approximate dimensions 0.144 mm×0.214 mm×0.451 mm, was used for the X-ray crystallographic analysis. Table 1 shows the corresponding data collection details.

A total of 2571 frames were collected. The total exposure time was 14.28 hours. The frames were integrated with the Bruker SAINT software package using a narrow-frame algorithm. The integration of the data using a monoclinic unit cell yielded a total of 14043 reflections to a maximum θ angle of 75.350 (0.80 Å resolution), of which 4554 were independent (average redundancy 3.084, completeness=99.3%, Rint=2.75%, Rsig=2.86%) and 4447 (97.65%) were greater than 2σ(F2). The final cell constants of a=25.6495(5) Å, b=6.93520(10) Å, c=15.3927(3) Å, β=125.5400(10)°, volume=2228.04(7) Å3, are based upon the refinement of the XYZ-centroids of 9909 reflections above 20 σ(I) with 7.057°<2θ<150.8°. Data were corrected for absorption effects using the Multi-Scan method (SADABS). The ratio of minimum to maximum apparent transmission was 0.734. The calculated minimum and maximum transmission coefficients (based on crystal size) are 0.5532 and 0.7539.

FIG. 1 is an ORTEP representation of Example 69. The structure was solved and refined using the Bruker SHELXTL Software Package, using the space group C 1 2 1, with Z=4 for the formula unit, C20H24Cl2N4O6. The final anisotropic full-matrix least-squares refinement on F2 with 307 variables converged at R1=2.97%, for the observed data and wR2=9.11% for all data. The goodness-of-fit was 1.016. The largest peak in the final difference electron density synthesis was 0.191 e−/Å3 and the largest hole was −0.210 e−/Å3 with an RMS deviation of 0.033 e−/Å3. On the basis of the final model, the calculated density was 1.453 g/cm3 and F(000), 1016 e−.

TABLE 2

Sample and crystal data for Example 69.

| | | |
|---|---|---|
| Chemical formula | C20H24Cl2N4O6 | |
| Formula weight | 487.33 g/mol | |
| Temperature | 296(2) K | |
| Wavelength | 1.54178 Å | |
| Crystal size | 0.144 × 0.214 × 0.451 mm | |
| Crystal habit | clear colourless block | |
| Crystal system | monoclinic | |
| Space group | C 1 2 1 | |
| Unit cell dimensions | a = 25.6495(5) Å | α = 90° |
| | b = 6.93520(10) Å | β = 125.5400(10)° |
| | c = 15.3927(3) Å | γ = 90° |
| Volume | 2228.04(7) Å3 | |
| Z | 4 | |
| Density (calculated) | 1.453 g/cm3 | |

TABLE 1

Data collection details for Example 69.

| axis | dx/mm | 2θ/° | ω/° | φ/° | χ/° | width/° | frames | time/s | wavelength/Å | volt/kV | current/mA | temp/K |
|---|---|---|---|---|---|---|---|---|---|---|---|---|
| Omega | 49.466 | 118.90 | −75.10 | 24.00 | 54.74 | 1.30 | 160 | 20.00 | 1.54184 | 45 | 0.7 | n/a |
| Omega | 49.466 | −58.14 | 107.86 | 270.00 | 54.74 | 1.30 | 160 | 20.00 | 1.54184 | 45 | 0.7 | n/a |
| Omega | 49.466 | 118.90 | −75.10 | 168.00 | 54.74 | 1.30 | 160 | 20.00 | 1.54184 | 45 | 0.7 | n/a |
| Omega | 49.466 | −58.14 | 107.86 | 180.00 | 54.74 | 1.30 | 160 | 20.00 | 1.54184 | 45 | 0.7 | n/a |
| Omega | 49.466 | 118.00 | −76.00 | 81.35 | 54.79 | 1.30 | 160 | 20.00 | 1.54184 | 45 | 0.7 | n/a |
| Omega | 49.466 | 118.90 | −75.10 | −24.00 | 54.74 | 1.30 | 160 | 20.00 | 1.54184 | 45 | 0.7 | n/a |
| Omega | 49.466 | −73.90 | 93.40 | 0.00 | 54.74 | 1.30 | 159 | 20.00 | 1.54184 | 45 | 0.7 | n/a |
| Omega | 49.466 | 118.90 | −75.10 | 48.00 | 54.74 | 1.30 | 160 | 20.00 | 1.54184 | 45 | 0.7 | n/a |
| Omega | 49.466 | 118.90 | −75.10 | 144.00 | 54.74 | 1.30 | 160 | 20.00 | 1.54184 | 45 | 0.7 | n/a |
| Omega | 49.466 | −28.84 | 137.15 | −120.00 | 54.74 | 1.30 | 160 | 20.00 | 1.54184 | 45 | 0.7 | n/a |
| Omega | 49.466 | −73.14 | 92.86 | 135.00 | 54.74 | 1.30 | 160 | 20.00 | 1.54184 | 45 | 0.7 | n/a |
| Omega | 49.466 | 118.90 | −75.10 | −96.00 | 54.74 | 1.30 | 160 | 20.00 | 1.54184 | 45 | 0.7 | n/a |
| Omega | 49.466 | 118.90 | −75.10 | 0.00 | 54.74 | 1.30 | 160 | 20.00 | 1.54184 | 45 | 0.7 | n/a |

TABLE 2-continued

Sample and crystal data for Example 69.

| | |
|---|---|
| Absorption coefficient | 3.018 mm−1 |
| F(000) | 1016 |

TABLE 3

Data collection and structure refinement for Example 69.

| | |
|---|---|
| Theta range for data collection | 3.53 to 75.35° |
| Index ranges | −32 <= h <= 32, −8 <= k <= 8, −19 <= l <= 18 |
| Reflections collected | 14043 |
| Independent reflections | 4554 [R(int) = 0.0275] |
| Coverage of independent reflections | 99.3% |
| Absorption correction | Multi-Scan |
| Max. and min. transmission | 0.7539 and 0.5532 |
| Structure solution technique | direct methods |
| Structure solution program | SHELXS-97 (Sheldrick 2008) |
| Refinement method | Full-matrix least-squares on F2 |
| Refinement program | SHELXL-2016/6 (Sheldrick, 2016) |
| Function minimized | Σ w(Fo2 − Fc2)2 |
| Data/restraints/parameters | 4554/1/307 |
| Goodness-of-fit on F2 | 1.016 |
| Final R indices | 4447 data; I > 2σ(I) R1 = 0.0297, wR2 = 0.0903 all data R1 = 0.0303, wR2 = 0.0911 |
| Weighting scheme where P = (Fo2 + 2Fc2)/3 | w = 1/[o2(Fo2) + (0.0672P)2 + 0.2961P] |
| Absolute structure parameter | −0.013(7) |
| Extinction coefficient | 0.0029(3) |
| Largest diff. peak and hole | 0.191 and −0.210 eÅ−3 |
| R.M.S. deviation from mean | 0.033 eÅ−3 |

TABLE 4

Atomic coordinates and equivalent isotropic atomic displacement parameters (Å2) for Example 69. (U(eq) is defined as one third of the trace of the orthogonalized Uij tensor).

| | x/a | y/b | z/c | U(eq) |
|---|---|---|---|---|
| Cl1 | 0.35444(4) | 0.57767(14) | 0.82068(5) | 0.0688(2) |
| Cl2 | 0.42821(5) | 0.97062(19) | 0.86236(7) | 0.0947(4) |
| N1 | 0.28071(8) | 0.2013(3) | 0.20080(13) | 0.0347(3) |
| N2 | 0.14374(9) | 0.5353(3) | 0.96656(16) | 0.0418(4) |
| N3 | 0.22705(9) | 0.5149(3) | 0.15096(15) | 0.0397(4) |
| N4 | 0.11352(9) | 0.2768(3) | 0.84518(15) | 0.0425(4) |
| O1 | 0.28645(10) | 0.6992(3) | 0.35704(14) | 0.0540(4) |
| O2 | 0.28926(7) | 0.2759(2) | 0.35549(12) | 0.0393(3) |
| O3 | 0.43543(8) | 0.2818(3) | 0.54089(13) | 0.0501(4) |
| O4 | 0.43071(7) | 0.3157(3) | 0.36167(13) | 0.0467(4) |
| O5 | 0.06795(10) | 0.4174(3) | 0.77306(15) | 0.0608(5) |
| O6 | 0.42197(8) | 0.3845(3) | 0.17727(15) | 0.0467(4) |
| C1 | 0.32247(10) | 0.6008(4) | 0.62135(19) | 0.0431(5) |
| C2 | 0.35505(11) | 0.6879(4) | 0.72081(18) | 0.0469(5) |
| C3 | 0.38713(12) | 0.8593(5) | 0.7383(2) | 0.0547(6) |
| C4 | 0.38647(14) | 0.9446(4) | 0.6564(2) | 0.0571(6) |
| C5 | 0.35449(12) | 0.8564(4) | 0.5575(2) | 0.0484(5) |
| C6 | 0.32297(10) | 0.6826(3) | 0.53989(17) | 0.0395(4) |
| C7 | 0.29073(10) | 0.5765(3) | 0.43443(17) | 0.0410(4) |
| C8 | 0.32804(9) | 0.3923(3) | 0.44995(16) | 0.0348(4) |
| C9 | 0.39239(9) | 0.4216(3) | 0.46593(16) | 0.0375(4) |
| C10 | 0.37585(9) | 0.3794(3) | 0.35449(16) | 0.0350(4) |
| C11 | 0.32502(9) | 0.2233(3) | 0.31546(16) | 0.0342(4) |

TABLE 4-continued

Atomic coordinates and equivalent isotropic atomic displacement parameters (Å2) for Example 69. (U(eq) is defined as one third of the trace of the orthogonalized Uij tensor).

| | x/a | y/b | z/c | U(eq) |
|---|---|---|---|---|
| C12 | 0.27246(10) | 0.0310(3) | 0.14751(18) | 0.0389(4) |
| C13 | 0.22389(10) | 0.0518(3) | 0.04226(17) | 0.0377(4) |
| C14 | 0.19972(9) | 0.2416(3) | 0.02951(15) | 0.0328(4) |
| C15 | 0.14938(9) | 0.3491(3) | 0.94056(16) | 0.0357(4) |
| C16 | 0.18155(11) | 0.6061(3) | 0.06833(18) | 0.0410(4) |
| C17 | 0.23567(9) | 0.3300(3) | 0.12866(16) | 0.0327(4) |
| C18 | 0.03657(16) | 0.3483(5) | 0.6682(2) | 0.0659(8) |
| C19 | 0.48310(13) | 0.3875(5) | 0.1943(2) | 0.0589(7) |
| C20 | 0.47807(19) | 0.4426(9) | 0.0974(3) | 0.0883(12) |

TABLE 5

Hydrogen atomic coordinates and isotropic atomic displacement parameters (Å2) for Example 69.

| | x/a | y/b | z/c | U(eq) |
|---|---|---|---|---|
| H2N | 0.1159(15) | 0.607(5) | −0.080(3) | 0.05 |
| H1O | 0.2679(19) | 0.649(6) | 0.306(3) | 0.065 |
| H3O | 0.4679(17) | 0.307(5) | 0.544(3) | 0.06 |
| H4O | 0.4277(16) | 0.339(5) | 0.309(3) | 0.056 |
| H6O | 0.4087(15) | 0.513(5) | 0.162(3) | 0.056 |
| H1A | 0.3002 | 0.4866 | 0.6093 | 0.052 |
| H4A | 0.4075 | 1.0612 | 0.6678 | 0.069 |
| H5A | 0.3541 | 0.9138 | 0.5025 | 0.058 |
| H7A | 0.2473 | 0.5409 | 0.4104 | 0.049 |
| H8A | 0.3354 | 0.3213 | 0.5112 | 0.042 |
| H9A | 0.4087 | 0.5530 | 0.4895 | 0.045 |
| H10A | 0.3575 | 0.4940 | 0.3090 | 0.042 |
| H11A | 0.3462 | 0.0995 | 0.3468 | 0.041 |
| H12A | 0.2964 | −0.0806 | 0.1788 | 0.047 |
| H13A | 0.2093 | −0.0405 | −0.0110 | 0.045 |
| H16A | 0.1736 | 0.7317 | 0.0788 | 0.049 |
| H18A | 0.0072 | 0.4443 | −0.3810 | 0.099 |
| H18B | 0.0135 | 0.2328 | −0.3400 | 0.099 |
| H18C | 0.0676 | 0.3205 | −0.3460 | 0.099 |
| H19A | 0.5025 | 0.2608 | 0.2172 | 0.071 |
| H19B | 0.5109 | 0.4782 | 0.2509 | 0.071 |
| H20A | 0.5186 | 0.4229 | 0.1086 | 0.133 |
| H20B | 0.4663 | 0.5761 | 0.0818 | 0.133 |
| H20C | 0.4460 | 0.3648 | 0.0385 | 0.133 |

X-Ray Powder Diffraction (XRPD) of Example 92A

Characterization of the crystalline form prepared in Example 92A by an X-ray diffraction pattern using CuKa radiation as having diffraction peaks (2-theta values) (SCAN: 3.0/45.0/0.02/0.6 (sec), Cu(30 kV, 5 mA), I(max)= 472) as described in Table 6 below.

TABLE 6

X-ray powder diffraction peaks of crystalline Example 92A PEAK: 21-pts/Parabolic Filter, Threshold = 3.0, Cutoff = 0.1%, BG = 3/1.0, Peak-Top = Summit

| 2-Theta | d(A) | BG | Height | I % | Area | I % | FWHM |
|---|---|---|---|---|---|---|---|
| 9.321 | 9.4806 | 46 | 30 | 7 | 474 | 7.4 | 0.269 |
| 10.78 | 8.2 | 45 | 112 | 26.1 | 1591 | 24.9 | 0.241 |
| 12.178 | 7.2618 | 42 | 50 | 11.7 | 723 | 11.3 | 0.246 |
| 14.078 | 6.2857 | 40 | 54 | 12.6 | 869 | 13.6 | 0.274 |
| 15.56 | 5.6902 | 39 | 43 | 10 | 637 | 10 | 0.252 |
| 17.44 | 5.0807 | 49 | 28 | 6.5 | 492 | 7.7 | 0.299 |
| 18.058 | 4.9082 | 43 | 429 | 100 | 6401 | 100 | 0.254 |
| 18.679 | 4.7465 | 43 | 103 | 24 | 1639 | 25.6 | 0.271 |
| 19.559 | 4.5349 | 43 | 49 | 11.4 | 1075 | 16.8 | 0.373 |
| 19.939 | 4.4492 | 44 | 163 | 38 | 2583 | 40.4 | 0.269 |
| 20.281 | 4.375 | 44 | 32 | 7.5 | 1094 | 17.1 | 0.581 |
| 21.04 | 4.2189 | 42 | 32 | 7.5 | 452 | 7.1 | 0.24 |

TABLE 6-continued

X-ray powder diffraction peaks of crystalline Example 92A
PEAK: 21-pts/Parabolic Filter, Threshold = 3.0, Cutoff =
0.1%, BG = 3/1.0, Peak-Top = Summit

| 2-Theta | d(A) | BG | Height | I % | Area | I % | FWHM |
|---|---|---|---|---|---|---|---|
| 21.92 | 4.0515 | 37 | 92 | 21.4 | 1366 | 21.3 | 0.252 |
| 23.539 | 3.7763 | 50 | 67 | 15.6 | 599 | 9.4 | 0.152 |
| 23.921 | 3.717 | 44 | 50 | 11.7 | 1097 | 17.1 | 0.373 |
| 24.599 | 3.616 | 47 | 109 | 25.4 | 1272 | 19.9 | 0.198 |
| 25.579 | 3.4796 | 44 | 149 | 34.7 | 3200 | 50 | 0.365 |
| 26.22 | 3.396 | 53 | 91 | 21.2 | 838 | 13.1 | 0.157 |
| 27.659 | 3.2225 | 39 | 119 | 27.7 | 1890 | 29.5 | 0.27 |
| 28.421 | 3.1378 | 43 | 39 | 9.1 | 697 | 10.9 | 0.304 |
| 29.358 | 3.0397 | 40 | 36 | 8.4 | 412 | 6.4 | 0.195 |
| 30.061 | 2.9702 | 37 | 54 | 12.6 | 656 | 10.2 | 0.207 |
| 31.761 | 2.815 | 39 | 28 | 6.5 | 570 | 8.9 | 0.346 |
| 34.859 | 2.5716 | 27 | 38 | 8.9 | 559 | 8.7 | 0.25 |

Examples of Formula III and Formula IV

Synthesis of Int-1

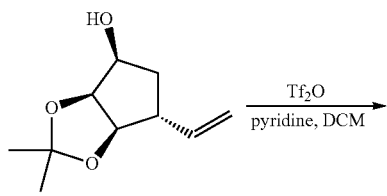

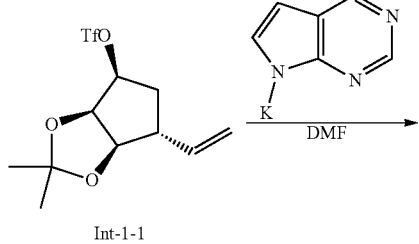

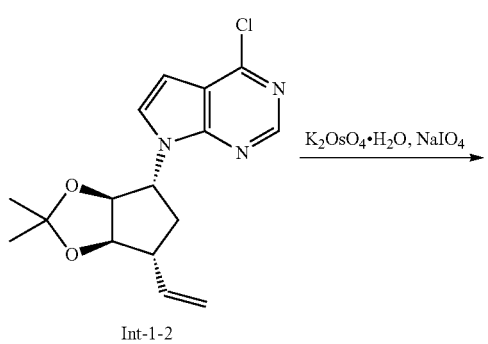

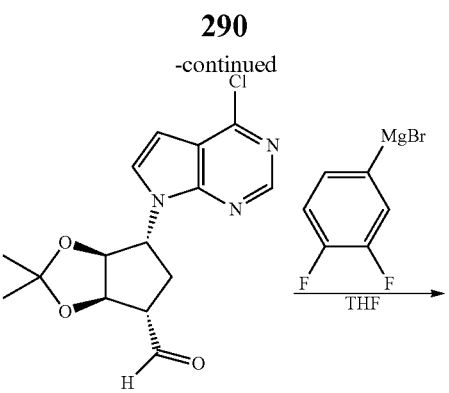

Int-1-3

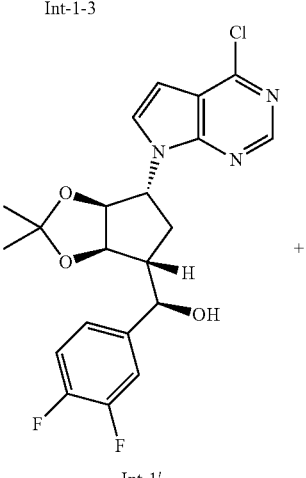

Int-1'

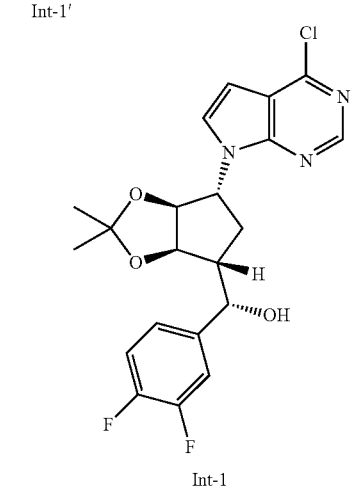

Int-1

Step 1. Synthesis of [(3aR,4S,6R, 6aR)-2,2-dimethyl-6-vinyl-4,5,6,6a-tetrahydro-3aH-cyclopenta[d][1,3]dioxol-4-yl] trifluorometh-anesulfonate (Int-1-1)

To a mixture of (3aS,4S,6R,6aR)-2,2-dimethyl-6-vinyl-4,5,6,6a-tetrahydro-3aH-cyclopenta[d][1,3]dioxol-4-ol (2000.00 mg, 10.86 mmol, prepared according to *J. Org. Chem.,* 2004, vol. 69, 3993-3996) in DCM (20 mL) was added the pyridine (4293.55 mg, 54.28 mmol), then $Tf_2O$ (4594.04 mg, 16.28 mmol) in DCM (10.00 mL) was added slowly to the mixture at 0° C. and the reaction was stirred for 0.5 hour at rt. TLC (PE:EA=10:1) showed the start materials was consumed completely and a new spot was on TLC. The mixture was washed with NH₄Cl solution and the organic layer was dried over Na₂SO₄ and concentrated in vacuo. The residue was purified by silica gel column (PE:EA=22:1) to give the desired product [(3aR,4S,6R, 6aR)-2,2-dimethyl-6-vinyl-4,5,6,6a-tetrahydro-3aH-cyclopenta[d][1,3]dioxol-4-yl] trifluorometh-anesulfonate (Int-1-1) (2.89 g, 9.14 mmol, 84.17% yield) and used directly in the next step.

Step 2. Synthesis of 7-[(3aS,4R,6R,6aR)-2,2-dimethyl-6-vinyl-4,5,6,6a-tetrahydro-3aH-cyclopenta[d][1,3]dioxol-4-yl]-4-chloro-pyrrolo[2,3-d]pyrimidine (Int-1-2)

To a solution of (4-chloropyrrolo[2,3-d]pyrimidin-7-yl) potassium (2166.92 mg, 11.31 mmol) in DMF (22.5 mL) was added [(3aR,4S,6R,6aR)-2,2-dimethyl-6-vinyl-4,5,6,6a-tetrahydro-3aH-cyclopenta[d][1,3]dioxol-4-yl] trifluoromethanesulfonate (Int-1-1) (2.98 g, 9.42 mmol) in DMF (7.5 mL) dropwise at 0° C. Then the mixture was stirred at 25° C. for 16 hrs. LCMS showed Int-1-2 is the major product in the reaction mixture. The mixture was diluted by EA (300.00 mL), washed with H₂O (30.00 mL×5) and NaCl aqueous solution (50.00 mL). The combined organic layers were dried over Na₂SO₄ and concentrated in vacuo. The residue was purified by silica gel column (PE:EA=15:1) to give the desired product 7-[(3aS,4R,6R,6aR)-2,2-dimethyl-6-vinyl-4,5,6,6a-tetrahydro-3aH-cyclopenta[d][1,3]dioxol-4-yl]-4-chloro-pyrrolo[2,3-d]pyrimidine (Int-1-2) (2.00 g, 6.13 mmol, 65.09% yield) as white solid. LCMS [M+H]: 320.1.

Step 3. Synthesis of (3aS,4R,6S,6aR)-4-(4-chloro-pyrrolo[2,3-d]pyrimidin-7-yl)-2,2-dimethyl-4,5,6,6a-tetrahydro-3aH-cyclopenta[d][1,3]dioxole-6-carbaldehyde (Int-1-3)

To a mixture of 7-[(3aS,4R,6R,6aR)-2,2-dimethyl-6-vinyl-4,5,6,6a-tetrahydro-3aH-cyclopenta [d][1,3]dioxol-4-yl]-4-chloro-pyrrolo[2,3-d] pyrimidine (Int-1-2) (1.6 g, 5.00 mmol) in acetone (25.0 mL), methanol (25.0 mL), water (25.0 mL) was added K₂OsO₄.2H₂O (184.3 mg, 0.5 mmol) and NaIO₄ (2140.3 mg, 10.01 mmol), then the mixture was stirred at 20° C. for 18 hrs. The mixture was filtered and the filtrate was concentrated in vacuo. The residue was dissolved in THF/H₂O (75.00 mL, v:v=2:1) and the NaIO₄ (2140.0 mg) was added. The mixture was stirred at 25° C. for 1 h. LCMS showed 39% 4 was in the mixture. The mixture was filtered and the aqueous phase was extracted with EA (50.0 mL×2). The combined organic layers were dried over Na₂SO₄, filtered and concentrated under vacuum. The crude (3aS,4R,6S,6aR)-4-(4-chloropyrrolo[2,3-d]pyrimidin-7-yl)-2,2-dimethyl-4,5,6,6a-tetrahydro-3aH-cyclopenta[d][1,3]dioxole-6-carbaldehyde (Int-1-3) (2000.00 mg, 2.75 mmol, 55.06% yield) was obtained. LCMS [M+H]: 322.1.

Step 4. Synthesis of (S)-[(3aS,4R,6R,6aR)-4-(4-chloropyrrolo[2,3-d]pyrimidin-7-yl)-2,2-dimethyl-4,5,6,6a-tetrahydro-3aH-cyclopenta[d][1,3]dioxol-6-yl]-(3,4-difluorophenyl)methanol (Int-1)

To a solution of (3aS,4R,6S,6aR)-4-(4-chloropyrrolo[2,3-d]pyrimidin-7-yl)-2,2-dimethyl-4,5,6,6a-tetrahydro-3aH-cyclopenta[d][1,3]dioxole-6-carbaldehyde (Int-1-3) (1.95 g, 2.67 mmol) in THF (20.00 mL) was added bromo-(3,4-difluorophenyl)magnesium (8.00 mL, 8.00 mmol) at 0° C. The solution was stirred at 0° C. for 1 h. LC-MS showed desired products are the major peak. The mixture was diluted by H₂O (30.00 mL) and EA (60.00 mL). EA layer was separated, washed with H₂O (30.00 mL) and NaCl aqueous solution (saturated, 30.00 mL), dried over Na₂SO₄, filtered, and concentrated under vacuum. The residue was purified by column (PE:EA=5:1 to PE:EA=3:1) to afford (R)-[(3aS,4R,6R,6aR)-4-(4-chloropyrrolo[2,3-d]pyrimidin-7-yl)-2,2-dimethyl-4,5,6,6a-tetrahydro-3aH-cyclopenta[d][1,3]dioxol-6-yl]-(3,4-difluorophenyl)methanol (Int-1') (380 mg, 0.87 mmol, 32.70% yield), and (S)-[(3aS,4R,6R,6aR)-4-(4-chloropyrrolo[2,3-d]pyrimidin-7-yl)-2,2-dimethyl-4,5,6,6a-tetrahydro-3aH-cyclopenta[d][1,3]dioxol-6-yl]-(3,4-difluorophenyl)methanol (Int-1) (450 mg, 1.03 mmol, 38.7% yield).

Synthesis of Int-2

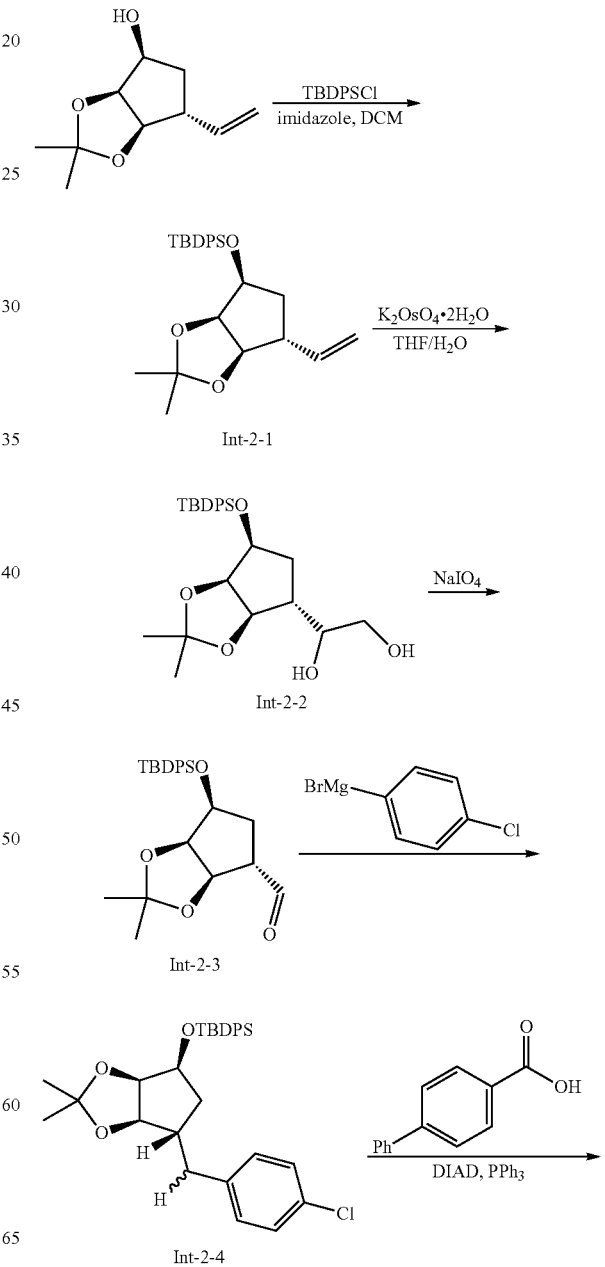

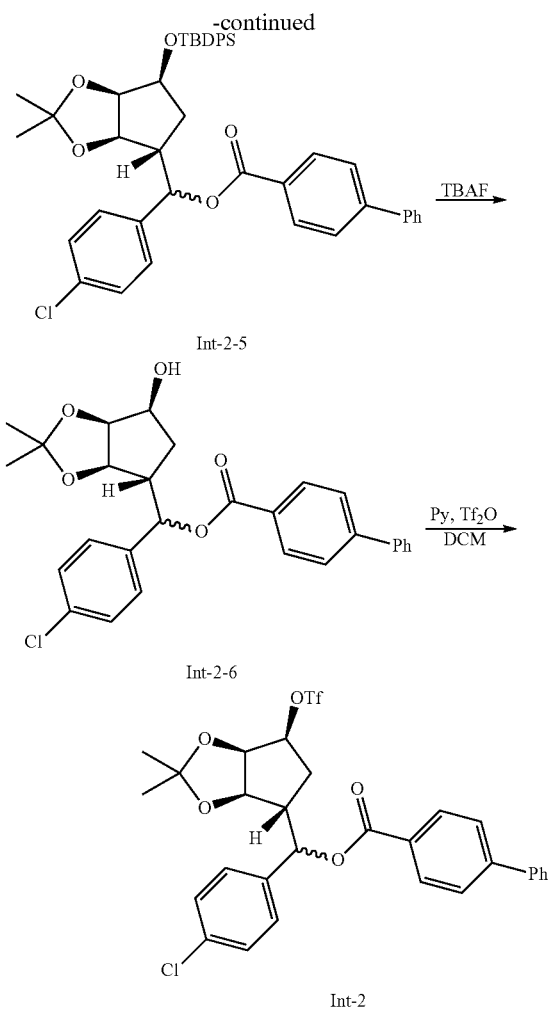

Step 1: Synthesis of Compound Int-2-1

To a solution of (3aS,4S,6R,6aR)-2,2-dimethyl-6-vinyl-4,5,6,6a-tetrahydro-3aH-cyclopenta[d][1,3]dioxol-4-ol (2.5 g, 13.6 mmol, prepared according to J. Org. Chem., 2004, vol. 69, 3993-3996) in DCM (10 mL) was added the imidazole (1.85 g, 27.1 mmol) and TBDPSCl (5.6 g, 20 mmol), then the mixture was stirred at 25° C. for 2 h. TLC (PE:EtOAc=10:1) showed the starting materials was consumed completed and a new spot was detected. The reaction was concentrated to dryness and the residue was diluted with EtOAc (100 ml), which was washed with water (50 ml×2) and brine (40 ml). The combined organic layers were dried over $Na_2SO_4$ before concentration to dryness. The residue was purified by flash column chromatography (PE:EtOAc=40:1 to 20:1) to afford Int-2-1 (5.6 g, 13.25 mmol, 97.6%) as a colorless oil. $^1$H NMR (400 MHz, CDCl$_3$): δ 7.76-7.71 (m, 4H), 7.43-7.35 (m, 6H), 5.57-5.49 (m, 1H), 4.83 (d, 1H), 4.74 (d, 1H), 4.27-4.21 (m, 2H), 4.04-3.99 (m, 1H), 2.56 (t, 1H), 2.08-2.00 (m, 1H), 1.59-1.52 (m, 1H), 1.59 (s, 3H), 1.30 (s, 3H), 1.07 (s, 9H).

Step 2: Synthesis of Compound Int-2-2

To a solution of compound Int-2-1 (5.6 g, 13 mmol) in THF (100 mL) and H$_2$O (50 mL) was added NMO (2.3 g, 20 mmol) and K$_2$OsO$_4$.2H$_2$O (488 mg, 1.33 mmol), then the reaction was stirred at 25° C. overnight. TLC (PE:EtOAc=1:1) showed the starting materials was consumed completely and a new spot was detected. EtOAc (20 mL) was added to the mixture and the organic layer was washed with saturated Na$_2$SO$_3$ solution (2 mL) and brine (10 mL). The organic layer was dried over Na$_2$SO$_4$, concentrated in vacuo to afford a residue. The residue was purified by silica gel chromatography eluted with petroleum ether:EtOAc=3:1 to 1:1 to afford Int-2-2 (4.6 g, 9.44 mmol, 71.25%) as a colorless oil. LCMS [M+23] 479.2; $^1$H NMR (400 MHz, CDCl$_3$): δ 7.76-7.71 (m, 4H), 7.44-7.35 (m, 6H), 4.28-4.11 (m, 3H), 3.50-3.33 (m, 3H), 2.10-2.04 (m, 1H), 1.94-1.88 (m, 1H), 1.58-1.52 (m, 1H), 1.54 (s, 3H), 1.31 (s, 3H), 1.08 (s, 9H).

Step 3: Synthesis of Compound Int-2-3

To a solution of compound Int-2-2 (4.6 g, 10. mmol) in THF (50 mL) and water (25 mL) was added NaIO$_4$ (6.46 g, 30.2 mmol), then the mixture was stirred at 25° C. for 2 h. TLC (PE:EtOAc=3:1) showed the starting materials was consumed and a new spot was detected. The mixture was poured into EtOAc (100 ml) and the organic layer was washed with water (50 ml×2) and brine (50 ml). The organic layer was dried over Na$_2$SO$_4$ and concentrated in vacuo to give the crude Int-2-3 (4.0 g, 9.42 mmol, 93.52%) as a colorless oil, which was used in the next step without further purification. $^1$H NMR (400 MHz, CDCl$_3$): δ 9.47 (s, 1H), 7.74-7.68 (m, 4H), 7.45-7.34 (m, 6H), 4.70 (d, 1H), 4.18-4.13 (m, 1H), 3.81-3.76 (m, 3H), 2.77 (d, 1H), 3.50-3.33 (m, 3H), 2.16-2.04 (m, 1H), 1.92-1.88 (m, 1H), 1.53 (s, 3H), 1.30 (s, 3H), 1.07 (s, 9H).

Step 4: Synthesis of Compound Int-2-4

To a solution of compound Int-2-3 (4.0 g, 9.42 mmol) in dry THF (20 mL) was added Bromo (4-chlorophenyl)magnesium (1M in THF, 47.1 mL, 47.1 mmol), then the reaction was stirred at 25° C. for 1 h. TLC (PE:EtOAc=3:1) showed the starting material was consumed completely and a new spot was detected. H$_2$O (1 ml) was added to quench the reaction and the mixture was diluted with EtOAc (50 ml), washed with H$_2$O (40 ml×2) and brine (30 ml×2). The organic layer was separated and dried over Na$_2$SO$_4$ before concentration to dryness. The residue was purified by silica gel chromatography eluted with petroleum ether:EtOAc=5:1 to 3:1 to afford Int-2-4 (3.5 g, 6.52 mmol, 69.17%) as a white solid. $^1$H NMR (400 MHz, CDCl$_3$): δ 7.75-7.68 (m, 4H), 7.46-7.30 (m, 6H), 7.24-6.97 (m, 4H), 4.63-4.55 (m, 1H), 4.38-4.03 (m, 3H), 2.25-2.23 (m, 1H), 1.83-1.75 (m, 2H), 1.54 (s, 3H, two peaks from epimers), 1.31 (s, 3H, two peaks from epimers), 1.03 (s, 9H, two peaks from epimers).

Step 5: Synthesis of Compound Int-2-5

To a solution of compound Int-2-4 (3.5 g, 6.52 mmol) in toluene (100 mL) was added PPh$_3$ (2.56 g, 9.77 mmol), 4-phenylbenzoic acid (1.94 g, 9.77 mmol), DIAD (1.98 g, 9.77 mmol) at 0° C., then the mixture was stirred at 20° C. for 2 h. TLC (PE:EtOAc=10:1) showed the starting materials was consumed completely and a new spot was detected. The mixture was concentrated in vacuo and the residue was purified by silica gel chromatography eluted with petroleum ether:EtOAc=30:1 to 20:1 to afford Int-2-5 (4.60 g, 6.41 mmol, 98.4%) as a white solid. $^1$H NMR (400 MHz, CDCl$_3$): δ 8.25-7.01 (m, 23H), 5.85-5.37 (m, 1H), 4.45-4.27

(m, 2H), 4.14-4.09 (m, 1H), 2.54-2.49 (m, 1H), 2.04-1.97 (m, 1H), 1.67-1.63 (m, 1H), 1.56 (s, 3H, two peaks from epimers), 1.28 (s, 3H, two peaks from epimers), 1.04 (s, 9H, two peaks from epimers).

Step 6: Synthesis of Compound Int-2-6

To a solution of compound Int-2-5 (4.60 g, 6.41 mmol) in THF (20 mL) was added tetrabutylammonium fluoride (1 μM in THF, 32 mL, 32 mmol), then the mixture was stirred at 25° C. overnight. TLC (PE:EtOAc=3:1) showed the starting materials was almost consumed completely. The solution was concentrated in vacuo and purified by silica gel chromatography eluted with petroleum ether:EtOAc=10:1 to 5:1 to afford Int-2-6 (1.60 g, 3.34 mmol, 52.1%) as a white solid. $^1$H NMR (400 MHz, CDCl$_3$): δ 8.13-7.26 (m, 13H), 6.11-5.73 (m, 1H), 4.63-4.46 (m, 2H), 4.29-4.11 (m, 1H), 2.78-2.75 (m, 1H), 2.50-2.39 (m, 1H), 2.04-1.91 (m, 1H), 1.53 (s, 3H, two peaks from epimers), 1.33 (s, 3H, two peaks from epimers).

Step 7: Synthesis of Compound Int-2

To a solution of compound Int-2-6 (1.60 g, 3.34 mmol) in DCM (20 mL) was added the pyridine (1.4 mL, 16.7 mmol), then Tf$_2$O (1.41 g, 5.01 mmol) was added slowly to the mixture and stirred at rt for 2 h. TLC (PE:EtOAc=10:1) showed the starting materials was consumed and a new spot was detected. The mixture was purified by silica gel chromatography eluted with petroleum ether:EtOAc=20:1 to 10:1 to give the desired product Int-2 (1.80 g, 2.95 mmol, 88.2%) as a white solid. $^1$H NMR (400 MHz, CDCl$_3$): δ 8.13-7.28 (m, 13H), 6.16-5.82 (m, 1H), 5.34-5.07 (m, 1H), 4.72-4.54 (m, 2H), 2.84-2.82 (m, 1H), 2.34-2.12 (m, 2H), 1.53 (s, 3H, two peaks from epimers), 1.31 (s, 3H, two peaks from epimers).

Synthesis of Int-3

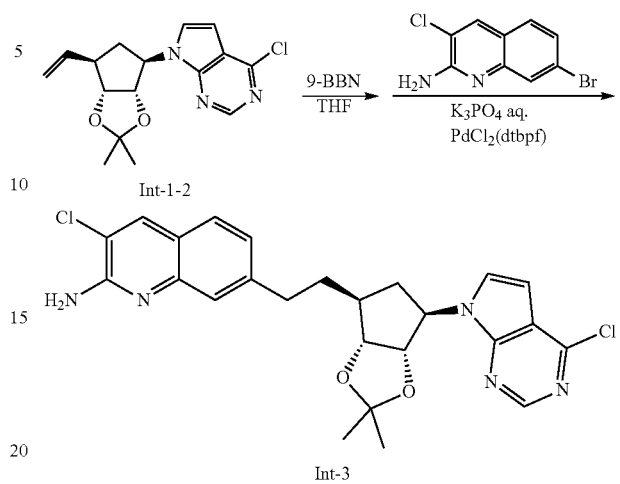

A solution of compound Int-1-2 (0.65 g, 2.03 mmol, 1 eq.) and 9-BBN (0.5 μM, 12.20 mL, 3 eq.) was stirred at 75° C. for 45 min. LC-MS showed compound Int-1-2 was consumed completely. To the reaction solution was added K$_3$PO$_4$ (1.24 g, 5.82 mmol, 3.04 eq.), 7-bromo-3-chloroquinolin-2-amine (493.03 mg, 1.91 mmol, 1 eq.), H$_2$O (2.4 mL), THF (12 mL) and ditert-butyl(cyclopentyl)phosphane; dichloropalladium; iron (124.78 mg, 191.46 umol, 0.1 eq.). The mixture was sealed and stirred at 75° C. for 12 h. LC-MS showed several new peaks and desired compound was detected. The mixture was diluted with H$_2$O (50 mL), and extracted with EtOAc (50 mL*3). The combined organic phase was washed with saturated NaCl (50 mL*2), dried with anhydrous Na$_2$SO$_4$, and concentrated in vacuo. The residue was purified by column chromatography (SiO$_2$, Petroleum ether/Ethyl acetate=50:1 to 1:1). Compound Int-3 (0.2 g, 264.85 umol, 13.83% yield, 66% LCMS purity) was obtained as a yellow solid checked. LCMS: (M+H$^+$): 498.1.

Synthesis of Int-4

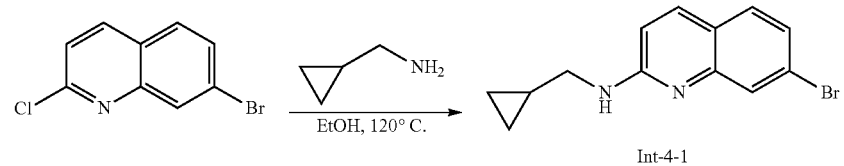

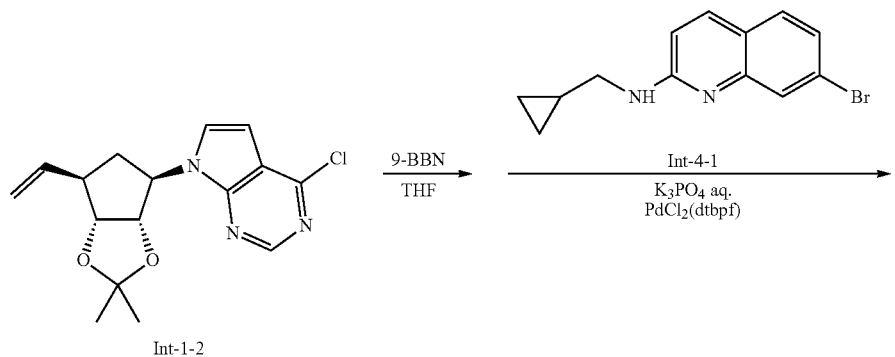

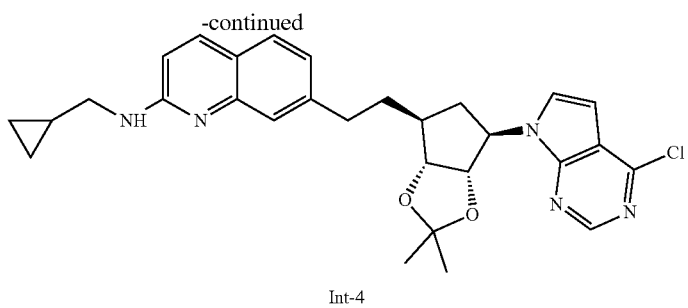

Int-4

Step 1. Synthesis of Int-4-1

A mixture of 7-bromo-2-chloro-quinoline (2 g, 8.25 mmol, 1 eq.) and cyclopropylmethanamine (6.15 g, 86.53 mmol, 6 mL, 10.49 eq.) in EtOH (10 mL) was stirred at 120° C. for 12 hrs. TLC showed the reaction was complete. The mixture was concentrated. The residue was purified by column chromatography (SiO2, Petroleum ether/Ethyl acetate=10:1 to 1:1). Int-4-1 (2.2 g, 7.63 mmol, 92.52% yield, 96.127% purity) was obtained as a yellow solid. $^1$H NMR (400 MHz, CHLOROFORM-d) δ=7.63 (d, J=1.8 Hz, 1H), 7.53 (d, J=8.9 Hz, 1H), 7.20 (d, J=8.4 Hz, 1H), 7.09-7.05 (m, 1H), 6.40 (d, J=8.9 Hz, 1H), 4.66 (br s, 1H), 3.13 (dd, J=5.3, 7.1 Hz, 2H), 0.91 (tquin, J=4.8, 7.5 Hz, 1H), 0.41-0.31 (m, 2H), 0.13-0.03 (m, 2H); LCMS: (M+H$^+$): 276.9, 278.9; LCMS purity: 96.12%; TLC (Petroleum ether: Ethyl acetate=3:1) R$_f$=0.60.

Step 2. Synthesis of Int-4

A mixture of Int-1-2 (1.5 g, 4.69 mmol, 1 eq.) in 9-BBN (0.5 μM, 30 mL, 3.20 eq.) was stirred at 75° C. for 1 hr. LCMS showed the starting material was consumed. It was cooled to 25° C. The solution was used directly in the next step. To the above solution in 30 mL THE was added 7-bromo-N-(cyclopropylmethyl)quinolin-2-amine (Int-4-1) (1.56 g, 5.61 mmol, 1.2 eq.), K$_3$PO$_4$ (3.02 g, 14.22 mmol, 3.04 eq.) and ditert-butyl(cyclopentyl)phosphane; dichloropalladium; iron (0.2 g, 306.87 umol, 0.066 eq.), H$_2$O (7.8 mL) and THE (60 mL). The mixture was stirred at 75° C. for 12 hr under N$_2$. LCMS showed the reaction was completed. It was cooled to 20° C. and concentrated at 45° C. The residue was purified by column chromatography (SiO$_2$, Petroleum ether/Ethyl acetate=15/1 to 3/1). Int-4 (0.5 g, 965.16 umol, 20.64% yield) was obtained as a brown oil. $^1$H NMR (400 MHz, CHLOROFORM-d) δ=8.56 (s, 1H), 7.70 (d, J=8.8 Hz, 1H), 7.48-7.38 (m, 2H), 7.21 (d, J=3.7 Hz, 1H), 7.01 (d, J=8.2 Hz, 1H), 6.57-6.49 (m, 2H), 4.98-4.81 (m, 2H), 4.75 (br s, 1H), 4.50-4.40 (m, 1H), 3.34-3.18 (m, 2H), 2.85-2.70 (m, 2H), 2.42 (td, J=6.0, 11.8 Hz, 1H), 2.23-2.13 (m, 1H), 2.03-1.94 (m, 1H), 1.86-1.73 (m, 2H), 1.50 (s, 3H), 1.24 (s, 3H), 1.11-1.00 (m, 1H), 0.54-0.45 (m, 2H), 0.23 (q, J=4.8 Hz, 2H); LCMS: (M+H$^+$): 518.0; TLC (Petroleum ether:Ethyl acetate=2:1) Rf=0.24.

Example 25-B. 7-[(1R,2S,3R,4R)-4-[(S)-(4-chlorophenyl)-hydroxy-methyl]-2,3-dihydroxy-cyclopentyl]-1H-pyrrolo[2,3-d]pyrimidin-4-one hydrazone hydrochloride (Ex. 25-B)

Int-2 ⟶

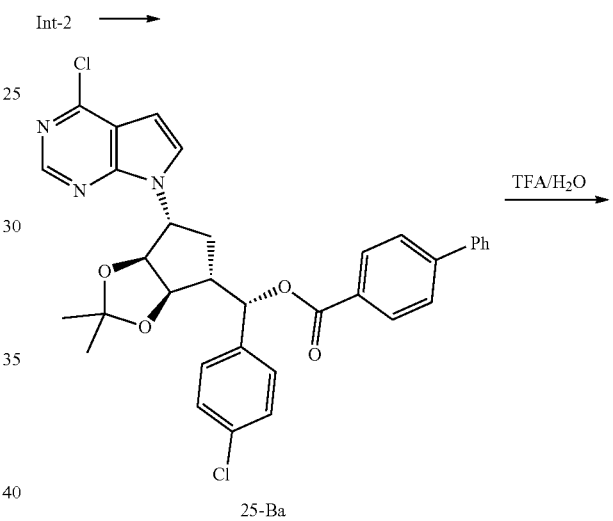

25-Ba

TFA/H$_2$O ⟶

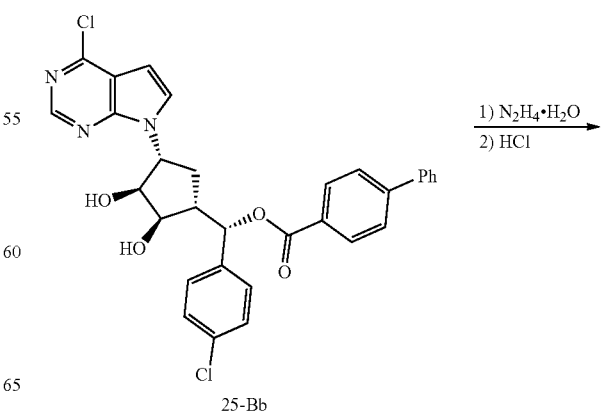

25-Bb

1) N$_2$H$_4$·H$_2$O
2) HCl ⟶

-continued

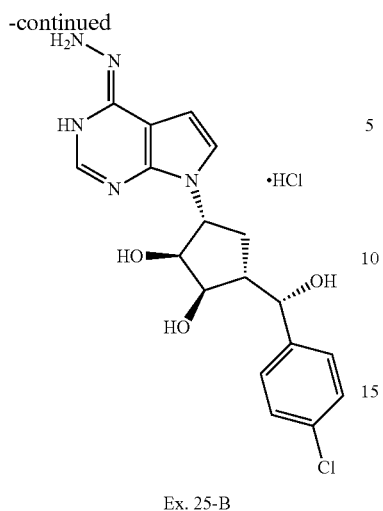

Ex. 25-B a) Synthesis of [(S)-[(3aS,4R,6R,6aR)-4-(4-chloro-pyrrolo[2,3-d]pyrimidin-7-yl)-2,2-dimethyl -4,5,6,6a-tetrahydro-3aH-cyclopenta[d][1,3]dioxol-6-yl]-(4-chlorophenyl)methyl] 4-phenylbenzoate (25-Ba)

Compound 25-Ba was prepared similarly to that of Int-1-2.

b) Synthesis of [(S)-(4-chlorophenyl)-[(1S,2R,3S,4R)-4-(4-chloropyrrolo[2,3-d] pyrimidin-7-yl)-2,3-dihydroxy-cyclopentyl]methyl] 4-phenylbenzoate (25-Bb)

To a solution of [(S)-[(3aS,4R,6R,6aR)-4-(4-chloropyrrolo[2,3-d]pyrimidin-7-yl)-2,2-dimethyl -4,5,6,6a-tetrahydro-3aH-cyclopenta[d][1,3]dioxol-6-yl]-(4-chlorophenyl)methyl] 4-phenylbenzoate (25-Ba) (210.0 mg, 0.34 mmol) in THF (2.0 mL), TFA (1.0 mL, 13.51 mmol) in water (1.0 mL, 55.49 mmol) was added. The mixture was stirred at 25° C. for 4 hrs. LCMS showed 83% desired product was detected in 254 nm. The solvent was removed, and the mixture was extracted with EA (30.0 mL×3). The combined organic layers were dried over $Na_2SO_4$ and concentrated in vacuum to give the crude [(S)-(4-chlorophenyl)-[(1S,2R,3S,4R)-4-(4-chloropyrrolo[2,3-d] pyrimidin-7-yl)-2,3-dihydroxy-cyclopentyl]methyl] 4-phenylbenzoate (25-Bb) (130.0 mg, 0.22 mmol, 66.12% yield) as yellow solid which was used in the next step directly. LCMS [M+H]: 574.1.

c) Synthesis of 7-[(1R,2S,3R,4R)-4-[(S)-(4-chloro-phenyl)-hydr oxy-methyl]-2,3-dihydroxy-cyclopen-tyl]-1H-pyrrolo[2,3-d]pyrimidin-4-one hydrazone hydro chloride (Ex. 25-B)

To a solution of [(S)-(4-chlorophenyl)-[(1S,2R,3S,4R)-4-(4-chloropyrrolo[2,3-d]pyrimidin-7-yl)-2,3-dihydroxy-cyclopentyl]methyl] 4-phenylbenzoate (25-Bb) (40.0 mg, 0.06 mmol) in ethanol (1.0 mL), hydrazine hydrate (2.5 mL, 51.23 mmol) was added. The mixture was stirred at 25° C. for 16 hrs. LCMS (SYZ001-50-R1) showed the reaction was completed. The mixture was adjusted to pH 2 with 4 μM HCl aqueous solution. The mixture was purified by prep-HPLC eluting with $CH_3CN/H_2O$ (0.1% TFA contained) from 5/95 to 95/5 to give 7-[(1R,2S,3R,4R)-4-[(S)-(4-chlorophenyl)-hydr oxy-methyl]-2,3-dihydroxy-cyclopentyl]-1H-pyrrolo[2,3-d]pyrimidin-4-one hydrazone hydro chloride (Ex. 25-B) (3.7 mg, 0.01 mmol, 13.89% yield) as a white solid. LCMS [M+H]: 390.1. $^1$H NMR (400 MHz, $CD_3OD$): δ 8.19 (s, 1H), 7.51 (s, 1H), 7.32-7.43 (m, 4H), 6.79 (s, 1H), 5.04-5.11 (m, 1H), 4.68 (d, J=6.8 Hz, 1H), 4.40 (m, 1H), 4.16 (m, 1H), 2.40-2.44 (m, 1H), 2.11-2.19 (m, 1H), 1.73-1.81 (m, 1H).

Example 28-B. 7-[(1R,2S,3R,4R)-4-[(S)-(4-chloro-phenyl)-hydroxy-methyl]-2,3-dihydroxy-cyclopen-tyl]-5-fluoro-H-pyrrolo[2,3-d]pyrimidin-4-one hydrazone hydrochloride (Ex. 28-B)

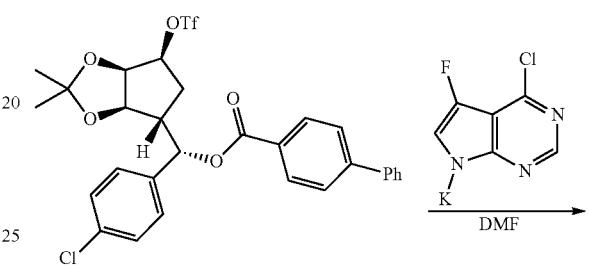

Int-2, S-epimer

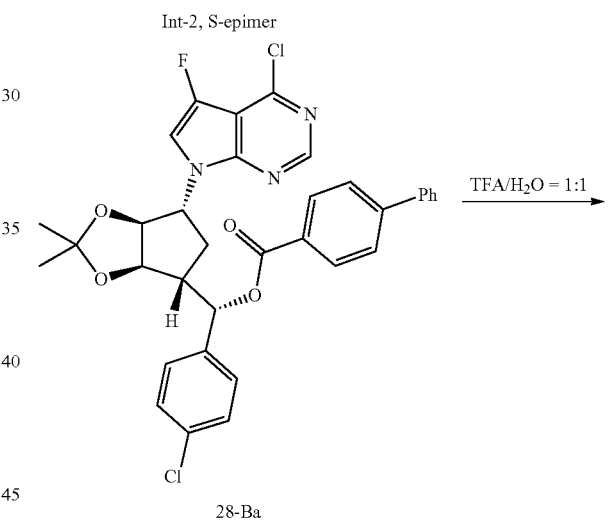

28-Ba

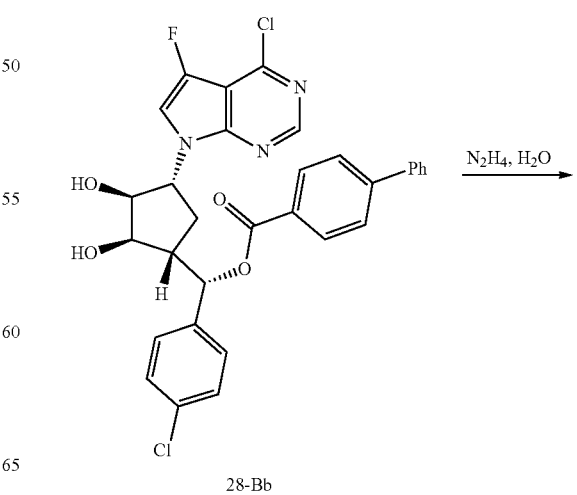

28-Bb

301

-continued

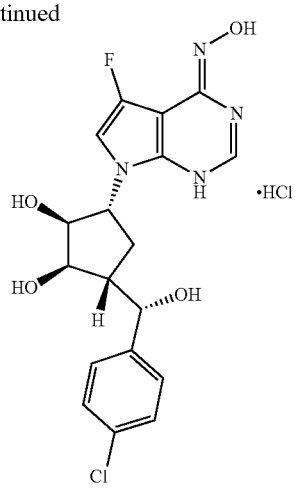

Ex. 28-B a) Synthesis of 7-[(3aS,4S,6R,6aR)-6-[(S)-(4-chlorophenyl)-[(4-phenylphenyl)methoxy]methyl]-2,2-dimethyl-4,5,6,6a-tetrahydro-3aH-cyclopenta[d][1,3]dioxol-4-yl]-4-chloro-5-fluoro-pyrrolo[2,3-d]pyrimidine(28-Ba)

To a solution of [(3aR,4S,6R,6aR)-6-[(S)-(4-chlorophenyl)-[(4-phenylphenyl)methoxy]methyl]-2,2-dimethyl-4,5,6,6a-tetrahydro-3aH-cyclopenta[d][1,3]dioxol-4-yl]trifluoromethanesulfonate (Int-2, S-epimer) (199.4 mg, 0.33 mmol) in DMF (10.0 mL) was added (4-chloro-5-fluoropyrrolo[2,3-d]pyrimidin-7-yl)potassium (70.0 mg, 0.33 mmol), then stirred at 25° C. for 4 hrs. After the reaction was complete, the reaction mixture was concentrated in vacuum, taken into water, and extracted with EA (20.0 mL). The organic layer was concentrated in vacuum to give crude 7-[(3aS,4S,6R,6aR)-6-[(S)-(4-chlorophenyl)-[(4-phenylphenyl)methoxy]methyl]-2,2-dimethyl-4,5,6,6a-tetrahydro-3aH-cyclopenta[d][1,3]dioxol-4-yl]-4-chloro-5-fluoro-pyrrolo[2,3-d]pyrimidine (28-Ba) (200.0 mg, 0.27 mmol, 82.3% yield) which was used in the next step directly. LCMS [M+H]: 632.2.

b) Synthesis of [(S)-[(1S,2R,3S,4R)-4-(4-chloro-5-fluoro-pyrrolo[2,3-d]pyrimidin-7-yl)-2,3-dihydroxy-cyclopentyl]-(4-chlorophenyl)methyl] 4-phenylbenzoate (28-Bb)

To a solution of [(S)-[(3aS,4R,6R,6aR)-4-(4-chloro-5-fluoro-pyrrolo[2,3-d]pyrimidin-7-yl)-2,2-dimethyl-4,5,6,6a-tetrahydro-3aH-cyclopenta[d][1,3]dioxol-6-yl]-(4-chlorophenyl)methyl] 4-phenylbenzoate (28-Ba) (200.0 mg, 0.27 mmol) in THF (3.0 mL) and water (25.0 mL) was added TFA (5.0 mL, 67.53 mmol). The reaction mixture was stirred at 20° C. for 12 hrs. After the reaction was complete, the reaction mixture was concentrated in vacuum and extracted with EA (30.0 mL). The organic layer was dried over $Na_2SO_4$, filtered and concentrated in vacuum to give the crude [(S)-[(1S,2R,3S,4R)-4-(4-chloro-5-fluoro-pyrrolo[2,3-d]pyrimidin-7-yl)-2,3-dihydroxy-cyclopentyl]-(4-chlorophenyl)methyl] 4-phenylbenzoate (28-Bb) (70.0 mg, 0.07 mmol) as yellow oil which was used in the next step directly. LCMS [M+H]: 592.3.

302 c) Synthesis of 7-[(1R,2S,3R,4R)-4-[(S)-(4-chlorophenyl)-hydroxy-methyl]-2,3-dihydroxy-cyclopentyl]-5-fluoro-H-pyrrolo[2,3-d]pyrimidin-4-one hydrazone hydrochloride (Ex. 28-B)

To a solution of [(S)-[(1S,2R,3S,4R)-4-(4-chloro-5-fluoro-pyrrolo[2,3-d]pyrimidin-7-yl)-2,3-dihydroxy-cyclopentyl]-(4-chlorophenyl)methyl] 4-phenylbenzoate (70.0 mg, 0.07 mmol) in ethanol (3.0 mL) was added $N_2H_4 \cdot H_2O$ (3.0 mL, 61.73 mmol). The mixture was stirred at 20° C. for 2 hrs. After the reaction was complete, the mixture was concentrated in vacuum to give the residue, which was purified by prep-HPLC (0.1% TFA, 10-40% MeCN/$H_2O$) to afford the pure product as TFA salt. HCl (0.5 mL, 1 µM) was added to the solution and lyophilized to afford 7-[(1R,2S,3R,4R)-4-[(S)-(4-chlorophenyl)-hydroxy-methyl]-2,3-dihydroxy-cyclopentyl]-5-fluoro-H-pyrrolo[2,3-d]pyrimidin-4-one hydrazone hydrochloride (Ex. 28-B) (9.5 mg, 0.02 mmol, 30.2% yield) as yellow solid. LCMS [M+H]: 409.3. $^1$H NMR (400 MHz, $CD_3OD$-d4): δ 8.22 (s, 1H), 7.46-7.33 (m, 5H), 5.13-5.14 (m, 1H), 4.68 (d, J=6.8 Hz, 1H), 4.37 (m, 1H), 4.18 (d, J=3.2 Hz, 1H), 2.43 (in, 1H), 2.13 (in, 1H), 1.73 (in, 1H).

Example 37-B. 7-[(1R,2S,3R,4R)-4-[(S)-(3,4-difluorophenyl)-hydroxy-methyl]-2,3-dihydroxy-cyclopentyl]-1H-pyrrolo[2,3-d]pyrimidin-4-one hydrazone hydrochloride (Ex. 37-B)

37-Ba

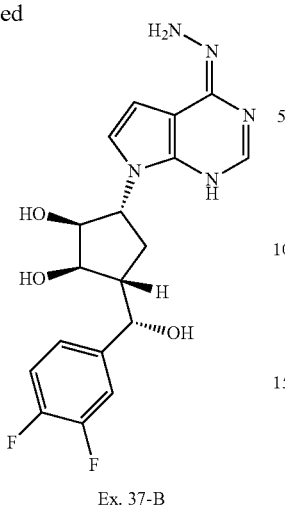

Ex. 37-B a) Synthesis of (1R,2S,3R,5R)-3-(4-chloropyrrolo[2,3-d]pyrimidin-7-yl)-5-[(S)-(3,4-difluorophen-yl)-hydroxy-methyl]cyclopentane-1,2-diol (37-Ba)

Compound 37-Ba was prepared by treated Int-1 with either TFA/H$_2$O or aq. HCl in methanol.

b) Synthesis of 7-[(1R,2S,3R,4R)-4-[(S)-(3,4-difluorophenyl)-hydroxy-methyl]-2,3-dihydroxy-cyclopentyl]-1H-pyrrolo[2,3-d]pyrimidin-4-one hydrazone hydrochloride (Ex. 37-B)

To a solution of (1R,2S,3R,5R)-3-(4-chloropyrrolo[2,3-d]pyrimidin-7-yl)-5-[(S)-(3,4-difluorophen-yl)-hydroxy-methyl]cyclopentane-1,2-diol (37-Ba) (79.00 mg, 0.20 mmol) in ethanol (3.00 mL) was added hydrazine hydrate (0.10 mL, 2.10 mmol). The mixture was stirred at 20° C. for 1 h. LC-MS showed the reaction was not complete, and additional hydrazine hydrate (0.20 mL, 4.12 mmol) was added. The mixture was stirred for another 1 h at 20° C. and LC-MS showed 55% product in the reaction mixture. Another batch of hydrazine hydrate (0.10 mL, 2.06 mmol) was added, and the mixture was stirred for another 1 h at 20° C. LC-MS showed the desired product is the major peak. The mixture was purified by prep-HPLC (0.1% TFA, H$_2$O:CH$_3$CN from 90:10 to 5:95), then 0.05 mL of conc. HCl was added. The mixture was lyophilized to afford 7-[(1R,2S,3R,4R)-4-[(S)-(3,4-difluorophenyl)-hydroxy-methyl]-2,3-dihydroxy-cyclopentyl]-1H-pyrrolo[2,3-d]pyrimidin-4-one hydrazone hydrochloride (Ex. 37-B) (30.6 mg, 0.07 mmol, 35.56% yield) as white solid. LCMS [M+H]: 392.3. $^1$HNMR (DMSO-d6, 400 MHz): δ 10.99 (b, 1H), 8.24 (s, 1H), 7.61-7.62 (m, 1H), 7.34-7.44 (m, 2H), 7.24-7.25 (m, 1H), 6.91-6.92 (m, 1H), 4.92-4.99 (m, 1H), 4.56-4.57 (m, 1H), 4.19-4.23 (m, 1H), 3.92-3.93 (m, 1H), 2.23-2.25 (m, 1H), 1.97-2.02 (m, 1H), 1.54-1.60 (m, 1H).

Example 49-B. (1S,2R,3R,5R)-3-[(S)-(4-chlorophenyl)-hydroxy-methyl]-5-[(4Z)-4-methoxyimino-1H-pyrrolo[2,3-d]pyrimidin-7-yl]cyclopentane-1,2-diol hydrochloride (Ex. 49-B)

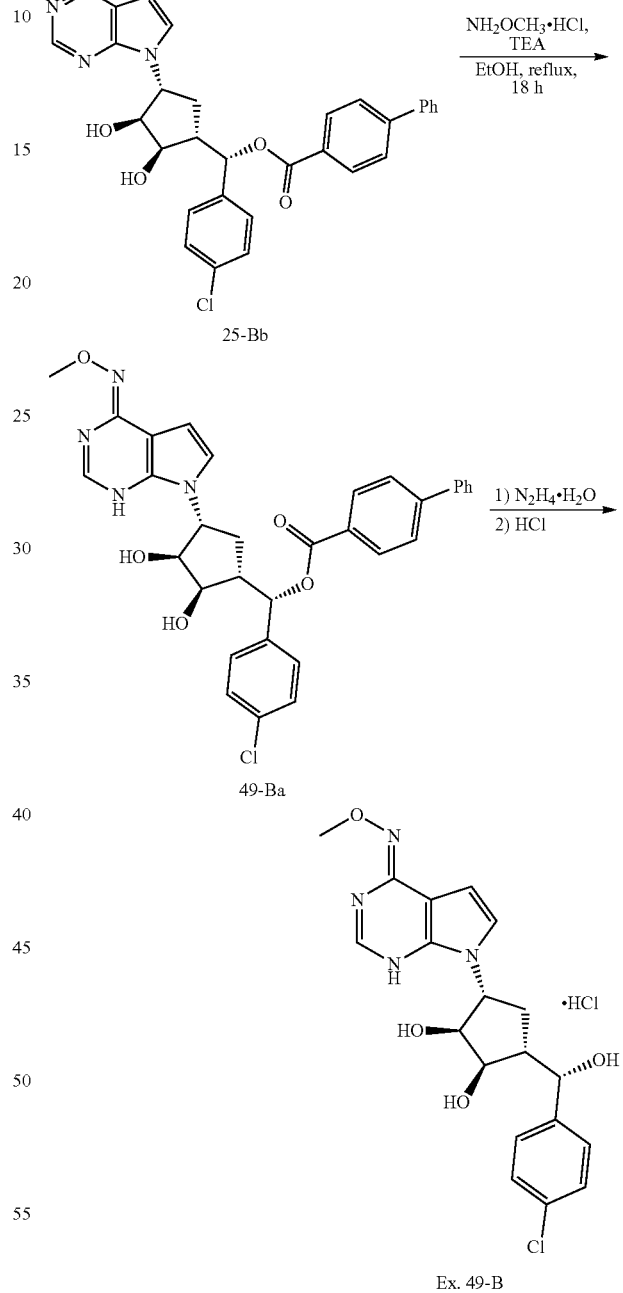

a) Synthesis of [(S)-(4-chlorophenyl)-[(1S,2R,3S,4R)-2,3-dihydroxy-4-[(4E)-4-methoxyimino-1H-pyrrolo[2,3-d]pyrimidin-7-yl]cyclopentyl]methyl] 4-phenylbenzoate (49-Ba)

To a solution of [(S)-(4-chlorophenyl)-[(1S,2R,3S,4R)-4-(4-chloropyrrolo[2,3-d]pyrimidin-7-yl)-2,3-dihydroxy-cyclopentyl]methyl] 4-phenylbenzoate (25-Bb) (20.0 mg, 0.03 mmol) in ethanol (10.0 mL) was added the TEA (5.0 mL, 0.03 mmol) and NH$_2$OCH$_3$—HCl (90.0 mg, 1.08 mmol) in a seal vessel. The mixture was stirred at 90° C. for 16 hrs. LCMS showed the starting material was almost consumed and the desired product was detected. The mixture was concentrated in vacuum and the residue was extracted with EA (20.0 mL×3) and the organic layers were concentrated to give the crude product [(S)-(4-chlorophenyl)-[(1S,2R,3S,4R)-2,3-dihydroxy-4-[(4E)-4-methoxyimino-1H-pyrrolo[2,3-d]pyrimidin-7-yl]cyclopentyl]methyl] 4-phenylbenzoate (49-Ba) (22.0 mg, 0.02 mmol, 73.95% yield) and the crude product was used directly for the next steps. LCMS [M+H]: 585.2.

b) Synthesis of (1S,2R,3R,5R)-3-[(S)-(4-chlorophenyl)-hydroxy-methyl]-5-[(4Z)-4-methoxyimino-1H-pyrrolo[2,3-d]pyrimidin-7-yl]cyclopentane-1,2-diol hydrochloride (Ex. 49-B)

To a solution of [(S)-(4-chlorophenyl)-[(1S,2R,3S,4R)-2,3-dihydroxy-4-[(4Z)-4-methoxyimino-1H-pyrrolo[2,3-d]pyrimidin-7-yl]cyclopentyl]methyl] 4-phenylbenzoate (49-Ba) (0.04 mL, 0.02 mmol) in ethanol (1.0 mL), hydrazine hydrate (0.2 mL, 4.12 mmol) was added, and the mixture was stirred at 25° C. for 16 hrs. LCMS showed the starting material was almost consumed. The mixture was purified by prep-HPLC eluting with CH$_3$CN/H$_2$O (0.1% TFA contained) from 5/95 to 95/5 to give the desired TFA salt as white solid. The solid was dissolved in 1 μM HCl aq. (3.0 mL) and lyophilized to give (1S,2R,3R,5R)-3-[(S)-(4-chlorophenyl)-hydroxy-methyl]-5-[(4Z)-4-methoxyimino-1H-pyrrolo[2,3-d]pyrimidin-7-yl]cyclopentane-1,2-diol hydrochloride (Ex. 49-B) (2.8 mg, 0.0057 mmol, 29.13% yield) as white solid. LCMS [M+H]: 405.1. $^1$H NMR (400 MHz, CD$_3$OD-d4): δ 8.12 (s, 1H), 7.33-7.44 (m, 5H), 6.67 (d, J=3.6 Hz, 1H), 5.00-5.07 (m, 1H), 4.68 (d, J=2.8 Hz, 1H), 4.37-4.41 (m, 1H), 4.14-4.17 (m, 1H), 3.92 (s, 3H), 2.40-2.46 (m, 1H), 2.11-2.19 (m, 1H), 1.72-1.18 (m, 1H).

Example 50-B. 7-[(1R,2S,3R,4R)-4-[(S)-(4-chlorophenyl)-hydroxy-methyl]-2,3-dihydroxy-cyclopentyl]-1H-pyrrolo[2,3-d]pyrimidin-4-one oxime hydrochloride (Ex. 50-B)

Example 50-B was prepared similarly to that of Ex. 49-B. LCMS [M+H]: 391.1. $^1$H NMR (400 MHz, DMSO-d6) δ 8.87 (br, 2H), 8.23 (s, 1H), 7.62 (d, J=3.6 Hz, 1H), 7.42-7.36 (m, 4H), 6.92 (d, J=3.6 Hz, 1H), 4.95 (m, 1H), 4.55 (d, J=6.8 Hz, 1H), 4.22 (m, 1H), 3.94 (d, J=4.8 Hz, 1H), 2.24-2.51 (m, 1H), 2.01-1.96 (m, 1H), 1.59-1.55 (m, 1H).

Example 79-B. (1S,2R,3S,5R)-3-(2-(2-((cyclopropylmethyl)amino)quinolin-7-yl)ethyl)-5-(4-(1-methylhydrazineyl)-7H-pyrrolo[2,3-d]pyrimidin-7-yl)cyclopentane-1,2-diol (79-B)

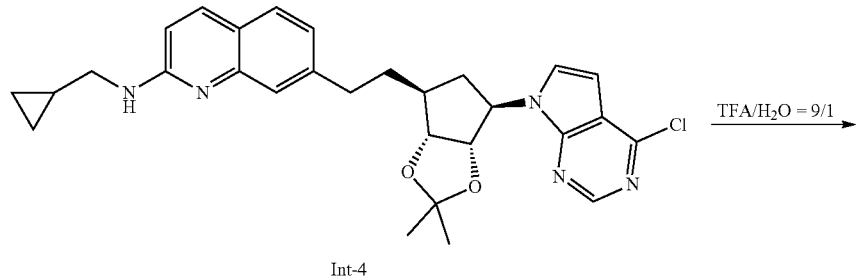

Int-4

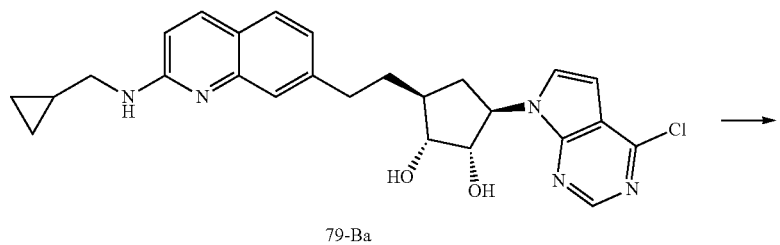

79-Ba

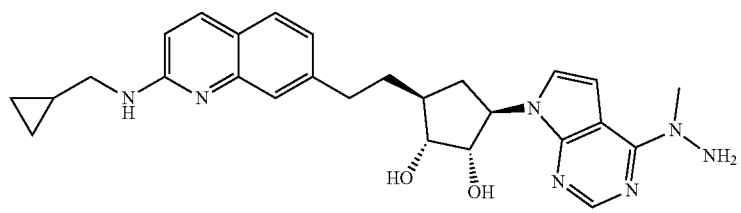

Ex. 79-B a) Synthesis of compound 79-Ba

A mixture of compound 1 (0.035 g, 67.56 umol, 1 eq.) in TFA (2 mL) and H$_2$O (0.22 mL) was stirred at 20° C. for 10 min. LCMS showed the reaction was completed, and the desired product was detected. The mixture was concentrated at 25° C. directly. The crude product compound 79-Ba (0.03 g, crude) was used into the next step without further purification (as a brown oil). LCMS: (M+H$^+$): 478.2 b) Synthesis of (1S,2R,3S,5R)-3-(2-(2-((cyclopropylmethyl)amino)quinolin-7-yl)ethyl)-5-(4-(1-methylhydrazineyl)-7H-pyrrolo[2,3-d]pyrimidin-7-yl)cyclopentane-1,2-diol (79-B)

To a solution of compound 2 (0.03 g, 62.76 umol, 1 eq.) in dioxane (4 mL) was added methylhydrazine (291.65 mg, 2.53 mmol, 333 uL, 40.3 eq.). The mixture was stirred at 100° C. for 12 hr. LCMS showed the reaction was completed. It was concentrated to give the crude product. It was purified by prep-HPLC (HCl condition) to give the product. Ex. 79-B (14 mg, 27.10 umol, 43.19% yield, 94.4% purity) was obtained as a colorless oil. $^1$H NMR (400 MHz, DMSO-d$_6$) δ=12.85 (br s, 1H), 9.63 (br s, 1H), 7.89 (s, 1H), 7.85 (br d, J=9.3 Hz, 1H), 7.79 (br s, 1H), 7.42 (br d, J=7.1 Hz, 2H), 7.00 (br d, J=7.5 Hz, 1H), 6.82 (br d, J=9.0 Hz, 1H), 6.75-6.65 (m, 1H), 4.67-4.54 (m, 1H), 3.86 (dd, J=5.8, 8.3 Hz, 1H), 2.56-2.32 (m, 2H), 2.02-1.84 (m, 1H), 1.66-1.46 (m, 2H), 1.45-1.28 (m, 1H), 1.23-1.07 (m, 1H), 0.82 (br s, 1H), 0.20 (br d, J=7.1 Hz, 2H), 0.01 (br d, J=4.2 Hz, 2H); $^1$H NMR (400 MHz, DMSO-d$_6$+D$_2$O) δ=7.96-7.80 (m, 2H), 7.57 (br s, 1H), 7.45 (br d, J=8.2 Hz, 1H), 7.39 (br d, J=3.3 Hz, 1H), 7.02 (br d, J=8.2 Hz, 1H), 6.81-6.67 (m, 2H), 4.67-4.54 (m, 1H), 3.86 (dd, J=6.0, 8.4 Hz, 1H), 3.44-3.38 (m, 2H), 3.10 (br d, J=6.6 Hz, 2H), 2.55-2.35 (m, 2H), 2.02-1.85 (m, 1H), 1.68-1.47 (m, 2H), 1.46-1.31 (m, 1H), 1.27-1.11 (m, 1H), 0.82 (br s, 1H), 0.23 (br d, J=7.1 Hz, 2H), 0.01 (br d, J=4.6 Hz, 2H); LCMS: (M+H$^+$): 488.2, LCMS purity: 97.61%; HPLC purity: 94.47%.

Example 84-B. 7-((1R,2S,3R,4S)-2,3-dihydroxy-4-(2-(2-(methylamino)quinolin-7-yl)ethyl)cyclopentyl)-1,7-dihydro-4H-pyrrolo[2,3-d]pyrimidin-4-one O-methyl oxime (84-B)

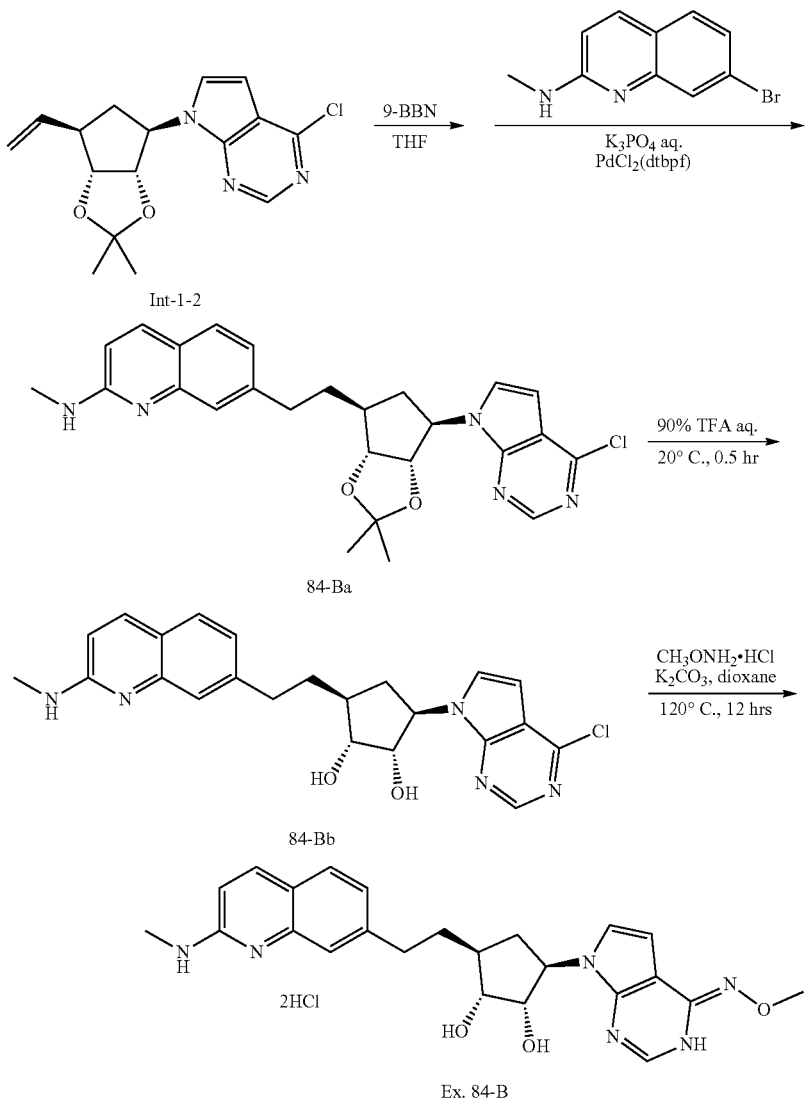

a) Synthesis of compound 84-Ba

A solution of Int-1-2 (0.2 g, 625 umol, 1 eq.) and 9-BBN (0.5 μM, 3.75 mL, 3 eq.) was stirred at 75° C. for 45 min. LC-MS showed Int-1-2 was consumed completely. One main peak with desired MS was detected. Without work up and purification, the reaction solution was used in the next step directly. To the reaction solution was added $K_3PO_4$ (402 mg, 1.90 mmol, 3.04 eq.), 7-bromo-N-methyl-quinolin-2-amine (177.42 mg, 748.32 umol, 1.2 eq.), and ditert-butyl (cyclopentyl) phosphane; dichloropalladium; iron (40.64 mg, 62.36 umol, 0.1 eq.), $H_2O$ (0.8 mL) and THF (4 mL). The mixture was stirred at 75° C. for 12 hr. LC-MS showed several new peaks and one main peak with desired MS was detected. The mixture was extracted with EtOAc (30 mL*3) and washed with saturated NaCl (20 mL). The combined organic phase was dried with anhydrous $Na_2SO_4$ and concentrated in vacuo. The residue was purified by column chromatography ($SiO_2$, Petroleum ether/Ethyl acetate=50:1 to 1:1). Compound 84-Ba (0.1 g, 171.55 umol, 27.51% yield, 82% purity) was obtained as a yellow oil. $^1$H NMR (400 MHz, DMSO-d6) δ=8.63 (s, 1H) 7.93-7.99 (m, 1H) 7.74 (d, J=9.04 Hz, 1H) 7.49 (d, J=7.94 Hz, 1H) 7.35 (s, 1H) 7.01 (d, J=7.94 Hz, 1H) 6.90 (br d, J=4.85 Hz, 1H) 6.71 (d, J=3.53 Hz, 1H) 6.64 (d, J=8.82 Hz, 1H) 5.05 (br d, J=7.06 Hz, 1H) 4.87-4.94 (m, 1H) 3.57 (br t, J=6.50 Hz, 3H) 2.85 (d, J=4.85 Hz, 3H) 2.72 (br t, J=7.61 Hz, 2H) 2.64 (br d, J=1.76 Hz, 1H) 1.72-1.76 (m, 3H) 0.81 (dt, J=16.87, 6.89 Hz, 3H); LCMS: (M+H$^+$): 478.0.

b) Synthesis of Compound 84-Bb

A solution of compound 84-Ba (0.1 g, 209.21 umol, 1 eq.) in TFA (0.45 mL) and $H_2O$ (0.05 mL) was stirred at 20° C. for 0.5 hr. LC-MS showed compound 84-Ba was consumed completely. One main peak with desired MS was detected. The reaction was concentrated in vacuo. The residue was dissolved in EtOAc (5 mL), and saturated NaHCO$_3$(10 mL) was added dropwise. The mixture was washed with saturated NaCl solution (10 mL*2), extracted with EtOAc (10 mL*3). The combined organic phase was dried with anhydrous $Na_2SO_4$, concentrated in vacuo. No purification, alkaline compound 84-Bb (0.1 g, crude) was obtained as a yellow solid. LCMS: (M+H$^+$): 438.0.

c) Synthesis of 7-((1R,2S,3R,4S)-2,3-dihydroxy-4-(2-(2-(methylamino)quinolin-7-yl)ethyl)cyclopentyl)-1,7-dihydro-4H-pyrrolo[2,3-d]pyrimidin-4-one O-methyl oxime (84-B)

To a solution of compound 84-Bb (0.07 g, 165.14 umol, 1 eq.) in dioxane (53 mL) was added O-methyl hydroxylamine; hydrochloride (1.38 g, 16.51 mmol, 1.25 mL, 100 eq.) and $K_2CO_3$ (3.42 g, 24.77 mmol, 150 eq.). The mixture was stirred at 120° C. for 12 hr. LC-MS showed compound 84-Bb was consumed completely. Several new peaks were shown on LC-MS desired compound was detected. The reaction was concentrated in vacuo. The residue was dissolved in MeOH (20 mL), filtered and concentrated in vacuo. The residue was purified by prep-HPLC. Ex. 84-B (0.0249 g, 43.93 umol, 26.60% yield, 92% purity, 2 HCl salt) was obtained as a brown solid. $^1$H NMR (400 MHz, DMSO-d6) δ=12.86 (br s, 1H) 9.89 (br s, 1H) 8.09-8.30 (m, 2H) 8.01 (br s, 1H) 7.82 (br d, J=8.19 Hz, 1H) 7.64 (br s, 1H) 7.39 (br d, J=7.70 Hz, 1H) 6.97-7.17 (m, 1H) 6.80 (br s, 1H) 4.80-5.01 (m, 1H) 4.17-4.28 (m, 1H) 3.86 (s, 3H) 3.73-3.79 (m, 2H) 3.16 (br d, J=3.91 Hz, 2H) 2.71-2.89 (m, 3H) 2.68 (br s, 1H) 2.22-2.36 (m, 1H) 1.84-2.05 (m, 2H) 1.67-1.81 (m, 1H) 1.46-1.63 (m, 1H); $^1$H NMR (400 MHz, DMSO-d6) δ=8.14-8.31 (m, 2H) 7.92 (br s, 1H) 7.82 (br d, J=7.83 Hz, 1H) 7.64 (br d, J=3.30 Hz, 1H) 7.39 (br d, J=7.95 Hz, 1H) 7.05 (br d, J=9.05 Hz, 1H) 6.76 (d, J=3.42 Hz, 1H) 4.80-5.00 (m, 1H) 4.20 (dd, J=8.01, 5.93 Hz, 1H) 3.86 (s, 3H) 3.73-3.78 (m, 1H) 3.13 (br s, 3H) 2.74-2.89 (m, 3H) 2.24-2.36 (m, 1H) 1.84-2.03 (m, 2H) 1.69-1.82 (m, 1H) 1.47-1.61 (m, 1H); LCMS: (M+H$^+$): 449.2; HPLC purity: 88.74%.

Example 85-B. 7-((1R,2S,3R,4S)-4-(2-(2-aminoquinolin-7-yl)ethyl)-2,3-dihydroxycyclopentyl)-1,7-dihydro-4H-pyrrolo[2,3-d]pyrimidin-4-one O-methyl oxime (85-B)

Ex. 85-B (2HCl salt), a brown solid, was prepared similarly to that of Ex. 84-B. $^1$H NMR (400 MHz, DMSO-d6) δ=14.23 (br s, 1H) 8.78-9.33 (m, 1H) 8.34 (d, J=9.29 Hz, 1H) 8.28 (s, 1H) 7.85 (d, J=8.19 Hz, 1H) 7.67 (d, J=3.55 Hz, 1H) 7.55 (s, 1H) 7.40 (dd, J=8.13, 1.16 Hz, 1H) 7.06 (d, J=9.29 Hz, 1H) 6.83 (d, J=3.42 Hz, 1H) 4.81-5.01 (m, 1H) 4.15-4.28 (m, 1H) 3.87 (s, 3H) 3.70-3.80 (m, 2H) 2.75-2.90 (m, 2H) 2.65-2.70 (m, 1H) 2.23-2.36 (m, 1H) 1.83-2.01 (m, 3H) 1.70-1.81 (m, 1H) 1.68-1.68 (m, 1H) 1.51-1.61 (m, 1H); 1H NMR (400 MHz, DMSO-d6) δ=8.30 (br d, J=9.26 Hz, 1H) 8.23 (s, 1H) 7.80 (br d, J=7.94 Hz, 1H) 7.62 (br d, J=3.53 Hz, 1H) 7.48 (s, 1H) 7.35 (br d, J=8.16 Hz, 1H) 6.98 (d, J=9.26 Hz, 1H) 6.72 (d, J=3.31 Hz, 1H) 4.74-5.01 (m, 1H) 4.15 (br dd, J=8.16, 5.95 Hz, 1H) 3.81 (s, 3H) 2.69-2.85 (m, 2H) 2.14-2.35 (m, 1H) 1.77-2.00 (m, 2H) 1.71 (br d, J=5.51 Hz, 1H) 1.41-1.60 (m, 1H); LCMS: (M+H$^+$): 435.2; LCMS purity: 97.88%; HPLC purity: 100.00%.

Example 86-B. (Z)-7-((1R,2S,3R,4S)-4-(2-(2-amino-3-chloroquinolin-7-yl)ethyl)-2,3-dihydroxycyclopentyl)-3,7-dihydro-4H-pyrrolo[2,3-d]pyrimidin-4-one O-methyl oxime (86-B)

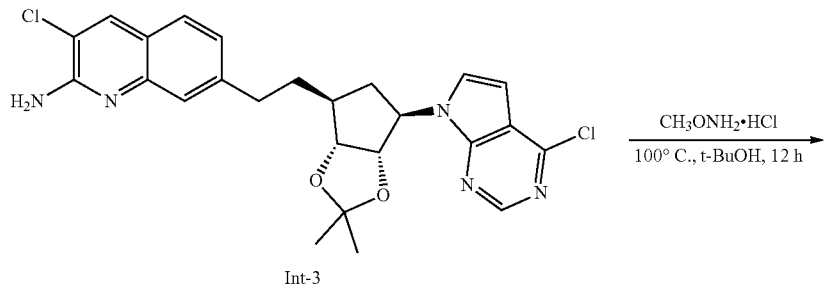

Int-3

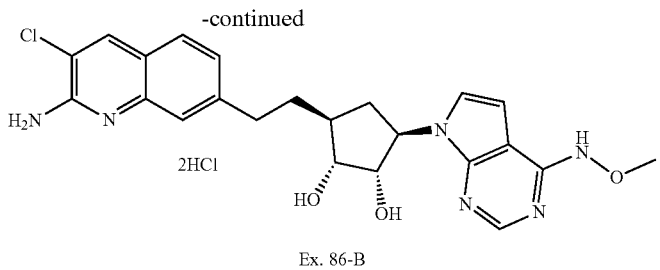

Ex. 86-B

To a solution of Int-3 (0.04 g, 80.26 umol, 1 eq.) in t-BuOH (2 mL) was added O-methyl hydroxyl amine hydrochloride (53.62 mg, 642 umol, 48.75 uL, 8 eq.). The mixture was stirred at 100° C. for 12 h. LC-MS showed compound 15 was consumed completely. Several new peaks were shown on LC-MS and desired compound was detected. The mixture was concentrated in vacuo, and dissolved in THF (1 mL). The mixture was purified by prep-HPLC (HCl condition, column: Luna C18 100*30 5 u; mobile phase: [water (0.05% HCl)-ACN]; B %: 10%-40%, 10 min). Ex. 86-B (0.01786 g, 36.87 umol, 45.94% yield, 96.8% HPLC purity, 2HCl salt) was obtained as a brown solid. $^1$H NMR (400 MHz, DMSO-$d_6$) δ=8.72 (br s, 1H), 8.69 (s, 1H), 8.24 (s, 1H), 7.81 (d, J=8.33 Hz, 1H), 7.64 (br d, J=3.51 Hz, 1H), 7.54 (s, 1H), 7.40 (d, J=8.33 Hz, 1H), 6.79 (d, J=3.07 Hz, 1H), 4.81-4.95 (m, 1H), 4.11-4.22 (m, 1H), 3.84 (s, 2H), 3.68-3.76 (m, 1H), 2.75-2.84 (m, 2H), 2.18-2.29 (m, 1H), 1.89 (br d, J=6.58 Hz, 2H), 1.66-1.76 (m, 1H), 1.46-1.59 (m, 1H); $^1$H NMR (400 MHz, DMSO-$d_6$+$D_2$O) δ=8.67 (s, 1H), 8.24 (s, 1H), 7.81 (d, J=8.33 Hz, 1H), 7.63 (d, J=3.51 Hz, 1H), 7.54 (s, 1H), 7.40 (d, J=8.77 Hz, 1H), 6.72 (d, J=3.07 Hz, 1H), 4.78-4.95 (m, 1H), 4.13-4.20 (m, 1H), 3.83 (s, 3H), 3.69-3.75 (m, 1H), 2.73-2.84 (m, 2H), 2.16-2.28 (m, 1H), 1.88 (br s, 2H), 1.72 (br d, J=8.77 Hz, 1H), 1.44-1.57 (m, 1H); LCMS: (M+H$^+$): 469.2; HPLC purity: 96.80%.

Example 87-B. 7-((1R,2S,3R,4S)-4-(2-(2-((cyclopropylmethyl)amino)quinolin-7-yl)ethyl)-2,3-dihydroxycyclopentyl)-1,7-dihydro-4H-pyrrolo[2,3-d]pyrimidin-4-one oxime (87-B)

Ex. 87-B was prepared similarly to that of Ex. 79-B. $^1$H NMR (400 MHz, DMSO-$d_6$) δ=7.80 (s, 1H), 7.53 (d, J=8.8 Hz, 1H), 7.27 (d, J=8.2 Hz, 1H), 7.09 (s, 1H), 7.03 (d, J=3.5 Hz, 1H), 6.84-6.73 (m, 2H), 6.67 (br s, 2H), 6.48 (d, J=9.0 Hz, 1H), 6.31 (d, J=3.5 Hz, 1H), 4.64-4.48 (m, 2H), 4.41 (br d, J=4.6 Hz, 1H), 4.02-3.91 (m, 1H), 3.52 (br d, J=4.6 Hz, 1H), 3.02 (t, J=6.1 Hz, 2H), 2.57-2.38 (m, 2H), 2.02 (td, J=7.8, 12.6 Hz, 1H), 1.80-1.57 (m, 2H), 1.54-1.40 (m, 1H), 1.36-1.21 (m, 1H), 0.94-0.77 (m, 1H), 0.28-0.17 (m, 2H), 0.07-0.05 (m, 2H); $^1$H NMR (400 MHz, DMSO-$d_6$+$D_2$O) δ=7.80 (s, 1H), 7.55 (d, J=8.8 Hz, 1H), 7.29 (d, J=7.9 Hz, 1H), 7.11 (s, 1H), 7.04 (d, J=3.5 Hz, 1H), 6.80 (dd, J=1.2, 8.0 Hz, 1H), 6.49 (d, J=9.0 Hz, 1H), 6.34 (d, J=3.5 Hz, 1H), 4.65-4.52 (m, 1H), 4.03-3.92 (m, 1H), 3.52 (br t, J=5.1 Hz, 1H), 3.02 (d, J=6.8 Hz, 2H), 2.58-2.40 (m, 2H), 2.02 (td, J=7.7, 12.5 Hz, 1H), 1.80-1.58 (m, 2H), 1.56-1.41 (m, 1H), 1.35-1.22 (m, 1H), 0.94-0.81 (m, 1H), 0.29-0.19 (m, 2H), 0.06-0.03 (m, 2H); LCMS purity: 94.46%; HPLC purity: 94.92%.

Example 88-B. 7-((1R,2S,3R,4R)-4-((S)-(3,4-difluorophenyl)(hydroxy)methyl)-2,3-dihydroxycyclopentyl)-1,7-dihydro-4H-pyrrolo[2,3-d]pyrimidin-4-one oxime (88-B)

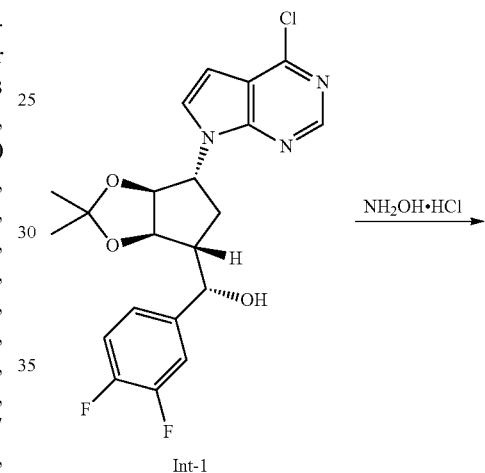

Int-1

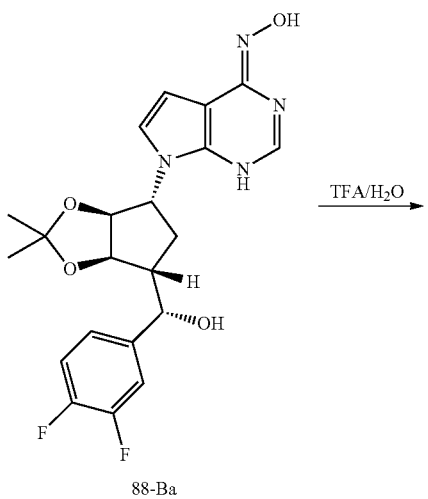

88-Ba

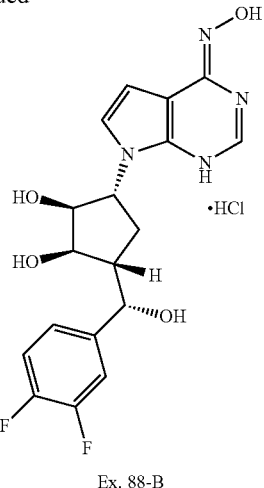

Ex. 88-B a) Synthesis of 7-[(3aS,4R,6R,6aR)-6-[(S)-(3,4-difluorophenyl)-hydroxy-methyl]-2,2-dimethyl-4,5,6,6a-tetrahydro-3aH-cyclopenta[d][1,3]dioxol-4-yl]-1H-pyrrolo[2,3-d]pyrimidin-4-one oxime (88-Ba)

To a solution of (S)-[(3aS,4R,6R,6aR)-4-(4-chloropyrrolo[2,3-d]pyrimidin-7-yl)-2,2-dimethyl-4,5,6,6a-tetrahydro-3aH-cyclopenta[d][1,3]dioxol-6-yl]-(3,4-difluorophenyl)methanol (Int-1) (80.0 mg, 0.18 mmol) in ethanol (5.0 mL) was added TEA (370.8 mg, 3.67 mmol) and hydroxylamine hydrochloride (127.6 mg, 1.84 mmol). The mixture stirred at 80° C. for 16 hrs. LC-MS showed about 65% product was in the reaction mixture. The solvent was removed under vacuum, diluted by H$_2$O (10.0 mL) and DCM (30.0 mL), separated, the DCM layer was washed with H$_2$O (10.0 mL×2) and NaCl aqueous solution (saturated, 20.00 mL), dried over Na$_2$SO$_4$, filtered, and concentrated under vacuum to afford 7-[(3aS,4R,6R,6aR)-6-[(S)-(3,4-difluorophenyl)-hydroxy-methyl]-2,2-dimethyl-4,5,6,6a-tetrahydro-3aH-cyclopenta[d][1,3]dioxol-4-yl]-1H-pyrrolo[2,3-d]pyrimidin-4-one oxime (88-Ba) (80.00 mg, crude). LCMS [M+H]: 433.3.

b) Synthesis of 7-((1R,2S,3R,4R)-4-((S)-(3,4-difluorophenyl)(hydroxy)methyl)-2,3-dihydroxycyclopentyl)-1,7-dihydro-4H-pyrrolo[2,3-d]pyrimidin-4-one oxime (88-B)

To a solution of 7-[(3aS,4R,6R,6aR)-6-[(S)-(3,4-difluorophenyl)-hydroxy-methyl]-2,2-dimethyl-4,5,6,6a-tetrahydro-3aH-cyclopenta[d][1,3]dioxol-4-yl]-1H-pyrrolo[2,3-d]pyrimidin-4-one oxime (88-Ba) (80.0 mg, 0.19 mmol) in water (2.00 mL) was added TFA (1.30 mL, 16.87 mmol). The mixture was stirred at 25° C. for 0.5 h. LC-MS showed the reaction was complete. The mixture was purified by prep-HPLC (0.1% TFA, H$_2$O:CH$_3$CN from 90:10 to 5:95) to afford 7-[(1R,2S,3R,4R)-4-[(S)-(3,4-difluorophenyl)-hydroxy-methyl]-2,3-dihydroxy-cyclopentyl]-1H-pyrrolo[2,3-d]pyrimidin-4-one oxime hydrochloride (Ex. 88-B) (12 mg, 0.03 mmol, 14.39% yield) as light yellow solid. LCMS [M+H]: 393.3. $^1$HNMR (DMSO-d6+D$_2$O, 400 MHz): δ 8.26 (s, 1H), 7.63-7.64 (m, 1H), 7.32-7.42 (m, 2H), 7.23-7.24 (m, 1H), 6.85-6.86 (m, 1H), 4.91-4.99 (m, 1H), 4.55-4.57 (m, 1H), 4.19-4.23 (m, 1H), 3.91-3.93 (m, 1H), 2.22-2.28 (m, 1H), 1.96-2.03 (m, 1H), 1.53-1.61 (m, 1H).

Example 89-B. 7-((1R,2S,3R,4R)-4-((S)-(3,4-difluorophenyl)(hydroxy)methyl)-2,3-dihydroxycyclopentyl)-1,7-dihydro-4H-pyrrolo[2,3-d]pyrimidin-4-one O-methyl oxime (89-B)

To a solution of (S)-[(3aS,4R,6R,6aR)-4-(4-chloropyrrolo[2,3-d]pyrimidin-7-yl)-2,2-dimethyl-4,5,6,6a-tetrahydro-3aH-cyclopenta[d][1,3]dioxol-6-yl]-(3,4-difluorophenyl)methanol (Int-1) (80.00 mg, 0.18 mmol) in 1-butanol (2.00 mL) was added O-methylhydroxylamine hydrochloride (80.00 mg, 0.96 mmol) and K$_2$CO$_3$ (200.00 mg, 1.45 mmol). The mixture was stirred at 100° C. for 2 hrs. LC-MS (ZYX001-86-R1) showed 30% of product was in the reaction mixture. The mixture was purified by prep-HPLC (0.1% TFA, H$_2$O:CH$_3$CN from 90:10 to 5:95.), then 0.05 mL of conc. HCl was added and lyophilized to afford (1S,2R,3R,5R)-3-[(S)-(3,4-difluorophenyl)-hydroxy-methyl]-5-[(4Z)-4-methoxyimino-1H-pyrrolo[2,3-d]pyrimidin-7-yl]cyclopentane-1,2-diol hydrochloride (Ex. 89-B) (4.20 mg, 0.009 mmol, 5.01% yield) as yellow solid. LCMS [M+H]: 407.2. $^1$HNMR (DMSO-d6+D20, 400 MHz): δ 8.25 (s, 1H), 7.59-7.60 (m, 1H), 7.34-7.43 (m, 2H), 7.23-7.24 (m, 1H), 6.71-6.73 (m, 1H), 4.91-4.98 (m, 1H), 4.56-4.58 (m, 1H), 4.20-4.24 (m, 1H), 3.89-3.95 (m, 1H), 3.86 (s, 3H), 2.22-2.28 (m, 1H), 1.96-2.04 (m, 1H), 1.52-1.60 (m, 1H).

Example 90-B. 7-((1R,2S,3R,4S)-4-(2-(2-((cyclopropylmethyl)amino)quinolin-7-yl)ethyl)-2,3-dihydroxycyclopentyl)-1,7-dihydro-4H-pyrrolo[2,3-d]pyrimidin-4-one O-methyl oxime (90-B)

Example 90-B (HCl salt) was prepared similarly to that of 87-B. $^1$H NMR (400 MHz, DMSO-d$_6$) δ=12.98 (br s, 1H), 9.87 (br s, 1H), 8.32-8.16 (m, 2H), 8.04 (br s, 1H), 7.81 (br d, J=7.7 Hz, 1H), 7.66 (br d, J=2.3 Hz, 1H), 7.45-7.34 (m, 1H), 7.22-7.08 (m, 1H), 6.84 (br s, 1H), 5.00-4.85 (m, 1H), 4.21 (dd, J=5.9, 8.1 Hz, 1H), 3.87 (s, 2H), 3.78-3.73 (m, 2H), 2.90-2.71 (m, 2H), 2.35-2.23 (m, 1H), 2.35-2.23 (m, 1H), 2.03-1.83 (m, 2H), 1.81-1.67 (m, 1H), 1.62-1.48 (m, 1H), 1.25-1.08 (m, 1H), 0.59 (br d, J=7.3 Hz, 2H), 0.37 (q, J=4.6 Hz, 2H); $^1$H NMR (400 MHz, DMSO-d$_6$+D$_2$O) δ=8.31-8.15 (m, 2H), 7.90 (br s, 1H), 7.79 (br d, J=8.3 Hz, 1H), 7.65 (d, J=3.5 Hz, 1H), 7.36 (br d, J=8.3 Hz, 1H), 7.08 (br d, J=9.2 Hz, 1H), 6.77 (d, J=3.5 Hz, 1H), 4.95-4.83 (m, 1H), 4.18 (dd, J=5.7, 8.3 Hz, 1H), 3.84 (s, 3H), 3.76-3.70 (m, 1H), 2.78 (dt, J=7.0, 14.0 Hz, 2H), 2.34-2.19 (m, 1H), 2.00-1.80 (m, 2H), 1.74 (br s, 1H), 1.59-1.45 (m, 1H), 1.16 (br s, 1H), 0.57 (br d, J=7.0 Hz, 2H), 0.39-0.27 (m, 2H); LCMS: (M+H$^+$): 489.2; LCMS purity: 96.0%;

Example 91-B. (1S,2R,3S,5R)-3-(2-(2-((cyclopropylmethyl)amino)quinolin-7-yl)ethyl)-5-((Z)-4-(2-methylhydrazineylidene)-1,4-dihydro-7H-pyrrolo[2,3-d]pyrimidin-7-yl)cyclopentane-1,2-diol (91-B)

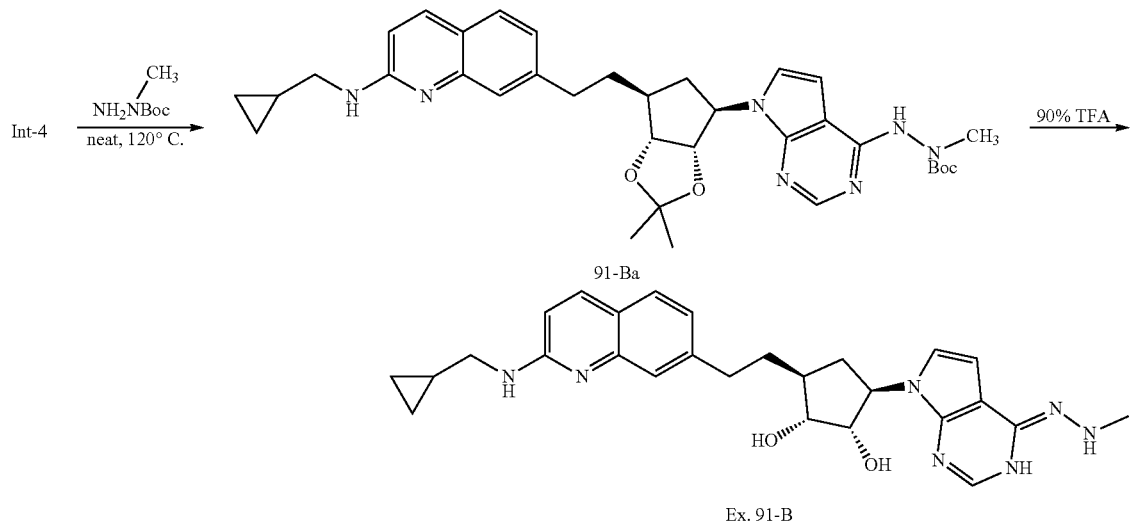

a) Synthesis of Compound 91-Ba

A mixture of Int-4 (0.06 g, 115.82 umol, 1 eq), N-methyl-N-Boc hydrazine (2.96 g, 20.21 mmol, 3 mL, 174.53 eq) was purged with $N_2$ for 3 times, and then the mixture was stirred at 110° C. for 12 hr under $N_2$ atmosphere. LCMS showed it was almost completed and the desired product was detected. The mixture was lyophilized to give a brown oil (200 mg), which was purified with by prep-HPLC under alkaline condition to give a white solid (45 mg).

b) Synthesis of (1S,2R,3S,5R)-3-(2-(2-((cyclopropylmethyl)amino)quinolin-7-yl)ethyl)-5-((Z)-4-(2-methylhydrazineylidene)-1,4-dihydro-7H-pyrrolo[2,3-d]pyrimidin-7-yl)cyclopentane-1,2-diol (91-B)

A mixture of compound 91-Ba (30 mg, 47.79 umol, 1 eq) in TFA (0.9 mL) and $H_2O$ (0.1 mL) was degassed and purged with $N_2$ for 3 times, and then the mixture was stirred at 20° C. for 5 min under $N_2$ atmosphere. LCMS showed it was completed. It was concentrated at 25° C. and purified by prep-HPLC under acid condition to give a white solid (column: Boston Green ODS 150*30 5 u; mobile phase: [water (0.05% HCl)-ACN]; B %: 10%-40%, 1 min). 19.37 mg Ex. 91-B was obtained as a white solid. 1H NMR (400 MHz, DMSO-d6) δ ppm 12.93 (br s, 1H) 11.27 (br s, 1H) 9.82 (br s, 1H) 8.16-8.28 (m, 2H) 8.01 (br s, 1H) 7.81 (br d, J=7.95 Hz, 1H) 7.70 (d, J=3.55 Hz, 1H) 7.38 (br d, J=8.31 Hz, 1H) 7.12 (br d, J=9.05 Hz, 1H) 6.98 (br d, J=3.30 Hz, 1H) 4.80-5.04 (m, 1H) 4.21 (dd, J=8.19, 5.87 Hz, 1H) 3.71-3.83 (m, 1H) 2.74-2.92 (m, 2H) 2.67 (s, 4H) 2.21-2.36 (m, 1H) 1.70-2.04 (m, 3H) 1.48-1.63 (m, 1H) 1.11-1.25 (m, 1H) 0.59 (br d, J=7.09 Hz, 2H) 0.37 (br d, J=4.89 Hz, 2H); $^1$H NMR (400 MHz, DMSO-d6) δ ppm 8.17-8.31 (m, 2H) 7.89 (br s, 1H) 7.81 (br d, J=8.07 Hz, 1H) 7.69 (d, J=3.67 Hz, 1H) 7.38 (br d, J=7.95 Hz, 1H) 7.09 (br d, J=9.54 Hz, 1H) 6.93 (br d, J=3.18 Hz, 1H) 4.80-5.01 (m, 1H) 4.20 (dd, J=8.25, 5.93 Hz, 1H) 3.70-3.79 (m, 1H) 2.72-2.91 (m, 2H) 2.61-2.69 (m, 3H) 2.20-2.37 (m, 1H) 1.68-2.02 (m, 3H) 1.47-1.62 (m, 1H) 1.20 (br d, J=18.71 Hz, 1H) 0.59 (br d, J=6.97 Hz, 2H) 0.36 (q, J=4.69 Hz, 2H); LCMS: (M+H$^+$): 488.2; LCMS purity: 97.0%; HPLC purity: 93.9%.

Example 92-B. 7-((1R,2S,3R,4R)-4-((S)-(3,4-dichlorophenyl)(hydroxy)methyl)-2,3-dihydroxycyclopentyl)-1,7-dihydro-4H-pyrrolo[2,3-d]pyrimidin-4-one O-methyl oxime (92-B)

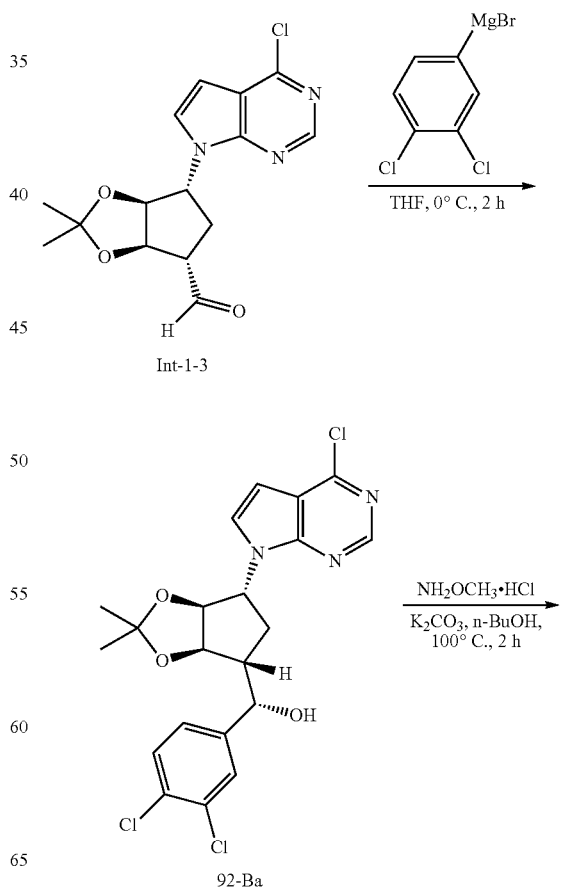

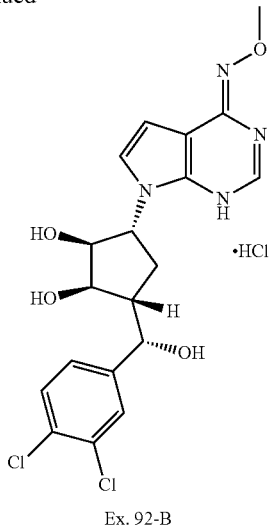

Ex. 92-B a) Synthesis of (S)-[(3aS,4R,6R,6aR) -4-(4-chloro-pyrrolo[2,3-d]pyrimidin-7-yl)-2,2-dimethyl-4,5,6,6a-tetrahydro-3aH-cyclopenta[d][1,3]dioxol-6-yl]-(3,4-dichlorophenyl)methanol (92-Ba)

To a solution of (3aS,4R,6S,6aR)-4-(4-chloropyrrolo[2,3-d]pyrimidin-7-yl)-2,2-dimethyl-4,5,6,6a-tetrahydro-3aH-cyclopenta[d][1,3]dioxole-6-carbaldehyde (Int-1-3) (2.63 g, 3.76 mmol) in THF (20.0 mL) was added bromo-(3,4-dichlorophenyl)magnesium (22.5 mL, 11.27 mmol) at 0° C. The reaction mixture was stirred at 0° C. for 1 h. LCMS showed the reaction was completed. The reaction mixture was added H$_2$O (30.0 mL) and EA (60.0 mL), washed with H$_2$O (30.0 mL), brine (30.0 mL), dried over Na$_2$SO$_4$, filtered, concentrated in vacuum to give crude product which was purified by silica gel column chromatography (PE: EA=5:1 to 3:1) to give (S)-[(3aS,4R,6R,6aR)-4-(4-chloro-pyrrolo[2,3-d]pyrimidin-7-yl)-2,2-dimethyl-4,5,6,6a-tetrahydro-3aH-cyclopenta[d][1,3]dioxol-6-yl]-(3,4-dichlorophenyl)methanol (92-Ba) (450.0 mg, 0.96 mmol, 25.6% yield). LCMS [M+H]: 468.1.

b) Synthesis of (1S,2R,3R,5R)-3-[(S) -(3,4-dichlorophenyl)-hydroxy-methyl]-5-[(4Z)-4-methoxy-imino-1H-pyrrolo[2,3-d]pyrimidin-7-yl]cyclopentane-1,2-diol hydrochloride (Ex. 94-B)

To a solution of (S)-[(3aS,4R,6R,6aR)-4-(4-chloropyrrolo [2,3-d]pyrimidin-7-yl)-2,2-dimethyl-4,5,6,6a-tetrahydro-3aH-cyclopenta[d][1,3]dioxol-6-yl]-(3,4-dichlorophenyl) methanol (150.0 mg, 0.32 mmol) in 1-butanol (5.0 mL) was added O-Methylhydroxylamine hydrochloride (133.6 mg, 1.60 mmol), K$_2$CO$_3$ (353.3 mg, 2.56 mmol). The mixture was stirred at 100° C. for 2 h. LCMS showed the reaction was completed. The mixture was purified by prep-HPLC to afford (1S,2R,3R,5R)-3-[(S) -(3,4-dichlorophenyl)-hydroxy-methyl]-5-[(4Z)-4-methoxyimino-1H-pyrrolo[2,3-d] pyrimidin-7-yl]cyclopentane-1,2-diol hydrochloride (Ex. 94-B) (16.0 mg, 0.03 mmol, 10.1% yield) as a white solid. LCMS [M+H]: 439.1. $^1$H NMR (400 MHz, DMSO-d$_6$+ D$_2$O): δ 8.59 (s, 1H), 7.58-7.63 (m, 3H), 7.38-7.40 (m, 1H), 6.72-6.73 (m, 1H), 4.91-4.98 (m, 1H), 4.58-4.60 (m, 1H), 4.19-4.23 (m, 1H), 3.89-3.90 (m, 1H), 3.86 (s, 3H), 2.22-2.28 (m, 1H), 1.99-2.07 (m, 1H), 1.55-1.63 (m, 1H).

Example 93-B. 7-((1R,2S,3R,4R)-4-((S)-(3,4-dichlorophenyl)(hydroxy)methyl)-2,3-dihydroxycyclopentyl)-1,7-dihydro-4H-pyrrolo[2,3-d]pyrimidin-4-one oxime (93-B)

Example 93-B, a light yellow solid, was prepared similarly to that of Ex. 92-B. LCMS [M+H]: 425.1. $^1$H NMR (400 MHz, DMSO-d$_6$+D$_2$O): S 8.27 (s, 1H), 7.58-7.64 (m, 3H), 7.38-7.40 (m, 1H), 6.80-6.81 (m, 1H), 4.93-5.00 (m, 1H), 4.58-4.60 (m, 1H), 4.19-4.23 (m, 1H), 3.90-3.91 (m, 1H), 2.23-2.28 (m, 1H), 2.00-2.07 (m, 1H), 1.55-1.63 (m, 1H).

Example 94-B. 7-((1R,2S,3R,4S)-4-((S)-1-(3,4-dichlorophenyl)-1-hydroxyethyl)-2,3-dihydroxycyclopentyl)-1,7-dihydro-4H-pyrrolo[2,3-d]pyrimidin-4-one oxime (94-B)

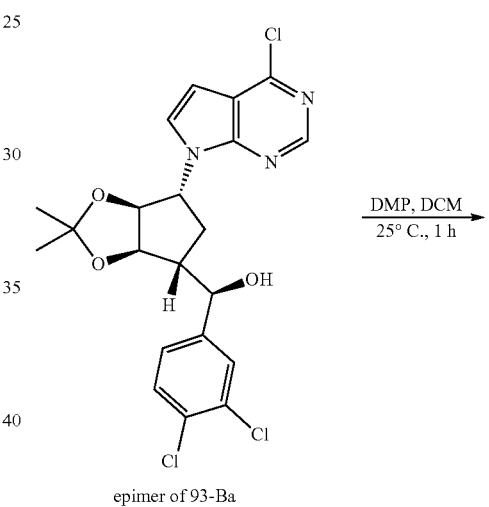

epimer of 93-Ba

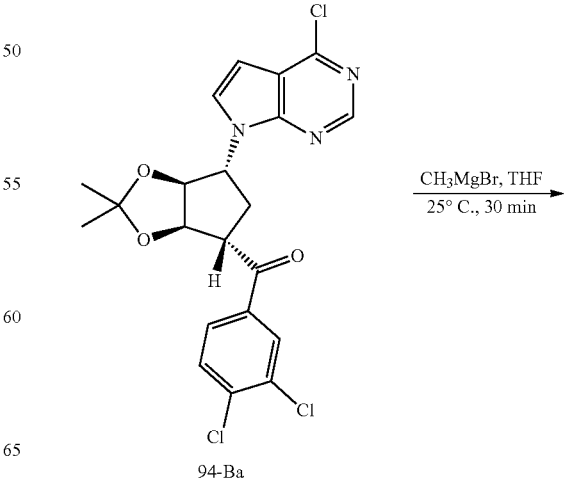

94-Ba

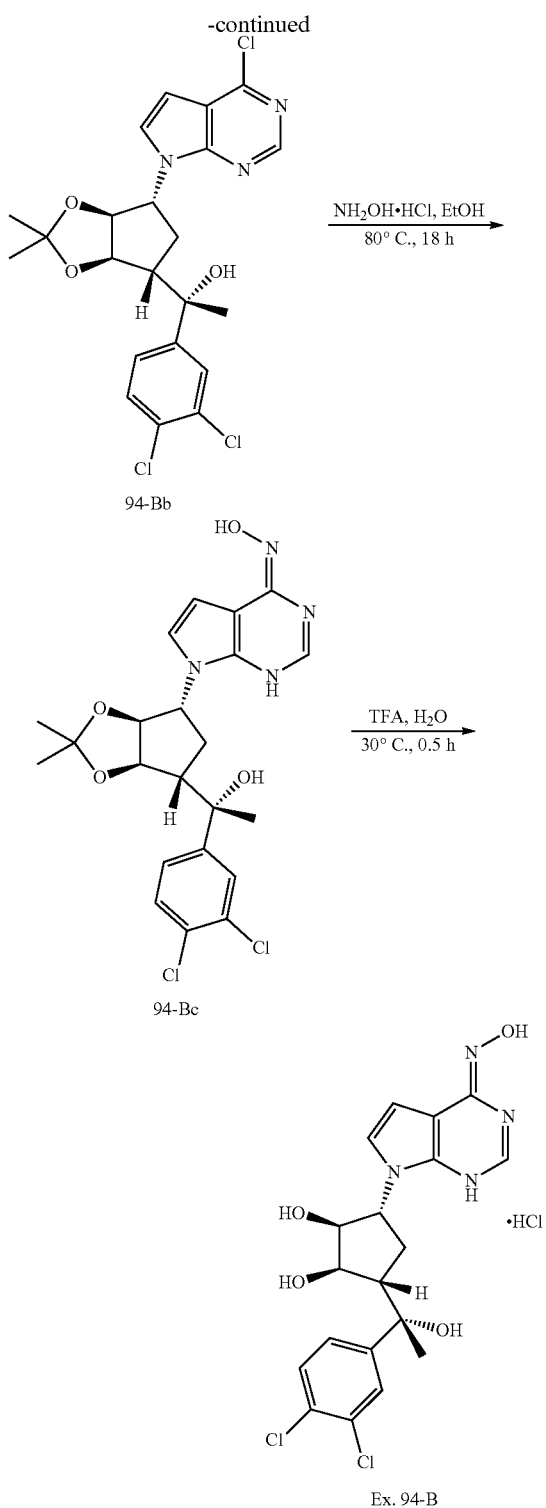

Ex. 94-B a) Synthesis of [(3aS,4R,6S,6aR)-4-(4-chloropyrrolo[2,3-d]pyrimidin-7-yl)-2,2-dimethyl-4,5,6,6a-tetrahydro-3aH-cyclopenta[d][1,3]dioxol-6-yl]-(3,4-dichlorophenyl)methanone (94-Ba)

To a solution of (R)-[(3aS,4R,6R,6aR)-4-(4-chloropyrrolo[2,3-d]pyrimidin-7-yl)-2,2-dimethyl-4,5,6,6a-tetrahydro-3aH-cyclopenta[d][1,3]dioxol-6-yl]-(3,4-dichlorophenyl)methanol (epimer of 93-Ba, isolated from the reaction of step a, Ex. 93-B) (450.0 mg, 0.96 mmol) in DCM (10.0 mL) was added Dess-Martin periodinane (1221.5 mg, 2.88 mmol) at 0° C., then the mixture warmed to 25° C. naturally and stirred at 25° C. for 1 h. LCMS showed the reaction was completed. NaHCO₃aqueous (30.00 mL) was added to the mixture. The reaction mixture was extracted with DCM (50.0 mL×3). The organic layers were dried over Na₂SO₄, filtered, concentrated in vacuum to give crude product which was purified by column (PE:EA=8:1) to give [(3aS,4R,6S,6aR)-4-(4-chloropyrrolo[2,3-d]pyrimidin-7-yl)-2,2-dimethyl-4,5,6,6a-tetrahydro-3aH-cyclopenta[d][1,3]dioxol-6-yl]-(3,4-dichlorophenyl)methanone (94-Ba) (340.0 mg, 0.73 mmol, 75.9% yield) as a white solid. LCMS [M+H]: 466.1.

b) Synthesis of (1S)-1-[(3aS,4R,6S,6aR)-4-(4-chloropyrrolo[2,3-d]pyrimidin-7-yl)-2,2-dimethyl-4,5,6,6a-tetrahydro-3aH-cyclopenta[d][1,3]dioxol-6-yl]-1-(3,4-dichlorophenyl)ethanol (94-Bb)

To a solution of [(3aS,4R,6S,6aR)-4-(4-chloropyrrolo[2,3-d]pyrimidin-7-yl)-2,2-dimethyl-4,5,6,6a-tetrahydro-3aH-cyclopenta[d][1,3]dioxol-6-yl]-(3,4-dichlorophenyl)methanone (94-Ba) (340.0 mg, 0.73 mmol) in TH (7.00 mL) was dropwise added bromo(methyl)magnesium (0.7 mL, 2.19 mmol) at 0° C., then the mixture warmed to 25° C. naturally and stirred at 25° C. for 30 mins. TLC showed the reaction was completed. The reaction mixture was added NH₄Cl aqueous (10.00 mL), extracted with EA (30.0 mL×3). The organic layers were dried over Na₂SO₄, filtered, concentrated in vacuum to give crude product which was purified by column (PE:EA=7:1 to PE:EA=5:1) to give (1S)-1-[(3aS,4R,6S,6aR)-4-(4-chloropyrrolo[2,3-d]pyrimidin-7-yl)-2,2-dimethyl-4,5,6,6a-tetrahydro-3aH-cyclopenta[d][1,3]dioxol-6-yl]-1-(3,4-dichlorophenyl)ethanol (94-Bb) (140.0 mg, 0.29 mmol, 39.8% yield). LCMS [M+H]: 482.1.

c) Synthesis of 7-[(3aS,4R,6S,6aR)-6-[(1S)-1-(3,4-dichlorophenyl)-1-hydroxy-ethyl]-2,2-dimethyl-4,5,6,6a-tetrahydro-3aH-cyclopenta[d][1,3]dioxol-4-yl]-1H-pyrrolo [2,3-d]pyrimidin-4-one oxime (94-Bc)

To a solution of (1S)-1-[(3aS,4R,6S,6aR)-4-(4-chloropyrrolo[2,3-d]pyrimidin-7-yl)-2,2-dimethyl-4,5,6,6a-tetrahydro-3aH-cyclopenta[d][1,3]dioxol-6-yl]-1-(3,4-dichlorophenyl)ethanol (94-Bb) (140.0 mg, 0.29 mmol) in ethanol (8.00 mL) was added TEA (586.9 mg, 5.80 mmol) and hydroxylamine hydrochloride (201.5 mg, 2.90 mmol), then the mixture was stirred at 80° C. for 16 h. LCMS showed the reaction mixture was done. The reaction mixture was concentrated in vacuum and added EA (50.0 mL). The organic layer was washed with brine (30.00 mL×3), dried over Na₂SO₄, concentrated in vacuum to give crude product 7-[(3aS,4R,6S,6aR)-6-[(1S)-1-(3,4-dichlorophenyl)-1-hydroxy-ethyl]-2,2-dimethyl-4,5,6,6a-tetrahydro-3aH-cyclopenta[d][1,3]dioxol-4-yl]-1H-pyrrolo [2,3-d] pyrimidin-4-one oxime (94-Bc) (140.0 mg, 0.23 mmol, 81.0% yield). LCMS [M+H]: 479.2.

d) Synthesis of 7-[(1R,2S,3R,4S)-4-[(1S)-1-(3,4-dichlorophenyl)-1-hydroxy-ethyl]-2,3-dihydroxy-cyclopentyl]-1H-pyrrolo[2,3-d]pyrimidin-4-one oxime hydrochloride (Ex. 94-B)

To a solution of 7-[(3aS,4R,6S,6aR)-6-[(1S)-1-(3,4-dichlorophenyl)-1-hydroxy-ethyl]-2,2-dimethyl-4,5,6,6a-tetrahydro-3aH-cyclopenta[d][1,3]dioxol-4-yl]-1H-pyrrolo[2,3-d]pyrimidin-4-one oxime (94-Bc) (140.0 mg, 0.24 mmol) in Water (3.0 mL) was added TFA (2.0 mL, 25.96 mmol), the reaction was stirred at 30° C. for 0.5 h. LCMS showed the reaction was completed. The mixture was sent to pre-HPLC to give 7-[(1R,2S,3R,4S)-4-[(1S)-1-(3,4-dichlorophenyl)-1-hydroxy-ethyl]-2,3-dihydroxy -cyclopentyl]-1H-pyrrolo[2,3-d]pyrimidin-4-one oxime hydrochloride (Ex. 94-B) (23.0 mg, 0.048 mmol, 20.5% yield) as a white solid. LCMS [M+H]: 439.1. $^1$H NMR (400 MHz, DMSO-$d_6$+$D_2O$): δ 8.27 (s, 1H), 7.73-7.7.75 (m, 1H), 7.59-7.61 (m, 2H), 7.48-7.50 (m, 1H), 6.81-6.82 (m, 1H), 4.97-4.99 (m, 1H), 4.02-4.05 (m, 1H), 3.50-3.51 (m, 1H), 2.36-2.41 (m, 1H), 2.18-2.24 (m, 1H), 1.93-1.95 (m, 1H), 1.36 (s, 3H).

Examples of Formula V and Formula VI

Example 1-C. (2R,3R,4S,5S)-2-(6-amino-9H-purin-9-yl)-5-((R)-1-(3,4-dichlorophenyl)-1-hydroxyethyl)tetrahydrofuran-3,4-diol (1-C)

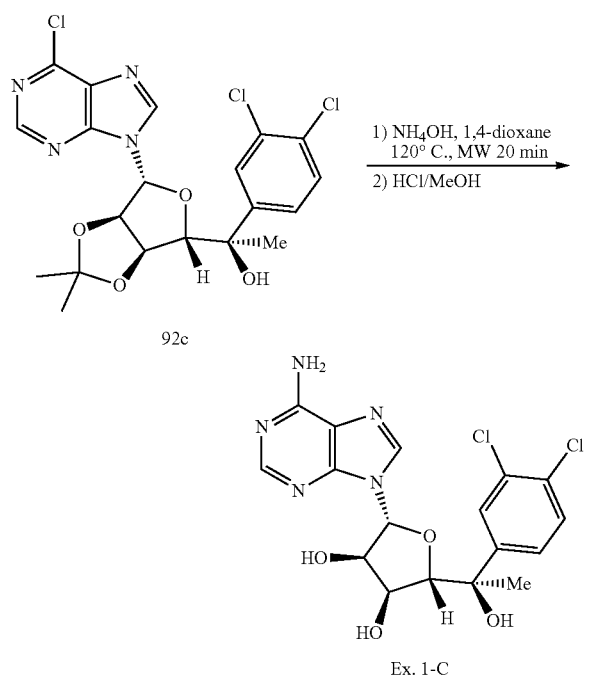

A mixture of (1R)-1-[(3aR,4R,6S,6aR)-4-(6-aminopurin-9-yl)-2,2-dimethyl-3a,4,6,6a-tetrahydrofuro[3,4-d][1,3]dioxol-6-yl]-1-(3,4-dichlorophenyl)ethanol (92c) (160.mg, 0.3400 mmol) and 1 μM HCl in MeOH (1 mL) was stirred at RT overnight. LCMS and TLC (9:1 DCM:MeOH) showed product formed and small amount of remaining st.m. The reaction mixture was concentrated and the crude product was purified on a 12 g column, eluted with 0-14% MeOH/DCM to give (2R,3R,4S,5S)-2-(6-aminopurin-9-yl)-5-[(1R)-1-(3,4-dichlorophenyl)-1-hydroxy-ethyl]tetrahydrofuran-3,4-diol (Ex 1-C) (117 mg, 0.26 mmol, 76% yield) as a light yellow solid. LCMS (M+H$^+$) 426/428/430. $^1$HNMR (400 MHz, Methanol-$d_4$) δ 8.64 (s, 1H), 8.46 (s, 1H), 7.75 (d, J=2.0 Hz, 1H), 7.53-7.45 (m, 2H), 6.12 (d, J=6.8 Hz, 1H), 4.68 (dd, J=6.8, 5.2 Hz, 1H), 4.31 (d, J=2.0 Hz, 1H), 4.03 (dd, J=5.2, 2.0 Hz, 1H), 1.59 (s, 3H).

Example 2-C. (2R,3R,4S,5S)-2-(6-amino-9H-purin-9-yl)-5-((R)-1-(4-chloro-3-methylphenyl)-1-hydroxyethyl)tetrahydrofuran-3,4-diol (2-C)

Example 2-C was synthesized via similar procedures of Example 1-C except for substituting (3,4-Dichlorophenyl)magnesium bromide with (4-chloro-3-methylphenyl)magnesium bromide in step 2. LCMS (M+H$^+$) 406/408. $^1$H NMR (600 MHz, Methanol-$d_4$) δ 8.51 (s, 1H), 8.46-8.34 (m, 2H), 7.50 (d, J=2.1 Hz, 1H), 7.42-7.22 (m, 2H), 6.07 (d, J=7.3 Hz, 1H), 4.74 (dd, J=5.2, 7.3 Hz, 1H), 4.34 (d, J=1.5 Hz, 1H), 4.00 (dd, J=1.4, 5.2 Hz, 1H), 2.40 (s, 3H), 1.57 (s, 3H).

Example 3-C. (2R,3R,4S,5S)-2-(4-amino-5-fluoro-7H-pyrrolo[2,3-d]pyrimidin-7-yl)-5-((R)-1-(3,4-dichlorophenyl)-1-hydroxyethyl)tetrahydrofuran-3,4-diol (3-C)

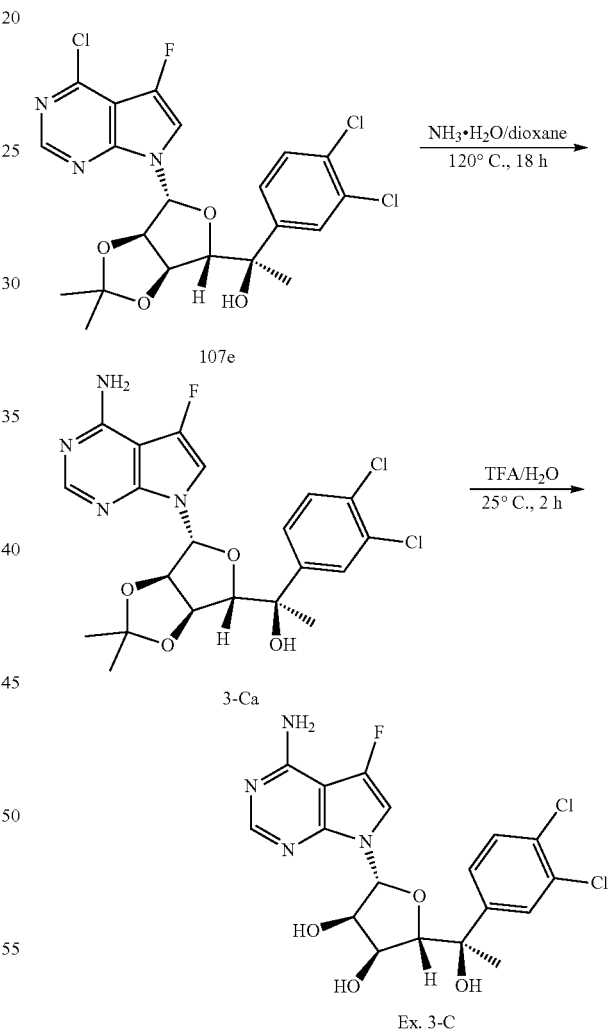

Step 1. Synthesis of (1R)-1-[(3aR,4R,6S,6aR)-4-(4-amino-5-fluoro-pyrrolo[2,3-d]pyrimidin-7-yl)-2,2-dimethyl-3a,4,6,6a-tetrahydrofuro[3,4-d][1,3]dioxol-6-yl]-1-(3,4-dichlorophenyl)ethanol(3-Ca)

To a solution of (1R)-1-[(3aR,4R,6S,6aR)-4-(4-chloro-5-fluoro-pyrrolo[2,3-d]pyrimidin-7-yl)-2,2-dimethyl-3a,4,6, 6a-tetrahydrofuro[3,4-d][1,3]dioxol-6-yl]-1-(3,4-dichlorophenyl)ethanol (107e) (100.0 mg, 0.20 mmol) in 1,4-Dioxane (1.0 mL) was added NH$_4$H (2.0 mL, 30.0%, 52.0 mmol). The mixture was stirred at 120° C. for 16 h in sealed tube. The solvent was removed in vacuum to give crude product which was purified by reversed-phase combi-flash eluted with MeCN in water from 10.0% to 70.0 to give (1R)-1-[(3aR,4R,6S,6aR)-4-(4-amino-5-fluoro-pyrrolo[2,3-d]pyrimidin-7-yl)-2,2-dimethyl-3a,4,6,6a-tetrahydrofuro[3,4-d][1,3]dioxol-6-yl]-1-(3,4-dichlorophenyl) ethanol (3-Ca) (80.0 mg, 0.17 mmol, 83.2% yield) as a gray solid. LCMS [M+H]: 483.1.

Step 2. Synthesis of(2R,3R,4S,5S)-2-(4-amino-5-fluoro-pyrrolo-[2,3-d]pyrimidin-7-yl)-5-[(1R)-1-(3,4-dichlorophenyl)-1-hydroxy-ethyl]tetrahydrofuran-3,4-diol(3-C)

To a solution of (1R)-1-[(3aR,4R,6S,6aR)-4-(4-amino-5-fluoro-pyrrolo[2,3-d]pyrimidin-7-yl)-2,2-dimethyl-3a,4,6,6a-tetrahydrofuro[3,4-d][1,3]dioxol-6-yl]-1-(3,4-dichlorophenyl)ethanol (80.0 mg, 0.17 mmol) in Water (1.0 mL) was added TFA (0.50 mL, 6.73 mmol). The mixture was stirred at 25° C. for 1 h. The solvent was removed in vacuum to give crude which was purified by pre-HPLC, eluted with MeCN in water from MeCN in water (0.1% NH$_3$.H$_2$O) from 10.0% to 80.0% to afford (2R,3R,4S,5S)-2-(4-amino-5-fluoro-pyrrolo-[2,3-d]pyrimidin-7-yl)-5-[(1R)-1-(3,4-dichlorophenyl)-1-hydroxy-ethyl]tetrahydrofuran-3,4-diol (Ex. 3-C) (51.1 mg, 0.11 mmol, 68.6% yield) as a white solid. LCMS [M+H]: 443.1. $^1$H NMR (400 MHz, DMSO-d$_6$+D$_2$O): δ 8.10 (s, 1H), 7.77 (d, J=1.7 Hz, 1H), 7.62 (d, J=8.4 Hz, 1H), 7.52 (d, J=8.4 Hz, 1H), 7.34 (s, 1H), 5.92 (d, J=7.6 Hz, 1H), 4.45-4.42 (m, 1H), 4.09 (brs, 1H), 3.68 (d, J=5.1 Hz, 1H), 1.43 (s, 3H). $^{19}$F NMR (377 MHz, DMSO-d$_6$): -168.17 (s, 1F).

Example 5-C. (2R,3R,4S,5R)-2-(4-amino-7H-pyrrolo[2,3-d]pyrimidin-7-yl)-5-((S)-1-(4-chlorophenyl)ethyl)tetrahydrofuran-3,4-diolhydrochloride (5-C)

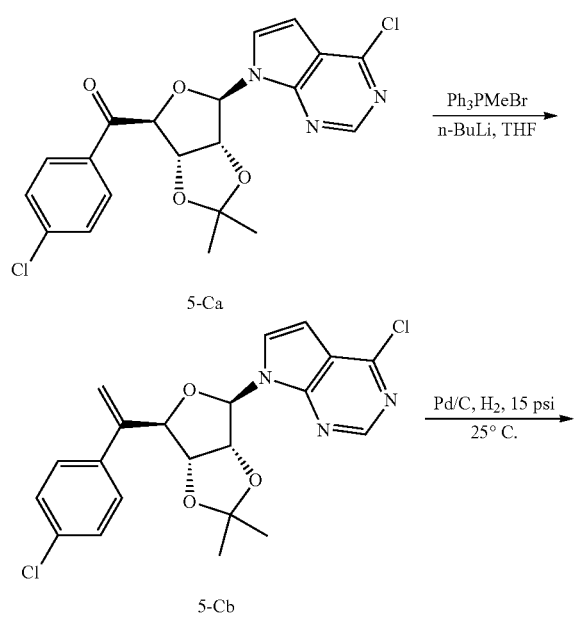

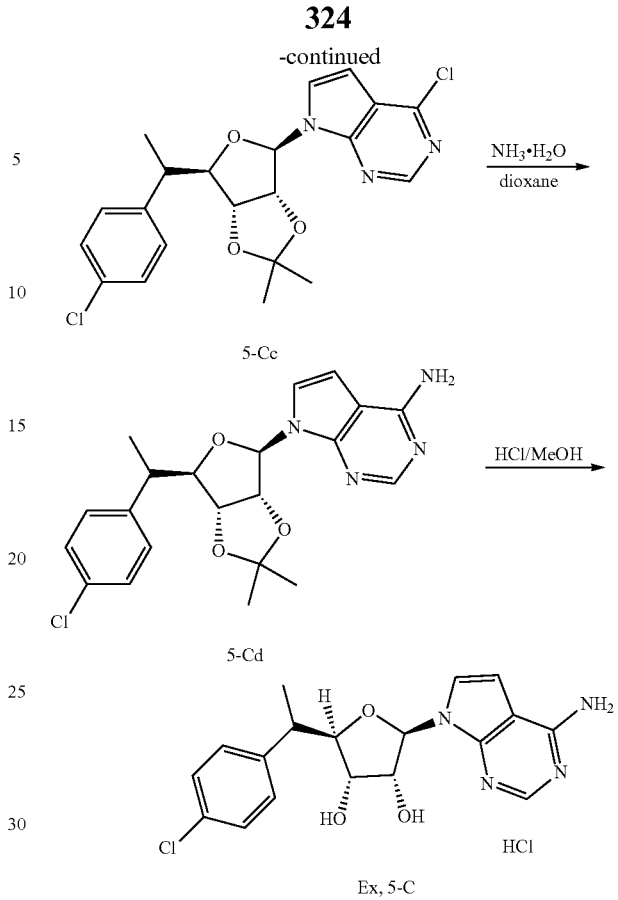

Step 1. Preparation of 4-chloro-7-((3aR,4R,6R,6aR)-6-(1-(4-chlorophenyl)vinyl)-2,2-dimethyltetrahydrofuro[3,4-d][1,3]dioxol-4-yl)-7H-pyrrolo[2,3-d]pyrimidine (5-Cb)

To a solution of Ph$_3$PMeBr (428 mg, 1.20 mmol, 1.04 eq.) in THF (15 mL) at −78° C. is added n-BuLi (2.5 μM, 479 uL, 1.04 eq.) slowly. The mixture is stirred at 0° C. for 30 minutes, and then cooled to −78° C. To the reaction mixture is added compound 5-Ca (0.5 g, 1.15 mmol, 1 eq.) in THF (4 mL). The reaction mixture is allowed to warm to 25° C. and stirred for 5.5 h. LC-MS showed no compound 5-Ca was remained. Several new peaks were shown on LC-MS and desired compound 5-Cb was detected. The reaction mixture was quenched by addition water (20 mL) at −60° C., and then diluted with EtOAc (20 mL) and extracted with EtOAc (20 mL*2). The combined organic layers were dried over Na$_2$SO$_4$, filtered and concentrated under reduced pressure to give a residue. The crude compound 5-Cb (750 mg, crude) was as yellow solid and used into the next step without further purification. LCMS: (M+H$^+$): 432.0, 434.0.

Step 2. Preparation of 4-chloro-7-((3aR,4R,6R,6aR)-6-((S)-1-(4-chlorophenyl)ethyl)-2,2-dimethyl-tetrahydrofuro[3,4-d][1,3]dioxol-4-yl)-7H-pyrrolo[2,3-d]pyrimidine (5-Cc)

To a solution of compound 5-Cb (50 mg, 116 umol, 1 eq) in THF (2 mL) was added Pd/C (0.01 g, 50% purity) under N$_2$. The suspension was degassed under vacuum and purged with H2 several times. The mixture was stirred under H2 (15 psi) at 25° C. for 15 min. LC-MS showed no compound 5-Cb was remained. Several new peaks were shown on LC-MS and desired compound was detected. The reaction mixture was filtered and the filtrate was concentrated. The crude compound 5-Cc (32 mg, crude) was as yellow oil and used into the next step without further purification. LCMS: (M+H$^+$): 434.0, 436.0.

Step 3. Preparation of 7-((3aR,4R,6R,6aR)-6-((S)-1-(4-chlorophenyl)ethyl)-2,2-dimethyltetrahydrofuro[3,4-d][1,3]dioxol-4-yl)-7H-pyrrolo[2,3-d]pyrimidin-4-amine (5-Cd)

A mixture of compound 5-Cc (32 mg, 74 umol, 1 eq.) in $NH_3·H_2O$ (1.86 g, 13.3 mmol, 2.04 mL, 25% purity, 180 eq.) and dioxane (2 mL) was stirred at 100° C. for 12 h. LC-MS showed no compound 5-Cc was remained. Several new peaks were shown on LC-MS and 64% of desired compound was detected. The reaction mixture was concentrated under reduced pressure to remove solvent. The residue was diluted with MeOH (5 mL*5) and concentrated under reduced pressure to give a residue. The crude product compound 5-Cd (30 mg, crude) was as yellow oil and used into the next step without further purification. LCMS: (M+H$^+$): 415.1.

Step 4. Preparation of (2R,3R,4S,5R)-2-(4-amino-7H-pyrrolo[2,3-d]pyrimidin-7-yl)-5-((S)-1-(4-chlorophenyl)ethyl)tetrahydrofuran-3,4-diol hydrochloride (5-C)

To compound 5-Cd (30 mg, 72.31 umol, 1 eq.) was added HCl/MeOH (4 μM, 1.81 mL, 100 eq.) in one portion at 0° C. The mixture was stirred at 25° C. for 10 min. LC-MS showed no compound 5-Cd was remained. Several new peaks were shown on LC-MS and desired compound was detected. The reaction mixture was concentrated under reduced pressure to remove solvent. The residue was purified by prep-HPLC (HCl condition). HPLC column: Luna C18 100*30 5 u; mobile phase: [water (0.05% HCl)-ACN]; B %: 20%-40%, 10 min. Compound 5-C (3.54 mg, 8.32 umol, 11.5% yield, 96.63% LCMS purity, HCl) was obtained as a white gum. $^1$H NMR (400 MHz, DMSO-d$_6$) δ=8.34 (s, 1H), 7.42 (d, J=3.1 Hz, 1H), 7.33-7.17 (m, 4H), 6.98 (br d, J=3.1 Hz, 1H), 5.99 (d, J=6.0 Hz, 1H), 4.26 (br t, J=5.4 Hz, 1H), 4.04 (br d, J=4.4 Hz, 1H), 4.01-3.94 (m, 1H), 3.12-3.02 (m, 1H), 1.26 (br d, J=6.8 Hz, 3H); 1H NMR (400 MHz, DMSO-d$_6$+D$_2$O) δ=8.32 (s, 1H), 7.45-7.37 (m, 1H), 7.29-7.19 (m, 4H), 6.94 (d, J=3.5 Hz, 1H), 5.98 (d, J=6.0 Hz, 1H), 4.25 (br t, J=5.6 Hz, 1H), 4.07-4.02 (m, 2H), 3.98 (br dd, J=3.7, 8.1 Hz, 3H), 3.10-3.01 (m, 2H), 1.25 (br d, J=7.0 Hz, 3H); LCMS: (M+H$^+$): 375.1; HPLC purity: 97.35%; SFC purity: 100.0%.

Example 15-C. (2R,3R,4S,5S)-2-(4-amino-5-fluoro-7H-pyrrolo[2,3-d]pyrimidin-7-yl)-5-((R)-1-(4-chloro-3-fluorophenyl)-1-hydroxyethyl)tetrahydrofuran-3,4-diol (15-C)

Example 15-C was prepared following the similar procedures of Ex. 3-C except for substituting 107e with (1R)-1-[(3aR,4R,6S,6aR)-4-(4-chloro-5-fluoro-pyrrolo[2,3-d]pyrimidin-7-yl)-2,2-dimethyl-3a,4,6,6a-tetrahydrofuro[3,4-d][1,3]dioxol-6-yl]-1-(4-chloro-3-fluorophenyl)ethanol. LCMS [M+H]: 427.2 $^1$H NMR (400 MHz, DMSO-d6): δ=8.09 (s, 1H), 7.54-7.58 (m, 2H), 7.41 (d, J=8.4 Hz, 1H), 7.37 (s, 1H), 7.12 (brs, 2H), 6.53 (s, 1H), 5.91 (d, J=8.0 Hz, 1H), 5.16 (brs, 1H), 4.84 (brs, 1H), 4.44 (brs, 1H), 4.10 (s, 1H), 1H), 3.66 (brs, 1H), 1.42 (s, 3H). $^1$H NMR (400 MHz, DMSO-d6+D$_2$O): δ=8.09 (s, 1H), 7.54-7.58 (m, 2H), 7.41 (d, J=8.4 Hz, 1H), 7.37 (s, 1H), 5.92 (d, J=8.0 Hz, 1H), 4.42-4.46 (m, 1H), 4.09 (s, 1H), 3.66 (d, J=5.2 Hz, 1H), 1.42 (s, 3H). $^{19}$F NMR (377 MHz, DMSO-d6): δ −116.62 (s, 1F), -168.22 (s, 1F).

Example 21-C. (2R,3R,4S,5S)-2-(4-amino-7H-pyrrolo[2,3-d]pyrimidin-7-yl)-5-((S)-1-(5-chlorothiophen-2-yl)-1-hydroxyethyl)tetrahydrofuran-3,4-diol (21-C)

Example 21-C was synthesized via similar procedures of Example 1-C. $^1$H NMR (400 MHz, Methanol-d$_4$) δ 8.09 (s, 1H), 7.23 (d, J=3.7 Hz, 1H), 6.87 (d, J=3.8 Hz, 1H), 6.80 (d, J=3.8 Hz, 1H), 6.59 (d, J=3.6 Hz, 1H), 5.85 (d, J=8.0 Hz, 1H), 4.82 (dd, J=5.2, 8.0 Hz, 1H), 4.19 (s, 1H), 4.14 (d, J=5.3 Hz, 1H), 1.54 (s, 3H).

Biochemical Assay Protocol

Compounds were solubilized, and 3-fold diluted in 100% DMSO. These diluted compounds were further diluted in the assay buffer (50 mM Tris-HCl, pH 8.5, 50 mM NaCl, 5 mM MgCl$_2$, 0.01% Brij35, 1 mM DTT, 1% DMSO) for 10-dose IC$_{50}$ mode at a concentration 10-fold greater than the desired assay concentration. Standard reactions were performed in a total volume of 50 in assay buffer, with histone H2A (5 μM final) as substrate. To this was added the PRMT5/MEP50 complex diluted to provide a final assay concentration of 5 nM and the compounds were allowed to preincubate for 15 to 20 minutes at room temperature. The reaction was initiated by adding S-[3H-methyl]-adenosyl-L-methionine (PerkinElmer) to final concentration of 1 μM. Following a 60 minutes incubation at 30° C., the reaction was stopped by adding 100 μL of 20% TCA. Each reaction was spotted onto filter plate (MultiScreen FB Filter Plate, Millipore), and washed 5 times with PBS buffer, Scintillation fluid was added to the filter plate and read in a scintillation counter. IC$_{50}$ values were determined by fitting the data to the standard 4 parameters with Hill Slope using GraphPad Prism software.

Cellular Assay Protocol

Cell Treatment and Western Blotting for Detecting Symmetric Di-Methyl Arginine (sDMA) and Histone H3R8 Dimethyl Symmetric (H3R8me2s) Marks Initial compounds screening in A549 cells: Compounds were dissolved in DMSO to make 10 mM stock and further diluted to 0.1, and 1 mM. A549 cells were maintained in PRMI 1640 (Corning Cellgro, Catalog #: 10-040-CV) medium supplemented with 10% v/v FBS (GE Healthcare, Catalog #: SH30910.03). One day before experiment, 1.25× 10$^5$ cells were seeded in 6 well plate in 3 mL medium and incubated overnight. The next day, medium was changed and 3 uL of compound solution was added (1:1,000 dilution, 0.1 and 1 uM final concentration; DMSO concentration: 0.1%), and incubated for 3 days. Cells incubated with DMSO was used as a vehicle control. Cells were washed once with PBS, trypsinized in 150 uL 0.25% Trypsin (Corning, Catalog #: 25-053-CI), neutralized with 1 mL complete medium, transferred to microcentrifuge tubes and collected. Cell pellet was then resuspended in 15 uL PBS, lysed in 4% SDS, and homogenized by passing through homogenizer column (Omega Biotek, Catalog #: HCR003). Total protein concentrations were determined by BCA assay (ThermoFisher Scientific, Catalog #: 23225). Lysates were mixed with 5× Laemmli buffer and boiled for 5 min. Forty ug of total protein was separated on SDS-PAGE gels (Bio-Rad, catalog #: 4568083, 4568043), transferred to PVDF membrane, blocked with 5% dry milk (Bio-Rad, Catalog #:

1706404) in TBS with 0.1% v/v Tween 20 (TBST) for 1 hour at room temperature (RT), and incubated with primary antibodies (sDMA: Cell signaling, Catalog #: 13222, 1:3,000; H3R8me2s: Epigentek, Catalog #: A-3706-100, 1:2,000; β-Actin: Abcam, Catalog #: ab8227, 1:10,000) in 5% dry milk in TBST at 4° C. for overnight. The next day, membranes were washed with TBST, 5×5 min, and incubated withhP conjugated seconded antibody (GE Healthcare; Catalog #: NA934-1ML; 1:5,000) for 2 hours at RT, followed by 5×5 min washes with TBST, and incubation with ECL substrates (Bio-Rad, Catalog #: 1705061, 1705062). Chemiluminescent signal was captured with FluoChem HD2 imager (Proteinsimple) and analyzed by ImageJ.

To determine enzyme inhibition $IC_{50}$ values using Western Blot analysis, Granta cells were seeded at density of $5\times10^5$ cells/mL in 3 mL medium (PRMI+10% v/v FBS). Nine-point 3-fold serial dilutions of compound were added to cells (3 ul, 1:1,000 dilution, DMSO concentration was 0.1%; final top concentration was 10 or 1 uM, depending on compounds potency) and incubated for 3 days. Cells incubated with DMSO was used as a vehicle control. Cells were harvested and subjected to western blot analysis as described above. SmD3me2s and H3R8me2s bands were quantified by ImageJ. Signals were normalized to β-Actin and DMSO control. $IC_{50}$ values were calculated using Graphpad Prism.

Cell Proliferation Assay to Determine $IC_{50}$ on Granta-519 Cells

Granta-519 cells were maintained in PRMI 1640 (Corning Cellgro, Catalog #: 10-040-CV) medium supplemented with 10% v/v FBS (GE Healthcare, Catalog #: SH30910.03). Compounds were dissolved in DMSO to make 10 mM stocks and stored at −20° C. Nine-point, 3-fold serial dilutions were made with DMSO with top concentration at 1 mM (working stocks).

On day of experiment, compound working stocks were further diluted at 1:50 with fresh medium in 96 well plate, and 10 μL of diluted drugs were added to a new 96 well plate for proliferation assay. Cells growing at exponential phase were spun down at 1500 rpm for 4 min and resuspend in fresh medium to reach a density of $0.5\times10^6$ cells/ml. 200 ul of cells were added to 96 well plate containing diluted drugs and incubated for 3 days. DMSO was used a vehicle control.

One day 3, 10 μL of Cell Counting Kit-8 (CCK-8, Jojindo, CK04-13) solution was added to a new 96 well plate. Cells incubated with drugs for 3 days were resuspended by pipetting up and down, and 100 μL of cells were transferred to 96 well plate containing CCK-8 reagent to measure viable cells. Plates were incubated in $C_{O2}$ incubator for 2 hours and OD450 values were measured with a microplate reader (iMark microplate reader, Bio-Rad).

For re-plating, compound working stocks were diluted at 1:50 with fresh medium and 10 μL of diluted drugs were added to anew 96 well plate. Cells from Day 3plate (50 ul) were added to 96 well plate containing fresh drug and additional 150 of fresh medium was added to reach 200 ul volume. Plate was returned to $CO_2$ incubator and incubated for 3more days. Viable cells measurement and re-plating were repeated on day 6, and the final viable cells measurement was taken on day 10.

Percentage of viable cells, relative to DMSO vehicle control, were calculated and plotted in Graphpad Prism ([Inhibitor] vs. normalized response-Variable slope) to determine proliferation $IC_{50}$ values on day 10.

TABLE 7

Biochemical and cellular potency (in Granta-519 cell line)

| Ex. No | PRMT5/ MEP50 $IC_{50}$ (μM) | PRMT5/ MEP50_N | sDMA $IC_{50}$ (μM) | sDMA_N | Proliferation $IC_{50}$ (μM) | Proliferation_N |
|---|---|---|---|---|---|---|
| 20 | 0.0006 | 2 | 120 | 2 | 0.098 | 2 |
| 36 | 17.3 | 3 | 102 | 9 | 0.144 | 5 |
| 37 | 0.0024 | 1 | 0.008 | 3 | 0.022 | 1 |
| 52 | 0.188 | 1 | 39% inhibition @ 1 uM | 1 | | |
| 39 | 0.18 | 1 | | | | |
| 62 | 0.0086 | 2 | 0.045 | 4 | 0.063 | 2 |
| 63 | 0.0007 | 2 | 0.0108 | 2 | | |
| 64 | 0.0083 | 2 | 0.093 | 1 | | |
| 54 | 0.0256 | 1 | 55% inhibition @ 1 uM | | | |
| 53 | 0.526 | 1 | | | | |
| 65 | 0.0019 | 1 | 0.016 | 2 | | |
| 66 | 0.0004 | 1 | 0.0018 | 1 | | |
| 67 | 0.0006 | 1 | 0.01 | 1 | | |
| 68 | 0.035 | 1 | 0.09 | 2 | | |
| 69 | 0.0018 | 3 | 0.028 | 3 | 0.032 | 5 |
| 70 | 0.0102 | 1 | 0.048 | 2 | 0.13 | 1 |
| 59 | 0.0028 | 2 | 0.045 | 1 | | |
| 71 | 0.0139 | 1 | 0.26 | 1 | | |
| 72 | 0.0028 | 1 | 0.041 | 1 | | |
| 73 | 0.0097 | 1 | 0.313 | 1 | | |
| 74 | 0.0756 | 1 | | | | |
| 75 | 0.0954 | 1 | | | | |
| 76 | 0.0027 | 1 | | | | |
| 77 | 0.1176 | 1 | | | | |
| 78 | 0.0031 | 1 | 0.033 | 1 | | |
| 61 | 0.0026 | 2 | 0.033 | 2 | 0.047 | 1 |
| 79 | 6.46 | 1 | | | | |
| 60 | 0.0377 | 1 | 0.438 | 1 | | |
| 80 | 0.0007 | 1 | 0.018 | 1 | | |

TABLE 7-continued

Biochemical and cellular potency (in Granta-519 cell line)

| Ex. No | PRMT5/MEP50 IC$_{50}$ (μM) | PRMT5/MEP50_N | sDMA IC$_{50}$ (μM) | sDMA_N | Proliferation IC$_{50}$ (μM) | Proliferation_N |
|---|---|---|---|---|---|---|
| 81 | 0.0003 | 1 | 0.009 | 1 | | |
| 82 | 0.0039 | 1 | 0.011 | 1 | | |
| 83 | 0.0291 | 1 | 0.097 | 1 | | |
| 92 | 1.97 | 2 | | | | |
| 93 | 0.92 | 3 | | | | |
| 94 | 1.62 | 1 | | | | |
| 95 | 0.699 | 1 | | | | |
| 96 | | | 0.142 | 1 | | |
| 97 | 0.042 | 1 | | | | |
| 98 | 0.0084 | 1 | 0.009 | | | |
| 99 | 0.0024 | 1 | 0.0084 | 1 | 0.094 | 2 |
| 100 | 1.77 | 1 | | | | |
| 101 | 0.308 | 1 | | | | |
| 102 | 0.436 | 1 | 3.36 | 1 | | |
| 103 | 0.0296 | 1 | 0.0579 | 1 | 0.062 | 1 |
| 104 | 0.0102 | 1 | | | | |
| 105 | 0.0002 | 1 | | | | |
| 106 | 0.113 | 1 | | | | |
| 107 | 0.028 | 1 | | | | |
| 108 | 0.0096 | 1 | 0.131 | 1 | 0.415 | 1 |

TABLE 8

Biochemical and cellular potency (in Granta cell line) - Compounds of Formula III and Formula IV

| Ex. No | PRTMT5/MEP50 IC$_{50}$ μM | PRTMT5/MEP50_N | sDMA IC$_{50}$ μM | sDMA_N | Prolif. IC$_{50}$ μM | Prolif_N |
|---|---|---|---|---|---|---|
| 25-B | 0.047 | 1 | ~3 | 1 | | |
| 28-B | 1.16 | 1 | | | | |
| 37-B | 0.0063 | 1 | 100 | 1 | | |
| 49-B | 0.543 | 1 | | | | |
| 50-B | 0.0117 | 1 | ~0.6 | 1 | | |
| 79-B | 0.0082 | 1 | 0.097 | 1 | | |
| 84-B | 0.0027 | 1 | 0.016 | 1 | | |
| 85-B | 0.00064 | 1 | 0.0009 | 1 | | |
| 86-B | 0.0002 | 1 | 0.003 | 1 | | |
| 87-B | 0.00033 | 1 | 0.0017 | 1 | | |
| 88-B | 0.037 | 1 | | | | |
| 89-B | 0.095 | 1 | | | | |
| 90-B | 0.00082 | 1 | 0.028 | 1 | 0.229 | 1 |
| 91-B | 0.0032 | 1 | 0.0468 | 1 | | |
| 92-B | 0.0199 | 1 | 0.335 | 1 | | |
| 93-B | 0.0023 | 1 | | | | |
| 94-B | 0.0034 | 1 | 0.053 | 1 | | |

TABLE 9

Biochemical and cellular potency (in Granta cell line) - Compounds of Formula V and Formula VI

| Ex. No | PRTMT5/MEP50 IC$_{50}$ μM | PRTMT5/MEP50_N | sDMA IC$_{50}$ μM | sDMA_N | Prolif. IC$_{50}$ μM | Prolif_N |
|---|---|---|---|---|---|---|
| 1-C | 0.0036 | 2 | 0.0082 | 2 | 0.044 | 2 |
| 2-C | 0.0135 | 1 | 0.013 | 1 | | |
| 3-C | 0.0009 | 1 | 0.0038 | 1 | | |
| 5-C | 0.037 | 1 | 0.091 | 1 | | |
| 6-C | 0.0069 | 1 | 0.093 | 1 | | |
| 15-C | 0.001 | 1 | 0.0019 | 1 | | |
| 21-C | 0.0009 | 1 | 0.007 | 1 | | |

FaSSIF Solubility

Compounds were first dispersed in freshly prepared FaSSIF (http://biorelevant.com/site_media/upload/documents/How_to_make_FaSSIF_FeSSIF_and_FaSSGF.pdf) buffer in 1 mg/mL respectively, and the standard samples were prepared by preparing 1 mg/mL of test compounds in DMSO. The compounds were then sufficient mixed by vortex mixer for 30 sec, and agitated at 25° C. using 300 rpm form 4 hour in thermo mixer. After incubation, the prepared samples were centrifuged at 10000 rpm for 10 min to remove the undissolved solid, the resulting supernatants were applied to HPLC. The actual concentrations of the compounds were evaluated by measuring the peak area, and the solubility (S) of compounds was calculated according to following equation:

$$S=C_{smp}=C_{std}*(A_{smp}/A_{std})*(V_{std}/V_{smp})$$

Where C is the sample concentration in μg/mL, A is the peak area, and V is the injection volume.

Warfarin (10-25 μg/mL), Atovaquone (<2 μg/mL) and Nimesulide (100-200 μg/mL) are positive controls in this experiment.

Example 36 was measured to have a FaSSIF solubility of 912.1 μg/mL.

Example 92A was measured to have an average of FaSSIF solubility of 54.7 μg/mL (n=4).

In Vivo Pharmacokinetic Properties of Example 36.

In a rat (SD, male, non-fasted) non-crossover cassette PK study, Example 36 was dosed at 0.25 mg/kg via i.v. administration (N=3) and 2 mg/kg via oral gauge (p.o.) (N=3) with other 3 compounds. It showed average T2 of 1.2 h, Vss of 1.1 L/kg, blood clearance of 12.3 mL/min/kg in the i.v. group; it showed average dose normalized AUC of 1738 ng*h*kg/mL/mg and >120% of oral bioavailability in the p.o. group.

In Vivo Pharmacokinetic Properties of Example 92.

In a rat (SD, male, non-fasted) non-crossover PK study, Example 92 was dosed at 1 mg/kg (DMA: 20% HPBCD=5:95, solution) via i.v. administration (N=2) and 1 mg/kg (0.5% Na CMC+0.5% Tween80, solution) via oral gauge (p.o.) (N=2). It showed average T2 of 1.84 hr, Vss of 1.13 L/kg, blood clearance of 11.3 mL/min/kg in the i.v. group; it showed average dose normalized $AUC_{0-inf}$ of 2184 ng*h*kg/mL/mg and >100% of oral bioavailability in the p.o. group; The metabolite (Ex. 1-C) was detected in blood samples. It showed T/2 of 5.01 hr, $T_{max}$ of 8.00 hr, average of $AUC_{0-inf}$ of 284 ng*h*kg/mL/mg.

In Vivo Pharmacodynamic Effect of Example 36 in Granta-519 Mouse Xenograft Model.

Granta-519 cells was maintained in DMEM medium supplemented with 10% fetal bovine serum and 2 mM L-Glutamine at 37° C. in an atmosphere of 5% $C_{O2}$ in air. Cells in exponential growth phase were harvested and 1×10⁷ cells in 0.1 mL of PBS with Matrigel (1:1) were injected subcutaneously at the right lower flank region of each mouse for tumor development. The treatments were started when the mean tumor size reaches approximately 300-400 mm³. Mice were assigned into groups using StudyDirector™ software (Studylog Systems, Inc. CA, USA) and one optimal randomization design (generated by either Matched distribution or Stratified method) that shows minimal group to group variation in tumor volume was selected for group allocation. Example 36 or vehicle (0.5% methylcellulose+0.1% Tween 80) were administered orally (BID for Example 36, QD for vehicle) at a dose of 25 mg/kg for 6 days. Body weights and tumor size were measured thrice weekly after randomization. Animals were euthanized 4 hours after last dosing on day 6, and blood and tumor samples were collected for analysis.

To measure sDMA levels in tumor samples, tumors from each mouse were weighted and homogenized in RIPA buffer supplemented with protease inhibitor (cOmplete™, EDTA-free Protease Inhibitor Cocktail, Roche). Lysate were centrifuged at 14,000 rpm for 30 min at 4° C. to remove debris. Total protein concentrations of lysate were determined by BCA assay (ThermoFisher Scientific, Catalog #: 23225). Equal amount of total proteins from each tumor were separated on SDS-PAGE gel, and sDMA levels were determined by WB as described previously.

Following this protocol, Example 36 showed an average of 97% (N=5, p<0.0001) inhibition of sDMA.

Example 92 or vehicle (0.5% Na CMC+0.5% Tween80, suspension) were administered orally (QD for Example 92, QD for vehicle) at a dose of 50 mg/kg for 14 days. Body weights and tumor size were measured every 3 to 4 days after randomization. Animals were euthanized 4 hours after last dosing, and blood and tumor samples were collected for analysis.

Following this protocol, Example 92 showed an average of 74% (N=5) tumor growth inhibition at 50 mg/kg with body weight loss of 1%; the metabolite (Ex. 1-C) was detected in all blood and tumor samples. It also showed >90% inhibition of sDMA in tumor samples. In a separate experiment, the metabolite (Ex. 1-C) showed an average of 61% (N=5) tumor growth inhibition at 30 mg/kg with body weight gain of 6%; It showed no detectable amount of sDMA in tumor samples.

The disclosure pertains to the following aspects:

Aspect 1. A compound of Formula I or Formula II:

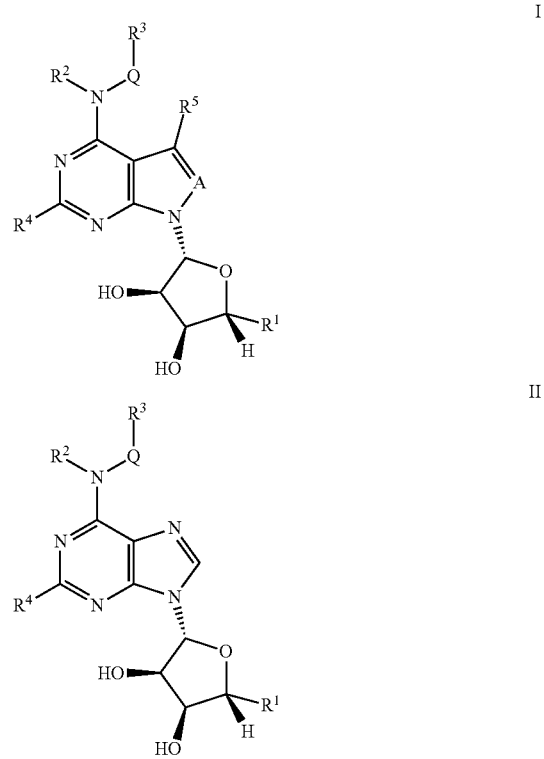

or a pharmaceutically acceptable salt or solvate thereof; wherein

A is CH or N;

Q is NH, NR$^6$ or O;

R$^1$ is —C$_0$-C$_6$alk-C$_3$-C$_6$cycloalkyl, —C$_0$-C$_6$alk-C$_3$-C$_6$halocycloalkyl; —C$_2$-C$_6$alkenyl, —C$_2$-C$_6$haloalkenyl, —C$_0$-C$_6$alk-C$_1$-C$_6$alkyl, —C$_0$-C$_6$alk-C$_1$-C$_6$haloalkyl, —C$_0$-C$_6$alk-C≡CH, —C$_0$-C$_6$alk-C≡C—C$_1$-C$_6$alkyl, —C$_0$-C$_6$alk-C≡C—C$_1$-C$_6$haloalkyl, —C$_0$-C$_6$alk-C≡C—C$_3$-C$_6$cycloalkyl, —C$_1$-C$_6$alk-aryl, —C$_1$-C$_6$alk-S—C$_1$-C$_6$alkyl, —C$_1$-C$_6$alk-S—C$_1$-C$_6$haloalkyl, —C$_1$-C$_6$alk-S—C$_3$-C$_6$cycloalkyl; —C$_1$-C$_6$alk-S—C$_3$-C$_6$halocycloalkyl; —C$_1$-C$_6$alk-O—C$_1$-C$_6$alkyl, —C$_1$-C$_6$alk-O—C$_3$-C$_6$cycloalkyl, —C$_1$-C$_6$alk-S—CH$_2$-aryl, or —C$_1$-C$_6$alk-C(O)NH-aryl;

R$^2$ is H, —C$_1$-C$_6$alkyl, —C$_1$-C$_6$haloalkyl, or —C$_0$-C$_6$alk-C$_3$-C$_6$cycloalkyl;

R$^3$ is H, —C$_1$-C$_6$alkyl, —C$_1$-C$_6$haloalkyl, —C$_0$-C$_6$alk-C$_3$-C$_6$cycloalkyl, —C(O)R$^7$, —C(O)OR$^7$, or —C(O)NR$^{8a}$R$^{8b}$;

R$^4$ is H, halo, —C$_1$-C$_6$alkyl, or NH$_2$;

R$^5$ is H, halo, CN, —C$_1$-C$_6$alkyl, —C$_2$-C$_4$alkenyl, —C$_2$-C$_4$haloalkenyl, C$_2$-C$_4$cyanoalkenyl, —C$_0$-C$_6$alk-C≡CH, —C$_0$-C$_6$alk-C≡C—C$_1$-C$_6$alkyl, —C$_1$-C$_4$haloalkyl, —C$_2$-C$_6$heterocycloalkyl, oxo-substituted-C$_2$-C$_6$heterocycloalkyl, —C$_3$-C$_6$cycloalkyl, —C$_0$-C$_3$alk-C(O)R$^9$, —CR$^8$R$^{8'}$CN, —CH$_2$NR$^8$R$^{8'}$, —C$_0$-C$_6$alk-OH, —NR$^8$R$^{8'}$, —N(R$^9$)CN, —O—C$_1$-C$_4$alkyl, —NR$^9$CONR$^8$R$^{8'}$, —OCONR$^8$R$^{8'}$, or —NR$^9$C(O)OR$^{9a}$;

R$^6$ is —C$_1$-C$_6$alkyl or —C$_0$-C$_6$alk-C$_3$-C$_6$cycloalkyl;

R$^7$ is H, C$_1$-C$_6$alkyl, or C$_0$-C$_6$alk-C$_3$-C$_6$cycloalkyl;

R$^{8a}$ and R$^{8b}$ are each independently H, C$_1$-C$_6$alkyl, or —C$_0$-C$_6$alk-OC$_1$-C$_6$alkyl, or R$^{8a}$ and R$^1$, together with the atom to which they are attached, form a C$_2$-C$_6$heterocycloalkyl ring;

R$^8$ and R$^{8'}$ are each independently H, C$_1$-C$_6$alkyl, or —C$_0$-C$_6$alk-OC$_1$-C$_6$alkyl; or R$^8$ and R$^{8'}$, together with the atom to which they are attached, form a C$_3$-C$_6$cycloalkyl ring or a C$_2$-C$_6$heterocycloalkyl ring;

R$^9$ is H, —C$_1$-C$_6$alkyl, or —C$_0$-C$_6$alk-C$_3$-C$_6$cycloalkyl; and

R$^{9a}$ is —C$_1$-C$_6$alkyl, or C$_0$-C$_6$alk-C$_3$-C$_6$cycloalkyl.

Aspect 2. The compound of aspect 1 wherein R$^1$ is —C$_0$-C$_6$alk-C$_1$-C$_6$alkyl.

Aspect 3. The compound of aspect 2 wherein the —C$_0$-C$_6$alk-C$_1$-C$_6$alkyl is —CH(OH)—C$_1$-C$_6$alkyl, —CH(F)—C$_1$-C$_6$alkyl, —CH(NH$_2$)—C$_1$-C$_6$alkyl, —CH(Me)-C$_1$-C$_6$alkyl, or —C(Me)(OH)—C$_1$-C$_6$alkyl.

Aspect 4. The compound of aspect 1 wherein R$_1$ is —C$_0$-C$_6$alk-C$_1$-C$_6$haloalkyl.

Aspect 5. The compound of aspect 4 wherein the —C$_0$-C$_6$alk-C$_1$-C$_6$haloalkyl is —CH(OH)—C$_1$-C$_6$haloalkyl, —CH(F)—C$_1$-C$_6$haloalkyl, —CH(NH$_2$)—C$_1$-C$_6$haloalkyl, —CH(Me)-C$_1$-C$_6$haloalkyl, or —C(Me)(OH)—C$_1$-C$_6$haloalkyl.

Aspect 6. The compound of aspect 1 wherein R$_1$ is —C$_0$-C$_6$alk-C≡CH.

Aspect 7. The compound of aspect 6 wherein the —C$_0$-C$_6$alk-C≡CH is —CH(OH)—C≡CH, —CH(F)—C—CH, —CH(NH$_2$)—C≡CH, —CH(Me)-C≡CH, or —C(Me)(OH)—C≡CH.

Aspect 8. The compound of aspect 1 wherein R$_1$ is —C$_1$-C$_6$alk-C≡C—C$_1$-C$_6$alkyl.

Aspect 9. The compound of aspect 8 wherein the —C$_0$-C$_6$alk-C≡C—C$_1$-C$_6$alkyl is —CH(OH)—C≡C—C$_1$-C$_6$alkyl, —CH(F)—C≡C—C$_1$-C$_6$alkyl, —CH(NH$_2$)—C≡C—C$_1$-C$_6$alkyl, —CH(Me)-C≡C—C$_1$-C$_6$alkyl, or —C(Me)(OH)—C≡C—C$_1$-C$_6$alkyl.

Aspect 10. The compound of aspect 9, wherein the —C$_0$-C$_6$alk-C≡C—C$_1$-C$_6$alkyl is —CH(OH)—C≡C—CH$_3$, —CH(F)—C≡C—CH$_3$, —CH(NH$_2$)—C≡C—CH$_3$, —CH(Me)-C≡C—CH$_3$, or —C(Me)(OH)—C≡C—CH$_3$.

Aspect 11. The compound of aspect 1 wherein R$_1$ is —C$_1$-C$_6$alk-C≡C—C$_1$-C$_6$haloalkyl.

Aspect 12. The compound of aspect 11 wherein the —C$_0$-C$_6$alk-C≡C—C$_1$-C$_6$haloalkyl is —CH(OH)—C≡C—C$_1$-C$_6$haloalkyl, —CH(F)—C≡C—C$_1$-C$_6$haloalkyl, —CH(NH$_2$)—C≡C—C$_1$-C$_6$haloalkyl, —CH(Me)-C≡C—C$_1$-C$_6$haloalkyl, or —C(Me)(OH)—C≡C—C$_1$-C$_6$haloalkyl.

Aspect 13. The compound of aspect 12, wherein the —C$_0$-C$_6$alk-C≡C—C$_1$-C$_6$haloalkyl is —CH(OH)—C≡C—CF$_3$, —CH(F)—C≡C—CF$_3$, —CH(NH$_2$)—C≡C—CF$_3$, —CH(Me)-C≡C—CF$_3$, or —C(Me)(OH)—C≡C—CF$_3$.

Aspect 14. The compound of aspect 1 wherein R$_1$ is —C$_0$-C$_6$alk-C≡C—C$_3$-C$_6$cycloalkyl.

Aspect 15. The compound of aspect 14 wherein the —C$_0$-C$_6$alk-C≡C—C$_3$-C$_6$cycloalkyl is —CH(OH)—C≡C—C$_3$-C$_6$cycloalkyl, —CH(F)—C≡C—C$_3$-C$_6$cycloalkyl, —CH(NH$_2$)—C≡C—C$_3$-C$_6$cycloalkyl, —CH(Me)-C≡C—C$_3$-C$_6$cycloalkyl, or —C(Me)(OH)—C≡C—C$_3$-C$_6$cycloalkyl.

Aspect 16. The compound of aspect 15, wherein the —C$_0$-C$_6$alk-C≡C—C$_3$-C$_6$cycloalkyl is —CH(OH)—C≡C-cyclopropyl, —CH(F)—C≡C-cyclopropyl, —CH(NH$_2$)—C≡C-cyclopropyl, —CH(Me)-C≡C-cyclopropyl, or —C(Me)(OH)—C≡C-cyclopropyl.

Aspect 17. The compound of aspect 1 wherein R$_1$ is —C$_1$-C$_6$alk-aryl.

Aspect 18. The compound of aspect 17 wherein the —C$_1$-C$_6$alk-aryl is —CH(OH)-aryl, —CH(F)-aryl, —CH(NH$_2$)-aryl, —CH(Me)-aryl, or —C(Me)(OH)-aryl.

Aspect 19. The compound of aspect 18 wherein the —C$_1$-C$_6$alk-aryl is —CH(OH)-4-chlorophenyl, —CH(OH)-3,4-dichlorophenyl, —CH(OH)-3,4-difluorophenyl, —CH(OH)-3-fluoro-4-chlorophenyl, —CH(OH)-3-chloro-4-fluorophenyl, —CH(F)-4-chlorophenyl, —CH(F)-3,4-dichlorophenyl, —CH(F)-3,4-difluorophenyl, —CH(F)-3-fluoro-4-chlorophenyl, —CH(F)-3-chloro-4-fluorophenyl, —CH(NH$_2$)-4-chlorophenyl, —CH(NH$_2$)-3,4-dichlorophenyl, —CH(NH$_2$)-3,4-difluorophenyl, —CH(NH$_2$)-3-fluoro-4-chlorophenyl, —CH(NH$_2$)-3-chloro-4-fluorophenyl, —CH(Me)-4-chlorophenyl, —CH(Me)-3,4-dichlorophenyl, —CH(Me)-3,4-difluorophenyl, —CH(Me)-3-fluoro-4-chlorophenyl, —CH(Me)-3-chloro-4-fluorophenyl, —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, or —C(Me)(OH)-3-chloro-4-fluorophenyl.

Aspect 20. The compound of any one of aspects 1 to 19 wherein R$^2$ is H.

Aspect 21. The compound of any one of aspects 1 to 19 wherein R$^2$ is C$_1$-C$_6$ alkyl.

Aspect 22. The compound of any one of aspects 1 to 21 wherein R$^3$ is H.

Aspect 23. The compound of any one of aspects 1 to 21 wherein R$^3$ is —C$_1$-C$_6$alkyl.

Aspect 24. The compound of any one of aspects 1 to 21 wherein R$^3$ is —C(O)R$^7$.

Aspect 25. The compound of aspect 24 wherein R$^7$ is C$_1$-C$_6$alkyl.

Aspect 26. The compound of any one of aspects 1 to 25 wherein R$^4$ is H.

Aspect 27. The compound of any one of aspects 1 to 26 wherein Q is NH.

Aspect 28. The compound of any one of aspects 1 to 26 wherein Q is O.

Aspect 29. The compound of any one of aspects 1 to 28 which is a compound of Formula I.

Aspect 30. The compound of aspect 29 wherein A is CH.

Aspect 31. The compound of aspect 29 wherein A is N.

Aspect 32. The compound of any one of aspects 29-31 wherein $R^5$ is H.

Aspect 33. The compound of any one of aspects 29-31 wherein $R^5$ is halo.

Aspect 34. The compound of any one of aspects 29-31 wherein $R^5$ is —$C_1$-$C_6$alkyl.

Aspect 35. The compound of any one of aspects 1 to 28 that is a compound of Formula II.

Aspect 36. A pharmaceutical composition comprising a compound according to any one of aspects 1-35 and a pharmaceutically acceptable excipient.

Aspect 37. A method of inhibiting a protein arginine methyltransferase 5 (PRMT5) enzyme, comprising: contacting the PRMT5 enzyme with an effective amount of a compound of any one of any one of aspects 1 to 35.

Aspect 38. A method of treating a disease or disorder associated with aberrant PRMT5 activity in a subject comprising administering to the subject, a compound of any one of aspects 1 to 35.

Aspect 39. The method of aspect 38, wherein the disease or disorder associated with aberrant PRMT5 activity is breast cancer, lung cancer, pancreatic cancer, prostate cancer, colon cancer, ovarian cancer, uterine cancer, cervical cancer, leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), myelodysplastic syndrome (MDS), epidermoid cancer, or hemoglobinopathies such as b-thalassemia and sickle cell disease (SCD).

Aspect 40. A compound of Formula I or Formula II

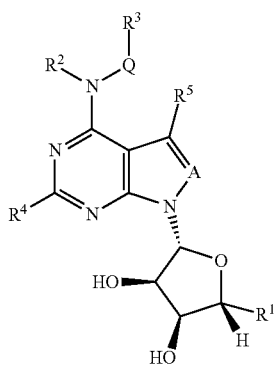

I

-continued

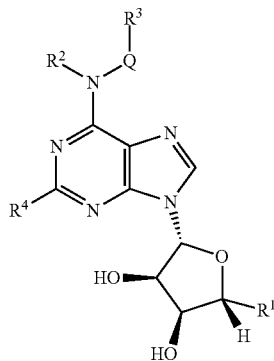

II or a pharmaceutically acceptable salt or solvate thereof; wherein

A is CH or N;

Q is NH, $NR^6$ or O;

$R^1$ is —$C_0$-$C_6$alk-$C_3$-$C_6$cycloalkyl, —$C_0$-$C_6$alk-$C_3$-$C_6$halocycloalkyl; —$C_2$-$C_6$alkenyl, —$C_2$-$C_6$haloalkenyl, —$C_0$-$C_6$alk-$C_1$-$C_6$alkyl, —$C_0$-$C_6$alk-$C_1$-$C_6$haloalkyl, —$C_0$-$C_6$alk-C≡CH, —$C_0$-$C_6$alk-C≡C—$C_1$-$C_6$alkyl, —$C_0$-$C_6$alk-C≡C—$C_1$-$C_6$haloalkyl, —$C_0$-$C_6$alk-C≡C—$C_3$-$C_6$cycloalkyl, —$C_1$-$C_6$alk-aryl, —$C_1$-$C_6$alk-S—$C_1$-$C_6$alkyl, —$C_1$-$C_6$alk-S—$C_1$-$C_6$haloalkyl, —$C_1$-$C_6$alk-S—$C_3$-$C_6$cycloalkyl; —$C_1$-$C_6$alk-S—$C_3$-$C_6$halocycloalkyl; —$C_1$-$C_6$alk-O—$C_1$-$C_6$alkyl, —$C_1$-$C_6$alk-O—$C_3$-$C_6$cycloalkyl, —$C_1$-$C_6$alk-S—$CH_2$-aryl, or —$C_1$-$C_6$alk-C(O)NH-aryl;

$R^2$ is H, —$C_1$-$C_6$alkyl, —$C_1$-$C_6$haloalkyl, or —$C_0$-$C_6$alk-$C_3$-$C_6$cycloalkyl;

$R^3$ is H, —$C_1$-$C_6$alkyl, —$C_1$-$C_6$haloalkyl, —$C_0$-$C_6$alk-$C_3$-$C_6$cycloalkyl, —$C(O)R^7$, —$C(O)OR^7$, or —$C(O)NR^{8a}R^{8b}$;

$R^4$ is H, halo, —$C_1$-$C_6$alkyl, or $NH_2$;

$R^5$ is H, halo, CN, —$C_1$-$C_6$alkyl, —$C_2$-$C_4$alkenyl, —$C_2$-$C_4$haloalkenyl, $C_2$-$C_4$cyanoalkenyl, —$C_0$-$C_6$alk-C≡CH, —$C_0$-$C_6$alk-C≡C—$C_1$-$C_6$alkyl, —$C_1$-$C_4$haloalkyl, —$C_2$-$C_6$heterocycloalkyl, oxo-substituted-$C_2$-$C_6$heterocycloalkyl, —$C_3$-$C_6$cycloalkyl, —$C_0$-$C_3$alk-C(O)$R^9$, —$CR^8R^{8'}$CN, —$CH_2NR^8R^{8'}$, —$C_0$-$C_6$alk-OH, —$NR^8R^{8'}$, —$N(R^9)$CN, —O—$C_1$-$C_4$alkyl, —$NR^9CONR^8R^{8'}$, —$OCONR^8R^{8'}$, or —$NR^9C(O)OR^{9a}$;

$R^6$ is —$C_1$-$C_6$alkyl or —$C_0$-$C_6$alk-$C_3$-$C_6$cycloalkyl;

$R^7$ is H, $C_1$-$C_6$alkyl, or $C_0$-$C_6$alk-$C_3$-$C_6$cycloalkyl;

$R^{8a}$ and $R^{8b}$ are each independently H, $C_1$-$C_6$alkyl, or —$C_0$-$C_6$alk-$OC_1$-$C_6$alkyl, or $R^{8a}$ and R, together with the atom to which they are attached, form a $C_2$-$C_6$heterocycloalkyl ring;

$R^8$ and $R^{8'}$ are each independently H, $C_1$-$C_6$alkyl, or —$C_0$-$C_6$alk-$OC_1$-$C_6$alkyl;

or $R^8$ and $R^{8'}$, together with the atom to which they are attached, form a $C_3$-$C_6$cycloalkyl ring or a $C_2$-$C_6$heterocycloalkyl ring;

$R^9$ is H, —$C_1$-$C_6$alkyl, or —$C_0$-$C_6$alk-$C_3$-$C_6$cycloalkyl; and $R^{9a}$ is —$C_1$-$C_6$alkyl, or $C_0$-$C_6$alk-$C_3$-$C_6$cycloalkyl.

Aspect 41. The compound of aspect 40 wherein $R_1$ is —$C_0$-$C_6$alk-$C_1$-$C_6$alkyl.

Aspect 42. The compound of aspect 41 wherein the —$C_0$-$C_6$alk-$C_1$-$C_6$alkyl is —CH(OH)—$C_1$-$C_6$alkyl, —CH (F)—$C_1$-$C_6$alkyl, —CH($NH_2$)—$C_1$-$C_6$alkyl, —CH(Me)-$C_1$-$C_6$alkyl, or —C(Me)(OH)—$C_1$-$C_6$alkyl.

Aspect 43. The compound of aspect 40 wherein $R_1$ is —$C_0$-$C_6$alk-$C_1$-$C_6$haloalkyl.

Aspect 44. The compound of aspect 43 wherein the —$C_0$-$C_6$alk-$C_1$-$C_6$haloalkyl is —CH(OH)—$C_1$-$C_6$haloalkyl, —CH(F)—$C_1$-$C_6$haloalkyl, —CH($NH_2$)—$C_1$-$C_6$haloalkyl, —CH(Me)-$C_1$-$C_6$haloalkyl, or —C(Me)(OH)—$C_1$-$C_6$haloalkyl.

Aspect 45. The compound of aspect 40 wherein $R_1$ is —$C_0$-$C_6$alk-C≡CH.

Aspect 46. The compound of aspect 45 wherein the —$C_0$-$C_6$alk-C≡CH is —CH(OH)—C≡CH, —CH(F)—C≡CH, —CH($NH_2$)—C≡CH, —CH(Me)-C≡CH, or —C(Me)(OH)—C≡CH.

Aspect 47. The compound of aspect 40 wherein $R_1$ is —$C_1$-$C_6$alk-C≡C—$C_1$-$C_6$alkyl.

Aspect 48. The compound of aspect 47 wherein the —$C_0$-$C_6$alk-C≡C—$C_1$-$C_6$alkyl is —CH(OH)—C≡C—$C_1$-$C_6$alkyl, —CH(F)—C≡C—$C_1$-$C_6$alkyl, —CH($NH_2$)—C≡C—$C_1$-$C_6$alkyl, —CH(Me)-C≡C—$C_1$-$C_6$alkyl, or —C(Me)(OH)—C≡C—$C_1$-$C_6$alkyl.

Aspect 49. The compound of aspect 48, wherein the —$C_0$-$C_6$alk-C≡C—$C_1$-$C_6$alkyl is —CH(OH)—C≡C—$CH_3$, —CH(F)—C≡C—$CH_3$, —CH($NH_2$)—C≡C—$CH_3$, —CH(Me)-C≡C—$CH_3$, or —C(Me)(OH)—C≡C—$CH_3$.

Aspect 50. The compound of aspect 40 wherein $R_1$ is —$C_1$-$C_6$alk-C≡C—$C_1$-$C_6$haloalkyl.

Aspect 51. The compound of aspect 50 wherein the —$C_0$-$C_6$alk-C≡C—$C_1$-$C_6$haloalkyl is —CH(OH)—C≡C—$C_1$-$C_6$haloalkyl, —CH(F)—C≡C—$C_1$-$C_6$haloalkyl, —CH($NH_2$)—C≡C—$C_1$-$C_6$haloalkyl, —CH(Me)-C≡C—$C_1$-$C_6$haloalkyl, or —C(Me)(OH)—C≡C—$C_1$-$C_6$haloalkyl.

Aspect 52. The compound of aspect 51, wherein the —$C_0$-$C_6$alk-C≡C—$C_1$-$C_6$haloalkyl is —CH(OH)—C≡C—$CF_3$, —CH(F)—C≡C—$CF_3$, —CH($NH_2$)—C≡C—$CF_3$, —CH(Me)-C≡C—$CF_3$, or —C(Me)(OH)—C≡C—$CF_3$.

Aspect 53. The compound of aspect 40 wherein $R_1$ is —$C_1$-$C_6$alk-C≡C—$C_3$-$C_6$cycloalkyl.

Aspect 54. The compound of aspect 53 wherein the —$C_0$-$C_6$alk-C≡C—$C_3$-$C_6$cycloalkyl is —CH(OH)—C≡C—$C_3$-$C_6$cycloalkyl, —CH(F)—C≡C—$C_3$-$C_6$cycloalkyl, —CH($NH_2$)—C≡C—$C_3$-$C_6$cycloalkyl, —CH(Me)-C≡C—$C_3$-$C_6$cycloalkyl, or —C(Me)(OH)—C≡C—$C_3$-$C_6$cycloalkyl.

Aspect 55. The compound of aspect 54, wherein the —$C_0$-$C_6$alk-C≡C—$C_3$-$C_6$cycloalkyl is —CH(OH)—C≡C-cyclopropyl, —CH(F)—C≡C-cyclopropyl, —CH($NH_2$)—C≡C-cyclopropyl, —CH(Me)-C≡C-cyclopropyl, or —C(Me)(OH)—C≡C-cyclopropyl.

Aspect 56. The compound of aspect 40 wherein $R_1$ is —$C_1$-$C_6$alk-aryl.

Aspect 57. The compound of aspect 56 wherein the —$C_1$-$C_6$alk-aryl is —CH(OH)-aryl, —CH(F)-aryl, —CH($NH_2$)-aryl, —CH(Me)-aryl, or —C(Me)(OH)-aryl.

Aspect 58. The compound of aspect 57 wherein the —$C_1$-$C_6$alk-aryl is —CH(OH)-4-chlorophenyl, —CH(OH)-3,4-dichlorophenyl, —CH(OH)-3,4-difluorophenyl, —CH(OH)-3-fluoro-4-chlorophenyl, —CH(OH)-3-chloro-4-fluorophenyl, —CH(F)-4-chlorophenyl, —CH(F)-3,4-dichlorophenyl, —CH(F)-3,4-difluorophenyl, —CH(F)-3-fluoro-4-chlorophenyl, —CH(F)-3-chloro-4-fluorophenyl, —CH($NH_2$)-4-chlorophenyl, —CH($NH_2$)-3,4-dichlorophenyl, —CH($NH_2$)-3,4-difluorophenyl, —CH($NH_2$)-3-fluoro-4-chlorophenyl, —CH($NH_2$)-3-chloro-4-fluorophenyl, —CH(Me)-4-chlorophenyl, —CH(Me)-3,4-dichlorophenyl, —CH(Me)-3,4-difluorophenyl, —CH(Me)-3-fluoro-4-chlorophenyl, —CH(Me)-3-chloro-4-fluorophenyl, —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, or —C(Me)(OH)-3-chloro-4-fluorophenyl.

Aspect 59. The compound of any one of aspects 40 to 58 wherein $R^2$ is H.

Aspect 60. The compound of any one of aspects 40 to 58 wherein $R^2$ is $C_1$-$C_6$ alkyl.

Aspect 61. The compound of any one of aspects 40 to 60 wherein $R^3$ is H.

Aspect 62. The compound of any one of aspects 40 to 60 wherein $R^3$ is —$C_1$-$C_6$alkyl.

Aspect 63. The compound of any one of aspects 40 to 60 wherein $R^3$ is —C(O)$R^7$.

Aspect 64. The compound of aspect 63 wherein $R^7$ is $C_1$-$C_6$alkyl.

Aspect 65. The compound of any one of aspects 40 to 64 wherein $R^4$ is H.

Aspect 66. The compound of any one of aspects 40 to 65 wherein Q is NH.

Aspect 67. The compound of any one of aspects 40 to 65 wherein Q is O.

Aspect 68. The compound of any one of aspects 40 to 67 which is a compound of Formula I.

Aspect 69. The compound of aspect 68 wherein A is CH.

Aspect 70. The compound of aspect 68 wherein A is N.

Aspect 71. The compound of any one of aspects 68-70 wherein $R^5$ is H.

Aspect 72. The compound of any one of aspects 68-70 wherein $R^5$ is halo.

Aspect 73. The compound of any one of aspects 68-70 wherein $R^5$ is —$C_1$-$C_6$alkyl.

Aspect 74. The compound of any one of aspects 40 to 67 that is a compound of Formula II.

Aspect 75. A pharmaceutical composition comprising a compound according to any one of aspects 40-74 and a pharmaceutically acceptable excipient.

Aspect 76. A method of inhibiting a protein arginine methyltransferase 5 (PRMT5) enzyme, comprising: contacting the PRMT5 enzyme with an effective amount of a compound of any one of any one of aspects 40 to 74.

Aspect 77. A method of treating a disease or disorder associated with aberrant PRMT5 activity in a subject comprising administering to the subject, a compound of any one of aspects 40 to 74.

Aspect 78. The method of aspect 77, wherein the disease or disorder associated with aberrant PRMT5 activity is breast cancer, lung cancer, pancreatic cancer, prostate cancer, colon cancer, ovarian cancer, uterine cancer, cervical cancer, leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), myelodysplastic syndrome (MDS), epidermoid cancer, or hemoglobinopathies such as b-thalassemia and sickle cell disease (SCD).

Aspect 79. A compound of Formula I or Formula II:

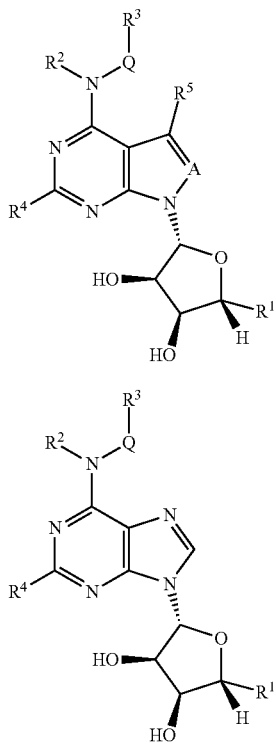

or a pharmaceutically acceptable salt or solvate thereof; wherein

A is CH or N;

Q is NH, $NR^6$ or O;

$R^1$ is —$C_0$-$C_6$alk-$C_3$-$C_6$cycloalkyl, —$C_0$-$C_6$alk-$C_3$-$C_6$halocycloalkyl; —$C_2$-$C_6$alkenyl, —$C_2$-$C_6$haloalkenyl, —$C_0$-$C_6$alk-$C_1$-$C_6$alkyl, —$C_0$-$C_6$alk-$C_1$-$C_6$haloalkyl, —$C_0$-$C_6$alk-C≡CH, —$C_0$-$C_6$alk-C≡C—$C_1$-$C_6$alkyl, —$C_0$-$C_6$alk-C≡C—$C_1$-$C_6$haloalkyl, —$C_0$-$C_6$alk-C≡C—$C_3$-$C_6$cycloalkyl, —$C_1$-$C_6$alk-aryl, —$C_1$-$C_6$alk-S—$C_1$-$C_6$alkyl, —$C_1$-$C_6$alk-S—$C_1$-$C_6$haloalkyl, —$C_1$-$C_6$alk-S—$C_3$-$C_6$cycloalkyl; —$C_1$-$C_6$alk-S—$C_3$-$C_6$halocycloalkyl; —$C_1$-$C_6$alk-O—$C_1$-$C_6$alkyl, —$C_1$-$C_6$alk-O—$C_3$-$C_6$cycloalkyl, —$C_1$-$C_6$alk-S—$CH_2$-aryl, —$C_1$-$C_6$alk-C(O)NH-aryl, —$C_0$-$C_6$alk-heteroaryl, —$C_1$-$C_6$alk-O-heteroaryl, —$C_1$-$C_6$alk-S-heteroaryl, or —$C_1$-$C_6$alk-NH-heteroaryl;

$R^2$ is H, —$C_1$-$C_6$alkyl, —$C_1$-$C_6$haloalkyl, or —$C_0$-$C_6$alk-$C_3$-$C_6$cycloalkyl;

$R^3$ is H, —$C_1$-$C_6$alkyl, —$C_1$-$C_6$haloalkyl, —$C_0$-$C_6$alk-$C_3$-$C_6$cycloalkyl, —C(O)$R^7$, —C(O)O$R^7$, or —C(O)$NR^{8a}R^{8b}$;

$R^4$ is H, halo, —$C_1$-$C_6$alkyl, or $NH_2$;

$R^5$ is H, halo, CN, —$C_1$-$C_6$alkyl, —$C_2$-$C_4$alkenyl, —$C_2$-$C_4$haloalkenyl, —$C_2$-$C_4$cyanoalkenyl, —$C_0$-$C_6$alk-C≡CH, —$C_0$-$C_6$alk-C≡C—$C_1$-$C_6$alkyl, —$C_1$-$C_4$haloalkyl, —$C_2$-$C_6$heterocycloalkyl, oxo-substituted-$C_2$-$C_6$heterocycloalkyl, —$C_3$-$C_6$cycloalkyl, —$C_0$-$C_3$alk-C(O)$R^9$, —$CR^8R^{8'}$CN, —$CH_2NR^8R^{8'}$, —$C_0$-$C_6$alk-OH, —$NR^8R^{8'}$, —N($R^9$)CN, —O—$C_1$-$C_4$alkyl, —$NR^9CONR^8R^{8'}$, —$OCONR^8R^{8'}$, or —$NR^9C(O)OR^{9a}$;

$R^6$ is —$C_1$-$C_6$alkyl or —$C_0$-$C_6$alk-$C_3$-$C_6$cycloalkyl;

$R^7$ is H, $C_1$-$C_6$alkyl, or $C_0$-$C_6$alk-$C_3$-$C_6$cycloalkyl;

$R^{8a}$ and $R^{8b}$ are each independently H, $C_1$-$C_6$alkyl, or —$C_0$-$C_6$alk-O$C_1$-$C_6$alkyl, or $R^{8a}$ and R, together with the atom to which they are attached, form a $C_2$-$C_6$heterocycloalkyl ring;

$R^8$ and $R^{8'}$ are each independently H, $C_1$-$C_6$alkyl, or —$C_0$-$C_6$alk-O$C_1$-$C_6$alkyl;

or $R^8$ and $R^{8'}$, together with the atom to which they are attached, form a $C_3$-$C_6$cycloalkyl ring or a $C_2$-$C_6$heterocycloalkyl ring;

$R^9$ is H, —$C_1$-$C_6$alkyl, or —$C_0$-$C_6$alk-$C_3$-$C_6$cycloalkyl; and $R^{9a}$ is —$C_1$-$C_6$alkyl, or $C_0$-$C_6$alk-$C_3$-$C_6$cycloalkyl.

Aspect 80. The compound of aspect 79 wherein $R^1$ is —$C_0$-$C_6$alk-$C_1$-$C_6$alkyl.

Aspect 81. The compound of aspect 80 wherein the —$C_0$-$C_6$alk-$C_1$-$C_6$alkyl is —CH(OH)—$C_1$-$C_6$alkyl, —CH(F)—$C_1$-$C_6$alkyl, —CH($NH_2$)—$C_1$-$C_6$alkyl, —CH(Me)-$C_1$-$C_6$alkyl, or —C(Me)(OH)—$C_1$-$C_6$alkyl.

Aspect 82. The compound of aspect 79 wherein $R^1$ is —$C_0$-$C_6$alk-$C_1$-$C_6$haloalkyl.

Aspect 83. The compound of aspect 82 wherein the —$C_0$-$C_6$alk-$C_1$-$C_6$haloalkyl is —CH(OH)—$C_1$-$C_6$haloalkyl, —CH(F)—$C_1$-$C_6$haloalkyl, —CH($NH_2$)—$C_1$-$C_6$haloalkyl, —CH(Me)-$C_1$-$C_6$haloalkyl, or —C(Me)(OH)—$C_1$-$C_6$haloalkyl.

Aspect 84. The compound of aspect 79 wherein $R^1$ is —$C_0$-$C_6$alk-C≡CH.

Aspect 85. The compound of aspect 84 wherein the —$C_0$-$C_6$alk-C≡CH is —CH(OH)—C≡CH, —CH(F)—C≡CH, —CH($NH_2$)—C≡CH, —CH(Me)-C≡CH, or —C(Me)(OH)—C≡CH.

Aspect 86. The compound of aspect 79 wherein $R^1$ is —$C_0$-$C_6$alk-C≡C—$C_1$-$C_6$alkyl.

Aspect 87. The compound of aspect 86 wherein the —$C_0$-$C_6$alk-C≡C—$C_1$-$C_6$alkyl is —CH(OH)—C≡C—$C_1$-$C_6$alkyl, —CH(F)—C≡C—$C_1$-$C_6$alkyl, —CH($NH_2$)—C≡C—$C_1$-$C_6$alkyl, —CH(Me)-C≡C—$C_1$-$C_6$alkyl, or —C(Me)(OH)—C≡C—$C_1$-$C_6$alkyl.

Aspect 88. The compound of aspect 87, wherein the —$C_0$-$C_6$alk-C≡C—$C_1$-$C_6$alkyl is —CH(OH)—C≡C—$CH_3$, —CH(F)—C≡C—$CH_3$, —CH($NH_2$)—C≡C—$CH_3$, —CH(Me)-C≡C—$CH_3$, or —C(Me)(OH)—C≡C—$CH_3$.

Aspect 89. The compound of aspect 79 wherein $R_1$ is —$C_1$-$C_6$alk-C≡C—$C_1$-$C_6$haloalkyl.

Aspect 90. The compound of aspect 89 wherein the —$C_0$-$C_6$alk-C≡C—$C_1$-$C_6$haloalkyl is —CH(OH)—C≡C—$C_1$-$C_6$haloalkyl, —CH(F)—C≡C—$C_1$-$C_6$haloalkyl, —CH($NH_2$)—C≡C—$C_1$-$C_6$haloalkyl, —CH(Me)-C≡C—$C_1$-$C_6$haloalkyl, or —C(Me)(OH)—C≡C—$C_1$-$C_6$haloalkyl.

Aspect 91. The compound of aspect 90, wherein the —$C_0$-$C_6$alk-C≡C—$C_1$-$C_6$haloalkyl is —CH(OH)—C≡C—$CF_3$, —CH(F)—C≡C—$CF_3$, —CH($NH_2$)—C≡C—$CF_3$, —CH(Me)-C≡C—$CF_3$, or —C(Me)(OH)—C≡C—$CF_3$.

Aspect 92. The compound of aspect 79 wherein $R_1$ is —$C_1$-$C_6$alk-C≡C—$C_3$-$C_6$cycloalkyl.

Aspect 93. The compound of aspect 92 wherein the —$C_0$-$C_6$alk-C≡C—$C_3$-$C_6$cycloalkyl is —CH(OH)—C≡C—$C_3$-$C_6$cycloalkyl, —CH(F)—C≡C—$C_3$-$C_6$cycloalkyl, —CH($NH_2$)—C≡C—$C_3$-$C_6$cycloalkyl, —CH(Me)-C≡C—$C_3$-$C_6$cycloalkyl, or —C(Me)(OH)—C≡C—$C_3$-$C_6$cycloalkyl.

Aspect 94. The compound of aspect 93, wherein the —$C_0$-$C_6$alk-C≡C—$C_3$-$C_6$cycloalkyl is —CH(OH)—C—C-cyclopropyl, —CH(F)—C≡C-cyclopropyl, —CH($NH_2$)—

C≡C-cyclopropyl, —CH(Me)-C≡C-cyclopropyl, or —C(Me)(OH)—C≡C-cyclopropyl.

Aspect 95. The compound of aspect 78 wherein R₁ is —C₁-C₆alk-aryl.

Aspect 96. The compound of aspect 95 wherein the —C₁-C₆alk-aryl is —CH(OH)-aryl, —C(OCH₃)-aryl, —CH(F)-aryl, —CH(NH₂)-aryl, —CH(Me)-aryl, or —C(Me)(OH)-aryl.

Aspect 97. The compound of aspect 96 wherein the —C₁-C₆alk-aryl is —CH(OH)-4-chlorophenyl, —CH(OH)-3,4-dichlorophenyl, —CH(OH)-3,4-difluorophenyl, —CH(OH)-3-fluoro-4-chlorophenyl, —CH(OH)-3-chloro-4-fluorophenyl, —CH(OH)-4-(trifluoromethyl)phenyl, —CH(OH)-3-fluoro-4-(trifluoromethyl)phenyl, —C(CF₃)(OH)-4-chlorophenyl, —CH(OH)-3-methyl-4-chlorophenyl, —CH(OH)-2,3-dihydrobenzofuran-5-yl, —CH(OH)-benzo[d][1,3]dioxol-5-yl, —CH(F)-4-chlorophenyl, —CH(F)-3,4-dichlorophenyl, —CH(F)-3,4-difluorophenyl, —CH(F)-3-fluoro-4-chlorophenyl, —CH(F)-3-chloro-4-fluorophenyl, —CH(F)-4-(trifluoromethyl)phenyl, —CH(F)-3-fluoro-4-(trifluoromethyl)phenyl, —C(CF₃)(F)-4-chlorophenylphenyl, —CH(F)-3-methyl-4-chlorophenyl, —CH(F)-2,3-dihydrobenzofuran-5-yl, —CH(F)-benzo[d][1,3]dioxol-5-yl, —CH(NH₂)-4-chlorophenyl, —CH(NH₂)-3,4-dichlorophenyl, —CH(NH₂)-3,4-difluorophenyl, —CH(NH₂)-3-fluoro-4-chlorophenyl, —CH(NH₂)-3-chloro-4-fluorophenyl, —CH(NH₂)-4-(trifluoromethyl)phenyl, —CH(NH₂)-3-fluoro-4-(trifluoromethyl)phenyl, —C(CF₃)(NH₂)-4-chlorophenylphenyl, CH(NH₂)-3-methyl-4-chlorophenyl, —CH(NH₂)-2,3-dihydrobenzofuran-5-yl, —CH(NH₂)-benzo[d][1,3]dioxol-5-yl, —CH(Me)-4-chlorophenyl, —CH(Me)-3,4-dichlorophenyl, —CH(Me)-3,4-difluorophenyl, —CH(Me)-3-fluoro-4-chlorophenyl, —CH(Me)-3-chloro-4-fluorophenyl, —CH(Me)-4-(trifluoromethyl)phenyl, —CH(Me)-3-fluoro-4-(trifluoromethyl)phenyl, —CH(Me)-3-methyl-4-chlorophenyl, —C(CF₃)(Me)-4-chlorophenylphenyl, —CH(Me)-2,3-dihydrobenzofuran-5-yl, —CH(Me)-benzo[d][1,3]dioxol-5-yl, —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, —C(Me)(OH)-4-(trifluoromethyl)phenyl, —C(Me)(OH)-3-fluoro-4-(trifluoromethyl)phenyl, —C(Me)(OH)-3-methyl-4-chlorophenyl, —C(Me)(OH)-2,3-dihydrobenzofuran-5-yl, or —C(Me)(OH)-benzo[d][1,3]dioxol-5-yl.

Aspect 98. The compound of aspect 79, wherein $R^1$ is —C₀-C₆alk-heteroaryl, —C₁-C₆alk-O-heteroaryl, —C₁-C₆alk-S-heteroaryl, or —C₁-C₆alk-NH-heteroaryl.

Aspect 99. The compound of aspect 98 wherein the —C₀-C₆alk-heteroaryl is 2-(2-amino-3-bromoquinolin-7-yl)ethyl or 2-(2-amino-3-chloroquinolin-7-yl)ethyl.

Aspect 100. The compound of any one of aspects 79 to 99 wherein $R^2$ is H.

Aspect 101. The compound of any one of aspects 79 to 60 wherein $R^2$ is C₁-C₆ alkyl.

Aspect 102. The compound of any one of aspects 79 to 100 wherein $R^3$ is H.

Aspect 103. The compound of any one of aspects 79 to 100 wherein $R^3$ is —C₁-C₆alkyl.

Aspect 104. The compound of any one of aspects 79 to 100 wherein $R^3$ is —C(O)R⁷.

Aspect 105. The compound of aspect 104 wherein $R^7$ is C₁-C₆alkyl.

Aspect 106. The compound of any one of aspects 78 to 105 wherein $R^4$ is H.

Aspect 107. The compound of any one of aspects 78 to 106 wherein Q is NH.

Aspect 108. The compound of any one of aspects 78 to 106 wherein Q is O.

Aspect 109. The compound of any one of aspects 78 to 108 which is a compound of Formula I.

Aspect 110. The compound of aspect 109 wherein A is CH.

Aspect 111. The compound of aspect 109 wherein A is N.

Aspect 112. The compound of any one of aspects 109-111 wherein $R^5$ is H.

Aspect 113. The compound of any one of aspects 109-111 wherein $R^5$ is halo.

Aspect 114. The compound of any one of aspects 109-111 wherein $R^5$ is —C₁-C₆alkyl.

Aspect 115. The compound of any one of aspects 79 to 108 that is a compound of Formula II.

Aspect 116. A pharmaceutical composition comprising a compound according to any one of aspects 79-115 and a pharmaceutically acceptable excipient.

Aspect 117. A method of inhibiting a protein arginine methyltransferase 5 (PRMT5) enzyme, comprising: contacting the PRMT5 enzyme with an effective amount of a compound of any one of any one of aspects 79 to 115.

Aspect 118. A method of treating a disease or disorder associated with aberrant PRMT5 activity in a subject comprising administering to the subject, a compound of any one of aspects 79 to 115.

Aspect 119. The method of aspect 118, wherein the disease or disorder associated with aberrant PRMT5 activity is breast cancer, lung cancer, pancreatic cancer, prostate cancer, colon cancer, ovarian cancer, uterine cancer, cervical cancer, leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), myelodysplastic syndrome (MDS), epidermoid cancer, or hemoglobinopathies such as b-thalassemia and sickle cell disease (SCD).

Aspect 120. A compound of Formula III or Formula IV:

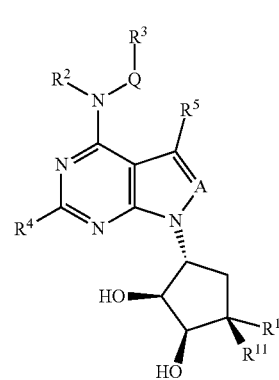

III

-continued

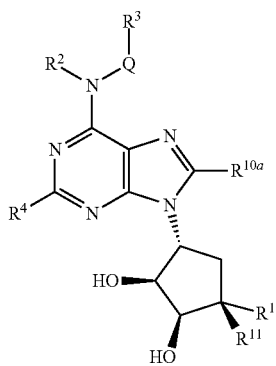

IV or a pharmaceutically acceptable salt or solvate thereof; wherein

A is CH, $CR^{10}$, or N;

Q is NH, $NR^6$, or O;

$R^1$ is —$C_0$-$C_6$alk-$C_3$-$C_6$cycloalkyl, —$C_0$-$C_6$alk-$C_3$-$C_6$halocycloalkyl, —$C_2$-$C_6$alkenyl, —$C_2$-$C_6$haloalkenyl, —$C_0$-$C_6$alk-$C_1$-$C_6$alkyl, —$C_0$-$C_6$alk-$C_1$-$C_6$haloalkyl, —$C_0$-$C_6$alk-C≡CH, —$C_0$-$C_6$alk-C≡C—$C_1$-$C_6$alkyl, —$C_0$-$C_6$alk-C≡C—$C_1$-$C_6$haloalkyl, —$C_0$-$C_6$alk-C≡C—$C_3$-$C_6$cycloalkyl, —$C_1$-$C_6$alk-aryl, —$C_1$-$C_6$alk-S—$C_1$-$C_6$alkyl, —$C_1$-$C_6$alk-S—$C_1$-$C_6$haloalkyl, —$C_1$-$C_6$alk-S—$C_3$-$C_6$cycloalkyl; —$C_1$-$C_6$alk-S—$C_3$-$C_6$halocycloalkyl; —$C_1$-$C_6$alk-O—$C_1$-$C_6$alkyl, —$C_1$-$C_6$alk-O—$C_3$-$C_6$cycloalkyl, —$C_1$-$C_6$alk-S—$CH_2$-aryl, —$C_1$-$C_6$alk-C(O)NH-aryl, —$C_0$-$C_6$alk-S-aryl, —$C_0$-$C_6$alk-S(O)aryl, —$C_0$-$C_6$alk-S(O)$_2$aryl, —$C_0$-$C_6$alk-Oaryl;

$R^2$ is H, —$C_1$-$C_6$alkyl, —$C_1$-$C_6$haloalkyl, or —$C_0$-$C_6$alk-$C_3$-$C_6$cycloalkyl;

$R^3$ is H, —$C_1$-$C_6$alkyl, —$C_1$-$C_6$haloalkyl, —$C_0$-$C_6$alk-$C_3$-$C_6$cycloalkyl, —C(O)$R^7$, —C(O)O$R^7$, or —C(O)NR$^{8a}$R$^{8b}$;

$R^4$ is H, halo, —$C_1$-$C_6$alkyl, or $NH_2$;

$R^5$ is H, halo, CN, —$C_1$-$C_6$alkyl, —$C_2$-$C_4$alkenyl, —$C_2$-$C_4$haloalkenyl, —$C_2$-$C_4$cyanoalkenyl, —$C_0$-$C_6$alk-C≡CH, —$C_0$-$C_6$alk-C≡C—$C_1$-$C_6$alkyl, —$C_1$-$C_4$haloalkyl, —$C_2$-$C_6$heterocycloalkyl, oxo-substituted-$C_2$-$C_6$heterocycloalkyl, —$C_3$-$C_6$cycloalkyl, —$C_0$-$C_3$alk-C(O)$R^9$, —CR$^8$R$^{8'}$CN, —$CH_2$NR$^8$R$^{8'}$, —$C_0$-$C_6$alk-OH, —NR$^8$R$^{8'}$, —N($R^9$)CN, —O—$C_1$-$C_4$alkyl, —NR$^9$CONR$^8$R$^{8'}$, —OCONR$^8$R$^{8'}$, or —NR$^9$C(O)OR$^{9a}$;

$R^6$ is $C_1$-$C_6$alkyl, or $C_0$-$C_6$alk-$C_3$-$C_6$cycloalkyl $R^7$ is H, $C_1$-$C_6$alkyl, or $C_0$-$C_6$alk-$C_3$-$C_6$cycloalkyl;

$R^{8a}$ and $R^{8b}$ are each independently H, $C_1$-$C_6$alkyl, or —$C_0$-$C_6$alk-O$C_1$-$C_6$alkyl, or $R^{8a}$ and R, together with the atom to which they are attached, form a $C_2$-$C_6$heterocycloalkyl ring;

$R^8$ and $R^{8'}$ are each independently H, $C_1$-$C_6$alkyl, or —$C_0$-$C_6$alk-O$C_1$-$C_6$alkyl;

or $R^8$ and $R^{8'}$, together with the atom to which they are attached, form a $C_3$-$C_6$cycloalkyl ring or a $C_2$-$C_6$heterocycloalky ring;

$R^9$ is H, —$C_1$-$C_6$alkyl, or $C_0$-$C_6$alk-$C_3$-$C_6$cycloalkyl;

$R^{9a}$ is —$C_1$-$C_6$alkyl, or $C_0$-$C_6$alk-$C_3$-$C_6$cycloalkyl;

$R^{10}$ is halo or —$C_1$-$C_6$alkyl;

$R^{10a}$ is H, halo, or —$C_1$-$C_6$alkyl; and $R^{11}$ is H, —$C_1$-$C_6$alkyl, —$C_1$-$C_6$haloalkyl, —$C_0$-$C_6$alk-$C_3$-$C_6$cycloalkyl, —$C_0$-$C_6$alk-$C_3$-$C_6$halocycloalkyl, —$C_0$-$C_6$alk-OH, —$C_0$-$C_6$alk-$NH_2$, —$C_0$-$C_6$alk-NH—$C_1$-$C_6$alkyl, —$C_0$-$C_6$alk-N($C_1$-$C_6$alkyl)-$C_1$-$C_6$alkyl, —$C_0$-$C_6$alk-NH—$C_3$-$C_6$cycloalkyl, or —$C_0$-$C_6$alk-N($C_1$-$C_6$alkyl)-$C_3$-$C_6$cycloalkyl;

or $R^{11}$ and $R^1$, together with the atom to which they are attached, form a $C_3$-$C_6$cycloalkyl ring or a heterocycloalkyl ring.

Aspect 121. The compound of aspect 120 wherein $R_1$ is —$C_0$-$C_6$alk-$C_1$-$C_6$alkyl.

Aspect 122. The compound of aspect 121 wherein the —$C_0$-$C_6$alk-$C_1$-$C_6$alkyl is —CH(OH)—$C_1$-$C_6$alkyl, —CH(F)—$C_1$-$C_6$alkyl, —CH($NH_2$)—$C_1$-$C_6$alkyl, —CH(Me)-$C_1$-$C_6$alkyl, or —C(Me)(OH)—$C_1$-$C_6$alkyl.

Aspect 123. The compound of aspect 120 wherein $R_1$ is —$C_0$-$C_6$alk-$C_1$-$C_6$haloalkyl.

Aspect 124. The compound of aspect 123 wherein the —$C_0$-$C_6$alk-$C_1$-$C_6$haloalkyl is —CH(OH)—$C_1$-$C_6$haloalkyl, —CH(F)—$C_1$-$C_6$haloalkyl, —CH($NH_2$)—$C_1$-$C_6$haloalkyl, —CH(Me)-$C_1$-$C_6$haloalkyl, or —C(Me)(OH)—$C_1$-$C_6$haloalkyl.

Aspect 125. The compound of aspect 120 wherein $R_1$ is —$C_0$-$C_6$alk-C≡CH.

Aspect 126. The compound of aspect 125 wherein the —$C_0$-$C_6$alk-C≡CH is —CH(OH)—C≡CH, —CH(F)—C≡CH, —CH($NH_2$)—C≡CH, —CH(Me)-C≡CH, or —C(Me)(OH)—C≡CH.

Aspect 127. The compound of aspect 120 wherein $R_1$ is —$C_1$-$C_6$alk-C≡C—$C_1$-$C_6$alkyl.

Aspect 128. The compound of aspect 127 wherein the —$C_0$-$C_6$alk-C≡C—$C_1$-$C_6$alkyl is —CH(OH)—C≡C—$C_1$-$C_6$alkyl, —CH(F)—C≡C—$C_1$-$C_6$alkyl, —CH($NH_2$)—C≡C—$C_1$-$C_6$alkyl, —CH(Me)-C≡C—$C_1$-$C_6$alkyl, or —C(Me)(OH)—C≡C—$C_1$-$C_6$alkyl.

Aspect 129. The compound of aspect 128 wherein the —$C_0$-$C_6$alk-C≡C—$C_1$-$C_6$alkyl is —CH(OH)—C≡C—$CH_3$, —CH(F)—C≡C—$CH_3$, —CH($NH_2$)—C≡C—$CH_3$, —CH(Me)-C≡C—$CH_3$, or —C(Me)(OH)—C≡C—$CH_3$.

Aspect 130. The compound of aspect 120 wherein $R_1$ is —$C_0$-$C_6$alk-C≡C—$C_1$-$C_6$haloalkyl.

Aspect 131. The compound of aspect 130 wherein the —$C_0$-$C_6$alk-C≡C—$C_1$-$C_6$haloalkyl is —CH(OH)—C≡C—$C_1$-$C_6$haloalkyl, —CH(F)—C≡C—$C_1$-$C_6$haloalkyl, —CH($NH_2$)—C≡C—$C_1$-$C_6$haloalkyl, —CH(Me)-C≡C—$C_1$-$C_6$haloalkyl, or —C(Me)(OH)—C≡C—$C_1$-$C_6$haloalkyl.

Aspect 132. The compound of aspect 131 wherein the —$C_0$-$C_6$alk-C≡C—$C_1$-$C_6$haloalkyl is —CH(OH)—C≡C—$CF_3$, —CH(F)—C≡C—$CF_3$, —CH($NH_2$)—C≡C—$CF_3$, —CH(Me)-C≡C—$CF_3$, or —C(Me)(OH)—C≡C—$CF_3$.

Aspect 133. The compound of aspect 120 wherein $R_1$ is —$C_1$-$C_6$alk-C≡C—$C_3$-$C_6$cycloalkyl.

Aspect 134. The compound of aspect 133 wherein the —$C_0$-$C_6$alk-C≡C—$C_3$-$C_6$cycloalkyl is —CH(OH)—C≡C—$C_3$-$C_6$cycloalkyl, —CH(F)—C≡C—$C_3$-$C_6$cycloalkyl, —CH($NH_2$)—C≡C—$C_3$-$C_6$cycloalkyl, —CH(Me)-C≡C—$C_3$-$C_6$cycloalkyl, or —C(Me)(OH)—C≡C—$C_3$-$C_6$cycloalkyl.

Aspect 135. The compound of aspect 134 wherein the —$C_0$-$C_6$alk-C≡C—$C_3$-$C_6$cycloalkyl is —CH(OH)—C≡C-cyclopropyl, —CH(F)—C≡C-cyclopropyl, —CH($NH_2$)—C≡C-cyclopropyl, —CH(Me)-C≡C-cyclopropyl, or —C(Me)(OH)—C≡C-cyclopropyl.

Aspect 136. The compound of aspect 120 wherein $R_1$ is —$C_1$-$C_6$alk-aryl.

Aspect 137. The compound of aspect 136 wherein the —$C_1$-$C_6$alk-aryl is —$CH_2$-aryl, —CH(OH)-aryl, —CH(F)-aryl, —CH($NH_2$)-aryl, —CH(Me)-aryl, or —C(Me)(OH)-aryl.

Aspect 138. The compound of aspect 137 wherein the —$C_1$-$C_6$alk-aryl is —$CH_2$-4-chlorophenyl, —$CH_2$-3,4-dichlorophenyl, —$CH_2$-3,4-difluorophenyl, —$CH_2$-3-fluoro-4-chlorophenyl, —$CH_2$-3-chloro-4-fluorophenyl, —CH(OH)-4-chlorophenyl, —CH(OH)-3,4-dichlorophenyl, —CH(OH)-3,4-difluorophenyl, —CH(OH)-3-fluoro-4-chlorophenyl, —CH(OH)-3-chloro-4-fluorophenyl, —CH(F)-4-chlorophenyl, —CH(F)-3,4-dichlorophenyl, —CH(F)-3,4-difluorophenyl, —CH(F)-3-fluoro-4-chlorophenyl, —CH(F)-3-chloro-4-fluorophenyl, —CH($NH_2$)-4-chlorophenyl, —CH($NH_2$)-3,4-dichlorophenyl, —CH($NH_2$)-3,4-difluorophenyl, —CH($NH_2$)-3-fluoro-4-chlorophenyl, —CH($NH_2$)-3-chloro-4-fluorophenyl, —CH(Me)-4-chlorophenyl, —CH(Me)-3,4-dichlorophenyl, —CH(Me)-3,4-difluorophenyl, —CH(Me)-3-fluoro-4-chlorophenyl, —CH(Me)-3-chloro-4-fluorophenyl, —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, or —C(Me)(OH)-3-chloro-4-fluorophenyl.

Aspect 139. The compound of aspect 120 wherein $R_1$ is —$C_0$-$C_6$alk-S-aryl.

Aspect 140. The compound of aspect 139 wherein the —$C_0$-$C_6$alk-S-aryl is —S-4-chlorophenyl, —S-3,4-dichlorophenyl, —S-3,4-difluorophenyl, —S-3-fluoro-4-chlorophenyl, or —S-3-chloro-4-fluorophenyl.

Aspect 141. The compound of aspect 120 wherein $R_1$ is —$C_0$-$C_6$alk-S(O)-aryl.

Aspect 142. The compound of aspect 141 wherein the —$C_0$-$C_6$alk-S(O)-aryl is —S(O)-4-chlorophenyl, —S(O)-3,4-dichlorophenyl, —S(O)-3,4-difluorophenyl, —S(O)-3-fluoro-4-chlorophenyl, or —S(O)-3-chloro-4-fluorophenyl.

Aspect 143. The compound of aspect 120 wherein $R_1$ is —$C_0$-$C_6$alk-$S(O)_2$-aryl.

Aspect 144. The compound of aspect 143 wherein the —$C_0$-$C_6$alk-$S(O)_2$-aryl is —$S(O)_2$-4-chlorophenyl, —$S(O)_2$-3,4-dichlorophenyl, —$S(O)_2$-3,4-difluorophenyl, —$S(O)_2$-3-fluoro-4-chlorophenyl, or —$S(O)_2$-3-chloro-4-fluorophenyl.

Aspect 145. The compound of aspect 120 wherein $R_1$ is —$C_0$-$C_6$alk-O-aryl.

Aspect 146. The compound of aspect 145 wherein the —$C_0$-$C_6$alk-O-aryl is —O-4-chlorophenyl, —O-3,4-dichlorophenyl, —O-3,4-difluorophenyl, —O-3-fluoro-4-chlorophenyl, or —O-3-chloro-4-fluorophenyl.

Aspect 147. The compound of any one of aspects 120 to 146 wherein $R^2$ is H.

Aspect 148. The compound of any one of aspects 120 to 146 wherein $R^2$ is $C_1$-$C_6$ alkyl.

Aspect 149. The compound of any one of aspects 120 to 148 wherein $R^3$ is H.

Aspect 150. The compound of any one of aspects 120 to 148 wherein $R^3$ is —$C_1$-$C_6$alkyl.

Aspect 151. The compound of any one of aspects 120 to 148 wherein $R^3$ is —C(O)$R^7$.

Aspect 152. The compound of aspect 151 wherein the $R^7$ is —$C_1$-$C_6$alkyl.

Aspect 153. The compound of any one of aspects 120 to 152 wherein $R^4$ is H.

Aspect 154. The compound of any one of aspects 120 to 153 wherein Q is NH.

Aspect 155. The compound of any one of aspects 120 to 153 wherein Q is O.

Aspect 156. The compound of any one of aspects 120 to 155 wherein $R^{11}$ is H.

Aspect 157. The compound of any one of aspects 120 to 156 which is a compound of Formula III.

Aspect 158. The compound of aspect 157 wherein A is CH.

Aspect 159. The compound of aspect 157 wherein A is N.

Aspect 160. The compound of aspect 157 wherein A is $CR^{10}$.

Aspect 161. The compound of aspect 160 wherein the $R^{10}$ is —$C_1$-$C_6$alkyl.

Aspect 162. The compound of any one of aspects 157 to 161 wherein $R^5$ is H.

Aspect 163. The compound of any one of aspects 157 to 161 wherein $R^5$ is halo.

Aspect 164. The compound of any one of aspects 157 to 161 wherein $R^5$ is —$C_1$-$C_6$alkyl.

Aspect 165. The compound of any one of aspects 120 to 156 which is a compound of Formula IV.

Aspect 166. The compound of aspect 165 where $R^{10a}$ is H.

Aspect 167. The compound of aspect 165 where $R^{10a}$ is —$C_1$-$C_6$alkyl.

Aspect 168. A pharmaceutical composition comprising a compound according to any one of aspects 120 to 167 and a pharmaceutically acceptable excipient.

Aspect 169. A method of inhibiting a protein arginine methyltransferase 5 (PRMT5) enzyme, comprising: contacting the PRMT5 enzyme with an effective amount of a compound of any one of any one of aspects 120 to 167.

Aspect 170. A method of treating a disease or disorder associated with aberrant PRMT5 activity in a subject comprising administering to the subject, a compound of any one of aspects 120 to 167.

Aspect 171. The method of aspect 170, wherein the disease or disorder associated with aberrant PRMT5 activity is breast cancer, lung cancer, pancreatic cancer, prostate cancer, colon cancer, ovarian cancer, uterine cancer, cervical cancer, leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), myelodysplastic syndrome (MDS), epidermoid cancer, or hemoglobinopathies such as b-thalassemia and sickle cell disease (SCD).

Aspect 172. A compound of Formula V or Formula VI:

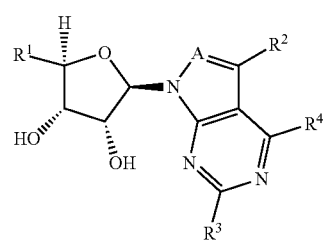

I

-continued

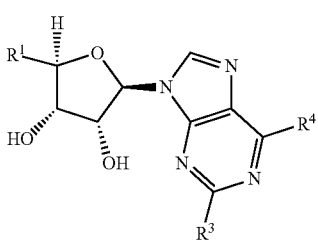

or a pharmaceutically acceptable salt or solvate thereof; wherein

A is CH or N;

$R^1$ is —$C_1$-$C_6$alk-aryl, —$C_1$-$C_6$alk-heteroaryl, —$C_1$-$C_6$alk-C≡CH, —$C_1$-$C_6$alk-C≡C—$C_1$-$C_6$alkyl, —$C_1$-$C_6$alk-C≡C—$C_1$-$C_6$haloalkyl, or —$C_1$-$C_6$alk-C≡C—$C_3$-$C_6$cycloalkyl;

$R^2$ is H, or halo;

$R^3$ is H, halo, $NH_2$, or $C_1$-$C_6$alkyl; and $R^4$ is $NH_2$ or $CH_3$.

Aspect 173. The compound of aspect 172, wherein $R^1$ is —CH(OH)-aryl, —CH(Me)-aryl, —C(Me)(OH)-aryl, —CH(CH$_2$OH)-aryl, —C(Me)(OH)-heteroaryl, or —CH(OH)—C≡C—$C_3$-$C_6$cycloalkyl.

Aspect 174. The compound of aspect 172, wherein $R^1$ is —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, —CH(Me)(OH)-3-methyl-4-chlorophenyl, —CH(Me)(OH)-3-fluoro-4-trifluoromethylphenyl, —CH(Me)(OH)-4-trifluoromethylphenyl, —CH(Me)(OH)-3-methyl-4-trifluoromethylphenyl, —CH(Me)(OH)-3-chloro-4-fluorophenyl, —CH(Me)-4-chlorophenyl, —CH(CH$_2$OH)-4-chlorophenyl, —C(Me)(OH)-5-chlorothiophen-2-yl, —CH(OH)—C≡C-cyclopropyl.

Aspect 175. The compound of any one of aspects 172 to 174, wherein $R^3$ is H.

Aspect 176. The compound of any one of aspects 172 to 175, wherein the compound is a compound of Formula V.

Aspect 177. The compound of aspect 176, wherein $R^2$ is H.

Aspect 178. The compound of aspect 176, wherein $R^2$ is halo.

Aspect 179. The compound of aspect 178, wherein halo is fluoro.

Aspect 180. The compound of any one of aspects 172 to 175, wherein the compound is a compound of Formula VI.

Aspect 181. The compound of any one of aspects 172 to 180, wherein $R^4$ is $NH_2$.

Aspect 182. The compound of any one of aspects 172 to 180, wherein $R^4$ is $CH_3$.

Aspect 183. A pharmaceutical composition comprising a compound according to any one of aspects 172 to 182 and a pharmaceutically acceptable excipient.

Aspect 184. A method of inhibiting a protein arginine methyltransferase 5 (PRMT5) enzyme, comprising: contacting the PRMT5 enzyme with an effective amount of a compound of any one of any one of aspects 172 to 182.

Aspect 185. A method of treating a disease or disorder associated with aberrant PRMT5 activity in a subject comprising administering to the subject, a compound of any one of aspects 172 to 182.

Aspect 186. The method of aspect 185, wherein the disease or disorder associated with aberrant PRMT5 activity is breast cancer, lung cancer, pancreatic cancer, prostate cancer, colon cancer, ovarian cancer, uterine cancer, cervical cancer, leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), myelodysplastic syndrome (MDS), epidermoid cancer, or hemoglobinopathies such as b-thalassemia and sickle cell disease (SCD).

Aspect 187. A compound of Formula I or Formula II:

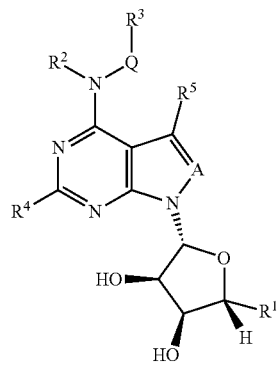

I

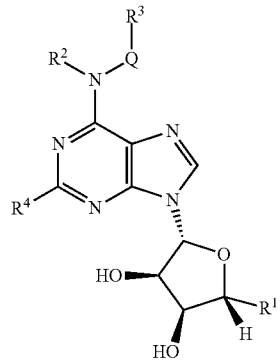

II or a pharmaceutically acceptable salt or solvate thereof; wherein

A is CH or N;

Q is NH, $NR^6$ or O;

$R^1$ is —$C_0$-$C_6$alk-$C_3$-$C_6$cycloalkyl, —$C_0$-$C_6$alk-$C_3$-$C_6$halocycloalkyl; —$C_2$-$C_6$alkenyl, —$C_2$-$C_6$haloalkenyl, —$C_0$-$C_6$alk-$C_1$-$C_6$alkyl, —$C_0$-$C_6$alk-$C_1$-$C_6$haloalkyl, —$C_0$-$C_6$alk-C≡CH, —$C_0$-$C_6$alk-C≡C—$C_1$-$C_6$alkyl, —$C_0$-$C_6$alk-C≡C—$C_1$-$C_6$haloalkyl, —$C_0$-$C_6$alk-C≡C—$C_3$-$C_6$cycloalkyl, —$C_1$-$C_6$alk-aryl, —$C_1$-$C_6$alk-S—$C_1$-$C_6$alkyl, —$C_1$-$C_6$alk-S—$C_1$-$C_6$haloalkyl, —$C_1$-$C_6$alk-S—$C_3$-$C_6$cycloalkyl; —$C_1$-$C_6$alk-S—$C_3$-$C_6$halocycloalkyl; —$C_1$-$C_6$alk-O—$C_1$-$C_6$alkyl, —$C_1$-$C_6$alk-O—$C_3$-$C_6$cycloalkyl, —$C_1$-$C_6$alk-S—$CH_2$-aryl, —$C_1$-$C_6$alk-C(O)NH-aryl, —$C_0$-$C_6$alk-heteroaryl, —$C_1$-$C_6$alk-O-heteroaryl, —$C_1$-$C_6$alk-S-heteroaryl, or —$C_1$-$C_6$alk-NH-heteroaryl;

$R^2$ is H, —$C_1$-$C_6$alkyl, —$C_1$-$C_6$haloalkyl, or —$C_0$-$C_6$alk-$C_3$-$C_6$cycloalkyl;

$R^3$ is H, —$C_1$-$C_6$alkyl, —$C_1$-$C_6$haloalkyl, —$C_0$-$C_6$alk-$C_3$-$C_6$cycloalkyl, —C(O)$R^7$, —C(O)O$R^7$, or —C(O)$NR^{8a}R^{8b}$;

$R^4$ is H, halo, —$C_1$-$C_6$alkyl, or —$NH_2$;

$R^5$ is H, halo, CN, —$C_1$-$C_6$alkyl, —$C_2$-$C_4$alkenyl, —$C_2$-$C_4$haloalkenyl, $C_2$-$C_4$cyanoalkenyl, —$C_0$-$C_6$alk-C≡CH, —$C_0$-$C_6$alk-C≡C—$C_1$-$C_6$alkyl, —$C_1$-$C_4$haloalkyl, —$C_2$-$C_6$heterocycloalkyl, oxo-substituted-$C_2$-$C_6$heterocycloalkyl, —$C_3$-$C_6$cycloalkyl, —$C_0$-$C_3$alk-C(O)$R^9$, —$CR^8R^{8'}$CN, —$CH_2NR^8R^{8'}$, —$C_0$-$C_6$alk-OH, —$NR^8R^{8'}$, —N($R^9$)CN, —O—$C_1$-$C_4$alkyl, —$NR^9CONR^8R^{8'}$, —$OCONR^8R^{8'}$, or —$NR^9C(O)OR^{9a}$;

$R^6$ is —$C_1$-$C_6$alkyl or —$C_0$-$C_6$alk-$C_3$-$C_6$cycloalkyl;

$R^7$ is H, $C_1$-$C_6$alkyl, or $C_0$-$C_6$alk-$C_3$-$C_6$cycloalkyl;

$R^{8a}$ and $R^{8b}$ are each independently H, $C_1$-$C_6$alkyl, or —$C_0$-$C_6$alk-O$C_1$-$C_6$alkyl, or $R^{8a}$ and R, together with the atom to which they are attached, form a $C_2$-$C_6$heterocycloalkyl ring;

$R^8$ and $R^{8'}$ are each independently H, $C_1$-$C_6$alkyl, or —$C_0$-$C_6$alk-O$C_1$-$C_6$alkyl;

or $R^8$ and $R^{8'}$, together with the atom to which they are attached, form a $C_3$-$C_6$cycloalkyl ring or a $C_2$-$C_6$heterocycloalkyl ring;

$R^9$ is H, —$C_1$-$C_6$alkyl, or —$C_0$-$C_6$alk-$C_3$-$C_6$cycloalkyl; and $R^{9a}$ is —$C_1$-$C_6$alkyl, or $C_0$-$C_6$alk-$C_3$-$C_6$cycloalkyl.

Aspect 188. The compound of aspect 187 wherein $R^1$ is —$C_0$-$C_6$alk-$C_1$-$C_6$alkyl.

Aspect 189. The compound of aspect 188 wherein the —$C_0$-$C_6$alk-$C_1$-$C_6$alkyl is —CH(OH)—$C_1$-$C_6$alkyl, —CH(F)—$C_1$-$C_6$alkyl, —CH(NH$_2$)—$C_1$-$C_6$alkyl, —CH(Me)-$C_1$-$C_6$alkyl, or —C(Me)(OH)—$C_1$-$C_6$alkyl.

Aspect 190. The compound of aspect 187 wherein $R^1$ is —$C_0$-$C_6$alk-$C_1$-$C_6$haloalkyl.

Aspect 191. The compound of aspect 190 wherein the —$C_0$-$C_6$alk-$C_1$-$C_6$haloalkyl is —CH(OH)—$C_1$-$C_6$haloalkyl, —CH(F)—$C_1$-$C_6$haloalkyl, —CH(NH$_2$)—$C_1$-$C_6$haloalkyl, —CH(Me)-$C_1$-$C_6$haloalkyl, or —C(Me)(OH)—$C_1$-$C_6$haloalkyl.

Aspect 192. The compound of aspect 187 wherein $R^1$ is —$C_0$-$C_6$alk-C≡CH.

Aspect 193. The compound of aspect 192 wherein the —$C_0$-$C_6$alk-C≡CH is —CH(OH)—C≡CH, —CH(F)—C≡CH, —CH(NH$_2$)—C≡CH, —CH(Me)-C≡CH, or —C(Me)(OH)—C≡CH.

Aspect 194. The compound of aspect 187 wherein $R^1$ is —$C_0$-$C_6$alk-C≡C—$C_1$-$C_6$alkyl.

Aspect 195. The compound of aspect 194 wherein the —$C_0$-$C_6$alk-C≡C—$C_1$-$C_6$alkyl is —CH(OH)—C≡C—$C_1$-$C_6$alkyl, —CH(F)—C≡C—$C_1$-$C_6$alkyl, —CH(NH$_2$)—C≡C—$C_1$-$C_6$alkyl, —CH(Me)-C≡C—$C_1$-$C_6$alkyl, or —C(Me)(OH)—C≡C—$C_1$-$C_6$alkyl.

Aspect 196. The compound of aspect 195, wherein the —$C_0$-$C_6$alk-C≡C—$C_1$-$C_6$alkyl is —CH(OH)—C≡C—CH$_3$, —CH(F)—C≡C—CH$_3$, —CH(NH$_2$)—C≡C—CH$_3$, —CH(Me)-C≡C—CH$_3$, or —C(Me)(OH)—C≡C—CH$_3$.

Aspect 197. The compound of aspect 187 wherein R$_1$ is —$C_0$-$C_6$alk-C≡C—$C_1$-$C_6$haloalkyl.

Aspect 198. The compound of aspect 197 wherein the —$C_0$-$C_6$alk-C≡C—$C_1$-$C_6$haloalkyl is —CH(OH)—C≡C—$C_1$-$C_6$haloalkyl, —CH(F)—C≡C—$C_1$-$C_6$haloalkyl, —CH(NH$_2$)—C≡C—$C_1$-$C_6$haloalkyl, —CH(Me)-C≡C—$C_1$-$C_6$haloalkyl, or —C(Me)(OH)—C≡C—$C_1$-$C_6$haloalkyl.

Aspect 199. The compound of aspect 198, wherein the —$C_1$-$C_6$alk-C≡C—$C_1$-$C_6$haloalkyl is —CH(OH)—C≡C—CF$_3$, —CH(F)—C≡C—CF$_3$, —CH(NH$_2$)—C≡C—CF$_3$, —CH(Me)-C≡C—CF$_3$, or —C(Me)(OH)—C≡C—CF$_3$.

Aspect 200. The compound of aspect 187 wherein R$_1$ is —$C_0$-$C_6$alk-C≡C—$C_3$-$C_6$cycloalkyl.

Aspect 201. The compound of aspect 200 wherein the —$C_1$-$C_6$alk-C≡C—$C_3$-$C_6$cycloalkyl is —CH(OH)—C≡C—$C_3$-$C_6$cycloalkyl, —CH(F)—C≡C—$C_3$-$C_6$cycloalkyl, —CH(NH$_2$)—C≡C—$C_3$-$C_6$cycloalkyl, —CH(Me)-C≡C—$C_3$-$C_6$cycloalkyl, or —C(Me)(OH)—C≡C—$C_3$-$C_6$cycloalkyl.

Aspect 202. The compound of aspect 201, wherein the —$C_1$-$C_6$alk-C≡C—$C_3$-$C_6$cycloalkyl is —CH(OH)—C≡C-cyclopropyl, —CH(F)—C≡C-cyclopropyl, —CH(NH$_2$)—C≡C-cyclopropyl, —CH(Me)-C C-cyclopropyl, or —C(Me)(OH)—C≡C-cyclopropyl.

Aspect 203. The compound of aspect 187 wherein R$_1$ is —$C_1$-$C_6$alk-aryl.

Aspect 204. The compound of aspect 203 wherein the —$C_1$-$C_6$alk-aryl is —CH(OH)-aryl, —C(OCH$_3$)-aryl, —CH(F)-aryl, —CH(NH$_2$)-aryl, —CH(Me)-aryl, or —C(Me)(OH)-aryl.

Aspect 205. The compound of aspect 204 wherein the —$C_1$-$C_6$alk-aryl is —CH(OH)-4-chlorophenyl, —CH(OH)-3,4-dichlorophenyl, —CH(OH)-3,4-difluorophenyl, —CH(OH)-3-fluoro-4-chlorophenyl, —CH(OH)-3-chloro-4-fluorophenyl, —CH(OH)-4-(trifluoromethyl)phenyl, —CH(OH)-3-fluoro-4-(trifluoromethyl)phenyl, —C(CF$_3$)(OH)-4-chlorophenyl, —CH(OH)-3-methyl-4-chlorophenyl, —CH(OH)-3-methyl-4-(trifluoromethyl)phenyl, —CH(OH)-2,3-dihydrobenzofuran-5-yl, —CH(OH)-benzo[d][1,3]dioxol-5-yl, —CH(F)-4-chlorophenyl, —CH(F)-3,4-dichlorophenyl, —CH(F)-3,4-difluorophenyl, —CH(F)-3-fluoro-4-chlorophenyl, —CH(F)-3-chloro-4-fluorophenyl, —CH(F)-4-(trifluoromethyl)phenyl, —CH(F)-3-fluoro-4-(trifluoromethyl)phenyl, —C(CF$_3$)(F)-4-chlorophenylphenyl, —CH(F)-3-methyl-4-chlorophenyl, —CH(F)-3-methyl-4-(trifluoromethyl)phenyl, —CH(F)-2,3-dihydrobenzofuran-5-yl, —CH(F)-benzo[d][1,3]dioxol-5-yl, —CH(NH$_2$)-4-chlorophenyl, —CH(NH$_2$)-3,4-dichlorophenyl, —CH(NH$_2$)-3,4-difluorophenyl, —CH(NH$_2$)-3-fluoro-4-chlorophenyl, —CH(NH$_2$)-3-chloro-4-fluorophenyl, —CH(NH$_2$)-4-(trifluoromethyl)phenyl, —CH(NH$_2$)-3-fluoro-4-(trifluoromethyl)phenyl, —C(CF$_3$)(NH$_2$)-4-chlorophenylphenyl, CH(NH$_2$)-3-methyl-4-chlorophenyl, —CH(NH$_2$)-3-methyl-4-(trifluoromethyl)phenyl, —CH(NH$_2$)-2,3-dihydrobenzofuran-5-yl, —CH(NH$_2$)-benzo[d][1,3]dioxol-5-yl, —CH(Me)-4-chlorophenyl, —CH(Me)-3,4-dichlorophenyl, —CH(Me)-3,4-difluorophenyl, —CH(Me)-3-fluoro-4-chlorophenyl, —CH(Me)-3-chloro-4-fluorophenyl, —CH(Me)-4-(trifluoromethyl)phenyl, —CH(Me)-3-fluoro-4-(trifluoromethyl)phenyl, —CH(Me)-3-methyl-4-chlorophenyl, —CH(Me)-3-methyl-4-(trifluoromethyl)phenyl, —C(CF$_3$)(Me)-4-chlorophenylphenyl, —CH(Me)-2,3-dihydrobenzofuran-5-yl, —CH(Me)-benzo[d][1,3]dioxol-5-yl, —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, —C(Me)(OH)-4-(trifluoromethyl)phenyl, —C(Me)(OH)-3-fluoro-4-(trifluoromethyl)phenyl, —C(Me)(OH)-3-methyl-4-chlorophenyl, —C(Me)(OH)-3-methyl-4-(trifluoromethyl)phenyl, —C(Me)(OH)-2,3-dihydrobenzofuran-5-yl, or —C(Me)(OH)-benzo[d][1,3]dioxol-5-yl.

Aspect 206. The compound of aspect 187, wherein R$_1$ is —$C_0$-$C_6$alk-heteroaryl, —$C_1$-$C_6$alk-O-heteroaryl, —$C_1$-$C_6$alk-S-heteroaryl, or —$C_1$-$C_6$alk-NH-heteroaryl.

Aspect 207. The compound of aspect 206 wherein the —C₀-C₆alk-heteroaryl is 2-(2-amino-3-bromoquinolin-7-yl)ethyl or 2-(2-amino-3-chloroquinolin-7-yl)ethyl.

Aspect 208. The compound of any one of aspects 187 to 207 wherein R² is H.

Aspect 209. The compound of any one of aspects 187 to 207 wherein R² is C₁-C₆ alkyl.

Aspect 210. The compound of any one of aspects 187 to 208 wherein R³ is H.

Aspect 211. The compound of any one of aspects 187 to 208 wherein R³ is —C₁-C₆alkyl or —C₁-C₆haloalkyl.

Aspect 212. The compound of any one of aspects 187 to 208 wherein R³ is —C(O)R⁷.

Aspect 213. The compound of aspect 212 wherein R⁷ is C₁-C₆alkyl.

Aspect 214. The compound of any one of aspects 187 to 213 wherein R⁴ is H.

Aspect 215. The compound of any one of aspects 187 to 214 wherein Q is NH.

Aspect 216. The compound of any one of aspects 187 to 214 wherein Q is O.

Aspect 217. The compound of any one of aspects 187 to 216 which is a compound of Formula I.

Aspect 218. The compound of aspect 217 wherein A is CH.

Aspect 219. The compound of aspect 217 wherein A is N.

Aspect 220. The compound of any one of aspects 217-219 wherein R⁵ is H.

Aspect 221. The compound of any one of aspects 217-219 wherein R⁵ is halo.

Aspect 222. The compound of any one of aspects 217-219 wherein R⁵ is —C₁-C₆alkyl.

Aspect 223. The compound of any one of aspects 187 to 216 that is a compound of Formula II.

Aspect 224. A pharmaceutical composition comprising a compound according to any one of aspects 187-223 and a pharmaceutically acceptable excipient.

Aspect 225. A method of inhibiting a protein arginine methyltransferase 5 (PRMT5) enzyme, comprising: contacting the PRMT5 enzyme with an effective amount of a compound of any one of any one of aspects 187 to 223.

Aspect 226. A method of treating a disease or disorder associated with aberrant PRMT5 activity in a subject comprising administering to the subject, a compound of any one of aspects 187 to 223.

Aspect 227. The method of aspect 226, wherein the disease or disorder associated with aberrant PRMT5 activity is breast cancer, lung cancer, pancreatic cancer, prostate cancer, colon cancer, ovarian cancer, uterine cancer, cervical cancer, leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), myelodysplastic syndrome (MDS), epidermoid cancer, hemoglobinopathies such as b-thalassemia and sickle cell disease (SCD), CDKN2A deleted cancers; 9P deleted cancers; MTAP deleted cancers; glioblastoma, NSCLC, head and neck cancer, bladder cancer, or hepatocellular carcinoma.

Aspect 228. A compound of Formula III or Formula IV:

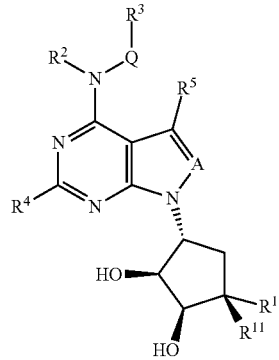

III

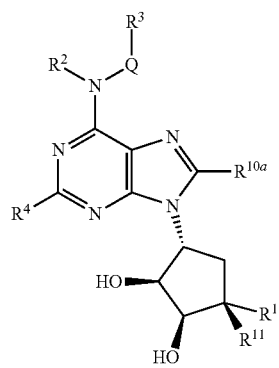

IV or a pharmaceutically acceptable salt or solvate thereof;
wherein
A is CH, CR¹⁰, or N;
Q is NH, NR⁶, or O;
R¹ is —C₀-C₆alk-C₃-C₆cycloalkyl, —C₀-C₆alk-C₃-C₆halocycloalkyl, —C₂-C₆alkenyl, —C₂-C₆haloalkenyl, —C₀-C₆alk-C₁-C₆alkyl, —C₀-C₆alk-C₁-C₆haloalkyl, —C₀-C₆alk-C≡CH, —C₀-C₆alk-C≡C—C₁-C₆alkyl, —C₀-C₆alk-C≡C—C₁-C₆haloalkyl, —C₀-C₆alk-C≡C—C₃-C₆cycloalkyl, —C₁-C₆alk-aryl, —C₁-C₆alk-S—C₁-C₆alkyl, —C₁-C₆alk-S—C₁-C₆haloalkyl, —C₁-C₆alk-S—C₃-C₆cycloalkyl; —C₁-C₆alk-S—C₃-C₆halocycloalkyl; —C₁-C₆alk-O—C₁-C₆alkyl, —C₁-C₆alk-O—C₃-C₆cycloalkyl, —C₁-C₆alk-S—CH₂-aryl, —C₁-C₆alk-C(O)NH-aryl, —C₀-C₆alk-S-aryl, —C₀-C₆alk-S(O)aryl, —C₀-C₆alk-S(O)₂aryl, —C₀-C₆alk-Oaryl, —C₀-C₆alk-heteroaryl, —C₁-C₆alk-O-heteroaryl, —C₁-C₆alk-S-heteroaryl, or —C₁-C₆alk-NH-heteroaryl;
R² is H, —C₁-C₆alkyl, —C₁-C₆haloalkyl, or —C₀-C₆alk-C₃-C₆cycloalkyl;
R³ is H, —C₁-C₆alkyl, —C₁-C₆haloalkyl, —C₀-C₆alk-C₃-C₆cycloalkyl, —C(O)R⁷, —C(O)OR⁷, or —C(O)NR⁸ᵃR⁸ᵇ;
R⁴ is H, halo, —C₁-C₆alkyl, or NH₂;
R⁵ is H, halo, CN, —C₁-C₆alkyl, —C₂-C₄alkenyl, —C₂-C₄haloalkenyl, C₂-C₄cyanoalkenyl, —C₀-C₆alk-C≡CH, —C₀-C₆alk-C≡C—C₁-C₆alkyl, —C₁-C₄haloalkyl, —C₂-C₆heterocycloalkyl, oxo-substituted-C₂-C₆heterocycloalkyl, —C₃-C₆cycloalkyl, —C₀-C₃alk-C(O)R⁹, —CR⁸R⁸'CN, —CH₂NR⁸R⁸', —C₀-C₆alk-OH, —NR⁸R⁸', —N(R⁹)CN, —O—C₁-C₄alkyl, —NR⁹CONR⁸R⁸', —OCONR⁸R⁸', or —NR⁹C(O)OR⁹ᵃ;

$R^6$ is $C_1$-$C_6$alkyl, or $C_0$-$C_6$alk-$C_3$-$C_6$cycloalkyl $R^7$ is H, $C_1$-$C_6$alkyl, or $C_0$-$C_6$alk-$C_3$-$C_6$cycloalkyl;

$R^{8a}$ and $R^{8b}$ are each independently H, $C_1$-$C_6$alkyl, or —$C_0$-$C_6$alk-O$C_1$-$C_6$alkyl, or $R^{8a}$ and $R^1$, together with the atom to which they are attached, form a $C_2$-$C_6$heterocycloalkyl ring;

$R^8$ and $R^{8'}$ are each independently H, $C_1$-$C_6$alkyl, or —$C_0$-$C_6$alk-O$C_1$-$C_6$alkyl;

or $R^8$ and $R^{8'}$, together with the atom to which they are attached, form a $C_3$-$C_6$cycloalkyl ring or a $C_2$-$C_6$heterocycloalky ring;

$R^9$ is H, —$C_1$-$C_6$alkyl, or $C_0$-$C_6$alk-$C_3$-$C_6$cycloalkyl;

$R^{9a}$ is —$C_1$-$C_6$alkyl, or $C_0$-$C_6$alk-$C_3$-$C_6$cycloalkyl;

$R^{10}$ is halo or —$C_1$-$C_6$alkyl;

$R^{10a}$ is H, halo, or —$C_1$-$C_6$alkyl; and $R^{11}$ is H, —$C_1$-$C_6$alkyl, —$C_1$-$C_6$haloalkyl, —$C_0$-$C_6$alk-$C_3$-$C_6$cycloalkyl, —$C_0$-$C_6$alk-$C_3$-$C_6$halocycloalkyl, —$C_0$-$C_6$alk-OH, —$C_0$-$C_6$alk-NH$_2$, —$C_0$-$C_6$alk-NH—$C_1$-$C_6$alkyl, —$C_0$-$C_6$alk-N($C_1$-$C_6$alkyl)-$C_1$-$C_6$alkyl, —$C_0$-$C_6$alk-NH—$C_3$-$C_6$cycloalkyl, or —$C_0$-$C_6$alk-N($C_1$-$C_6$alkyl)-$C_3$-$C_6$cycloalkyl;

or $R^{11}$ and $R^1$, together with the atom to which they are attached, form a $C_3$-$C_6$cycloalkyl ring or a heterocycloalkyl ring.

Aspect 229. The compound of aspect 228 wherein $R_1$ is —$C_0$-$C_6$alk-$C_1$-$C_6$alkyl.

Aspect 230. The compound of aspect 229 wherein the —$C_0$-$C_6$alk-$C_1$-$C_6$alkyl is —CH(OH)—$C_1$-$C_6$alkyl, —CH(F)—$C_1$-$C_6$alkyl, —CH(NH$_2$)—$C_1$-$C_6$alkyl, —CH(Me)-$C_1$-$C_6$alkyl, or —C(Me)(OH)—$C_1$-$C_6$alkyl.

Aspect 231. The compound of aspect 228 wherein $R_1$ is —$C_0$-$C_6$alk-$C_1$-$C_6$haloalkyl.

Aspect 232. The compound of aspect 231 wherein the —$C_0$-$C_6$alk-$C_1$-$C_6$haloalkyl is —CH(OH)—$C_1$-$C_6$haloalkyl, —CH(F)—$C_1$-$C_6$haloalkyl, —CH(NH$_2$)—$C_1$-$C_6$haloalkyl, —CH(Me)-$C_1$-$C_6$haloalkyl, or —C(Me)(OH)—$C_1$-$C_6$haloalkyl.

Aspect 233. The compound of aspect 228 wherein $R_1$ is —$C_0$-$C_6$alk-C≡CH.

Aspect 234. The compound of aspect 233 wherein the —$C_0$-$C_6$alk-C≡CH is —CH(OH)—C≡CH, —CH(F)—C≡CH, —CH(NH$_2$)—C≡CH, —CH(Me)-C≡CH, or —C(Me)(OH)—C≡CH.

Aspect 235. The compound of aspect 228 wherein $R_1$ is —$C_0$-$C_6$alk-C≡C—$C_1$-$C_6$alkyl.

Aspect 236. The compound of aspect 235 wherein the —$C_0$-$C_6$alk-C≡C—$C_1$-$C_6$alkyl is —CH(OH)—C≡C—$C_1$-$C_6$alkyl, —CH(F)—C≡C—$C_1$-$C_6$alkyl, —CH(NH$_2$)—C≡C—$C_1$-$C_6$alkyl, —CH(Me)-C≡C—$C_1$-$C_6$alkyl, or —C(Me)(OH)—C≡C—$C_1$-$C_6$alkyl.

Aspect 237. The compound of aspect 236 wherein the —$C_0$-$C_6$alk-C≡C—$C_1$-$C_6$alkyl is —CH(OH)—C≡C—CH$_3$, —CH(F)—C≡C—CH$_3$, —CH(NH$_2$)—C≡C—CH$_3$, —CH(Me)-C≡C—CH$_3$, or —C(Me)(OH)—C≡C—CH$_3$.

Aspect 238. The compound of aspect 228 wherein $R_1$ is —$C_0$-$C_6$alk-C≡C—$C_1$-$C_6$haloalkyl.

Aspect 239. The compound of aspect 238 wherein the —$C_0$-$C_6$alk-C≡C—$C_1$-$C_6$haloalkyl is —CH(OH)—C≡C—$C_1$-$C_6$haloalkyl, —CH(F)—C≡C—$C_1$-$C_6$haloalkyl, —CH(NH$_2$)—C≡C—$C_1$-$C_6$haloalkyl, —CH(Me)-C≡C—$C_1$-$C_6$haloalkyl, or —C(Me)(OH)—C≡C—$C_1$-$C_6$haloalkyl.

Aspect 240. The compound of aspect 239 wherein the —$C_0$-$C_6$alk-C≡C—$C_1$-$C_6$haloalkyl is —CH(OH)—C≡C—CF$_3$, —CH(F)—C≡C—CF$_3$, —CH(NH$_2$)—C≡C—CF$_3$, —CH(Me)-C≡C—CF$_3$, or —C(Me)(OH)—C≡C—CF$_3$.

Aspect 241. The compound of aspect 228 wherein $R_1$ is —$C_1$-$C_6$alk-C≡C—$C_3$-$C_6$cycloalkyl.

Aspect 242. The compound of aspect 241 wherein the —$C_0$-$C_6$alk-C≡C—$C_3$-$C_6$cycloalkyl is —CH(OH)—C≡C—$C_3$-$C_6$cycloalkyl, —CH(F)—C≡C—$C_3$-$C_6$cycloalkyl, —CH(NH$_2$)—C≡C—$C_3$-$C_6$cycloalkyl, —CH(Me)-C≡C—$C_3$-$C_6$cycloalkyl, or —C(Me)(OH)—C≡C—$C_3$-$C_6$cycloalkyl.

Aspect 243. The compound of aspect 242 wherein the —$C_0$-$C_6$alk-C≡C—$C_3$-$C_6$cycloalkyl is —CH(OH)—C≡C-cyclopropyl, —CH(F)—C≡C-cyclopropyl, —CH(NH$_2$)—C≡C-cyclopropyl, —CH(Me)-C C-cyclopropyl, or —C(Me)(OH)—C≡C-cyclopropyl.

Aspect 244. The compound of aspect 228 wherein $R_1$ is —$C_1$-$C_6$alk-aryl.

Aspect 245. The compound of aspect 244 wherein the —$C_1$-$C_6$alk-aryl is —CH$_2$-aryl, —CH(OH)-aryl, —CH(F)-aryl, —CH(NH$_2$)-aryl, —CH(Me)-aryl, or —C(Me)(OH)-aryl.

Aspect 246. The compound of aspect 245 wherein the —$C_1$-$C_6$alk-aryl is —CH$_2$-4-chlorophenyl, —CH$_2$-3,4-dichlorophenyl, —CH$_2$-3,4-difluorophenyl, —CH$_2$-3-fluoro-4-chlorophenyl, —CH$_2$-3-chloro-4-fluorophenyl, —CH(OH)-4-chlorophenyl, —CH(OH)-3,4-dichlorophenyl, —CH(OH)-3,4-difluorophenyl, —CH(OH)-3-fluoro-4-chlorophenyl, —CH(OH)-3-chloro-4-fluorophenyl, —CH(F)-4-chlorophenyl, —CH(F)-3,4-dichlorophenyl, —CH(F)-3,4-difluorophenyl, —CH(F)-3-fluoro-4-chlorophenyl, —CH(F)-3-chloro-4-fluorophenyl, —CH(NH$_2$)-4-chlorophenyl, —CH(NH$_2$)-3,4-dichlorophenyl, —CH(NH$_2$)-3,4-difluorophenyl, —CH(NH$_2$)-3-fluoro-4-chlorophenyl, —CH(NH$_2$)-3-chloro-4-fluorophenyl, —CH(Me)-4-chlorophenyl, —CH(Me)-3,4-dichlorophenyl, —CH(Me)-3,4-difluorophenyl, —CH(Me)-3-fluoro-4-chlorophenyl, —CH(Me)-3-chloro-4-fluorophenyl, —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, or —C(Me)(OH)-3-chloro-4-fluorophenyl.

Aspect 247. The compound of aspect 228 wherein $R_1$ is —$C_0$-$C_6$alk-S-aryl.

Aspect 248. The compound of aspect 247 wherein the —$C_0$-$C_6$alk-S-aryl is —S-4-chlorophenyl, —S-3,4-dichlorophenyl, —S-3,4-difluorophenyl, —S-3-fluoro-4-chlorophenyl, or —S-3-chloro-4-fluorophenyl.

Aspect 249. The compound of aspect 228 wherein $R_1$ is —$C_0$-$C_6$alk-S(O)-aryl.

Aspect 250. The compound of aspect 249 wherein the —$C_0$-$C_6$alk-S(O)-aryl is —S(O)-4-chlorophenyl, —S(O)-3,4-dichlorophenyl, —S(O)-3,4-difluorophenyl, —S(O)-3-fluoro-4-chlorophenyl, or —S(O)-3-chloro-4-fluorophenyl.

Aspect 251. The compound of aspect 228 wherein $R_1$ is —$C_0$-$C_6$alk-S(O)$_2$-aryl.

Aspect 252. The compound of aspect 251 wherein the —$C_0$-$C_6$alk-S(O)$_2$-aryl is —S(O)$_2$-4-chlorophenyl, —S(O)$_2$-3,4-dichlorophenyl, —S(O)$_2$-3,4-difluorophenyl, —S(O)$_2$-3-fluoro-4-chlorophenyl, or —S(O)$_2$-3-chloro-4-fluorophenyl.

Aspect 253. The compound of aspect 228 wherein $R_1$ is —$C_0$-$C_6$alk-O-aryl.

Aspect 254. The compound of aspect 253 wherein the —$C_0$-$C_6$alk-O-aryl is —O-4-chlorophenyl, —O-3,4-dichlorophenyl, —O-3,4-difluorophenyl, —O-3-fluoro-4-chlorophenyl, or —O-3-chloro-4-fluorophenyl.

Aspect 255. The compound of aspect 228, wherein $R_1$ is —$C_0$-$C_6$alk-heteroaryl.

Aspect 256. The compound of aspect 255 wherein the —C$_0$-C$_6$alk-heteroaryl is 2-(2-amino-3-bromoquinolin-7-yl)ethyl, 2-(2-amino-3-chloroquinolin-7-yl)ethyl, 2-(2-((cyclopropylmethyl)amino)quinolin-7-yl)ethyl, 2-(2-(methylamino)quinolin-7-yl)ethyl, or 2-(2-aminoquinolin-7-yl)ethyl.

Aspect 257. The compound of aspect 228, wherein R$_1$ is —C$_1$-C$_6$alk-O-heteroaryl.

Aspect 258. The compound of aspect 257, wherein the —C$_1$-C$_6$alk-O-heteroaryl is ((2-amino-3-bromoquinolin-7-yl)oxy)methyl.

Aspect 259. The compound of aspect 228, wherein R$_1$ is —C$_1$-C$_6$alk-S-heteroaryl.

Aspect 260. The compound of aspect 259, wherein the —C$_1$-C$_6$alk-S-heteroaryl is ((2-amino-3-bromoquinolin-7-yl)thio)methyl.

Aspect 261. The compound of aspect 228, wherein R$^1$ is —C$_1$-C$_6$alk-NH-heteroaryl.

Aspect 262. The compound of aspect 261, wherein the —C$_1$-C$_6$alk-NH-heteroaryl is 2-amino-3-bromoquinolin-7-yl)amino)methyl.

Aspect 263. The compound of any one of aspects 28 to 262 wherein R$^2$ is H.

Aspect 264. The compound of any one of aspects 228 to 262 wherein R$^2$ is C$_1$-C$_6$ alkyl.

Aspect 265. The compound of any one of aspects 228 to 264 wherein R$^3$ is H.

Aspect 266. The compound of any one of aspects 228 to 264 wherein R$^3$ is —C$_1$-C$_6$alkyl.

Aspect 267. The compound of any one of aspects 228 to 264 wherein R$^3$ is —C(O)R$^7$.

Aspect 268. The compound of aspect 267 wherein the R$^7$ is —C$_1$-C$_6$alkyl.

Aspect 269. The compound of any one of aspects 228 to 268 wherein R$^4$ is H.

Aspect 270. The compound of any one of aspects 228 to 269 wherein Q is NH.

Aspect 271. The compound of any one of aspects 228 to 269 wherein Q is O.

Aspect 272. The compound of any one of aspects 228 to 271 wherein R$^{11}$ is H.

Aspect 273. The compound of any one of aspects 228 to 272 which is a compound of Formula III.

Aspect 274. The compound of aspect 273 wherein A is CH.

Aspect 275. The compound of aspect 273 wherein A is N.

Aspect 276. The compound of aspect 273 wherein A is CR$^{10}$.

Aspect 277. The compound of aspect 276 wherein the R$^{10}$ is —C$_1$-C$_6$alkyl.

Aspect 278. The compound of any one of aspects 273 to 277 wherein R$^5$ is H.

Aspect 279. The compound of any one of aspects 273 to 277 wherein R$^5$ is halo.

Aspect 280. The compound of any one of aspects 273 to 277 wherein R$^5$ is —C$_1$-C$_6$alkyl.

Aspect 281. The compound of any one of aspects 228 to 280 which is a compound of Formula IV.

Aspect 282. The compound of aspect 281 where R$^{10a}$ is H.

Aspect 283. The compound of aspect 281 where R$^{10}$ is —C$_1$-C$_6$alkyl.

Aspect 284. A pharmaceutical composition comprising a compound according to any one of aspects 228 to 283 and a pharmaceutically acceptable excipient.

Aspect 285. A method of inhibiting a protein arginine methyltransferase 5 (PRMT5) enzyme, comprising: contacting the PRMT5 enzyme with an effective amount of a compound of any one of any one of aspects 228 to 283.

Aspect 286. A method of treating a disease or disorder associated with aberrant PRMT5 activity in a subject comprising administering to the subject, a compound of any one of aspects 228 to 283.

Aspect 287. The method of aspect 286, wherein the disease or disorder associated with aberrant PRMT5 activity is breast cancer, lung cancer, pancreatic cancer, prostate cancer, colon cancer, ovarian cancer, uterine cancer, cervical cancer, leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), myelodysplastic syndrome (MDS), epidermoid cancer, hemoglobinopathies such as b-thalassemia and sickle cell disease (SCD), CDKN2A deleted cancers; 9P deleted cancers; MTAP deleted cancers; glioblastoma, NSCLC, head and neck cancer, bladder cancer, or hepatocellular carcinoma.

Aspect 288. A compound of Formula V or Formula VI:

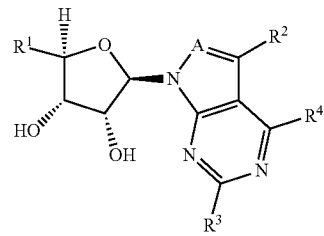

V

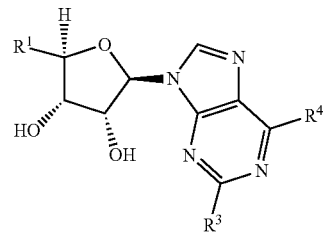

VI or a pharmaceutically acceptable salt or solvate thereof; wherein

A is CH or N;

R$^1$ is —C$_1$-C$_6$alk-aryl, —C$_1$-C$_6$alk-heteroaryl, —C$_1$-C$_6$alk-C≡CH, —C$_1$-C$_6$alk-C≡C—C$_1$-C$_6$alkyl, —C$_1$-C$_6$alk-C≡C—C$_1$-C$_6$haloalkyl, or —C$_1$-C$_6$alk-C≡C—C$_3$-C$_6$cycloalkyl;

R$^2$ is H, or halo;

R$^3$ is H, halo, NH$_2$, or C$_1$-C$_6$alkyl; and

R$^4$ is NH$_2$ or CH$_3$.

Aspect 289. The compound of aspect 288, wherein R$^1$ is —CH(OH)-aryl, —CH(Me)-aryl, —C(Me)(OH)-aryl, —CH(CH$_2$OH)-aryl, —C(Me)(OH)-heteroaryl, or —CH(OH)—C≡C—C$_3$-C$_6$cycloalkyl.

Aspect 290. The compound of aspect 288, wherein R$^1$ is —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, —CH(Me)(OH)-3-methyl-4-chlorophenyl, —CH(Me)(OH)-3-fluoro-4-trifluoromethylphenyl, —CH(Me)(OH)-4-trifluoromethylphenyl, —CH(Me)(OH)-3-methyl-4-trifluoromethylphenyl, —CH(Me)(OH)-3-chloro-4-fluorophenyl, —CH(Me)-4-chlorophenyl, —CH(CH$_2$OH)-4-chlorophenyl, —C(Me)(OH)-5-chlorothiophen-2-yl, —CH(OH)—C C-cyclopropyl.

Aspect 291. The compound of any one of aspects 288 to 290, wherein R$^3$ is H.

Aspect 292. The compound of any one of aspects 288 to 291, wherein the compound is a compound of Formula V.

Aspect 293. The compound of aspect 292, wherein R$^2$ is H.

Aspect 294. The compound of aspect 292, wherein R$^2$ is halo.

Aspect 295. The compound of aspect 294, wherein halo is fluoro.

Aspect 296. The compound of any one of aspects 288 to 292, wherein the compound is a compound of Formula VI.

Aspect 297. The compound of any one of aspects 288 to 296, wherein R$^4$ is NH$_2$.

Aspect 298. The compound of any one of aspects 288 to 296, wherein R$^4$ is CH$_3$.

Aspect 299. A pharmaceutical composition comprising a compound according to any one of aspects 288 to 298 and a pharmaceutically acceptable excipient.

Aspect 300. A method of inhibiting a protein arginine methyltransferase 5 (PRMT5) enzyme, comprising: contacting the PRMT5 enzyme with an effective amount of a compound of any one of any one of aspects 288 to 298.

Aspect 301. A method of treating a disease or disorder associated with aberrant PRMT5 activity in a subject comprising administering to the subject, a compound of any one of aspects 288 to 298.

Aspect 302. The method of aspect 301, wherein the disease or disorder associated with aberrant PRMT5 activity is breast cancer, lung cancer, pancreatic cancer, prostate cancer, colon cancer, ovarian cancer, uterine cancer, cervical cancer, leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), myelodysplastic syndrome (MDS), epidermoid cancer, hemoglobinopathies such as b-thalassemia and sickle cell disease (SCD), CDKN2A deleted cancers; 9P deleted cancers; MTAP deleted cancers; glioblastoma, NSCLC, head and neck cancer, bladder cancer, or hepatocellular carcinoma.

What is claimed:
1. A compound of Formula I or Formula II:

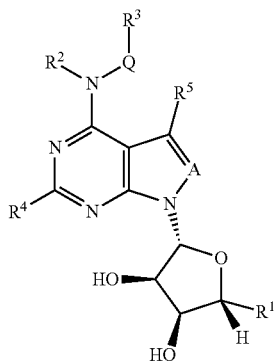

I

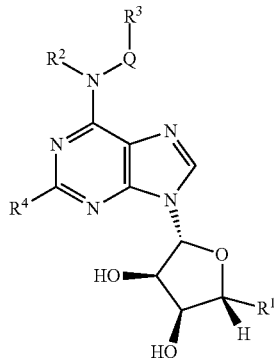

II or a pharmaceutically acceptable salt or solvate thereof;
wherein
A is CH or N;
Q is NH, NR$^6$ or O;
R$^1$ is —C$_0$-C$_6$alk-C$_3$-C$_6$cycloalkyl, —C$_0$-C$_6$alk-C$_3$-C$_6$halocycloalkyl; —C$_2$-C$_6$haloalkenyl, CH(OH)—C$_1$-C$_6$alkyl, —CH(F)—C$_1$-C$_6$alkyl, —CH(NH$_2$)—C$_1$-C$_6$alkyl, —CH(Me)-C$_1$-C$_6$alkyl, —C(Me)(OH)—C$_1$-C$_6$alkyl, —CH(OH)—C$_1$-C$_6$haloalkyl, —CH(F)—C$_1$-C$_6$haloalkyl, —CH(NH$_2$)—C$_1$-C$_6$haloalkyl, —CH(Me)-C$_1$-C$_6$haloalkyl, —C(Me)(OH)—C$_1$-C$_6$haloalkyl, —C$_0$-C$_6$alk-C≡CH, —C$_0$-C$_6$alk-C≡C—C$_1$-C$_6$alkyl, —C$_0$-C$_6$alk-C≡C—C$_1$-C$_6$haloalkyl, —C$_0$-C$_6$alk-C≡C—C$_3$-C$_6$cycloalkyl, —C$_1$-C$_6$alk-aryl, —C$_1$-C$_6$alk-S—C$_1$-C$_6$alkyl, —C$_1$-C$_6$alk-S—C$_1$-C$_6$haloalkyl, —C$_1$-C$_6$alk-S—C$_3$-C$_6$cycloalkyl; —C$_1$-C$_6$alk-S—C$_3$-C$_6$halocycloalkyl; —C$_1$-C$_6$alk-O—C$_3$-C$_6$cycloalkyl, —C$_1$-C$_6$alk-S—CH$_2$-aryl, —C$_1$-C$_6$alk-C(O)NH-aryl, 2-(2-amino-3-bromoquinolin-7-yl)ethyl or 2-(2-amino-3-chloroquinolin-7-yl)ethyl-C$_1$-C$_6$alk-O-heteroaryl, —C$_1$-C$_6$alk-S-heteroaryl, or —C$_1$-C$_6$alk-NH-heteroaryl;
R$^2$ is H, —C$_1$-C$_6$alkyl, —C$_1$-C$_6$haloalkyl, or —C$_0$-C$_6$alk-C$_3$-C$_6$cycloalkyl;
R$^3$ is H, —C$_1$-C$_6$alkyl, —C$_1$-C$_6$haloalkyl, —C$_0$-C$_6$alk-C$_3$-C$_6$cycloalkyl, —C(O)R$^7$, —C(O)OR$^7$ or —C(O)NR$^{8a}$R$^{8b}$;
R$^4$ is H, halo, —C$_1$-C$_6$alkyl, or NH$_2$;
R$^5$ is H, halo, CN, —C$_1$-C$_6$alkyl, —C$_2$-C$_4$alkenyl, —C$_2$-C$_4$haloalkenyl, C$_2$-C$_4$cyanoalkenyl, —C$_0$-C$_6$alk-C≡CH, —C$_0$-C$_6$alk-C≡C—C$_1$-C$_6$alkyl, —C$_1$-C$_4$haloalkyl, —C$_2$-C$_6$heterocycloalkyl, oxo-substituted-C$_2$-C$_6$heterocycloalkyl, —C$_3$-C$_6$cycloalkyl, —C$_0$-C$_3$alk-C(O)R$^9$, —CR$^8$R$^{8'}$CN, —CH$_2$NR$^8$R$^{8'}$, —C$_0$-C$_6$alk-OH, —NR$^8$R$^{8'}$, —N(R$^9$)CN, —O—C$_1$-C$_4$alkyl, —NR$^9$CONR$^8$R$^{8'}$, —OCONR$^8$R$^{8'}$, or —NR$^9$C(O)OR$^{9a}$;
R$^6$ is —C$_1$-C$_6$alkyl or —C$_0$-C$_6$alk-C$_3$-C$_6$cycloalkyl;
R$^7$ is H, C$_1$-C$_6$alkyl, or C$_0$-C$_6$alk-C$_3$-C$_6$cycloalkyl;
R$^{8a}$ and R$^{8b}$ are each independently H, C$_1$-C$_6$alkyl, or —C$_0$-C$_6$alk-OC$_1$-C$_6$alkyl, or R$^{8a}$ and R$^{8b}$, together with the atom to which they are attached, form a C$_2$-C$_6$heterocycloalkyl ring;
R$^8$ and R$^{8'}$ are each independently H, C$_1$-C$_6$alkyl, or —C$_0$-C$_6$alk-OC$_1$-C$_6$alkyl;
or R$^8$ and R$^{8'}$, together with the atom to which they are attached, form a C$_3$-C$_6$cycloalkyl ring or a C$_2$-C$_6$heterocycloalkyl ring;
R$^9$ is H, —C$_1$-C$_6$alkyl, or —C$_0$-C$_6$alk-C$_3$-C$_6$cycloalkyl; and
R$^{9a}$ is —C$_1$-C$_6$alkyl, or C$_0$-C$_6$alk-C$_3$-C$_6$cycloalkyl.

2. The compound according to claim 1, or a pharmaceutically acceptable salt or solvate thereof, wherein $R^1$ is —CH(OH)-aryl, —C(Me)(OH)-aryl, —CH(OH)-3,4-dichlorophenyl, —CH(OH)-3,4-difluorophenyl, —CH(OH)-3-fluoro-4-chlorophenyl, —CH(OH)-3-chloro-4-fluorophenyl, —CH(OH)-4-(trifluoromethyl)phenyl, —CH(OH)-3-fluoro-4-(trifluoromethyl)phenyl, —CH(OH)-3-methyl-4-(trifluoromethyl)phenyl, —C(CF3)(OH)-4-chlorophenyl, —CH(OH)-3-methyl-4-chlorophenyl, —CH(OH)-2,3-dihydrobenzofuran-5-yl, —CH(OH)-benzo[d][1,3]dioxol-5-yl, —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, —C(Me)(OH)-4-(trifluoromethyl)phenyl, —C(Me)(OH)-3-fluoro-4-(trifluoromethyl)phenyl, —C(Me)(OH)-3-methyl-4-(trifluoromethyl)phenyl, —C(Me)(OH)-3-methyl-4-chlorophenyl, —C(Me)(OH)-2,3-dihydrobenzofuran-5-yl, or —C(Me)(OH)-benzo[d][1,3]dioxol-5-yl.

3. The compound according to claim 2, or a pharmaceutically acceptable salt or solvate thereof, wherein $R^1$ is CH(OH)-3,4-dichlorophenyl- or —C(Me)(OH)-3,4-dichlorophenyl.

4. The compound of claim 3, or a pharmaceutically acceptable salt or solvate thereof, wherein said compound is

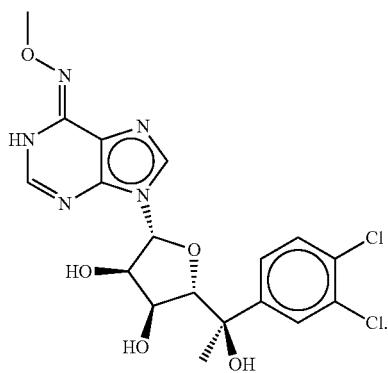

5. The compound of claim 3, or a pharmaceutically acceptable salt or solvate thereof, wherein said compound is

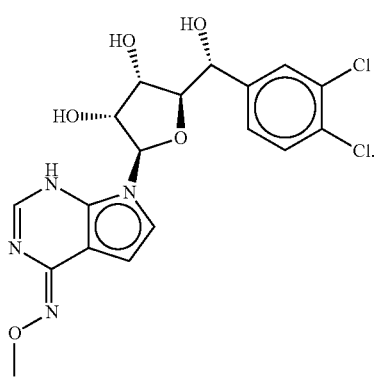

6. The compound of claim 3, or a pharmaceutically acceptable salt or solvate thereof, wherein said compound is

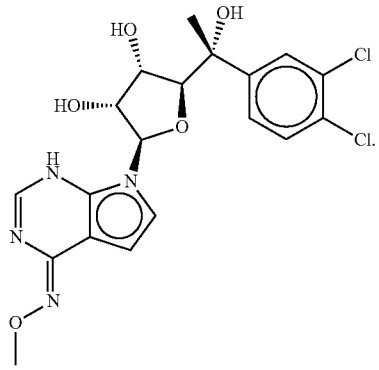

7. The compound of claim 1, or a pharmaceutically acceptable salt or solvate thereof, wherein $R^2$ is H or $C_1$-$C_6$ alkyl.

8. The compound of claim 1, or a pharmaceutically acceptable salt or solvate thereof, wherein $R^3$ is H or —$C_1$-$C_6$alkyl.

9. The compound of claim 1, or a pharmaceutically acceptable salt or solvate thereof, wherein $R^4$ is H.

10. The compound of claim 1, or a pharmaceutically acceptable salt or solvate thereof, wherein Q is NH or O.

11. The compound of claim 1, or a pharmaceutically acceptable salt or solvate thereof, wherein $R^5$ is H, halo, or —$C_1$-$C_6$alkyl.

12. A pharmaceutical composition comprising a compound according to claim 1, or a pharmaceutically acceptable salt or solvate thereof, and a pharmaceutically acceptable excipient.

13. A method of inhibiting a protein arginine methyltransferase 5 (PRMT5) enzyme, comprising: contacting the PRMT5 enzyme with an effective amount of a compound of claim 1, or a pharmaceutically acceptable salt or solvate thereof.

14. A method of treating a disease or disorder associated with aberrant PRMT5 activity in a subject comprising administering to the subject, a compound of claim 1, or a pharmaceutically acceptable salt or solvate thereof, wherein the disease or disorder associated with aberrant PRMT5 activity is breast cancer, lung cancer, pancreatic cancer, prostate cancer, colon cancer, ovarian cancer, uterine cancer, cervical cancer, leukemia, acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), myelodysplastic syndrome (MDS), epidermoid cancer, hemoglobinopathies, b-thalassemia, sickle cell disease (SCD), CDKN2A deleted cancers; 9P deleted cancers; MTAP deleted cancers; glioblastoma, NSCLC, head and neck cancer, bladder cancer, or hepatocellular carcinoma.

15. A compound of Formula V or Formula VI:

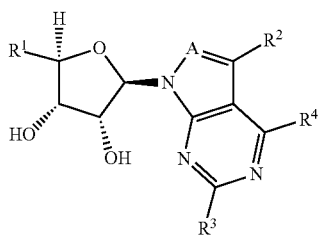

V

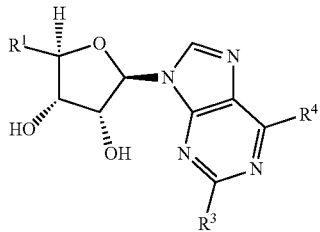

VI or a pharmaceutically acceptable salt or solvate thereof;
wherein
A is CH or N;
R¹ is —$C_1$-$C_6$alk-C≡C—$C_1$-$C_6$alkyl, —$C_1$-$C_6$alk-C≡C—$C_1$-$C_6$haloalkyl, —$C_1$-$C_6$alk-C≡C—$C_3$-$C_6$cycloalkyl, —CH(Me)-aryl, —CH($CH_2$OH)-aryl, —C(Me)(OH)-heteroaryl, —CH(OH)—C≡C—$C_3$-$C_6$cycloalkyl, —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, —CH(Me)(OH)-3-methyl-4-chlorophenyl, —CH(Me)(OH)-3-fluoro-4-trifluoromethylphenyl, —CH(Me)(OH)-4-trifluoromethylphenyl, —CH(Me)(OH)-3-methyl-4-trifluoromethylphenyl, —CH(Me)(OH)-3-chloro-4-fluorophenyl, —CH(Me)-4-chlorophenyl, —CH($CH_2$OH)-4-chlorophenyl, —C(Me)(OH)-5-chlorothiophen-2-yl, or —CH(OH)—C≡C-cyclopropyl;
R² is halo;
R³ is H, halo, $NH_2$, or $C_1$-$C_6$alkyl; and
R⁴ is $NH_2$ or $CH_3$.

16. The compound of claim 15, or a pharmaceutically acceptable salt or solvate thereof, wherein $R_1$ is —C(Me)(OH)-4-chlorophenyl, —C(Me)(OH)-3,4-dichlorophenyl, —C(Me)(OH)-3,4-difluorophenyl, —C(Me)(OH)-3-fluoro-4-chlorophenyl, —C(Me)(OH)-3-chloro-4-fluorophenyl, —CH(Me)(OH)-3-methyl-4-chlorophenyl, —CH(Me)(OH)-3-fluoro-4-trifluoromethylphenyl, —CH(Me)(OH)-4-trifluoromethylphenyl, —CH(Me)(OH)-3-methyl-4-trifluoromethylphenyl, or —CH(Me)(OH)-3-chloro-4-fluorophenyl.

17. The compound of claim 16, a pharmaceutically acceptable salt or solvate thereof, wherein said compound is

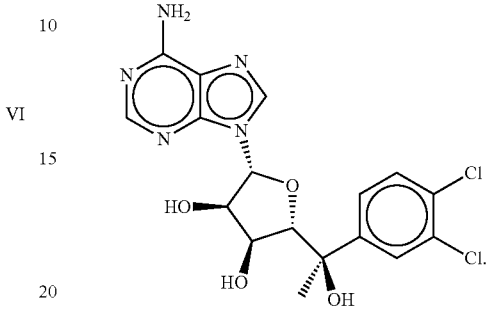

18. A pharmaceutical composition comprising a compound according to claim 15, or a pharmaceutically acceptable salt or solvate thereof, and a pharmaceutically acceptable excipient.

19. A method of inhibiting a protein arginine methyltransferase 5 (PRMT5) enzyme, comprising: contacting the PRMT5 enzyme with an effective amount of a compound of claim 15, or a pharmaceutically acceptable salt or solvate thereof.

20. A method of treating a disease or disorder associated with aberrant PRMT5 activity in a subject comprising administering to the subject, a compound of claim 15, or a pharmaceutically acceptable salt or solvate thereof, wherein the disease or disorder associated with aberrant PRMT5 activity is breast cancer, lung cancer, pancreatic cancer, prostate cancer, colon cancer, ovarian cancer, uterine cancer, cervical cancer, leukemia, acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), myelodysplastic syndrome (MDS), epidermoid cancer, hemoglobinopathies, b-thalassemia, sickle cell disease (SCD), CDKN2A deleted cancers; 9P deleted cancers; MTAP deleted cancers; glioblastoma, NSCLC, head and neck cancer, bladder cancer, or hepatocellular carcinoma.

* * * * *